US012509492B2

(12) United States Patent
Gersbach et al.

(10) Patent No.: US 12,509,492 B2
(45) Date of Patent: Dec. 30, 2025

(54) GENOME ENGINEERING WITH CRISPR-CAS SYSTEMS IN EUKARYOTES

(71) Applicants: Duke University, Durham, NC (US); North Carolina State University, Raleigh, NC (US)

(72) Inventors: Charles A. Gersbach, Durham, NC (US); Adrian Pickar Oliver, Rougemont, NC (US); Rodolphe Barrangou, Raleigh, NC (US)

(73) Assignees: Duke University, Durham, NC (US); North Carolina State University, Raleigh, NC (US)

( * ) Notice: Subject to any disclaimer, the term of this patent is extended or adjusted under 35 U.S.C. 154(b) by 1261 days.

(21) Appl. No.: 16/963,034

(22) PCT Filed: Jan. 19, 2019

(86) PCT No.: PCT/US2019/014386

§ 371 (c)(1),
(2) Date: Jul. 17, 2020

(87) PCT Pub. No.: WO2019/144061

PCT Pub. Date: Jul. 25, 2019

(65) Prior Publication Data

US 2020/0347105 A1 Nov. 5, 2020

Related U.S. Application Data

(60) Provisional application No. 62/683,595, filed on Jun. 11, 2018, provisional application No. 62/683,586, filed on Jun. 11, 2018, provisional application No. 62/671,413, filed on May 14, 2018, provisional application No. 62/619,477, filed on Jan. 19, 2018, provisional application No. 62/619,398, filed on Jan. 19, 2018.

(51) Int. Cl.

| | |
|---|---|
| ***C07K 14/47*** | (2006.01) |
| ***C07K 14/245*** | (2006.01) |
| ***C12N 9/22*** | (2006.01) |
| ***C12N 15/11*** | (2006.01) |
| ***C12N 15/90*** | (2006.01) |

(52) U.S. Cl.

CPC ........ *C07K 14/4702* (2013.01); *C07K 14/245* (2013.01); *C12N 9/22* (2013.01); *C12N 15/11* (2013.01); *C12N 15/907* (2013.01); *C07K 2319/09* (2013.01); *C07K 2319/43* (2013.01); *C07K 2319/71* (2013.01); *C07K 2319/85* (2013.01); *C12N 2310/20* (2017.05); *C12N 2800/80* (2013.01)

(58) Field of Classification Search

None

See application file for complete search history.

(56) References Cited

U.S. PATENT DOCUMENTS

| | | | |
|---|---|---|---|
| 3,687,808 | A | 8/1972 | Merigan, Jr. |
| 4,469,863 | A | 9/1984 | Ts'o et al. |
| 4,476,301 | A | 10/1984 | Imbach et al. |
| 4,501,729 | A | 2/1985 | Boucher et al. |
| 4,554,101 | A | 11/1985 | Hopp |
| 4,587,044 | A | 5/1986 | Miller et al. |
| 4,605,735 | A | 8/1986 | Miyoshi et al. |
| 4,667,025 | A | 5/1987 | Miyoshi et al. |
| 4,737,323 | A | 4/1988 | Martin et al. |
| 4,762,779 | A | 8/1988 | Snitman |
| 4,789,737 | A | 12/1988 | Miyoshi et al. |
| 4,824,941 | A | 4/1989 | Gordon et al. |
| 4,828,979 | A | 5/1989 | Klevan et al. |
| 4,835,263 | A | 5/1989 | Nguyen et al. |
| 4,845,205 | A | 7/1989 | Huynh et al. |
| 4,876,335 | A | 10/1989 | Yamane et al. |
| 4,904,582 | A | 2/1990 | Tullis |
| 4,948,882 | A | 8/1990 | Ruth |
| 4,958,013 | A | 9/1990 | Letsinger |
| 5,013,830 | A | 5/1991 | Ohsuka et al. |
| 5,023,243 | A | 6/1991 | Tullis |
| 5,034,506 | A | 7/1991 | Summerton et al. |
| 5,082,830 | A | 1/1992 | Brakel et al. |
| 5,109,124 | A | 4/1992 | Ramachandran et al. |

(Continued)

FOREIGN PATENT DOCUMENTS

| | | | |
|---|---|---|---|
| AU | 2022318664 | A1 | 2/2024 |
| CA | 2749305 | A1 | 7/2010 |

(Continued)

OTHER PUBLICATIONS

US 11,898,176 B2, 02/2024, Gersbach et al. (withdrawn)

(Continued)

*Primary Examiner* — Christopher M Babic
*Assistant Examiner* — Kimberly A Aron
(74) *Attorney, Agent, or Firm* — Michael Best & Friedrich LLP

(57) ABSTRACT

Disclosed herein are Type I Clustered Regularly Interspaced Short Palindromic Repeats (CRISPR)/CRISPR-associated (Cas) programmable systems and methods of using said Type I CRISPR/Cas programmable systems for activating gene expression, repressing gene expression, and gene editing. The disclosure relates to compositions that include Type I CRISPR-Cas fusion proteins designed for transcriptional activation, transcriptional repression, and/or gene editing of target genes in eukaryotic cells. The disclosure relates to Type I Clustered Regularly Interspaced Short Palindromic Repeats (CRISPR)/CRISPR-associated (Cas) transcriptional activation system related compositions and methods of using said Type I CRISPR/Cas transcriptional activation system related compositions for activating gene expression. The disclosure relates to compositions that include a Type I CRISPR-Cas fusion protein designed for transcriptional activation of target genes in eukaryotic cells.

12 Claims, 27 Drawing Sheets

Specification includes a Sequence Listing.

(56) References Cited

U.S. PATENT DOCUMENTS

| | | | |
|---|---|---|---|
| 5,112,963 | A | 5/1992 | Pieles et al. |
| 5,118,802 | A | 6/1992 | Smith et al. |
| 5,130,302 | A | 7/1992 | Spielvogel et al. |
| 5,134,066 | A | 7/1992 | Rogers et al. |
| 5,138,045 | A | 8/1992 | Cook et al. |
| 5,149,797 | A | 9/1992 | Pederson et al. |
| 5,166,315 | A | 11/1992 | Summerton et al. |
| 5,175,273 | A | 12/1992 | Bischofberger et al. |
| 5,177,196 | A | 1/1993 | Meyer et al. |
| 5,185,444 | A | 2/1993 | Summerton et al. |
| 5,188,897 | A | 2/1993 | Suhadolnik et al. |
| 5,214,134 | A | 5/1993 | Weis et al. |
| 5,214,136 | A | 5/1993 | Lin et al. |
| 5,216,141 | A | 6/1993 | Benner |
| 5,218,105 | A | 6/1993 | Cook et al. |
| 5,219,740 | A | 6/1993 | Miller et al. |
| 5,220,007 | A | 6/1993 | Pederson et al. |
| 5,235,033 | A | 8/1993 | Summerton et al. |
| 5,245,022 | A | 9/1993 | Weis et al. |
| 5,254,469 | A | 10/1993 | Warren, III |
| 5,256,775 | A | 10/1993 | Froehler |
| 5,258,506 | A | 11/1993 | Urdea et al. |
| 5,262,536 | A | 11/1993 | Hobbs, Jr. |
| 5,264,423 | A | 11/1993 | Cohen et al. |
| 5,264,562 | A | 11/1993 | Matteucci |
| 5,264,564 | A | 11/1993 | Matteucci |
| 5,272,250 | A | 12/1993 | Spielvogel et al. |
| 5,276,019 | A | 1/1994 | Cohen et al. |
| 5,278,302 | A | 1/1994 | Caruthers et al. |
| 5,286,717 | A | 2/1994 | Cohen et al. |
| 5,292,873 | A | 3/1994 | Rokita et al. |
| 5,317,098 | A | 5/1994 | Shizuya et al. |
| 5,321,131 | A | 6/1994 | Agrawal et al. |
| 5,366,878 | A | 11/1994 | Pederson et al. |
| 5,367,066 | A | 11/1994 | Urdea et al. |
| 5,371,241 | A | 12/1994 | Brush |
| 5,391,723 | A | 2/1995 | Priest |
| 5,399,676 | A | 3/1995 | Froehler |
| 5,403,711 | A | 4/1995 | Walder et al. |
| 5,405,938 | A | 4/1995 | Summerton et al. |
| 5,405,939 | A | 4/1995 | Suhadolnik et al. |
| 5,414,077 | A | 5/1995 | Lin et al. |
| 5,416,203 | A | 5/1995 | Letsinger |
| 5,432,272 | A | 7/1995 | Benner |
| 5,434,257 | A | 7/1995 | Matteucci et al. |
| 5,451,463 | A | 9/1995 | Nelson et al. |
| 5,453,496 | A | 9/1995 | Caruthers et al. |
| 5,455,233 | A | 10/1995 | Spielvogel et al. |
| 5,457,187 | A | 10/1995 | Gmeiner et al. |
| 5,459,255 | A | 10/1995 | Cook et al. |
| 5,466,677 | A | 11/1995 | Baxter et al. |
| 5,470,967 | A | 11/1995 | Huie et al. |
| 5,476,925 | A | 12/1995 | Letsinger et al. |
| 5,478,745 | A | 12/1995 | Samulski et al. |
| 5,484,908 | A | 1/1996 | Froehler et al. |
| 5,486,603 | A | 1/1996 | Buhr |
| 5,489,677 | A | 2/1996 | Sanghvi et al. |
| 5,491,133 | A | 2/1996 | Walder et al. |
| 5,502,177 | A | 3/1996 | Matteucci et al. |
| 5,510,473 | A | 4/1996 | Camerini-otero et al. |
| 5,510,475 | A | 4/1996 | Agrawal et al. |
| 5,512,439 | A | 4/1996 | Horner et al. |
| 5,512,667 | A | 4/1996 | Reed et al. |
| 5,514,785 | A | 5/1996 | Van Ness et al. |
| 5,519,126 | A | 5/1996 | Hecht |
| 5,525,465 | A | 6/1996 | Haralambidis et al. |
| 5,525,711 | A | 6/1996 | Hawkins et al. |
| 5,536,821 | A | 7/1996 | Agrawal et al. |
| 5,541,306 | A | 7/1996 | Agrawal et al. |
| 5,541,307 | A | 7/1996 | Cook et al. |
| 5,541,313 | A | 7/1996 | Ruth |
| 5,545,730 | A | 8/1996 | Urdea et al. |
| 5,550,111 | A | 8/1996 | Suhadolnik et al. |
| 5,552,538 | A | 9/1996 | Urdea et al. |
| 5,552,540 | A | 9/1996 | Haralambidis |
| 5,561,225 | A | 10/1996 | Maddry et al. |
| 5,563,253 | A | 10/1996 | Agrawal et al. |
| 5,565,350 | A | 10/1996 | Kmiec |
| 5,565,552 | A | 10/1996 | Magda et al. |
| 5,567,810 | A | 10/1996 | Weis et al. |
| 5,571,799 | A | 11/1996 | Tkachuk et al. |
| 5,574,142 | A | 11/1996 | Meyer et al. |
| 5,578,717 | A | 11/1996 | Urdea et al. |
| 5,578,718 | A | 11/1996 | Cook et al. |
| 5,580,731 | A | 12/1996 | Chang et al. |
| 5,585,481 | A | 12/1996 | Arnold, Jr. et al. |
| 5,587,361 | A | 12/1996 | Cook et al. |
| 5,587,371 | A | 12/1996 | Sessler et al. |
| 5,587,469 | A | 12/1996 | Cook et al. |
| 5,591,584 | A | 1/1997 | Chang et al. |
| 5,593,972 | A | 1/1997 | Weiner et al. |
| 5,595,726 | A | 1/1997 | Magda et al. |
| 5,596,086 | A | 1/1997 | Matteucci et al. |
| 5,596,091 | A | 1/1997 | Switzer |
| 5,597,696 | A | 1/1997 | Linn et al. |
| 5,599,923 | A | 2/1997 | Sessler et al. |
| 5,599,928 | A | 2/1997 | Hemmi et al. |
| 5,602,240 | A | 2/1997 | De Mesmaeker et al. |
| 5,608,046 | A | 3/1997 | Cook et al. |
| 5,610,289 | A | 3/1997 | Cook et al. |
| 5,614,617 | A | 3/1997 | Cook et al. |
| 5,618,704 | A | 4/1997 | Sanghvi et al. |
| 5,623,065 | A | 4/1997 | Cook et al. |
| 5,623,070 | A | 4/1997 | Cook et al. |
| 5,625,050 | A | 4/1997 | Beaton et al. |
| 5,633,360 | A | 5/1997 | Bischofberger et al. |
| 5,652,355 | A | 7/1997 | Metelev et al. |
| 5,652,356 | A | 7/1997 | Agrawal |
| 5,663,312 | A | 9/1997 | Chaturvedula et al. |
| 5,677,437 | A | 10/1997 | Teng et al. |
| 5,677,439 | A | 10/1997 | Weis et al. |
| 5,681,941 | A | 10/1997 | Cook et al. |
| 5,688,941 | A | 11/1997 | Cook et al. |
| 5,700,922 | A | 12/1997 | Cook et al. |
| 5,714,331 | A | 2/1998 | Buchardt et al. |
| 5,719,262 | A | 2/1998 | Buchardt et al. |
| 5,750,692 | A | 5/1998 | Cook et al. |
| 5,773,700 | A | 6/1998 | Van Grinsven et al. |
| 5,962,428 | A | 10/1999 | Carrano et al. |
| 6,140,081 | A | 10/2000 | Barbas |
| 6,207,453 | B1 | 3/2001 | Maass et al. |
| 6,268,490 | B1 | 7/2001 | Imanishi et al. |
| 6,287,860 | B1 | 9/2001 | Monia et al. |
| 6,453,242 | B1 | 9/2002 | Eisenberg et al. |
| 6,462,254 | B1 | 10/2002 | Vernachio et al. |
| 6,534,261 | B1 | 3/2003 | Cox, III et al. |
| 6,734,291 | B2 | 5/2004 | Kochkine et al. |
| 6,770,748 | B2 | 8/2004 | Imanishi et al. |
| 6,794,499 | B2 | 9/2004 | Wengel et al. |
| 7,034,133 | B2 | 4/2006 | Wengel et al. |
| 7,053,207 | B2 | 5/2006 | Wengel |
| 7,060,809 | B2 | 6/2006 | Wengel et al. |
| 7,074,596 | B2 | 7/2006 | Darzynkiewicz et al. |
| 7,084,125 | B2 | 8/2006 | Wengel |
| 7,449,561 | B1 | 11/2008 | Sommer et al. |
| 7,572,582 | B2 | 8/2009 | Wengel et al. |
| 7,728,118 | B2 | 6/2010 | Wood et al. |
| 7,745,651 | B2 | 6/2010 | Heyes et al. |
| 7,799,565 | B2 | 9/2010 | Maclachlan et al. |
| 8,278,036 | B2 | 10/2012 | Kariko et al. |
| 8,450,107 | B1 | 5/2013 | Zhang et al. |
| 8,586,526 | B2 | 11/2013 | Gregory et al. |
| 8,889,356 | B2 | 11/2014 | Zhang |
| 9,139,554 | B2 | 9/2015 | Hope et al. |
| 9,458,205 | B2 | 10/2016 | Gregory et al. |
| 9,890,364 | B2 | 2/2018 | Joung et al. |
| 10,266,850 | B2 | 4/2019 | Doudna et al. |
| 11,421,251 | B2 | 8/2022 | Gersbach et al. |
| 11,427,817 | B2 | 8/2022 | Josephs et al. |
| 11,970,710 | B2 | 4/2024 | Gersbach et al. |
| 11,976,307 | B2 | 5/2024 | Gersbach et al. |
| 2002/0160940 | A1 | 10/2002 | Case et al. |
| 2003/0124102 | A1 | 7/2003 | Rudnicki et al. |
| 2004/0142025 | A1 | 7/2004 | Maclachlan et al. |

(56) References Cited

U.S. PATENT DOCUMENTS

| | | | |
|---|---|---|---|
| 2004/0175727 | A1 | 9/2004 | Draghia-Akli et al. |
| 2004/0192593 | A1 | 9/2004 | Draghia-Akli et al. |
| 2004/0204345 | A1 | 10/2004 | Case et al. |
| 2005/0079512 | A1 | 4/2005 | Emerson et al. |
| 2006/0068395 | A1 | 3/2006 | Wood et al. |
| 2006/0171924 | A1 | 8/2006 | Luo et al. |
| 2006/0211647 | A1 | 9/2006 | Khan |
| 2006/0270595 | A1 | 11/2006 | Jullien et al. |
| 2007/0042031 | A1 | 2/2007 | Maclachlan et al. |
| 2007/0042462 | A1 | 2/2007 | Hildinger |
| 2007/0059795 | A1 | 3/2007 | Moore et al. |
| 2007/0185042 | A1 | 8/2007 | Tsai et al. |
| 2007/0192880 | A1 | 8/2007 | Muyan et al. |
| 2008/0070299 | A1 | 3/2008 | Wood et al. |
| 2008/0090291 | A1 | 4/2008 | Wood et al. |
| 2009/0018031 | A1 | 1/2009 | Trinklein et al. |
| 2010/0035968 | A1 | 2/2010 | Rasmussen et al. |
| 2010/0076057 | A1 | 3/2010 | Sontheimer et al. |
| 2010/0261175 | A1 | 10/2010 | Rasmussen et al. |
| 2010/0267018 | A1 | 10/2010 | Wengel et al. |
| 2011/0145940 | A1 | 6/2011 | Voytas et al. |
| 2011/0197290 | A1 | 8/2011 | Fahrenkrug et al. |
| 2011/0263682 | A1 | 10/2011 | De Kimpe et al. |
| 2011/0301073 | A1 | 12/2011 | Gregory et al. |
| 2012/0207744 | A1 | 8/2012 | Mendlein et al. |
| 2013/0274129 | A1 | 10/2013 | Katzen et al. |
| 2014/0179006 | A1 | 6/2014 | Zhang |
| 2014/0234975 | A1 | 8/2014 | Silva et al. |
| 2014/0295557 | A1 | 10/2014 | Joung et al. |
| 2014/0315862 | A1 | 10/2014 | Kaye |
| 2014/0356956 | A1 | 12/2014 | Church et al. |
| 2015/0024499 | A1 | 1/2015 | Brouns et al. |
| 2015/0044772 | A1 | 2/2015 | Zhao |
| 2015/0045413 | A1 | 2/2015 | De Visser et al. |
| 2015/0056705 | A1 | 2/2015 | Conway et al. |
| 2015/0159178 | A1 | 6/2015 | Green et al. |
| 2015/0225717 | A1 | 8/2015 | Lee et al. |
| 2015/0252358 | A1 | 9/2015 | Maeder et al. |
| 2016/0002634 | A1 | 1/2016 | Sazani et al. |
| 2016/0040189 | A1 | 2/2016 | Kennedy et al. |
| 2016/0058889 | A1 | 3/2016 | Olson et al. |
| 2016/0177278 | A1 | 6/2016 | Wolfe et al. |
| 2016/0199419 | A1 | 7/2016 | Miura |
| 2016/0281166 | A1 | 9/2016 | Bhattacharjee et al. |
| 2016/0354487 | A1 | 12/2016 | Zhang et al. |
| 2017/0002316 | A1 | 1/2017 | Gascón Jiménez et al. |
| 2017/0204407 | A1 | 7/2017 | Gilbert et al. |
| 2017/0283831 | A1 | 10/2017 | Zhang et al. |
| 2017/0362635 | A1 | 12/2017 | Chamberlain et al. |
| 2018/0073012 | A1 | 3/2018 | Liu et al. |
| 2018/0127780 | A1 | 5/2018 | Liu et al. |
| 2018/0135023 | A1 | 5/2018 | Wang et al. |
| 2018/0135109 | A1 | 5/2018 | Jayaram et al. |
| 2018/0201951 | A1 | 7/2018 | Guilak et al. |
| 2018/0237771 | A1 | 8/2018 | Kim et al. |
| 2018/0251735 | A1 | 9/2018 | Ko |
| 2018/0271069 | A1 | 9/2018 | Min et al. |
| 2018/0280539 | A1 | 10/2018 | Debs et al. |
| 2018/0298380 | A1 | 10/2018 | Gao et al. |
| 2018/0305689 | A1 | 10/2018 | Sætrom et al. |
| 2018/0305704 | A1 | 10/2018 | Zhang |
| 2018/0305719 | A1 | 10/2018 | Perez-Pinera et al. |
| 2018/0319850 | A1 | 11/2018 | Payne et al. |
| 2018/0327740 | A1 | 11/2018 | Gifford et al. |
| 2018/0334685 | A1 | 11/2018 | Yeo et al. |
| 2018/0355332 | A1 | 12/2018 | Steinberg et al. |
| 2019/0032049 | A1 | 1/2019 | Naldini et al. |
| 2019/0038776 | A1 | 2/2019 | Pyle et al. |
| 2019/0048337 | A1 | 2/2019 | Hsu et al. |
| 2019/0062790 | A1 | 2/2019 | Doudna et al. |
| 2019/0078119 | A1 | 3/2019 | Wilson et al. |
| 2019/0106710 | A1 | 4/2019 | Zhang et al. |
| 2019/0167815 | A1 | 6/2019 | Holmes et al. |
| 2019/0183932 | A1 | 6/2019 | Mackall et al. |
| 2019/0192691 | A1 | 6/2019 | Barrett et al. |
| 2019/0201402 | A1 | 7/2019 | Jiang et al. |
| 2019/0225955 | A1 | 7/2019 | Liu et al. |
| 2019/0248854 | A1 | 8/2019 | Tremblay et al. |
| 2019/0264232 | A1 | 8/2019 | Hou et al. |
| 2019/0374655 | A1 | 12/2019 | Kabadi et al. |
| 2020/0002731 | A1 | 1/2020 | Frendewey et al. |
| 2020/0056206 | A1 | 2/2020 | Tremblay et al. |
| 2020/0063105 | A1 | 2/2020 | Ng et al. |
| 2020/0080108 | A1 | 3/2020 | Jaskula-Ranga et al. |
| 2020/0080112 | A1 | 3/2020 | Zhang et al. |
| 2020/0123533 | A1 | 4/2020 | Wang et al. |
| 2020/0216549 | A1 | 7/2020 | Fukumura et al. |
| 2020/0216810 | A1 | 7/2020 | Metelitsa et al. |
| 2020/0260698 | A1 | 8/2020 | Kyrychenko et al. |
| 2020/0275641 | A1 | 9/2020 | Min et al. |
| 2020/0361877 | A1 | 11/2020 | Mahajan et al. |
| 2021/0024895 | A1 | 1/2021 | Kariko et al. |
| 2021/0054448 | A1 | 2/2021 | Ng et al. |
| 2021/0254049 | A1 | 8/2021 | Wang et al. |
| 2021/0277379 | A1 | 9/2021 | Gaudelli et al. |
| 2021/0322577 | A1 | 10/2021 | Lande et al. |
| 2021/0363525 | A1 | 11/2021 | Sætrom et al. |
| 2022/0098561 | A1 | 3/2022 | Gersbach et al. |
| 2022/0177879 | A1 | 6/2022 | Gersbach et al. |
| 2022/0184229 | A1 | 6/2022 | Gersbach et al. |
| 2022/0186199 | A1 | 6/2022 | Cotta-Ramusino et al. |
| 2022/0195406 | A1 | 6/2022 | Gersbach et al. |
| 2022/0244244 | A1 | 8/2022 | Schmedt et al. |
| 2022/0249626 | A1 | 8/2022 | Kmiec et al. |
| 2022/0305141 | A1 | 9/2022 | Gersbach et al. |
| 2022/0307015 | A1 | 9/2022 | Gersbach et al. |
| 2022/0364124 | A1 | 11/2022 | Gersbach et al. |
| 2022/0396790 | A1 | 12/2022 | Gersbach et al. |
| 2023/0032846 | A1 | 2/2023 | Gersbach et al. |
| 2023/0047669 | A1 | 2/2023 | Josephs et al. |
| 2023/0201375 | A1 | 6/2023 | Gersbach et al. |
| 2023/0257723 | A1 | 8/2023 | Gersbach et al. |
| 2023/0304000 | A1 | 9/2023 | Josephs et al. |
| 2023/0348870 | A1 | 11/2023 | Gersbach et al. |
| 2023/0349888 | A1 | 11/2023 | Gersbach et al. |
| 2023/0383270 | A1 | 11/2023 | Gersbach et al. |
| 2023/0383297 | A1 | 11/2023 | Gersbach et al. |
| 2023/0392132 | A1 | 12/2023 | Gersbach et al. |
| 2024/0026352 | A1 | 1/2024 | Gersbach et al. |
| 2024/0052328 | A1 | 2/2024 | Kwon et al. |
| 2024/0058425 | A1 | 2/2024 | Gersbach et al. |
| 2024/0067968 | A1 | 2/2024 | Cosgrove et al. |
| 2024/0141341 | A1 | 5/2024 | Gersbach et al. |
| 2024/0279628 | A1 | 8/2024 | Gersbach et al. |
| 2025/0114482 | A1 | 4/2025 | Gersbach et al. |

FOREIGN PATENT DOCUMENTS

| | | | |
|---|---|---|---|
| CA | 2981508 | A1 | 10/2016 |
| CA | 3086885 | A1 | 7/2019 |
| CA | 3101477 | A1 | 12/2019 |
| EP | 3009511 | A2 | 4/2016 |
| EP | 3199632 | A1 | 8/2017 |
| EP | 3712272 | A1 | 9/2020 |
| EP | 3209783 | B1 | 11/2021 |
| EP | 3995584 | A1 | 5/2022 |
| JP | 2013-509159 | A | 3/2013 |
| JP | 2015-534817 | A | 12/2015 |
| JP | 2016-521452 | A2 | 7/2016 |
| JP | 2016-521975 | A | 7/2016 |
| JP | 2016-523082 | A | 8/2016 |
| JP | 2018-011546 | A | 1/2018 |
| JP | 2019-103393 | A | 6/2019 |
| JP | 2020-517247 | A | 6/2020 |
| KR | 20190134673 | A | 12/2019 |
| WO | WO1991/18114 | A1 | 11/1991 |
| WO | WO1992/000387 | A1 | 1/1992 |
| WO | WO1993/007883 | A1 | 4/1993 |
| WO | 1993/024640 | A2 | 12/1993 |
| WO | 1994/016737 | A1 | 8/1994 |
| WO | WO1998/053058 | A1 | 11/1998 |
| WO | WO1998/053059 | A1 | 11/1998 |
| WO | WO1998/053060 | A1 | 11/1998 |
| WO | WO 2000/028004 | A1 | 5/2000 |

(56) References Cited

FOREIGN PATENT DOCUMENTS

| | | | |
|---|---|---|---|
| WO | 2001/083793 | A2 | 11/2001 |
| WO | WO2001/083783 | A2 | 11/2001 |
| WO | WO 2001/092551 | A2 | 12/2001 |
| WO | WO2002/016536 | A1 | 2/2002 |
| WO | WO2003/016496 | A2 | 2/2003 |
| WO | WO2003/072788 | A1 | 9/2003 |
| WO | 2004/018632 | A2 | 3/2004 |
| WO | WO2007/019301 | A2 | 2/2007 |
| WO | WO2008/006028 | A2 | 1/2008 |
| WO | WO2008/070859 | A2 | 6/2008 |
| WO | WO2010/144740 | A1 | 12/2010 |
| WO | WO2011/036640 | A2 | 3/2011 |
| WO | 2011/141820 | A1 | 11/2011 |
| WO | 2011/146121 | A1 | 11/2011 |
| WO | WO2011/154427 | A1 | 12/2011 |
| WO | WO2012/136476 | A1 | 10/2012 |
| WO | 2013/098244 | A1 | 7/2013 |
| WO | WO2014/018423 | A2 | 1/2014 |
| WO | WO2014/059255 | A1 | 4/2014 |
| WO | WO2014/065596 | A1 | 5/2014 |
| WO | WO2014/081855 | A1 | 5/2014 |
| WO | 2014/089290 | A1 | 6/2014 |
| WO | 2014/093622 | A2 | 6/2014 |
| WO | 2014/093712 | A1 | 6/2014 |
| WO | 2014/099744 | A1 | 6/2014 |
| WO | WO2014/093479 | A1 | 6/2014 |
| WO | WO2014/093595 | A1 | 6/2014 |
| WO | WO2014/093709 | A1 | 6/2014 |
| WO | WO2014/144592 | A2 | 9/2014 |
| WO | 2014/197568 | A2 | 12/2014 |
| WO | 2014/197748 | A2 | 12/2014 |
| WO | WO2014/204726 | A1 | 12/2014 |
| WO | 2015/006747 | A2 | 1/2015 |
| WO | 2015/021457 | A2 | 2/2015 |
| WO | 2015/035139 | A2 | 3/2015 |
| WO | WO2015/035136 | A2 | 3/2015 |
| WO | WO2015/048690 | A1 | 4/2015 |
| WO | WO2015/070083 | A1 | 5/2015 |
| WO | 2015/089462 | A1 | 6/2015 |
| WO | WO2015/089427 | A1 | 6/2015 |
| WO | 2015/155686 | A2 | 10/2015 |
| WO | WO2015/161276 | A2 | 10/2015 |
| WO | 2015/195621 | A1 | 12/2015 |
| WO | 2016/011080 | A2 | 1/2016 |
| WO | WO2016/011070 | A2 | 1/2016 |
| WO | WO2016/049258 | A2 | 3/2016 |
| WO | WO 2016/054326 | A1 | 4/2016 |
| WO | WO2016/063264 | A1 | 4/2016 |
| WO | WO2016/070070 | A1 | 5/2016 |
| WO | WO2016/081924 | A1 | 5/2016 |
| WO | WO2016/114972 | A1 | 7/2016 |
| WO | WO2016/123578 | A1 | 8/2016 |
| WO | WO2016/161380 | A1 | 10/2016 |
| WO | 2016/182893 | A1 | 11/2016 |
| WO | 2016/205613 | A1 | 12/2016 |
| WO | WO2016/187717 | A1 | 12/2016 |
| WO | 2017/016915 | A1 | 2/2017 |
| WO | WO2017/049266 | A2 | 3/2017 |
| WO | WO2017/049407 | A1 | 3/2017 |
| WO | 2017/066497 | A2 | 4/2017 |
| WO | WO2017/070632 | A2 | 4/2017 |
| WO | WO2017/072590 | A1 | 5/2017 |
| WO | WO2017/075478 | A2 | 5/2017 |
| WO | WO2017/139505 | A2 | 8/2017 |
| WO | WO2017/165859 | A1 | 9/2017 |
| WO | 2017/180976 | A1 | 10/2017 |
| WO | 2018/005805 | A1 | 1/2018 |
| WO | 2018/017483 | A1 | 1/2018 |
| WO | WO2018/002812 | A1 | 1/2018 |
| WO | WO 2018/013932 | A1 | 1/2018 |
| WO | WO2018/017751 | A1 | 1/2018 |
| WO | WO2018/035388 | A1 | 2/2018 |
| WO | WO2018/035495 | A1 | 2/2018 |
| WO | 2018/039145 | A1 | 3/2018 |
| WO | WO2018/081504 | A1 | 5/2018 |
| WO | WO2018/098480 | A1 | 5/2018 |
| WO | 2018/107003 | A1 | 6/2018 |
| WO | 2018/129486 | A2 | 7/2018 |
| WO | WO2018/129296 | A1 | 7/2018 |
| WO | WO2018/162702 | A1 | 9/2018 |
| WO | 2018/179578 | A1 | 10/2018 |
| WO | 2018/195073 | A2 | 10/2018 |
| WO | WO2018/191388 | A1 | 10/2018 |
| WO | 2019/009682 | A2 | 1/2019 |
| WO | WO2019/002590 | A1 | 1/2019 |
| WO | WO 2019/014230 | A1 | 1/2019 |
| WO | WO2019/023291 | A2 | 1/2019 |
| WO | WO 2019/036599 | A1 | 2/2019 |
| WO | WO 2019/038776 | A1 | 2/2019 |
| WO | 2019/046755 | A1 | 3/2019 |
| WO | WO2019/067786 | A1 | 4/2019 |
| WO | WO2019/077001 | A1 | 4/2019 |
| WO | WO2019/079514 | A1 | 4/2019 |
| WO | WO2019/084050 | A1 | 5/2019 |
| WO | WO2019/092505 | A1 | 5/2019 |
| WO | 2019/113472 | A1 | 6/2019 |
| WO | 2019/120283 | A1 | 6/2019 |
| WO | WO2019/123014 | A1 | 6/2019 |
| WO | WO2019/136216 | A1 | 7/2019 |
| WO | 2019/152609 | A1 | 8/2019 |
| WO | 2019/204750 | A1 | 10/2019 |
| WO | WO2019/213626 | A1 | 11/2019 |
| WO | WO2019/232069 | A1 | 12/2019 |
| WO | 2020/018918 | A1 | 1/2020 |
| WO | 2020/086881 | A1 | 4/2020 |
| WO | 2020/101042 | A1 | 5/2020 |
| WO | 2020/106916 | A1 | 5/2020 |
| WO | WO2020/124257 | A1 | 6/2020 |
| WO | WO 2020/132226 | A1 | 6/2020 |
| WO | 2020/168133 | A1 | 8/2020 |
| WO | WO2020/163396 | A1 | 8/2020 |
| WO | WO2020/257665 | A1 | 12/2020 |
| WO | WO2021/055956 | A1 | 3/2021 |
| WO | 2021/076744 | A1 | 4/2021 |
| WO | WO2021/222328 | A1 | 11/2021 |
| WO | 2022/038264 | A1 | 2/2022 |
| WO | 2022/055946 | A1 | 3/2022 |
| WO | WO2022/087321 | A1 | 4/2022 |
| WO | WO 2022/103935 | A1 | 5/2022 |
| WO | WO2022/104159 | A1 | 5/2022 |
| WO | 2022/133062 | A1 | 6/2022 |
| WO | WO2022/187288 | A2 | 9/2022 |
| WO | 2023/283631 | A2 | 1/2023 |
| WO | WO 2023/010133 | A2 | 2/2023 |
| WO | WO 2023/137471 | A1 | 7/2023 |
| WO | WO 2023/137472 | A2 | 7/2023 |
| WO | 2023/164670 | A2 | 8/2023 |
| WO | 2023/164671 | A2 | 8/2023 |
| WO | WO2023/200998 | A2 | 10/2023 |
| WO | WO 2024/015881 | A2 | 1/2024 |
| WO | WO2024/040253 | A1 | 2/2024 |
| WO | WO 2024/064642 | A2 | 3/2024 |
| WO | WO2024/081937 | A1 | 4/2024 |
| WO | 2024/092258 | A2 | 5/2024 |
| WO | WO 2024/040254 | A3 | 5/2024 |
| WO | WO 2024/220947 | A2 | 10/2024 |
| WO | WO 2025/038982 | A2 | 2/2025 |
| WO | WO 2025/049903 | A2 | 3/2025 |

OTHER PUBLICATIONS

Kotterman et al., 2014 (Nature Reviews, vol. 15, p. 445-451).*
Shim et al., 2017 (Current Gene Therapy, vol. 17, No. 5, p. 1-18).*
Lenzi et al., 2014 (NCBI Bookshelf, A Service of the National Library of Medicine, National Institute of Health, Oversight and Review of Clinical Gene Transfer Protocols: Assessing the Role of the Recombinant DNA Advisory Committee. Washington (DC): National Academies Press (US), pp. 1-16).*
Dunbar et al., 2018 (Science, vol. 359, eaan4672, p. 1-10).*
Bulcha et al., 2021 (Signal Transduction and Targeted Therapy, 6:53, p. 1-24).*
Gersbach et al., 2017 (Geneseq Accession No. BDV61294, computer printout, pp. 1-3) (Gersbach SEQ ID No. 377).*

(56) References Cited

OTHER PUBLICATIONS

Gersbach et al., 2017 (Geneseq Accession No. BDV61295, computer printout, pp. 1-3) (Gersbach SEQ ID No. 378).*
Gersbach et al., 2017 (Geneseq Accession No. BDV61296, computer printout, pp. 1-3) (Gersbach SEQ ID No. 379).*
Gersbach et al., 2017 (Geneseq Accession No. BDV61297, computer printout, pp. 1-3) (Gersbach SEQ ID No. 380).*
Gersbach et al., 2017 (Geneseq Accession No. BDV61311, computer printout, pp. 1-3) (Gersbach SEQ ID No. 381).*
Hideki et al., 2018 (Geneseq Accession No. BFK30060, computer printout, pp. 1-3).*
Adikusuma et al., "Versatile single-step-assembly CRISPR/Cas9 vectors for dual gRNA expression," 2017, 12(12): e0187236.
Carcagno et al., "Neurogenin3 Restricts Serotonergic Neuron Differentiation to the Hindbrain," The Journal of Neuroscience, 2014, 34(46): 15223-15233.
Kalsner et al., "Prader-Willi, Angelman, and 15q11-q13 Duplication Syndromes," Pediatric Clinics of North America United States, 2015, 62(3): 587-606.
Ohta et al., "Imprinting-Mutation Mechanisms in Prader-Willi Syndrome," The American Journal of Human Genetics, 1999, 64(2): 397-413.
Yang et al., "A dual AAV system enables the Cas9-mediates correction of a metabolic liver disease in newborn mice," Nature Biotechnology, 2016, 34(3): 334-338.
Black et al., "Synthetic transcription factors for cell fate reprogramming," Current Opinion in Genetics & Development 2018, 52, 13-21.
'T Hoen et al., "Generation and characterization of transgenic mice with the full-length human DMD gene," J. Biol. Chem., 2008, 283: 5899-5907.
Aartsma-Rus et al., "Antisense-mediated exon skipping: a versatile tool with therapeutic and research applications," RNA, 2007, 13: 1609-1624.
Aartsma-Rus et al., "Exploring the frontiers of therapeutic exon skipping for Duchenne muscular dystrophy by double targeting within one or multiple exons," Mol Ther, 2006, 14: 401-407.
Aartsma-Rus et al., "Theoretic applicability of antisense-mediated exon skipping for Duchenne muscular dystrophy mutations," Hum Mutat, 2009, 30: 293-299.
Acosta et al., "Use of two gRNAs for CRISPR/Cas9 improves bi-allelic homologous recombination efficiency in mouse embryonic stem cells," Genesis, 2018, 56(5): 1-8.
Adamson et al., "A Multiplexed Single-Cell CRISPR Screening Platform Enables Systematic Dissection of the Unfolded Protein Response," Cell, 2016, 167: 1867-1882 e1821.
Adamson et al., "A Multiplexed Single-Cell CRISPR Screening Platform Enables Systematic Dissection of the Unfolded Protein Response," Cell, 2016, 167: 1867-1882.e21.
Adler et al., "Nonviral direct conversion of primary mouse embryonic fibroblasts to neuronal cells," Molecular therapy, 2012 Nucleic acids 1, e32.
Aguilar et al., "Transcriptional and Chromatin Dynamics of Muscle Regeneration after Severe Trauma," Stem Cell Rep, 2016, 7: 983-997.
Ahlenius et al., "FoxO3 regulates neuronal reprogramming of cells from postnatal and aging mice," Proc Natl Acad Sci U S A, 2016, 113: 8514-8519.
Aiuti et al., "Lentiviral hematopoietic stem cell gene therapy in patients with Wiskott-Aldrich syndrome," Science, 2013, 341(6148): 1233151.
Albuquerque et al., "Mammalian nicotinic acetylcholine receptors: from structure to function," Physiol Rev, 2009, 89: 73-120.
Aloia, "Epigenetic Regulation of Cell-Fate Changes That Determine Adult Liver Regeneration After Injury," Front. Cell Dev. Biol., 2021, 9: 643055.
Amabile et al., "Inheritable Silencing of Endogenous Genes by Hit-and-Run Targeted Epigenetic Editing," Cell, 2016, 167(1): 219-232.e14.
Amabile et al., "Permanent Epigenetic Silencing of Human Genes With Artificial Transcriptional Repressors,", Molecular Therapy, 2015, 23(Suppl. 1): S275.
Amoasii et al., "Gene editing restores dystrophin expression in a canine model of Duchenne muscular dystrophy," Science, 2018, 362: 86-91.
Amoasii et al., "Single-cut genome editing restores dystrophin expression in a new mouse model of muscular dystrophy," Sci Transl Med, Nov. 2017, 9(418): eaan8081.
Anders et al., "Differential expression analysis for sequence count data," Genome biology 11, 2010, R106.
Andersen et al., "Dual role of delta-like 1 homolog (DLK1) in skeletal muscle development and adult muscle regeneration," Development, 2013, 140: 3743-3753.
Anguela et al., "Robust ZFN-mediated genome editing in adult hemophilic mice," Blood, 2013, 122: 3283-3287.
Aoki et al., "Bodywide skipping of exons 45-55 in dystrophic mdx52 mice by systemic antisense delivery," Proc Natl Acad Sci USA, 2012, 109: 13763-13768.
Arechavala-Gomeza et al., "Comparative analysis of antisense oligonucleotide sequences for targeted skipping of exon 51 during dystrophin pre-mRNA splicing in human muscle," Human Gene Therapy, 2007, 18: 798-810.
Arnett et al., "Adeno-associated viral vectors do not efficiently target muscle satellite cells," Molecular Therapy Methods & Clinical Development, 2014, 1: 14038.
Asokan et al., "Reengineering a receptor footprint of adeno-associated virus enables selective and systemic gene transfer to muscle," Nat Biotechnol, 2010, 28: 79-82.
Asrani et al., "Burden of liver diseases in the world," J Hepatol, 2019, 70(1): 151-171.
Bae et al., "Cas-OFFinder: a fast and versatile algorithm that searches for potential off-target sites of Cas9 RNA-guided endonucleases," Bioinformatics, 2014, 30: 1473-1475.
Balboa et al., "Conditionally Stabilized dCas9 Activator for Controlling Gene Expression in Human Cell Reprogramming and Differentiation," Stem Cell Rep, 2015, 5: 448-459.
Baratta et al., "Cellular organization of normal mouse liver: a histological, quantitative immunocytochemical, and fine structural analysis," Histochem Cell Biol, 2009, 131(6): 713-726.
Barberi et al., "Derivation of engraftable skeletal myoblasts from human embryonic stem cells," Nat Med, 2007, 13: 642-648.
Barr et al., "Predominant Expression of Alternative PAX3 and PAX7 Forms in Myogenic and Neural Tumor Cell Lines," Cancer Res, 1999, 59: 5443-5448.
Barrangou et al., "CRISPR provides acquired resistance against viruses in prokaryotes," Science, 2007, 315(5819): 1709-1712.
Bartel et al., "Isolation of new ribozymes from a large pool of random sequences," Science, 1993, 261(5127): 1411-1418.
Bartsevich et al., "Engineered zinc finger proteins for controlling stem cell fate," Stem Cells, 2003, 21: 632-637.
Bauer et al., "An erythroid enhancer of BCL11A subject to genetic variation determines fetal hemoglobin level," Science 342, 2013, 253-257.
Beaudry et al., "Directed evolution of an RNA enzyme," Science, 1992, 257(5070): 635-641.
Beerli et al., "Chemically regulated zinc finger transcription factors," J Biol Chem, 2000, 275(42): 32617-27.
Beerli et al., "Engineering polydactyl zinc-finger transcription factors," Nat Biotechnol, 2002, 20: 135-141.
Beerli et al., "Positive and negative regulation of endogenous genes by designed transcription factors," Proc Natl Acad Sci USA, 2000, 97: 1495-1500.
Beerli et al., "Toward controlling gene expression at will: specific regulation of the erbB-2/HER-2 promoter by using polydactyl zinc finger proteins constructed from modular building blocks," Proc Natl Acad Sci USA, 1998, 95: 14628-14633.
Beltran et al., "Re-activation of a dormant tumor suppressor gene maspin by designed transcription factors," Oncogene, 2007, 26: 2791-2798.
Benedetti et al., "Repair or Replace? Exploiting Novel Gene and Cell Therapy Strategies for Muscular Dystrophies," FEBS Journal, 2013, 280: 4263-4280.

(56) References Cited

OTHER PUBLICATIONS

Bengtsson et al., "Muscle-specific CRISPR/Cas9 dystrophin gene editing ameliorates pathophysiology in a mouse model for Duchenne muscular dystrophy," Nat Commun, 2017, 8: 1-10.
Berghella et al., "Reversible immortalization of human myogenic cells by site-specific excision of a retrovirally transferred oncogene," Human gene therapy, 1999, 10: 1607-1617.
Bernstein et al., "An integrated encyclopedia of DNA elements in the human genome," Nature, 2012, 489: 57-74.
Bhakta et al., "Highly active zinc-finger nucleases by extended modular assembly," Genome Res, 2013, 530-538.
Bidou et al., "Sense from nonsense: therapies for premature stop codon diseases," Trends in Molecular Medicine, 2012, 18: 679-688.
Bieth et al., "Highly restricted deletion of the SNORD116 region is implicated in Prader-Willi Syndrome, " Eur J Hum Genet, 2015, 23: 252-255.
Bittel et al., "Prader-Willi syndrome: clinical genetics, cytogenetics and molecular biology," Expert Rev Mol Med, 2005, 7(14): 1-20.
Black et al., "Targeted Epigenetic Remodeling of Endogenous Loci by CRISPR/Cas9-Based Transcriptional Activators Directly Converts Fibroblasts to Neuronal Cells," Cell Stem Cell, 2016, 19: 406-414.
Bladen et al., "The TREAT-NMD DMD Global Database: analysis of more than 7,000 Duchenne muscular dystrophy mutations," Human Mutation, 2015, 36(4):395-402.
Blancafort et al., "Scanning the human genome with combinatorial transcription factor libraries," Nat Biotechnol, 2003, 21: 269-274.
Blancafort et al., "Writing and rewriting the epigenetic code of cancer cells: from engineered proteins to small molecules," Mol. Pharmacol., 2013, 83(3): 563-576.
Boch et al., "Breaking the code of DNA binding specificity of TAL-type III effectors," Science, 2009, 326: 1509.
Boldrin et al., "Donor satellite cell engraftment is significantly augmented when the host niche is preserved and endogenous satellite cells are incapacitated," Stem Cells, 2012, 30: 1971-1984.
Bowles et al., "Phase 1 Gene Therapy for Duchenne Muscular Dystrophy Using a Translation Optimized AAV Vector," Molecular Therapy, 2012, 20: 443-455.
Braasch et al., "Novel Antisense and Peptide Nucleic Acid Strategies for Controlling Gene Expression," Biochemistry, 2002, 41: 4503-4510.
Breaker et al., "Inventing and improving ribozyme function rational design versus iterative selection methods," TIBTECH, 1994, 12: 268-274.
Breaker, "Are engineered proteins getting competition from RNA? ," Curr. Op. Biotech., 1996, 7(4): 442-448.
Briguet et al., "Histological parameters for the quantitative assessment of muscular dystrophy in the mdx-mouse," Neuromuscul. Disord., 2004, 14: 675-682.
Briner et al., "Guide RNA Functional Modules Direct Cas9 Activity and Orthogonality," Molecular Cell, 2014, 56(2): 333-339.
Brummelkamp et al., "A system for stable expression of short interfering RNAs in mammalian cells," Science, 2002, 296(5567): 550-553.
Brunet et al., "Chromosomal translocations induced at specific loci in human stem cells," Proc Natl Acad Sci USA, 2009, 106: 10620-10625.
Brunger et al., "CRISPR/Cas9 Editing of Murine Induced Pluripotent Stem Cells for Engineering Inflammation-Resistant Tissues," Arthritis Rheumatol, 2017, 69: 1111-1121.
Brunger et al., "Genome Engineering of Stem Cells for Autonomously Regulated, Closed-Loop Delivery of Biologic Drugs," Stem Cell Reports, 2017, 8: 1202-1213.
Buenrostro et al., "Transposition of native chromatin for fast and sensitive epigenomic profiling of open chromatin, DNA-binding proteins and nucleosome position," Nat Methods, 2013, 10: 1213-1218.
Buiting, "Prader-Willi syndrome and Angelman syndrome," Am J Med Genet C Semin Med Genet, 2010, 154C(3): 365-376.
Buler et al., "Energy-sensing factors coactivator peroxisome proliferator-activated receptor gamma coactivator 1-alpha (PGC-1 alpha) and AMP-activated protein kinase control expression of inflammatory mediators in liver," The Journal of Biological Chemistry, 2012, 287(3): 1847-1860.
Bultmann et al., "Targeted transcriptional activation of silent oct4 pluripotency gene by combining designer TALEs and inhibition of epigenetic modifiers," Nucleic Acids Res, 2012, 40: 5368-5377.
Burnett et al., "Deficiency in prohormone convertase PC1 impairs prohormone processing in Prader-Willi syndrome," J Clin Invest, 2017, 127: 293-305.
Busskamp et al., "Rapid neurogenesis through transcriptional activation in human stem cells," Mol Syst Biol, 2014, 10: 760.
Cano-Rodriguez et al., "Writing of H3K4Me3 overcomes epigenetic silencing in a sustained but context-dependent manner," Nat Commun, 2016, 7: 12284.
Carroll, "A CRISPR approach to gene targeting," Molecular Therapy, 2012, 20: 1658-1660.
Cassidy et al., "Prader-Willi syndrome," Eur J Hum Genet, 2009, 17(1): 3-13.
Cassidy et al., "Prader-Willi syndrome," Genet Med, 2012, 14: 10-26.
Cencic et al., "Protospacer adjacent motif (PAM)-distal sequences engage CRISPR Cas9 DNA target cleavage," PLoS one, 2014, 9, e109213, 13 pages.
Cerletti et al., "Highly efficient, functional engraftment of skeletal muscle stem cells in dystrophic muscles," Cell, 2008, 134: 37-47.
Cermak et al., "Efficient design and assembly of custom TALEN and other TAL effector-based constructs for DNA targeting," Nucleic Acids Res, 2011, 30: e82.
Chal et al., "Differentiation of pluripotent stem cells to muscle fiber to model Duchenne muscular dystrophy," Nat Biotechnol, 2015, 33: 962-969.
Chamberlain et al., "Progress toward Gene Therapy for Duchenne Muscular Dystrophy, " Mol. Ther., 2017, 25: 1125-1131.
Chanda et al., "Generation of induced neuronal cells by the single reprogramming factor ASCL1," Stem Cell Reports, 2014, 3: 282-296.
Chang et al., "Integrating Combinatorial Lipid Nanoparticle and Chemically Modified Protein for Intracellular Delivery and Genome Editing," Acc. Chem. Res., 2019, 52: 665-675.
Chapdelaine et al., "Meganucleases can restore the reading frame of a mutual dystrophin," Gene therapy, 2010, 17: 846-858.
Cheloufi et al., "The histone chaperone CAF-1 safeguards somatic cell identity," Nature, 2015, 528: 218-224.
Chen et al., "Acetylation of RelA at discrete sites regulates distinct nuclear functions of NF-kB," The EMBO Journal, 2002, 21(23): 6539-6548.
Chen et al., "Dynamic imaging of genomic loci in living human cells by an optimized CRISPR/Cas systemm," Cell, 2013, 155: 1479-1491.
Chen et al., "Enrichr: interactive and collaborative HTML5 gene list enrichment analysis tool," BMC Bioinformatics, 2013, 14: 128.
Chen et al., "Genome-wide CRISPR screen in a mouse model of tumor growth and metastasis," Cell, 2015, 160: 1246-1260.
Chen et al., "microRNA-1 and microRNA-206 regulate skeletal muscle satellite cell proliferation and differentiation by repressing Pax7," J Cell Biol, 2010, 190: 867-879.
Chen et al., "Vitamin D receptor suppresses proliferation and metastasis in renal cell carcinoma cell lines via regulating the expression of the epithelial Ca2+ channel TRPV5," PLoS One, 2018, 13: e0195844.
Cheng et al., "Multiplexed activation of endogenous genes by CRISPR-on, an RNA-guided transcriptional activator system," Cell Res, 2013, 23(10): 1163-1171.
Childers et al., "Gene therapy prolongs survival and restores function in murine and canine models of myotubular myopathy," Sci Transl Med, 2014, 6: 220ra210.
Cho et al., "Analysis of off-target effects of CRISPR/Cas-derived RNA-guided endonucleases and nickases," Genome Res, 2014, 24: 132-141.

(56) References Cited

OTHER PUBLICATIONS

Cho et al., "Targeted genome engineering in human cells with the Cas9 RNA-guided endonuclease," Nat Biotechnol 2013, 31: 230-232.
Christian et al., "Targeting DNA double-strand breaks with TAL effector nucleases," Genetics, 2010, 186: 757-761.
Christoffersen et al., "Ribozymes as human therapeutic agents," J. Med. Chem., 1995, 38(12): 2023-2037.
Chronis et al., "Cooperative Binding of Transcription Factors Orchestrates Reprogramming," Cell, 2017, 168: 442-459 e420.
Cirak et al., "Exon skipping and dystrophin restoration in patients with Duchenne muscular dystrophy after systemic phosphorodiamidate morpholino oligomer treatment: an open-label, phase 2, dose-escalation study," Lancet, 2011, 378: 595-605.
Concise Encyclopedia of Polymer Science And Engineering, 1990, pp. 858-859.
Cong et al., "Multiplex Genome Engineering Using CRISPR/Cas Systems," Science, 2013, 339: 819-823.
Cooper et al., "Improved induction of immune tolerance to factor IX by hepatic AAV-8 gene transfer," Hum Gene Ther, 2009, 20: 767-776.
Corces et al., "The chromatin accessibility landscape of primary human cancers," Science, 2018, 362(6413): eaav1898.
Cordier et al., "Muscle-specific promoters may be necessary for adeno-associated virus-mediated gene transfer in the treatment of muscular dystrophies," Hum. Gene Ther., 2001, 12: 205-215.
Cornu et al., "DNA-binding specificity is a major determinant of the activity and toxicity of zinc-finger nucleases," Mol Ther, 2008, 16: 352-358.
Cornu et al., "Quantification of zinc finger nuclease-associated toxicity," Meth Mol Biol, 2010, 649: 237-245.
Cradick et al., "CRISPR/Cas9 systems targeting beta-globin and CCR5 genes have substantial off-target activity," Nucleic Acids Res, 2013, 41(20): 9584-92.
Crooke et al., "Pharmacokinetic properties of several novel oligonucleotide analogs in mice," J. Pharmacol. Exp. Ther., 1996, 277(2): 923-937.
Cruvinel et al., "Reactivation of maternal SNORD116 cluster via SETDB1 knockdown in Prader-Willi syndrome iPSCs," Hum Mol Genet, 2014, 23: 4674-4685.
Dahlman et al., "Orthogonal gene knockout and activation with a catalytically active Cas9 nuclease," Nat Biotechnol, 2015, 33(11): 1159-1161, correction in Nat Biotechnol, Apr. 2016, 34(4): 441.
D'Alessio et al., "A Systematic Approach to Identify Candidate Transcription Factors that Control Cell Identity," Stem Cell Reports, 2015, 5: 763-775.
Daley et al., "CRISPhieRmix: a hierarchical mixture model for CRISPR pooled screens," Genome Biol, 2018, 19: 159.
Darabi et al., "Functional skeletal muscle regeneration from differentiating embryonic stem cells," Nat Med, 2008, 14: 134-143.
Darabi et al., "Human ES- and iPS-derived myogenic progenitors restore dystrophin and improve contractility upon transplantation in dystrophic mice," Cell Stem Cell, 2012, 10: 610-619.
Darmanis et al., "A survey of human brain transcriptome diversity at the single cell level," Proc Natl Acad Sci U S A, 2015, 112: 7285-7290.
Datlinger et al., "Pooled CRISPR screening with single-cell transcriptome readout," Nat. Methods, 2017, 14: 297-301.
De Mesmaeker et al., "Antisense Oligonucleotides," Ace. Chem. Res., 1995, 28: 366-374.
De Smith et al., "A deletion of the HBII-85 class of small nucleolar RNAs (snoRNAs) is associated with hyperphagia, obesity and hypogonadism," Hum Mol Genet, 2009, 18: 3257-3265.
Deconinck et al., "Utrophin-Dystrophin-Deficient Mice as a Model for Duchenne Muscular Dystrophy," Cell, 1997, 90(4): 717-727.
Dempster et al., "Extracting Biological Insights from the Project Achilles Genome-Scale CRISPR Screens in Cancer Cell Lines," Cold Spring Harbor Laboratory, 2019, 35 pages.
Dezawa et al., "Bone marrow stromal cells generate muscle cells and repair muscle degeneration," Science Signaling, 2005, 309: 314-317.
Diao et al., "A new class of temporarily phenotypic enhancers identified by CRISPR/Cas9-mediated genetic screening," Genome Res, 2016, 26: 397-405.
Ding et al., "A TALEN Genome-Editing System for Generating Human Stem Cell-Based Disease Models," Cell Stem Cell, 2013, 12: 238-251.
Ding et al., "Enhanced efficiency of human pluripotent stem cell genome editing through replacing TALENs with CRISPRs," Cell Stem Cell, 2013, 12: 393-394.
Dirks et al., "Triggered amplification by hybridization chain reaction," Proceedings of the National Academy of Sciences of the United States of America, 2004, 101(43): 15275-15278.
Dixit et al., "Perturb-Seq: Dissecting Molecular Circuits with Scalable Single-Cell RNA Profiling of Pooled Genetic Screens," Cell, 2016, 167: 1853-1866.e17.
Doyle et al., "TAL Effector-Nucleotide Targeter (TALE-NT) 2.0: tools for TAL effector design and target prediction," Nucleic Acids Res, 2012, 40: W117-122.
Doyon et al., "Enhancing zinc-finger-nuclease activity with improved obligate heterodimeric architectures," Nat Methods, 2010, 8: 74-79.
Du et al., "Genetic interaction mapping in mammalian cells using CRISPR interference," Nat Methods, 2017, 14: 577-580.
Duan et al., "Expanding AAV packaging capacity with transsplicing or overlapping vectors: a quantitative comparison," Molecular Therapy, 2001, 4: 383-391.
Duan et al., "Genome-wide identification of CRISPR/Cas9 off-targets in human genome," Cell research, 2014, 24(8): 1009-12.
Duan, "Systemic AAV Micro-dystrophin Gene Therapy for Duchenne Muscular Dystrophy," Molecular Therapy, 2018, 26(10): 2337-2356.
Duker et al., "Paternally inherited microdeletion at 15q11.2 confirms a significant role for the SNORD116 C/D box snoRNA cluster in Prader-Willi syndrome," Eur J Hum Genet, 2010, 18: 1196-1201.
Dumont et al., "Dystrophin expression in muscle stem cells regulates their polarity and asymmetric division," Nat Med, 2015, 21: 1455-1463.
Dumont et al., "Intrinsic and extrinsic mechanisms regulating satellite cell function," Development, 2015, 142: 1572-1581.
Dunbar et al., "Gene therapy comes of age," Science, 2018, 359: eaan4672.
Dykeman, "An implementation of the Gillespie algorithm for RNA kinetics with logarithmic time update," Nucleic Acids Research, 2015, 45(12): 5708-5715.
Edelstein et al., "Gene therapy clinical trials worldwide 1989-2004—an overview," J. Gene Med., 2004, 6: 597-602.
Eguchi et al., "Reprogramming cell fate with a genome-scale library of artificial transcription factors," Proc Natl Acad Sci U S A, 2016, 113: E8257-E8266.
Englisch et al., Chemically Modified Oligonucleotides as Probes and Inhibitors, Angewandle Chemie, International Edition, 1991, 30(6): 613-629.
Eraslan et al., "Deep learning: new computational modelling techniques for genomics," Nat. Rev. Genet., 2019, 20: 389-403.
Ernsberger, "Role of neurotrophin signalling in the differentiation of neurons from dorsal root ganglia and sympathetic ganglia," Cell Tissue Res, 2009, 336: 349-384.
Erwin et al., "Synthetic transcription elongation factors license transcription across repressive chromatin," Science, 2017, 358: 1617-1622.
Fagerlund et al., "The Cpf1 CRISPR-Cas protein expands genome-editing tools," Genome Biology, 2015, 16:251.
Fairclough et al., "Therapy for Duchenne muscular dystrophy: renewed optimism from genetic approaches," Nat. Rev. Genet., 2013, 14: 373-378.
Farasat et al., "A Biophysical Model of CRISPR/Cas9 Activity for Rational Design of Genome Editing and Gene Regulation," PLOS Computational Biology, 2016, 12(1):e1004724.
Farasat, "Sequence-to-Function Models for Efficient Optimization of Metabolic Pathways and Genetic Circuits," Ph. D. Thesis, 2015, 254 pages.

(56) References Cited

OTHER PUBLICATIONS

Farinelli et al., "Lentiviral vectors for the treatment of primary immunodeficiencies," J Inherit Metab Dis, 2014, 37: 525-533.
Farzadfard et al., "Tunable and Multifunctional Eukaryotic Transcription Factors Based on CRISPR/Cas," ACS Synth Biol, 2013, 604-613.
FDA approval brings first gene therapy to the United States, <https://www.fda.gov/newsevents/newsroom/pressannouncements/ucm574058.htm> (Aug. 30, 2017).
FDA approves first drug for spinal muscular atrophy, <https://www.fda.gov/newsevents/newsroom/pressannouncements/ucm534611.htm> (Dec. 23, 2016).
FDA approves first-of-its kind targeted RNA-based therapy to treat a rare disease, <https://www.fda.gov/newsevents/newsroom/pressannouncements/ucm616518.htm> (Aug. 10, 2018).
FDA approves novel gene therapy to treat patients with a rare form of inherited vision loss, <https://www.fda.gov/newsevents/newsroom/pressannouncements/ucm589467.htm> (Dec. 18, 2017).
FDA grants accelerated approval to first drug for Duchenne muscular dystrophy, <https://www.fda.gov/newsevents/newsroom/pressannouncements/ucm521263.htm> (Sep. 19, 2016).
Flamm et al., "RNA folding at elementary step resolution," Rna, 2000, 6: 325-338.
Flandin et al., "Lhx6 and Lhx8 coordinately induce neuronal expression of Shh that controls the generation of interneuron progenitors," Neuron, 2011, 70: 939-950.
Flanigan et al., "Mutational spectrum of DMD mutations in dystrophinopathy patients: application of modern diagnostic techniques to a large cohort," Human mutation, 2009, 30: 1657-1666.
Fluiter et al., "Filling the gap in LNA antisense oligo gapmers: the effects of unlocked nucleic acid (UNA) and 4'-C-hydroxymethyl-DNA modifications on RNase H recruitment and efficacy of an LNA gapmer, " Mol. Biosyst., 2009, 5: 838-843.
Fonfara et al., "Phylogeny of Cas9 determines functional exchangeability of dual-RNA and Cas9 among orthologous type II CRISPR-Cas systems," Nucleic Acids Res, 2013, 42(4): 2577-2590.
Forget, "Molecular basis of hereditary persistence of fetal hemoglobin," Ann N Y Acad Sci, 1998, 850, 38-44.
Frank et al., "HDAC inhibitors cause site-specific chromatin remodeling at PU.1-bound enhancers in K562 cells," Epigenetics Chromatin, 2016, 9: 15.
Friedland et al., "Characterization of *Staphylococcus aureus* Cas9: a smaller Cas9 for all-in-one adeno-associated virus delivery and paired nickase applications," Genome Biology, 2015, 16(16):257, 10 pages.
Friedland et al., "*Staphyloccocus aureus* Cas9: An Alternative Cas9 for Genome Editing Applications," Molecular Therapy, 2015, 23(Suppl. 1): S224.
Friedland et al., "*Staphyloccocus aureus* Cas9: An Alternative Cas9 for Genome Editing Applications," Retrieved from the Internet: <http://www.editasmedicine.com/data/documents/ASGCT%20poster 2015 Ari.pdf> Retrieved on Feb. 28, 2018.
Fu et al., "High-frequency off-target mutagenesis induced by CRISPR-Cas nucleases in human cells," Nat Biotechnol, 2013, 31(9): 822-826.
Fu et al., "Improving CRISPR-Cas nuclease specificity using truncated guide RNAs," Nat Biotechnol, 2014, 32: 279-284.
Fu et al., "Landscape of target: guide homology effects on Cas9-mediated cleavage," Nucleic Acids Research, 2014, 42(22): 13778-13787.
Fulco et al., "Activity-by-contact model of enhancer-promoter regulation from thousands of CRISPR perturbations," Nature Genetics, 2019, 51: 1664-1669.
Fulco et al., "Systematic mapping of functional enhancer-promoter connections with CRISPR interference," Science, 2016, 354: 769-773.
Fulmer-Smentek et al., "Association of acetylated histones with paternally expressed genes in the Prader-Willi deletion region," Hum Mol Genet, 2001, 10: 645-652.
Gait, "Oligoribonucleotides," Antisense Research and Applications, 1993, Chapter 16, pp. 290-299.
Gaj et al., "Structure-Guided Reprogramming of Serine Recombinase DNA Sequence Specificity," Proc Natl Acad Sci U S A, 2011, 108(2): 498-503.
Gaj et al., "Targeted gene knockout by direct delivery of zinc-finger nuclease proteins," Nature Methods, 2012, 9(8): 805-807.
Gaj et al., "ZFN, TALEN, and CRISPR/Cas-based methods for genome engineering," Trends Biotechnol, 2013, 31: 397-405.
Gao et al., "Complex transcriptional modulation with orthogonal and inducible dCas9 regulators," Nat Methods, 2016, 13: 1043-1049.
Garg et al., "Engineering synthetic TAL effectors with orthogonal target sites," Nucleic Acids Res, 2012, 40: 7584-7595.
Gascon et al., "Direct Neuronal Reprogramming: Achievements, Hurdles, and New Roads to Success," Cell Stem Cell, 2017, 21: 18-34.
Gasperini et al., "A Genome-wide Framework for Mapping Gene Regulation via Cellular Genetic Screens," Cell, 2018, 176(1-2); 377-390.e19.
Gaudelli et al., "Directed evolution of adenine base editors with increased activity and therapeutic application," Nat Biotechnol, Jul. 2020, 38(7): 892-900.
Gaudelli et al., "Programmable base editing of A•T to G•C in genomic DNA without DNA cleavage," Nature, Nov. 2017, 551(7681): 464-471.
Gebeyehu et al., "Novel biotinylated nucleotide—analogs for labeling and colorimetric detection of DNA," Nucl. Acids Res., 1987, 15(11): 4513-4534.
Gee et al., "Cellular Reprogramming Genome Editing, and Alternative CRISPR Cas9 Technologies for Precise Gene Therapy of Duchenne Muscular Dystrophy," Stem Cells International, 2017, pp. 1-11.
Gemberling et al., "Transgenic mice for in vivo epigenome editing with CRISPR-based systems," Nat Methods, 2021, 18(8): 965-974.
GenBank Accession AF214528.1 (2000).
GenBank Accession No. AK019325 (2010).
GenBank Accession No. BB730912 (2001).
GenBank Accession No. BC010291 (2006).
GenBank Accession No. BC026642.1 (2007).
GenBank Accession No. BI143915 (2011).
GenBank Accession No. NM_020562.1 (2004).
GenBank Accession X51934.1 (1997).
Gersbach et al., "Targeted plasmid integration into the human genome by an engineered zinc-finger recombinase," Nucleic Acids Res, 2011, 39: 7868-7878.
Gertz et al., "Transposase mediated construction of RNA-seq libraries," Genome Res, 2012, 22: 134-141.
Ghisletti et al., "Identification and characterization of enhancers controlling the inflammatory gene expression program in macrophages," Immunity, 2010, 32: 317-328.
Gibson et al., "Enzymatic assembly of DNA molecules up to several hundred kilobases," Nature Methods, 2009, 6(5): 343-345.
Gillespie, "A general method for numerically simulating the stochastic time evolution of coupled chemical reactions," Journal of computational physics, 1976, 22: 403-434.
Gilman et al., "Distal CCAAT box deletion in the A gamma globin gene of two black adolescents with elevated fetal A gamma globin," Nucleic Acids Res 16, 1988, 10635-10642.
Goemans et al., "Systemic administration of PRO051 in Duchenne's muscular dystrophy," The New England journal of medicine, 2011, 364: 1513-1522.
Goldstein et al., "In Situ Modification of Tissue Stem and Progenitor Cell Genomes," Cell Reports, 2019, 27: 1254-1264.e7.
Gou et al., "A novel approach for the construction of multiple shRNA expression vectors," J Gene Med, 2007, 9(9): 751-63.
Gräslund et al., "Exploring strategies for the design of artificial transcription factors: targeting sites proximal to known regulatory regions for the induction of gamma-globin expression and the treatment of sickle cell disease," J Biol Chem, 2005, 280: 3707-3714.

(56) References Cited

OTHER PUBLICATIONS

Gray et al., "G quadruplexes are genomewide targets of transcriptional helicases XPB and XPD," Nat. Chem. Biol, 2014, 10: 313-318.
Gregorevic et al., "Systemic delivery of genes to striated muscles using adeno-associated viral vectors," Nat Med, 2004, 10: 828-834.
Gregorevic et al., "Systemic microdystrophin gene delivery improves skeletal muscle structure and function in old dystrophic mdx mice," Mol Ther, 2008, 16: 657-664.
Guo et al., "Directed evolution of an enhanced and highly efficient Fokl cleavage domain for zinc finger nucleases," J Mol Biol, 2010, 400: 96-107.
Guo et al., "Harnessing accurate non-homologous end joining for efficient prease deletion in CRISPR/Cas9-mediated genome editing," Genome Biology, 2018, 19: 170, 20 pages.
Guo, J et al., "Directed evolution of an enhanced and highly efficient Fokl cleavage domain for zinc finger nucleases," J Mol Biol, 2010, 400(1): 96-107.
Guschin et al., "A rapid and general assay for monitoring endogenous gene modification," Methods Mol Biol, 2010, 649: 247-256.
Hacein-Bey-Abina et al., "LMO2-associated clonal T cell proliferation in two patients after gene therapy for SCID-X1," Science, 2003, 302: 415-419.
Hakim et al., "Evaluation of Muscle Function of the Extensor Digitorum Longus Muscle Ex vivo and Tibialis Anterior Muscle In situ in Mice," J. Vis. Exp., 2013, 1-8.
Hakim et al., "Systemic gene transfer reveals distinctive muscle transduction profile of tyrosine mutant AAV-1, -6, and -9 in neonatal dogs," Mol. Ther. Methods Clin. Dev., 2014, 1:14002.
Hall et al., "Prevention of Muscle Aging by Myofiber-Associated Satellite Cell Transplantation," Sci Transl Med, 2010, 2: 57ra83.
Hardy et al., "Comparative Study of Injury Models for Studying Muscle Regeneration in Mice," PLoS ONE, 2016, 11: e0147198.
Harper et al., "Modular flexibility of dystrophin: implications for gene therapy of Duchenne muscular dystrophy," Nat. Med., 2002, 8: 253-261.
Harrow et al., "GENCODE: The reference human genome annotation for The ENCODE Project," Genome Res, 2012, 22: 1760-1774.
Hart et al., "High-Resolution CRISPR Screens Reveal Fitness Genes and Genotype-Specific Cancer Liabilities," Cell, 2015, 163: 1515-1526.
Hayward et al., "Whole-genome landscapes of major melanoma subtypes," Nature, 2017, 545: 175-180.
He et al., "Molecular Genetic Mechanisms of Hereditary Spherocytosis: Current Perspectives," Acta Haematol., 2018, 139: 60-66.
Heagerty et al., "Time-dependent ROC curves for censored survival data and a diagnostic marker," Biometrics, 2000, 56(2): 337-344.
Heasman, "Morpholino oligos: making sense of antisense?," Dev. Biol., 2002, 243(2): 209-214.
Henning et al., "Epigenetic control of CD8 + T cell differentiation," Nat Rev Immunol, 2018, 18(5): 340-356.
Hilton et al., "Enabling functional genomics with genome engineering," Genome Research, 2015, 25(10):1442-1455.
Himeda et al., "Design and Testing of Regulatory Cassettes for Optimal Activity in Skeletal and Cardiac Muscles," Methods Mol Biol, 2011, 709: 3-19 (Published Online Dec. 2010).
Hockemeyer et al., "Efficient targeting of expressed and silent genes in human ESCs and iPSCs using zinc-finger nucleases," Nat Biotechnol, 2009, 27(9): 851-857.
Hockemeyer et al., "Genetic engineering of human pluripotent cells using TALE nucleases," Nat Biotechnol, 2011, 29: 731-734.
Hoffman et al., "Dystrophin: the protein product of the Duchenne muscular dystrophy locus," Cell, 1987, 51: 919.
Hori et al., "Simple and reproducible hepatectomy in the mouse using the clip technique," World J Gastroenterol, 2012, 18(22): 2767-2774.
Hou et al., "Efficient genome engineering in human pluripotent stem cells using Cas9 from Neisseria meningitidis," Proc Natl Acad Sci USA, 2013, 110: 15644-15649.
Howarth et al., "A monovalent streptavidin with a single femtomolar biotin binding site," Nature methods, 2006, 3(4): 267-273.
Hsu et al., "Dissecting Neural Function Using Targeted Genome Engineering Technologies", ACS Chem. Neurosci., 2012, 3: 603-610.
Hsu et al., "DNA targeting specificity of RNA-guided Cas9 nucleases," Nature Biotechnology, 2013, 31: 827-832.
Hsu et al., "Development and applications of CRISPR-Cas9 for genome engineering," Cell, 2014, 157: 1262-1278.
Huang et al., "Generation and comparison of CRISPR-Cas9 and Cre-mediated genetically engineered mouse models of sarcoma," Nature Communications, 2017, 8(15999): 1-11.
Huang et al., "Impaired respiratory function in mdx and mdx/utrn+/− mice," Muscle & Nerve, 2011, 43(2): 263-267.
Humbert et al., "Targeted gene therapies: tools, applications, optimization", Critical Reviews in Biochemistry and Molecular Biology, 2012, 47(3): 264-281.
Huntriss et al., "Imprinted expression of SNRPN in human preimplantation embryos," Am J Hum Genet, 1998, 63: 1009-1014.
Hwang et al., "Efficient genome editing in zebrafish using CRISPR-Cas system," Nat Biotechnol, 2013, 31(3): 227-9.
Inoue et al., "Runx transcription factors in neuronal development," Neural Dev, 2008, 3: 20.
Isaac et al., "Dystrophin and utrophin "double knockout" dystrophic mice exhibit a spectrum of degenerative musculoskeletal abnormalities," Journal of Orthopaedic Research, 2013, 31(3): 343-349.
Iyombe-Engembe et al., "Efficient Restoration of the Dystrophin Gene Reading Frame and Protein Structure in DMD Myoblasts Using the CinDel Method," Molecular Therapy—Nucleic Acids, 2016, 5:e283.
Jansen et al., "Identification of genes that are associated with DNA repeats in prokaryotes," Mol Microbiol, 2002, 43(6): 1565-1575.
Jeltsch et al., "Application of DNA methyltransferases in targeted DNA methylation," Appl. Microbiol. Biotechnol., 2007, 75(6): 1233-1240.
Jepsen et al., "Locked nucleic acid: a potent nucleic acid analog in therapeutics and biotechnology," Oligonucleotides, 2004, 14(2): 130-146.
Jiang et al., "A Cas9-guide RNA complex preorganized for target DNA recognition," Science, 2015, 348, 1477-1481.
Jiang et al., "Notch signaling deficiency underlies age-dependent depletion of satellite cells in muscular dystrophy," Disease Models & Mechanisms, 2014, 7: 997-1004.
Jimenez et al., "Activation of the beta-globin locus control region precedes commitment to the erythroid lineage," Proceedings of the National Academy of Sciences, 1992, 89: 10618-10622.
Jinek et al., "A programmable dual-RNA-guided DNA endonuclease in adaptive bacterial immunity," Science, 2012, 337: 816-821.
Jinek et al., "RNA-programmed genome editing in human cells," eLife, 2013, 2: e00471.
Jinek et al., "Structures of Cas9 endonucleases reveal RNA-mediated conformational activation," Science, 2014, 343(6176): 1247997.
Jiwlawat et al., "Current Progress and Challenges for Skeletal Muscle Differentiation from Human Pluripotent Stem Cells Using Transgene-Free Approaches," Stem Cells Int, Apr. 2018, Article ID 6241681, 18 pages.
Jobling et al., "Chitayat-Hall and Schaaf-Yang syndromes:a common aetiology: expanding the phenotype of MAGEL2-related disorders," J Med Genet, 2018, 55: 316-321.
Jooss et al., "Transduction of dendritic cells by DNA viral vectors directs the immune response to transgene products in muscle fibers," J. Virol., 1998, 72: 4212-4223.
Josephs et al., "Structure and specificity of the RNA-guided endonuclease Cas9 during DNA interrogation, target binding and cleavage," Nucleic Acids Research, 2015, 43(18): 8924-8941.
Joung et al., "TALENs: a widely applicable technology for targeted genome editing," Nature Reviews Molecular Cell Biology, 2013, 14: 49-55.
Joyce, "Amplification, mutation and selection of catalytic RNA," Gene, 1989, 82(1): 83-87.
Joyce, "Directed molecular evolution," Scientific American, 1992, 267(6): 90-97.

(56) References Cited

OTHER PUBLICATIONS

Jurkowska and Jeltsch, "Silencing of Gene Expression by Targeted DNA Methylation: Concepts and Approaches," Methods Mol. Biol. 649, 2010, Chapter 9: 149-161.
Kabadi et al., "Engineering Synthetic TALE and CRISPR/Cas9 Transcription Factors for Regulating Gene Expression," Methods, 2014, 69(2): 188-197.
Kabanov et al., "A new class of antivirals: antisense oligonucleotides combined with a hydrophobic substituent effectively inhibit influenza virus reproduction and synthesis of virus- specific proteins in MDCK cells," FEBS Lett., 1990, 259: 327-330.
Kauppinen et al., "Locked nucleic acid (LNA): High affinity targeting of RNA for diagnostics and therapeutics," Drug Discov Today Technol, 2005, 2(3): 287-290.
Kayali et al., "Site-directed gene repair of the dystrophin gene mediated by PNA-ssODNs," Human Molecular Genetics, 2010, 19(16): 3266-3281.
Kearns et al., "Cas9 effector-mediated regulation of transcription and differentiation in human pluripotent stem cells," Development, 2014, 141(1): 219-23.
Keefe et al., "Muscle stem cells contribute to myofibers in sedentary adult mice," Nat Commun, 2015, 6: 7087.
Keil et al., "Brain transcriptome databases: a user's guide," J Neurosci, 2018, 38(10): 2399-2412.
Kempfer et al., "Methods for mapping 3D chromosome architecture," Nat. Rev. Genet., 2020, 21: 207-226.
Keys et al., "A genome-wide screen in the mouse liver reveals sex-specific and cell non-autonomous regulation of cell fitness," bioRxiv preprint doi: https://doi.org/10.1101/2021.01.30.428976, posted Feb. 1, 2021.
Khambata-Ford et al., "Identification of Promoter Regions in the Human Genome by Using a Retroviral Plasmid Library-Based Functional Reporter Gene Assay," Genome Research, 2003, 13: 1765-1774.
Khodakov et al., "Protected DNA strand displacement for enhanced single nucleotide discrimination in double-stranded DNA," Scientific reports, 2015, 5: 8721.
Khurana et al., "Role of non-coding sequence variants in cancer," Nat. Rev. Genet., 2016, 17: 93-108.
Kim et al., "Epigenetic therapy of Prader-Willi Syndrome," Transl Res, 2019, 208: 105-118.
Kim et al., "Expansion and Purification Are Critical for the Therapeutic Application of Pluripotent Stem Cell-Derived Myogenic Progenitors," Stem Cell Rep, 2017, 9: 12-22.
Kim et al., "Histone acetylation contributes to chromatin looping between the locus control region and globin gene by influencing hypersensitive site formation," Biochim Biophys Acta, 2013, 1829: 963-969.
Kim et al., "Surrogate reporters for enrichment of cells with nuclease-induced mutations," Nat Methods, 2011, 8: 941-943.
Kim et al., "TALENs and ZFNs are associated with different mutation signatures," Nat Methods, 2013, 10(3): 185.
Kim et al., "Targeting the histone methyltransferase G9a activates imprinted genes and improves survival of a mouse model of Prader-Willi syndrome," Nat Med, 2017, 23: 213-222.
Kim et al., "Engineering and Application of Zinc Finger Proteins and TALEs for Biomedical Research," Mol Cells, 2017, 40(8): 533-541.
Kimura et al., "Cell-lineage regulated myogenesis for dystrophin replacement: a novel therapeutic approach for treatment of muscular dystrophy," Hum Mol Genet, 2008, 17: 2507- 2517.
Klann et al., "CRISPR-based methods for high-throughput annotation of regulatory DNA," Curr Opin Biotechnol, 2018, 52: 32-41.
Klann et al., "Genome-wide annotation of gene regulatory elements linked to cell fitness," bioRxiv doi: 10.1101/2021.03.08.434470. Preprint posted Mar. 9, 2021, 42 pages.
Kleinstiver et al., "Broadening the targeting range of Staphylococcus aureus CRISPR-Cas9 by modifying PAM recognition," Nature Biotechnology, 2015, 33(12): 1293-1298.
Kleinstiver et al., "Engineered CRISPR-Cas9 nucleases with altered PAM specificities," Nature, 2015, 523(7561): 481-485.
Kleinstiver et al., "Genome-wide specificities of CRISPR-Cas Cpf1 nucleases in human cells," Nature Biotechnology, 2016, 34(8):869-874.
Koblan et al., "Improving cytidine and adenine base editors by expression optimization and ancestral reconstruction," Oct. 2018, 36(9): 843-846.
Kocak, "Synthetic Transcription Factors and their Effects on Endogenous DNA Methylation in Human Cells," Thesis submitted in partial fulfillment of the requirements for the degree of Master of Science in the Department of Biomedical Engineering in the Graduate School of Duke University, 2013, p. 1-29.
Kocher et al., "Phylogenetic Analysis of the SNORD116 Locus," Genes, 2017, 8(12): 358.
Kodaka et al., "Skeletal Muscle Cell Induction from Pluripotent Stem Cells," Stem Cells Int, Apr. 2017, Article ID 1376151, 16 pages.
Koerber et al., "DNA shuffling of adeno-associated virus yields functionally diverse viral progeny," Mol Ther, 2008, 16: 1703-1709.
Komor et al., "Programmable editing of a target base in genomic DNA without double-stranded DNA cleavage," Nature, 2016, 533(7603): 420-424.
Konermann et al., "Optical control of mammalian endogenous transcription and epigenetic states," Nature, 2013, 500(7463): 472-6.
Konieczny et al., "Gene and cell-mediated therapies for muscular dystrophy," Muscle Nerve, 2013, 47: 649-663.
Koo et al., "Functional Rescue of Dystrophin Deficiency in Mice Caused by Frameshift Mutations Using Campylobacter jejuni Cas9," Molecular Therapy, 2018 26(6): 1529-1538.
Koopmans et al., "SynGO: An Evidence-Based, Expert-Curated Knowledge Base for the Synapse," Neuron, 2019, 103: 217-234 e214.
Koppanati et al., "Improvement of the mdx mouse dystrophic phenotype by systemic in utero AAV8 delivery of a minidystrophin gene," Gene Ther, 2010, 17: 1355-1362.
Kornberg et al., "DNA Replication," 1980, pp. 75-77.
Koshkin et al., "LNA (Locked Nucleic Acids): Synthesis of the adenine, cytosine, guanine, 5-methylcytosine, thymine and uracil bicyclonucleoside monomers, oligomerisation, and unprecedented nucleic acid recognition," Tetrahedron, 1998, 54(14): 3607-3630.
Kreis et al., "The Multifaceted p21 (Cip1/Waf1/CDKN1A) in Cell Differentiation, Migration and Cancer Therapy," Cancers (Basel), 2019, 11(9): 1220.
Kubokawa et al., "Molecular characterization of the 5'-UTR of retinal dystrophin reveals a cryptic intron that regulates translational activity," Molecular Vision, 2010, 16: 2590-2597.
Kuhnel et al., "Tumor-specific adenoviral gene therapy: Transcriptional repression of gene expression by utilizing p53-signal transduction pathways," Cancer Gene Ther., 2004, 11: 28-40.
Kumar et al., "Artificial evolution and natural ribozymes," FASEB Journal, 1995, 9: 1183-1195.
Kurreck, "Antisense technologies. Improvement through novel chemical modifications," European Journal of Biochemistry, 2003, 270(8): 1628-1644.
Kwa et al., "Chromatin modifying agents—the cutting edge of anticancer therapy," Drug Discovery Today, 2011, 16(13/14):543-547.
Kwon et al., "Myogenic Progenitor Cell Lineage Specification by CRISPR/Cas9-Based Transcriptional Activators," Stem cell reports, 2020, 14: 755-769.
Lacerra et al., "Restoration of hemoglobin A synthesis in erythroid cells from peripheral blood of thalassemic patients," Proc. Natl. Acad. Sci., 2000, 97(17): 9591-9596.
Lai et al., "Partial restoration of cardiac function with ΔPDZ nNOS in aged mdx model of Duchenne cardiomyopathy," Hum Mol Genet., 2014, 23(12): 3189-3199.
Lake et al., "Integrative single-cell analysis of transcriptional and epigenetic states in the human adult brain," Nat Biotechnol, 2018, 36: 70-80.

(56) References Cited

OTHER PUBLICATIONS

Lam et al., "Rapid and Efficient Differentiation of Human Pluripotent Stem Cells into Intermediate Mesoderm That Forms Tubules Expressing Kidney Proximal Tubular Markers," J Am Soc Nephrol JASN, 2014, 25: 1211-1225.
Lambert et al., "The Human Transcription Factors," Cell, 2018, 172: 650-665.
Lamey et al., "Pax genes in myogenesis: alternate transcripts add complexity," Histol Histopathol, 2004, 19: 1289-1300.
Landry et al., "Expression of the leukemia oncogene Lmo2 is controlled by an array of tissue-specific elements dispersed over 100 kb and bound by Tal1/Lmo2, Ets, and Gata factors," Blood, 2009, 113: 5783-5792.
Langmead et al., "Ultrafast and memory-efficient alignment of short DNA sequences to the human genome," Genome biology, 2009, 10: R25.
Langouet et al., "Zinc finger protein 274 regulates imprinted expression of transcripts in Prader-Willi syndrome neurons," Hum Mol Genet, 2018, 27: 505-515.
Larson et al., "CRISPR interference (CRISPRi) for sequence-editing control of gene expression," Nat Protoc, 2013, 8(11): 2180-96.
Latta-Mahieu et al., "Gene transfer of a chimeric trans-activator is immunogenic and results in short-lived transgene expression," Human Gene Therapy, 2002, 13(13): 1611-1620.
Lattanzi et al., "High efficiency myogenic conversion of human fibroblasts by adenoviral vector-mediated MyoD gene transfer. An alternative strategy for ex vivo gene therapy of primary myopathies," The Journal of clinical investigation, 1998, 101: 2119-2128.
Laumont et al., "Noncoding regions are the main source of targetable tumor-specific antigens," Sci. Transl. Med., 2018, 10(470): eaau5516, 11 pages.
Lawrence et al., "Discovery and saturation analysis of cancer genes across 21 tumour types," Nature, 2014, 505: 495-501.
Lee et al., "Activation of innate immunity is required for efficient nuclear reprogramming," Cell, 2012, 151: 547-558.
Lee et al., "Expression of small interfering RNAs targeted against HIV-1 rev transcripts in human cells," Nature Biotechnol, 2002, 20(5): 500-505.
Lee et al., "Nanoparticle delivery of Cas9 ribonucleoprotein and donor DNA in vivo induces homology-directed DNA repair," Nat Biomed Eng, 2017, 1: 889-901.
Lee et al., "Targeted chromosomal deletions in human cells using zinc finger nucleases," Genome research, 2010, 20: 81-89.
Lenoir et al., "PICKLES: the database of pooled in-vitro CRISPR knockout library essentiality screens," Nucleic Acids Res, 2018, 46: D776-D780.
Lesnik et al., "Relative thermodynamic stability of DNA, RNA, and DNA: RNA hybrid duplexes: relationship with base composition and structure," Biochemistry, 1995, 34(34): 10807-10815.
Letsinger et al., "Cholesteryl-conjugated oligonucleotides: synthesis, properties, and activity as inhibitors of replication of human immunodeficiency virus in cell culture," Proc. Natl. Acad. Sci. USA, 1989, 86(17): 6553-6556.
Levin et al., "Position-dependent effects of locked nucleic acid (LNA) on DNA sequencing and PCR primers," Nuc. Acids. Res., 2006, 34: e142.
Li et al., "In vivo genome editing restores haemostasis in a mouse model of haemophilia," Nature, 2011, 475: 217-221.
Li et al., "Chimeric DNA methyltransferases target DNA methylation to specific DNA sequences and repress expression of target genes," Nucleic Acids Res., 2007, 35(1): 100-112.
Li et al., "Engineering and selection of shuffled AAV genomes: a new strategy for producing targeted biological nanoparticles," Mol Ther, 2008, 16: 1252-1260.
Li et al., "Ex vivo cell-based CRISPR/Cas9 genome editing for therapeutic applications," Biomaterials, 2020, 234: 119711.
Li et al., "Marginal level dystrophin expression improves clinical outcome in a strain of dystrophin/utrophin double knockout mice," PLoS One, 2010, 5: e15286.
Li et al., "Modularly assembled designer TAL effector nucleases for targeted gene knockout and gene replacement in eukaryotes," Nucleic Acids Research, 2011, 39(14): 6315-6325.
Li et al., "Precise correction of the dystrophin gene in duchenne muscular dystrophy patient induced pluripotent stem cells by TALEN and CRISPR-Cas9," Stem Cell Reports, 2015, 4: 143-154.
Li et al., "Preservation of muscle force in Mdx3cv mice correlates with low-level expression of a near full-length dystrophin protein," Am. J. Pathol., 2008, 172: 1332-1341.
Li et al., "RSEM: accurate transcript quantification from RNA-Seq data with or without a reference genome," BMC Bioinformatics, 2011, 12: 323.
Li et al., "Synthetic muscle promoters: activities exceeding naturally occurring regulatory sequences," Nature Biotechnology, 1999, 17: 241-245.
Li et al., "The autism-related gene SNRPN regulates cortical and spine development via controlling nuclear receptor Nr4a1," Sci Rep, 2016, 6: 29878.
Li et al., "Transcription activator-like effector hybrids for conditional control and rewiring of chromosomal transgene expression," Scientific reports, 2012, 2: 897.
Lian et al., "Robust cardiomyocyte differentiation from human pluripotent stem cells via temporal modulation of canonical Wnt signaling," Proc Natl Acad Sci, 2012, 109: E1848-E1857.
Liang et al., "Engineering biological systems with synthetic RNA molecules," Mol Cell, 2011, 43: 915-926.
Liao et al., "In Vivo Target Gene Activation via CRISPR/Cas9-Mediated Trans-epigenetic Modulation," Cell, 2017, 171: 1495-1507.
Liao et al., "The Subread aligner: fast, accurate and scalable read mapping by seed-and-vote," Nucleic Acids Res, 2013, 41: e108.
Lim et al., "Application of CRISPR/Cas9 for the Treatment of Duchenne Muscular Dystrophy," Journal of Personalized Medicine, 2018, 8(4): 1-20.
Limberis et al., "Transduction efficiencies of novel AAV vectors in mouse airway epithelium in vivo and human ciliated airway epithelium in vitro," Molecular therapy: the journal of the American Society of Gene Therapy, 2009, 17: 294-301.
Lin et al., "Essential Role of the 58-kDa Microspherule Protein in the Modulation of Daxx-dependent Transcriptional Repression as Revealed by Nucleolar Sequestration," J Biol Chem, 2002, 277: 25446-25456.
Liu et al., "Adeno-associated virus-mediated microdystrophin expression protects young mdx muscle from contraction-induced injury," Mol. Ther., 2005, 11: 245-256.
Liu et al., "CRISPR Activation Screens Systematically Identify Factors that Drive Neuronal Fate and Reprogramming," Cell Stem Cell, 2018, 23: 758-771 e758.
Liu et al., "CRISPR-Based Chromatin Remodeling of the Endogenous Oct4 or Sox2 Locus Enables Reprogramming to Pluripotency," Cell Stem Cell, 2018, 22: 252-261 e254.
Liu et al., "Editing DNA Methylation in the Mammalian Genome," Cell, Sep. 2016, 167(1): 233-247.
Liu et al., "Monte Carlo simulation for single RNA unfolding by force," Biophysical journal, 2005, 88(1): 76-84.
Lohmueller et al., "A tunable zinc finger-based framework for Boolean logic computation in mammalian cells," Nucleic Acids Res, 2012, 40: 5180-5187.
Long et al., "Postnatal genome editing partially restores dystrophin expression in a mouse model of muscular dystrophy," Science, 2016, 351(6271): 400-403.
Lovric et al., "Terminal Differentiation of Cardiac and Skeletal Myocytes Induces Permissivity to AAV Transduction by Relieving Inhibition Imposed by DNA Damage Response Proteins," Molecular Therapy, 2012, 2087-2097.
Lu et al., "The status of exon skipping as a therapeutic approach to duchenne muscular dystrophy," Molecular Therapy, 2011, 19: 9-15.
Lund et al. "Promoter-targeted phage display selections with preassembled synthetic zinc finger libraries for endogenous gene regulation." Journal of Molecular Biology, 2004, 340: 599-613.
Luo et al., "Repurposing endogenous type I CRISPR-Cas systems for programmable gene repression," Nucleic Acids Research, 2014, 43(1): 674-681.

(56) References Cited

OTHER PUBLICATIONS

Luo et al., "Synthetic DNA delivery systems," Nature Biotechnology, 2000, 18: 33-37.
Ma et al., "Targeted gene suppression by inducing de novo DNA methylation in the gene promoter," Epigenetics Chromatin, 2014, 7: 20.
Machinek et al., "Programmable energy landscapes for kinetic control of DNA strand displacement," Nature communications, 2014, 5: 5324, 9 pages.
Macpherson et al., "Flexible guide-RNA design for CRISPR applications using Protospacer Workbench," Nature biotechnology, 2015, 33(8): 805-806.
Madigan et al., "Engineering AAV receptor footprints for gene therapy," Curr Opin Virol, 2016, 18: 89-96.
Madisen et al., "A robust and high-throughput Cre reporting and characterization system for the whole mouse brain," Nat Neurosci, 2010, 13: 133-140.
Maeder et al., "CRISPR RNA-guided activation of endogenous human genes," Nat Methods, 2013, 10: 977-979.
Maeder, "Targeted DNA demethylation and activation of endogenous genes using programmable TALE-TET1 fusion proteins," Nat Biotechnol, 2013, 31(12): 1137-42.
Magli et al., "PAX7 Targets, CD54, Integrin a9B1, and SDC2, Allow Isolation of Human ESC/iPSC-Derived Myogenic Progenitors," Cell Rep, 2017, 19: 2867-2877.
Maheshri et al., "Directed evolution of adeno-associated virus yields enhanced gene delivery vectors," Nat Biotechnol, 2006, 24: 198-204.
Majzner et al., "Clinical lessons learned from the first leg of the Car T cell journey," Nature Medicine, 2019, 25(9): 1341-1355.
Mali et al., "Cas9 as a versatile tool for engineering biology," Nat Methods, 2013, 10(10): 957- 63.
Mali et al., "CAS9 transcriptional activators for target specificity screening and paired nickases for cooperative genome engineering," Nat Biotechnol, 2013, 31(9): 833-8.
Mali et al., "RNA-Guided Human Genome Engineering via Cas9," Science, 2013, 339: 823-826.
Mamchaoui et al., "Immortalized pathological human myoblasts: towards a universal tool for the study of neuromuscular disorders," Skelet Muscle, 2011, 1: 1-11.
Mann et al., "Improved antisense oligonucleotide induced exon skipping in the mdx mouse model of muscular dystrophy," J. Gene Med., 2002, 4: 644-654.
Manning et al., "What has the mdx mouse model of duchenne muscular dystrophy contributed to our understanding of this disease? ," Journal of Muscle Research and Cell Motility, 2015, 36: 155-167.
Manoharan et al., "Chemical Modifications to Improve Uptake and Bioavailability of Antisense Oligonucleotides," Ann. N. Y. Acad. Sci., 1992, 660: 306-309.
Manoharan et al., "Cholic acid-oligonucleotide conjugates for antisense applications," Bioorg. Med. Chem. Let., 1994, 4(8): 1053-1060.
Manoharan et al., "Introduction of a lipophilic thioether tether in the minor groove of nucleic acids for antisense applications," Bioorg. Med. Chem. Let., 1993, 3(12): 2765-2770.
Manoharan et al., "Lipidic Nucleic Acids," Tetrahedron Lett, 1995, 36: 3651-3654.
Manoharan et al., "Oligonucleotide Conjugates: Alteration of the Pharmacokinetic Properties of Antisense Agents," Nucleosides & Nucleotides, 1995, 14: 969-973.
Martin et al., "A New Access to 2'-O-Alkylated Ribonucleosides and Properties of 2'-O-Alkylated Oligoribonucleotides," Helv. Chim. Acta, 1995, 78: 486-504.
Maruyama et al., "Epigenetic Regulation of Cell Type-Specific Expression Patterns in the Human Mammary Epithelium," PLoS Genetics, 2011, 7(4): e1001369, 15 pages.
Mastellos et al., "Inducing and characterizing liver regeneration in mice: Reliable models, essential "readouts" and critical perspectives," Curr Protoc Mouse Biol., 2013, 3(3): 141-170.
Mathews et al., "Expanded sequence dependence of thermodynamic parameters improves prediction of RNA secondary structure," Journal of Molecular Biology, 1999, 288(5): 911-940.
Maurano et al., "Systematic localization of common disease-associated variation in regulatory DNA," Science, 2012, 337: 1190-1195.
Maxwell et al., "A detailed cell-free transcription-translation-based assay to decipher CRISPR protospacer-adjacent motifs," Methods, 2018, 143: 48-57.
McCarthy et al., "Schaaf-Yang syndrome overview: Report of 78 individuals," Am J Med Genet A, 2018, 176(12): 2564-2574.
Mcfadden et al., "The Hand1 and Hand2 transcription factors regulate expansion of the embryonic cardiac ventricles in a gene dosage-dependent manner," Development, 2005, 132: 189-201.
McGreevy et al., "Animal models of Duchenne muscular dystrophy: from basic mechanisms to gene therapy," Disease Models Mechanisms, 2015, 8(3): 195-213.
McTigue et al., "Sequence-dependent thermodynamic parameters for locked nucleic acid (LNA)-DNA duplex formation," Biochemistry, 2004, 43(18): 5388-5405.
Mendell et al., "Dystrophin immunity in Duchenne's muscular dystrophy," New England Journal of Medicine, 2010, 363: 1429-1437.
Mendenhall et al., "Locus-specific editing of histone modification at endogenous enhancers," Nat Biotechnol, 2013, 31(12): 1133-6.
Mercer et al., "Regulation of Endogenous Human Gene Expression by Ligand-Inducible TALE Transcription Factors," ACS Synth Biol, 2013.
Mertens et al., "Evaluating cell reprogramming, differentiation and conversion technologies in neuroscience," Nat Rev Neurosci, 2016, 17: 424-437.
Mevissen et al., "Molecular basis of Lys11-polyubiquitin specificity in the deubiquitinase Cezanne," Nature, 2016, 538(7625): 402-405.
Miller et al., "A TALE nuclease architecture for efficient genome editing," Nat Biotechnol, 2011, 29: 143-148.
Miller et al., "Transcriptional landscape of the prenatal human brain," Nature, 2014, 508: 199-206.
Min et al., "CRISPR Correction of Duchene Muscular Dystrophy," Annual Review of Medicine, Epub Oct. 2018, 70: 239-255.
Mishra et al., "Improved leishmanicidal effect of phosphorotioate antisense oligonucleotides by LDL-mediated delivery," Biochim. Biophys. Acta, 1995, 1264(2): 229-237.
Miyagishi et al., "U6 promoter-driven siRNAs with four uridine 3' overhangs efficiently suppress targeted gene expression in mammalian cells," Nature Biotechnol, 2002, 20(5): 497-500.
Mojica et al., "Intervening sequences of regularly spaced prokaryotic repeats derive from foreign genetic elements," J Molec Evolution, 2005, 60(2): 174-182.
Montalbano et al., "High-Throughput Approaches to Pinpoint Function within the Noncoding Genome," Mol. Cell, 2017, 68: 44-59.
Montarras, "Direct Isolation of Satellite Cells for Skeletal Muscle Regeneration," Science, 2005, 309: 2064-2067.
Moore et al., "Transcription Activator-like Effectors: A Toolkit for Synthetic Biology," ACS Synth Biol, 2014, 3(10): 708-716.
Morris et al., "Dissecting engineered cell types and enhancing cell fate conversion via CellNet," Cell, 2014, 158: 889-902.
Moscou et al., "A simple cipher governs DNA recognition by TAL effectors," Science, 2009, 326: 1501.
Muir et al., "Engraftment potential of dermal fibroblasts following in vivo myogenic conversion in immunocompetent dystrophic skeletal muscle," Mol. Ther. Methods Clin. Dev., 2014, 1:14025.
Murphy et al., "The in vitro transcription of the 7SK RNA gene by RNA polymerase III is dependable only on the presence of an upstream promoter," Cell, 1987, 51: 81-87.
Mussolino et al., "A novel TALE nuclease scaffold enables high genome editing activity in combination with low toxicity," Nucleic Acids Res, 2011, 39: 9283-9293.
Myslinski et al., "An unusually compact external promoter for RNA polymerase III transcription of the human H1RNA gene," Nucleic Acids Res, 2001, 29: 2502-2509.
Naguibneva et al., "An LNA-based loss-of-function assay for micro-RNAs," Biomed Pharmacother, 2006, 60: 633-638.

(56) References Cited

OTHER PUBLICATIONS

Najm et al., "Orthologous CRISPR-Cas9 enzymes for combinatorial genetic screens," Nat Biotechnol, 2018, 36: 179-189.
Naldini, "Gene therapy returns to centre stage," Nature, 2015, 526: 351-360.
Nance et al., "AAV9 Edits Muscle Stem Cells in Normal and Dystrophic Adult Mice," Molecular Therapy, 2019, 27: 1568-1585.
Nasevicius et al., "Effective targeted gene 'knockdown' in zebrafish," Nat. Genet., 2000, 26(2): 216-220.
Negroni et al., "In Vivo Myogenic Potential of Human CD133+ Muscle-derived Stem Cells: A Quantitative Study," Molecular Therapy, 2009, 17: 1771-1778.
Nelson et al., "Engineering Delivery Vehicles for Genome Editing," Annual review of chemical and biomolecular engineering, 2016, 7: 637-662.
Nelson et al., "Genome engineering: a new approach to gene therapy for neuromuscular disorders," Nat Rev Neurol, 2017, 13: 647-661.
Nelson et al., "Local and Systemic Gene Editing in a Mouse Model of Duchenne Muscular Dystrophy," Molecular Therapy, 2016, 24(Supp 1):S191.
Nelson et al., "Long-term evaluation of AAV-CRISPR genome editing for Duchenne muscular dystrophy," Nature Medicine, 2019, 25(3): 427-432.
Nguyen et al., "Transcriptional Enhancers in the Regulation of T Cell Differentiation," Front. Immunol., 2015, 6: 462.
Nielsen et al., "Sequence-selective recognition of DNA by strand displacement with a thymine-substituted polyamide," Science, 1991, 254: 1497-1500.
Nikfarjam et al., "A Model of Partial Hepatectomy in Mice," Journal of Investigative Surgery, 2004, 17(5): 291-294.
Nishimasu et al., "Crystal structure of cas9 in complex with guide RNA and target DNA Cell," 2014, 156(5): 935-49.
Nowotny et al., "Crystal structures of RNase H bound to an RNA/DNA hybrid: substrate specificity and metal-dependent catalysis," Cell, 2005, 121(7): 1005-1016.
Nuñez et al., "Genome-wide programmable transcriptional memory by CRISPR-based epigenome editing," Cell, 2021, 184(9): P2503-2519.
O'Brien et al., "GT-Scan: identifying unique genomic targets," Bioinformatics, 2014, 30: 2673-2675.
Oberhauser et al., "Effective incorporation of 2'-O-methyl-oligoribonucleotides into liposomes and enhanced cell association through modification with thiocholesterol," Nucl. Acids Res., 1992, 20(3): 533-538.
Obika et al., "Stability and structural features of the duplexes containing nucleoside analogues with a fixed N-type conformation, 2'-O,4'-C-methyleneribonucleosides," Tetrahedron Lett. 1998, 39(30): 5401-5404.
O'Connell et al., "Programmable RNA recognition and cleavage by CRISPR/Cas9," Nature, 2014, 516: 263-266.
Odom et al., "Microutrophin Delivery Through rAAV6 Increases Lifespan and Improves Muscle Function in Dystrophic Dystrophin/Utrophin-deficient Mice," Molecular Therapy, 2008, 16(9): 1539-1545.
O'Geen et al., "dCas9-based epigenome editing suggests acquisition of histone methylation is not sufficient for target gene repression," Nucleic Acids Res, 2017, 45: 9901-9916.
O'Geen et al., "Ezh2-dCas9 and KRAB-dCas9 enable engineering of epigenetic memory in a context-dependent manner," Epigenetics Chromatin, 2019, 12: 26.
Ohshima et al., "Nucleotide sequence of mouse genomic loci including a gene or pseudogene for U6 (4.85) nuclear RNA," Nucleic Acids Res, 1981, 9: 5145-5158.
Olguin et al., "Pax-7 up-regulation inhibits myogenesis and cell cycle progression in satellite cells: a potential mechanism for self-renewal," Dev Biol, 2004, 275: 375-388.
Orgel, "Selection in vitro," Proc. R. Soc. B, 1979, 205: 435-442.
Orlando et al., "Promoter capture Hi-C-based identification of recurrent noncoding mutations in colorectal cancer," Nat. Genet., 2018, 50: 1375-1380.
Orom et al., "LNA-modified oligonucleotides mediate specific inhibition of microRNA function," Gene, 2006, 372: 137-141.
Ousterout et al., "Correction of dystrophin expression in cells from duchenne muscular dystrophy patients through genomic excision of exon 51 by zinc finger nucleases," Molecular Therapy 23, 2015, 523-532.
Ousterout et al., "Multiplex CRISPR/Cas9-based genome editing for correction of dystrophin mutations that cause Duchenne muscular dystrophy," Nature Communications, 2015, 6:6244.
Ousterout et al., "Reading frame correction by targeted genome editing restores dystrophin expression in cells from Duchenne muscular dystrophy patients," Mol Ther, 2013, 21: 1718-1726.
Ousterout, "Genetic Correction of Duchenne Muscular Dystrophy using Engineered Nucleases," Dept. of Biomedical Engineering Duke University (Dissertation), 2014, pp. 1-204.
Paddison et al., "Short hairpin RNAs (shRNAs) induce sequence-specific silencing in mammalian cells," Genes & Dev, 2002, 16(8): 948-958.
Paez-Espino et al., "CRISPR immunity drives rapid phage genome evolution in *Streptococcus thermophilus*," mBio, 2015, 6(2): e00262-15.
Palu et al., "In pursuit of new developments for gene therapy of human diseases," J. Biotechnol., 1999, 68: 1-13.
Pang et al., "Induction of human neuronal cells by defined transcription factors," Nature, 2011, 476: 220-223.
Papapetrou, "Induced pluripotent stem cells, past and future," Science, 2016, 353: 991-992.
Papayannakos et al., "Understanding lentiviral vector chromatin targeting: working to reduce insertional mutagenic potential for gene therapy," Gene Ther, 2013, 20(6): 581-8.
Parekh et al., "Mapping Cellular Reprogramming via Pooled Overexpression Screens with Paired Fitness and Single-Cell RNA-Sequencing Readout," Cell Systems, 2018, 7: 548-555.e548.
Park et al., "Multi-Parametric MRI at 14T for Muscular Dystrophy Mice Treated with AAV Vector-Mediated Gene Therapy," PLoS ONE, 2015, 10(4): e0124914.
Park et al., "Phenotypic alteration of eukaryotic cells using randomized libraries of artificial transcription factors," Nat Biotechnol, 2003, 21: 1208-1214.
Pattanayak et al., "High-throughput profiling of off-target DNA cleavage reveals RNA-programmed Cas9 nuclease specificity," Nat Biotechnol, 2013, 31(9): 839-43.
Paul et al., "Effective expression of small interfering RNA in human cells," Nature Biotechnol, 2002, 20(5): 505-508.
Pawlikowski et al., "Regulation of skeletal muscle stem cells by fibroblast growth factors," Dev Dyn, 2017, 246: 359-367.
Peault et al., "Stem and progenitor cells in skeletal muscle development, maintenance, and therapy," Molecular Therapy, 2007, 15: 867-877.
Penczek et al., "Three-dimensional reconstruction of single particles embedded in ice," Ultramicroscopy, 1992, 40, 33-53.
Perez et al., "Establishment of HIV-1 resistance in CD4+ T cells by genome editing using zinc-finger nucleases," Nature biotechnology, 2008, 26: 808-816.
Perez-Pinera et al., "Advances in targeted genome editing," Current Opinion in Chemical Biology, 2012, 16: 268-277.
Perez-Pinera et al., "Gene targeting to the ROSA26 locus directed by engineered zinc finger nucleases," Nucleic Acids Research, 2012, 40: 3741-3752.
Perez-Pinera et al., "RNA-guided gene activation by CRISPR-Cas9-based transcription factors," Nat Methods, 2013, 10: 973-976.
Perez-Pinera et al., "Synergistic and tunable human gene activation by combinations of synthetic transcription factors," Nature Methods, 2013, 10(3): 239-244, including pp. 1/12-12-12 of Supplementary Material.
Perez-Pinera et al., "Synergistic Transcriptional Activation by Combinations of Engineered TALEs" presented at the American Society of Gene & Cell Therapy's 15th Annual Meeting in Philadelphia, Pennsylvania, May 19, 2012, Abstract 855.

(56) References Cited

OTHER PUBLICATIONS

Persons, "Lentiviral vector gene therapy: effective and safe?" Mol Ther, 2010, 18(5): 861-2.
Pichavant et al., "Current status of pharmaceutical and genetic therapeutic approaches to treat DMD," Molecular Therapy, 2011, 19: 830-840.
Pigozzo et al., "Revertant Fibers in the mdx Murine Model of Duchenne Muscular Dystrophy: An Age- and Muscle-Related Reappraisal," PLoS One, 2013, 8(8): e72147.
Pinello et al., "Analyzing CRISPR genome-editing experiments with CRISPResso," Nat Biotechnol, 2016, 34(7):695-697.
Polstein et al., "A light-inducible CRISPR-Cas9 system for control of endogenous gene activation," Nature Chemical Biology, 2015, 11: 198-200.
Polstein et al., "Light-inducible spatiotemporal control of gene activation by customizable zinc finger transcription factors," J Am Chem Soc, 2012, 134(40): 16480-3.
Ponting et al., "Evolution and functions of long noncoding RNAs," Cell, 2009, 136(4): 629-641.
Popplewell et al., "Gene correction of a duchenne muscular dystrophy mutation by meganuclease-enhanced exon knock-in," Hum Gene Ther, 2013, 24: 692-701.
Povero et al., "Lipid-induced toxicity stimulates hepatocytes to release angiogenic microparticles that require Vanin-1 for uptake by endothelial cells," Sci Signal, 2013, 6(296): ra88.
Powell et al., "A Prader-Willi locus IncRNA cloud modulates diurnal genes and energy expenditure," Hum Molec Genet, 2013, 22: 4318-4328.
Prykhozhij et al., "CRISPR MultiTargeter: A Web Tool to Find Common and Unique CRISPR Single Guide RNA Targets in a Set of Similar Sequences," PLoS One, 2015, 10(3): e0119372.
Puccini et al., "Colorectal cancer: epigenetic alterations and their clinical implications", Biochim Biophys Acta, 2017, vol. 1868, No. 2, pp. 439-448.
Qi et al., "Repurposing CRISPR as an RNA-guided platform for sequence-specific control of gene expression," Cell, 2013, 152: 1173-1183.
Rackham et al., "A predictive computational framework for direct reprogramming between human cell types," Nature Genetics, 2016, 48: 331-335.
Rajagopal et al., "High-throughput mapping of regulatory DNA," Nat. Biotechnol, 2016, 34: 167-174.
Ramachandran et al., "Nitric Oxide Signaling Pathway in Duchenne Muscular Dystrophy Mice: Upregulation of L-arginine Transport," Biochem. J., 2012, 449: 133-142.
Ran et al., "Double nicking by RNA-guided CRISPR Cas9 for enhanced genome editing specificity," Cell, 2013, 154(6): 1380-9.
Ran et al., "Genome engineering using the CRISPR-Cas9 system," Nature Protocols, 2013, 8(11): 2281-2308.
Rao et al., "Engineering human pluripotent stem cells into a functional skeletal muscle tissue," Nat Commun, 2018, 9: 126.
Ratcliff et al., "A novel single-molecule study to determine protein-protein-protein association constants," Journal of the American Chemical Society, 2001, 123(24): 5632-5635.
Rauscher et al., "GenomeCRISPR—a database for high-throughput CRISPR/Cas9 screens," Nucleic Acids Res, 2017, 45: D679-D686.
Rebar et al., "Induction of angiogenesis in a mouse model using engineered transcription factors," Nat Med, 2002, 8: 1427-1432.
Reyon et al., "FLASH assembly of TALENs for high-throughput genome editing," Nat Biotechnol, 2012, 30: 460-465.
Rheinbay et al., "Analyses of non-coding somatic drivers in 2,658 cancer whole genomes," Nature, 2020, 578: 102-111.
Rhodes et al., "G-quadruplexes and their regulatory roles in biology," Nucleic Acids Res, 2015, 43: 8627-8637.
Richter et al., "Phage-assisted evolution of an adenine base editor with improved Cas domain compatibility and activity," Nat Biotechnol, Jul. 2020, 38(7): 883-891.
Riordan et al., "Application of CRISPR/Cas9 for biomedical discoveries," Cell & Bioscience, 2015, 5(1):11 pages.
Rmilah et al., "Understanding the marvels behind liver regeneration," Wiley Interdiscip Rev Dev Biol., 2019, 8(3): e340.
Roadmap Epigenomics Consortium, "Integrative analysis of 111 reference human epigenomes," Nature, 2015, 518: 317-330.
Rodriguez et al., "Clustering by fast search and find of density peaks," Science, 2014, 344(6191): 1492-1496.
Roudaut et al., "Restriction of calpain3 expression to the skeletal muscle prevents cardiac toxicity and corrects pathology in a murine model of limb-girdle muscular dystrophy," Circulation, 2013, 128: 1094-1104.
Rousseau et al., "Endonucleases: tools to correct the dystrophin gene" The Journal of Gene Medicine, 2011, 13: 522-537.
Rutkauskas et al., "Directional R-loop formation by the CRISPR-Cas surveillance complex cascade provides efficient off-target site rejection," Cell reports, 2015, 10, 1534-1543.
Sacco et al., "Short Telomeres and Stem Cell Exhaustion Model Duchenne Muscular Dystrophy in mdx/mTR Mice," Cell, 2010, 143: 1059-1071.
Sagal et al., "Proneural transcription factor Atoh1 drives highly efficient differentiation of human pluripotent stem cells into dopaminergic neurons," Stem Cells Transl Med, 2014, 3: 888-898.
Sahoo et al., "Prader-Willi phenotype caused by paternal deficiency for the HBII-85 C/D box small nucleolar RNA cluster," Nat Genet, 2008, 40: 719-721.
Saito et al., "Specific activation of microRNA-127 with downregulation of the proto-oncogene BCL6 by chromatin-modifying drugs in human cancer cells," Cancer Cell, 2006, 9: 435-443.
Saitoh et al., "Parent-of-Origin Histone Acetylation and Reactivation of a Key Imprinted Gene Locus in Prader-Willi Syndrome," Am J Hum Genet, 2000, 66: 1958-1962.
Salmon et al., "Production and titration of lentiviral vectors," Curr Protoc Hum Genet, 2007, Chapter 12, Unit 12.10, Supplement 54, 24 pages.
Salmon et al., "Production and titration of lentiviral vectors," Curr Protoc Neurosci, 2006, Chapter 4: Unit 4 21.
Salva et al., "Design of tissue-specific regulatory cassettes for high-level rAAV-mediated expression in skeletal and cardiac muscle," Mol. Ther., 2007, 15:320-329.
Sambasivan et al., "Embryonic founders of adult muscle stem cells are primed by the determination gene Mrf4," Developmental Biology, 2013, 381: 241-255.
Sambrook et al., "Molecular Cloning and Laboratory manual," Second Ed., Cold Spring Harbor, 1989, pp. 16.7-16.8.
Sanghvi et al., "Heterocyclic Base Modifications in Nucleic Acids and their Applications in Antisense Oligonucleotides," 1993, Antisense Research and Applications, Chapter 15, pp. 274-285.
Sanjana et al., "High-resolution interrogation of functional elements in the noncoding genome," Science, 2016, 353: 1545-1549.
Sanson et al., "Optimized libraries for CRISPR-Cas9 genetic screens with multiple modalities," Nat Commun, 2018, 9: 5416.
Santalucia et al., "Improved nearest-neighbor parameters for predicting DNA duplex stability," Biochemistry, 1996, 35(11): 3555-3562.
Schaaf et al., "Truncating mutations of MAGEL2 cause Prader-Willi phenotypes and autism," Nat Genet, 2013, 45(11): 1405-1408.
Schifrut et al., "Genome-wide CRISPR Screens in Primary Human T Cells Reveal Key Regulators of Immune Function," Cell, 2018, 175(7): 1958-1971.e15.
Schmid-Burgk et al., "A ligation-independent cloning technique for high-throughput of transcription activator-like effector genes," Nat Biotechnol, 2012, 31: 76-81.
Schmidt et al., "GenomeRNAi: a database for cell-based and in vivo RNAi phenotypes, 2013 update," Nucleic Acids Res, 2013, 41: D1021-6.
Schmittgen et al., "Analyzing real-time PCR data by the comparative CT method," Nature Protocols, 2008, 3(6): 1101-1108.
Scholze et al., "TAL effectors are remote controls for gene activation," Current Opinion in Microbiology, 2011, 14: 47-53.
Schreck et al., "DNA hairpins destabilize duplexes primarily by promoting melting rather than by inhibiting hybridization," Nucleic Acids Research, 2015, 43(13): 6181-6190.

(56) References Cited

OTHER PUBLICATIONS

Schreck et al., "DNA hairpins primarily promote duplex melting rather than inhibiting hybridization," 2014, arXiv preprint arXiv:1408.4401.
Schultz et al., "Recombinant adeno-associated virus transduction and integration," Molecular Therapy, 2008, 16: 1189-1199.
Sebastiano et al., "In Situ Genetic Correction of the Sickle Cell Anemia Mutation in Human Induced Pluripotent Stem Cells Using Engineered Zinc Finger Nucleases," Stem Cells, 2011, 29: 1717-1726.
Segal and Meckler, "Genome Engineering at the Dawn of the Golden Age," Annu. Rev. Genomics Hum. Genet., 2013, 14: 135-158.
Seidel et al., "Chromatin-modifying agents in anti-cancer therapy," Biochimie, 2012, 94: 2264-2279.
Sengupta et al., "Super-Enhancer-Driven Transcriptional Dependencies in Cancer," Trends Cancer Res, 2017, 3: 269-281.
Sentmanat et al., "A Survey of Validation Strategies for CRISPR-Cas9 Editing," Scientific Reports, 2018, 8: 888.
Sequence alignment: SEQ ID No. 102920 (2019).
Sequence alignment: SEQ ID No. 102921 (2019).
Sequence alignment: SEQ ID No. 103735 (2019).
Sequence alignment: SEQ ID No. 103736 (2019).
Serra et al., "Predicting thermodynamic properties of RNA," Methods in Enzymology, 1995, 259: 242-261.
Shalem et al., "Genome-scale CRISPR-Cas9 knockout screening in human cells," Science, 2014, 343: 84-87.
Sharma et al., "Efficiency of nonhomologous DNA and joining varies among somatic tissues, despite similarity in mechanism," Cellular and Molecular Life Science, 2011, 68: 661-676.
Sharma et al., "In vivo genome editing of the albumin locus as a platform for protein replacement therapy," Blood, 2015, 126: 1777-1784.
Shea et al., "Synthesis, hybridization properties and antiviral activity of lipid- oligodeoxynucleotide conjugates," Nucl. Acids Res, 1990, 18: 3777-3783.
Shelton et al., "Derivation and Expansion of PAX7-Positive Muscle Progenitors from Human and Mouse Embryonic Stem Cells," Stem Cell Rep, 2014, 3: 516-529.
Shen et al., "Combinatorial CRISPR-Cas9 screens for de novo mapping of genetic interactions," Nat Methods, 2017, 14: 573-576.
Shen et al., "Engraftment of a galactose receptor footprint onto adeno-associated viral capsids improves transduction efficiency," J Biol Chem, 2013, 288(40): 28814-28823.
Shin et al., "Microdystrophin Ameliorates Muscular Dystrophy in the Canine Model of Duchenne Muscular Dystrophy," Mol. Ther., 2013, 21: 750-757.
Shlyakhtenko et al., "Silatrane-based surface chemistry for immobilization of DNA, protein-DNA complexes and other biological materials," Ultramicroscopy, 2003, 97: 279-287.
Siddique et al., "Targeted methylation and gene silencing of VEGF-A in human cells by using a designed Dnmt3a-Dnmt3L single-chain fusion protein with increased DNA methylation activity," J. Mol. Biol., 2013, 425(3): 479-491.
Silva et al., "Meganucleases and other tools for targeted genome engineering: perspective and challenges for gene therapy," Current gene therapy, 2011, 11: 11-27.
Skene et al., "Genetic identification of brain cell types underlying schizophrenia," Nat Genet, 2018, 50: 825-833.
Soejima et al., "Imprinting centers, chromatin structure, and disease," J Cell Biochem, 2005, 95(2): 226-233.
Şöllü et al., "Autonomous zinc-finger nuclease pairs for targeted chromosomal deletion," Nucleic acids research, 2010, 38: 8269-8276.
Song et al., "Dnase-seq: a high-resolution technique for mapping active gene regulatory elements across the genome from mammalian cells," Cold Spring Harbor protocols 2010, pdb prot5384.
Song et al., "Non-immunogenic utrophin gene therapy for the treatment of muscular dystrophy animal models," Nature Medicine, 2019, 25(10): 1505-1511.
Song et al., "Open chromatin defined by DNasel and FAIRE identifies regulatory elements that shape cell-type identify," Genome Res, 2011, 21: 1757-1767.
Stanton et al., "Chemical modification study of antisense gapmers," Nucleic Acid Ther., 2012, 22(5): 344-359.
Stemmer et al., "CCTop: An Intuitive, Flexible and Reliable CRISPR/Cas9 Target Prediction Tool," PLoS One, 2015, 10(4): e0124633.
Stephens, "False discovery rates: a new deal," Biostatistics, 2017, 18: 275-294.
Stepper et al., "Efficient targeted DNA methylation with chimeric dCas9-Dnmt3a-Dnmt3L methyltransferase," Nucleic Acids Res., 2017, 45(4): 1703-1713.
Stolzenburg et al., "Targeted silencing of the oncogenic transcription factor SOX2 in breast cancer," Nucleic Acids Res., 2012, 40(14): 6725-6740.
Stuelsatz et al., "A Contemporary Atlas of the Mouse Diaphragm: Myogenicity, Vascularity, and the Pax3 Connection" J Histochem Cytochem, 2012, 60(9): 638-657.
Sugimoto et al., "Thermodynamic parameters to predict stability of RNA/DNA hybrid duplexes," Biochemistry, 1995, 34: 11211-11216.
Sugimoto et al., "Thermodynamics-structure relationship of single mismatches in RNA/DNA duplexes," Biochemistry, 2000, 39: 11270-11281.
Sui et al., "A Dna vector-based RNAi technology to suppress gene expression in mammalian cells," PNAS, 2002, 99(8): 5515-5520.
Sun et al., "Optimized TAL effector nucleases (TALENs) for use in treatment of sickle cell disease," Molecular bioSystems, 2012, 8: 1255-1263.
Sun et al., "Phage mutations in response to CRISPR diversification in a bacterial population," Environmental microbiology, 2013, 15(2): 463-470.
Sur et al., "The role of enhancers in cancer," Nat. Rev. Cancer., 2016, 16: 483-493.
Sutcliffe et al., "Deletions of a differentially methylated CpG island at the SNRPN gene define a putative imprinting control region," Nature Genetics, 1994, 8: 52-58.
Suzuki et al., "In vivo genome editing via CRISPR/Cas9 mediated homology-independent targeted integration," Nature, 2016, 540: 144-149.
Svinarchuk et al., "Inhibition of HIV proliferation in MT-4 cells by antisense oligonucleotide conjugated to lipophilic groups," Biochimie, 1993, 75: 49-54.
Szczelkun et al., "Direct observation of R-loop formation by single RNA-guided Cas9 and Cascade effector complexes," Proceedings of the National Academy of Sciences, 2014, 6 pages.
Szostak, "in Vitro Genes," TIBS, 1993, 17: 89-93.
Szyf, "Epigenetics, DNA methylation, and chromatin modifying drugs," Annual Review of Pharmacology and Toxicology, 2009, 49: 243-263.
Takahashi et al., "A decade of transcription factor-mediated reprogramming to pluripotency," Nature Reviews, 2016, 17: 183-193.
Takahashi et al., "Induction of pluripotent stem cells from mouse embryonic and adult fibroblast cultures by defined factors," Cell, 2006, 126: 663-676.
Takeshima et al., "Mutation spectrum of the dystrophin gene in 442 Duchene/Becker muscular dystrophy cases from one Japanese referral center," Journal of Human Genetics, 2010, 55: 379-388.
Tam et al., "Benefits and limitations of genome-wide association studies," Nat. Rev. Genet., 2019, 20: 467-484.
Tan et al., "Efficient derivation of lateral plate and paraxial mesoderm subtypes from human embryonic stem cells through GSKi-mediated differentiation," Stem Cells Dev, 2013, 22: 1893-1906.
Tan et al., "Rationally engineered *Staphylococcus aureus* Cas9 nucleases with high genome-wide specificity," Proc. Nat. Acad. Sci. USA, 2019, 116(46): 20969-20976.
Taniguchi-Ikeda et al., "Pathogenic exon-trapping by SVA retrotransposon and rescue in Fukuyama muscular dystrophy," Nature, 2011, 478: 127-131.
Tebas et al., "Gene editing of CCR5 in autologous CD4 T cells of persons infected with HIV," N Engl J Med, 2014, 370: 901-910.
Tedesco et al., "Repairing skeletal muscle: regenerative potential of skeletal muscle stem cells," J Clin Invest, 2010, 120: 11-19.

(56) References Cited

OTHER PUBLICATIONS

Tedesco et al., "Stem Cell-Mediated Transfer of a Human Artificial Chromosome Ameliorates Musculat Dystrophy," Science Translational Medicine, 2011, 3(96): 96ra78.
Tedesco et al., "Transplantation of Genetically Corrected Human iPSC-Derived Progenitors in Mice with Limb-Girdle Muscular Dystrophy," Science Translational Medicine, 2012, 4: 140ra189.
Teratani-Ota et al., "Induction of specific neuron types by overexpression of single transcription factors," In Vitro Cell Dev Biol Anim, 2016, 52(9): 961-973.
Theodorou et al., "A high throughput embryonic stem cell screen identifies Oct-2 as a bifunctional regulator of neuronal differentiation," Genes Dev, 2009, 23: 575-588.
Thorgeirsson et al., "A variant associated with nicotine dependence, lung cancer and peripheral arterial disease," Nature, 2008, 452: 638-642.
Tian et al., "CRISPR Interference-Based Platform for Multimodal Genetic Screens in Human iPSC-Derived Neurons," Neuron, 2019, 104: 239-255 e212.
Tinsley et al., "Amelioration of the dystrophic phenotype of mdx mice using a truncated utrophin transgene," Nature, 1996, 384(6607): 349-353.
Tracy, "Human DNA sequence from clone RP11-34D15 on chromosome 10, complete sequence," Genbank entry, National Center for Biotechnology Information, <https://www.ncbi.nlm.nih.gov/nucleotide/AL139819.8> 2012.
Tsai et al., "GUIDE-seq enables genome-wide profiling of off-target cleavage by CRISPR-Cas nucleases," Nature biotechnology, 2015, 33(2): 187-197.
Tsuchiya et al., "The "Spanning Protocol": A new DNA extraction method for efficient single-cell genetic diagnosis," Journal of Assisted Reproduction Genetics, 2005, 22(11-12):407-14.
Tsunemoto et al., "Diverse reprogramming codes for neuronal identity," Nature, 2018, 557: 375-380.
Tycko et al., "Screening *S. aureus* CRISPR-Cas9 Paired Guide RNAs for Efficient Targeted Deletion in Duchenne Muscular Dystrophy," Editas, Poster presented on May 5, 2016.
U.S. Appl. No. 17/471,935, filed Sep. 10, 2021, by Gersbach et al.
U.S. Appl. No. 17/636,750, filed Feb. 18, 2022, by Gersbach et al.
U.S. Appl. No. 17/636,754, filed Feb. 18, 2022, by Gersbach et al.
Urnov et al., "Highly efficient endogenous human gene correction using designed zinc-finger nucleases," Nature, 2005, 435: 646-651.
Urrutia, "KRAB-containing zinc-finger repressor proteins," Genome Biol., 2003, 4(10): 231.
Usman et al., "Catalytic RNA (Ribozymes) as Drugs," Ann. Rep. Med. Chem., 1995, Chapter 30, pp. 285-294.
Van Arensbergen et al., "Genome-wide mapping autonomous promoter activity in human cells," Nature Biotechnology, 2017, 35(2): 145-153.
Van Deutekom et al., "Advances in Duchenne muscular dystrophy gene therapy," Nat. Rev. Genet., 2003, 4: 774-783.
Van Putten et al., "Low dystrophin levels in heart can delay heart failure in mdx mice," J Mol Cell Cardiol, 2014, 69C: 17-23.
Van Putten et al., "Low dystrophin levels increase survival and improve muscle pathology and function in dystrophin/utrophin double-knockout mice," FASEB J, 2013, 27: 2484-2495.
Vaquerizas et al., "A census of human transcription factors: function, expression and evolution," Nat Rev Genet, 2009, 10: 252-263.
Veltrop et al., "A dystrophic Duchenne mouse model for testing human antisense oligonucleotides," PLoS One, 2018, 13(2): e0193289, 18 pages.
Verkhusha et al., "GFP-like flourescent proteins and chromoproteins of the class Anthozoa," Protein Structures: Kaleidoscope of Structural Properties and Functions, 2003, 405-439.
Verma et al., "Gene Therapy: Twenty-first century medicine," Annual Review of Biochemistry, 2005, 74: 711-738.
Verma et al., "Gene therapy-promises, problems and prospects," Nature, 1997, 389: 239-242.
Vierbuchen et al., "Direct conversion of fibroblasts to functional neurons by defined factors," Nature, 2010, 463: 1035-1041.
Vierbuchen et al., "Direct lineage conversions: unnatural but useful? ," Nat Biotechnol, 2011, 29: 892-907.
Vierbuchen et al., "Molecular roadblocks for cellular reprogramming," Mol Cell, 2012, 47: 827-838.
Vorobyov et al., "Expression of two protein isoforms of PAX7 is controlled by competing cleavage-polyadenylation and splicing," Gene, 2004, 342: 107-112.
Waddell et al., "DIk1 Is Necessary for Proper Skeletal Muscle Development and Regeneration," PLoS ONE, 2010, 5(11): e15055.
Waldrop et al., "Update in Duchenne and Becker muscular dystrophy," Current Opinion in Neurology, 2019, 32: 722-727.
Wang et al., "Adeno-associated virus serotype 8 efficiently delivers genes to muscle and heart," Nat. Biotechnol., 2005, 23: 321-328.
Wang et al., "Adeno-associated virus vector carrying human minidystrophin genes effectively ameliorates muscular dystrophy in mdx mouse model," Proc Natl Acad Sci USA, 2000, 97(25): 13714-13719.
Wang et al., "Construction and analysis of compact muscle-specific promoters for AAV vectors," Gene Ther, 2008, 15: 1489-1499.
Wang et al., "Cyclohexene Nucleic Acids (CeNA): Serum Stable Oligonucleotides that Activate RNase H and Increase Duplex Stability with Complementary RNA," J. Am. Chem. Soc., 2000, 122: 8595-8602.
Wang et al., "Gene Essentiality Profiling Reveals Gene Networks and Synthetic Lethal Interactions with Oncogenic Ras," Cell, 2017, 168: 890-903.e15.
Wang et al., "Genetic screens in human cells using the CRISPR-Cas9 system," Science, 2014, 343: 80-84.
Wang et al., "Identification and characterization of essential genes in the human genome," Science, 2015, 350: 1096-1101.
Wang et al., "One-Step Generation of Mice Carrying Mutations in Multiple Genes by CRISPR-Cas-Mediated Genome Engineering," Cell, 2013, 153(4): 910-8.
Wang et al., "Potential of Epigenetic Therapy for Pader-Willi Syndrome," Trends in Pharmacological Sciences, 2019, 40(9): 605-608.
Wang et al., "Systemic human minidystrophin gene transfer improves functions and life span of dystrophin and dystrophin/utrophin-deficient mice," J. Orthop. Res., 2009, 27: 421-426.
Wang et al., "Unbiased detection of off-target cleavage by CRISPR-Cas9 and TALENs using integrase-defective lentiviral vectors," Nature biotechnology, 2015, 33(2): 175-8.
Wapinski et al., "Hierarchical mechanisms for direct reprogramming of fibroblasts to neurons," Cell, 2013, 155: 621-635.
Watkins et al., "Thermodynamic contributions of single internal rA.dA, rC.dC, rG.dG and rU.dT mismatches in RNA/DNA duplexes," Nucleic acids research, 2011, 39(5): 1894-1902.
Wei et al., "Targeting Regnase-1 programs long-lived effector T cells for cancer therapy," Nature, 2019, 576(7787): 471-476.
Wein et al., "Efficient bypass of mutations in dysferlin deficient patient cells by antisense-induced exon skipping," Hum Mutat, 2010, 31: 136-142.
Welch et al., "PTC124 targets genetic disorders caused by nonsense mutations," Nature, 2007, 447: 87-91.
Weltner et al., "Human pluripotent reprogramming with CRISPR activators," Nat Commun Lond, 2018, 9: 1-12.
Westendorp et al., "E2F7 represses a network of oscillating cell cycle genes to control S-phase progression," Nucleic Acids Res, 2012, 40: 3511-3523.
Wienert et al., "Editing the genome to introduce a beneficial naturally occurring mutation associated with increased fetal globin," Nat Commun 6, 2015, 7085.
Wiggins et al., "High flexibility of DNA on short length scales probed by atomic force microscopy," Nature nanotechnology, 2006, 1(2): 137-141.
Wilbie et al., "Delivery Aspects of CRISPR/Cas for in Vivo Genome Editing," Acc Chem Res, 2019, 52(6): 1555-1564.
Wiles et al., "CRISPR-Cas9_mediated genome editing and guide RNA design," Mammalian Genome, 2015, 26(9): 501-510.
Willmann et al., "Mammalian animal models for Duchenne muscular dystrophy," Neuromuscular Disorders, 2009, 19(4): 241-249.

(56) References Cited

OTHER PUBLICATIONS

Wood, "Neuromuscular disease: CRISPR/Cas9 gene-editing platform corrects mutations associated with Duchenne muscular dystrophy," Nature Reviews Neurology, 2015, 11(4):184.
Wu et al., "A Myogenic Double-Reporter Human Pluripotent Stem Cell Line Allows Prospective Isolation of Skeletal Muscle Progenitors," Cell Rep, 2018, 25: 1966-1981.e4.
Wu et al., "Genome-wide binding of the CRISPR endonuclease Cas9 in mammalian cells," Nature biotechnology, 2014, 32(7): 670-6.
Wu et al., "Induction of anion exchanger-1 translation and its opposite roles in the carcinogenesis of gastric cancer cells and differentiation of K562 cells," Oncogene, 2010, 29: 1987-1996.
Wu et al., "Unusual Processing Generates SPA LncRNAs that Sequester Multiple RNA Binding Proteins," Mol Cell, 2016, 64: 534-548.
Wüst et al., "Metabolic Maturation during Muscle Stem Cell Differentiation Is Achieved by miR-1/133a-Mediated Inhibition of the Dlk1-Dio3 Mega Gene Cluster," Cell Metab, 2018, 27: 1026-1039.e6.
Wylie et al., "Distinct transcriptomes define rostral and caudal serotonin neurons," J Neurosci, 2010, 30: 670-684.
Xie et al., "Multiplexed Engineering and Analysis of Combinatorial Enhancer Activity in Single Cells," Mol. Cell, 2017, 66: 285-299.e5.
Xie et al., "sgRNAcas9: a software package for designing CRISPR sgRNA and evaluating potential off-target cleavage sites," PLoS One, 2014, 9(6): e100448.
Xu et al., "CRISPR-mediated Genome Editing Restores Dystrophin Expression and Function in mdx Mice," Molecular Therapy: The Journal of the American Society of Gene Therapy, 2016, 24(3):564-569.
Xu et al., "Direct lineage reprogramming: strategies, mechanisms, and applications," Cell Stem Cell, 2015, 16: 119-134.
Xu et al., "Human Satellite Cell Transplantation and Regeneration from Diverse Skeletal Muscles," Stem Cell Rep, 2015, 5: 419-434.
Xu et al., "Recent advances in neuroepigenetic editing," Curr Opin Neurobiol, 2019, 59: 26-33.
Xue et al., "Synthetic mRNAs Drive Highly Efficient iPS Cell Differentiation to Dopaminergic Neurons," Stem Cells Transl Med, 2019, 8: 112-123.
Yan et al., "Drugging the Undruggable: Transcription Therapy for Cancer," Biochim Biophys Acta, 2013, 1835(1): 76-85.
Yang et al., "Determination of protein-DNA binding constants and specificities from statistical analyses of single molecules: MutS-DNA interactions," Nucleic acids research, 2005, 33(13): 4322-4334.
Yang et al., "Gene Reactivation by 5-Aza-2'-Deoxycytidine-Induced Demethylation Requires SRCAP-Mediated HZA.Z Insertion to Establish Nucleosome Depleted Regions", PLoS Genetics, 2012, vol. 8, Issue 3, e1002604, 12 pages.
Yang et al., "Generation of pure GABAergic neurons by transcription factor programming," Nat Methods, 2017, 14: 621-628.
Yang et al., "Optimization of scarless human stem cell genome editing," Nucleic Acids Res, 2013, 41(19): 9049-9061.
Yin et al., "Long noncoding RNAs with snoRNA ends," Mol Cell, 2012, 48(2): 219-230.
Yin et al., "Programming biomolecular self-assembly pathways," Nature, 2008, 451(7176): 318-323.
You et al., "Design of LNA probes that improve mismatch discrimination," Nuc. Acids. Res., 2006, 34(8): e60.
Young et al., "A Single CRISPR-Cas9 Deletion Strategy that Targets he Majority of DMD Patients Restores Dystrophin Function in hiPSC-Derived Muscle Cells," Cell Stem Cell, 2016, 18: 533-540.
Young et al., "Creation of a Novel Humanized Dystrophic Mouse Model of Duchenne Muscular Dystrophy and Application of a CRISPR/Cas9 Gene Editing Therapy," Journal of Neuronuscular Diseases, 2017, 4(2): 139-145.
Younossi et al., "Epidemiology of chronic liver diseases in the USA in the past three decades," Gut, 2020, 69(3): 564-568.
Yu et al., "RNA interference by expression of short-interfering RNAs and hairpin RNAs in mammalian cells," PNAS, 2002, 99(9): 6047-6052.
Yusa et al., "Targeted gene correction of a1-antitrypsin deficiency in induced pluripotent stem cells," Nature, 2011, 478: 391-394.
Zenser et al., "A new TAP system for isolation of plant protein complexes and subsequent mass-spec analysis," <https://www.sigmaaldrich.com/deepweb/assets/sigmaaldrich/product/documents/388/028/flag_ha_tap_poster.pdf> published 2008, printed as pp. 1/4-4/4.
Zetsche et al., "Cpf1 Is a Single RNA-Guided Endonuclease of a Class 2 CRISPR-Cas System," Cell, 2015, 163(3):759-71.
Zhang et al. "Efficient construction of sequence-specific TAL effectors for modulating mammalian transcription," Nat Biotechnol, 2011, 29: 149-153.
Zhang et al., "Comprehensive Structure-Function Study of Neurogenin3 Disease-Causing Alleles during Human Pancreas and Intestinal Organoid Development," Dev Cell, 2019, 50(3): 367-380.e7.
Zhang et al., "Efficient precise knockin with a double cute HDR donor after CRISPR/Cas9-mediated double-stranded DNA cleavage," Genome Biol, 2017 18(35): 18 pages.
Zhang et al., "Gene activation in human cells using CRISPR/Cpf1-p300 and CRISPR/Cpf1-SunTag systems," Protein Cell, 2018, 9: 380-383.
Zhang et al., "Myoediting: Toward Prevention of Muscular Dystrophy by Therapeutic Genome Editing," Physiological Reviews, 2018, 98(3): 1205-1240.
Zhang et al., "Rapid single-step induction of functional neurons from human pluripotent stem cells," Neuron, 2013, 78: 785-798.
Zhao et al., "Intracellular delivery of artificial transcription factors fused to the protein transduction domain of HIV-1 Tat," Protein Expr Purif, 2013, 90(1): 27-33.
Zhao et al., "The LIM-homeobox gene Lhx8 is required for the development of many cholinergic neurons in the mouse forebrain," Proc Natl Acad Sci U S A, 2003, 100: 9005-9010.
Zheng et al., "Foxp3 in control of the regulatory T cell lineage," Nat. Immunol. 2007, 8: 457-462.
Zhou et al., "Haploinsufficiency of utrophin gene worsens skeletal muscle inflammation and fibrosis in mdx mice," Journal of the Neurological Sciences, 2008, 264(1): 106-111.
Zhu et al., "Cellular senescence in human telomerase reverse transcriptase and cyclin-dependent kinase 4: consequences in aging muscle and therapeutic strategies for muscular dystrophies," Aging cell, 2007, 6: 515-523.
Zhu et al., "The role of histone deacetylase 7 (HDAC7) in cancer cell proliferation: regulation on c-Myc," J. Mol. Med, 2011, 89: 279-289.
Zou et al., "Site-specific gene correction of a point mutation in human iPS cells derived from an adult patient with sickle cell disease," Blood, 2011, 118: 4599-4608.
United States Patent Office Notice of Allowance for U.S. Appl. No. 15/766,912 dated Jun. 15, 2022 (8 pages).
United States Patent Office Notice of Allowance for U.S. Appl. No. 15/766,912 dated Jan. 19, 2023 (8 pages).
Trinklein et al., "Identification and functional analysis of human transcriptional promoters," Genome Research, 2003, 13(2): 308-312.
Park et al., "Cas-Designer: a web-based tool for choice of CRISPR-Cas9 target sites," Bioinformatics, 2015, 31(24): 4014-4016.
Shen et al., "Massively parallel cis-regulatory analysis in the mammalian central nervous system," Genome Research, 2015, 26(2): 238-255.
Chhatwal et al., "Identification of cell-type-specific promoters within the brain using lentiviral vectors," Gene Therapy, 2007, 14(7): 575-583.
United States Patent Office Notice of Allowance for U.S. Appl. No. 15/766,912 dated Aug. 25, 2023 (8 pages).
Ousterout et al., "Genetic Correction of Duchenne Muscular Dystrophy Using Zinc Finger Nucleases," Mol. Ther., 2013, vol. 21, Supplement 1, 292, p. S111-S112.
Rousseau et al., "New TALENs To Correct the Reading Frame of Exon 54 of the Dystrophin Gene," Mol. Ther., 2013, vol. 21, Supplement 1, 293, p. S112.

(56) References Cited

OTHER PUBLICATIONS

United States Patent Office Supplemental Notice of Allowance for U.S. Appl. No. 15/766,912 dated Mar. 30, 2022 (4 pages).
Yu et al., “Dystrophin-deficient large animal models: translational research and exon skipping,” Am J Transl Res, 2015, 7(8): 1314-1331.
United States Patent Office Notice of Allowance for U.S. Appl. No. 15/766,912 dated May 5, 2023 (7 pages).
United States Patent Office Notice of Allowance for U.S. Appl. No. 16/837,395 dated Apr. 13, 2022 (12 pages).
United States Patent Office Supplemental Notice of Allowance for U.S. Appl. No. 16/837,395 dated May 12, 2022 (5 pages).
Fuku et al., “Restoration of Dystrophin Protein Expression by Exon Skipping Utilizing CRISPR-Cas9 in Myoblasts Derived from DMD Patient iPS Cells,” Methods Mol Biol, 2018, Chapter 12, pp. 191-217.
Min et al., “CRISPR Correction of Duchene Muscular Dystrophy Exon 44 Deletion Mutations in Mice and Human Cells,” Science Advances, 2019, 5: eaav4324.
NCBI Reference Sequence NG_028016.2 (2013).
NCBI Reference Sequence NM_004020.2 (2010).
NCBI Reference Sequence XM011532698.1 (2015).
Robinson-Hamm et al., “Gene therapies that restore dystrophin expression for the treatment of Duchenne muscular dystrophy,” Human Genetics, 2016, 135(9): 1029-1040.
U.S. Appl. No. 17/879,506, filed Aug. 2, 2022, by Josephs et al.
U.S. Appl. No. 17/922,751, filed Nov. 1, 2022, by Iglesias et al.
Blakemore et al., “Editing of Human Genes May Begin by Year’s End in the U.S.” Smithsonian.com, <https://www.smithsonianmag.com/smart-news/editing-human-genes-may-begin-years-end-US-180959532/?no-ist> 2016.
Briner et al., “Lactobacillus buchneri genotyping on the basis of clustered regularly interspaced short palindromic repeat (CRISPR) locus diversity,” Appl. Environ. Microbiol., 2014, 80: 994-1001.
Chen et al., “Targeted activation of diverse CRISPR-Cas systems for mammalian genome editing via proximal CRISPR targeting,” Nature Communications, 2017, 8: 14958.
Crawford et al., “Genome-wide mapping of DNase hypersensitive sites using massively parallel signature sequencing (MPSS),” Genome Res, 2006, 16: 123-131.
Esvelt et al., “Orthogonal Cas9 proteins for RNA-guided gene regulation and editing,” Nat. Methods, 2013, 10: 1116-1121.
Gasiunas et al., “Cas9-crRNA ribonucleoprotein complex mediates specific DNA cleavage for adaptive immunity in bacteria,” Proc. Natl. Acad. Sci., 2012, 109: E2579-E2586.
Genbank Accenssion AP006627.1 (2016).
Genbank Accession BA000004.3 (2016).
Genbank Accenssion BAB04055.1 (2016).
GenBank Accession No. AAC75803.1 (2018).
GenBank Accession No. AIN33136.1 (2014).
GenBank Accession No. BAB04055.1 (2017).
GenBank Accession No. EOT14076.1 (2013).
Gomaa et al., “Programmable Removal of Bacterial Strains by Use of Genome-Targeting CRISPR-Cas Systems,” 2014, mBio 5(1): e00928-13.
Gonda “Aerosols for delivery of therapeutic and diagnostic agents to the respiratory tract,” Critical Reviews in Therapeutic Drug Carrier Systems, 1990 6:273-313.
Gong et al., “Molecular insights into DNA interference by CRISPR-associated nuclease-helicase Cas3,” Proc Natl Acad Sci U S A, 2014, 111(46):16359-64.
Grissa et al., “CRISPRFinder: a web tool to identify clustered regularly interspaced short palindromic repeats,” Nucleic Acids Res., 2007, 35(Web Server issue):W52-57.
Henikoff et al., “Amino acid substitution matrices from protein blocks,” Proc. Natl. Acad. Sci. USA, 1992, 89: 10915-9.
Hilton et al., “Epigenome editing by a CRISPR-Cas9-based acetyltransferase activates genes from promoters and enhancers,” Nat. Biotechnol, 2015, 33: 510-517.
Hsu et al., “Development and applications of CRISPR-Cas9 for genome engineering,” Cell, 2014, 157(6):1262-78.
Jiang et al., “RNA-guided editing of bacterial genomes using CRISPR-Cas systems,” Nat. Biotechnol., 2013, 31:233-239.
Karlin et al., “Applications and statistics for multiple high-scoring segments in molecular sequences,” Proc. Natl. Acad. Sci. USA, 1993, 90: 5873-77.
Kyte et al., “A simple method for displaying the hydropathic character of a protein,” J. Mol. Biol., 1982, 157:105-132.
Levskaya et al., “Synthetic biology: engineering *Escherichia coli* to see light,” Nature, 2005, 438:441-442.
Mader et al., “CRISPR RNA-guided activation of endogenous human genes,” Nature Methods, 2013, 10(10): 977-979.
Makarova et al., “An updated evolutionary classification of CRISPR-Cas systems,” Nature Reviews Microbiology, 2015, 13:722-736.
Makarova et al., “Evolution and classification of the CRISPR-Cas systems,” Nature Reviews Microbiology, 2011, pp. 467-477.
Mojica et al., “Short motif sequences determine the targets of the prokaryotic CRISPR defence system,” Microbiology, 2009, 155: 733-740.
Murray et al., “Codon usage in plant genes,” Nucl. Acids Res., 1989, 17:477-498.
Nam et al., “Cas5d protein processes pre-crRNA and assembles into a Cascade-like interference complex in Subtype I-C/Dvulg CRISPR-Cas system,” Structure, 2012, 20:1574-1584.
Piacentino et al., “X-Linked Inhibitor of Apoptosis Protein-Mediated Attenuation of Apoptosis, Using a Novel Cardiac- Enhanced Adeno-Associated Viral Vector,” Human Gene Therapy, 2012, 23: 635-646.
Raeburn et al., “Techniques for drug delivery to the airways, and the assessment of lung function in animal models,” J. Pharmacol. Toxicol. Meth., 1992, 27:143-159.
Russa et al. “The New State of the Art: Cas9 for Gene Activation and Repression,” Molecular and Cellular Biology, 2015, 35(22):3800-3809.
Semenova et al., “The Cas6e ribonuclease is not required for interference and adaptation by the *E. coli* type I-E CRISPR-Cas system,” Nucleic Acids Res, 2015, 43(12):6049-61.
Seto et al., “Gene replacement therapies for duchenne muscular dystrophy using adeno-associated viral vectors,” Current Gene Therapy, 2012, 12: 139-151.
Simpson, “Contacts between *Escherichia coli* RNA polymerase and thymines in the lac UV5 promoter,” Proc. Natl. Acad. Sci. USA, 1979, 76: 3233-3237.
Spitz et al., “Transcription factors: from enhancer binding to developmental control,” Nat Rev Genet, 2012, 13: 613-26.
Takami et al., “Complete Genome Sequence of the Alkaliphilic Bacterium Bacillus halodurans and Genomic Sequence Comparison with Bacillus subtilis,” Nucleic Acids Research, 2000, 28(21): 4317-4331.
Tyle, “Iontophoretic Devices for Drug Delivery,” Pharm. Res., 1986, 3: 318-326.
Van der Oost et al., “Unravelling the structural and mechanistic basis of CRISPR-Cas systems,” Nature Reviews Microbiology, 2014, 12: 479-492.
Wada et al., “Codon usage tabulated from the GenBank genetic sequence data,” Nucl. Acids Res., 1990, 18: 2367-2411.
Wherry, “T cell exhaustion,” Nat.Immunology, 2011, 12: 492-499.
Zhao et al., “High-efficiency transfection of primary human and mouse T lymphocytes using RNA electroporation, ” Mol. Ther., 2006, 13: 151-159.
International Search Report and Written Opinion for Application No. PCT/US2016/056925 dated Apr. 28, 2017 (30 pages).
International Search Report and Written Opinion for Application No. PCT/US2019/014386 dated Jun. 26, 2019 (16 pages).
Abaandou et al., “Affecting HEK293 Cell Growth and Production Performance by Modifying the Expression of Specific Genes,” Cells, 2021, 10: 1667, 21 pages.
Alerasool et al., “An efficient KRAB domain for CRISPRi applications in human cells,” Nat Methods, 2020, 17: 1093-1096.

(56) References Cited

OTHER PUBLICATIONS

Alonso-Camino et al., "CARbodies: Human Antibodies Against Cell Surface Tumor Antigens Selected From Repertoires Displayed on T Cell Chimeric Antigen Receptors," Mol Ther Nucl Acids, 2013, 2: e93, 11 pages.
Azuma et al., "Robust expansion of human hepatocytes in Fah-/-/Rag2-/-/112rg-/-mice" Nat Biotechnol., 2007, 25(8): 903-910.
Bhakta et al., "The generation of zinc finger proteins by modular assembly," Methods Mol. Biol., 2010, 649: 3-30.
Bloomfield, "Quasi-Elastic Light Scattering Applications in Biochemistry and Biology," Ann. Rev. Biophys. Bioeng., 1981, 10: 421-450.
Boris-Lawrie et al., "Recent advances in retrovirus vector technology," Cur. Opin. Genet. Develop., 1993, 3: 102-109.
Bouhairie et al., "Familial hypercholesterolemia," Cardiol. Clin., 2015, 33(2): 169-179.
Braliou et al., "The v-ErbA oncoprotein quenches the activity of an erythroid-specific enhancer," Oncogene, 2001, 20(7): 775-87.
Brash et al., "Strontium phosphate transfection of human cells in primary culture: stable expression of the simian virus 40 large-T-antigen gene in primary human bronchial epithelial cells," Mol. Cell Biol., 1987, 7(5): 2031-2034.
Broude et al., "p21 (CDKN1A) is a negative regulator of p53 stability," Cell Cycle, 2007, 6(12): 1468-1471.
Buckingham, M et al. "The role of Pax genes in the development of tissues and organs: Pax3 and Pax7 regulate muscle progenitor cell functions." Annu. Rev. Cell Dev. Biol. 23 (2007): 645-673.
Burns et al., "Vesicular stomatitis virus G glycoprotein pseudotyped retroviral vectors: concentration to very high titer and efficient gene transfer into mammalian and nonmammalian cells," Proc. Natl. Acad. Sci. USA, 1993, 90: 8033-8037.
Cano-Rodriguez et al., "Epigenetic Editing: On the Verge of Reprogramming Gene Expression at Will," Curr Genet Med Rep, 2016, 4: 170-179.
Carlens et al., "Ex vivo T lymphocyte expansion for retroviral transduction: influence of serum-free media on variations in cell expansion rates and lymphocyte subset distribution," Exp Hematol, 2000, 28(10): 1137-46.
Cavalieri et al., "Human T lymphocytes transduced by lentiviral vectors in the absence of TCR activation maintain an intact immune competence," Blood, 2003, 102(2): 497-505.
Aubert et al. "553. AAV-Mediated Delivery of HSV-Specific Homing Endonucleases To Neurons of the Trigeminal Ganglia for HSV-1 Inhibition." Molecular Therapy 22 (2014).
Chen et al., "Fusion protein linkers: property, design and functionality," Adv. Drug Deliv. Rev., 2013, 65(10): 1357-1369.
Chicaybam et al., "An efficient low cost method for gene transfer to T lymphocytes, " PLoS ONE, 2013, 8(3): e60298, 11 pages.
Chylinski et al., "The tracrRNA and Cas9 families of type II CRISPR-Cas immunity systems," RNA Biol., 2013, 10(5): 726-737.
Cooper et al., "T-cell clones can be rendered specific for CD19: toward the selective augmentation of the graft-versus-B-lineage leukemia effect," Blood, 2003, 101(4): 1637-1644.
Cortes-Mancera et al., "Gene-Targeted DNA Methylation: Towards Long-Lasting Reprogramming of Gene Expression?" Adv Exp Med Biol., 2022, 1389: 515-533.
Das et al., "Tet-On Systems For Doxycycline-inducible Gene Expression," Current Gene Therapy, 2016, 16: 156-167.
Defesche et al., "Familial hypercholesterolaemia," Nat. Rev. Dis. Primers, 2017, 3: 17093, 20 pages.
Deng et al., "Highly sensitive electrochemical methyltransferase activity assay," Anal Chem., 2014, 86: 2117-2123.
Fuks, "DNA methylation and histone modifications: teaming up to silence genes," Current Opinion in Genetics & Development, 2005, 15(5): 490-495.
Gersbach et al., "Synthetic zinc finger proteins: the advent of targeted gene regulation and genome modification technologies," Acc. Chem. Res., 2014, 47(8): 2309-18.
Gowher et al., "Mechanism of stimulation of catalytic activity of Dnmt3A and Dnmt3B DNA-(cytosine-C5)-methyltransferases by Dnmt3L," J. Biol. Chem., 2005, 280(14): 13341-13348.
Gowher et al., "Molecular enzymology of the catalytic domains of the Dnmt3a and Dnmt3b DNA methyltransferases," J. Biol. Chem., 2002, 277(23): 20409-20414.
Hochstrasser et al., "CasA mediates Cas3-catalyzed target degradation during CRISPR RNA-guided interference," PNAS, 2014, 111(18): 6618-23.
Huang et al., "Ch 9: DNA transposons for modification of human primary T lymphocytes," Methods Mol Biol, 2009, 506: 115-126.
Jia et al., "Structure of Dnmt3a bound to Dnmt3L suggests a model for de novo DNA methylation," Nature, 2007, 449(7159): 248-251.
Johnston, "Biolistic transformation: microbes to mice," Nature, 1990, 346: 776-777.
Kao et al., "Ectopic DNMT3L triggers assembly of a repressive complex for retroviral silencing in somatic cells," J Virol., 2014, 88(18): 10680-95.
Kim et al., "Zinc-fingers and homeoboxes 1 (ZHX1) binds DNA methyltransferase (Dnmt) 3B to enhance DNMT3B-mediated transcriptional repression," Biochemical and Biophysical Research Communications, 2007, 355(2): 318-323.
Koste et al., "T-cell receptor transfer into human T cells with ecotropic retroviral vectors," Gene Ther, 2014, 21(5): 533-538.
Lagace, "PCSK9 and LDLR degradation: regulatory mechanisms in circulation and in cells," Curr. Opin. Lipidol., 2014, 25(5): 387-393.
Lei et al., "Targeted DNA methylation in vivo using an engineered dCas9-MQ1 fusion protein," Nat. Commun, 2017, 8: 16026, 10 pages.
Li et al., "Development of fluorescent methods for DNA methyltransferase assay," Methods Appl. Fluoresc., 2017, 5: 012002, 8 pages.
Li et al., "The histone methyltransferase SETDB1 and the DNA methyltransferase DNMT3A interact directly and localize to promoters silenced in cancer cells," J. Biol. Chem., 2006, 281(28): 19489-19500.
Liu et al., "Design of polydactyl zinc-finger proteins for unique addressing within complex genomes," PNAS, 1997, 94(11): 5525-5530.
Ma et al., "Pol III Promoters to Express Small RNAs: Delineation of Transcription Initiation," Molecular Therapy—Nucleic Acids, 2014, 3: e161, 11 pages.
Makarova et al., "Annotation and Classification of CRISPR-Cas Systems," Methods Mol. Biol, 2015, 1311: 47-75.
Manuri et al., "piggyBac transposon/transposase system to generate CD19-specific T cells for the treatment of B-lineage malignancies," Hum Gene Ther, 2010, 21(4): 427-437.
Mavrothalassitis et al., "Proteins of the ETS family with transcriptional repressor activity," Oncogene, 2000, 19: 6524-6532.
Miller et al., "Improved retroviral vectors for gene transfer and expression," BioTechniques, 1989, 7(9): 980-990.
Miller, "Retrovirus packaging cells," Human Gene Therapy, 1990, 1: 5-14.
Milone et al., "Clinical use of lentiviral vectors," Leukemia, 2018, 32(7): 1529-1541.
Mok et al., "Stabilized plasmid-lipid particles: factors influencing plasmid entrapment and transfection properties," Biochimica et Biophysica Acta, 1999, 1419(2): 137-150.
Moon et al., "Recent advances in the CRISPR genome editing tool set," Exp. Mol. Med., 2019, 51(11): 130, 11 pages.
Moussa et al., "Here to stay: Writing lasting epigenetic memories," Cell, 2021, 184(9): 2281-2283.
Murphy et al., "The Transcriptional Repressive Activity of KRAB Zinc Finger Proteins Does Not Correlate with Their Ability to Recruit TRIM28, " PLoS ONE, 2016, 11(9): e0163555, 19 pages.
O'Geen et al., "Determinants of heritable gene silencing for KRAB-dCas9 + DNMT3 and Ezh2-dCas9 + DNMT3 hit-and-run epigenome editing," Nucleic Acids Res, 2022, 50(6): 3239-3253.
Orth et al., "Structural basis of gene regulation by the tetracycline inducible Tet repressor-operator system," natural structural biology, 2000, 7(3): 215-219.
Park et al., "Treating cancer with genetically engineered T cells," Trends Biotechnol, 2011, 29(11): 550-557.

(56) References Cited

OTHER PUBLICATIONS

Peterson et al., "PCSK9 function and physiology," J. Lipid Res., 2008, 49(6): 1152-1156.
Pickar-Oliver et al., "The next generation of CRISPR-Cas technologies and applications," Nature Reviews Molecular Cell Biology, 2019, 20(8): 490-507.
Poh et al., "DNA Methyltransferase Activity Assays: Advances and Challenges," Theranostics, 2016, 6(3): 369-391.
Poirier et al., "The proprotein convertase PCSK9 induces the degradation of low density lipoprotein receptor (LDLR) and its closest family members VLDLR and ApoER2"J. Biol. Chem., 2008, 283: 2363-2372.
Policarpi et al., "Epigenetic editing: Dissecting chromatin function in context," Bioessays, 2021, 43(5): e2000316, 16 pages.
Saha et al., "The NIH Somatic Cell Genome Editing program," Nature, 2021, 592: 195-204.
Scarpa et al., "Characterization of recombinant helper retroviruses from moloney-based vectors in ecotropic and amphotropic packaging cell lines," Virology, 1991, 180: 849-852.
Schellenberger et al., "A recombinant polypeptide extends the in vivo half-life of peptides and proteins in a tunable manner," Nature Biotechnology, 2009, 27(12): 1186-1190.
Sharma et al., "Efficient Sleeping Beauty DNA Transposition From DNA Minicircles," Molec Ther Nucl Acids, 2013, 2(2): e74, 10 pages.
Stepper, "Dissertation: CRISPR-Cas9 fusions for synthetic epigenetics," Von der Fakultat 4: Energie-, Verfahrens-und Biotechnik, Institut für Biochemie und Technische Biochemie der Universität Stuttgart, 2020, 148 pages.
Thakore et al., "385. Inhibiting the Myostatin Signaling Pathway using CRISPR/Cas9-Based Repressors." Molecular Therapy 2016, 24: S153.
Tycko et al., "High-Throughput Discovery and Characterization of Human Transcriptional Effectors," Cell, 2020, 183(7): 2020-2035.
Van Tedeloo et al., "High-level transgene expression in primary human T lymphocytes and adult bone marrow CD34+ cells via electroporation-mediated gene delivery," Gene Therapy, 2000, 7(16): 1431-1437.
Verhoeyen et al., "Ch 8: Lentiviral vector gene transfer into human T cells," Methods Mol Biol, 2009, 506: 97-114.
Wang et al., "Phenotypic and functional attributes of lentivirus modified CD19-specific human CD8+ central memory T cells manufactured at clinical scale," J. Immunother, 2012, 35(9): 689-701.
Wright et al., "Rational design of a split-Cas9 enzyme complex," PNAS, 2015, 112(10): 2984-2989.
Wright et al., "Standardized reagents and protocols for engineering zinc finger nucleases by modular assembly," Nat. Protoc., 2006, 1(3): 1637-1652.
Zetsche et al., "A split-Cas9 architecture for inducible genome editing and transcription modulation," Nat. Biotechnol, 2015, 33(2): 139-142.
Echevarria et al., "Exon-skipping advances for Duchenne muscular dystrophy," Human Molecular Genetics, 2018, 27(R2): R163-R172.
Miller, "Non-viral CRISPR/Cas gene editing in vitro and in vivo enabled by synthetic nanoparticle co-delivery of Cas9 mRNA and sgRNA," Angew Chem Int Engl, 2017, 56(4): 1059-1063.
Ryu et al., "Adenine base editing in mouse embryos and an adult mouse model of Duchenne muscular dystrophy," Nature Biotechnology, 2018, 36(6): 536-539.
Rees et al., "Base editing: precision chemistry on the genome and transcriptome of living cells," Nature Reviews Genetics, 2018, 19(12): 770-788.
Nelson et al., "Long-term evaluation of genome editing for Duchenne muscular dystrophy," Duke Presentation, 2019, 123 pages. Retrieved from the Internet: <https://static.seekingalpha.com/uploads/sa_presentations/453/41453/original.pdf>.
Young, "Development of a Therapeutic CRISPR/Cas9 Plataform for Duchenne Muscular Dystrophy," UCLA Electronic Theses and Dissertations, Jan. 1, 2018, 136 pages.
Kwon et al., "In Vivo Gene Editing of Muscle Stem Cells with Adeno-Associated Viral Vectors in a Mouse Model of Duchenne Muscular Dystrophy," Molecular Therapy, 2020, 19: 320-329.
Duchêne et al., "CRISPR-Induced Deletion with SaCas Restores Dystrophin Expression in Dystrophic Models In Vitro and In Vivo," Molecular Therapy: The Journal of the American Society of Gene Therapy, 2018, 26(11): 2604-2616.
Liao, "Targeted disruption of DNMT1, DNMT3A and DNMT3B in human embryonic stem cells," Nature Genetics, 2015, 47(5): 469-478.
Long et al., "Correction of Diverse Muscular Dystrohpy Mutations in Human Engineered Heart Muscle by Single-Site Genome Editing," Sci Adv, 2018, 4(1): eaap9004.
Maggio et al., "Adenoviral vectors encoding CRISPR/Cas9 multiplexes rescue dystrophin synthesis in unselected populations of DMD muscle cells," Scientific Reports, 2016, 6: 37051.
Swiech et al., "In vivo interrogation of gene function in the mammalian brain using CRISPR-Cas9," Nature Biotechnology, 2014, 33(1): 102-106 (Supplementary Information included).
Thule et al., "Engineered Insulin Secretion in Human Primary Thyroid Cells," Molecular Therapy, 2012, 20(Supplement 1): S164, Article 421.
Chao et al., "Several log increase in therapeutic transgene delivery by distinct adeno-associated viral serotype vectors," (2000) Molecular Therapy 2:619.
Chen et al., "In vivo CD8+ T cell CRISPR screening reveals control by Fli1 in infection and cancer," Cell, 2021, 184(5): 1262-1280.
Corces et al., "An improved ATAC-seq protocol reduces background and enables interrogation of frozen tissues," Nature Methods. 2017, 14: 959-962.
Galletti et al., "Two subsets of stem-like CD8+ memory T cell progenitors with distinct fate commitments in humans," Nature Immunology, 2020, 21: 1552-1562.
Gao et al., "Clades of Adeno-Associated Viruses Are Widely Disseminated in Human Tissues," (2004) J. Virology 78:6381-6388.
GenBank Accession No. AF028704.1, (1998).
GenBank Accession No. AF028705.1, (1998).
GenBank Accession No. AF043303.1, (2010).
GenBank Accession No. AF063497.1, (1999).
GenBank Accession No. AF288061.1, (2001).
GenBank Accession No. AF513851.1, (2002).
GenBank Accession No. AFS13852.1, (2015).
GenBank Accession No. AH009962.2, (2016).
GenBank Accession No. AY028223.1, (2001).
GenBank Accession No. AY028226.1, (2001).
GenBank Accession No. AY530579.1, (2004).
GenBank Accession No. J01901.1, (1993).
GenBank Accession No. J02275.1, (1995).
GenBank Accession No. NC_000883.2, (2018).
GenBank Accession No. NC_001358.1, (2015).
GenBank Accession No. NC_001401, (2018).
GenBank Accession No. NC_001510.1, (2018).
GenBank Accession No. NC_001540.1, (2018).
GenBank Accession No. NC_001701.1, (2018).
GenBank Accession No. NC_001729, (2018).
GenBank Accession No. NC_001829.1, (2018).
GenBank Accession No. NC_001862.1, (2004).
GenBank Accession No. NC_001863.1, (2004).
GenBank Accession No. NC_002077, (2018).
GenBank Accession No. NC_006152.1, (2018).
GenBank Accession No. NC_006261.1, (2018).
GenBank Accession No. U89790.1, (1997).
GenBank Accession No. X01457.1, (2005).
Hao et al., "Integrated analysis of multimodal single-cell data," Cell, 2021, 184: 3573-3587.e29.
Hart et al., "Kruppel-like factors in lymphocyte biology," J Immunol, 2012, 188(2): 521-526.
Joung et al., "Transcription Factor Atlas of Directed Differentiation," Cell, 2023, 186(1): 209-229.e26.
Jung et al. "BLIMP1 and NR4A3 transcription factors reciprocally regulate antitumor Car T cell stemness and exhaustion," Cancer Immunotherapy, 2022, 14: eabn7336.

(56) References Cited

OTHER PUBLICATIONS

Kaminskiy et al., "Neglected, yet significant role of FOXP1 in T-cell quiescence, differentiation and exhaustion," Front. Immunol, 2022, 13: 971045.
Krishna et al., "Stem-like CD8 T cells mediate response of adoptive cell immunotherapy against human cancer," Science, 2020, 370: 1328-1334.
Kuleshov et al., "Enrichr: a comprehensive gene set enrichment analysis web server 2016 update," Nucleic Acids Research, 2016, 44: 90-97.
Liao et al., "featureCounts: an efficient general purpose program for assigning sequence reads to genomic features," Bioinformatics, 2013, 30(7): 923-30.
Martin et al., "CCR7 Deficiency in NOD Mice Leads to Thyroiditis and Primary Hyperthyroidism," The Journal of Immunology, 2009, 183(5): 3073-3080.
Mimitou et al., "Expanding the CITE-seq tool-kit: Detection of proteins, transcriptomes, clonotypes and CRISPR perturbations with multiplexing, in a single assay," Nat. Methods, 2019, 16: 409-412.
Mori et al., "Two novel adeno-associated viruses from cynomolgus monkey: pseudotyping characterization of capsid protein," (2004) Virology 330: 375-383.
Muzyczka, "Use of adeno-associated virus as a general transduction vector for mammalian cells," (1992) Curr. Topics Microbial. Immunol. 158: 97-129.
Philip et al., "Chromatin states define tumour-specific T cell dysfunction and reprogramming," Nature, 2017, 545: 452-456.
Pritykin et al., "A unified atlas of CD8 T cell dysfunctional states in cancer and infection," Mol. Cell 2021, 81: 2477-2493.
Ramirez et al., "deepTools: a flexible platform for exploring deep-sequencing data," Nucleic Acids Research, 2014, 42:W187-91.
Schubert et al., "Autosomal dominant immune dysregulation syndrome in humans with CTLA4 mutations," Nature Medicine, 2014, 20(2): 1410-1416.
Sen et al., "The epigenetic landscape of T cell exhaustion," Science, 2016, 354(6316): 1165-1169.
Vojta et al., "Repurposing the CRISPR-Cas9 system for targeted DNA methylation," Nucleic Acids Research, 2016, 44(12): 5615-5628.
Wherry et al., "Molecular Signature of CD8+ T Cell Exhaustion during Chronic Viral Infection," Immunity, 2007, 27(4): 670-684.
Woolf et al., "Runx3 and Runx1 are required for CD8 T cell development during thymopoiesis," PNAS, 2003, 100(13): 7731-7736.
Yang et al., "The transcriptional regulators Id2 and Id3 control the formation of distinct memory CD8+ T cell subsets," Nat Immunol, 2011, 12: 1221-1229.
Yu et al., "ChIPseeker: an R/Bioconductor package for ChIP peak annotation, comparison and visualization," Bioinformatics, 2015, 31(14): 2382-2383.
Yuan et al., "Genetic Modulation of RNA Splicing with a CRISPR-Guided Cytidine Deaminase," Molecular Cell, 2018, 72(2): 380-394.
Zhang et al., "Model-based analysis of ChIP-Seq (MACS)," Genome Biology, 2008, 9(9): R137.
Zheng et al., "Landscape of Infiltrating T Cells in Liver Cancer Revealed by Single-Cell Sequencing," Cell, 2017, 169: 1342-1356.
Liu et al., "A CRISPR-Cas9 Strategy for Activating the Saccharopolyspora erythraea Erythromycin Biosynthetic Gene Cluster with Knock-in Bidirectional Promoters," ACS Synth. Biol. 2019, 8(5): 1134-1143.
Miyazaki et al., "Characterization of deletion breakpoints in patients with dystrophinopathy carrying a deletion of exons 45-55 of the Duchenne muscular dystrophy (DMD) gene," Journal of Human Genetics, 2009, 54: 127-130.
Razzouk, "CRISPR-Cas9: A cornerstone for the evolution of precision medicine," Annal of Human Genetics, 2018, 82(6): 331-357.
Simeonov et al., "Discovery of stimulation-responsive immune enhancers with CRISPR activation," Nature, 2017, 549(7670): 111-115.
Ahern, "Biochemical, Reagents Kits Offer Scientists Good Return on Investment," The Scientist Magazine, (accessed at https://www.the-scientist.com/technology/biochemical-reagents-kits-offer-scientists-good-return-on-investment-58425 on Dec. 14, 2023) (Year: 1995).
Bennett et al., "Detection of mutations in the dystrophin gene via automated DHPLC screening and direct sequencing," BMC Genet, 2001, 2: 17.
Bikard et al., "Programmable repression and activation of bacterial gene expression using an engineered CRISPR-Cas system," Nucleic Acids Research, 2013, 41(15): 7429-7437.
Echigoya et al., "Multiple Exon Skipping in the Duchenne Muscular Dystrophy Hot Spots: Prospects and Challenges," J Pers Med, 2018, 8(4): 41.
Jangid et al., "Biodirectional promoters exhibit characteristic chromatin modification signature associated with transcription elongation in both sense and antisense directions," BMC Genomics, 2018, 19: 313.
Mitsunobu et al., "Beyond Native Cas9: Manipulating Genomic Information and Function," Trends in Biotechnology, 2017, 35(10): 986-996.
NCBI Reference Sequence: NG_012232.1, "*Homo sapiens* dystrophin (DMD), RefSeqGene (LRG_199) on chromosome X," National Library of Medicine (accessed at: https://www.ncbi.nlm.nih.gov/nuccore/NG_012232.1/) (Year: 1993).
NCBI Reference Sequence: WP_038431314.1 "type II CRISPR RNA-guided endonuclease Cas9 [*Streptococcus pyogenes*]," National Library of Medicine (accessed at: https://www.ncbi.nlm.nih.gov/protein/WP_038431314.1) (Year: 2005).
Pinder et al., "Nuclear domain 'knock-in' screen for the evaluation and identification of small molecule enhancers of CRISPR-based genome editing," Nucleic Acids Research, 2015, 43(19): 9379-9392.
Shimo et al., "A novel human muscle cell model of Duchenne muscular dystrophy created by CRISPR/Cas9 and evaluation of antisense-mediated exon skipping," Journal of Human Genetics, 2018, 63: 365-375.
Tremblay et al., "Gene Editing for Duchenne Muscular Dystrophy Using the CRISPR/Cas9 Technology: The Importance of Fine-tuning the Approach," Molecular Therapy, The Journal of the American Society of Gene Therapy, 2016, 24(11): 1888-1889.
Warnock et al., "Introduction to Viral Vectors," Viral Vectors for Gene Therapy: Methods in Molecular Biology, 2011, vol. 737, Chapter 1, 25 pages.
European Patent Office Action for Application No. 19741214.1 dated Jan. 2, 2025 (5 pages).
Abdennur et al., "Cooler: scalable storage for Hi-C data and other genomically labeled arrays," Bioinformatics, 2020, 36: 311-316.
Achterberg et al., "The nano-scale mechanical properties of the extracellular matrix regulate dermal fibroblast function," J. Invest. Dermatol, 2014, 134: 1862-1872.
Akter et al., "FAM98A associates with DDX1-C14orf166-FAM98B in a novel complex involved in colorectal cancer progression," Int. J. Biochem. Cell Biol., 2017, 84: 1-13.
Andreu et al.," Mechanical force application to the nucleus regulates nucleocytoplasmic transport," Nat. Cell Biol., 2022, 24: 896-905.
Arda et al., "Quantitative assessment of normal soft-tissue elasticity using shear-wave ultrasound elastography," AJR Am. J. Roentgenol., 2011, 197: 532-536.
Aubel et al., "Mammalian synthetic biology—from tools to therapies," BioEssays, 2010, 32(4): 332-345.
Babic et al., "CYR61, a product of a growth factor-inducible immediate early gene, promotes angiogenesis and tumor growth," Proc. Natl. Acad. Sci. U.S.A., 1998, 95: 6355-6360.
Baek et al., "DNA-free two-gene knockout in Chlamydomonas reinhardtii via CRISPR-Cas9 ribonucleoproteins," Scientific Reports, 2016, 6:30620.
Balko et al., "Activation of MAPK pathways due to DUSP4 loss promotes cancer stem cell-like phenotypes in basal-like breast cancer," Cancer Res, 2013, 73: 6346-6358.

(56) References Cited

OTHER PUBLICATIONS

Behan et al., "Prioritization of cancer therapeutic targets using CRISPR-Cas9 screens," Nature, 2019, 568: 511-516.
Benabdallah et al., "Decreased Enhancer-Promoter Proximity Accompanying Enhancer Activation," Mol. Cell, 2019, 76: 473-484.e7.
Beningo et al., "Traction forces of fibroblasts are regulated by the Rho-dependent kinase but not by the myosin light chain kinase," Arch. Biochem. Biophys., 2006, 456: 224-231.
Berginski et al., "The Focal Adhesion Analysis Server: a web tool for analyzing focal adhesion dynamics," F1000Res., 2013, 2: 68.
Bischoff et al., "RanGAP1 induces GTPase activity of nuclear Ras-related Ran," Proc. Natl. Acad. Sci. U.S.A., 1994, 91: 2587-2591.
Bolger et al., "Trimmomatic: a flexible trimmer for Illumina sequence data," Bioinformatics, 2014, 30: 2114-2120.
Braun et al., "Rapid and reversible epigenome editing by endogenous chromatin regulators," Nat Commun, 2017, 8(1): 560.
Canver et al., "BCL11A enhancer dissection by Cas9-mediated in situ saturating mutagenesis," Nature, 2015, 527: 192-197.
Chang et al., "GEF-H1 couples nocodazole-induced microtubule disassembly to cell contractility via RhoA," Mol Biol Cell, 2008, 19: 2147-2153.
Chang et al., "The SWI/SNF complex is a mechanoregulated inhibitor of YAP and TAZ," Nature, 2018, 563: 265-269.
Chen et al., "Connective Tissue Growth Factor: From Molecular Understandings to Drug Discovery," Front Cell Dev Biol, 2020, 8: 593269.
Chen et al., "Geometric control of cell life and death," Science, 1997, 276: 1425-1428.
Chen, "Mechanotransduction—a field pulling together?" J. Cell Sci., 2008, 121: 3285-3292.
Chrzanowska-Wodnicka et al., "Rho-stimulated contractility drives the formation of stress fibers and focal adhesions," J Cell Biol, 1996, 133: 1403-1415.
Clement et al., "CRISPResso2 provides accurate and rapid genome editing sequence analysis," Nat. Biotechnol., 2019, 37: 224-226.
Corces et al., "Omni-ATAC-seq: improved ATAC-seq protocol," Protocol exchange, [Preprint] 2017.
Cosgrove et al., "Mechanosensitive genomic enhancers potentiate the cellular response to matrix stiffnes," Posted Jan. 10, 2024. bioRxiv Jan. 10, 2024:2024.01.10.574997.
Darnell et al. "RNA-seq reveals diverse effects of substrate stiffness on mesenchymal stem cells," Biomaterials, 2018, 181: 182-188.
Devos et al., "Practical Limits of Fuction Prediction," PROTEINS: Structure, Function, and Genetics, 2000, 41: 98-107.
Ding et al., "Improving CRISPR-Cas9 Genome Editing Efficiency by Fusion with Chromatin- Modulating Peptides," Crispr J, 2019, 2: 51-63.
Dobin et al., "STAR: ultrafast universal RNA-seq aligner," Bioinformatics, 2013, 29: 15-21.
Dupont et al., "Mechanical regulation of chromatin and transcription," Nat. Rev. Genet., 2022, 23: 624-643.
Dupont et al., "Role of YAP/TAZ in mechanotransduction," Nature, 2011, 474: 179-183.
Durand et al., "Juicer Provides a One-Click System for Analyzing Loop-Resolution Hi-C Experiments," Cell Syst, 2016, 3: 95-98.
Effendi et al., "Connective Tissue Growth Factor in Idiopathic Pulmonary Fibrosis: Breaking the Bridge," Int. J. Mol. Sci., 2022, 23.
Ehrbar et al., "Elucidating the role of matrix stiffness in 3D cell migration and remodeling," Biophys. J., 2011, 100: 284-293.
Elosegui-Artola et al., "Force triggers YAP nuclear entry by regulating transport across nuclear pores," Cell, 2017, 171: 1397-1410.e14.
Encode Project Consortium, "An integrated encyclopedia of DNA elements in the human genome," Nature, 2012, 2012, 489: 57-74.
Encode Project Consortium, "Expanded encyclopaedias of DNA elements in the human and mouse genomes," Nature, 2020, 583: 699-710.
Engler et al., "Matrix elasticity directs stem cell lineage specification," Cell, 2006, 126: 677-689.
Ernst et al., "ChromHMM: automating chromatin-state discovery and characterization," Nat Methods, 2012, 9: 215-216.
Fan et al., "Hsp90{beta} and p130(cas): novel regulatory factors of MMP-13 expression in human osteoarthritic chondrocytes," Ann. Rheum. Dis., 2009, 68: 976-982.
Finak et al., "MAST: a flexible statistical framework for assessing transcriptional changes and characterizing heterogeneity in single-cell RNA sequencing data," Genome Biol., 2015, 16: 278.
Fiore et al., "Publisher Correction: Mechanics of a multilayer epithelium instruct tumour architecture and function," Nature, 2020, 586: E9.
Freeberg et al., "Mechanical Feed-Forward Loops Contribute to Idiopathic Pulmonary Fibrosis," Am. J. Pathol., 2021, 191: 18-25.
Fulco et al., "Activity-by-contact model of enhancer-promoter regulation from thousands of CRISPR perturbations," Nat. Genet., 2019, 51: 1664-1669.
Galli et al., "YAP Drives Growth by Controlling Transcriptional Pause Release from Dynamic Enhancers," Molecular Cell, 2015, 60(2): P328-337.
Gasperini et al., "A Genome-wide Framework for Mapping Gene Regulation via Cellular Genetic Screens," Cell, 2019, 176: 377-390.e19.
GenBank Accession No. U94396.1 "Human dystrophin (DMD) gene, exon 44 and partial cds," 2016.
Gilbert et al., "CRISPR-mediated modular RNA-guided regulation of transcription in eukaryotes," Cell, 2013, 154: 442-451.
Gordon et al., "lentiMPRA and MPRAflow for high-throughput functional characterization of gene regulatory elements," Nat. Protoc., 2020, 15(8): 2387-2412.
Habermann et al., "Single-cell RNA sequencing reveals profibrotic roles of distinct epithelial and mesenchymal lineages in pulmonary fibrosis," Sci Adv, 2020, 6: eaba197.
Hall et al., "Polarity of the CRISPR roadblock to transcription," Nat. Struct. Mol. Biol., 2022, 29: 1217-1227.
Han et al., "CRISPR screens in cancer spheroids identify 3D growth-specific vulnerabilities," Nature, 2020, 580: 136-141.
Hanmandlu et al., "Transcriptomic and Epigenetic Profiling of Fibroblasts in Idiopathic Pulmonary Fibrosis," Am J Respir Cell Mol Biol, 2022, 66(1): 53-63.
Heinz et al., "Simple combinations of lineage-determining transcription factors prime cis- regulatory elements required for macrophage and B cell identities," Mol. Cell, 2010, 38: 576-589.
Heinz et al., "The selection and function of cell type-specific enhancers," Nat. Rev. Mol. Cell Biol., 2015, 16: 144-154.
Heo et al., "Differentiation alters stem cell nuclear architecture, mechanics, and mechano- sensitivity," Elife, 2016, 5.
Herrera et al., "Extracellular matrix as a driver of progressive fibrosis," J. Clin. Invest., 2018, 128: 45-53.
Ho et al., "Lamin A/C and emerin regulate MKL1-SRF activity by modulating actin dynamics," Nature, 2013, 497: 507-511.
Hoffman et al., "Dynamic molecular processes mediate cellular mechanotransduction," Nature, 2011, 475: 316-323.
Horlbeck et al., "Compact and highly active next-generation libraries for CRISPR-mediated gene repression and activation," Elife, 2016, 5: e19760.
Humphrey et al., "Mechanotransduction and extracellular matrix homeostasis," Nat. Rev. Mol. Cell Biol., 2014, 15: 802-812.
Isaac et al., "Nucleosome breathing and remodeling constrain CRISPR-Cas9 function," Elife, 2016, 5: e13450.
Jang et al., "Mechanical cue-induced YAP instructs Skp2-dependent cell cycle exit and oncogenic signaling, " Embo J., 2017, 36: 2510-2528.
Jeffrey et al., "Targeting dual-specificity phosphatases: manipulating MAP kinase signalling and immune responses," Nat. Rev. Drug Discov., 2007, 6: 391-403.
Jiang et al., "Systematic investigation of cytokine signaling activity at the tissue and single-cell levels," Nat. Methods, 2021, 18: 1181-1191.
Johne et al., "Spred1 and TESK1—two new interaction partners of the kinase MARKK/TAO1 that link the microtubule and actin cytoskeleton," Mol. Biol. Cell, 2008, 19: 1391-1403.

(56) References Cited

OTHER PUBLICATIONS

Jones et al., "Mechanoepigenetic regulation of extracellular matrix homeostasis via Yap and Taz," Proc. Natl. Acad. Sci. U.S.A., 2023, 120: e2211947120.
Jones et al., "No place like home: anatomy and function of the stem cell niche," Nat. Rev. Mol. Cell Biol., 2008, 9: 11-21.
Jones et al., "ZNF416 is a pivotal transcriptional regulator of fibroblast mechanoactivation," J. Cell Biol., 2021, 220.
Juric et al., "MAPS: Model-based analysis of long-range chromatin interactions from PLAC-seq and HiChIP experiments," PLoS Comput. Biol., 2019, 15: e1006982.
Katsura et al., "Human Lung Stem Cell-Based Alveolospheres Provide Insights into SARS-COV-2-Mediated Interferon Responses and Pneumocyte Dysfunction," Cell Stem Cell, 2020, 27(6): 890-904.e8.
Kechin et al., "cutPrimers: A New Tool for Accurate Cutting of Primers from Reads of Targeted Next Generation Sequencing," J. Comput. Biol., 2017, 24: 1138-1143.
Khemlina et al., "The biology of Hepatocellular carcinoma: implications for genomic and immune therapies," Mol. Cancer, 2017, 16: 149.
Kisselev, "Polypeptide Release Factors in Prokaryotes and Eukaryotes: Same Function, Different Structure," Structure, 2002, 10: 8-9.
Klann et al., "CRISPR-Cas9 epigenome editing enables high-throughput screening for functional regulatory elements in the human genome," Nat. Biotechnol., 2017, 35: 561-568.
Korkmaz et al., "Functional genetic screens for enhancer elements in the human genome using CRISPR-Cas9," Nat. Biotechnol., 2016, 34: 192-198.
Krietenstein et al., "Ultrastructural Details of Mammalian Chromosome Architecture," Mol. Cell, 2020, 78(3): 554-565.e7.
Kurppa et al., "Treatment-Induced Tumor Dormancy through YAP-Mediated Transcriptional Reprogramming of the Apoptotic Pathway," Cancer Cell, 2020, 37: 104-122.e12.
Langmead, "Aligning short sequencing reads with Bowtie," Curr. Protoc. Bioinformatics, 2010, Chapter 11, Unit 11.7.
Lau et al., "In vivo epigenome editing and transcriptional modulation using CRISPR technology," Transgenic Res. 2018, 27(6): 489-509.
Le et al., "Mechanical regulation of transcription controls Polycomb-mediated gene silencing during lineage commitment, " Nature Cell Biology, 2016, 18(8): 864-875.
Lee et al., "The novel PIAS-like protein hZimp10 is a transcriptional co-activator of the p53 tumor suppressor," Nucleic Acids Res., 2007, 35: 4523-4534.
Leight et al., "Matrix rigidity regulates a switch between TGF-B1-induced apoptosis and epithelial-mesenchymal transition," Mol. Biol. Cell, 2012, 23: 781-791.
Li et al., "MicroRNA-21 preserves the fibrotic mechanical memory of mesenchymal stem cells," Nat. Mater., 2017, 16: 379-389.
Liao et al., "featureCounts: an efficient general purpose program for assigning sequence reads to genomic features," Bioinformatics, 2014, 30: 923-930.
Liu et al., "Modulating chromatin accessibility by transactivation and targeting proximal dsgRNAs enhances Cas9 editing efficiency in vivo," Genome Biol, 2019, 20(1): 145.
Love et al., "Moderated estimation of fold change and dispersion for RNA-seq data with DESeq2," Genome Biol., 2014, 15: 550.
Ma et al., "Mechanotransduction and anoikis: death and the homeless cell," Cell Cycle, 2008, 7: 2462-2465.
McBeath et al., "Cell shape, cytoskeletal tension, and RhoA regulate stem cell lineage commitment," Dev. Cell, 2004, 6: 483-495.
McDowell et al., "Glucocorticoid receptor recruits to enhancers and drives activation by motif-directed binding," Genome Res., 2018, 28: 1272-1284.
Meng et al., "RAP2 mediates mechanoresponses of the Hippo pathway," Nature, 2018, 560: 655-660.
Meyers et al., "Computational correction of copy No. effect improves specificity of CRISPR-Cas9 essentiality screens in cancer cells," Nat. Genet., 2017, 49: 1779-1784.
Miano, "Serum response factor: toggling between disparate programs of gene expression," J. Mol. Cell. Cardiol., 2003, 35: 577-593.
Mifsud et al., "Mapping long-range promoter contacts in human cells with high-resolution capture Hi-C," Nat. Genet., 2015, 47: 598-606.
Miralles et al., "Actin dynamics control SRF activity by regulation of its coactivator MAL," Cell, 2003, 113: 329-342.
Miroshnikova et al., "Emerging roles of mechanical forces in chromatin regulation," J. Cell Sci., 2017, 130: 2243-2250.
Molineros et al., "Mechanistic Characterization of Variants Identifies an hnRNP-K-Regulated Transcriptional Enhancer Contributing to SLE Susceptibility," Front. Immunol., 2019, 10: 1066.
Moore et al., "Regulation and Relevance of Myofibroblast Responses in Idiopathic Pulmonary Fibrosis," Curr. Pathobiol. Rep., 2013, 1: 199-208.
Morrison et al., "Stem cells and niches: mechanisms that promote stem cell maintenance throughout life," Cell, 2008, 132: 598-611.
Muerdter et al., "Resolving systematic errors in widely used enhancer activity assays in human cells," Nat. Methods, 2018, 15: 141-149.
Murthy et al., "Human distal lung maps and lineage hierarchies reveal a bipotent progenitor," Nature, 2022, 604(7904): 111-119.
Namavar et al., "Classification, diagnosis and potential mechanisms in pontocerebellar hypoplasia," Orphanet J. Rare Dis., 2011, 6: 50.
Nava et al., "Heterochromatin-Driven Nuclear Softening Protects the Genome against Mechanical Stress-Induced Damage," Cell, 2020, 181: 800-817.e22.
Noonan et al., "Genomics of long-range regulatory elements," Annu. Rev. Genomics Hum. Genet., 2010, 11: 1-23.
Oliver-De La Cruz et al., "Substrate mechanics controls adipogenesis through YAP phosphorylation by dictating cell spreading, " Biomaterials, 2019, 205: 64-80.
Open2C et al., "Pairtools: From sequencing data to chromosome contacts, " PLoS Comput. Biol., 2024, 20: e1012164.
Paoli et al., "Anoikis molecular pathways and its role in cancer progression," Biochim. Biophys. Acta, 2013, 1833: 3481-3498.
Parker et al., "Fibrotic extracellular matrix activates a profibrotic positive feedback loop," J. Clin. Invest., 2014, 124: 1622-1635.
Paszek et al., "Tensional homeostasis and the malignant phenotype," Cancer Cell, 2005, 8: 241-254.
Paulmann et al., "The OTUD6B-LIN28B-MYC axis determines the proliferative state in multiple myeloma," Embo J., 2022, 41: e110871.
Pelham Jr et al., "Cell locomotion and focal adhesions are regulated by substrate flexibility," Proc. Natl. Acad. Sci. U.S.A., 1997, 94: 13661-13665.
Piccolo et al., "The biology of YAP/TAZ: hippo signaling and beyond, " Physiol. Rev., 2014, 94: 1287-1312.
Plikus et al., "Fibroblasts: Origins, definitions, and functions in health and disease," Cell, 2021, 184: 3852-3872.
Quinlan et al., "BEDTools: a flexible suite of utilities for comparing genomic features," Bioinformatics, 2010, 26: 841-842.
Quinlan, "BEDTools: The Swiss-Army Tool for Genome Feature Analysis," Curr. Protoc. Bioinformatics, 2014, 47: 11.12.1-34.
Ramírez et al., "deepTools: a flexible platform for exploring deep-sequencing data," Nucleic Acids Res., 2014, 42: W187-91.
Ritterhoff et al., "The RanBP2/RanGAP1*SUMO1/Ubc9 Sumo E3 ligase is a disassembly machine for Crm1-dependent nuclear export complexes," Nat. Commun., 2016, 7: 11482.
Robinson et al., "edgeR: a Bioconductor package for differential expression analysis of digital gene expression data," Bioinformatics, 2010, 26: 139-140.
Royer et al., "Mechanobiology in the Comorbidities of Ehlers Danlos Syndrome," Front Cell Dev Biol, 2022, 10: 874840.
Sanson et al., "Optimized libraries for CRISPR-Cas9 genetic screens with multiple modalities," Nat. Commun., 2018, 9: 1-15.
Sanyal et al., "The long-range interaction landscape of gene promoters," Nature, 2012, 489: 109-113.
Schmelzle et al., "Functional role and oncogene-regulated expression of the BH3-only factor Bmf in mammary epithelial anoikis and morphogenesis," Proc. Natl. Acad. Sci. U.S.A., 2007, 104: 3787-3792.

(56) References Cited

OTHER PUBLICATIONS

Seo et al., "RNAi-based functional selection identifies novel cell migration determinants dependent on PI3K and AKT pathways," Nat. Commun., 2014, 5: 5217.
Simeonov et al., "Discovery of stimulation-responsive immune enhancers with CRISPR activation," Nature, 2017, 549: 111-115.
Sollis et al., "The NHGRI-EBI Gwas Catalog: knowledgebase and deposition resource," Nucleic Acids Res., 2023, 51: D977-D985.
Song et al., "B-catenin induces A549 alveolar epithelial cell mesenchymal transition during pulmonary fibrosis," Mol. Med. Rep., 2015, 11: 2703-2710.
Stowers et al., "Matrix stiffness induces a tumorigenic phenotype in mammary epithelium through changes in chromatin accessibility," Nat Biomed Eng, 2019, 3: 1009-1019.
Stuart et al., "Comprehensive Integration of Single-Cell Data," Cell, 2019, 177: 1888-1902.e21.
Sun et al., "Effects of Matrix Stiffness on the Morphology, Adhesion, Proliferation and Osteogenic Differentiation of Mesenchymal Stem Cells," Int. J. Med. Sci., 2018, 15: 257-268.
Sun et al., "Force-induced gene up-regulation does not follow the weak power law but depends on H3K9 demethylation," Sci Adv, 2020, 6: eaay9095.
Swift et al., "Nuclear lamin-A scales with tissue stiffness and enhances matrix-directed differentiation," Science, 2013, 341: 1240104.
Tajik et al., "Transcription upregulation via force-induced direct stretching of chromatin," Nat. Mater., 2016, 15: 1287-1296.
Thakore et al., "Highly specific epigenome editing by CRISPR-Cas9 repressors for silencing of distal regulatory elements," Nat. Methods, 2015, 12: 1143-1149.
Torrungruang et al., "DNA binding and gene activation properties of the Nmp4 nuclear matrix transcription factors," J. Biol. Chem., 2002, 277: 16153-16159.
Tycko et al., "Mitigation of off-target toxicity in CRISPR-Cas9 screens for essential non-coding elements," Nat. Commun., 2019, 10: 4063.
Vartiainen et al., "Nuclear actin regulates dynamic subcellular localization and activity of the SRF cofactor MAL," Science, 2007, 316: 1749-1752.
Vicente-Manzanares et al., "Non-muscle myosin II takes centre stage in cell adhesion and migration" Nat. Rev. Mol. Cell Biol., 2009, 10: 778-790.
Vierbuchen et al., "AP-1 Transcription Factors and the BAF Complex Mediate Signal-Dependent Enhancer Selection," Mol. Cell, 2017, 68: 1067-1082.e12.
Vishwanath et al., "Mechanisms of aortic carboxypeptidase-like protein secretion and identification of an intracellularly retained variant associated with Ehlers-Danlos syndrome," J. Biol. Chem., 2020, 295: 9725-9735.
Wei et al., "HiCAR is a robust and sensitive method to analyze open-chromatin-associated genome organization," Mol. Cell, 2022, 82: 1225-1238.e6.
Wells, "Tissue mechanics and fibrosis," Biochim. Biophys. Acta, 2013, 1832: 884-890.
Witkowski et al., "Conversion of a β-Ketoacyl Synthase to a Malonyl Decarboxylase by Replacement of the Active-Site Cysteine with Glutamine," Biochemistry, 1999, 38: 11643- 11650.
Yan et al., "Zinc finger protein 384 enhances colorectal cancer metastasis by upregulating MMP2," Oncol. Rep., 2022, 47.
Yao et al., "The ENCODE4 Consortium, Multi-center integrated analysis of non-coding CRISPR screens," https://doi.org/10.1101/2022.12.21.520137, posted Dec. 22, 2022.
Yu et al., "ChIPseeker: an R/Bioconductor package for ChIP peak annotation, comparison and visualization," Bioinformatics, 2015, 31: 2382-2383.
Zanconato et al., "Genome-wide association between YAP/TAZ/TEAD and AP-1 at enhancers drives oncogenic growth," Nat. Cell Biol., 2015, 17: 1218-1227.
Zhang et al., "BAALC-AS1/G3BP2/c-Myc feedback loop promotes cell proliferation in esophageal squamous cell carcinoma," Cancer Commun., 2021, 41: 240-257.
Zhang et al., "Model-based analysis of ChIP-Seq (MACS)," Genome Biol., 2008, 9: R137.
Zhang et al., "The matricellular protein Cyr61 is a key mediator of platelet-derived growth factor- induced cell migration," J. Biol. Chem., 2015, 290: 8232-8242.
Zhao et al., "Cell detachment activates the Hippo pathway via cytoskeleton reorganization to induce anoikis," Genes Dev., 2012, 26: 54-68.
Zhao et al., "Substrate stiffness regulated migration and angiogenesis potential of A549 cells and HUVECs," J. Cell. Physiol, 2018, 233: 3407-3417.
Zhao et al., "TEAD mediates YAP-dependent gene induction and growth control," Genes Dev., 2008, 22: 1962-1971.
Zhou et al., "Novel identified associations of RGS1 and RASGRP1 variants in IgA Nephropathy," Sci. Rep., 2016, 6: 35781.
Lee et al., "Synthetically modified guide RNA and donor DNA are a versatile platform for CRISPR-Cas9 engineering," eLife, 2017, 6: e25312.
Kwon et al., "626. Directing Skeletal Myogenic Progenitor Cell Lineage Specification with CRISPR/Cas9 Transcriptional Activators," Molecular Therapy, 2016, 24: S248.
Jiang et al., "CRISPR-Cas9 Structures and Mechanisms," Annu Rev Biophys, 2017, 46: 505-529.
Mathias et al., "Unraveling Immune-Related IncRNAs in Breast Cancer Molecular Subtypes," Front. Oncol., 2021, 11: 692170.
Cui et al., "Long non-coding RNA LINC02613 is a prognostic biomarker for breast cancer and correlates with the cell cycle and immune infiltration based on TCGA data," Translational Cancer Research, 2022, 11(4): 615-628.
Hori et al., "Control of Regulatory T Cell Development by the Transcription Factor Foxp3," Science, 2003, 299: 1057-1061.
Reiner et al., "Epigenetics meets GPCR: inhibition of histone H3 methyltransferase (G9a) and histamine H3 receptor for Prader-Willi Syndrome," Scientific Reports, 2020, 10: 13558.
Burr et al., "Mitochondrial Protein Lipoylation and the 2-Oxoglutarate Dehydrogenase Complex Controls HIF1a Stability in Aerobic Conditions," Cell Metab, 2016, 24(5): 740-752.
Leandro et al., "DHTKD1 and OGDH display in vivo substrate overlap and form a hybrid ketoacid dehydrogenase complex," bioRxiv preprint version posted May 22, 2019.
Bailey et al., "ABHD11 maintains 2-oxoglutarate metabolism by preserving functional lipoylation of the 2-oxoglutarate dehydrogenase complex," Nature Communications, 2020, 11: 4046.
Chung et al., "Prader-Willi syndrome: reflections on seminal studies and future therapies," Open Biology, 2020, 10:200195.
Hesselson et al., "Suppression of Ptf1a Activity Induces Acinar-to-Endocrine Conversion," Current Biology, 2011, 21:712-717.

* cited by examiner

GTTTTAACTACTTATTATGAAATGTAAAT (SEQ ID NO: 73)

CRISPR Lm I-B

AP286

PAMs = CCA

| Strain | Spacer-CRISPR | PAM_protospacers | Phage |
|---|---|---|---|
| *L. monocytogenes* | 3-1 | TCAAA**CCA**ACAGATCAAACTCCGGAAGGGTGATTGTAAATGGC | LP-101 |
| | 8-1 | AATAC**CCA**AAAATAGGAGGAAATAAATTATGACTATCAAATTAA | LP-101 |
| | 9-2 | CTTGG**CCA**AGAGTTTCCAGCTGTAAGGCCAGATATTGATAATTTC | phage1034 |
| | 25-2 | ATATT**CCA**CCTCCACAATCACTCGGCTTTCTTCGTCTTTATCGAC | A118 |
| | 27-2 | AAGAT**CCA**GTCGCTAGAGCTAAAAAATGGATAGAGGAACAACAAG | vB_LmoS_293 |
| | 44-2 | CCAAA**CAA**GTTGAAAAGCGCACCATTGTTTTAATTTTTTTAATT | LP-030-2 |
| | 45-2 | CAAGT**CCA**TTTTGTCGCATAAATTCTTTGATGTGGCGGACTGACG | LP-114 |
| | 49-2 | CGGAG**CCT**TCGTTAATCATAATTGATGAAAGTCATCATGTGTTAG | LP-101 |

*Underlined bold nucleotides indicate the predicted PAM

**PAM prediction for CRISPR subtype I-B in *L. monocytogenes* Finland 1998**

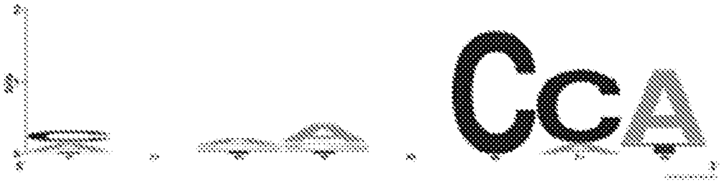

Average spacer length = 36bp, ranges from 33bp to 42bp

FIG. 12

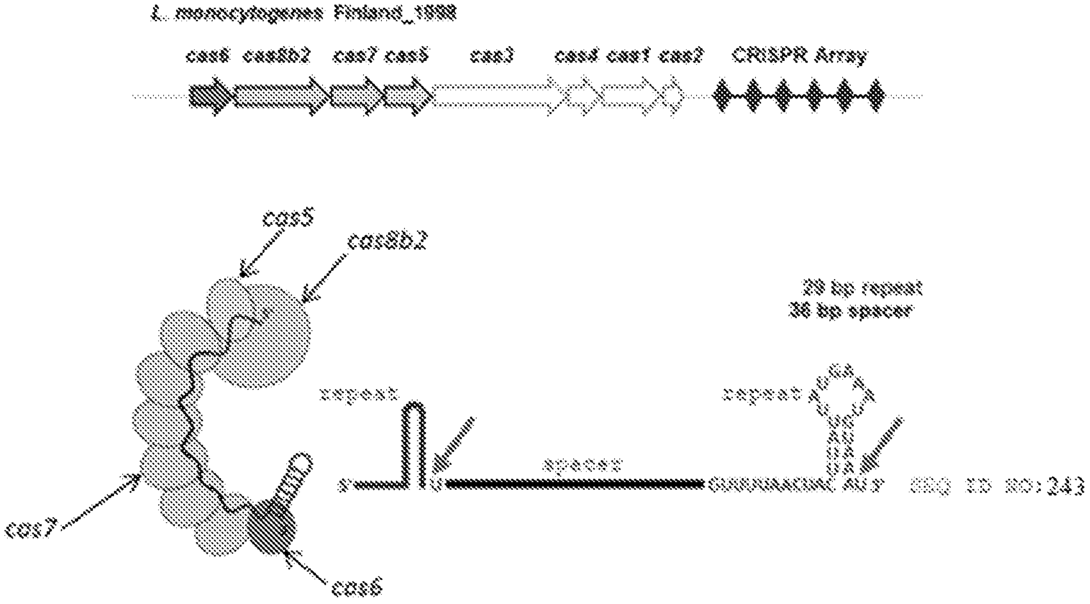

FIG. 13

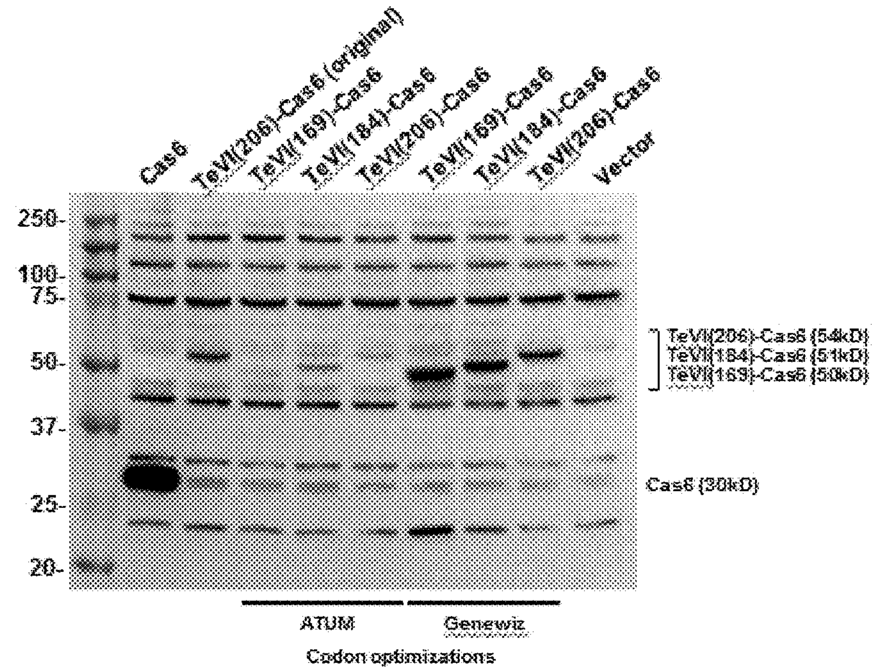
FIG. 28B
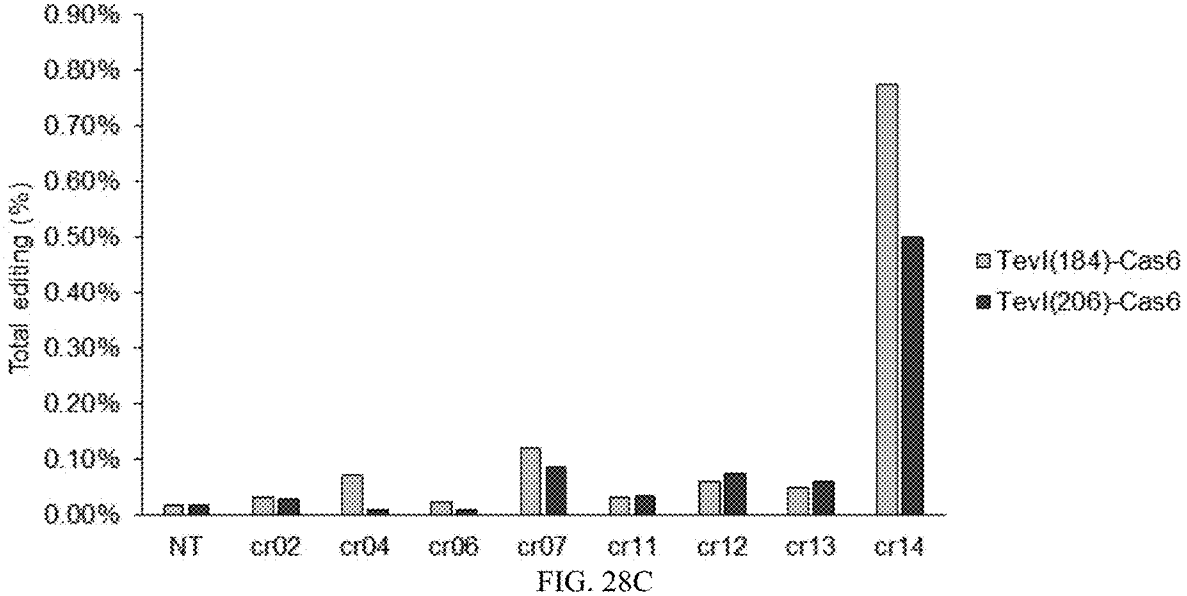
FIG. 28C
SEQ ID NO:301
GGAGGCTGGGCTCCTGCTTGTACTCTTCCAGGTGGCTCTGGAAGGAGGGGCAGCTCCACCCTGGGAGGGACTGTGGCCCAGGT
CCTCCGACCCGAGGACGAACATGAGAAGGTCCACCGAGACCTTCCTCCCCGTCGAGGTGGGACCCTCCCTGACACCGGGTCCA
FIG. 28D

GENOME ENGINEERING WITH CRISPR-CAS SYSTEMS IN EUKARYOTES

CROSS-REFERENCE

This patent application is the U.S. national stage entry, under 35 U.S.C. § 371, of International Application Number PCT/US2019/014386, filed Jan. 19, 2019, which claims the benefit of U.S. Provisional Application No. 62/619,398, filed Jan. 19, 2018, U.S. Provisional Application No. 62/619,477, filed Jan. 19, 2018, U.S. Provisional Application No. 62/671,413, filed May 14, 2018, U.S. Provisional Application No. 62/683,586, filed Jun. 11, 2018, and U.S. Provisional Application No. 62/683,595, filed Jun. 11, 2018, the entire contents of each of which are hereby incorporated by reference.

STATEMENT OF GOVERNMENT INTEREST

This invention was made with government support under federal grant numbers DP2-OD008586, R01DA036865, and T32GM008555 awarded by US National Institutes of Health and CBET-1151035 awarded by US National Science Foundation. The U.S. Government has certain rights to this invention.

SEQUENCE LISTING

This instant application includes a Sequence Listing which has been submitted electronically in ASCII format and is hereby incorporated by reference in its entirety. Said ASCII copy created on May 21, 2024, is named "028193-9283-US04 Sequence Listing_ST25.txt" and is 225,109 bytes in size.

TECHNICAL FIELD

The present disclosure relates to the field of gene expression alteration of target genes in eukaryotic cells using Clustered Regularly Interspaced Short Palindromic Repeats (CRISPR)/CRISPR-associated (Cas) based programmable systems. For example, Type I-E Clustered Regularly Interspaced Short Palindromic Repeats (CRISPR)/CRISPR-associated (Cas) transcriptional activation (Type I-E CRISPRa) systems. In some embodiments, the disclosure relates to CRISPR systems compositions, and methods of using said compositions. In some embodiments, such compositions can include fusion proteins. In some embodiments, the disclosure relates to Type I-E CRISPRa system compositions, and methods of using said compositions, that include Type I-E Cascade fusion proteins designed for transcriptional activation of target genes in eukaryotic cells.

The present disclosure also relates to the field of gene editing and gene expression modulation of target genes in cells using CRISPR systems. For example, *Listeria monocytogenes* Type I-B Clustered Regularly Interspaced Short Palindromic Repeats (CRISPR)/CRISPR-associated (Cas) based programmable systems, such as a *Listeria monocytogenes* Type I-B CRISPR-based programmable transcriptional activation (Type I-B CRISPRa) system. In some embodiments, the disclosure relates to *Listeria monocytogenes* Type I-B CRISPR-based programmable systems that include *Listeria monocytogenes* Type I-B Cascade polypeptide fusion proteins that can be designed to modulate gene expression of or to edit a target gene in a cell, such as in a eukaryotic cell.

BACKGROUND

The ability to modulate and perturb genetic information is indispensable for studying gene function and uncovering biological mechanisms. Targetable DNA-binding proteins that modify genomes at specific loci have led to tremendous advances in science, biotechnology, and medicine. The development of CRISPR systems for targeting DNA and RNA in diverse organisms has transformed biotechnology and biological research. Moreover, the CRISPR Revolution has highlighted bacterial adaptive immune systems as a rich and largely unexplored territory for discovery of new genome engineering technologies.

CRISPR-Cas systems are naturally adaptive immune systems found in bacteria and archaea. The CRISPR system is a nuclease system involved in defense against invading phages and plasmids that provides a form of acquired immunity. The CRISPR loci in microbial hosts contain a combination of CRISPR-associated (Cas) genes as well as non-coding RNA elements capable of programming the specificity of the CRISPR-mediated nucleic acid cleavage. Short segments of foreign DNA, called spacers, are incorporated into the genome between CRISPR repeats, and serve as a 'memory' of past exposures. The CRISPR (for clustered regularly interspaced short palindromic repeats) consists of alternating repeats and spacers and is often flanked by a set of cas (for CRISPR associated) genes. The CRISPR array is transcribed and processed into individual CRISPR RNAs that complex with the Cas proteins. The spacer portion of the CRISPR RNA (crRNA) then serves as a guide to recognize complementary foreign genetic material, which is cleaved by the Cas proteins.

Bioinformatics analyses have a revealed a diversity of CRISPR-Cas systems based on the set of cas genes and their phylogenetic relationship. The most recent classification system defines six different types (I through VI) where Type I represents over 50% of all identified systems in both bacteria and archaea. The Type I systems are further divided into six subtypes: I-A, I-B, I-C, I-D, I-E, and I-F. Type I CRISPR/Cas systems include a multi-subunit complex called Cascade (for complex associated with antiviral defense), Cas3 (a protein with nuclease, helicase, and exonuclease activity that is responsible for degradation of the target DNA), and crRNA (stabilizes Cascade complex and directs Cascade and Cas3 to DNA target). Cascade forms a complex with the crRNA, and the protein-RNA pair recognizes its genomic target by complementary base pairing between the 5' end of the crRNA sequence and a predefined DNA sequence, known as the protospacer. This complex is directed to homologous loci of pathogen DNA via regions encoded within the crRNA and protospacer-adjacent motifs (PAMs) within the pathogen genome. Base pairing occurs between the crRNA and the target DNA sequence leading to a conformational change. In the Type I-E system, the PAM is recognized by the CasA protein within Cascade, which then unwinds the flanking DNA to evaluate the extent of base pairing between the target and the spacer portion of the crRNA.

Sufficient recognition leads Cascade to recruit and activate Cas3. Cas3 then nicks the non-target strand and begins degrading the strand in a 3'-to-5' direction. By simply exchanging the crRNA, the Cas3 can be directed to new genomic targets. Despite the unique attributes and prevalence of Type I CRISPR/Cas systems, little work has been done to explore their potential use for genome engineering, and there remains a need for the ability to precisely regulate any gene in a eukaryotic cell.

SUMMARY

In some embodiments, the present disclosure is directed to system for modulating the activity of at least one target gene in a eukaryotic cell. In some embodiment, the system is a Type I system. In some embodiments, the present disclosure is directed to a Type I-E CRISPR-based programmable transcriptional activation (Type I-E CRISPRa) system composition for activating at least one target gene in a eukaryotic cell. In some embodiments, the composition comprises at least one polynucleotide sequence encoding: (a) a Cascade complex comprising three or more Cascade polypeptides of the Type I-E CRISPR/Cas system, or functional fragments thereof, wherein at least one Cascade polypeptide is fused to a second polypeptide domain having transcription activation activity; and/or (b) at least one crRNA, wherein the crRNA targets a target nucleotide sequence from the at least one target gene, wherein the at least one polynucleotide sequence is operably linked to a eukaryotic promoter, comprises a nuclear localization signal, and is codon-optimized, and wherein the at least one Cascade polypeptide fused to a second polypeptide domain is CasA or CasE. In some embodiments, the present disclosure is directed to an expression cassette or a vector comprising said Type I-E CRISPRa system, or subcomponents thereof. In some embodiments, the present disclosure is also directed to an expression cassette or a vector comprising at least one polynucleotide sequence of SEQ ID NO: 1, SEQ ID NO: 2, SEQ ID NO: 3, SEQ ID NO: 4, SEQ ID NO: 5, SEQ ID NO: 6; SEQ ID NO: 7, SEQ ID NO: 8, SEQ ID NO: 163, or combinations thereof. In some embodiments, the expression cassette or vector comprises a polynucleotide sequence having at least 60%, 70%, 80%, 90% or 95% sequence identity to SEQ ID NO: 1, SEQ ID NO: 2, SEQ ID NO: 3, SEQ ID NO: 4, SEQ ID NO: 5, SEQ ID NO: 6; SEQ ID NO: 7, SEQ ID NO: 8, SEQ ID NO: 163. In some embodiments, the disclosure is also directed to a host cell comprising said Type I-E CRISPRa system, or said expression cassettes or vectors. In some embodiments, the disclosure is also directed to a pharmaceutical composition comprising said Type I-E CRISPRa, said expression cassettes or vectors, or said host cell. In some embodiments, the disclosure is also directed to a method of activating the expression of a target gene in a eukaryotic cell. In some embodiments, the method comprises introducing to a cell said Type I-E CRISPRa system or said expression cassettes or vectors. In some embodiments, the disclosure is also directed to a kit. In some embodiments, the disclosure is directed to a kit for activating gene expression of at least one target gene in a eukaryotic cell. In some embodiments, the kit comprises said Type I-E CRISPRa system, said expression cassettes or vectors, or said host cell.

In some embodiments, the disclosure is directed to a system for genome engineering at least one target gene in a cell. In some embodiments, the disclosure is directed to a Type I-B Clustered Regularly Interspaced Short Palindromic Repeats (CRISPR)-based programmable system composition for genome engineering at least one target gene in a cell. In some embodiments, the composition comprises: (a)(i) a Cascade complex comprising three or more Cascade polypeptides of a Type I-B CRISPR/CRISPR-associated (Cas) system, or functional fragments thereof, or (ii) a nucleic acid sequence encoding a Cascade complex comprising three or more Cascade polypeptides of the Type I-B CRISPR/Cas system, or functional fragments thereof; and/or (b)(i) at least one crRNA or (ii) a nucleic acid sequence encoding at least one crRNA, wherein the at least one crRNA targets a target nucleotide sequence from the at least one target gene, and wherein at least one Cascade polypeptide is fused to a second polypeptide domain thereby generating a Cascade polypeptide fusion protein, wherein the second polypeptide domain has an activity selected from the group consisting of transcription activation activity, nuclease activity, nickase activity, transcription repression activity, transcription release factor activity, histone modification activity, nucleic acid association activity, methylase activity, and demethylase activity; wherein the at least one Cascade polypeptide in the Cascade polypeptide fusion protein is Cas5, Cas6, Cas7, or Cas8b2. In some embodiments, the disclosure is directed to an expression cassette or a vector comprising said Type I-B CRISPR-based programmable system, or subcomponents thereof. In some embodiments, the disclosure is directed to a host cell comprising said Type I-B CRISPR-based programmable system or said expression cassette or vector. In some embodiments, the disclosure is directed to a pharmaceutical composition comprising said Type I-B CRISPR-based programmable system, said expression cassette or vector, or said host cell. In some embodiments, the disclosure is directed to a kit. In some embodiments, the disclosure is directed to a kit for modulating gene expression or gene editing of at least one target gene in a cell, the kit comprising said Type I-B CRISPR-based programmable system or said expression cassette or vector. In some embodiments, the disclosure is directed to a method of modulating gene expression or gene editing of at least one target gene in a cell. In some embodiments, the disclosure the method comprises introducing to a cell said Type I-B CRISPR-based programmable system or said expression cassette or vector.

In some embodiments, the disclosure is directed to a method of modulating gene expression or gene editing of at least one target gene in a cell. In some embodiments, the method comprises introducing to a cell: (a)(i) a Cascade complex comprising three or more Cascade polypeptides of a Type I-B CRISPR/Cas system, or functional fragments thereof or (ii) a nucleic acid encoding a Cascade complex comprising three or more Cascade polypeptides of a Type I-B CRISPR/Cas system, or functional fragments thereof; and/or (b)(i) at least one crRNA or (ii) a nucleic acid encoding at least one crRNA, wherein the crRNA targets a target nucleotide sequence from the at least one target gene, and wherein at least one Cascade polypeptide is fused to a second polypeptide domain thereby generating a Cascade polypeptide fusion protein, wherein the second polypeptide domain has an activity selected from the group consisting of transcription activation activity, nuclease activity, nickase activity, transcription repression activity, transcription release factor activity, histone modification activity, nucleic acid association activity, methylase activity, and demethylase activity, and wherein the at least one Cascade polypeptide in the Cascade polypeptide fusion protein is Cas5, Cas6, Cas7, or Cas8b2. In some embodiments, the disclosure is directed to a modified lentiviral construct comprising at least one polynucleotide sequence of SEQ ID NOs 166-174, 179, 181-197, 258-261, or a combination thereof. In some embodiments, the modified lentiviral construct comprises a polynucleotide sequence having at least 60%, 70%, 80%, 90% or 95% sequence identity to SEQ ID NOs 166-174, 179, 181-197, 258-261. In some embodiments, the disclosure is directed to a modified lentiviral construct comprising at least one polynucleotide sequence of SEQ ID Nos: 270-275, or a combination thereof.

In some embodiments, the disclosure is directed to a Type I-B CRISPR-based programmable transcriptional activation (Type I-B CRISPRa) system composition for activating at least one target gene in a cell. In some embodiments, the composition comprises: (a)(i) a Cascade complex comprising three or more Cascade polypeptides of a Type I-B CRISPR/Cas system, or functional fragments thereof, or (ii) a nucleic acid sequence encoding a Cascade complex comprising three or more Cascade polypeptides of the Type I-B CRISPR/Cas system, or functional fragments thereof; and/or (b)(i) at least one crRNA or (ii) a nucleic acid encoding at least one crRNA, wherein the crRNA targets a target nucleotide sequence from the at least one target gene, and wherein at least one Cascade polypeptide is fused to a second polypeptide domain having transcription activation activity thereby generating a Cascade polypeptide fusion protein, and wherein the at least one Cascade polypeptide in the Cascade polypeptide fusion protein is Cas5, Cas6, Cas7, or Cas8b2. In some embodiments, the disclosure is directed to an expression cassette or a vector comprising said Type I-B CRISPRa system, or subcomponents thereof. In some embodiments, the disclosure is directed to an expression cassette or a vector comprising at least one polynucleotide sequence of SEQ ID NO: 166, SEQ ID NO: 167, SEQ ID NO: 168, SEQ ID NO: 169, SEQ ID NO: 171; SEQ ID NO: 172, SEQ ID NO: 173, SEQ ID NO: 174, SEQ ID NO: 179, SEQ ID NO: 258; SEQ ID NO: 259, SEQ ID NO: 260, SEQ ID NO: 261, or combinations thereof. In some embodiments, the expression cassette or a vector comprises a polynucleotide sequence having at least 60%, 70%, 80%, 90% or 95% sequence identity to SEQ ID NO: 166, SEQ ID NO: 167, SEQ ID NO: 168, SEQ ID NO: 169, SEQ ID NO: 171; SEQ ID NO: 172, SEQ ID NO: 173, SEQ ID NO: 174, SEQ ID NO: 179, SEQ ID NO: 258; SEQ ID NO: 259, SEQ ID NO: 260, SEQ ID NO: 261. In some embodiments, the disclosure is directed to a host cell comprising said Type I-B CRISPRa system or said expression cassette or vector. In some embodiments, the disclosure is directed to a pharmaceutical composition comprising said Type I-B CRISPRa system, said expression cassette or vector, or said host cell. In some embodiments, the disclosure is directed to a kit. In some embodiments, the disclosure is directed to a kit for activating gene expression of at least one target gene in a cell. In some embodiments, the kit comprises said Type I-B CRISPRa system or said expression cassette or vector. In some embodiments, the disclosure is directed to a method of activating the expression of a target gene in a cell. In some embodiments, the method comprises introducing to a cell said Type I-B CRISPRa system or said expression cassette or vector.

In some embodiments, the disclosure is directed to a method of activating the expression of a target gene in a cell. In some embodiments, the method comprises introducing to a cell: (a)(i) a Cascade complex comprising three or more Cascade polypeptides of a Type I-B CRISPR/Cas system, or functional fragments thereof, or (ii) a nucleic acid encoding a Cascade complex comprising three or more Cascade polypeptides of a Type I-B CRISPR/Cas system, or functional fragments thereof; and/or (b)(i) at least one crRNA or (ii) a nucleic acid encoding at least one crRNA, wherein the crRNA targets a target nucleotide sequence from the at least one target gene, and wherein at least one Cascade polypeptide is fused to a second polypeptide domain having transcription activation activity thereby generating a Cascade polypeptide fusion protein, and wherein the at least one Cascade polypeptide in the Cascade polypeptide fusion protein is Cas5, Cas6, Cas7, or Cas8b2.

These and other aspects of the disclosure are set forth in more detail in the description of the disclosure below.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 1A shows a schematic of Type I-E CRISPR-Cas system in *E. coli* K-12 showing Cascade stoichiometry and crRNA processing with the top arrows indicating cleavage processing sites in the repeat and the bottom arrows indicating the start and ends of the spacer sequences. FIG. 1B shows a schematic representation of processed crRNA with 5' PAM recognition (spacer sequence is between the arrows with repeat fragments on the other side of the arrows for the crRNA (SEQ ID NO: 139)) and base pairing at the DNA target site. FIG. 1C shows Cas subunits driven by human cytomegalovirus (CMV) promoter and pre-processed crRNA driven by U6 promoter for expression and processing in mammalian cells. FIG. 1D shows a Western blot showing expression of human codon-optimized individual Cas proteins and GAPDH loading control in human HEK293T cells. (* indicates second round of codon optimization). FIG. 1E shows co-Immunoprecipitation (IP) and western blot showing crRNA-dependent Cascade formation following co-transfection with V5-tagged CasC and Flag-tagged CasA, CasB, CasD, and CasE; IP was performed with α-V5 and detection was performed with α-V5 and α-Flag. FIG. 1F shows immunofluorescence imaging showing engineered Cas subunits with NLSs enables import into the human nucleus; scale bar, 25 nm. All samples processed at 3 days post-transfection. CMV, human cytomegalovirus; CoIP, Co-Immunoprecipitation; NLS, nuclear localization signal. FIG. 1G shows an updated schematic representation of processed crRNA with 5' PAM recognition (spacer sequence is between the arrows with repeat fragments on the other side of the arrows for the crRNA) and base pairing at the DNA target site.

FIG. 2A shows co-IP showing Cascade formation following co-transfection with plasmids encoding the crRNA, Flag-tagged Cascade subunits with V5-tagged CasC, and various Cas-p300 fusions. IP performed with α-V5 and western blot (IB) performed with α-V5 and α-Flag. FIG. 2B shows a schematic of the IL1RN locus along with tiled IL1RN crRNA target sites. ENCODE H3K27ac enrichment is indicated with the vertical range set to 400. The two IL1RN ChIP-qPCR amplicons are shown in corresponding locations. FIG. 2C shows relative IL1RN expression following co-transfection of individual crRNAs and Cascade with CasE-p300. FIG. 2D shows relative IL1RN expression following co-transfection of control crRNA (left bars) or cr26 (right bars) and Cascade with various Cas-p300 effectors. FIG. 2E shows ChIP-qPCR enrichment following co-transfection of individual crRNAs with Cascade and CasE-p300. IP performed with α-Flag and qPCR performed with primers for amplicon regions designated in FIG. 2B. All samples processed at 3 days post transfection. (Tukey-test following log transformation, $^{**}P<0.001$ and $^{*}P<0.05$ compared to Ctrl crRNA, n=3 biological replicates; error bars, SEM). TSS, Transcription start site; Ctrl crRNA, Control crRNA; IP, immunoprecipitation; IB, immunoblot; CMP, chromatin immunoprecipitation; qPCR, quantitative PCR.

FIG. 3A shows a schematic of the IL1RN locus along with IL1RN crRNA target sites. FIG. 3B shows relative IL1RN expression following co-transfection of individual crRNAs and Cascade with CasE-p300 fusion protein, unless otherwise noted. All samples processed at 3 days post-transfection. (Tukey-test following logarithmic transformation, **P<0.001, n.s. P>0.05 compared to Ctrl crRNA, n=3 biological replicates; error bars, SEM). TSS, transcription start site; Ctrl crRNA, Control crRNA; n.s., non-significant.

FIG. 5A shows a schematic of the IL1RN locus along with IL1RN crRNA and gRNA target sites. IL1RN ChIP-qPCR amplicons are shown in corresponding locations. FIG. 5B shows ChIP-qPCR enrichment following co-transfection of individual crRNAs (Ctrl crRNA, cr25, and cr26) with Cascade and CasE-p300 compared to dCas9 with gRNA-3. IP performed with α-Flag and qPCR performed with primers for amplicon regions designated in FIG. 5A. All samples processed at 3 days post-transfection. (Tukey-test among conditions for each ChIP-qPCR region, *P<0.05 compared to Ctrl crRNA, †P<0.05 compared to dCas9-p300+g3, n=3 biological replicates; error bars, SEM). TSS, Transcription start site; Ctrl crRNA, Control crRNA; ChIP, chromatin immunoprecipitation; qPCR, g3, gRNA-3.

FIG. 6A shows a schematic of the IL1RN locus along with IL1RN crRNA and gRNA target sites. FIG. 6B shows relative IL1RN expression following co-transfection of individual crRNAs and Cascade with CasE-p300 (left bars) or CasE-VPR fusions (right bars). FIG. 6C shows relative IL1RN expression following co-transfection of individual gRNAs with dCas9-p300 (left bars) or dCas9-VPR (right bars) fusions. All samples processed at 3 days post transfection. (Tukey-test, **P<0.001 compared to Ctrl crRNA, ††P<0.001 compared to same crRNA, n=3 biological replicates; error bars, SEM). TSS, transcription start site; Ctrl crRNA, Control crRNA; VPR, VP64-p65-Rta tripartite activator.

FIG. 7A shows a schematic of the HBG locus along with HBG crRNA target sites. FIG. 7B shows relative HBG expression following co-transfection of individual crRNAs and Cascade with CasE-p300 compared to dCas9-p300. All samples processed at 3 days post-transfection. (Tukey-test, *P<0.05 compared to Ctrl crRNA, n=3 biological replicates; error bars, SEM). TSS, transcription start site; Ctrl crRNA, Control crRNA.

FIG. 8A shows a schematic of the IL1RN locus along with IL1RN crRNA and gRNA target sites. FIG. 8B shows relative IL1RN expression following co-transfection of individual crRNAs, Cascade with CasE-p300, dCas9 (no effector), and individual gRNAs, where indicated. All samples processed at 3 days post transfection. (Tukey-test following logarithmic transformation, **P<0.001 compared to Cascade-p300 with Ctrl crRNA, ††T<0.001 compared to Cascade-p300 with cr19, n=3 biological replicates; error bars, SEM). TSS, transcription start site; Ctrl crRNA, Control crRNA.

FIG. 9A shows a schematic representation of *E. coli* K-12 processed crRNA with 5' PAM recognition and base pairing at the DNA target loci. FIG. 9B shows engineering of pre-processed crRNA driven by U6 promoter for expression and processing in mammalian cells. FIG. 9C shows illustration of pAPcrRNA cloning plasmid digested with SacII and XhoI. To insert repeat-spacer pairs, forward and reverse oligonucleotides encoding the palindromic repeat and crRNA spacers were synthesized. Annealed oligonucleotide pairs can be annealed, 5' phosphorylated with PNK and ligated into digested pAPcrRNA. Oligo, oligonucleotide. FIG. 9D shows an updated schematic representation of processed crRNA with 5' PAM recognition (spacer sequence is between the arrows with repeat fragments on the other side of the arrows for the crRNA) and base pairing at the DNA target site.

FIG. 10A shows a schematic of the IL1RN and HBG loci along with IL1RN and HBG crRNA target sites. FIG. 10B shows relative IL1RN and HBG expression following co-transfection of individual crRNAs or crRNA arrays and EcoCascade with CasE-p300. All samples processed at 3 days post-transfection. (Tukey-test, **P<0.001 compared to Ctrl crRNA, n=3 biological replicates; error bars, SEM). Numbers above bars indicate mean relative expression. TSS, transcription start site; Ctrl crRNA, Control crRNA.

FIG. 11A shows MA plot for ChIP-seq differential binding of Flag-tagged EcoCascade-p300 targeted to the IL1RN promoter with cr26 compared with binding of EcoCascade-p300 targeted to the IL1RN promoter with cr25 in HEK293T cells. Dark Grey data points indicate FDR<0.001 by differential DESeq2 analysis. FIG. 11B shows MA plot for the differential expression of EcoCascade-p300 targeted by cr26 versus EcoCascade targeted by cr26 in HEK293T cells. Dark Grey data points indicate FDR<0.01 by differential expression analysis. (n=3 biological replicates).

FIG. 12 shows the protospacers targeted by the CRISPR spacers of *L. monocytogenes* Finland 1998 (CRISPR subtype I-B) and a predicted PAM ("CCA"). The sequences of Spacer-CRISPR 3-1 (SEQ ID NO: 230), 8-1 (SEQ ID NO: 231), 9-2 (SEQ ID NO: 232), 25-2 (SEQ ID NO: 233), 27-2 (SEQ ID NO: 234), 44-2 (SEQ ID NO: 235), 45-2 (SEQ ID NO: 236), and 49-2 (SEQ ID NO: 237) are shown.

FIG. 13 shows a schematic of the LmoCascade complex and gene.

FIG. 14A shows a schematic of an embodiment forward strand (SEQ ID NO: 244) and reverse strand (SEQ ID NO: 245) of the target site with the crRNA (SEQ ID NO: 246). FIG. 14B shows a schematic of the vector design. FIG. 14C shows a schematic of an embodiment vector design of the crRNA containing plasmid with the Forward crRNA Oligo (SEQ ID NO: 248) and Reverse crRNA Oligo (SEQ ID NO: 249) shown within the partial sequences of the forward strand (SEQ ID NO: 250) and reverse strand (SEQ ID NO: 251) of the plasmid.

FIG. 22A shows a schematic of the HBG loci along with HBG crRNA target sites. FIG. 22B shows relative HBG expression following co-transfection of individual crRNAs or crRNA arrays and LmoCascade with Cas6-p300. All samples processed at 3 days post-transfection. (Tukey-test, **P<0.001 compared to Ctrl crRNA, *P<0.05 compared to Ctrl crRNA n=3 biological replicates; error bars, SEM). Numbers above bars indicate mean relative expression. TSS, transcription start site; Ctrl crRNA, Control crRNA.

FIG. 25A is a schematic of lentiviral construct for Type I-B LmoCascade crRNA expression. These constructs include eGFP-2A-Puro sequence to select for transduced cells for Puromycin resistance. FIG. 25B is an exemplary oligo sequence design used to clone crRNA library into lentiviral vector using NheI and AgeI restriction enzyme sites.

FIG. 26A shows endogenous HBE1 promoter tiling for targeting LmoCascade with Cas6-KRAB to repress HBE1 expression in human K562 cells. FIG. 26B shows LmoCascade expression in human K562 single cell clones following Blasticidin selection. These cells also contain an endogenous HBE-2A-mcherry reporter. Clone 2 was expanded for LmoCascade studies. FIG. 26C shows repression of mCherry mean fluorescence intensity (MFI) by flow cytometry in human K562s with endogenous HBE-2A-mcherry reporter and stable expression of LmoCascade-KRAB (clone 2 from previous slide). Cells were transduced with individual crRNA expressing lentiviruses in triplicate. Flow cytometry analysis was completed 6 days post transduction. FIG. 26D shows representative histogram plots. FIG. 26E shows repression of endogenous HBE expression in human K562s with endogenous HBE-2A-mcherry reporter and stable expression of LmoCascade-KRAB (clone 2 from previous slide). Cells were transduced with individual crRNA expressing lentiviruses in triplicate. RT-qPCR analysis was completed 6 days post transduction. **P<0.001, compared to Ctrl crRNA; *P<0.05, compared to Ctrl crRNA (Excluding cr04 from analysis).

FIG. 28B shows TeVI-Cas6 expression following codon optimization in human HEK293T cells. FIG. 28C shows TeVI-Cas6-mediated LmoCascade editing percentages via deep sequencing analysis of human HEK29T cells co-transfected with TeVI-LmoCascade and individual crRNAs targeting endogenous IL1RN promoter. FIG. 28D shows schematic of predicted editing motifs of TeVI-LmoCascade targeted to endogenous IL1RN promoter with cr14 spacer.

DETAILED DESCRIPTION

CRISPR/CAS Systems

Figure 1A:
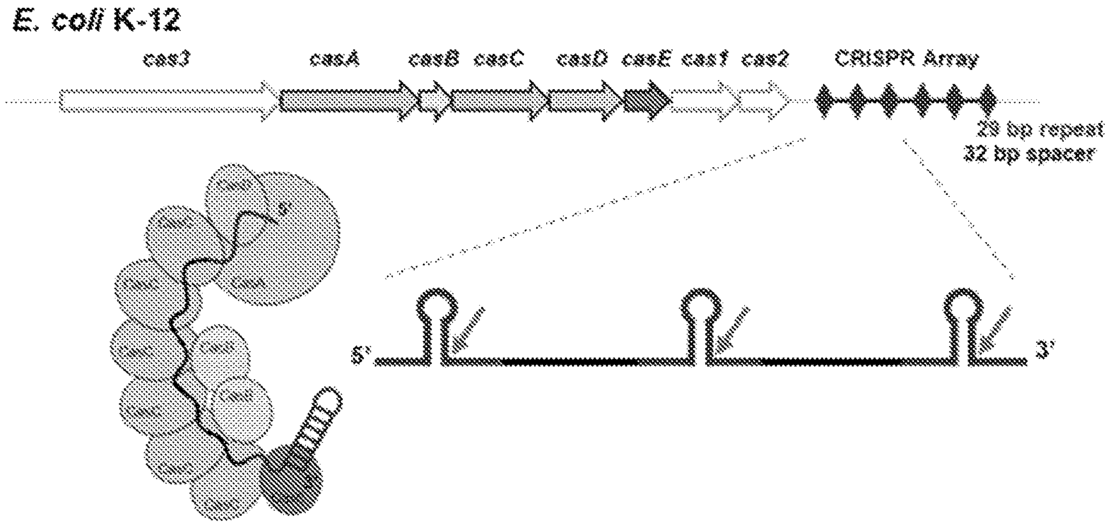
FIG. 1A-FIG. 1G show Type I-E Cascade expression and complex formation in human cells.

CRISPR-Cas systems are naturally adaptive immune systems found in bacteria and archaea. The CRISPR system is a nuclease system involved in defense against invading phages and plasmids that provides a form of acquired immunity. There is a diversity of CRISPR-Cas systems based on the set of cas genes and their phylogenetic relationship. There are at least six different types (I through VI) where Type I represents over 50% of all identified systems in both bacteria and archaea. In some embodiments, a Type I, Type II, Type II, Type IV, Type V, or Type VI CRISPR-Cas system is used herein. In some embodiments, the methods and compositions disclosed herein can be used with type I-A, I-B, I-C, I-D, I-E, or I-F systems.

With regard to Type I systems, Type I systems are divided into seven subtypes including: type I-A, type I-B, type I-C, type I-D, type I-E, type I-F, and type I-U. Type I CRISPR-Cas systems include a multi-subunit complex called Cascade (for complex associated with antiviral defense), Cas3 (a protein with nuclease, helicase, and exonuclease activity that is responsible for degradation of the target DNA), and crRNA (stabilizes Cascade complex and directs Cascade and Cas3 to DNA target). Cascade forms a complex with the crRNA, and the protein-RNA pair recognizes its genomic target by complementary base pairing between the 5' end of the crRNA sequence and a predefined protospacer. This complex is directed to homologous loci of pathogen DNA via regions encoded within the crRNA and protospacer-adjacent motifs (PAMs) within the pathogen genome. Base pairing occurs between the crRNA and the target DNA sequence leading to a conformational change. In the Type I-E system, the PAM is recognized by the CasA protein within Cascade, which then unwinds the flanking DNA to evaluate the extent of base pairing between the target and the spacer portion of the crRNA. Sufficient recognition leads Cascade to recruit and activate Cas3. Cas3 then nicks the non-target strand and begins degrading the strand in a 3'-to-5' direction.

In some embodiments, a type-I Cascade polypeptide disclosed herein have an amino acid sequence having substantial identity to a wild-type type-I Cascade polypeptide. In some embodiments, a Cascade polypeptide described herein is a functional fragment of any full length type-1 Cascade polypeptides. In some embodiments, the type I Cascade complex comprises type I-A Cascade polypeptides, type I-B Cascade polypeptides, type I-C Cascade polypeptides, type I-D Cascade polypeptides, type I-E Cascade polypeptides, type I-F Cascade polypeptides, or type I-U Cascade polypeptides.

In some embodiments, the type I Cascade complex comprises: (a) a nucleotide sequence encoding a Cas6b polypeptide, a nucleotide sequence encoding a Cas8b (Csh1) polypeptide, a nucleotide sequence encoding a Cas7 (Csh2) polypeptide, and a nucleotide sequence encoding a Cas5 polypeptide (Type 1-B); (b) a nucleotide sequence encoding a Cas5d polypeptide, a nucleotide sequence encoding a Cas8c (Csd1) polypeptide, and a nucleotide sequence encoding a Cas7 (Csd2) polypeptide (Type I-C); (c) a nucleotide sequence encoding a Cse1 (CasA) polypeptide, a nucleotide sequence encoding a Cse2 (CasB) polypeptide, a nucleotide sequence encoding a Cas7 (CasC) polypeptide, a nucleotide sequence encoding a Cas5 (CasD) polypeptide, and a nucleotide sequence encoding a Cas6e (CasE) polypeptide (Type 1-E); (d) a nucleotide sequence encoding a Cys1 polypeptide, a nucleotide sequence encoding a Cys2 polypeptide, a nucleotide sequence encoding a Cas7 (Cys3) polypeptide, and a nucleotide sequence encoding a Cas6f polypeptide (Type 1-F); (e) a nucleotide sequence encoding a Cas7 (Csa2) polypeptide, a nucleotide sequence encoding a Cas8a1 (Csx13) polypeptide or a Cas8a2 (Csx9) polypeptide, a nucleotide sequence encoding a Cas5 polypeptide, a nucleotide sequence encoding a Csa5 polypeptide, a nucleotide sequence encoding a Cas6a polypeptide, a nucleotide sequence encoding a Cas3' polypeptide, and a nucleotide sequence encoding a Cas3" polypeptide having no nuclease activity (Type I-A); and/or (f) a nucleotide sequence encoding a Cas1 Od (Csc3) polypeptide, a nucleotide sequence encoding a Csc2 polypeptide, a nucleotide sequence encoding a Csc1 polypeptide, and a nucleotide sequence encoding a Cas6d polypeptide (Type I-D).

As described herein, certain engineered Type I-E CRISPR/CRISPR-associated (Cas) transcriptional activation system compositions have been discovered to be useful for use as programmable transcriptional activators in eukaryotic cells and altering the expression of target genes. Targeted transcriptional modulation is important for perturbing gene function, designing gene regulatory networks, investigating the function of distal regulatory elements, manipulating cellular and organismal phenotypes, and inducing therapeutic changes to gene expression. Modifications of Type I-E systems provides a novel and modular RNA-guided platform for targeting DNA sequences in eukaryotes with certain advantages over Type II, such as greater specificity, processing crRNA arrays by Cascade for multiplexing, and multiplexing effector domains on the different Cascade subunits. The disclosed Type I-E CRISPR-based programmable transcriptional activation (Type I-E CRISPRa) systems provide DNA-targeting and gene regulation using a class I-E CRISPR system. The disclosed Type I-E CRISPRa systems involve the Type I-E Cascade complex (a multimeric complex consisting of three to five proteins that processes crRNA arrays), a Cascade fusion protein, and at least one crRNA.

As disclosed herein, certain engineered Type I-B CRISPR/CRISPR-associated (Cas) based programmable systems have been discovered for DNA-targeting and gene expression modification and/or gene editing. Modifications of Type I-B systems provides a novel and modular RNA-guided platform for targeting DNA sequences in cells, such as eukaryotic cells, with certain advantages over Type II CRISPR systems, such as greater specificity, processing crRNA arrays by Cascade for multiplexing, and multiplexing effector domains on the different Cascade subunits. Tethering functional domains to one or more components of Cascade allows specific DNA targeting to modify a gene target or modulate the expression of a gene target. For example, Type I-B CRISPR Cascade systems can be reprogrammed for RNA-guided transcriptional activation in cells, such as eukaryotic cells.

The disclosed Type I-B CRISPR-based programmable systems provide DNA-targeting and genome engineering using a newly discovered Type I-B CRISPR system from *Listeria monocytogenes*. The disclosed Type I-B CRISPR-based programmable systems involve the Type I-B Cascade complex (a multimeric complex consisting of three to four proteins that processes crRNA arrays), a Cascade polypeptide fusion protein, and at least one crRNA. Specifically, the effector complex from a *Listeria monocytogenes* Type I-B CRISPR/Cas system was repurposed and tethered to a functional domain, such as a transactivation domain. The effector complex targets DNA via a multi-component RNA-guided complex termed Cascade. In the Type I-B system, the PAM is recognized by the Cas8 protein within Cascade, which then unwinds the flanking DNA to evaluate the extent of base pairing between the target and the spacer portion of the crRNA. For example, in the *L. monocytogenes* Finland_1998 Type I-B CRISPR/Cas system, Cas8b2 recognizes the PAM.

Disclosed herein is a *L. monocytogenes* Type I-B CRISPR-based programmable transcriptional activation (Type I-B CRISPRa) system that has been discovered to provide DNA-targeting and transcriptional control of a target gene. By tethering a transactivation domain to Cascade to generate the Type I-B CRISPR-based programmable transcriptional activation system, the expression of targeted chromosomal genes in cells, such as eukaryotic cells, can be modulated and/or induced. For example, the tethering of transactivation domains to Cas5, Cas6, Cas7, or Cas8b2 polypeptides from the *L. monocytogenes* Type I-B CRISPR system produced fusion proteins that were surprisingly able to activated target genes. In addition, fusions containing the Cas5 polypeptide, Cas6 polypeptide, or Cas8b2 polypeptide showed unexpectedly greater activation of genes compared to fusions containing the Cas7 polypeptide. The disclosed Type I-B CRISPR-based programmable transcriptional activation systems are useful as programmable transcriptional activators in cells, such as eukaryotic cells, and altering the expression of target genes. Targeted transcriptional modulation is important for perturbing gene function, designing gene regulatory networks, investigating the function of distal regulatory elements, manipulating cellular and organismal phenotypes, and inducing therapeutic changes to gene expression.

The present disclosure expands the toolbox for engineering eukaryotic genomes and establishes Cascade as a novel Type I CRISPR-based technology for targeted gene regulation. The Type I-E CRISPR Cascade systems can be reprogrammed for RNA-guided transcriptional activation in eukaryotic cells, such as mammalian cells. The Type I variants of class I CRISPR systems are the most prevalent CRISPR loci in nature and target DNA via a multi-component RNA-guided complex termed Cascade. By tethering transactivation domains to Cascade, the expression of targeted endogenous genes can be induced in eukaryotic cells, such as human cells. For example, the tethering of transactivation domains to CasA or CasE polypeptides from the *E. coli* Type I-E CRISPR system showed unexpectedly greater activation of genes compared to CasB, CasC, or CasD polypeptides.

This new class of genome engineering tools has potential benefits that can add to the CRISPR engineering toolbox. For example, the promiscuous PAM recognition of Type I Cascade, located 5' of the spacer in contrast to the 3' PAM of Type II systems, enables a larger set of available CRISPR target sequences. The natural function of Cascade to process crRNAs suggests the possibility of using arrayed spacers for multiplexed genome engineering. Additionally, the preservation of complex formation observed after effector tethering suggests opportunities to utilize the Cascade complex stoichiometry for exploring synergistic activities of multiple effector domains.

The present disclosure now will be described hereinafter with reference to the accompanying drawings and examples, in which embodiments of the disclosure are shown. This description is not intended to be a detailed catalog of all the different ways in which the disclosure can be implemented, or all the features that can be added to the instant disclosure. For example, features illustrated with respect to one embodiment can be incorporated into other embodiments, and features illustrated with respect to a particular embodiment can be deleted from that embodiment. Thus, the disclosure contemplates that in some embodiments of the disclosure, any feature or combination of features set forth herein can be excluded or omitted. In addition, numerous variations and additions to the various embodiments suggested herein will be apparent to those skilled in the art in light of the instant disclosure, which do not depart from the instant disclosure. Hence, the following descriptions are intended to illustrate some particular embodiments of the disclosure, and not to exhaustively specify all permutations, combinations and variations thereof.

Unless the context indicates otherwise, it is specifically intended that the various features of the disclosure described herein can be used in any combination. Moreover, the present disclosure also contemplates that in some embodiments of the disclosure, any feature or combination of features set forth herein can be excluded or omitted. To illustrate, if the specification states that a composition comprises components A, B and C, it is specifically intended that any of A, B or C, or a combination thereof, can be omitted and disclaimed singularly or in any combination.

Definitions

The terms “comprise(s),” “include(s),” “having,” “has,” “can,” “contain(s),” and variants thereof, as used herein, are intended to be open-ended transitional phrases, terms, or words that do not preclude the possibility of additional acts or structures. The singular forms “a,” “an” and “the” include plural references unless the context clearly dictates otherwise. The present disclosure also contemplates other embodiments “comprising,” “consisting of” and “consisting essentially of,” the embodiments or elements presented herein, whether explicitly set forth or not.

Also as used herein, “and/or” refers to and encompasses any and all possible combinations of one or more of the associated listed items, as well as the lack of combinations when interpreted in the alternative (“or”).

The term “about,” as used herein when referring to a measurable value such as a dosage or time period and the like refers to variations of ±20%, ±10%, ±5%, ±1%, ±0.5%, or even ±0.1% of the specified amount.

As used herein, phrases such as “between X and Y” and “between about X and Y” should be interpreted to include X and Y. As used herein, phrases such as “between about X and Y” mean “between about X and about Y” and phrases such as “from about X to Y” mean “from about X to about Y.”

As used herein, the transitional phrase “consisting essentially of” means that the scope of a claim is to be interpreted to encompass the specified materials or steps recited in the claim and those that do not materially affect the basic and novel characteristic(s) of the claimed invention. Thus, the term “consisting essentially of” when used in a claim of this invention is not intended to be interpreted to be equivalent to “comprising.”

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

“Adeno-associated virus” or “AAV” as used interchangeably herein refers to a small virus belonging to the genus Dependovirus of the Parvoviridae family that infects humans and some other primate species. AAV is not currently known to cause disease and consequently the virus causes a very mild immune response.

“Binding region” as used herein refers to the region within a target nucleotide sequence that is recognized and bound by the Cascade.

As used herein, “chimeric” can refer to a nucleic acid molecule and/or a polypeptide in which at least two components are derived from different sources (e.g., different organisms, different coding regions). Also as used herein, chimeric refers to a construct comprising a polypeptide linked to a nucleic acid.

"Clustered Regularly Interspaced Short Palindromic Repeats" and "CRISPRs", as used interchangeably herein refers to loci containing multiple short direct repeats that are found in the genomes of approximately 40% of sequenced bacteria and 90% of sequenced archaea.

"Coding sequence" or "encoding nucleic acid" as used herein means the nucleic acids (RNA or DNA molecule) that comprise a nucleotide sequence which encodes a protein. The coding sequence can further include initiation and termination signals operably linked to regulatory elements including a promoter and polyadenylation signal capable of directing expression in the cells of an individual or mammal to which the nucleic acid is administered. The coding sequence can be codon optimized.

"Complement" or "complementary" as used herein means a nucleic acid can mean Watson-Crick (e.g., A-T/U and C-G) or Hoogsteen base pairing between nucleotides or nucleotide analogs of nucleic acid molecules. "Complementarity" refers to a property shared between two nucleic acid sequences, such that when they are aligned antiparallel to each other, the nucleotide bases at each position will be complementary. "Complement" as used herein can mean 100% complementarity (fully complementary) with the comparator nucleotide sequence or it can mean less than 100% complementarity (e.g., substantial complementarity) (e.g., about 80%, 81%, 82%, 83%, 84%, 85%, 86%, 87%, 88%, 89%, 90%, 91%, 92%, 93%, 94%, 95%, 96%, 97%, 98%, 99%, and the like, complementarity). Complement can also be used in terms of a "complement" to or "complementing" a mutation. The terms "complementary" or "complementarity," as used herein, refer to the natural binding of polynucleotides under permissive salt and temperature conditions by base-pairing. For example, the sequence "5'-A-G-T-3" binds to the complementary sequence "5'-A-C-T-3'." Complementarity between two single-stranded molecules can be "partial," in which only some of the nucleotides bind, or it can be complete when total complementarity exists between the single stranded molecules. The degree of complementarity between nucleic acid strands has significant effects on the efficiency and strength of hybridization between nucleic acid strands.

"Concurrently" means sufficiently close in time to produce a combined effect (that is, concurrently can be simultaneously, or it can be two or more events occurring within a short time period before or after each other). In some embodiments, the administration of two or more compounds "concurrently" means that the two compounds are administered closely enough in time that the presence of one alters the biological effects of the other. The two compounds can be administered in the same or different formulations or sequentially. Concurrent administration can be carried out by mixing the compounds prior to administration, or by administering the compounds in two different formulations, for example, at the same point in time but at different anatomic sites or using different routes of administration.

A "CRISPR RNA," "crRNA," or "CRISPR array" as used interchangeably herein refers to a nucleic acid molecule that comprises at least two repeat nucleotide sequences, or portions thereof, and at least one spacer sequence, wherein one of the two repeat nucleotide sequences, or a portion thereof, is linked to the 5' end of the spacer nucleotide sequence and the other of the two repeat nucleotide sequences, or portion thereof, is linked to the 3' end of the spacer nucleotide sequence. In a recombinant CRISPR array, the combination of repeat nucleotide sequences and spacer nucleotide sequences is synthetic, made by man and not found in nature.

As used herein, the terms "eliminate," "eliminated," and/or "eliminating" refer to complete cessation of the specified activity.

"Eukaryotic" or "eukaryotes" as used interchangeably herein refers to any organism whose cells contain a nucleus and other organelles enclosed within membranes. Eukaryotes have membrane-bound organelles, especially the nucleus, which contains the genetic material, and is enclosed by the nuclear envelope. Examples of eukaryotes include, but are not limited to, an animal, a mammal, an insect, a plant, a fungus, an insect, a bird, a fish, an amphibian, a reptile, or a cnidarian. In additional embodiments, a mammal can include, but is not limited to, a rodent, a horse, a dog a cat, a human, a non-human primate (e.g., monkeys, baboons, and chimpanzees), a goat, a pig, a cow (e.g., cattle), a sheep, laboratory animals (e.g., rats, mice, gerbils, hamsters, and the like) and the like. Non-limiting examples of birds useful with this disclosure include chickens, ducks, turkeys, geese, quails and birds kept as pets (e.g., parakeets, parrots, macaws, and the like). Additional embodiments can include, for example, mammalian and insect cell lines. Non-limiting examples of mammalian and insect cell lines include HEK293T cells, HeLa cells, CHO cells, MEF cells, 3T3 cells, Hi-5 cells, and Sf21 cells.

"Expression cassette" as used herein refers to a recombinant nucleic acid molecule comprising one or more polynucleotide sequence of interest (e.g., a polynucleotide sequence encoding the Type I-E CRISPRa system, or subcomponents thereof), wherein said recombinant nucleotide sequence is operably associated with at least a control sequence (e.g., a promoter). Thus, some aspects of the disclosure provide expression cassettes designed to express the nucleotides sequences of the disclosure. An expression cassette comprising a nucleotide sequence of interest can be chimeric, meaning that at least one of its components is heterologous with respect to at least one of its other components. An expression cassette can also be one that is naturally occurring but has been obtained in a recombinant form useful for heterologous expression.

As used herein, an extrachromosomal element means a double stranded nucleic acid element that is residing in a eukaryotic cell and is not integrated into any of the eukaryotic cell's chromosomes.

A "fragment" or "portion" of a nucleotide sequence will be understood to mean a nucleotide sequence of reduced length relative (e.g., reduced by 1, 2, 3, 4, 5, 6, 7, 8, 9, 10, 11, 12, 13, 14, 15, 16, 17, 18, 19, 20 or more nucleotides) to a reference nucleic acid or nucleotide sequence and comprising, consisting essentially of and/or consisting of a nucleotide sequence of contiguous nucleotides identical or almost identical (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identical) to the reference nucleic acid or nucleotide sequence. Such a nucleic acid fragment or portion according to the disclosure can be, where appropriate, included in a larger polynucleotide of which it is a constituent. In some embodiments, a fragment of a polynucleotide can be a functional fragment that encodes a polypeptide that retains its function (e.g., a fragment of a Cascade fusion protein, such as a fragment of a CasA fusion or CasE fusion protein, retains one or more of the activities of a full length CasA fusion or CasE fusion protein).

"Functional" and "full-functional" as used herein describes protein that has biological activity. A "functional gene" refers to a gene transcribed to mRNA, which is translated to a functional protein.

"Fusion protein" as used herein refers to a chimeric protein created through the joining of two or more genes that originally coded for separate proteins. The translation of the fusion gene results in a single polypeptide with functional properties derived from each of the original proteins.

As used herein, the term "gene" refers to a nucleic acid molecule capable of being used to produce mRNA, tRNA, rRNA, miRNA, anti-microRNA, regulatory RNA, and the like. Genes may or may not be capable of being used to produce a functional protein or gene product. Genes can include both coding and non-coding regions (e.g., introns, regulatory elements, promoters, enhancers, termination sequences and/or 5' and 3' untranslated regions). A gene can be "isolated" by which is meant a nucleic acid that is substantially or essentially free from components normally found in association with the nucleic acid in its natural state. Such components include other cellular material, culture medium from recombinant production, and/or various chemicals used in chemically synthesizing the nucleic acid.

"Genetic construct" as used herein refers to the DNA or RNA molecules that comprise a nucleotide sequence that encodes a protein. The coding sequence includes initiation and termination signals operably linked to regulatory elements including a promoter and polyadenylation signal capable of directing expression in the cells of the individual to whom the nucleic acid molecule is administered. As used herein, the term "expressible form" refers to gene constructs that contain the necessary regulatory elements operable linked to a coding sequence that encodes a protein such that when present in the cell of the individual, the coding sequence will be expressed.

"Genetic disease" as used herein refers to a disease, partially or completely, directly or indirectly, caused by one or more abnormalities in the genome, especially a condition that is present from birth. The abnormality can be a mutation, an insertion or a deletion. The abnormality can affect the coding sequence of the gene or its regulatory sequence. The genetic disease can be, but is not limited to DMD, hemophilia, cystic fibrosis, Huntington's chorea, familial hypercholesterolemia (LDL receptor defect), hepatoblastoma, Wilson's disease, congenital hepatic porphyria, inherited disorders of hepatic metabolism, Lesch Nyhan syndrome, sickle cell anemia, thalassaemias, xeroderma pigmentosum, Fanconi's anemia, retinitis pigmentosa, ataxia telangiectasia, Bloom's syndrome, retinoblastoma, and Tay-Sachs disease.

The term "genome" as used herein includes an organism's chromosomal/nuclear genome as well as any mitochondrial, and/or plasmid genome.

As used herein, hybridization, hybridize, hybridizing, and grammatical variations thereof, refer to the binding of two complementary nucleotide sequences or substantially complementary sequences in which some mismatched base pairs are present. The conditions for hybridization are well known in the art and vary based on the length of the nucleotide sequences and the degree of complementarity between the nucleotide sequences. In some embodiments, the conditions of hybridization can be high stringency, or they can be medium stringency or low stringency depending on the amount of complementarity and the length of the sequences to be hybridized. The conditions that constitute low, medium and high stringency for purposes of hybridization between nucleotide sequences are well known in the art (See, e.g., Gasiunas et al. (2012) *Proc. Natl. Acad. Sci.* 109:E2579-E2586; M. R. Green and J. Sambrook (2012) Molecular Cloning: A Laboratory Manual. 4th Ed., Cold Spring Harbor Laboratory Press, Cold Spring Harbor, NY).

A "hairpin sequence" as used herein refers to a nucleotide sequence comprising hairpins (e.g., that forms one or more hairpin structures). A hairpin (e.g., stem-loop, fold-back) refers to a nucleic acid molecule having a secondary structure that includes a region of nucleotides that form a single strand that are further flanked on either side by a double stranded-region. Such structures are well known in the art. As known in the art, the double stranded region can comprise some mismatches in base pairing or can be perfectly complementary. In some embodiments, a repeat nucleotide sequence comprises, consists essentially of, consists of a hairpin sequence that is located within said repeat nucleotide sequence (i.e., at least one nucleotide (e.g., one, two, three, four, five, six, seven, eight, nine, ten, or more) of the repeat nucleotide sequence is present on either side of the hairpin that is within said repeat nucleotide sequence). In some embodiments, a repeat sequence comprises a hairpin sequence.

A "heterologous" or a "recombinant" nucleotide sequence as used interchangeably herein refers to a nucleotide sequence not naturally associated with a host cell into which it is introduced, including non-naturally occurring multiple copies of a naturally occurring nucleotide sequence.

Different nucleic acids or proteins having homology are referred to herein as "homologues." The term homologue includes homologous sequences from the same and other species and orthologous sequences from the same and other species. "Homology" refers to the level of similarity between two or more nucleic acid and/or amino acid sequences in terms of percent of positional identity (i.e., sequence similarity or identity). Homology also refers to the concept of similar functional properties among different nucleic acids or proteins. Thus, the compositions and methods of the disclosure further comprise homologues to the nucleotide sequences and polypeptide sequences of this disclosure. "Orthologous," as used herein, refers to homologous nucleotide sequences and/or amino acid sequences in different species that arose from a common ancestral gene during speciation. A homologue of a nucleotide sequence or polypeptide of this disclosure has a substantial sequence identity (e.g., at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, and/or 100%) to the nucleotide sequence or polypeptide of the disclosure. Thus, for example, a homologue of a CRISPR array repeat sequence, a Type I-E Cascade polypeptide/polynucleotide and the like, can be about 70% homologous or more to any known CRISPR array repeat sequence or Type I-E Cascade polypeptide/polynucleotide, respectively. For example, a homologue of a polynucleotide sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, or SEQ ID NO: 163 has a substantial sequence identity (e.g., at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, and/or 100%) to SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, or SEQ ID NO: 163, respectively. Also, for example, a homologue of a CRISPR array repeat sequence, a Type I-B Cascade polypeptide/polynucleotide and the like, can be about 70% homologous or more to any known CRISPR array repeat sequence or Type I-B Cascade polypeptide/polynucleotide, respectively. For example, a homologue of a polynucleotide sequence of SEQ ID NO: 166, SEQ ID NO: 167, SEQ ID NO: 168, SEQ ID NO: 169, SEQ ID NO: 171; SEQ ID NO: 172, SEQ ID NO: 173, SEQ ID NO: 174, SEQ ID NO: 179, SEQ ID NO: 258; SEQ ID NO: 259, SEQ ID NO: 260, or SEQ ID NO: 261, has a substantial sequence identity (e.g., at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, and/or 100%) to SEQ ID NO: 166, SEQ ID NO: 167, SEQ ID NO: 168, SEQ ID NO: 169, SEQ ID NO: 171; SEQ ID NO: 172, SEQ ID NO: 173, SEQ ID NO: 174, SEQ ID NO: 179, SEQ ID NO: 258; SEQ ID NO: 259, SEQ ID NO: 260, or SEQ ID NO: 261, respectively. For example, a homologue of a polypeptide or amino acid sequence of SEQ ID NO: 175; SEQ ID NO: 176, SEQ ID NO: 177, or SEQ ID NO: 178, has a substantial sequence identity (e.g., at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, and/or 100%) to SEQ ID NO: 175, SEQ ID NO: 176, SEQ ID NO: 177, or SEQ ID NO: 178, respectively. Also, for example, a homologue of a polynucleotide sequence of SEQ ID NO: 282, SEQ ID NO: 283, SEQ ID NO: 284, SEQ ID NO: 285, SEQ ID NO: 286; SEQ ID NO: 287, SEQ ID NO: 288, SEQ ID NO: 289, SEQ ID NO: 290, SEQ ID NO: 291; SEQ ID NO: 292, SEQ ID NO: 293, SEQ ID NO: 294, SEQ ID NO: 295, SEQ ID NO: 296, or SEQ ID NO: 297, has a substantial sequence identity (e.g., at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, and/or 100%) to SEQ ID NO: 282, SEQ ID NO: 283, SEQ ID NO: 284, SEQ ID NO: 285, SEQ ID NO: 286; SEQ ID NO: 287, SEQ ID NO: 288, SEQ ID NO: 289, SEQ ID NO: 290, SEQ ID NO: 291; SEQ ID NO: 292, SEQ ID NO: 293, SEQ ID NO: 294, SEQ ID NO: 295, SEQ ID NO: 296, or SEQ ID NO: 297, respectively.

"Identical" or "identity" as used herein in the context of two or more nucleic acids or polypeptide sequences means that the sequences have a specified percentage of residues that are the same over a specified region. The percentage can be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of single sequence are included in the denominator but not the numerator of the calculation. When comparing DNA and RNA, thymine (T) and uracil (U) can be considered equivalent. Identity can be performed manually or by using a computer sequence algorithm such as BLAST or BLAST 2.0.

As used herein, the terms "increase," "increasing," "increased," "enhance," "enhanced," "enhancing," and "enhancement" (and grammatical variations thereof) describe an elevation of at least about 25%, 50%, 75%, 100%, 150%, 200%, 300%, 400%, 500% or more as compared to a control.

An "isolated" polynucleotide or an "isolated" polypeptide is a nucleotide sequence or polypeptide sequence that, by the hand of man, exists apart from its native environment and is therefore not a product of nature. In some embodiments, the polynucleotides and polypeptides of the disclosure are "isolated." An isolated polynucleotide or polypeptide can exist in a purified form that is at least partially separated from at least some of the other components of the naturally occurring organism or virus, for example, the cell or viral structural components or other polypeptides or polynucleotides commonly found associated with the polypeptide or polynucleotide. In representative embodiments, the isolated polynucleotide and/or the isolated polypeptide is at least about 1%, 5%, 10%, 20%, 30%, 40%, 50%, 60%, 70%, 80%, 90%, 95%, or more pure.

In other embodiments, an isolated polynucleotide or polypeptide can exist in a non-native environment such as, for example, a recombinant host cell. Thus, for example, with respect to nucleotide sequences, the term "isolated" means that it is separated from the chromosome and/or cell in which it naturally occurs. A polynucleotide is also isolated if it is separated from the chromosome and/or cell in which it naturally occurs in and is then inserted into a genetic context, a chromosome and/or a cell in which it does not naturally occur (e.g., a different host cell, different regulatory sequences, and/or different position in the genome than as found in nature). Accordingly, the polynucleotides and their encoded polypeptides are "isolated" in that, by the hand of man, they exist apart from their native environment and therefore are not products of nature, however, in some embodiments, they can be introduced into and exist in a recombinant host cell.

"Multicistronic" as used herein refers to a polynucleotide possessing more than one coding region to produce more than one protein from the same polynucleotide.

"Mutant gene" or "mutated gene" as used interchangeably herein refers to a gene that has undergone a detectable mutation. A mutant gene has undergone a change, such as the loss, gain, or exchange of genetic material, which affects the normal transmission and expression of the gene.

A "native" or "wild type" nucleic acid, nucleotide sequence, polypeptide or amino acid sequence refers to a naturally occurring or endogenous nucleic acid, nucleotide sequence, polypeptide or amino acid sequence. Thus, for example, a "wild type mRNA" is an mRNA that is naturally occurring in or endogenous to the organism. A "homologous" nucleic acid is a nucleotide sequence naturally associated with a host cell into which it is introduced.

"Normal gene" as used herein refers to a gene that has not undergone a change, such as a loss, gain, or exchange of genetic material. The normal gene undergoes normal gene transmission and gene expression.

"Nucleic acid" or "oligonucleotide" or "polynucleotide" as used herein means at least two nucleotides covalently linked together. The depiction of a single strand also defines the sequence of the complementary strand. Thus, a nucleic acid also encompasses the complementary strand of a depicted single strand. Many variants of a nucleic acid can be used for the same purpose as a given nucleic acid. Thus, a nucleic acid also encompasses substantially identical nucleic acids and complements thereof. A single strand provides a probe that can hybridize to a target sequence under stringent hybridization conditions. Thus, a nucleic acid also encompasses a probe that hybridizes under stringent hybridization conditions.

Nucleic acids can be single stranded or double stranded, or can contain portions of both double stranded and single stranded sequence. The nucleic acid can be DNA, both genomic and cDNA, RNA, or a hybrid, where the nucleic acid can contain combinations of deoxyribo- and ribo-nucleotides, and combinations of bases including uracil, adenine, thymine, cytosine, guanine, inosine, xanthine hypo-xanthine, isocytosine and isoguanine. Nucleic acids can be obtained by chemical synthesis methods or by recombinant methods.

Also as used herein, the terms "nucleic acid," "nucleic acid molecule," "nucleic acid construct," "nucleotide sequence" and "polynucleotide" refer to RNA or DNA that is linear or branched, single or double stranded, or a hybrid thereof. The term also encompasses RNA/DNA hybrids. When dsRNA is produced synthetically, less common bases, such as inosine, 5-methylcytosine, 6-methyladenine, hypo-xanthine and others can also be used for antisense, dsRNA, and ribozyme pairing. For example, polynucleotides that contain C-5 propyne analogues of uridine and cytidine have been shown to bind RNA with high affinity and to be potent antisense inhibitors of gene expression. Other modifications, such as modification to the phosphodiester backbone, or the 2'-hydroxy in the ribose sugar group of the RNA can also be made. The nucleic acid constructs of the present disclosure can be DNA or RNA, but are preferably DNA. Thus, although the nucleic acid constructs of this disclosure can be described and used in the form of DNA, depending on the intended use, they can also be described and used in the form of RNA.

A "synthetic" nucleic acid or polynucleotide, as used herein, refers to a nucleic acid or polynucleotide that is not found in nature but is constructed by the hand of man and as a consequence is not a product of nature.

A "nuclear localization signal," "nuclear localization sequence," or "NLS" as used interchangeably herein refers to an amino acid sequence that "tags" a protein for import into the cell nucleus by nuclear transport. Typically, this signal consists of one or more short sequences of positively charged lysines or arginines exposed on the protein surface. Different nuclear localized proteins can share the same NLS. An NLS has the opposite function of a nuclear export signal, which targets proteins out of the nucleus.

"Operably linked" or "operably associated" as used interchangeably herein means that the indicated elements, such as polynucleotide sequences on a single nucleic acid molecule, are functionally related to each other, and are also generally physically related. Thus, a first nucleotide sequence that is operably linked to a second nucleotide sequence means a situation when the first nucleotide sequence is placed in a functional relationship with the second nucleotide sequence. For instance, a promoter is operably associated with a nucleotide sequence if the promoter effects the transcription or expression of the nucleotide sequence. For example, a gene encoding a protein operably linked to a promoter means that the expression of the gene is under the control of a promoter with which it is spatially connected. A promoter can be positioned 5' (upstream) or 3' (downstream) of a gene under its control. The distance between the promoter and a gene can be approximately the same as the distance between that promoter and the gene it controls in the gene from which the promoter is derived. As is known in the art, variation in this distance can be accommodated without loss of promoter function. Those skilled in the art will appreciate that the control sequences (e.g., promoter) need not be contiguous with the nucleotide sequence to which it is operably associated, as long as the control sequences function to direct the expression thereof. Thus, for example, intervening untranslated, yet transcribed, sequences can be present between a promoter and a nucleotide sequence, and the promoter can still be considered "operably linked" to the nucleotide sequence.

"Partially-functional" as used herein describes a protein that is encoded by a mutant gene and has less biological activity than a functional protein but more than a non-functional protein.

As used herein, the term "percent sequence identity" or "percent identity" refers to the percentage of identical nucleotides in a linear polynucleotide of a reference ("query") polynucleotide molecule (or its complementary strand) as compared to a test ("subject") polynucleotide molecule (or its complementary strand) when the two sequences are optimally aligned. In some embodiments, "percent identity" can refer to the percentage of identical amino acids in an amino acid sequence.

As used herein, the term "polynucleotide" refers to a heteropolymer of nucleotides or the sequence of these nucleotides from the 5' to 3' end of a nucleic acid molecule and includes DNA or RNA molecules, including cDNA, a DNA fragment or portion, genomic DNA, synthetic (e.g., chemically synthesized) DNA, plasmid DNA, mRNA, and anti-sense RNA, any of which can be single stranded or double stranded. The terms "polynucleotide," "nucleotide sequence" "nucleic acid," "nucleic acid molecule," and "oligonucleotide" are also used interchangeably herein to refer to a heteropolymer of nucleotides. Except as otherwise indicated, nucleic acid molecules and/or polynucleotides provided herein are presented herein in the 5' to 3' direction, from left to right and are represented using the standard code for representing the nucleotide characters as set forth in the U.S. sequence rules, 37 CFR §§ 1.821-1.825 and the World Intellectual Property Organization (WIPO) Standard ST.25.

The terms "prevent," "preventing," and "prevention" (and grammatical variations thereof) refer to prevention and/or delay of the onset of an infection, disease, condition and/or a clinical symptom(s) in a subject and/or a reduction in the severity of the onset of the infection, disease, condition and/or clinical symptom(s) relative to what would occur in the absence of carrying out the methods of the disclosure prior to the onset of the disease, disorder and/or clinical symptom(s).

A "prevention effective" amount as used herein is an amount of an at least one polynucleotide or nucleic acid construct and a crRNA or CRISPR array and optionally a template, or a protein-RNA complex of the disclosure that is sufficient to reduce a viral load by at least about 10% to about 100%, and any range or value therein.

"Promoter" as used herein means a synthetic or naturally-derived molecule or nucleotide sequence which is capable of conferring, activating or enhancing expression of a nucleic acid sequence or construct in a cell. A promoter controls or regulates the transcription of a nucleotide sequence (i.e., a coding sequence) that is operably associated with the promoter. Typically, a "promoter" refers to a nucleotide sequence that contains a binding site for RNA polymerase and directs the initiation of transcription. In general, promoters are found 5', or upstream, relative to the start of the coding region of the corresponding coding sequence. The promoter region can comprise other elements that act as regulators of gene expression. These include, but are not limited to, a −35 element consensus sequence and a −10 consensus sequence (Simpson. 1979. *Proc. Natl. Acad. Sci. U.S.A.* 76:3233-3237). A promoter can comprise one or more specific transcriptional regulatory sequences to further enhance expression and/or to alter the spatial expression and/or temporal expression of same. A promoter can also comprise distal enhancer or repressor elements, which can be located as much as several thousand base pairs from the start site of transcription. A promoter can be derived from sources including viral, bacterial, fungal, plants, insects, and animals. Promoters can include, for example, constitutive, inducible, temporally regulated, developmentally regulated, chemically regulated promoters for use in the preparation of recombinant nucleic acid constructs, polynucleotides, expression cassettes and vectors comprising the polynucleotides and recombinant nucleic acid constructs of the disclosure. These various types of promoters are known in the art. A promoter can regulate the expression of a gene component constitutively, or differentially with respect to cell, the tissue or organ in which expression occurs or, with respect to the developmental stage at which expression occurs, or in response to external stimuli such as physiological stresses, pathogens, metal ions, or inducing agents.

A "protospacer sequence" refers to the portion of the target DNA (e.g., or target region in the genome) that is fully or substantially complementary (and hybridizes) to the spacer sequence of the CRISPR arrays. The protospacer sequence in a Type I system is directly flanked at the 3' end by a PAM. A spacer is designed to be complementary to the protospacer.

A "protospacer adjacent motif (PAM)" is a short motif of 2-4 base pairs present immediately 3' to the protospacer.

As used herein, the terms "reduce," "reduced," "reducing," "reduction," "diminish," "suppress," and "decrease" (and grammatical variations thereof), describe, for example, a decrease of at least about 5%, 10%, 15%, 20%, 25%, 35%, 50%, 75%, 80%, 85%, 90%, 95%, 97%, 98%, 99%, or 100% as compared to a control. In particular embodiments, the reduction results in no or essentially no (i.e., an insignificant amount, e.g., less than about 10% or even less than about 5%) detectable activity or amount.

A "repeat sequence" as used herein, refers to, for example, any repeat sequence of a wild-type Type I-E CRISPR-Cas locus or a repeat sequence of a synthetic CRISPR array.

As used herein "sequence identity" refers to the extent to which two optimally aligned polynucleotide or peptide sequences are invariant throughout a window of alignment of components, e.g., nucleotides or amino acids. "Identity" can be readily calculated by known methods including, but not limited to, those described in: *Computational Molecular Biology* (Lesk, A. M., ed.) Oxford University Press, New York (1988); *Biocomputing: Informatics and Genome Projects* (Smith, D. W., ed.) Academic Press, New York (1993); *Computer Analysis of Sequence Data, Part I* (Griffin, A. M., and Griffin, H. G., eds.) Humana Press, New Jersey (1994); *Sequence Analysis in Molecular Biology* (von Heinje, G., ed.) Academic Press (1987); and *Sequence Analysis Primer* (Gribskov, M. and Devereux, J., eds.) Stockton Press, New York (1991).

A "spacer nucleotide sequence" or "spacer sequence" as used interchangeably herein refers to a nucleotide sequence that is complementary to a target nucleotide sequence on a target gene. In some embodiments, a spacer nucleotide sequence of this disclosure can be about 15 nucleotides to about 150 nucleotides in length. In other embodiments, a spacer nucleotide sequence of this disclosure can be about 15 nucleotides to about 100 nucleotides in length (e.g., about 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 nucleotides or more). In some particular embodiments, a spacer nucleotide sequence can be a length of about 8 to about 150 nucleotides, about 8 to about 100 nucleotides, about 8 to about 50 nucleotides, about 8 to about 40 nucleotides, about 8 to about 30 nucleotides, about 8 to about 25 nucleotides, about 8 to about 20 nucleotides, about 10 to about 50 nucleotides, about 10 to about 40, about 10 to about 30, about 10 to about 25, about 10 to about 20, about 15 to about 50, at least about 8, at least about 10, at least about 15, at least about 20, at least about 25, at least about 30, at least about 35, at least about 40, at least about 50, at least about 60, at least about 70, at least about 80, at least about 90, at least about 100, at least about 110, at least about 120, at least about 130, at least about 140, at least about 150 nucleotides in length, or more, and any value or range therein.

"Subject" and "patient" as used herein interchangeably refers to any vertebrate, including, but is not limited to, a mammal (e.g., cow, pig, camel, llama, horse, goat, rabbit, sheep, hamsters, guinea pig, cat, dog, rat, and mouse, a non-human primate (for example, a monkey, such as a cynomolgus or rhesus monkey, chimpanzee, etc.) and a human). In some embodiments, the subject can be a human or a non-human. The subject or patient can be undergoing other forms of treatment. A "subject" of the disclosure includes any eukaryotic organism that has or is susceptible to an infection, disease or condition, for example, cancer or a viral infection. Thus, such a subject can be a mammal, an insect, an amphibian, a reptile, a bird, a fish, a fungus, a plant, or a nematode. Mammalian subjects include but are not limited to humans, non-human primates (e.g., gorilla, monkey, baboon, and chimpanzee, etc.), dogs, cats, goats, horses, pigs, cattle, sheep, and the like, and laboratory animals (e.g., rats, guinea pigs, mice, gerbils, hamsters, and the like). Avian subjects include but are not limited to chickens, ducks, turkeys, geese, quail, pheasants, and birds kept as pets (e.g., parakeets, parrots, macaws, cockatoos, canaries, and the like). Suitable subjects include both males and females and subjects of any age, including embryonic (e.g., in utero or in ovo), infant, juvenile, adolescent, adult and geriatric subjects. In some embodiments, a subject of this disclosure is a human.

A "subject in need" of the methods of the disclosure can be a subject known to have, suspected of having, or having an increased risk of developing an infection, disease, or condition, including secondary infections, caused by, for example, a virus.

A "sub-optimal protospacer sequence" refers to a target DNA to which a spacer is designed, wherein the spacer comprises greater than 50% complementarity and less than 100% complementarity to the protospacer sequence. The reduced complementarity can come from, for example, truncating the spacer sequence at the 5' end by up to about 5 nucleotides, introducing up to 5 mismatches within the non-seed region, or introducing up to 3 mismatches within the seed region.

A "sub-optimal PAM sequence" refers to a PAM sequence that allows DNA recognition but at a rate that is below an optimal PAM. Sub-optimal PAMs are commonly identified when applying high-throughput techniques for PAM elucidation. For instance, a suboptimal PAM for the Type I-E system in *E. coli* is TTTC.

As used herein, the phrase "substantially identical," or "substantial identity" and grammatical variations thereof in the context of two nucleic acid molecules, nucleotide sequences or protein sequences, refers to two or more sequences or subsequences that have at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, and/or 100% nucleotide or amino acid residue identity, when compared and aligned for maximum correspondence, as measured using one of the following sequence comparison algorithms or by visual inspection. In particular embodiments, substantial identity can refer to two or more sequences or subsequences that have at least about 70%, at least about 75%, at least about 80%, at least about 85%, at least about 90%, at least about 95, 96, 96, 97, 98, or 99% identity.

For sequence comparison, typically one sequence acts as a reference sequence to which test sequences are compared. When using a sequence comparison algorithm, test and reference sequences are entered into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

"Target enhancer" as used herein refers to enhancer that is targeted by a crRNA and Type I CRISPR-based programmable system, such as Type I-E CRISPRa system or Type I-B CRISPRa system. The target enhancer can be within the target region.

"Target regulatory element" as used herein refers to a regulatory element that is targeted by a crRNA and Type I CRISPRa system. The target regulatory element can be within the target region.

"Target gene" as used herein refers to any nucleotide sequence encoding a known or putative gene product. For example, the target gene can be a mutated gene or a normal gene involved in a genetic disease.

"Target nucleotide sequence," "target DNA," "target nucleic acid," "target region," or a "target region in the genome" as used interchangeably herein refers to the region of the target gene to which the Type I CRISPRa system is designed to bind and a region of an organism's genome that is fully complementary or substantially complementary (e.g., at least 70% complementary (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more)) to a spacer sequence in a CRISPR array of this disclosure. In some embodiments, a target region can be about 25 to about 100 consecutive nucleotides in length (e.g., about 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 nucleotides, or any value or range therein) which is located immediately 3' to a PAM sequence in the genome of the organism.

The terms "transformation," "transfection," and "transduction" as used interchangeably herein refer to the introduction of a heterologous nucleic acid molecule into a cell. Such introduction into a cell can be stable or transient. Thus, in some embodiments, a host cell or host organism is stably transformed with a polynucleotide of the disclosure. In other embodiments, a host cell or host organism is transiently transformed with a polynucleotide of the disclosure. "Transient transformation" in the context of a polynucleotide means that a polynucleotide is introduced into the cell and does not integrate into the genome of the cell. By "stably introducing" or "stably introduced" in the context of a polynucleotide introduced into a cell is intended that the introduced polynucleotide is stably incorporated into the genome of the cell, and thus the cell is stably transformed with the polynucleotide. "Stable transformation" or "stably transformed" as used herein means that a nucleic acid molecule is introduced into a cell and integrates into the genome of the cell. As such, the integrated nucleic acid molecule is capable of being inherited by the progeny thereof, more particularly, by the progeny of multiple successive generations. "Genome" as used herein also includes the nuclear, the plasmid and the plastid genome, and therefore includes integration of the nucleic acid construct into, for example, the chloroplast or mitochondrial genome. Stable transformation as used herein can also refer to a transgene that is maintained extrachromasomally, for example, as a minichromosome or a plasmid. In some embodiments, the nucleotide sequences, constructs, expression cassettes can be expressed transiently and/or they can be stably incorporated into the genome of the host organism.

"Transgene" as used herein refers to a gene or genetic material containing a gene sequence that has been isolated from one organism and is introduced into a different organism. This non-native segment of DNA can retain the ability to produce RNA or protein in the transgenic organism, or it can alter the normal function of the transgenic organism's genetic code. The introduction of a transgene has the potential to change the phenotype of an organism.

By the terms "treat," "treating," or "treatment," it is intended that the severity of the subject's condition is reduced or at least partially improved or modified and that some alleviation, mitigation or decrease in at least one clinical symptom is achieved, and/or there is a delay in the progression of the disease or condition, and/or delay of the onset of a disease or illness. With respect to an infection, a disease or a condition, the term refers to, e.g., a decrease in the symptoms or other manifestations of the infection, disease or condition. In some embodiments, treatment provides a reduction in symptoms or other manifestations of the infection, disease or condition by at least about 5%, e.g., about 10%, 15%, 20%, 25%, 30%, 35%, 40%, 45%, 50% or more.

The term "Type I-E polypeptide" refers to the polypeptides that make up a Type I-E CRISPR-Cas system. A Type I-E CRISPR-Cas system can comprise, consist essentially of, or consist of a nucleotide sequence encoding a CasA (Cse1) polypeptide, a nucleotide sequence encoding a CasB (Cse2) polypeptide, a nucleotide sequence encoding a CasC (Cas7) polypeptide, a nucleotide sequence encoding a CasD (Cas5) polypeptide, a nucleotide sequence encoding a CasE (Cas6e) polypeptide, and a nucleotide sequence encoding a Cas3 polypeptide. As used herein, "Type I-E polypeptide," "Type I-E CRISPR system polypeptide" or "polypeptides of a Type I-E CRISPR system" refers to any of a Cas3 polypeptide and any one or more of the Type I-E Clustered Regularly Interspaced Short Palindromic Repeats (CRISPR)-associated complex for antiviral defense ("Cascade") polypeptides.

"Type I-E CRISPR-associated complex for antiviral defense" or "Cascade" as used interchangeably herein refers to a complex of polypeptides involved in processing of pre-crRNAs and subsequent binding to the target DNA in Type I-E CRISPR-Cas systems. As used herein, "Type I-E Cascade polypeptides" refers to a complex of polypeptides involved in processing of CRISPR arrays and subsequent binding to the target DNA in Type I-E CRISPR-Cas systems. These polypeptides include the Cascade polypeptides of Type I subtype I-E. Non-limiting examples of Type I-E Cascade polypeptides include CasA (Cse1), CasB (Cse2), CasC (Cas7), CasD (Cas5) and/or CasE (Cas6e).

The term "Type I-B polypeptide" refers to the polypeptides that make up a Type I-B CRISPR-Cas system. A Type I-B CRISPR-Cas system can comprise, consist essentially of, or consist of a nucleotide sequence encoding a Cas5 polypeptide, a nucleotide sequence encoding a Cas6 polypeptide, a nucleotide sequence encoding a Cas7 polypeptide, a nucleotide sequence encoding a Cas8b2 polypeptide and a nucleotide sequence encoding a Cas3 polypeptide. As used herein, "Type I-B polypeptide," "Type I-B CRISPR system polypeptide" or "polypeptides of a Type I-B CRISPR system" refers to any of a Cas3 polypeptide and any one or more of the Type I-B Clustered Regularly Interspaced Short Palindromic Repeats (CRISPR)-associated complex for antiviral defense ("Cascade") polypeptides.

"Type I-B CRISPR-associated complex for antiviral defense" or "Cascade" as used interchangeably herein refers to a complex of polypeptides involved in processing of pre-crRNAs and subsequent binding to the target DNA in Type I-B CRISPR-Cas systems. As used herein, "Type I-B Cascade polypeptides" refers to a complex of polypeptides involved in processing of CRISPR arrays and subsequent binding to the target DNA in Type I-B CRISPR-Cas systems. These polypeptides include the Cascade polypeptides of Type I subtype I-B. Non-limiting examples of Type I-B Cascade polypeptides include Cas5, Cas6, Cas7, and/or Cas8b2.

"Variant" used herein with respect to a nucleic acid means (i) a portion or fragment of a referenced nucleotide sequence; (ii) the complement of a referenced nucleotide sequence or portion thereof; (iii) a nucleic acid that is substantially identical to a referenced nucleic acid or the complement thereof; or (iv) a nucleic acid that hybridizes under stringent conditions to the referenced nucleic acid, complement thereof, or a sequences substantially identical thereto.

"Variant" with respect to a peptide or polypeptide that differs in amino acid sequence by the insertion, deletion, or conservative substitution of amino acids, but retain at least one biological activity. Variant can also mean a protein with an amino acid sequence that is substantially identical to a referenced protein with an amino acid sequence that retains at least one biological activity. A conservative substitution of an amino acid, i.e., replacing an amino acid with a different amino acid of similar properties (e.g., hydrophilicity, degree and distribution of charged regions) is recognized in the art as typically involving a minor change. These minor changes can be identified, in part, by considering the hydropathic index of amino acids, as understood in the art. Kyte et al., *J. Mol. Biol.* 157:105-132 (1982). The hydropathic index of an amino acid is based on a consideration of its hydrophobicity and charge. It is known in the art that amino acids of similar hydropathic indexes can be substituted and still retain protein function. In one aspect, amino acids having hydropathic indexes of ±2 are substituted. The hydrophilicity of amino acids can also be used to reveal substitutions that would result in proteins retaining biological function. A consideration of the hydrophilicity of amino acids in the context of a peptide permits calculation of the greatest local average hydrophilicity of that peptide. Substitutions can be performed with amino acids having hydrophilicity values within ±2 of each other. Both the hydrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

"Vector" as used herein means a nucleic acid sequence containing an origin of replication. A vector can be a viral vector, bacteriophage, bacterial artificial chromosome or yeast artificial chromosome. A vector can be a DNA or RNA vector. A vector can be a self-replicating extrachromosomal vector, and preferably, is a DNA plasmid.

Unless otherwise defined, all technical and scientific terms used herein have the same meaning as commonly understood by one of ordinary skill in the art. In case of conflict, the present document, including definitions, will control. The terminology used in the description of the disclosure herein is for the purpose of describing particular embodiments only and is not intended to be limiting of the disclosure. Preferred methods and materials are described below, although methods and materials similar or equivalent to those described herein can be used in practice or testing of the present disclosure. All publications, patent applications, patents and other references mentioned herein are incorporated by reference in their entirety. The materials, methods, and examples disclosed herein are illustrative only and not intended to be limiting.

Type I CRISPR-Based Programmable System

In some embodiments, the present disclosure is directed to the use of CRISPR systems to modulate activity of a gene. The present disclosure is directed to Type I-E CRISPR-based programmable transcriptional activation ("Type I-E CRISPRa") system compositions for altering gene expression of a target gene in a eukaryotic cell. The Type I-E CRISPRa system can cause robust transcriptional activation of target genes from promoters and proximal and distal enhancers. The Type I-E CRISPRa system is highly specific and can be guided to the target gene using as few as one crRNA. The Type I-E CRISPRa system can activate the expression of one gene or a family of genes by targeting enhancers at distant locations in the genome.

In one aspect, the disclosed Type I-E CRISPRa system compositions include: (a) a Cascade complex comprising three or more Cascade polypeptides of the Type I-E CRISPR/Cas system, or functional fragments thereof, wherein at least one Cascade polypeptide is fused to a second polypeptide domain having transcription activation activity; and (b) at least one crRNA, wherein the crRNA targets a target nucleotide sequence within the target gene. The at least one Cascade polypeptide fused to a second polypeptide domain is CasA or CasE.

In another aspect, the disclosed Type I-E CRISPRa system compositions include at least one polynucleotide sequence encoding: (a) a Cascade complex comprising three or more Cascade polypeptides of the Type I-E CRISPR/Cas system, or functional fragments thereof, wherein at least one Cascade polypeptide is fused to a second polypeptide domain having transcription activation activity; and (b) at least one crRNA, wherein the crRNA targets a target nucleotide sequence within the target gene. The at least one polynucleotide sequence is operably linked to a eukaryotic promoter, comprises a nuclear localization signal, and is codon-optimized. The at least one Cascade polypeptide fused to a second polypeptide domain is CasA or CasE.

In some embodiments, the present disclosure is also directed to Type I-B CRISPR-based programmable system, and compositions thereof, for altering gene expression of a target gene or genome editing of a target gene in a cell, such as a eukaryotic cell. The disclosed Type I-B CRISPR-based programmable system composition can be used for genome engineering at least one target gene in a cell. The composition includes: (a)(i) a Cascade complex comprising three or more Cascade polypeptides of a Type I-B CRISPR/CRISPR-associated (Cas) system, or functional fragments thereof, or (ii) a nucleic acid encoding a Cascade complex comprising three or more Cascade polypeptides of a Type I-B CRISPR/CRISPR-associated (Cas) system, or functional fragments thereof, and/or (b)(i) at least one crRNA or (ii) a nucleic acid encoding at least one crRNA, wherein the crRNA targets a target nucleotide sequence from the at least one target gene. At least one Cascade polypeptide is fused to a second polypeptide domain thereby generating a Cascade polypeptide fusion protein. The second polypeptide domain has an activity selected from the group consisting of transcription activation activity, nuclease activity, transcription repression activity, transcription release factor activity, histone modification activity, nucleic acid association activity, methylase activity, and demethylase activity. The at least one Cascade polypeptide in the Cascade polypeptide fusion protein is Cas5, Cas6, Cas7, or Cas8b2. In some embodiments, the nucleic acid encoding the Cascade complex comprising three or more Cascade polypeptides of a Type I-B CRISPR/CRISPR-associated (Cas) system, or functional fragments thereof, and/or crRNA can be operably linked to a eukaryotic promoter, can include a nuclear localization signal, and can be codon-optimized for eukaryotic expression. In some embodiments, the nucleic acid of (a)(ii) and/or (b)(ii) comprises DNA or RNA.

Cascade Complex

In some embodiments, the disclosed Type I CRISPRa systems include a Cascade complex or at least one polynucleotide sequence encoding a Cascade complex. In some embodiments, the Cascade complex includes at least three Cascade polypeptides of the Type I CRISPR/Cas system, or functional fragments thereof. At least one Cascade polypeptide is fused to a second polypeptide domain thereby generating a Cascade polypeptide fusion protein. At least one Cascade polypeptide is fused to a second polypeptide domain having transcription activation activity.

Type I Cascade Polypeptides

The Type I-E Cascade polypeptides include, but are not limited to, a CasA (Cse1) polypeptide, a CasB (Cse2) polypeptide, a CasC (Cas7) polypeptide, a CasD (Cas5) polypeptide, and a CasE (Cas6e) polypeptide. In some embodiments, the Cascade complex includes a CasA polypeptide, a CasB polypeptide, a CasC polypeptide, a CasD polypeptide, a CasE polypeptide, combinations thereof, or functional fragments thereof. In some embodiments, the Cascade complex includes three Cascade polypeptides, four polypeptides, or five polypeptides of the Type I-E CRISPR/Cas system, or functional fragments thereof.

In some embodiments, the Type I-E CRISPR/Cas system can include a polynucleotide sequence encoding a CasA polypeptide, a polynucleotide sequence encoding a CasB polypeptide, a polynucleotide sequence encoding a CasC polypeptide, a polynucleotide sequence encoding a CasD polypeptide, a polynucleotide sequence encoding a CasE polypeptide, or combinations thereof. In some embodiments, each of the polynucleotide sequences encoding the Cascade polypeptides can be operably linked to a eukaryotic promoter, can include a nuclear localization signal, and can be operably linked to a terminator. In some embodiments, each of the polynucleotide sequences encoding the Cascade polypeptides can be codon optimized for expression in the host species. In some embodiments, the polynucleotide sequences encoding the Cascade polypeptides can be codon optimized versions of a CasA polypeptide, a CasB polypeptide, a CasC polypeptide, a CasD polypeptide, a CasE polypeptide, and/or combinations thereof. In some embodiments, two or more Cascade polypeptides, or functional fragments thereof, are fused to form a single polypeptide. In some embodiments, two or more Cascade polypeptides are encoded by a multicistronic polynucleotide sequence and separated by at least one 2A peptide.

Figure 1B:
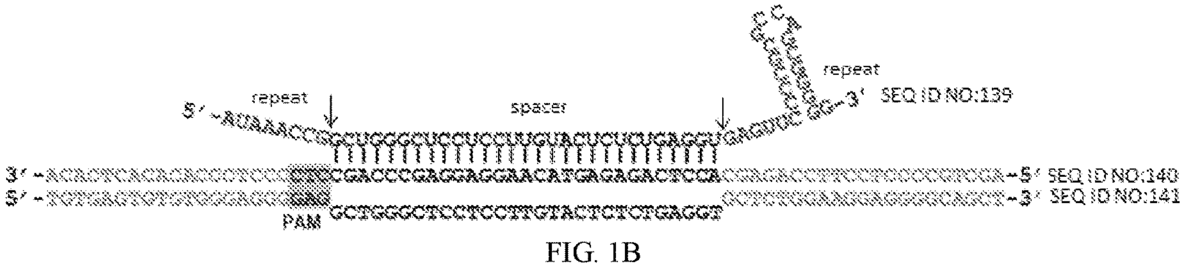

In some embodiments, the Cascade polypeptides are Cascade polypeptides of the *Escherichia coli* Type I-E CRISPR/Cas system. The Type I-E system of *Escherichia coli* K12 consists of eight cas genes and a downstream CRISPR array (FIG. 1A). Following transcription of the CRISPR array, the 29-bp repeat sequences flanking the variable spacer sequences are cleaved during crRNA processing. Together, five protein subunits (CasA to CasE) and the mature 61-nt crRNA form the 405-kDa CRISPR-associated complex for antiviral defense (Cascade) (FIG. 1A). Unlike Type II CRISPR systems, there is no tracrRNA required for complex formation. To bind to a target, Cascade surveils the DNA to find a protospacer-adjacent motif (PAM) upstream of a target sequence with complementarity to the crRNA spacer (FIG. 1B). In some embodiments, the Cascade polypeptide can be encoded by a polynucleotide sequence of SEQ ID NO: 1, SEQ ID NO: 2, SEQ ID NO: 3, SEQ ID NO: 4, SEQ ID NO: 5, or SEQ ID NO: 163. In some embodiments, the Cascade polypeptide can be encoded by a homologue of a polynucleotide sequence of SEQ ID NO: 1, SEQ ID NO: 2, SEQ ID NO: 3, SEQ ID NO: 4, SEQ ID NO: 5, or SEQ ID NO: 163.

In some embodiments, the Type I-B Cascade polypeptides disclosed herein include, but are not limited to, a Cas6 polypeptide, a Cas5 polypeptide, a Cas7 polypeptide, or a Cas8b2 polypeptide. In some embodiments, the Cascade complex includes a Cas5 polypeptide, a Cas6 polypeptide, a Cas7 polypeptide, a Cas8b2 polypeptide, combinations thereof, or functional fragments thereof. In some embodiments, the Cascade complex includes three Cascade polypeptides or four polypeptides of the Type I-B CRISPR/Cas system, or functional fragments thereof. Non-limiting examples of Type I-B polypeptides include Cas5, Cas6, Cas7, and/or Cas8b2.

In some embodiments, the Type I-B CRISPR/Cas system can include a polynucleotide sequence encoding a Cas5 polypeptide, a polynucleotide sequence encoding a Cas6 polypeptide, a polynucleotide sequence encoding a Cas7 polypeptide and/or a polynucleotide sequence encoding a Cas8b2 polypeptide, or combinations thereof. In some embodiments, the Cas5 polypeptide can include an amino acid sequence of SEQ ID NO: 175, the Cas6 polypeptide can include an amino acid sequence of SEQ ID NO: 176, the Cas7 polypeptide can include an amino acid sequence of SEQ ID NO: 176, and/or the Cas8b2 polypeptide can include an amino acid sequence of SEQ ID NO: 177. In some embodiments, the polynucleotide sequence encoding the Cas5 polypeptide can include a nucleotide sequence of SEQ ID NO: 258, the polynucleotide sequence encoding the Cas6 polypeptide can include a nucleotide sequence of SEQ ID NO: 259, the polynucleotide sequence encoding the Cas7 polypeptide can include a nucleotide sequence of SEQ ID NO: 260, and/or the polynucleotide sequence encoding the Cas8b2 polypeptide can include a nucleotide sequence of SEQ ID NO: 261.

In some embodiments, each of the polynucleotide sequences encoding the Cascade polypeptides can be operably linked to a eukaryotic promoter, can include a nuclear localization signal, and can be operably linked to a terminator. In some embodiments, each of the polynucleotide sequences encoding the Cascade polypeptides can be codon optimized for expression in the host species. In some embodiments, the polynucleotide sequences encoding the Cascade polypeptides can be codon optimized versions of a Cas5 polypeptide, a Cas6 polypeptide, a Cas7 polypeptide, a Cas8b2 polypeptide, and/or combinations thereof. In some embodiments, two or more Cascade polypeptides, or functional fragments thereof, are fused to form a single polypeptide. In some embodiments, two or more Cascade polypeptides are encoded by a multicistronic polynucleotide sequence and separated by at least one 2A peptide.

Figure 14A:
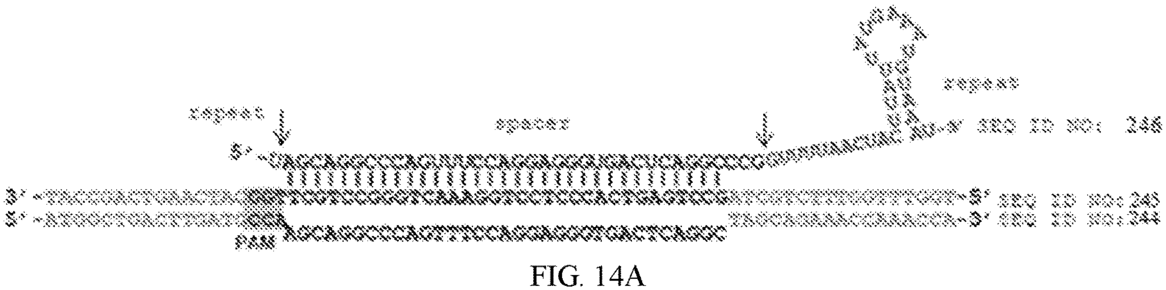
FIG. 14A-FIG. 14C show a schematic embodiments of LmoCascade crRNA cloning.

In some embodiments, the Cascade polypeptides are Cascade polypeptides of the *Listeria monocytogenes* Type I-B CRISPR/Cas system, such as *L. monocytogenes* Finland_1998 Type I-B CRISPR/Cas system. The Type I-B system of *Listeria monocytogenes* consists of eight cas genes and a downstream CRISPR array (FIG. 13). Following transcription of the CRISPR array, the 29-bp repeat sequences flanking the variable spacer sequences are cleaved during crRNA processing. Together, four protein subunits (Cas6, Cas8b2, Cas7, and Cas5) and the mature 65-nt crRNA form the CRISPR-associated complex for antiviral defense (Cascade) (FIG. 13). Unlike Type II CRISPR systems, there is no tracrRNA required for complex formation. To bind to a target, Cascade surveils the DNA to find a protospacer-adjacent motif (PAM) upstream of a target sequence with complementarity to the crRNA spacer (FIG. 14A).

In some embodiments, the Cascade polypeptide can be encoded by a polynucleotide sequence of SEQ ID NO: 166, SEQ ID NO: 167, SEQ ID NO: 168, SEQ ID NO: 169, SEQ ID NO: 258; SEQ ID NO: 259, SEQ ID NO: 260, or SEQ ID NO: 261. In some embodiments, the Cascade polypeptide can be encoded by a homologue of a polynucleotide sequence of SEQ ID NO: 166, SEQ ID NO: 167, SEQ ID NO: 168, SEQ ID NO: 169, SEQ ID NO: 258; SEQ ID NO: 259, SEQ ID NO: 260, or SEQ ID NO: 261. In some embodiments, the at least one polynucleotide sequence encoding the Cascade complex can include at least one polynucleotide sequence of SEQ ID NO: 166, SEQ ID NO: 167, SEQ ID NO: 168, SEQ ID NO: 169, or combinations thereof. In some embodiments, each of the polynucleotide sequences encoding the Cascade polypeptides can be operably linked to a eukaryotic promoter, can include a nuclear localization signal, and can be operably linked to a terminator.

In some embodiments, the Cascade complex can include a Cas5 polypeptide encoded by a polynucleotide sequence of SEQ ID NO: 166 or 258, a Cas7 polypeptide encoded by a polynucleotide sequence of SEQ ID NO: 168 or 260, a Cas8b2 polypeptide encoded by a polynucleotide sequence of SEQ ID NO: 169 or 261, and a Cas6-p300 fusion protein encoded by a polynucleotide sequence of SEQ ID NO: 174.

In some embodiments, the Cascade complex can include a Cas6 polypeptide encoded by a polynucleotide sequence of SEQ ID NO: 167 or 259, a Cas7 polypeptide encoded by a polynucleotide sequence of SEQ ID NO: 168 or 260, a Cas8b2 polypeptide encoded by a polynucleotide sequence of SEQ ID NO: 169 or 261, and a Cas5-p300 protein encoded by a polynucleotide sequence of SEQ ID NO: 171.

In some embodiments, the Cascade complex can include a Cas5 polypeptide encoded by a polynucleotide sequence of SEQ ID NO: 166 or 258, a Cas6 polypeptide encoded by a polynucleotide sequence of SEQ ID NO: 167 or 259, a Cas8b2 polypeptide encoded by a polynucleotide sequence of SEQ ID NO: 169 or 261, and a Cas7 fusion protein encoded by a polynucleotide sequence of SEQ ID NO: 172.

In some embodiments, the Cascade complex can include a Cas5 polypeptide encoded by a polynucleotide sequence of SEQ ID NO: 166 or 258, a Cas6 polypeptide encoded by a polynucleotide sequence of SEQ ID NO: 167 or 259, a Cas7 polypeptide encoded by a polynucleotide sequence of SEQ ID NO: 168 or 260, and a Cas8b2 fusion protein encoded by a polynucleotide sequence of SEQ ID NO: 173.

Cascade Fusion Protein

In some embodiments, at least one Cascade polypeptide is fused to a second polypeptide domain having transcription activation activity. In some embodiments, at least one Cascade polypeptide, such as CasA, CasB, CasC, CasD, and/or CasE, is fused to a second polypeptide domain having transcription activation activity, such as a polypeptide having histone acetyltransferase activity or a transactivation domain. In some embodiments, at least one Cascade polypeptide, such as CasA, CasB, CasC, CasD, and/or CasE, is fused to a second polypeptide domain having transcription repression activity.

In some embodiments, a polypeptide domain having histone acetyltransferase activity can include, but is not limited to, a p300 protein, CREB binding protein (CBP; an analog of p300), GCN5, or PCAF, or fragment thereof. In some embodiments, the polypeptide domain can include a core lysine-acetyltransferase domain of the human p300 protein, i.e., the p300 HAT Core (also known as "p300 Core domain"). In some embodiments, a polypeptide having a transactivation domain can include but is not limited to, VP16 protein, multiple VP16 proteins, such as a VP48 domain or VP64 domain, p65 domain of NF kappa B transcription activator, or VP64-p65-Rta tripartite activator (VPR) domain. In some embodiments, the second polypeptide domain having transcription activation activity can include a p300 core domain or VP64-p65-Rta tripartite activator (VPR) domain. In some embodiments, p300 core domain can include an amino acid sequence of the SEQ ID NO: 9 or a homologue thereof. In some embodiments, the VPR domain can include an amino acid sequence of the SEQ ID NO: 11 or a homologue thereof. In some embodiments, the second polypeptide domain having transcription activation activity can include an amino acid sequence of SEQ ID NO: 9 or SEQ ID NO: 11 or a homologue thereof.

In some embodiments, the at least one Cascade polypeptide fused to a second polypeptide domain to generate the Cascade fusion protein is CasA. In some embodiments, the at least one Cascade polypeptide fused to a second polypeptide to generate a Cascade fusion protein is CasE. In some embodiments, the second polypeptide domain is fused to the N terminus and/or the C terminus of the at least one Cascade polypeptide. In some embodiments, the Cascade fusion protein further comprises a linker connecting the at least one Cascade polypeptide to the second polypeptide domain. In some embodiments, the Cascade polypeptide fused to a second polypeptide domain having transcription activation activity can be encoded by a polynucleotide sequence of SEQ ID NO: 6, SEQ ID NO: 7, or SEQ ID NO: 8. In some embodiments, the Cascade polypeptide fused to a second polypeptide domain having transcription activation activity can be encoded by a homologue of a polynucleotide sequence of SEQ ID NO: 6, SEQ ID NO: 7, or SEQ ID NO: 8.

In some embodiments, the Cascade complex can include a CasA polypeptide, a CasB polypeptide, a CasC polypeptide, a CasD polypeptide, and a CasE polypeptide fused to a second polypeptide domain. In some embodiments, the Cascade complex can include a CasA polypeptide fused to a second polypeptide domain, a CasB polypeptide, a CasC polypeptide, a CasD polypeptide, and a CasE polypeptide.

In some embodiments, the Cascade complex can include a CasA polypeptide comprising a polypeptide sequence of SEQ ID NO: 1, or homologue thereof, a CasB polypeptide comprising a polypeptide sequence of SEQ ID NO: 2, or homologue thereof, a CasC polypeptide comprising a polypeptide sequence of SEQ ID NO: 3, SEQ ID NO: 163, or homologue thereof, a CasD polypeptide comprising a polypeptide sequence of SEQ ID NO: 4, or homologue thereof, and a CasE fusion protein comprising a polypeptide sequence of SEQ ID NO: 6, or homologue thereof. In some embodiments, the Cascade complex can include a CasA polypeptide comprising a polypeptide sequence of SEQ ID NO: 1, or homologue thereof, a CasB polypeptide comprising a polypeptide sequence of SEQ ID NO: 2, or homologue thereof, a CasC polypeptide comprising a polypeptide sequence of SEQ ID NO: 3, SEQ ID NO: 163, or homologue thereof, a CasD polypeptide comprising a polypeptide sequence of SEQ ID NO: 4, or homologue thereof, and a CasE fusion protein comprising a polypeptide sequence of SEQ ID NO: 7, or homologue thereof. In some embodiments, the Cascade complex can include a CasA fusion protein comprising a polypeptide sequence of SEQ ID NO:1, or homologue thereof, a CasB polypeptide comprising a polypeptide sequence of SEQ ID NO: 2, or homologue thereof, a CasC polypeptide comprising a polypeptide sequence of SEQ ID NO: 3, SEQ ID NO: 163, or homologue thereof, a CasD polypeptide comprising a polypeptide sequence of SEQ ID NO: 4, or homologue thereof, and a CasE polypeptide comprising a polypeptide sequence of SEQ ID NO: 5, or homologue thereof.

In some embodiments, the Type I-B CRISPR-based programmable system includes a Cascade polypeptide fusion protein. The Cascade polypeptide fusion protein can include two heterologous polypeptide domains, a first polypeptide domain, such as at least one Type I-B Cascade polypeptide, and a second polypeptide domain. In some embodiments, the first polypeptide domain comprises at least one Type I-B Cascade polypeptide, and a second polypeptide domain that has an activity selected from the group consisting of transcription activation activity, nuclease activity, transcription repression activity, transcription release factor activity, histone modification activity, nucleic acid association activity, methylase activity, and demethylase activity. In some embodiments, the first polypeptide domain comprises at least one Type I-B Cascade polypeptide and the second polypeptide domain comprises a label or tag. In some embodiments, the second polypeptide domain is fused to the N-terminal end of the first polypeptide domain. In some embodiments, the second polypeptide domain is fused to the C-terminal end of the first polypeptide domain. In some embodiments, the Cascade polypeptide fusion protein further comprises a linker connecting the at least one Cascade polypeptide to the second polypeptide domain.

In some embodiments, the second polypeptide domain may have histone modification activity. A histone modification is a covalent post-translational modification (PTM) to histone proteins which includes methylation, phosphorylation, acetylation, ubiquitylation, and sumoylation. The PTMs made to histones can impact gene expression by altering chromatin structure or recruiting histone modifiers. Histones act to package DNA, which wraps around eight histones, into chromosomes. Histone modifications are involved in biological processes such as transcriptional activation/inactivation, chromosome packaging, and DNA damage/repair. The second polypeptide domain may have histone acetyltransferase, histone deacetylase, histone demethylase, or histone methyltransferase activity.

In some embodiments, the histone acetyltransferase may be p300 or CREB-binding protein (CBP; an analog of p300), GCN5, KAT6A, KAT8, or PCAF, or fragment thereof. In some embodiments, the second polypeptide domain can include a p300 core domain. In some embodiments, the second polypeptide domain can include an amino acid sequence of SEQ ID NO: 180. In some embodiments, the Cascade polypeptide fusion protein can be a Cas5-p300 fusion protein, a Cas6-p300 fusion protein, a Cas7-p300 fusion protein, or a Cas8b2-p300 fusion protein. In some embodiments, the Cascade polypeptide fusion protein can include an amino acid sequence encoded by a polynucleotide sequence of SEQ ID NO: 171, SEQ ID NO: 172, SEQ ID NO: 173, or SEQ ID NO: 174. In some embodiments, the Cascade polypeptide fusion protein can include an amino acid sequence encoded by a homologue of a polynucleotide sequence of SEQ ID NO: 171, SEQ ID NO: 172, SEQ ID NO: 173, or SEQ ID NO: 174.

In some embodiments, the histone deacetylase may be Sirtuin-6 (SIRT6). In some embodiments, the histone methyltransferases may be SET Domain Bifurcated 2 (SETDB2) or Euchromatic histone-lysine N-methyltransferase 2 (EHMT2). In some embodiments, the histone demethylase may be PHD finger protein 8 (PHF8) or Lysine Demethylase 4D (KDM4D).

The second polypeptide domain may have transcription activation activity, i.e., a transactivation domain. For example, the transactivation domain may include a VP16 protein, multiple VP16 proteins, such as a VP48 domain or VP64 domain, or p65 domain of NF kappa B transcription activator activity.

The second polypeptide domain may have nuclease activity or nickase activity. A nuclease, or a protein having nuclease activity, is an enzyme capable of cleaving the phosphodiester bonds between the nucleotide subunits of nucleic acids. Nucleases are usually further divided into endonucleases and exonucleases, although some of the enzymes may fall in both categories. Well known nucleases are deoxyribonuclease and ribonuclease. In some embodiments, the second polypeptide domain can have nuclease activity and/or nickase activity that is the same as the nuclease activity of the Cas3 protein. In some embodiments, the second polypeptide domain can have nuclease activity and/or nickase activity that is different from the nuclease activity of the Cas3 protein. Tethering a second polypeptide domain having nuclease activity and/or nickase activity to Cascade eliminates the need for Cas3 and thus an extra component to the system.

In some embodiments, the second polypeptide domain may have nickase activity. A nickase, or a protein having nickase activity, is an enzyme capable of introducing a single-strand cut of a polynucleotide sequence. In some embodiments, the second polypeptide domain having nickase activity is a Cas9 having a mutation to generate a nickase, as known in the art. In some embodiments, the second polypeptide domain having nickase activity is Cas3.

In some embodiments, the second polypeptide domain can have a nuclease domain from FokI or ITev-I. In some embodiments, the second polypeptide domain can have a monomeric or dimeric form of Fold. In some embodiments, a first monomeric form of Fold is fused to a first Cascade polypeptide and a second monomeric form of Fold is fused to a second Cascade polypeptide. In some embodiments, the second polypeptide domain can include a linker separating the two Fold domains, wherein the linker is of sufficient length to allow dimerization of the two FokI domains.

The second polypeptide domain may have transcription repression activity. The second polypeptide domain may have a Kruppel associated box activity, such as a KRAB domain, ERF repressor domain activity, Mxi1 repressor domain activity, SID4X repressor domain activity, Mad-SID repressor domain activity or TATA box binding protein activity.

In some embodiments, the second polypeptide domain may have transcription release factor activity. The second polypeptide domain may have eukaryotic release factor 1 (ERF1) activity or eukaryotic release factor 3 (ERF3) activity.

In some embodiments, the second polypeptide domain may have nucleic acid association activity or nucleic acid binding protein-DNA-binding domain (DBD) is an independently folded protein domain that contains at least one motif that recognizes double- or single-stranded DNA. A DBD can recognize a specific DNA sequence (a recognition sequence) or have a general affinity to DNA. nucleic acid association region selected from the group consisting of helix-turn-helix region, leucine zipper region, winged helix region, winged helix-turn-helix region, helix-loop-helix region, immunoglobulin fold, B3 domain, Zinc finger, HMG-box, Wor3 domain, TAL effector DNA-binding domain.

The second polypeptide domain may have methylase activity, which involves transferring a methyl group to DNA, RNA, protein, small molecule, cytosine or adenine. The second polypeptide domain may include a DNA methyltransferase. In some embodiments, the methylase activity domain can be DNA (cytosine-5)-methyltransferase 3A (DNMT3a). DNMT3a is an enzyme that catalyzes the transfer of methyl groups to specific CpG structures in DNA. The enzyme is encoded in humans by the DNMT3A gene. In some embodiment, the second polypeptide domain can cause methylation of DNA either directly or indirectly.

The second polypeptide domain may have demethylase activity. The second polypeptide domain may include an enzyme that remove methyl (CH3-) groups from nucleic acids, proteins (in particular histones), and other molecules. Alternatively, the second polypeptide may covert the methyl group to hydroxymethylcytosine in a mechanism for demethylating DNA. The second polypeptide may catalyze this reaction. For example, the second polypeptide that catalyzes this reaction may be Ten-eleven translocation methylcytosine dioxygenase 1 (Tet1) or Lysine-specific histone demethylase 1 (LSD1). In some embodiment, the second polypeptide domain can cause demethylation of DNA either directly or indirectly.

Tag or Label

In some embodiments, the polynucleotide sequence encoding the Cascade polypeptide and/or Cascade fusion protein can further include a polynucleotide sequence encoding a tag or label. For example, the polynucleotide sequence can include a polynucleotides sequence that encodes a Cascade polypeptide fused to a tag or label. In some embodiments, each of the Cascade polypeptides is fused to a tag or label. In some embodiments the tag can be an epitope tag. For examples, the epitope tag can include FLAG, such as FLAG (SEQ ID NO: 147), 3×FLAG, HA (SEQ ID NO: 148), myc (SEQ ID NO: 149), V5 (SEQ ID NO: 150), E-tag (SEQ ID NO: 151), VSV-g (SEQ ID NO: 152), 6×His (SEQ ID NO: 153), HSV (SEQ ID NO: 154), a homologue of any of these or a combination thereof.

In some embodiments, the polynucleotide sequence encoding the Cascade polypeptide and/or Cascade polypeptide fusion protein can further include a polynucleotide sequence encoding a tag or label. For example, the polynucleotide sequence can include a polynucleotides sequence that encodes a Cascade polypeptide fused to a tag or label. In some embodiments, each of the Cascade polypeptides is fused to a tag or label. In some embodiments the tag can be an epitope tag. For examples, the epitope tag can include FLAG, such as FLAG (DYKDDDDK; SEQ ID NO: 220) and 3×FLAG, HA (YPYDVPDYAC; SEQ ID NO: 252), myc (EQKLISEEDLC; SEQ ID NO: 253), V5 (GKPIPNPLLGLDST; SEQ ID NO: 222), E-tag (GAPVPYPDPLEPR; SEQ ID NO: 254), VSV-g (YTDIEMNRLGK; SEQ ID NO: 255), 6×His (HHHHHH; SEQ ID NO: 256), and HSV (QPELAPEDPEDC; SEQ ID NO: 257). In some embodiments, the FLAG can be encoded by a polynucleotide sequence of GACTATAAGGATGATGACGACAAG (SEQ ID NO: 215), GACTACAAGGACGACGACGATAAG (SEQ ID NO: 216), GACTACAAGGACGATGATGACAAG (SEQ ID NO: 217), GATTACAAGGACGATGACGACAAA (SEQ ID NO: 218), GATTACAAAGACGATGACGATAAG (SEQ ID NO: 219) or a homologue thereof. In some embodiments, the V5 can be encoded by a polynucleotide sequence of GGCAAGCC-TATACCTAACCCTTTGCTCGGGCTGGACTCCACC (SEQ ID NO: 221).

crRNA

In some embodiments, the Type I CRISPRa system includes at least one crRNA or a polynucleotide sequence encoding at least one crRNA. A "CRISPR RNA," "crRNA," or "CRISPR array" as used interchangeably herein refers to a nucleic acid molecule that comprises at least two repeat nucleotide sequences, or portions thereof, and at least one spacer sequence, wherein one of the two repeat nucleotide sequences, or a portion thereof, is linked to the 5' end of the spacer nucleotide sequence and the other of the two repeat nucleotide sequences, or portion thereof, is linked to the 3' end of the spacer nucleotide sequence. A repeat sequence useful with the disclosed compositions can be any known or later identified repeat sequence of a Type I CRISPR-Cas locus or it can be a synthetic repeat designed to function in a Type I CRISPRa system. A repeat sequence can comprise a hairpin structure and/or a stem loop structure. Thus, in some embodiments, a repeat sequence can be identical to or substantially identical to a repeat sequence from a wild-type Type I CRISPR locus. A repeat sequence from a wild-type Type I CRISPR locus can be determined through established algorithms, such as using the CRISPRfinder offered through CRISPRdb (see, Grissa et al. *Nucleic Acids Res.* 35(Web Server issue):W52-7).

In some embodiments, a repeat sequence or portion thereof is linked to the 3' end of a spacer sequence. In other embodiments, a repeat sequence or portion thereof is linked to the 5' end of a spacer-repeat sequence, thereby forming a repeat-spacer-repeat sequence.

In some embodiments, a repeat sequence comprises, consists essentially of, or consists of at least one nucleotide (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or more nucleotides, or any range therein) depending on the particular repeat and whether the CRISPR array comprising the repeat is processed or unprocessed. In some embodiments, a repeat sequence comprises, consists essentially of, or consists of at least about one to about 40 nucleotides. In still other embodiments, a repeat sequence comprises, consists essentially of, or consists of at least about 8 nucleotides to about 40 nucleotides, or any range or value therein. In further embodiments, a repeat sequence can comprise, consist essentially of, or consist of about 10 nucleotides to about 40 nucleotides, about 15 nucleotides to about 40 nucleotides, about 20 nucleotides to about 40 nucleotides, about 25 nucleotides to about 40 nucleotides, about 1 to about 35 nucleotides, about 10 to about 35 nucleotides, about 15 to about 35 nucleotides, about 20 to about 35 nucleotides, about 25 to about 35 nucleotides, about 20 to about 30 nucleotides, and/or about 25 to about 30 nucleotides, or any range or value therein. In representative embodiments, a repeat sequence can comprise, consist essentially of, or consist of about 25 nucleotides to about 38 nucleotides, or any range or value therein. When more than one spacer sequence is present in a CRISPR array, each spacer nucleotide sequence is separated from another by a repeat sequence.

In some embodiments, a repeat sequence linked to the 5' or to the 3' end of a spacer sequence can comprise a portion of a repeat sequence (e.g., 1, 2, 3, 4, 5, 6, 7, 8, 9, 10, 11, 12, 13, 14, 15 or more contiguous nucleotides of a wild type repeat sequence). In some embodiments, a portion of a repeat sequence linked to the 5' end of a spacer sequence can be about five to about ten consecutive nucleotides in length (e.g., about 5, 6, 7, 8, 9, 10 nucleotides) and have at least 90% identity (e.g., at least about 90%, 91%, 92%, 93%, 94%, 95%, 96%, 97%, 98%, 99%, or more) to the same region (e.g., 5' end) of a wild type repeat nucleotide sequence. In representative embodiments, a repeat sequence linked to the 5' end of a spacer sequence can be about eight consecutive nucleotides in length and have at least 90% identity (e.g., at least about 90%, 91%, 92%, 93%, 94%, 95%, 96%, 97%, 98%, 99%, or more) to the same region (e.g., 5' end) of a wild type repeat nucleotide sequence. In representative embodiments, a repeat sequence linked to the 3' end of a spacer sequence in a CRISPR array for Type I-E system can comprise a portion of consecutive nucleotides of a Type I-E repeat sequence from the 5'-most end through the hairpin of the Type I-E repeat sequence (e.g., to the 3' end of the hairpin of the repeat sequence). In further embodiments, a repeat sequence linked to the 3' end of a spacer sequence in a CRISPR array for Type I-E system can comprise a portion of consecutive nucleotides of a Type I-E repeat sequence from the 5'-most end up to the base of the stem loop of the Type I-E repeat sequence (e.g., up to the 5' end of the stem loop structure of the repeat sequence). In another representative embodiment, a repeat sequence linked to the 3' end of a spacer sequence in a CRISPR array for Type I-B system can comprise a portion of consecutive nucleotides of a Type I-B repeat sequence from the 5'-most end through the hairpin of the Type I-B repeat sequence (e.g., to the 3' end of the hairpin of the repeat sequence). In further embodiments, a repeat sequence linked to the 3' end of a spacer sequence in a CRISPR array for Type I-B system can comprise a portion of consecutive nucleotides of a Type I-B repeat sequence from the 5'-most end up to the base of the stem loop of the Type I-B repeat sequence (e.g., up to the 5' end of the stem loop structure of the repeat sequence).

The design of a crRNA or CRISPR array will vary based on the planned use. The disclosed crRNA or CRISPR arrays are synthetic, made by man and not found in nature. In some embodiments, a crRNA or a CRISPR array can comprise, from 5' to 3', a repeat sequence (full length or portion thereof ("handle")), a spacer sequence, and a repeat sequence (full length or portion thereof). In some embodiments, a crRNA or a CRISPR array can comprise, from 5' to 3', a repeat sequence (full length or portion thereof ("handle")) and a spacer sequence. In some embodiments, the at least one polynucleotide sequence encoding the at least one crRNA can include a spacer nucleotide sequence linked to a repeat nucleotide sequence at its 5' end and at its 3' end. For example, the at least one polynucleotide sequence encoding the at least one crRNA can include from 5' to 3' a repeat nucleotide sequence (full length or portion thereof), a spacer nucleotide sequence, and a repeat nucleotide sequence (full length or portion thereof). In some embodiments, the polynucleotide sequence encoding the crRNA can include a repeat nucleotide sequence of SEQ ID NO: 145, SEQ ID NO: 146, or complement thereof. In some embodiments, the polynucleotide sequence encoding the crRNA can include a spacer sequence corresponding to at least one of SEQ ID NOs: 15-66, or combinations thereof or a homologue thereof. In some embodiments, the crRNA or CRISPR array can be operably linked to a eukaryotic promoter, can include a nuclear localization signal, and can be operably linked to a terminator. In some embodiments, the polynucleotide sequence encoding the crRNA can include a repeat nucleotide sequence of SEQ ID NO: 243, or complement thereof or a homologue thereof. In some embodiments, the polynucleotide sequence encoding the crRNA can include a spacer sequence corresponding to at least one of SEQ ID NOs: 181-197, or combinations thereof or a homologue thereof. In some embodiments, the polynucleotide sequence encoding the crRNA can include a spacer sequence corresponding to at least one of SEQ ID NOs: 270-275, or combinations thereof or a homologue thereof. In some embodiments, the crRNA or CRISPR array can be operably linked to a eukaryotic promoter, can include a nuclear localization signal, and can be operably linked to a terminator.

In some embodiments, a CRISPR array can comprise at least one spacer sequence having a 5' end and a 3' end and linked at its 3' end to the 5' end of at least one repeat sequence or a portion of the least one repeat sequence to form a "spacer-repeat sequence" having a 5' end and a 3' end. In other embodiments, a CRISPR array can comprise a "minimal CRISPR array," comprising a spacer having a 5' end and a 3' end and linked at its 5' end to a portion of a repeat sequence. In some embodiments, a CRISPR array can comprise a spacer-repeat sequence that comprises a further repeat sequence, or portion thereof, the further repeat sequence linked at its 3' end to the 5' end of a spacer-repeat sequence, thereby forming a "repeat-spacer-repeat sequence." In still further embodiments, a repeat-spacer-repeat sequence can be linked at the 3' end to at least one to up to about nine further spacer-repeat sequences (e.g., 1, 2, 3, 4, 5, 6, 7, 8, 9 additional consecutive spacer-repeat sequences). In such embodiments, each of the at least one up to nine additional consecutive spacer-repeat sequences, each having a 5' end and a 3' end, are linked at the 3' end to the 5' end of the next spacer-repeat sequence (e.g., a first spacer-repeat sequence linked at the 3' end to a second spacer-repeat sequence) and so on, to form, for example, a repeat-spacer-repeat-spacer-repeat with up to 10 spacer sequences alternating with up to 11 repeat sequences.

A CRISPR array of this disclosure can be "processed" or "unprocessed." An "unprocessed CRISPR array" can comprise at least one spacer linked at both the 5' end and at the 3' end to a full-length repeat sequence ("repeat-spacer-repeat" sequence). An unprocessed CRISPR array can comprise further spacer-repeat sequences linked to the 3' end of the repeat-spacer-repeat sequence (e.g., repeat-spacer-repeat-spacer-repeat-spacer-repeat-spacer-repeat and the like, up to about ten "spacer-repeat sequence" units). The design of a "processed CRISPR array will vary depending on its intended for use. Thus, in some embodiments, a "processed CRISPR array" can comprise a spacer sequence linked at its 5' end to the 3' end of a portion of consecutive nucleotides of a repeat sequence (e.g., "a handle"). In some embodiments, a processed CRISPR array can further comprise a full length repeat sequence or a portion of consecutive nucleotides of a repeat sequence, the full length repeat sequence or portion of a repeat sequence being linked at its 5' end to the 3' end of the spacer sequence.

In representative embodiments, an unprocessed CRISPR array can comprise a repeat sequence having a 5' end and a 3' end, and at least one spacer-repeat sequence having a 5' end and a 3' end, and the repeat sequence is linked at its 3' end to the 5' end of the at least one spacer-repeat sequence, wherein when more than one spacer-repeat sequence is present, the spacer-repeat sequences are consecutive to one another, each having a 5' end and a 3' end, and linked at the 3' end to the 5' end of the next spacer-repeat sequence. In some embodiments, an unprocessed CRISPR array can comprise up to nine additional consecutive spacer-repeat sequences, each having a 5' end and a 3' end and each linked at the 3' end to the 5' end of the next-spacer-repeat sequence. When processed, the leading repeat sequence is cleaved off, while the terminal repeat sequence is cleaved and retained with the spacer as part of Cascade.

In some aspects, a processed CRISPR array can be introduced with polypeptides of a Type I CRISPRa system. In representative aspects, a processed Type I-E crRNA can comprise, consist essentially of, or consist of: (A) a first portion of a Type I-E repeat sequence having a 5' end and a 3' end; (B) a spacer sequence having a 5' end and a 3' end; and (C) (i) a full length Type I-E repeat sequence having a 5' end and a 3' end, or (ii) a second portion of a Type II repeat sequence having a 5' end and a 3' end, the second portion of the Type I-E repeat sequence comprising: (a) a portion of consecutive nucleotides of a Type I-E repeat sequence from the 5'-most end of the Type I-E repeat sequence through the hairpin (e.g., the hairpin having a 5' end and a 3' end and the second portion comprising a portion of consecutive nucleotides of a Type I-E repeat sequence from the 5'-most end of the Type I-E repeat sequence through the 3' end of the hairpin), or (b) a portion of consecutive nucleotides of a Type I-E repeat sequence from the 5'-most end of the Type I-E repeat sequence up to the base (5' end) of the stem loop (e.g., the stem loop having a 5' end and a 3' end and the second portion comprising a portion of consecutive nucleotides of a Type I-E repeat sequence from the 5'-most end of the Type I-E repeat sequence up to the 5' end of the stem loop), wherein the spacer sequence is linked at its 5' end to the 3' end of the first portion of a Type I-E repeat sequence and linked at its 3' end to the 5' end of the full length Type I-E repeat or the 5' end of the second portion of a Type I-E repeat. In some embodiments, the first portion of a Type I-E repeat comprises from about 5 consecutive nucleotides to about 10 (e.g., 5, 6, 7, 8, 9, 10) consecutive nucleotides from the 3'-most end of the Type I-E repeat sequence. In representative embodiments, the first portion of a Type I-E repeat comprises about 8 consecutive nucleotides from the 3'-most end of the Type I-E repeat sequence. In some embodiments, a spacer of a Type I-E crRNA can be at least about 70% complementary to a target nucleic acid. In some embodiments, the spacer sequence of a Type I-E crRNA can comprise, consist essentially of, or consist of a length of about 25-100 nucleotides. In aspects of the disclosure, the spacer guides the Cascade complex to one strand of the target DNA.

In representative aspects, a processed Type I-B crRNA can comprise, consist essentially of, or consist of: (A) a first portion of a Type I-B repeat sequence having a 5' end and a 3' end; (B) a spacer sequence having a 5' end and a 3' end; and (C) a full length Type I-B repeat sequence having a 5' end and a 3' end, the second portion of the Type I-B repeat sequence comprising: (a) a portion of consecutive nucleotides of a Type I-B repeat sequence from the 5'-most end of the Type I-B repeat sequence through the hairpin (e.g., the hairpin having a 5' end and a 3' end and the second portion comprising a portion of consecutive nucleotides of a Type I-B repeat sequence from the 5'-most end of the Type I-B repeat sequence through the 3' end of the hairpin), or (b) a portion of consecutive nucleotides of a Type I-B repeat sequence from the 5'-most end of the Type I-B repeat sequence up to the base (5' end) of the stem loop (e.g., the stem loop having a 5' end and a 3' end and the second portion comprising a portion of consecutive nucleotides of a Type I-B repeat sequence from the 5'-most end of the Type I-B repeat sequence up to the 5' end of the stem loop), wherein the spacer sequence is linked at its 5' end to the 3' end of the first portion of a Type I-B repeat sequence and linked at its 3' end to the 5' end of the full length Type I-B repeat or the 5' end of the second portion of a Type I-B repeat. In some embodiments, the first portion of a Type I-B repeat comprises from about 5 consecutive nucleotides to about 10 (e.g., 5, 6, 7, 8, 9, 10) consecutive nucleotides from the 3'-most end of the Type I-B repeat sequence. In representative embodiments, the first portion of a Type I-B repeat comprises about 8 consecutive nucleotides from the 3'-most end of the Type I-B repeat sequence. In some embodiments, a spacer of a Type I-B crRNA can be at least about 70% complementary to a target nucleic acid. In some embodiments, the spacer sequence of a Type I-B crRNA can comprise, consist essentially of, or consist of a length of about 25-100 nucleotides. In aspects of the disclosure, the spacer guides the Cascade complex to one strand of the target DNA.

In some embodiments, the 5' region of a spacer sequence can be identical to a target DNA while the 3' region of the spacer can be substantially identical to the target DNA and therefore the overall complementarity of the spacer sequence to the target DNA is less than 100%. Thus, for example, the first 5, 6, 7, 8, 9, 10, 11, 12, 13, 14, 15, 16, and the like, nucleotides in the 3' region of, for example, a 20 nucleotide spacer sequence (seed region) can be 100% complementary to the target DNA, while the remaining nucleotides in the 5' region of the spacer sequence are substantially complementary (e.g., at least about 70% complementary) to the target DNA. In some embodiments, the first 5 to 12 nucleotides of the 3' end of the spacer sequence can be 100% complementary to the target DNA, while the remaining nucleotides in the 5' region of the spacer sequence are substantially complementary (e.g., at least about 50% complementary (e.g., 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more)) to the target DNA. In some embodiments, the 3' end of the spacer sequence can have about 75% to about 99% complementarity to the target DNA, while the remaining nucleotides in the 5' region of the spacer sequence can have at least about 50% to about 99% complementarity to the target DNA. In other embodiments, the first 7 to 10 nucleotides in the 3' end of the spacer sequence can have about 75% to about 99% complementarity to the target DNA, while the remaining nucleotides in the 5' region of the spacer sequence can have about 50% to about 99% complementarity to the target DNA. In other embodiments, the first 7 to 10 nucleotides in the 3' end of the spacer sequence can be fully (100%) complementary to the target DNA, while the remaining nucleotides in the 5' region of the spacer sequence can be substantially complementary (e.g., at least about 70% complementarity) to the target DNA. In representative embodiments, the first 10 nucleotides (within the seed region) of the spacer sequence can be 100% complementary to the target DNA, while the remaining nucleotides in the 5' region of the spacer sequence can be substantially complementary (e.g., at least about 70% complementary) to the target DNA. In an exemplary embodiment, the 5' region of a spacer sequence (e.g., the first 8 nucleotides at the 5' end, the first 10 nucleotides at the 5' end, the first 15 nucleotides at the 5' end, the first 20 nucleotides at the 5' end) can be about 75% identical or more (about 75% to about 100% identity) to a target DNA, while the remainder of the spacer sequence can be about 50% or more identical to the target DNA. Thus, for example, the first 8 nucleotides at the 5' end of a spacer sequence can be 100% identical to the target nucleotide sequence or it can have one or two mutations and therefore can be about 88% identical or about 75% identical to a target DNA, respectively, while the remainder of the spacer nucleotide sequence can be at least about 50% or more identical to the target DNA.

In some embodiments, a spacer sequence of this disclosure can be about 25 nucleotides to about 100 nucleotides in length for a CRISPR array (e.g., about 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 nucleotides, or any value or range therein). In some particular embodiments, a spacer nucleotide sequence can be a length of about 25 to about 90 nucleotides, about 25 to about 80 nucleotides, about 25 to about 50 nucleotides, about 25 to about 40 nucleotides, about 25 to about 35 nucleotides, about 25 to about 30 nucleotides, at least about 25 nucleotides, at least about 30 nucleotides, at least about 35 nucleotides, at least about 40 nucleotides, at least about 50 nucleotides, at least about 60 nucleotides, at least about 70 nucleotides, at least about 80 nucleotides, at least about 90 nucleotides, at least about 100 nucleotides in length, or more, and any value or range therein. In some embodiments, spacers of increased length exhibit greater specificity, where specificity is defined by the fraction of mismatches needed to disrupt targeting.

In representative embodiments, a spacer sequence of a Type I-E CRISPR spacer-repeat nucleic acid of the disclosure comprises at least about 25 consecutive nucleotides of a target DNA or target nucleic acid, wherein at the 3' end of the spacer at least about 10 consecutive nucleotides of the at least about 25 consecutive nucleotides comprise at least about 90% complementarity to the target nucleic acid, wherein the target nucleic acid is adjacent to a protospacer adjacent motif (PAM) sequence in the genome of a bacterium or archaeon of interest. The motif varies widely between Type I-E subtypes. For instance, the Type I-E system in *E. coli* can recognize a 3-base motif (read 5' to 3) that includes, but is not limited to, AAG, AGG, ATG, GAG, and TAG. In some embodiments, the PAM can be a 4-base motif (read 5' to 3') that includes, but is not limited to, NAAC, CAAA, CATA, CAAT, AAAC, AAAA, CTTN, CCTN, CTCN, CATN, TTTG, TATG, ATTG, and GTTV (where N is any nucleotide and V is any nucleotide except T). The PAM is initially recognized by proteins within Cascade, DNA unwinding and evaluation of the base pairing between the CRISPR RNA spacer and the protospacer. Non-functional PAMs are never bound by Cascade, resulting in Cascade ignoring protospacers that are perfectly complementary to the CRISPR RNA spacer if flanked by this PAM. PAMs can be determined through bioinformatics analysis of the natural DNA targets of CRISPR arrays or through the experimental screening of potential PAM sequences through plasmid destruction.

In representative embodiments, a spacer sequence of a Type I-B CRISPR spacer-repeat nucleic acid of the disclosure comprises at least about 25 consecutive nucleotides of a target DNA or target nucleic acid, wherein at the 3' end of the spacer at least about 10 consecutive nucleotides of the at least about 25 consecutive nucleotides comprise at least about 90% complementarity to the target nucleic acid, wherein the target nucleic acid is adjacent to a protospacer adjacent motif (PAM) sequence in the genome of a bacterium or archaeon of interest. The motif varies widely between Type I-B subtypes. For instance, the Type I-B system in *L. monocytogenes* can recognize a 3-base motif (read 5' to 3) that includes, but is not limited to, CCA, CCT, and CAA (see e.g., FIG. 12). The PAM is initially recognized by proteins within Cascade, DNA unwinding and evaluation of the base pairing between the CRISPR RNA spacer and the protospacer. Non-functional PAMs are never bound by Cascade, resulting in Cascade ignoring protospacers that are perfectly complementary to the CRISPR RNA spacer if flanked by this PAM. PAMs can be determined through bioinformatics analysis of the natural DNA targets of CRISPR arrays or through the experimental screening of potential PAM sequences through plasmid destruction.

Type I crRNA arrays can include 61-67 nucleotide (nt) spacers complementary to a DNA target, flanked by 29-32 nt repeat sequences unique to the Type I-E subtype. Transcription of the crRNA array produces pre-crRNA that is processed via cleavage of a single site in each repeat sequence. The resulting mature crRNA includes of a 5' tail, the full-length spacer, and a 3' hairpin. In some embodiments, the Type I-E CRISPRa system can include a number of crRNA, singly or in a CRISPR array. In some embodiments, the Type I-E CRISPRa system can include at least 1 crRNA, at least 2 different crRNA, at least 3 different crRNA at least 4 different crRNA, at least 5 different crRNA, at least 6 different crRNA, at least 7 different crRNA, at least 8 different crRNA, at least 9 different crRNA, at least 10 different crRNAs, at least 11 different crRNAs, at least 12 different crRNAs, at least 13 different crRNAs, at least 14 different crRNAs, at least 15 different crRNAs, at least 16 different crRNAs, at least 17 different crRNAs, at least 18 different crRNAs, at least 18 different crRNAs, at least 20 different crRNAs, at least 25 different crRNAs, at least 30 different crRNAs, at least 35 different crRNAs, at least 40 different crRNAs, at least 45 different crRNAs, or at least 50 different crRNAs. For example, the Type I-E CRISPRa system can include between at least 1 crRNA to at least 50 different crRNAs, at least 1 crRNA to at least 45 different crRNAs, at least 1 crRNA to at least 40 different crRNAs, at least 1 crRNA to at least 35 different crRNAs, at least 1 crRNA to at least 30 different crRNAs, at least 1 crRNA to at least 25 different crRNAs, at least 1 crRNA to at least 20 different crRNAs, at least 1 crRNA to at least 16 different crRNAs, at least 1 crRNA to at least 12 different crRNAs, at least 1 crRNA to at least 8 different crRNAs, at least 1 crRNA to at least 4 different crRNAs, at least 4 crRNAs to at least 50 different crRNAs, at least 4 different crRNAs to at least 45 different crRNAs, at least 4 different crRNAs to at least 40 different crRNAs, at least 4 different crRNAs to at least 35 different crRNAs, at least 4 different crRNAs to at least 30 different crRNAs, at least 4 different crRNAs to at least 25 different crRNAs, at least 4 different crRNAs to at least 20 different crRNAs, at least 4 different crRNAs to at least 16 different crRNAs, at least 4 different crRNAs to at least 12 different crRNAs, at least 4 different crRNAs to at least 8 different crRNAs, at least 8 different crRNAs to at least 50 different crRNAs, at least 8 different crRNAs to at least 45 different crRNAs, at least 8 different crRNAs to at least 40 different crRNAs, at least 8 different crRNAs to at least 35 different crRNAs, at least 8 different crRNAs to at least 30 different crRNAs, at least 8 different crRNAs to at least 25 different crRNAs, at least 8 different crRNAs to at least 20 different crRNAs, at least 8 different crRNAs to at least 16 different crRNAs, or at least 8 different crRNAs to at least 12 different crRNAs.

In another aspect, the present disclosure provides a recombinant CRISPR array comprising two or more repeat nucleotide sequences and one or more spacer nucleotide sequence(s), wherein each spacer nucleotide sequence in said CRISPR array is linked at its 5' end and at its 3' end to a repeat nucleotide sequence. Accordingly, the repeat nucleotide sequences and spacer nucleotide sequences of the CRISPR array alternate with each other, e.g., 5' to 3', repeat, spacer, repeat, and the like.

In some embodiments, the spacer sequence can be fully complementary or substantially complementary (e.g., at least about 70% complementary (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more)) to a target DNA. Thus, in some embodiments, the spacer sequence can have one, two, three, four, or five mismatches as compared to the target DNA where the mismatches can be contiguous or noncontiguous. In some embodiments, the spacer sequence can have 70% identity to a target DNA. In other embodiments, the spacer nucleotide sequence can have 80% identity to a target DNA. In still other embodiments, the spacer nucleotide sequence can have 85%, 90%, 95%, 96%, 97%, 98%, 99% identity, and the like, to a target nucleotide sequence of a target gene. In representative embodiments, the spacer sequence has 100% complementarity to the target DNA. In particular embodiments, a spacer sequence has complete identity or substantial identity over a region of a target nucleotide sequence that is at least about 25 nucleotides to about 100 nucleotides in length.

A recombinant CRISPR array of the disclosure can be of any length and include any number of spacer nucleotide sequences alternating with repeat nucleotide sequences, as described above, necessary to achieve the desired level of activation of expression (e.g., activation of transcription) of one or more target genes. In some embodiments, a CRISPR array can include 1 to about 100 spacer nucleotide sequences, each linked on its 5' end and its 3' end to a repeat nucleotide sequence. Thus, in some embodiments, a recombinant CRISPR array of the disclosure can include 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, or more, spacer nucleotide sequences.

In some embodiments, the at least one spacer nucleotide sequence can be linked at its 3' end to a repeat sequence and linked at its 5' end to about 1 to about 8, about 1 to about 10, about 1 to about 15 nucleotides from the 3' end of a repeat nucleotide sequence (e.g., a portion of a repeat nucleotide sequence). In other embodiments, the at least one spacer nucleotide sequence can be linked at its 5' end to about 2 to about 6, or about 2 to about 4 nucleotides from the 3' end of a repeat nucleotide sequence.

In representative embodiments, the recombinant CRISPR array includes two or more (e.g., 2, 3, 4, 5, 6, 7, 8, 9, 10, or more, as described herein) spacer nucleotide sequences, each spacer nucleotide sequence flanked on its 3' and its 5' end by a repeat nucleotide sequence, and the at least two of the two or more spacer nucleotide sequences of said recombinant CRISPR array can each include a nucleotide sequence that is complementary to a different target nucleotide sequence from a single target gene (e.g., a different region of the same target gene). By targeting at least two different regions of a single target gene, a CRISPR array can be used to modify activation (e.g., increase or decrease the level of activation) of the expression of said target gene. More specifically, a CRISPR array having multiple spacer nucleotide sequences each of which are complementary to a different non-overlapping target nucleotide sequence from a single gene, can provide stronger/increased activation of expression of that target gene as compared with a CRISPR array having comparatively fewer spacer nucleotide sequences each of which are complementary to different target nucleotide sequences from a single target gene. The level of transcription activation can be further modified by designing a CRISPR array having spacer nucleotide sequences that are complementary to overlapping target nucleotide sequences within the same target gene. Overlapping spacer nucleotide sequences that are complementary to overlapping target nucleotide sequences within the same target gene can result in reduced activation of expression of that target gene as compared to a CRISPR array in which the spacer nucleotide sequences are complementary to different target nucleotide sequences within the same target gene but which said target nucleotide sequences do not overlap. In some embodiments, overlapping spacer sequences have a reduced effect on activation of expression than spacer sequences that do not overlap. Without wishing to be bound to any particular theory, the overlapping sequences can compete with one another and thereby reduce the level of activation as compared with non-overlapping sequences In addition to targeting different locations/regions on a single gene to modulate the activation of that gene, the length of the spacer or its complementarity to the target nucleotide sequence can be altered to modulate activation. Thus, for example, a shorter spacers or a spacer with less complementarity to a target nucleotide sequence can result in reduced activation as compared a longer spacer and/or a spacer with greater complementarity to a target nucleotide sequence, respectively.

Accordingly, in some embodiments, activation by a spacer can be increased by adding one or more nucleotides to the length of said spacer, said spacer resulting in increased activation when used with the recombinant nucleic acids of the disclosure as compared with the same spacer but without the additional nucleotides. In some embodiments, the length of the spacer can be increased by one to about 100 nucleotides, and/or any range or value therein (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, or more). In some embodiments, the length of the spacer can be increased by about 1 to about 40, about 5 to about 30, 10 to about 30, about 20 to about 30 nucleotides. In other embodiments, the length of the spacer can be increased by about 6 nucleotides, about 8 nucleotides, about 10 nucleotides, about 12 nucleotides, about 18 nucleotides, about 24 nucleotides, and the like.

In further embodiments, activation by a spacer can be decreased by reducing the length of said spacer by one or more nucleotides, said spacer resulting in decreased activation when used with the recombinant nucleic acids of the disclosure as compared with the same spacer but without a reduced number of nucleotides. Accordingly, in some embodiments, activation by a spacer can be decreased by decreasing the length of the spacer by 1 to about 100 nucleotides, and any range or value therein. In representative embodiments, the length of the spacer can be decreased by about 1 to about 40, about 5 to about 30, 10 to about 30, about 20 to about 30 nucleotides. In other embodiments, the length of the spacer can be decreased by about 6 nucleotides, about 8 nucleotides, about 10 nucleotides, about 12 nucleotides, about 18 nucleotides, about 24 nucleotides, and the like.

In further aspects, a spacer sequence of a CRISPR array of the disclosure can be complementary to a target nucleotide sequence that is from a coding strand or a plus (top) strand and/or from a non-coding strand or a minus (bottom) strand of a double stranded target gene. As demonstrated herein, designing a recombinant CRISPR array to include spacers targeting a coding/plus strand rather than a non-coding/minus strand, and vice versa, provides further modulation of activation with targeting of coding/plus strands providing increased or greater activation as compared to targeting of non-coding/minus strands of the same target gene.

These variations of a spacer nucleotide sequence of a CRISPR array construct as described herein and other variations are possible and can be used to modify activation of expression of a target gene. Any combination of the types of spacers described herein as well as other types of spacers can be used alone or in any combination for modulating the activation of expression of a target gene.

Variations in CRISPR array design can be used to achieve a desired level of activation of expression of a target gene. In other embodiments, a recombinant CRISPR array can be designed to include at least two spacer nucleotide sequences each of which include a nucleotide sequence that is complementary to a different target nucleotide sequence from a different target gene, thereby achieving activation of expression of different target genes using a single CRISPR array. Alternatively, different genes can be targeted for activation of expression using two or more recombinant CRISPR arrays. As would be readily understood, various recombinant CRISPR array designs can be constructed and introduced into a cell or an organism in single or in multiple recombinant CRISPR array constructs for use in modulating the expression of one or more target genes in said cell or organism. Thus, for example, various combinations of different types of spacer nucleotide sequences, as described herein, can be introduced on a single recombinant CRISPR array such that expression of one or more target genes can be modulated. Alternatively, in other embodiments, various spacer nucleotide sequences can be introduced on two or more recombinant CRISPR arrays modulating expression of one or more target genes.

In some embodiments, the crRNA can target a target enhancer or a target regulatory element. In some embodiments, the target enhancer or target regulatory element controls the gene expression of several target genes. In some embodiments, the target enhancer or target regulatory element controls a cell phenotype that involves the gene expression of one or more target genes. In some embodiments, the identity of one or more of the target genes is known. In some embodiments, the identity of one or more of the target genes is unknown.

In some embodiments, the crRNA can target a target region in a cis-regulatory region or trans-regulatory region of a target gene. In some embodiments, the target region is a distal or proximal cis-regulatory region of the target gene. In some embodiments, the target region is a distal or proximal trans-regulatory region of the target gene. In some embodiments, the crRNA can target an enhancer region, a promoter region, or a transcribed region of a target gene. For example, the crRNA can target the target region of at least one of interleukin-1 receptor antagonist gene (IL1RN) or human β-globin gene (HBG).

In some embodiments, the Type I CRISPRa system can activate genes at both proximal and distal locations relative the transcriptional start site (TSS). The Type I-E CRISPRa system can target a region that is at least about 1 base pair to about 100,000 base pairs, at least about 100 base pairs to about 100,000 base pairs, at least about 250 base pairs to about 100,000 base pairs, at least about 500 base pairs to about 100,000 base pairs, at least about 1,000 base pairs to about 100,000 base pairs, at least about 2,000 base pairs to about 100,000 base pairs, at least about 5,000 base pairs to about 100,000 base pairs, at least about 10,000 base pairs to about 100,000 base pairs, at least about 20,000 base pairs to about 100,000 base pairs, at least about 50,000 base pairs to about 100,000 base pairs, at least about 75,000 base pairs to about 100,000 base pairs, at least about 1 base pair to about 75,000 base pairs, at least about 100 base pairs to about 75,000 base pairs, at least about 250 base pairs to about 75,000 base pairs, at least about 500 base pairs to about 75,000 base pairs, at least about 1,000 base pairs to about 75,000 base pairs, at least about 2,000 base pairs to about 75,000 base pairs, at least about 5,000 base pairs to about 75,000 base pairs, at least about 10,000 base pairs to about 75,000 base pairs, at least about 20,000 base pairs to about 75,000 base pairs, at least about 50,000 base pairs to about 75,000 base pairs, at least about 1 base pair to about 50,000 base pairs, at least about 100 base pairs to about 50,000 base pairs, at least about 250 base pairs to about 50,000 base pairs, at least about 500 base pairs to about 50,000 base pairs, at least about 1,000 base pairs to about 50,000 base pairs, at least about 2,000 base pairs to about 50,000 base pairs, at least about 5,000 base pairs to about 50,000 base pairs, at least about 10,000 base pairs to about 50,000 base pairs, at least about 20,000 base pairs to about 50,000 base pairs, at least about 1 base pair to about 25,000 base pairs, at least about 100 base pairs to about 25,000 base pairs, at least about 250 base pairs to about 25,000 base pairs, at least about 500 base pairs to about 25,000 base pairs, at least about 1,000 base pairs to about 25,000 base pairs, at least about 2,000 base pairs to about 25,000 base pairs, at least about 5,000 base pairs to about 25,000 base pairs, at least about 10,000 base pairs to about 25,000 base pairs, at least about 20,000 base pairs to about 25,000 base pairs, at least about 1 base pair to about 10,000 base pairs, at least about 100 base pairs to about 10,000 base pairs, at least about 250 base pairs to about 10,000 base pairs, at least about 500 base pairs to about 10,000 base pairs, at least about 1,000 base pairs to about 10,000 base pairs, at least about 2,000 base pairs to about 10,000 base pairs, at least about 5,000 base pairs to about 10,000 base pairs, at least about 1 base pair to about 5,000 base pairs, at least about 100 base pairs to about 5,000 base pairs, at least about 250 base pairs to about 5,000 base pairs, at least about 500 base pairs to about 5,000 base pairs, at least about 1,000 base pairs to about 5,000 base pairs, or at least about 2,000 base pairs to about 5,000 base pairs upstream from the TSS. The Type I-E CRISPRa system can target a region that is at least about 1 base pair, at least about 100 base pairs, at least about 500 base pairs, at least about 1,000 base pairs, at least about 1,250 base pairs, at least about 2,000 base pairs, at least about 2,250 base pairs, at least about 2,500 base pairs, at least about 5,000 base pairs, at least about 10,000 base pairs, at least about 11,000 base pairs, at least about 20,000 base pairs, at least about 30,000 base pairs, at least about 46,000 base pairs, at least about 50,000 base pairs, at least about 54,000 base pairs, at least about 75,000 base pairs, or at least about 100,000 base pairs upstream from the TSS.

In some embodiments, the Type I CRISPRa system can target a region that is at least about 1 base pair to at least about 500 base pairs, at least about 1 base pair to at least about 250 base pairs, at least about 1 base pair to at least about 200 base pairs, at least about 1 base pair to at least about 100 base pairs, at least about 50 base pairs to at least about 500 base pairs, at least about 50 base pairs to at least about 250 base pairs at least about 50 base pairs to at least about 200 base pairs, at least about 50 base pairs to at least about 100 base pairs, at least about 100 base pairs to at least about 500 base pairs, at least about 100 base pairs to at least about 250 base pairs, or at least about 100 base pairs to at least about 200 base pairs downstream from the TSS. The Type I CRISPRa system can target a region that is at least about 1 base pair, at least about 2 base pairs, at least about 3 base pairs, at least about 4 base pairs, at least about 5 base pairs, at least about 10 base pairs, at least about 15 base pairs, at least about 20 base pairs, at least about 25 base pairs, at least about 30 base pairs, at least about 40 base pairs, at least about 50 base pairs, at least about 60 base pairs, at least about 70 base pairs, at least about 80 base pairs, at least about 90 base pairs, at least about 100 base pairs, at least about 110 base pairs, at least about 120, at least about 130, at least about 140 base pairs, at least about 150 base pairs, at least about 160 base pairs, at least about 170 base pairs, at least about 180 base pairs, at least about 190 base pairs, at least about 200 base pairs, at least about 210 base pairs, at least about 220, at least about 230, at least about 240 base pairs, or at least about 250 base pairs downstream from the TSS.

In some embodiments, the Type I CRISPRa system can target and bind a target region that is on the same chromosome as the target gene but more than 100,000 base pairs upstream or more than 250 base pairs downstream from the TSS. In some embodiments, the Type I CRISPRa system can target and bind a target region that is on a different chromosome from the target gene.

Compositions for Altering Gene Expression or Genome Editing of a Target Gene

In some embodiments, the present invention is directed to compositions for altering gene expression or genome editing of a target gene in a cell. The composition can include the Type I CRISPR-based programmable system, or at least one polynucleotide sequence coding said system, as disclosed above. The composition can also include a viral delivery system. For example, the viral delivery system can include an adeno-associated virus vector or a modified lentiviral vector.

In some embodiments, the present invention is directed to compositions for gene activation. The composition can include the Type I CRISPRa system, or at least one polynucleotide sequence coding said system or components of said system, as disclosed above. The composition can also include a viral delivery system. For example, the viral delivery system can include an adeno-associated virus vector or a modified lentiviral vector.

Methods of introducing a nucleic acid into a host cell are known in the art, and any known method can be used to introduce a nucleic acid (e.g., an expression construct) into a cell. Suitable methods include, include e.g., viral or bacteriophage infection, transfection, conjugation, protoplast fusion, polycation or lipid:nucleic acid conjugates, lipofection, electroporation, nucleofection, immunoliposomes, calcium phosphate precipitation, polyethyleneimine (PEI)-mediated transfection, DEAF-dextran mediated transfection, liposome-mediated transfection, particle gun technology, calcium phosphate precipitation, direct micro injection, nanoparticle-mediated nucleic acid delivery, and the like.

The vector can be expression vectors or systems to produce protein by routine techniques and readily available starting materials including Sambrook et al., Molecular Cloning and Laboratory Manual, Second Ed., Cold Spring Harbor (1989), which is incorporated fully by reference. In some embodiments the vector can comprise the nucleic acid sequence encoding the Type I CRISPRa system, including the nucleic acid sequence encoding the Cascade polypeptides, the nucleic acid sequence encoding the Cascade fusion protein, and the nucleic acid sequence encoding the at least one crRNA.

In some embodiments, the composition can be delivered by mRNA delivery and ribonucleoprotein (RNP) complex delivery. In some embodiments, the mRNA and/or RNP can be delivered into a cell using nanoparticles, electroportation, lipid carriers, and the like. In some embodiments, the compositions are delivered by mRNA and protein/RNA complexes (Ribonucleoprotein (RNP)). For example, the purified Type I Cascade polypeptides and Cascade fusion protein can be combined with one or more crRNAs to form an RNP complex.

Constructs and Plasmids

The compositions, as described above, can comprise genetic constructs that encodes the Type I CRISPRa system, as disclosed herein. The genetic construct, such as a plasmid, expression cassette or vector, can comprise a nucleic acid that encodes the Type I CRISPRa system, or subcomponents thereof, such as the Cascade fusion protein, the Type I Cascade polypeptides, and/or crRNA. The genetic construct can be present in the cell as a functioning extrachromosomal molecule. The genetic construct can be a linear minichromosome including centromere, telomeres or plasmids or cosmids. In some embodiments, the genetic construct can include at least one polynucleotide sequence of SEQ ID NO: 1, SEQ ID NO: 2, SEQ ID NO: 3, SEQ ID NO: 4, SEQ ID NO: 5, SEQ ID NO: 6; SEQ ID NO: 7, SEQ ID NO: 8, SEQ ID NO: 163, homologues thereof, and/or combinations thereof. In some embodiments, the genetic construct can include at least one polynucleotide sequence of SEQ ID NO: 166, SEQ ID NO: 167, SEQ ID NO: 168, SEQ ID NO: 169, SEQ ID NO: 171; SEQ ID NO: 172, SEQ ID NO: 173, SEQ ID NO: 174, SEQ ID NO: 179, SEQ ID NO: 258; SEQ ID NO: 259, SEQ ID NO: 260, SEQ ID NO: 261, homologues thereof, and/or combinations thereof. In some embodiments, the genetic construct can include at least one polynucleotide sequence of SEQ ID NO: 282, SEQ ID NO: 283, SEQ ID NO: 284, SEQ ID NO: 285, SEQ ID NO: 286; SEQ ID NO: 287, SEQ ID NO: 288, SEQ ID NO: 289, SEQ ID NO: 290, SEQ ID NO: 291; SEQ ID NO: 292, SEQ ID NO: 293, SEQ ID NO: 294, SEQ ID NO: 295, SEQ ID NO: 296, SEQ ID NO: 297, homologues thereof, and/or combinations thereof.

The genetic construct can also be part of a genome of a recombinant viral vector, including recombinant lentivirus, recombinant adenovirus, recombinant adenovirus associated virus, and recombinant herpes simplex virus (HSV). The genetic construct can be part of the genetic material in attenuated live microorganisms or recombinant microbial vectors which live in cells. The compositions, as described above, can comprise genetic constructs that encodes the modified Adeno-associated virus AAV vector and a nucleic acid sequence that encodes the Type I CRISPRa system, or subcomponents thereof, as disclosed herein. In some embodiments, the compositions, as described above, can comprise genetic constructs that encodes the modified adenovirus vector and a nucleic acid sequence that encodes the Type I CRISPRa system, or subcomponents thereof, as disclosed herein. The compositions, as described above, can comprise genetic constructs that encodes the modified lentiviral vector and a nucleic acid sequence that encodes the Type I CRISPRa system, or subcomponents thereof, as disclosed herein.

The nucleic acid sequences can make up a genetic construct that can be a vector. The vector can be capable of expressing the Cascade fusion protein, the Type I Cascade polypeptides, and/or crRNA in the cell of a mammal. The vector can be recombinant. The vector can comprise heterologous nucleic acid encoding the Cascade fusion protein, the Type I Cascade polypeptides, and/or crRNA. The vector can be a plasmid. The vector can be useful for transfecting cells with nucleic acid encoding the Cascade fusion protein, the Type I Cascade polypeptides, and/or crRNA, which the transformed host cell is cultured and maintained under conditions wherein expression of the Cascade fusion protein, the Type I Cascade polypeptides, and/or crRNA takes place.

In further embodiments of the disclosure, the genetic constructs and polynucleotides comprising CRISPR arrays and/or polynucleotides encoding the Cascade fusion protein and/or the Type I Cascade polypeptides can be operatively associated with a variety of promoters, terminators and other regulatory elements for expression in various organisms or cells. In some embodiments, the genetic constructs can comprise regulatory elements for gene expression of the coding sequences of the nucleic acid. In some embodiments, the regulatory elements can be a promoter, an enhancer, an initiation codon, a stop codon, or a polyadenylation signal.

In representative embodiments, at least one promoter and/or terminator can be operably linked to a polynucleotide of the disclosure. Any promoter useful with this disclosure can be used and includes, for example, promoters functional with the organism of interest including but not limited to constitutive, inducible, developmentally regulated, and the like, as described herein. A regulatory element as used herein can be endogenous or heterologous. In some embodiments, an endogenous regulatory element derived from the subject organism can be inserted into a genetic context in which it does not naturally occur (e.g., a different position in the genome than as found in nature), thereby producing a recombinant or non-native nucleic acid. Accordingly, in representative embodiments, a nucleic acid construct encoding polypeptides of a Type I Cascade system and/or Cascade fusion protein and having a 5' end and a 3' end, can further comprise a promoter operably linked to 5' end of the at least one polynucleotide or nucleic acid construct and a polyA signal operably linked to the 3' end of the at least one polynucleotide or nucleic acid construct.

In some aspects, the polynucleotide, or polynucleotides encoding the Type I CRISPRa system that is introduced into a eukaryotic cell are operably linked to a promoter and/or to a polyA signal as known in the art. Therefore, in some aspects, the nucleic acid constructs of the disclosure encoding the polypeptides of the Type I CRISPRa system having a 5' end and a 3' end can be operably linked at the 5' end to a promoter and at the 3' end to a polyA signal. In some aspects, the nucleic acid constructs of the disclosure can comprise 2A peptide sequences and/or internal ribosomal entry sites as known in the art for assisting with transformation/transfection. In some aspects, the nucleic acid constructs of the disclosure encoding the polypeptides of the Type I CRISPRa system can be introduced into a eukaryotic cell via a plasmid, a viral vector, or a nanoparticle. In some embodiments, the polynucleotide or genetic construct encoding the Type I CRISPRa system, or subcomponents thereof, can be introduced in one construct or in different constructs.

An expression cassette also can optionally include a transcriptional and/or translational termination region (i.e., termination region) that is functional in the selected host cell. A variety of transcriptional terminators is available for use in expression cassettes and can be responsible for the termination of transcription beyond the heterologous nucleotide sequence of interest. The termination region can be native to the transcriptional initiation region, can be native to the operably linked nucleotide sequence of interest, can be native to the host cell, or can be derived from another source (i.e., foreign or heterologous to the promoter, to the nucleotide sequence of interest, to the host, or any combination thereof). In some embodiments of this disclosure, terminators can be operably linked to a recombinant polynucleotide(s) encoding the Type I CRISPRa system or subcomponents thereof.

An expression cassette also can include a nucleotide sequence encoding a selectable marker, which can be used to select a transformed host cell. As used herein, "selectable marker" means a nucleotide sequence that when expressed imparts a distinct phenotype to the host cell expressing the marker and thus allows such transformed cells to be distinguished from those that do not have the marker. Such a nucleotide sequence can encode either a selectable or screenable marker, depending on whether the marker confers a trait that can be selected for by chemical means, such as by using a selective agent (e.g., an antibiotic and the like), or whether the marker is simply a trait that one can identify through observation or testing, such as by screening (e.g., fluorescence). Of course, many examples of suitable selectable markers are known in the art and can be used in the expression cassettes described herein.

In addition to expression cassettes, the recombinant polynucleotides described herein (e.g., polynucleotides comprising a CRISPR array and polynucleotides encoding Cascade polypeptides (i.e., Type I Cascade polynucleotides) and/or a Cascade fusion protein) can be used in connection with vectors. The term "vector" refers to a composition for transferring, delivering or introducing a nucleic acid (or nucleic acids) into a cell. A vector comprises a nucleic acid molecule comprising the nucleotide sequence(s) to be transferred, delivered or introduced. Vectors for use in transformation of host organisms are well known in the art. Non-limiting examples of general classes of vectors include but are not limited to a viral vector, a plasmid vector, a phage vector, a phagemid vector, a cosmid vector, a fosmid vector, a bacteriophage, an artificial chromosome, or an *Agrobacterium* binary vector in double or single stranded linear or circular form which may or may not be self transmissible or mobilizable. A vector as defined herein can transform a eukaryotic host either by integration into the cellular genome or exist as an extrachromosomal element (e.g., minichromosome). In some embodiments, the recombinant polynucleotides described herein can be delivered as a ribonucleoprotein complex.

Additionally included are shuttle vectors by which is meant a DNA vehicle capable, naturally or by design, of replication in two different host organisms, such as broad-host plasmids or shuttle vectors with multiple origins-of-replication. In some representative embodiments, the nucleic acid in the vector is under the control of, and operably linked to, an appropriate promoter or other regulatory elements for transcription in a host cell. The vector can be a bi-functional expression vector which functions in multiple hosts. In the case of genomic DNA, this can contain its own promoter or other regulatory elements and in the case of cDNA this can be under the control of an appropriate promoter or other regulatory elements for expression in the host cell. Accordingly, a polynucleotide of this disclosure and/or expression cassettes comprising polynucleotides of this disclosure can be comprised in vectors as described herein and as known in the art. In some embodiments, the recombinant polynucleotides described herein can be delivered as a ribonucleoprotein complex.

Coding sequences can be optimized for stability and high levels of expression. In some instances, codons are selected to reduce secondary structure formation of the RNA such as that formed due to intramolecular bonding.

The vector can comprise heterologous nucleic acid encoding the Type I CRISPRa system and can further comprise an initiation codon, which can be upstream of the Type I CRISPRa system, and a stop codon, which can be downstream of the Type I CRISPRa system. The initiation and termination codon can be in frame with the Type I CRISPRa system. The vector can also comprise a promoter that is operably linked to the Type I CRISPRa system.

The vector can also comprise a polyadenylation signal, which can be downstream of the Type I CRISPRa system. The polyadenylation signal can be a SV40 polyadenylation signal, LTR polyadenylation signal, bovine growth hormone (bGH) polyadenylation signal, human growth hormone (hGH) polyadenylation signal, or human β-globin polyadenylation signal. The SV40 polyadenylation signal can be a polyadenylation signal from a pCEP4 vector (Invitrogen, San Diego, CA).

The vector can also comprise an enhancer upstream of the Type I CRISPRa system. The enhancer can be necessary for DNA expression. The enhancer can be human actin, human myosin, human hemoglobin, human muscle creatine or a viral enhancer such as one from CMV, HA, RSV or EBV. Polynucleotide function enhancers are described in U.S. Pat. Nos. 5,593,972, 5,962,428, and WO94/016737, the contents of each are fully incorporated by reference. The vector can also comprise a mammalian origin of replication in order to maintain the vector extrachromosomally and produce multiple copies of the vector in a cell. The vector can also comprise a regulatory sequence, which can be well suited for gene expression in a mammalian or human cell into which the vector is administered. The vector can also comprise a reporter gene, such as green fluorescent protein ("GFP") and/or a selectable marker, such as hygromycin ("Hygro").

Eukaryotic Promoters

Exemplary promoters useful with this disclosure include promoters functional in a eukaryote. Non-limiting examples of a eukaryote include a mammal, an insect, an amphibian, a reptile, a bird, a fish, a fungus, a plant, and/or a nematode.

In some embodiments, expression of a construct of the disclosure can be made constitutive, inducible, temporally regulated, developmentally regulated, or chemically regulated using the recombinant nucleic acid constructs of the disclosure operatively linked to the appropriate promoter functional in an organism of interest. In representative embodiments, repression can be made reversible using the recombinant nucleic acid constructs of the disclosure operatively linked to, for example, an inducible promoter functional in an organism of interest.

The choice of promoter will vary depending on the quantitative, temporal and spatial requirements for expression, and also depending on the host cell to be transformed. Promoters for many different organisms are well known in the art. Based on the extensive knowledge present in the art, the appropriate promoter can be selected for the particular host organism of interest. Thus, for example, much is known about promoters upstream of highly constitutively expressed genes in model organisms and such knowledge can be readily accessed and implemented in other systems as appropriate.

In some embodiments of the disclosure, inducible promoters can be used. Thus, for example, chemical-regulated promoters can be used to modulate the expression of a gene in an organism through the application of an exogenous chemical regulator. Regulation of the expression of nucleotide sequences of the disclosure via promoters that are chemically regulated enables the RNAs and/or the polypeptides of the disclosure to be synthesized only when, for example, an organism is treated with the inducing chemicals. Depending upon the objective, the promoter can be a chemical-inducible promoter, where application of a chemical induces gene expression, or a chemical-repressible promoter, where application of the chemical represses gene expression. In some aspects, a promoter can also include a light-inducible promoter, where application of specific wavelengths of light induce gene expression (Levskaya et al. 2005. *Nature* 438:441-442).

Exemplary promoters include, but are not limited to, promoters functional in eukaryotes including, but are not limited to, constitutive promoters, e.g., viral promoters such as CMV, SV40 and RSV promoters, as well as regulatable promoters, e.g., an inducible or repressible promoter such as the tet promoter, the hsp70 promoter and a synthetic promoter regulated by CRE, including any fragment that has promoter activity. In some embodiments, the eukaryotic promoter can include RNA polymerase III U6 promoter or CMV promoter.

Exemplary promoters can include a promoter from phosphoglycerate kinase (PGK), glyceraldehyde-3-phosphate dehydrogenase (GAP), triose phosphate isomerase (TPI), galactose-regulon (GAL1, GAL10), alcohol dehydrogenase (ADH1, ADH2), phosphatase (PHOS), copper-activated metallothionine (CUP1), MFa1, PGK/a2 operator, TPI/a2 operator, GAP/GAL, PGK/GAL, GAP/ADH2, GAP/PHOS, iso-1-cytochrome c/glucocorticoid response element (CYC/GRE), phosphoglycerate kinase/androgen response element (PGK ARE), transcription elongation factor EF-1a (TEF1), triose phosphate dehydrogenase (TDH3), phosphoglycerate kinase 1 (PGK1), pyruvate kinase 1 (PYK1), and/or hexose transporter (HXT7). The promoter can also be a tissue specific promoter, such as a muscle or skin specific promoter, natural or synthetic. Examples of such promoters are described in US Patent Application Publication No. US20040175727, the contents of which are incorporated herein in its entirety.

Nuclear Localization Signal (NLS)

In further aspects, the nucleic acid constructs of the disclosure encoding the Cascade complex can include one or more nuclear localization signals linked to the polynucleotides to move the polynucleotides from the cytoplasm into the nucleus. In some aspects, the Cascade polypeptides of the Type I CRISPR-Cas system encoded by the nucleic acid constructs of the disclosure can include separate nuclear localization signals.

Nuclear localization signal can include, but is not limited to, the NLS sequence of SV40 Large T-antigen subunit (PKKKRKV (SEQ ID NO: 155), nucleoplasmin (AVKRPAATKKAGQAKKKKLD (SEQ ID NO: 156), or fragment of nucleoplasmin (such as KRPAATKKAGQAKKKK (SEQ ID NO: 164), EGL-13 (MSRRRKANPTKLSENAKKLAKEVEN (SEQ ID NO: 157)), c-Myc (PAAKRVKLD (SEQ ID NO: 158)), TUS-protein (KLKIKRPVK (SEQ ID NO: 159)), the acidic M9 domain of hnRNP A1, the sequence KIPIK in yeast transcription repressor Mata2, the complex signals of U snRNPs, or proline-tyrosine (PY)-NLSs. Other nuclear localization sequences include VQRKRQKLMP (SEQ ID NO: 160), SKKKKTKV (SEQ ID NO: 161), and/or GRKRKKRT (SEQ ID NO: 162). In some embodiments, the nuclear localization signal is encoded by a polynucleotide sequence of CCTAAGAAGAAACGCAAAGTG (SEQ ID NO: 12), CCTAAGAAAAAGAGGAAAGTA (SEQ ID NO: 13), CCTAAGAAGAAGCGCAAGGTG (SEQ ID NO: 14), or AAGCGACCTGCCGCCACAAAGAAGGCTGGACAGGCTAAGAAGAAGAAA (SEQ ID NO: 165).

Nuclear localization signal can include, but is not limited to, the NLS sequence of SV40 Large T-antigen subunit (PKKKRKV (SEQ ID NO: 227), nucleoplasmin (AVKRPAATKKAGQAKKKKLD (SEQ ID NO: 262), or fragment of nucleoplasmin (such as KRPAATKKAGQAKKKK (SEQ ID NO: 263), EGL-13 (MSRRRKANPTKLSENAKKLAKEVEN (SEQ ID NO: 264)), c-Myc (PAAKRVKLD (SEQ ID NO: 265)), TUS-protein (KLKIKRPVK (SEQ ID NO: 266)), the acidic M9 domain of hnRNP A1, the sequence KIPIK in yeast transcription repressor Mata2, the complex signals of U snRNPs, or proline-tyrosine (PY)-NLSs. Other nuclear localization sequences include KRPAATKKAGQAKKKK (SEQ ID NO: 229), VQRKRQKLMP (SEQ ID NO: 267), SKKKKTKV (SEQ ID NO: 268), and/or GRKRKKRT (SEQ ID NO: 269). In some embodiments, the nuclear localization signal is encoded by a polynucleotide sequence of CCCAAGAAGAAGCGCAAAGTC (SEQ ID NO: 223), CCAAAGAAAAAGCGCAAGGTC (SEQ ID NO: 224), CCCAAGAAGAAACGGAAAGTC (SEQ ID NO: 225), CCGAAGAAGAAGCGGAAGGTC (SEQ ID NO: 226), or AAGCGACCTGCCGCCACAAAGAAGGCTGGACAGGCTAAGAAGAAGAAA (SEQ ID NO: 228).

Codon Optimization

In some embodiments, the polynucleotide encoding the Cascade complex comprises a polynucleotide sequence which is optimized for expression in at least one selected host. Optimized sequences include sequences which are codon optimized, i.e., codons which are employed more frequently in one organism relative to another organism, e.g., a distantly related organism, as well as modifications to add or modify Kozak sequences and/or introns, and/or to remove undesirable sequences, for instance, potential transcription factor binding sites. Such optimized sequences can provide enhanced expression, e.g., increased levels of protein expression, when introduced into a host cell. Examples of optimized sequences are disclosed in U.S. Pat. No. 7,728,118 and U.S. Pat. Appl. Publ. Nos. 2008/0070299, 2008/0090291, and 2006/0068395, each of which is incorporated by reference herein. In some embodiments, the at least one polynucleotide sequence comprises a Kozak sequence.

In some embodiments, the polynucleotide includes a nucleic acid sequence that is optimized for expression in a mammalian host cell. In some embodiments, an optimized polynucleotide no longer hybridizes to the corresponding non-optimized sequence, e.g., does not hybridize to the non-optimized sequence under medium or high stringency conditions. The term "stringency" is used in reference to the conditions of temperature, ionic strength, and the presence of other compounds, under which nucleic acid hybridizations are conducted. With "high stringency" conditions, nucleic acid base pairing will occur only between nucleic acid fragments that have a high frequency of complementary base sequences. Thus, conditions of "medium" or "low" stringency are often used when it is desired that nucleic acids that are not completely complementary to one another be hybridized or annealed together. The art knows well that numerous equivalent conditions can be employed to comprise medium or low stringency conditions.

Any polynucleotide of this disclosure (e.g., a polynucleotide encoding a Cascade polypeptide or Cascade fusion protein) can be codon optimized for expression in any species of interest. Codon optimization is well known in the art and involves modification of a nucleotide sequence for codon usage bias using species-specific codon usage tables. The codon usage tables are generated based on a sequence analysis of the most highly expressed genes for the species of interest. When the nucleotide sequences are to be expressed in the nucleus, the codon usage tables are generated based on a sequence analysis of highly expressed nuclear genes for the species of interest. The modifications of the nucleotide sequences are determined by comparing the species-specific codon usage table with the codons present in the native polynucleotide sequences. As is understood in the art, codon optimization of a nucleotide sequence results in a nucleotide sequence having less than 100% identity (e.g., 50%, 60%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, and the like) to the native nucleotide sequence but which still encodes a polypeptide having the same function as that encoded by the original nucleotide sequence. Thus, in representative embodiments of the disclosure, a polynucleotide of this disclosure can be codon optimized for expression in the particular organism/species of interest.

In some embodiments, the polynucleotide has less than 90%, e.g., less than 80%, nucleic acid sequence identity to the corresponding non-optimized sequence and optionally encodes a polypeptide having at least 60%, e.g., at least 65%, 70%, 75%, 80%, 85%, 90%, 95%, 96%, 97%, 98%, 99%, or 100%, amino acid sequence identity with the polypeptide encoded by the non-optimized sequence. Constructs, e.g., expression cassettes, and vectors comprising the isolated nucleic acid molecule, e.g., with optimized nucleic acid sequence, as well as kits comprising the isolated nucleic acid molecule, construct or vector are also provided.

A polynucleotide comprising a nucleic acid sequence encoding the Type I CRISPRa system, a subcomponent or fragment thereof or a fusion thereof, is optionally optimized for expression in a particular host cell and also optionally operably linked to transcription regulatory sequences, e.g., one or more enhancers, a promoter, a transcription termination sequence or a combination thereof, to form an expression cassette.

In some embodiments, a nucleic acid sequence encoding the Type I CRISPRa system of the disclosure, a subcomponent or fragment thereof or a fusion thereof, is optimized by replacing codons with codons which are preferentially employed in a particular (selected) cell. Preferred codons have a relatively high codon usage frequency in a selected cell, and preferably their introduction results in the introduction of relatively few transcription factor binding sites for transcription factors present in the selected host cell, and relatively few other undesirable structural attributes. In some embodiments, examples of undesirable structural attributes include, but are not limited to, restriction enzyme sites, eukaryotic sequence elements, vertebrate promoter modules and transcription factor binding sites, response elements, *E. coli* sequence elements, mRNA secondary structure. Thus, the optimized nucleic acid product can have an improved level of expression due to improved codon usage frequency, and a reduced risk of inappropriate transcriptional behavior due to a reduced number of undesirable transcription regulatory sequences.

An isolated and optimized nucleic acid molecule can have a codon composition that differs from that of the corresponding wild-type nucleic acid sequence at more than 30%, 35%, 40% or more than 45%, e.g., 50%, 55%, 60% or more of the codons. Exemplary codons for use in the disclosure are those which are employed more frequently than at least one other codon for the same amino acid in a particular organism and, in some embodiments, are also not low-usage codons in that organism and are not low-usage codons in the organism used to clone or screen for the expression of the nucleic acid molecule. Moreover, codons for certain amino acids (i.e., those amino acids that have three or more codons), can include two or more codons that are employed more frequently than the other (non-preferred) codon(s). The presence of codons in the nucleic acid molecule that are employed more frequently in one organism than in another organism results in a nucleic acid molecule which, when introduced into the cells of the organism that employs those codons more frequently, is expressed in those cells at a level that is greater than the expression of the wild-type or parent nucleic acid sequence in those cells.

In some embodiments of the disclosure, the codons that are different are those employed more frequently in a mammal, while in still other embodiments, the codons that are different are those employed more frequently in a plant. Preferred codons for different organisms are known to the art. A particular type of mammal, e.g., a human, can have a different set of preferred codons than another type of mammal. Likewise, a particular type of plant can have a different set of preferred codons than another type of plant. In one embodiment of the disclosure, the majority of the codons that differ are ones that are preferred codons in a desired host cell. Preferred codons for organisms including mammals (e.g., humans) and plants are known to the art (e.g., Wada et al., Nucl. Acids Res., 18:2367 (1990); Murray et al., Nucl. Acids Res., 17:477 (1989)). In some embodiments, the sequences can be optimized using a computer programs such as those provided by ATUM/DNA2.0.

Modified Lentiviral Vector

The compositions for gene activation can include a modified lentiviral vector. The modified lentiviral vector can include one or more polynucleotide sequences encoding Cascade proteins and a separate polynucleotide sequence encoding at least one crRNA. The modified lentiviral vector can include a first polynucleotide sequence encoding a Type I CRISPRa system and a second polynucleotide sequence encoding at least one crRNA. The one or more polynucleotide sequences can be operably linked to a eukaryotic promoter. The promoter can be a constitutive promoter, an inducible promoter, a repressible promoter, or a regulatable promoter.

The modified lentiviral vector can include a multicistronic polynucleotide sequence. In some embodiments, the multicistronic polynucleotide sequence includes polynucleotide sequences encoding two or more Cascade polypeptides. The coding sequences can be separated by at least one 2A peptide or IRES. For example, the multicistronic polynucleotide can include between 2 and 6, between 2 and 5, between 2 and 4, between 3 and 6, between 3 and 5, or between 4 and 6 Cascade polypeptides each separated by at least one 2A peptide or IRES. In some embodiments, the modified lentiviral vector can include a first polynucleotide sequence that encodes a Cascade polypeptides and/or a Cascade fusion protein. In some embodiments, the modified lentiviral vector can include a polynucleotide sequence of SEQ ID NO: 1, SEQ ID NO: 2, SEQ ID NO: 3, SEQ ID NO: 4, SEQ ID NO: 5, SEQ ID NO: 6, SEQ ID NO: 7, or SEQ ID NO: 8, SEQ ID NO: 163, homologues thereof, or combinations thereof. In some embodiments, the modified lentiviral vector can include a polynucleotide sequence of SEQ ID NO: 166, SEQ ID NO: 167, SEQ ID NO: 168, SEQ ID NO: 169, SEQ ID NO: 171; SEQ ID NO: 172, SEQ ID NO: 173, SEQ ID NO: 174, SEQ ID NO: 179, SEQ ID NO: 258; SEQ ID NO: 259, SEQ ID NO: 260, SEQ ID NO: 261, homologues thereof, or combinations thereof.

In some embodiments, a second polynucleotide sequence can encode at least 1 crRNA. For example, the second polynucleotide sequence can encode at least 1 crRNA, at least 2 crRNAs, at least 3 crRNAs, at least 4 crRNAs, at least 5 crRNAs, at least 6 crRNAs, at least 7 crRNAs, at least 8 crRNAs, at least 9 crRNAs, at least 10 crRNAs, at least 11 crRNA, at least 12 crRNAs, at least 13 crRNAs, at least 14 crRNAs, at least 15 crRNAs, at least 16 crRNAs, at least 17 crRNAs, at least 18 crRNAs, at least 19 crRNAs, at least 20 crRNAs, at least 25 crRNA, at least 30 crRNAs, at least 35 crRNAs, at least 40 crRNAs, at least 45 crRNAs, or at least 50 crRNAs. In some embodiments, the second polynucleotide sequence can encode between 1 crRNA and 50 crRNAs, between 1 crRNA and 45 crRNAs, between 1 crRNA and 40 crRNAs, between 1 crRNA and 35 crRNAs, between 1 crRNA and 30 crRNAs, between 1 crRNA and 25 different crRNAs, between 1 crRNA and 20 crRNAs, between 1 crRNA and 16 crRNAs, between 1 crRNA and 8 different crRNAs, between 4 different crRNAs and 50 different crRNAs, between 4 different crRNAs and 45 different crRNAs, between 4 different crRNAs and 40 different crRNAs, between 4 different crRNAs and 35 different crRNAs, between 4 different crRNAs and 30 different crRNAs, between 4 different crRNAs and 25 different crRNAs, between 4 different crRNAs and 20 different crRNAs, between 4 different crRNAs and 16 different crRNAs, between 4 different crRNAs and 8 different crRNAs, between 8 different crRNAs and 50 different crRNAs, between 8 different crRNAs and 45 different crRNAs, between 8 different crRNAs and 40 different crRNAs, between 8 different crRNAs and 35 different crRNAs, between 8 different crRNAs and 30 different crRNAs, between 8 different crRNAs and 25 different crRNAs, between 8 different crRNAs and 20 different crRNAs, between 8 different crRNAs and 16 different crRNAs, between 16 different crRNAs and 50 different crRNAs, between 16 different crRNAs and 45 different crRNAs, between 16 different crRNAs and 40 different crRNAs, between 16 different crRNAs and 35 different crRNAs, between 16 different crRNAs and 30 different crRNAs, between 16 different crRNAs and 25 different crRNAs, or between 16 different crRNAs and 20 different crRNAs. In some embodiments, each of the polynucleotide sequences encoding the different crRNAs can be operably linked to a promoter. In some embodiments, the promoters that are operably linked to the different crRNAs can be the same promoter. In some embodiments, the promoters that are operably linked to the different crRNAs can be different promoters. The promoter can be a constitutive promoter, an inducible promoter, a repressible promoter, or a regulatable promoter. At least one crRNA can bind to a target gene or loci. If more than one crRNA is included, each of the crRNAs binds to a different target region within one target loci or each of the crRNA binds to a different target region within different gene loci.

Adeno-Associated Virus Vectors

In some embodiments, AAV can be used to deliver the compositions to the cell using various construct configurations. For example, AAV can deliver genetic constructs encoding Cascade polypeptides, Cascade fusion protein, and/or crRNA expression cassettes on separate vectors. The composition, as described above, includes a modified adeno-associated virus (AAV) vector. The modified AAV vector can be capable of delivering and expressing the site-specific nuclease in the cell of a mammal. For example, the modified AAV vector can be an AAV-SASTG vector (Piacentino et al. (2012) Human Gene Therapy 23:635-646). The modified AAV vector can be based on one or more of several capsid types, including AAV1, AAV2, AAV5, AAV6, AAV8, and AAV9. The modified AAV vector can be based on AAV2 pseudotype with alternative muscle-tropic AAV capsids, such as AAV2/1, AAV2/6, AAV2/7, AAV2/8, AAV2/9, AAV2.5 and AAV/SASTG vectors that efficiently transduce skeletal muscle or cardiac muscle by systemic and local delivery (Seto et al. Current Gene Therapy (2012) 12:139-151).

Target Genes

The Type I CRISPR-based programmable system can be designed to target any target gene or gene of interest. The Type I CRISPRa system can be designed to target and activate the expression of any target gene or gene of interest. In some embodiments, the target gene can be an endogenous gene or a transgene. In some embodiments, the target nucleotide sequence or target DNA is located adjacent to or flanked by a PAM (protospacer adjacent motif). In some embodiments, the target region is located on a different chromosome as the target gene.

In some embodiments, the crRNA targets the Cascade complex to the target gene or target nucleotide sequence. In some embodiments, the Type I CRISPRa system can include more than 1 crRNA that targets the target gene or target nucleotide sequence. In some embodiments, the Type I CRISPRa system can include more than 1 different crRNAs that targets the target gene or target nucleotide sequence. In some embodiments, the different crRNAs bind to different target regions. For example, the different crRNAs can bind to target regions of different target genes and the expression of two or more target genes are activated. Alternatively, the different crRNAs can bind to target regions of the same target gene and the expression of the target gene is activated.

In some embodiments, a target nucleotide sequence or target DNA can be in the genome of a eukaryotic cell (e.g., in a chromosome of the eukaryotic cell) or can be on an extrachromosomal element residing in the cell. In some aspects, the target nucleotide sequence or target DNA can be that of an infectious agent residing in the eukaryotic cell, as either incorporated into the chromosome of the eukaryotic cell or as, for example, an extrachromosomal element in the eukaryotic cell (e.g., a virus). In representative embodiments, the target nucleotide sequence or target DNA can be unique to a eukaryotic cell type (e.g., a mutation in a cancer cell), or unique to a species, genus, family or kingdom (e.g., a virus infecting a eukaryotic cell). In some embodiments, the target nucleotide sequence comprises all or a part of a nucleotide sequence encoding a promoter region of a gene or a complement thereof, or an enhancer region of a gene or a complement thereof.

In some embodiments, the crRNA targets a target nucleotide sequence comprising a polynucleotide sequence of any one of SEQ ID NOs: 105-122, or combinations thereof. In some embodiments, the crRNA targets a target nucleotide sequence comprising a polynucleotide sequence of any one of SEQ ID NOs: 198-214, or combinations thereof. In some embodiments, the crRNA targets a target nucleotide sequence comprising a polynucleotide sequence of any one of SEQ ID NOs: 276-281, or combinations thereof. In some embodiments, the target gene can be interleukin-1 receptor antagonist gene (IL1RN) or human β-globin gene (HBG).

Methods of Uses

Potential applications of the compositions are diverse across many areas of science and biotechnology. The disclosed compositions can be used to modulate mammalian gene expression, such as activate gene expression. The disclosed compositions can be used to transdifferentiate or induce the differentiation of a cell by activating gene expression. Examples of activation of genes related to cell and gene therapy, genetic reprogramming, and regenerative medicine are provided. RNA-guided transcriptional activators can be used to reprogram cell lineage specification. Activation of endogenous genes encoding the key regulators of cell fate, rather than forced overexpression of these factors, can potentially lead to more rapid, efficient, stable, or specific methods for genetic reprogramming, transdifferentiation, and/or induced differentiation. The present disclosure finds use in agricultural, veterinary and medical applications as well as research applications.

Methods of Activating Gene Expression

In some embodiments, the present disclosure provides a method for activating the expression of a target gene, such as an endogenous eukaryotic gene, based on targeting a transcriptional activator to promoters via RNA using a Type I CRISPRa system, as described above. Cascade functions with the crRNA to locate and bind to a complimentary DNA target sequence. Transcriptional regulation can be enhanced by generating various fusions on the Cascade molecules with domains having transcription activation activity. This is fundamentally different from previously described methods based on engineering sequence-specific DNA-binding proteins and can provide opportunities for targeted gene regulation. The crRNAs can also be transfected directly to cells following in vitro transcription. Multiple crRNAs can target a single promoter or simultaneous target multiple promoters. In some embodiments, the Type I CRISPRa system can be used for targeted multiplexed transactivation of different genes. In some embodiments, the Type I CRISPRa system can be used to activate IL1RN and HBG genes. Recognition of genomic target sites with RNAs, rather than proteins, can also circumvent limitations of targeting epigenetically modified sites, such as methylated DNA.

In some embodiments, the method can include administering to a cell or subject a Type I CRISPRa system, or a polynucleotide or vector encoding said Type I CRISPRa system, as described above. The method can include administering a Type I CRISPRa system, such as administering Cascade polypeptides, a Cascade fusion protein containing transcription activation domain, and/or crRNA, or a nucleotide sequence encoding said Cascade polypeptides, a Cascade fusion protein containing transcription activation domain, and/or crRNA.

In some embodiments, the present disclosure also provides a method of activating the expression of a target gene in a cell, such as a eukaryotic cell, the method comprising introducing to a cell: (a) at least one polynucleotide sequence encoding a Cascade complex comprising three or more Cascade polypeptides of a Type I CRISPR/Cas system, or functional fragments thereof, and/or (b) at least one crRNA. In some embodiments, at least one Cascade polypeptide is fused to a second polypeptide domain having transcription activation activity thereby generating a Cascade polypeptide fusion protein. In some embodiments, the crRNA targets a target nucleotide sequence from the at least one target gene. In some embodiments, the at least one polynucleotide sequence is operably linked to a eukaryotic promoter, comprises a nuclear localization signal, and is codon-optimized for expression in a eukaryotic host cell. In some embodiments, the at least one Cascade polypeptide in the Cascade polypeptide fusion protein is Cas5, Cas6, Cas7, or Cas8b2.

In some embodiments, the Cascade complex can include a Cas5 polypeptide encoded by a polynucleotide sequence of SEQ ID NO: 166 or 258, a Cas7 polypeptide encoded by a polynucleotide sequence of SEQ ID NO: 168 or 260, a Cas8b2 polypeptide encoded by a polynucleotide sequence of SEQ ID NO: 169 or 261, and/or a Cas6-p300 fusion protein encoded by a polynucleotide sequence of SEQ ID NO: 174.

In some embodiments, the Cascade complex can include a Cas6 polypeptide encoded by a polynucleotide sequence of SEQ ID NO: 167 or 259, a Cas7 polypeptide encoded by a polynucleotide sequence of SEQ ID NO: 168 or 260, a Cas8b2 polypeptide encoded by a polynucleotide sequence of SEQ ID NO: 169 or 261, and/or a Cas5-p300 protein encoded by a polynucleotide sequence of SEQ ID NO: 171.

In some embodiments, the Cascade complex can include a Cas5 polypeptide encoded by a polynucleotide sequence of SEQ ID NO: 166 or 258, a Cas6 polypeptide encoded by a polynucleotide sequence of SEQ ID NO: 167 or 259, a Cas8b2 polypeptide encoded by a polynucleotide sequence of SEQ ID NO: 169 or 261, and/or a Cas7 fusion protein encoded by a polynucleotide sequence of SEQ ID NO: 172.

In some embodiments, the Cascade complex can include a Cas5 polypeptide encoded by a polynucleotide sequence of SEQ ID NO: 166 or 258, a Cas6 polypeptide encoded by a polynucleotide sequence of SEQ ID NO: 167 or 259, a Cas7 polypeptide encoded by a polynucleotide sequence of SEQ ID NO: 168 or 260, and/or a Cas8b2 fusion protein encoded by a polynucleotide sequence of SEQ ID NO: 173.

In some embodiments, the method can include introducing to the cell in step (a): a Cas5 expression vector or cassette comprising a polynucleotide sequence encoding a Cas5 polypeptide, a Cas6 expression vector or cassette comprising a polynucleotide sequence encoding a Cas6 polypeptide, a Cas7 expression vector or cassette comprising a polynucleotide sequence encoding a Cas7 polypeptide, a Cas8b2 expression vector or cassette comprising a polynucleotide sequence encoding a Cas8b2 polypeptide, or a combination thereof, and a Cas5 fusion expression vector or cassette comprising a polynucleotide sequence encoding a Cas5 fusion protein, a Cas6 fusion expression vector or cassette comprising a polynucleotide sequence encoding a Cas6 fusion protein, a Cas7 fusion expression vector or cassette comprising a polynucleotide sequence encoding a Cas7 fusion protein, or a Cas8b2 fusion expression vector or cassette comprising a polynucleotide sequence encoding a Cas8b2 fusion protein.

In some embodiments, the Cas5 expression vector or cassette or Cas5 fusion expression vector or cassette, the Cas6 expression vector or cassette or Cas6 fusion expression vector or cassette, the Cas7 expression vector or cassette or Cas7 fusion expression vector or cassette, and/or the Cas8b2 expression vector or cassette or Cas8b2 fusion expression vector or cassette are administered to the cell in a ratio of 50-150:50-150:60-185:50-15, respectively.

In some embodiments, the Cas5 expression vector or cassette or Cas5 fusion expression vector or cassette, the Cas6 expression vector or cassette or Cas6 fusion expression vector or cassette, the Cas7 expression vector or cassette or Cas7 fusion expression vector or cassette, and/or the Cas8b2 expression vector or cassette or Cas8b2 fusion expression vector or cassette are administered to the cell in a ratio of: 75 of the Cas5 expression vector or cassette or Cas5 fusion expression vector or cassette:150 of the Cas6 expression vector or cassette or Cas6 fusion expression vector or cassette:150 of the Cas7 expression vector or cassette or Cas7 fusion expression vector or cassette:50 of the Cas8b2 expression vector or cassette or Cas8b2 fusion expression vector or cassette; 60 of the Cas5 expression vector or cassette or Cas5 fusion expression vector or cassette:185 of the Cas6 expression vector or cassette or Cas6 fusion expression vector or cassette:130 of the Cas7 expression vector or cassette or Cas7 fusion expression vector or cassette:150 of the Cas8b2 expression vector or cassette or Cas8b2 fusion expression vector or cassette; 75 of the Cas5 expression vector or cassette or Cas5 fusion expression vector or cassette:150 of the Cas6 expression vector or cassette or Cas6 fusion expression vector or cassette:50:150 of the Cas8b2 expression vector or cassette or Cas8b2 fusion expression vector or cassette or 150 the Cas5 expression vector or cassette or Cas5 fusion expression vector or cassette:100 of the Cas6 expression vector or cassette or Cas6 fusion expression vector or cassette:50 of the Cas7 expression vector or cassette or Cas7 fusion expression vector or cassette:100 of the Cas8b2 expression vector or cassette or Cas8b2 fusion expression vector or cassette.

In some embodiments, the method comprises introducing to the cell in step (b) a crRNA expression vector or cassette comprising the crRNA sequence.

In some embodiments, the Cas5 expression vector or cassette or Cas5 fusion expression vector or cassette, the Cas6 expression vector or cassette or Cas6 fusion expression vector or cassette, the Cas7 expression vector or cassette or Cas7 fusion expression vector or cassette, the Cas8b2 expression vector or cassette or Cas8b2 fusion expression vector or cassette, and the crRNA expression vector or cassette are administered to the cell in a ratio of 50-150: 50150:60-185:50-15: 50-150, respectively.

In some embodiments, the Cas5 expression vector or cassette or Cas5 fusion expression vector or cassette, the Cas6 expression vector or cassette or Cas6 fusion expression vector or cassette, the Cas7 expression vector or cassette or Cas7 fusion expression vector or cassette, the Cas8b2 expression vector or cassette or Cas8b2 fusion expression vector or cassette, and the crRNA expression vector or cassette are administered to the cell in a ratio of:

75 of the Cas5 expression vector or cassette or Cas5 fusion expression vector or cassette:150 of the Cas6 expression vector or cassette or Cas6 fusion expression vector or cassette:150 of the Cas7 expression vector or cassette or Cas7 fusion expression vector or cassette:50 of the Cas8b2 expression vector or cassette or Cas8b2 fusion expression vector or cassette:100 of the crRNA expression vector or cassette; 60 of the Cas5 expression vector or cassette or Cas5 fusion expression vector or cassette:185 of the Cas6 expression vector or cassette or Cas6 fusion expression vector or cassette:130 of the Cas7 expression vector or cassette or Cas7 fusion expression vector or cassette:150 of the Cas8b2 expression vector or cassette or Cas8b2 fusion expression vector or cassette:100 of the crRNA expression vector or cassette; 75 of the Cas5 expression vector or cassette or Cas5 fusion expression vector or cassette:150 of the Cas6 expression vector or cassette or Cas6 fusion expression vector or cassette:50:150 of the Cas8b2 expression vector or cassette or Cas8b2 fusion expression vector or cassette:100 of the crRNA expression vector or cassette; or 150 of the Cas5 expression vector or cassette or Cas5 fusion expression vector or cassette:100 of the Cas6 expression vector or cassette or Cas6 fusion expression vector or cassette:50 of the Cas7 expression vector or cassette or Cas7 fusion expression vector or cassette:100 of the Cas8b2 expression vector or cassette or Cas8b2 fusion expression vector or cassette:100 of the crRNA expression vector or cassette.

Methods of Repressing Gene Expression

The present disclosure provides a method for repressing the expression of a target gene, such as an endogenous eukaryotic gene, based on targeting a transcriptional repressor to promoters via RNA using a Type I CRISPR-based programmable system, as described above. Cascade functions with the crRNA to locate and bind to a complimentary DNA target sequence. Transcriptional regulation can be enhanced by generating various fusions on the Cascade molecules with domains having transcription repressor activity. This is fundamentally different from previously described methods based on engineering sequence-specific DNA-binding proteins and can provide opportunities for targeted gene regulation. The crRNAs can also be transfected directly to cells following in vitro transcription. Multiple crRNAs can target a single promoter or simultaneous target multiple promoters. Recognition of genomic target sites with RNAs, rather than proteins, can also circumvent limitations of targeting epigenetically modified sites, such as methylated DNA.

The method can include administering to a cell or subject a Type I CRISPR-based programmable system, or a polynucleotide or vector encoding said Type I CRISPR-based programmable system, as described above. The method can include administering a Type I CRISPR-based programmable system, such as administering Cascade polypeptides, a Cascade polypeptide fusion protein containing transcription activation domain, and/or crRNA, or a nucleotide sequence encoding said Cascade polypeptides, a Cascade polypeptide fusion protein containing transcription activation domain, and/or crRNA.

Methods of Gene Editing

In some embodiments, the present disclosure provides a method of editing a target gene, such as an endogenous eukaryotic gene, based on targeting a nuclease to a target region in the target gene via RNA using a Type I CRISPR-based programmable system, as described above, in which the Cascade polypeptide fusion protein includes a site-specific nuclease (a Type I CRISPR-nuclease system). In some embodiments, the Type I CRISPR-nuclease system can be used to introduce site-specific double strand breaks or single strand breaks at targeted genomic loci. Site-specific double-strand breaks are created when the Type I CRISPR-nuclease system binds to a target DNA sequences, thereby permitting cleavage of the target DNA. This DNA cleavage may stimulate the natural DNA-repair machinery, leading to one of two possible repair pathways: homology-directed repair (HDR) or the non-homologous end joining (NHEJ) pathway.

In some embodiments, the present disclosure is directed to genome editing with a Type I CRISPR-nuclease system without a repair template, which can efficiently correct the reading frame and restore the expression of a functional protein involved in a genetic disease. The disclosed Type I CRISPR-nuclease system may involve using homology-directed repair or nuclease-mediated non-homologous end joining (NHEJ)-based correction approaches, which enable efficient correction in proliferation-limited primary cell lines that may not be amenable to homologous recombination or selection-based gene correction. This strategy integrates the rapid and robust assembly of active site-specific nucleases with an efficient gene editing method for the treatment of genetic diseases caused by mutations in nonessential coding regions that cause frameshifts, premature stop codons, aberrant splice donor sites or aberrant splice acceptor sites.

Combination with dCas9

A Cas9 protein is an endonuclease that cleaves nucleic acid and is encoded by the CRISPR loci and is involved in the Type II CRISPR system. In some embodiments, the methods described above can further include introducing to the cell an inactivated Cas9 protein (such as dCas9 protein), or a polynucleotide sequence encoding an inactivated Cas9 protein, and a gRNA.

The Cas9 protein can be from any bacterial or archaea species, such as *Streptococcus pyogenes, Streptococcus thermophiles*, or *Neisseria meningitides*. The Cas9 protein can be mutated so that the nuclease activity is inactivated. In some embodiments, an inactivated Cas9 protein from *Streptococcus pyogenes* can be used. In some embodiments, the inactivate Cas9 protein is dCas9 (SEQ ID NO: 10), which is a Cas9 protein that has the amino acid substitutions D10A and H840A and has its nuclease activity inactivated.

In some embodiments, the gRNA provides the targeting of the Cas9 to a target region, target nucleotide sequence, or target DNA. The gRNA is a fusion of two noncoding RNAs: a crRNA and a tracrRNA. In some embodiments, the gRNA can target any desired DNA sequence by exchanging the sequence encoding a 20 bp protospacer which confers targeting specificity through complementary base pairing with the desired DNA target. In some embodiments, the gRNA mimics the naturally occurring crRNA:tracrRNA duplex involved in the Type II Effector system. This duplex, which can include, for example, a 42-nucleotide crRNA and a 75-nucleotide tracrRNA, acts as a guide for the Cas9.

In some embodiments, the gRNA can target and bind a target region of a target gene or target nucleotide sequence. In some embodiments, the gRNA can target the same target region or target nucleotide sequence as the crRNA. In some embodiments, the gRNA can target a different target region or different target nucleotide sequence from the crRNA. In some embodiments, the gRNA can target a region or target nucleotide sequence that is at least about 1 base pair to about 5,000 base pairs, at least about 1 base pair to about 1,000 base pairs, at least about 1 base pair to about 500 base pairs, at least about 1 base pair to about 100 base pairs, at least about 1 base pair to about 50 base pairs, at least about 1 base pair to about 25 base pairs, at least about 1 base pair to about 15 base pairs, or at least about 1 base pair to about 10 base pairs upstream or downstream from the target region or target nucleotide sequence of the crRNA. In some embodiments, the gRNA can target a region at least about 1 base pair, at least about 5 base pairs, at least about 10 base pairs, at least about 15 base pairs, at least about 20 base pairs, at least about 25 base pairs, at least about 30 base pairs, at least about 35 base pairs, at least about 40 base pairs, at least about 45 base pairs, at least about 50 base pairs, at least about 55 base pairs, at least about 60 base pairs, at least about 65 base pairs, at least about 70 base pairs, at least about 75 base pairs, at least about 80 base pairs, at least about 85 base pairs, at least about 90 base pairs, at least about 95 base pairs, at least about 100 base pairs, at least about 150 base pairs, at least about 200 base pairs, at least about 250 base pairs, at least about 300 base pairs, at least about 400 base pairs, at least about 500 base pairs, at least about 600 base pairs, at least about 700 base pairs, at least about 800 base pairs, at least about 900 base pairs, or at least about 100 base pairs upstream or downstream from the target region or target nucleotide sequence of the crRNA.

In some embodiments, at least one gRNA can target and bind a target region or target nucleotide sequence. In some embodiments, between 1 and 20 gRNAs can be used. For example, between 1 gRNA and 20 gRNAs, between 1 gRNA and 15 gRNAs, between 1 gRNA and 10 gRNAs, between 1 gRNA and 5 gRNAs, between 2 gRNAs and 20 gRNAs, between 2 gRNAs and 15 gRNAs, between 2 gRNAs and 10 gRNAs, between 2 gRNAs and 5 gRNAs, between 5 gRNAs and 20 gRNAs, between 5 gRNAs and 15 gRNAs, or between 5 gRNAs and 10 gRNAs are activated by at least one gRNA. In some embodiments, at least 1 gRNA, at least 2 gRNAs, at least 3 gRNAs, at least 4 gRNAs, at least 5 gene, at least 6 gRNAs, at least 7 gRNAs, at least 8 gRNAs, at least 9 gene, at least 10 gRNAs, at least 11 gRNAs, at least 12 gRNAs, at least 13 gene, at least 14 gRNAs, at least 15 gRNAs, or at least 20 gRNAs can be used.

In some embodiments, the dCas9 protein comprises an amino acid sequence of SEQ ID NO: 10 and the gRNA comprises a polynucleotide sequences corresponding to SEQ ID NO: 67, SEQ ID NO: 68, SEQ ID NO: 69, or SEQ ID NO 70.

Methods of Treating a Disease

In some embodiments, the present disclosure is directed to a method of treating a subject in need thereof. In some embodiments, the subject can have a disease, such as a disease selected from a variety of acute and chronic diseases including but not limited to genetic, degenerative, or autoimmune diseases and obesity related conditions. In some embodiments, the method comprises administering to a tissue of a subject the Type I CRISPRa system, or polynucleotide encoding said system, in a eukaryotic cell or subject, as described above. In some embodiments, the Type I CRISPRa system can be used to activate genes that compensate for genetic defects. In some embodiments, the Type I CRISPRa system can be used in ex vivo cell engineering for cell therapy application. The disease can be a genetic disease, an infectious disease cause by an infectious agent, a viral infection, or cancer.

"Effective amount" as used herein refers to an amount of a nucleic acid construct, CRISPR array, and optionally, a template, or a protein-RNA complex of the disclosure that is sufficient to produce a desired effect, which can be a therapeutic and/or beneficial effect. The effective amount will vary with the age, general condition of the subject, the severity of the condition being treated, the particular agent administered, the duration of the treatment, the nature of any concurrent treatment, the pharmaceutically acceptable carrier used, and like factors within the knowledge and expertise of those skilled in the art. As appropriate, an "effective amount" in any individual case can be determined by one of skill in the art by reference to the pertinent texts and literature and/or by using routine experimentation. In representative embodiments, an effective amount of a nucleic acid construct, CRISPR array, and optional templates, or a protein-RNA complex of the disclosure can be about 1 nM to 10 μM. In representative embodiments, an effective amount can be an amount that reduces the amount of cancer cells in a eukaryotic organism by about 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, or 100%, and any value or range therein. In some embodiments, an effective amount can be an amount that reduces the amount of an infectious agent (e.g., a virus) in or on a eukaryotic organism by about 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, or 100%, and any value or range therein.

A "therapeutically effective" amount as used herein is an amount that provides some improvement or benefit to the subject. Alternatively stated, a "therapeutically effective" amount is an amount that will provide some alleviation, mitigation, or decrease in at least one clinical symptom in the subject. Those skilled in the art will appreciate that the therapeutic effects need not be complete or curative, as long as some benefit is provided to the subject. In some embodiments, a therapeutically effective amount of an at least one polynucleotide or nucleic acid construct and a crRNA or CRISPR array of the disclosure can be about 1 nM to 10 μM. In representative embodiments, a therapeutically effective amount can be an amount that reduces the amount of an infectious agent (e.g., a virus) in or on a eukaryotic organism by about 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, or 100%, and any value or range therein. In additional representative embodiments, an therapeutically effective amount can be an amount that reduces the amount of cancer cells in a eukaryotic organism by about 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, or 100%, and any value or range therein.

Further, with respect to an infection, a disease or a condition, the terms "treat," "treating," or "treatment of" and the like refer to, e.g., elimination of or a decrease in the presence or amount of, for example, a virus, cells comprising viral DNA or cancer cells in a subject. Thus, by treating the infection, disease, and/or condition in the subject, the infection, disease, and/or condition is ameliorated, alleviated, severity reduced, symptoms reduced and the like as compared to a similar subject not treated with the chimeric constructs of this disclosure, thereby treating the infection, disease and/or condition. In some embodiments, the presence of a virus, cancer cell, or cell comprising viral DNA can be reduced by about 10% to about 100% (e.g., 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, or 100%, or any value or range therein) following introduction of an at least one polynucleotide or nucleic acid construct and a crRNA or CRISPR array of this disclosure.

In some embodiments, a subject in need of treatment can be identified by, for example, well-established hallmarks of an infection, such as fever, pulse, culture of organisms, and the like, or a subject can be treated prior to infection to prevent or reduce the likelihood of infection in the subject.

Pharmaceutical Compositions

In some embodiments, the composition can be in a pharmaceutical composition. The pharmaceutical composition can comprise about 1 ng to about 10 mg of DNA encoding the Type I CRISPRa system or Type I CRISPRa system protein component. The pharmaceutical composition can comprise about 1 ng to about 10 mg of the expression cassette, vector or host cell, as described above. The pharmaceutical composition can comprise about 1 ng to about 10 mg of the DNA of the modified lentiviral vector. The pharmaceutical compositions according to the present disclosure are formulated according to the mode of administration to be used. In cases where pharmaceutical compositions are injectable pharmaceutical compositions, they are sterile, pyrogen free and particulate free. An isotonic formulation is preferably used. Generally, additives for isotonicity can include sodium chloride, dextrose, mannitol, sorbitol and lactose. In some cases, isotonic solutions such as phosphate buffered saline are preferred. Stabilizers include gelatin and albumin. In some embodiments, a vasoconstriction agent is added to the formulation.

In some embodiments, the composition can further comprise a pharmaceutically acceptable excipient. The pharmaceutically acceptable excipient can be functional molecules as vehicles, adjuvants, carriers, or diluents. The pharmaceutically acceptable excipient can be a transfection facilitating agent, which can include surface active agents, such as immune-stimulating complexes (ISCOMS), Freunds incomplete adjuvant, LPS analog including monophosphoryl lipid A, muramyl peptides, quinone analogs, vesicles such as squalene and squalene, hyaluronic acid, lipids, liposomes, calcium ions, viral proteins, polyanions, polycations, or nanoparticles, or other known transfection facilitating agents.

The transfection facilitating agent is a polyanion, polycation, including poly-L-glutamate (LGS), or lipid. The transfection facilitating agent is poly-L-glutamate, and more preferably, the poly-L-glutamate is present in the composition of the present disclosure at a concentration less than 6 mg/ml. The transfection facilitating agent can also include surface active agents such as immune-stimulating complexes (ISCOMS), Freunds incomplete adjuvant, LPS analog including monophosphoryl lipid A, muramyl peptides, quinone analogs and vesicles such as squalene and squalene, and hyaluronic acid can also be used administered in conjunction with the genetic construct. In some embodiments, the DNA vector encoding the composition can also include a transfection facilitating agent such as lipids, liposomes, including lecithin liposomes or other liposomes known in the art, as a DNA-liposome mixture (see for example WO9324640), calcium ions, viral proteins, polyanions, polycations, or nanoparticles, or other known transfection facilitating agents. Preferably, the transfection facilitating agent is a polyanion, polycation, including poly-L-glutamate (LGS), or lipid.

As a further aspect, the disclosure provides pharmaceutical compositions and methods of administering the same to treat viral infections or-cancer. The pharmaceutical composition can comprise any of the reagents discussed above in a pharmaceutically acceptable carrier.

By "pharmaceutically acceptable" it is meant a material that is not biologically or otherwise undesirable, i.e., the material can be administered to a subject without causing any undesirable biological effects such as toxicity.

The compositions of the disclosure can optionally comprise medicinal agents, pharmaceutical agents, carriers, adjuvants, dispersing agents, diluents, and the like.

In some embodiments, the nucleic acid constructs, CRISPR arrays, templates and/or protein-RNA complexes of the disclosure can be formulated for administration in a pharmaceutical carrier in accordance with known techniques. See, e.g., Remington, *The Science and Practice of Pharmacy* ($21^{th}$ Ed. 2005). In the manufacture of a pharmaceutical composition, the nucleic acid constructs, CRISPR arrays, templates and/or protein-RNA complexes are typically admixed with, inter alia, an acceptable carrier. The carrier can be a solid (including a powder) or a liquid, or both, and is preferably formulated with the compound as a unit-dose composition, for example, a tablet, which can contain from 0.01 or 0.5% to 95% or 99% by weight of the compound. One or more compounds can be incorporated in the compositions of the disclosure, which can be prepared by any of the well-known techniques of pharmacy.

A further aspect of the disclosure is a method of treating subjects in vivo, comprising administering to a subject a pharmaceutical composition comprising nucleic acid constructs, CRISPR arrays, optionally templates, and/or protein-RNA complexes of the disclosure in a pharmaceutically acceptable carrier, wherein the pharmaceutical composition is administered in a therapeutically effective amount. Administration of the compounds of the present disclosure to a eukaryotic subject in need thereof can be by any means known in the art for administering compounds.

The nucleic acid constructs, CRISPR arrays, and optionally templates, and/or protein-RNA complexes of the disclosure and compositions thereof include those suitable for oral, rectal, topical, buccal (e.g., sub-lingual), vaginal, parenteral (e.g., subcutaneous, intramuscular including skeletal muscle, cardiac muscle, diaphragm muscle and smooth muscle, intradermal, intravenous, intraperitoneal), topical (i.e., both skin and mucosal surfaces, including airway surfaces), intranasal, transdermal, intraarticular, intrathecal, and inhalation administration, administration to the liver by intraportal delivery, as well as direct organ injection (e.g., into the liver, into the brain for delivery to the central nervous system, into the pancreas, or into a tumor or the tissue surrounding a tumor). In some embodiments, the composition is delivered to the site of tissue infection. The most suitable route in any given case will depend on the nature and severity of the condition being treated and on the nature of the particular compound which is being used.

In some embodiments, for oral administration, the nucleic acid constructs, CRISPR arrays, and optionally templates and/or protein-RNA complexes can be administered in solid dosage forms, such as capsules, tablets, and powders, or in liquid dosage forms, such as elixirs, syrups, and suspensions. The nucleic acid constructs, CRISPR arrays, and optionally templates and/or protein-RNA complexes can be encapsulated in gelatin capsules together with inactive ingredients and powdered carriers, such as glucose, lactose, sucrose, mannitol, starch, cellulose or cellulose derivatives, magnesium stearate, stearic acid, sodium saccharin, talcum, magnesium carbonate and the like. Examples of additional inactive ingredients that can be added to provide desirable color, taste, stability, buffering capacity, dispersion or other known desirable features are red iron oxide, silica gel, sodium lauryl sulfate, titanium dioxide, edible white ink and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric-coated for selective disintegration in the gastrointestinal tract. Liquid dosage forms for oral administration can contain coloring and flavoring to increase patient acceptance.

Compositions suitable for buccal (sub-lingual) administration include lozenges comprising the compound in a flavored base, usually sucrose and acacia or tragacanth; and pastilles comprising the compound in an inert base such as gelatin and glycerin or sucrose and acacia.

Compositions of the present disclosure suitable for parenteral administration comprise sterile aqueous and non-aqueous injection solutions of the compound, which preparations are preferably isotonic with the blood of the intended recipient. These preparations can contain anti-oxidants, buffers, bacteriostats and solutes which render the composition isotonic with the blood of the intended recipient. Aqueous and non-aqueous sterile suspensions can include suspending agents and thickening agents. The compositions can be presented in unit\dose or multi-dose containers, for example sealed ampoules and vials, and can be stored in a freeze-dried (lyophilized) condition requiring only the addition of the sterile liquid carrier, for example, saline or water-for-injection immediately prior to use.

Extemporaneous injection solutions and suspensions can be prepared from sterile powders, granules and tablets of the kind previously described. For example, in one aspect of the present disclosure, there is provided an injectable, stable, sterile composition comprising a compound of the disclosure, in a unit dosage form in a sealed container. The compound or salt is provided in the form of a lyophilizate which is capable of being reconstituted with a suitable pharmaceutically acceptable carrier to form a liquid composition suitable for injection thereof into a subject. The unit dosage form typically comprises from about 10 mg to about 10 grams of the compound or salt. When the compound or salt is substantially water-insoluble, a sufficient amount of emulsifying agent which is pharmaceutically acceptable can be employed in sufficient quantity to emulsify the compound or salt in an aqueous carrier. One such useful emulsifying agent is phosphatidyl choline.

Compositions suitable for rectal administration are preferably presented as unit dose suppositories. These can be prepared by admixing the compound with one or more conventional solid carriers, for example, cocoa butter, and then shaping the resulting mixture.

Compositions suitable for topical application to the skin preferably take the form of an ointment, cream, lotion, paste, gel, spray, aerosol, or oil. Carriers which can be used include petroleum jelly, lanoline, polyethylene glycols, alcohols, transdermal enhancers, and combinations of two or more thereof.

Compositions suitable for transdermal administration can be presented as discrete patches adapted to remain in intimate contact with the epidermis of the recipient for a prolonged period of time. Compositions suitable for transdermal administration can also be delivered by iontophoresis (see, for example, Tyle, *Pharm. Res.* 3:318 (1986)) and typically take the form of an optionally buffered aqueous solution of the compound. Suitable compositions comprise citrate or bis\tris buffer (pH 6) or ethanol/water and contain from 0.1 to 0.2M of the compound.

The nucleic acid constructs, CRISPR arrays, and optionally templates and/or protein-RNA complexes of the disclosure can alternatively be formulated for nasal administration or otherwise administered to the lungs of a subject by any suitable means, e.g., administered by an aerosol suspension of respirable particles comprising the compound, which the subject inhales. The respirable particles can be liquid or solid. The term "aerosol" includes any gas-borne suspended phase, which is capable of being inhaled into the bronchioles or nasal passages. Specifically, aerosol includes a gas-borne suspension of droplets, as can be produced in a metered dose inhaler or nebulizer, or in a mist sprayer. Aerosol also includes a dry powder composition suspended in air or other carrier gas, which can be delivered by insufflation from an inhaler device, for example. See Ganderton & Jones, *Drug Delivery to the Respiratory Tract*, Ellis Horwood (1987); Gonda (1990) *Critical Reviews in Therapeutic Drug Carrier Systems* 6:273-313; and Raeburn et al., *J. Pharmacol. Toxicol. Meth.* 27:143 (1992). Aerosols of liquid particles comprising the compound can be produced by any suitable means, such as with a pressure-driven aerosol nebulizer or an ultrasonic nebulizer, as is known to those of skill in the art. See, e.g., U.S. Pat. No. 4,501,729. Aerosols of solid particles comprising the compound can likewise be produced with any solid particulate medicament aerosol generator, by techniques known in the pharmaceutical art.

Alternatively, one can administer the nucleic acid constructs, CRISPR arrays, and optionally templates and/or protein-RNA complexes in a local rather than systemic manner, for example, in a depot or sustained-release composition.

Further, the present disclosure provides liposomal formulations of the nucleic acid constructs, CRISPR arrays, and optionally templates and/or protein-RNA complexes of the disclosure disclosed herein. The technology for forming liposomal suspensions is well known in the art. As aqueous-soluble material, using conventional liposome technology, the nucleic acid constructs, CRISPR arrays, and optionally templates and/or protein-RNA complexes of the disclosure can be incorporated into lipid vesicles. In such an instance, due to the water solubility of the compound, the compound will be substantially entrained within the hydrophilic center or core of the liposomes. The lipid layer employed can be of any conventional composition and can either contain cholesterol or can be cholesterol-free. The liposomes which are produced can be reduced in size through the use of, for example, standard sonication and homogenization techniques. The liposomal compositions containing the compound disclosed herein can be lyophilized to produce a lyophilizate, which can be reconstituted with a pharmaceutically acceptable carrier, such as water, to regenerate a liposomal suspension.

In some embodiments, the pharmaceutical composition comprising the nucleic acid constructs, CRISPR arrays, and optionally templates and/or protein-RNA complexes of the disclosure can contain other additives, such as pH-adjusting additives. In particular, useful pH-adjusting agents include acids, such as hydrochloric acid, bases or buffers, such as sodium lactate, sodium acetate, sodium phosphate, sodium citrate, sodium borate, or sodium gluconate. Further, the compositions can contain microbial preservatives. Useful microbial preservatives include methylparaben, propylparaben, and benzyl alcohol. The microbial preservative is typically employed when the composition is placed in a vial designed for multidose use. Other additives that are well known in the art include, e.g., detackifiers, anti-foaming agents, antioxidants (e.g., ascorbyl palmitate, butyl hydroxy anisole (BHA), butyl hydroxy toluene (BHT) and tocopherols, e.g., α-tocopherol (vitamin E)), preservatives, chelating agents (e.g., EDTA and/or EGTA), viscomodulators, tonicifiers (e.g., a sugar such as sucrose, lactose, and/or mannitol), flavorants, colorants, odorants, opacifiers, suspending agents, binders, fillers, plasticizers, lubricants, and mixtures thereof. The amounts of such additives can be readily determined by one skilled in the art, according to the particular properties desired.

In some embodiments, the additive can also comprise a thickening agent. Suitable thickening agents can be those known and employed in the art, including, e.g., pharmaceutically acceptable polymeric materials and inorganic thickening agents. Exemplary thickening agents for use in the present pharmaceutical compositions include polyacrylate and polyacrylate co-polymer resins, for example poly-acrylic acid and poly-acrylic acid/methacrylic acid resins; celluloses and cellulose derivatives including: alkyl celluloses, e.g., methyl-, ethyl- and propyl-celluloses; hydroxy-alkyl-celluloses, e.g., hydroxypropyl-celluloses and hydroxypropylalkyl-celluloses such as hydroxypropyl-methyl-celluloses; acylated celluloses, e.g., cellulose-acetates, cellulose-acetatephthallates, cellulose-acetatesuccinates and hydroxypropylmethyl-cellulose phthallates; and salts thereof such as sodium-carboxymethyl-celluloses; polyvinylpyrrolidones, including for example poly-N-vinylpyrrolidones and vinylpyrrolidone co-polymers such as vinylpyrrolidone-vinylacetate co-polymers; polyvinyl resins, e.g., including polyvinylacetates and alcohols, as well as other polymeric materials including gum traganth, gum arabicum, alginates, e.g., alginic acid, and salts thereof, e.g., sodium alginates; and inorganic thickening agents such as atapulgite, bentonite and silicates including hydrophilic silicon dioxide products, e.g., alkylated (for example methylated) silica gels, in particular colloidal silicon dioxide products. Such thickening agents as described above can be included, e.g., to provide a sustained release effect. However, where oral administration is intended, the use of thickening agents as aforesaid will generally not be required and is generally less preferred. Use of thickening agents is, on the other hand, indicated, e.g., where topical application is foreseen.

In particular embodiments, the nucleic acid constructs, CRISPR arrays, and-optionally templates and/or protein-RNA complexes of the disclosure can be administered to the subject in a therapeutically effective amount, as that term is defined above. Dosages of pharmaceutically active compounds can be determined by methods known in the art, see, e.g., Remington, *The Science And Practice of Pharmacy* ($21^{th}$ Ed. 2005). The therapeutically effective dosage of any specific compound will vary somewhat from compound to compound, and patient to patient, and will depend upon the condition of the patient and the route of delivery. In one embodiment, the compound is administered at a dose of about 0.001 to about 10 mg/kg body weight, e.g., about 0.001, 0.005, 0.01, 0.05, 0.1, 0.2, 0.3, 0.4, 0.5, 0.6, 0.7, 0.8, 0.9, 1, 2, 3, 4, 5, 6, 7, 8, 9, or 10 mg/kg. In some instances, the dose can be even lower, e.g., as low as 0.0005 or 0.0001 mg/kg or lower. In some instances, the dose can be even higher, e.g., as high as 20, 50, 100, 500, or 1000 mg/kg or higher. The present disclosure encompasses every sub-range within the cited ranges and amounts.

Methods of Delivery

Provided herein is a method for delivering the pharmaceutical formulations, preferably compositions described above, for providing genetic constructs. The delivery of the compositions can be the transfection or electroporation of the composition as a nucleic acid molecule that is expressed in the cell and delivered to the surface of the cell. The nucleic acid molecules can be electroporated using BioRad Gene Pulser Xcell or Amaxa Nucleofector IIb devices. Several different buffers can be used, including BioRad electroporation solution, Sigma phosphate-buffered saline product #D8537 (PBS), Invitrogen OptiMEM I (OM), or Amaxa Nucleofector solution V (N. V.). Transfections can include a transfection reagent, such as Lipofectamine 2000.

Upon delivery of the composition to the tissue, and thereupon the vector into the cells of the mammal, the transfected cells will express the Type I Cascade polypeptides and/or Cascade fusion protein of Type I CRISPRa system. The composition can be administered to a mammal to alter gene expression or to re-engineer or alter the genome. The mammal can be human, non-human primate, cow, pig, sheep, goat, antelope, bison, water buffalo, bovids, deer, hedgehogs, elephants, llama, alpaca, mice, rats, or chicken, and preferably human, cow, pig, or chicken.

"Introducing," "introduce," "introduced" (and grammatical variations thereof) in the context of a polynucleotide of interest (e.g., the polynucleotide encoding the Type I-E Cascade polypeptides, Cascade fusion protein, and/or crRNA or CRISPR array) means presenting a polynucleotide of interest to a host organism or a cell of the organism (e.g., host cell such as a eukaryotic cell) in such a manner that the polynucleotide gains access to the interior of a cell and includes such terms as transformation" and/or "transfection." Where more than one polynucleotide is to be introduced these polynucleotides can be assembled as part of a single polynucleotide or nucleic acid construct, or as separate polynucleotide or nucleic acid constructs, and can be located on the same or different expression constructs or transformation vectors. Thus, in some aspects, a eukaryotic cell can be transformed or transfected with a polynucleotide encoding the Type I CRISPRa system, thereby expressing the Type I Cascade polypeptides, Cascade fusion protein, as well as at least one crRNA or CRISPR array.

The terms "transformation" and "transfection" as used herein refer to the introduction of a heterologous polynucleotide into a cell (e.g., polynucleotides encoding the Type I-E Cascade polypeptides, Cascade fusion protein, and/or crRNA or CRISPR array). Such introduction into a cell can be stable or transient. Thus, in some embodiments, a host cell or host organism is stably transformed with a nucleic acid molecule of the disclosure (DNA or RNA (e.g., mRNA)) or a ribonucleoprotein complex. In other embodiments, a host cell or host organism is transiently transformed with a recombinant nucleic acid molecule of the disclosure (DNA or RNA (e.g., mRNA)) or a ribonucleoprotein complex.

"Transient transformation" in the context of a polynucleotide means that a polynucleotide is introduced into the cell and does not integrate into the genome of the cell and cannot be maintained through antibiotic selection or addictive systems.

By "stably introducing" or "stably introduced" in the context of a polynucleotide introduced into a cell is intended that the introduced polynucleotide is stably incorporated into the genome of the cell, and thus the cell is stably transformed with the polynucleotide.

"Stable transformation" or "stably transformed" as used herein means that a nucleic acid molecule is introduced into a cell and integrates into the genome of the cell. As such, the integrated nucleic acid molecule is capable of being inherited by the progeny thereof, more particularly, by the progeny of multiple successive generations. "Genome" as used herein also includes the nuclear and the plasmid genome, and therefore includes integration of the nucleic acid construct into, for example, the plasmid genome. Stable transformation as used herein can also refer to a transgene that is maintained extrachromasomally, for example, as a minichromosome.

Transient transformation can be detected by, for example, an enzyme-linked immunosorbent assay (ELISA) or Western blot, which can detect the presence of a peptide or polypeptide encoded by one or more transgene introduced into an organism. Stable transformation of a cell can be detected by, for example, a Southern blot hybridization assay of genomic DNA of the cell with nucleic acid sequences which specifically hybridize with a nucleotide sequence of a transgene introduced into a eukaryotic organism. Stable transformation of a cell can be detected by, for example, a Northern blot hybridization assay of RNA of the cell with nucleic acid sequences which specifically hybridize with a nucleotide sequence of a transgene introduced into the cell. Stable transformation of a cell can also be detected by, e.g., a polymerase chain reaction (PCR) or other amplification reactions as are well known in the art, employing specific primer sequences that hybridize with target sequence(s) of a transgene, resulting in amplification of the transgene sequence, which can be detected according to standard methods. Transformation can also be detected by direct sequencing and/or hybridization protocols well known in the art.

The polynucleotides of the disclosure (e.g., polynucleotides encoding the Type I Cascade polypeptides, Cascade fusion protein, and/or crRNA or CRISPR array) can be introduced into a eukaryotic cell by any method known to those of skill in the art. Exemplary methods of transformation include transformation via electroporation of competent cells, passive uptake by competent cells, chemical transformation of competent cells, as well as any other electrical, chemical, physical (mechanical) and/or biological mechanism that results in the introduction of nucleic acid into a cell, including any combination thereof. In some aspects, transformation of a cell can comprise nuclear transformation. In other aspects, transformation of a cell can comprise plastid transformation. Procedures for transforming eukaryotic organisms are well known and routine in the art and are described throughout the literature.

A nucleotide sequence (e.g., nucleotide sequences comprising the crRNA nucleic acids and those encoding the Type I Cascade polypeptides and/or Cascade fusion protein), can therefore be introduced into a host cell in any number of ways that are well known in the art to generate a eukaryote comprising, for example, a Type I CRISPRa system as described herein. The methods of the disclosure do not depend on a particular method for introducing one or more nucleotide sequences into an organism, only that they gain access to the interior of the cell. Where more than one nucleotide sequence is to be introduced, they can be assembled as part of a single nucleic acid construct, or as separate nucleic acid constructs, and can be located on the same or different nucleic acid constructs. Accordingly, the nucleotide sequences can be introduced into the cell of interest in a single transformation event, or in separate transformation events.

In additional aspects, a plant can be transformed with at least one polynucleotide or nucleic acid construct comprising the Type I CRISPRa system targeting nematodes and/or or fungi. The at least one polynucleotide or nucleic acid construct and crRNA or CRISPR array can be constitutively expressed or specifically expressed in various plant parts including leaves and/or roots. A nematode and/or fungus feeding on the transformed plant can then consume the at least one polynucleotide or nucleic acid construct comprising the Type I CRISPRa system and CRISPR array targeting nematodes and/or fungi, thereby killing the nematode or fungus.

The vector encoding the Type I CRISPRa system protein component, i.e., Cascade polypeptides, can be delivered to the mammal by DNA injection (also referred to as DNA vaccination) with and without in vivo electroporation, liposome mediated, nanoparticle facilitated, and/or recombinant vectors. The recombinant vector can be delivered by any viral mode. The viral mode can be recombinant lentivirus, recombinant adenovirus, and/or recombinant adeno-associated virus. The nucleotide encoding a Type I CRISPRa system protein component, i.e., Cascade polypeptides can be introduced into a cell to alter gene expression of a gene, such as activate endogenous genes.

Routes of Administration

The compositions can be administered to a subject by different routes including orally, parenterally, sublingually, transdermally, rectally, transmucosally, topically, via inhalation, via buccal administration, intrapleurally, intravenous, intraarterial, intraperitoneal, subcutaneous, intramuscular, intranasal intrathecal, and intraarticular or combinations thereof. For veterinary use, the composition can be administered as a suitably acceptable formulation in accordance with normal veterinary practice. In some embodiments, the veterinarian can readily determine the dosing regimen and route of administration that is most appropriate for a particular animal. The compositions can be administered by traditional syringes, needleless injection devices, "microprojectile bombardment gone guns", or other physical methods such as electroporation ("EP"), "hydrodynamic method", or ultrasound.

The composition can be delivered to the mammal by several technologies including DNA injection (also referred to as DNA vaccination) with and without in vivo electroporation, liposome mediated, nanoparticle facilitated, recombinant vectors such as recombinant lentivirus, recombinant adenovirus, and recombinant adenovirus associated virus.

Cell Types

In some embodiments, the present disclosure is directed to a host cell that includes the Type I-E CRISPRa system or the expression cassette or vector encoding said system, as described above. Any of these delivery methods and/or routes of administration could be utilized with a myriad of eukaryotic cell types, for example, those cell types currently under investigation for cell-based therapies. A eukaryotic cell useful with the disclosed compositions and methods can be any eukaryotic cell from any eukaryotic organism and/or in a eukaryotic organism. Non-limiting examples of eukaryotic organisms include mammals, insects, amphibians, reptiles, birds, fish, fungi, plants, and/or nematodes. In some embodiments, the mammal is a human. Cell types can be fibroblasts, pluripotent stem cells, cardiomyocytes, hepatocytes, chondrocytes, mesenchymal progenitor cells, hematopoetic stem cells, smooth muscle cells, or K562 human erythroid leukemia cell line.

Kits

In some embodiments, provided herein are kits, which can be used to activate gene expression of a target gene. In some embodiments, the kit comprises a Type I CRISPRa system or compositions for activating gene expression comprising said system, as described above, and instructions for using said systems or compositions. Instructions included in kits can be affixed to packaging material or can be included as a package insert. While the instructions are typically written or printed materials they are not limited to such. Any medium capable of storing such instructions and communicating them to an end user is contemplated by this disclosure. Such media include, but are not limited to, electronic storage media (e.g., magnetic discs, tapes, cartridges, chips), optical media (e.g., CD ROM), and the like. As used herein, the term "instructions" can include the address of an internet site that provides the instructions. The composition for activating gene expression of a target gene in eukaryotic cells can include a polynucleotide nucleotide sequence encoding the Type I CRISPRa system, as described above. The composition for modulating gene expression of a target gene in eukaryotic cells can include a modified lentiviral vector and a nucleotide sequence encoding Type I CRISPRa system, as described above. The kit can further include donor DNA, a crRNA, or a transgene, as described above.

Clauses

For reasons of completeness, various aspects of the disclosure are set out in the following numbered clause:

Clause 1. A Type I-E CRISPR-based programmable transcriptional activation (Type I-E CRISPRa) system composition for activating at least one target gene in a eukaryotic cell, the composition comprising at least one polynucleotide sequence encoding: (a) a Cascade complex comprising three or more Cascade polypeptides of the Type I-E CRISPR/Cas system, or functional fragments thereof, wherein at least one Cascade polypeptide is fused to a second polypeptide domain having transcription activation activity; and/or (b) at least one crRNA, wherein the crRNA targets a target nucleotide sequence from the at least one target gene, wherein the at least one polynucleotide sequence is operably linked to a eukaryotic promoter, comprises a nuclear localization signal, and is codon-optimized, and wherein the at least one Cascade polypeptide fused to a second polypeptide domain is CasA or CasE.

Clause 2. The Type I-E CRISPRa system composition of clause 1, wherein the second polypeptide domain is fused to the N terminus and/or the C terminus of the at least one Cascade polypeptide.

Clause 3. The Type I-E CRISPRa system composition of clause 1 or 2, further comprising a linker connecting the at least one Cascade polypeptide to the second polypeptide domain.

Clause 4. The Type I-E CRISPRa system composition of any one of clauses 1-3, wherein the second polypeptide domain comprises a p300 core domain or VP64-p65-Rta tripartite activator (VPR) domain.

Clause 5. The Type I-E CRISPRa system composition of any one of clauses 1-4, wherein the second polypeptide domain comprises an amino acid sequence of SEQ ID NO: 9 or SEQ ID NO: 11.

Clause 6. The Type I-E CRISPRa system composition of any one of clauses 1-5, wherein the at least one polynucleotide sequence encoding the Cascade complex comprises: a polynucleotide sequence encoding a CasB polypeptide, a polynucleotide sequence encoding a CasC polypeptide, a polynucleotide sequence encoding a CasD polypeptide and/or a polynucleotide sequence encoding a CasE polypeptide.

Clause 7. The Type I-E CRISPRa system composition of clause 6, wherein each of the polynucleotide sequences encoding the Cascade polypeptides is operably linked to a eukaryotic promoter, comprises a nuclear localization signal, and is operably linked to a terminator.

Clause 8. The Type I-E CRISPRa system composition of any one of clauses 1-7, wherein two or more Cascade polypeptides, or functional fragments thereof, are fused to form a single polypeptide.

Clause 9. The Type I-E CRISPRa system composition of any one of clauses 1-8, wherein two or more Cascade polypeptides are encoded by a multicistronic polynucleotide sequence and separated by at least one 2A peptide.

Clause 10. The Type I-E CRISPRa system composition of any one of clauses 1-9, wherein the three or more Cascade polypeptides comprises Cascade polypeptides of *Escherichia coli* Type I-E CRISPR/Cas system.

Clause 11. The Type I-E CRISPRa system composition of any one of clauses 1-10, wherein the at least one Cascade polypeptide fused to a second polypeptide domain comprises SEQ ID NO: 6, SEQ ID NO: 7, or SEQ ID NO: 8.

Clause 12. The Type I-E CRISPRa system composition of any one of clauses 1-11, wherein the at least one polynucleotide sequence encoding the Cascade complex comprises at least one polynucleotide sequence of SEQ ID NO: 1, SEQ ID NO: 2, SEQ ID NO: 3, SEQ ID NO: 4, SEQ ID NO: 5, SEQ ID NO: 163, or combinations thereof.

Clause 13. The Type I-E CRISPRa system composition of any one of clauses 1-12, wherein the least one polynucleotide sequence further comprises a polynucleotide sequence encoding an epitope tag.

Clause 14. The Type I-E CRISPRa system composition of clause 13, wherein the epitope tag comprises FLAG (SEQ ID NO: 147), 3×FLAG, HA (SEQ ID NO: 148), myc (SEQ ID NO: 149), V5 (SEQ ID NO: 150), E-tag (SEQ ID NO: 151), VSV-g (SEQ ID NO: 152), 6×His (SEQ ID NO: 153), or HSV (SEQ ID NO: 154).

Clause 15. The Type I-E CRISPRa system composition of any one of clauses 1-14, wherein the at least one polynucleotide sequence encoding the at least one crRNA comprises a spacer nucleotide sequence linked to a repeat nucleotide sequence at its 5' end and at its 3' end.

Clause 16. The Type I-E CRISPRa system composition of any one of clauses 1-14, wherein the at least one polynucleotide sequence encoding the at least one crRNA comprises a recombinant CRISPR array comprising two or more repeat nucleotide sequences and one or more spacer nucleotide sequence(s), wherein each spacer nucleotide sequence in said CRISPR array is linked at its 5' end and at its 3' end to a repeat nucleotide sequence.

Clause 17. The Type I-E CRISPRa system composition of clause 16, wherein the recombinant CRISPR array is operably linked to a eukaryotic promoter, comprises a nuclear localization signal, and is operably linked to a terminator.

Clause 18. The Type I-E CRISPRa system of clause 17, wherein at least two of the one or more spacer nucleotide sequence(s) each comprise a nucleotide sequence that is complementary to a different target nucleotide sequence from a single target gene.

Clause 19. The Type I-E CRISPRa system of clause 17, wherein at least two of the one or more spacer nucleotide sequence(s) each comprise a nucleotide sequence that is complementary to a different target nucleotide sequence from a different target gene.

Clause 20. The Type I-E CRISPRa system of any one of clauses 1-19, wherein the target nucleotide sequence is located on a coding or a plus strand of a double stranded nucleotide sequence.

Clause 21. The Type I-E CRISPRa system of any one of clauses 1-19, wherein the target nucleotide sequence is located on a non-coding or a minus strand of a double stranded nucleotide sequence.

Clause 22. The Type I-E CRISPRa system of any one of clauses 1-21, wherein the target nucleotide sequence comprises all or a part of a nucleotide sequence encoding a promoter region of a gene or a complement thereof, or an enhancer region of a gene or a complement thereof.

Clause 23. The Type I-E CRISPRa system of any one of clauses 1-22, wherein the at least one target gene is an endogenous gene or a transgene.

Clause 24. The Type I-E CRISPRa system of any one of clauses 1-23, wherein the eukaryotic promoter comprises a RNA polymerase III U6 promoter or CMV promoter.

Clause 25. The Type I-E CRISPRa system of any one of clauses 1-24, wherein the at least one polynucleotide sequence comprises a Kozak sequence.

Clause 26. The Type I-E CRISPRa system of any one of clauses 1-25, wherein the nuclear localization signal comprises a polynucleotide sequence of SEQ ID NO: 12, SEQ ID NO: 13, or SEQ ID NO: 14, or SEQ ID NO: 165.

Clause 27. The Type I-E CRISPRa system of any one of clauses 1-26, wherein the least one crRNA comprises a polynucleotide sequence of SEQ ID NOs 15-66.

Clause 28. The Type I-E CRISPRa system of any one of clauses 1-27, wherein the Cascade complex comprises: a CasA polypeptide comprising a polypeptide sequence of SEQ ID NO: 1, a CasB polypeptide comprising a polypeptide sequence of SEQ ID NO: 2, a CasC polypeptide comprising a polypeptide sequence of SEQ ID NO: 3 or SEQ ID NO: 163, a CasD polypeptide comprising a polypeptide sequence of SEQ ID NO: 4, and a CasE fusion protein comprising a polypeptide sequence of SEQ ID NO: 6; a CasA polypeptide comprising a polypeptide sequence of SEQ ID NO: 1, a CasB polypeptide comprising a polypeptide sequence of SEQ ID NO: 2, a CasC polypeptide comprising a polypeptide sequence of SEQ ID NO: 3 or SEQ ID NO: 163, a CasD polypeptide comprising a polypeptide sequence of SEQ ID NO: 4, and a CasE fusion protein comprising a polypeptide sequence of SEQ ID NO: 7; or a CasA fusion protein comprising a polypeptide sequence of SEQ ID NO: 8, a CasB polypeptide comprising a polypeptide sequence of SEQ ID NO: 2, a CasC polypeptide comprising a polypeptide sequence of SEQ ID NO: 3 or SEQ ID NO: 163, a CasD polypeptide comprising a polypeptide sequence of SEQ ID NO: 4, and a CasE polypeptide comprising a polypeptide sequence of SEQ ID NO: 5.

Clause 29. An expression cassette or a vector comprising the Type I-E CRISPRa system of any one of clauses 1-28, or subcomponents thereof.

Clause 30. An expression cassette or a vector comprising at least one polynucleotide sequence of SEQ ID NO: 1, SEQ ID NO: 2, SEQ ID NO: 3, SEQ ID NO: 4, SEQ ID NO: 5, SEQ ID NO: 6; SEQ ID NO: 7, SEQ ID NO: 8, SEQ ID NO: 163, or combinations thereof.

Clause 31. A host cell comprising the Type I-E CRISPRa system of any one of clauses 1-28 or the expression cassette or vector of clause 29 or 30.

Clause 32. A pharmaceutical composition comprising the Type I-E CRISPRa system of any one of clauses 1-28, the expression cassette or vector of clause 29 or 30, or the host cell of clause 31.

Clause 33. A method of activating the expression of a target gene in a eukaryotic cell, the method comprising introducing to a cell the Type I-E CRISPRa system of any one of clauses 1-28 or the expression cassette or vector of clause 29 or 30.

Clause 34. The method of clause 33, wherein the Type I-E CRISPRa comprises at least one polynucleotide encoding a Cascade complex and at least one crRNA.

Clause 35. The method of clause 33 or 34, wherein the Type I-E CRISPRa system comprises two or more crRNAs.

Clause 36. The method of clause 33 or 34, wherein the Type I-E CRISPRa Cas system comprises between one and ten different crRNAs.

Clause 37. The method of clause 36, wherein the different crRNAs bind to different target nucleotide sequences within the target gene.

Clause 38. The method of clause 37, wherein the different target nucleotide sequences are separated by at least one nucleotide.

Clause 39. The method of clause 37, wherein the different target nucleotide sequences are separated by about 15 to about 700 base pairs.

Clause 40. The method of clause 36, wherein each of the different crRNAs bind to at least one different target genes.

Clause 41. The method of clause 40, wherein the different target genes are located on same chromosome.

Clause 42. The method of clause 40, wherein the different target genes are located on different chromosomes.

Clause 43. The method of clause 36, wherein at least one target nucleotide sequence is within a non-open chromatin region, an open chromatin region, a promoter region of the target gene, an enhancer region of the target gene, or a region upstream of a transcription start site of the target gene.

Clause 44. The method of clause 36, wherein at least one target nucleotide sequence is located between about 1 to about 1000 base pairs upstream of a transcription start site of a target gene.

Clause 45. The method of any one of clauses 33-44, wherein the target nucleotide sequence is immediately 3' to a protospacer adjacent motif (PAM).

Clause 46. The method of clause 45, wherein the PAM comprises AAG, AGG, ATG, GAG, or TAG.

Clause 47. The method any one of clauses 33-46, wherein the eukaryotic cell is in a eukaryotic organism.

Clause 48. The method of clause 47, wherein the eukaryotic organism is a mammal, an insect, an amphibian, a reptile, a bird, a fish, a fungus, a plant, or a nematode.

Clause 49. The method of clause 48, wherein the mammal is a human.

Clause 50. The method of any one of clauses 33-49, wherein the Type I-E CRISPRa system, or subcomponents thereof, is introduced in one construct or in different constructs.

Clause 51. The method of any one of clauses 33-50, further comprising introducing to the cell: a dCas9 protein or a polynucleotide sequence encoding a dCas9 protein; and a gRNA.

Clause 52. The method of clause 51, wherein the dCas9 protein comprises an amino acid sequence of SEQ ID NO: 10, or functional fragment thereof, and the gRNA comprises a polynucleotide sequence corresponding to SEQ ID NO: 67, SEQ ID NO: 68, SEQ ID NO: 69, or SEQ ID NO 70.

Clause 53. A kit for activating gene expression of at least one target gene in a eukaryotic cell, the kit comprising the Type I-E CRISPRa system of any one of clauses 1-28, the expression cassette or vector of clause 29 or 30, or the host cell of clause 31.

Further discloses herein are compositions for modulating gene expression using Type I-B systems.

Clause 1. A Type I-B Clustered Regularly Interspaced Short Palindromic Repeats (CRISPR)-based programmable system composition for genome engineering at least one target gene in a cell, the composition comprising: (a)(i) a Cascade complex comprising three or more Cascade polypeptides of a Type I-B CRISPR/CRISPR-associated (Cas)

system, or functional fragments thereof, or (ii) a nucleic acid sequence encoding a Cascade complex comprising three or more Cascade polypeptides of the Type I-B CRISPR/Cas system, or functional fragments thereof; and/or (b)(i) at least one crRNA or (ii) a nucleic acid sequence encoding at least one crRNA, wherein the at least one crRNA targets a target nucleotide sequence from the at least one target gene, and wherein at least one Cascade polypeptide is fused to a second polypeptide domain thereby generating a Cascade polypeptide fusion protein, wherein the second polypeptide domain has an activity selected from the group consisting of transcription activation activity, nuclease activity, nickase activity, transcription repression activity, transcription release factor activity, histone modification activity, nucleic acid association activity, methylase activity, and demethylase activity; wherein the at least one Cascade polypeptide in the Cascade polypeptide fusion protein is Cas5, Cas6, Cas7, or Cas8b2.

Clause 2. The Type I-B CRISPR-based programmable system composition of clause 1, wherein the cell is a eukaryotic cell.

Clause 3. The Type I-B CRISPR-based programmable system composition of clause 1 or 2, wherein the nucleic acid sequence encoding the Cascade complex is operably linked to a eukaryotic promoter, comprises a nuclear localization signal, and is codon-optimized for eukaryotic expression.

Clause 4. The Type I-B CRISPR-based programmable system composition of any one of clauses 1-3, wherein the second polypeptide domain is fused to the N terminus and/or the C terminus of the at least one Cascade polypeptide.

Clause 5. The Type I-B CRISPR-based programmable system composition of any one of clauses 1-4, further comprising a linker connecting the at least one Cascade polypeptide to the second polypeptide domain.

Clause 6. The Type I-B CRISPR-based programmable system composition of any one of clauses 1-5, wherein the Cascade complex comprises: a CasB polypeptide, a CasC polypeptide, a CasD polypeptide and/or a CasE polypeptide.

Clause 7. The Type I-B CRISPR-based programmable system composition of any one of clauses 1-5, wherein the nucleic acid sequence encoding the Cascade complex comprises: a polynucleotide sequence encoding a Cas5 polypeptide, a polynucleotide sequence encoding a Cas6 polypeptide, a polynucleotide sequence encoding a Cas7 polypeptide and/or a polynucleotide sequence encoding a Cas8b2 polypeptide.

Clause 8. The Type I-B CRISPR-based programmable system composition of clause 6 or 7, wherein the Cas5 polypeptide comprises an amino acid sequence of SEQ ID NO: 175, the Cas6 polypeptide comprises an amino acid sequence of SEQ ID NO: 176, the Cas7 polypeptide comprises an amino acid sequence of SEQ ID NO: 176, and/or the Cas8b2 polypeptide comprises an amino acid sequence of SEQ ID NO: 177.

Clause 9. The Type I-B CRISPR-based programmable system composition of clause 7, wherein the polynucleotide sequence encoding the Cas5 polypeptide comprises a nucleotide sequence of SEQ ID NO: 258, the polynucleotide sequence encoding the Cas6 polypeptide comprises a nucleotide sequence of SEQ ID NO: 259, the polynucleotide sequence encoding the Cas7 polypeptide comprises a nucleotide sequence of SEQ ID NO: 260, and/or the polynucleotide sequence encoding the Cas8b2 polypeptide comprises a nucleotide sequence of SEQ ID NO: 261.

Clause 10. The Type I-B CRISPR-based programmable system composition of clause 9, wherein each of the polynucleotide sequences encoding the Cascade polypeptides is operably linked to a eukaryotic promoter, comprises a nuclear localization signal, and is operably linked to a terminator.

Clause 11. The Type I-B CRISPR-based programmable system composition of any one of clauses 1-10, wherein two or more Cascade polypeptides are encoded by a multicistronic polynucleotide sequence and separated by at least one 2A peptide.

Clause 12. The Type I-B CRISPR-based programmable system composition of clause 11, wherein a lentiviral vector comprises the multicistronic polynucleotide sequence.

Clause 13. The Type I-B CRISPR-based programmable system composition of any one of clauses 1-12, wherein the three or more Cascade polypeptides comprises Cascade polypeptides of a Type I-B CRISPR/Cas system from *Listeria monocytogenes.*

Clause 14. The Type I-B CRISPR-based programmable system composition of any one of clauses 1-13, wherein the three or more Cascade polypeptides comprises Cascade polypeptides of a *Listeria monocytogenes* Finland_1998 Type I-B CRISPR/Cas system.

Clause 15. The Type I-B CRISPR-based programmable system composition of any one of clauses 1-14, wherein the second polypeptide domain has transcription activation activity.

Clause 16. The Type I-B CRISPR-based programmable system composition of any one of clauses 1-15, wherein the second polypeptide domain comprises a p300 core domain.

Clause 17. Type I-B CRISPR-based programmable system of any one of clauses 116, wherein the second polypeptide domain comprises an amino acid sequence of SEQ ID NO: 180.

Clause 18. The Type I-B CRISPR-based programmable system composition of any one of clauses 1-17, wherein the Cascade polypeptide fusion protein is a Cas5-p300 fusion protein, a Cas6-p300 fusion protein, a Cas7-p300 fusion protein, or a Cas8b2-p300 fusion protein.

Clause 19. The Type I-B CRISPR-based programmable system composition of any one of clauses 1-18, wherein the Cascade polypeptide fusion protein comprises an amino acid sequence encoded by a polynucleotide sequence of SEQ ID NO: 171, SEQ ID NO: 172, SEQ ID NO: 173, or SEQ ID NO: 174.

Clause 20. The Type I-B CRISPR-based programmable system composition of any one of clauses 1-19, wherein the at least one polynucleotide sequence encoding the Cascade complex comprises at least one polynucleotide sequence of SEQ ID NO: 166, SEQ ID NO: 167, SEQ ID NO: 168, SEQ ID NO: 169, or combinations thereof.

Clause 21. The Type I-B CRISPR-based programmable system composition of any one of clauses 1-14, wherein the second polypeptide domain has nuclease activity or nickase activity.

Clause 22. The Type I-B CRISPR-based programmable system composition of any one of clauses 1-21, wherein the at least one polynucleotide sequence encoding the at least one crRNA comprises a spacer nucleotide sequence linked to a repeat nucleotide sequence at its 5' end and at its 3' end.

Clause 23. The Type I-B CRISPR-based programmable system composition of any one of clauses 1-22, wherein the at least one polynucleotide sequence encoding the at least one crRNA comprises a recombinant CRISPR array comprising two or more repeat nucleotide sequences and one or more spacer nucleotide sequence(s), wherein each spacer nucleotide sequence in said CRISPR array is linked at its 5' end and at its 3' end to a repeat nucleotide sequence.

Clause 24. The Type I-B CRISPR-based programmable system composition of clause 23, wherein the recombinant CRISPR array is operably linked to a eukaryotic promoter, comprises a nuclear localization signal, and is operably linked to a terminator.

Clause 25. The Type I-B CRISPR-based programmable system of clause 24, wherein at least two of the one or more spacer nucleotide sequence(s) each comprise a nucleotide sequence that is complementary to a different target nucleotide sequence from a single target gene.

Clause 26. The Type I-B CRISPR-based programmable system of clause 25, wherein at least two of the one or more spacer nucleotide sequence(s) each comprise a nucleotide sequence that is complementary to a different target nucleotide sequence from a different target gene.

Clause 27. The Type I-B CRISPR-based programmable system of any one of clauses 1-26, wherein the target nucleotide sequence is located on a coding or a plus strand of a double stranded nucleotide sequence.

Clause 28. The Type I-B CRISPR-based programmable system of any one of clauses 1-26, wherein the target nucleotide sequence is located on a non-coding or a minus strand of a double stranded nucleotide sequence.

Clause 29. The Type I-B CRISPR-based programmable system of any one of clauses 1-28, wherein the target nucleotide sequence comprises all or a part of a nucleotide sequence encoding a promoter region of a gene or a complement thereof, or an enhancer region of a gene or a complement thereof.

Clause 30. The Type I-B CRISPR-based programmable system of any one of clauses 1-29, wherein the at least one target gene is an endogenous gene or a transgene.

Clause 31. The Type I-B CRISPR-based programmable system of any one of clauses 1-30, wherein the nucleic acid of (a)(ii) and/or (b)(ii) comprises DNA or RNA.

Clause 32. An expression cassette or a vector comprising the Type I-B CRISPR-based programmable system of any one of clauses 1-31, or subcomponents thereof.

Clause 33. A host cell comprising the Type I-B CRISPR-based programmable system of any one of clauses 1-31 or the expression cassette or vector of clause 32.

Clause 34. A pharmaceutical composition comprising the Type I-B CRISPR-based programmable system of any one of clauses 1-31, the expression cassette or vector of clause 32, or the host cell of clause 33.

Clause 35. A kit for modulating gene expression or gene editing of at least one target gene in a cell, the kit comprising the Type I-B CRISPR-based programmable system of any one of clauses 1-31 or the expression cassette or vector of clause 32.

Clause 36. A method of modulating gene expression or gene editing of at least one target gene in a cell, the method comprising introducing to a cell the Type I-B CRISPR-based programmable system of any one of clauses 1-31 or the expression cassette or vector of clause 32.

Clause 37. A method of modulating gene expression or gene editing of at least one target gene in a cell, the method comprising introducing to a cell: (a)(i) a Cascade complex comprising three or more Cascade polypeptides of a Type I-B CRISPR/Cas system, or functional fragments thereof or (ii) a nucleic acid encoding a Cascade complex comprising three or more Cascade polypeptides of a Type I-B CRISPR/Cas system, or functional fragments thereof; and/or (b)(i) at least one crRNA or (ii) a nucleic acid encoding at least one crRNA, wherein the crRNA targets a target nucleotide sequence from the at least one target gene, and wherein at least one Cascade polypeptide is fused to a second polypeptide domain thereby generating a Cascade polypeptide fusion protein, wherein the second polypeptide domain has an activity selected from the group consisting of transcription activation activity, nuclease activity, nickase activity, transcription repression activity, transcription release factor activity, histone modification activity, nucleic acid association activity, methylase activity, and demethylase activity, and wherein the at least one Cascade polypeptide in the Cascade polypeptide fusion protein is Cas5, Cas6, Cas7, or Cas8b2

Clause 38. The method of clause 37, wherein the cell is a eukaryotic cell.

Clause 39. The method of clause 37 or 38, wherein the at least one polynucleotide sequence is operably linked to a eukaryotic promoter, comprises a nuclear localization signal, and is codon-optimized for eukaryotic expression.

Clause 40. The method of any one of clauses 36-39, wherein the nucleic acid of (a)(ii) and/or (b)(ii) comprises DNA or RNA.

Clause 41. A modified lentiviral construct comprising at least one polynucleotide sequence of SEQ ID NOs 166-174, 179, 181-197, 258-261, or a combination thereof.

Clause 42. A Type I-B CRISPR-based programmable transcriptional activation (Type I-B CRISPRa) system composition for activating at least one target gene in a cell, the composition comprising: (a)(i) a Cascade complex comprising three or more Cascade polypeptides of a Type I-B CRISPR/Cas system, or functional fragments thereof, or (ii) a nucleic acid sequence encoding a Cascade complex comprising three or more Cascade polypeptides of the Type I-B CRISPR/Cas system, or functional fragments thereof; and/or (b)(i) at least one crRNA or (ii) a nucleic acid encoding at least one crRNA, wherein the crRNA targets a target nucleotide sequence from the at least one target gene, and wherein at least one Cascade polypeptide is fused to a second polypeptide domain having transcription activation activity thereby generating a Cascade polypeptide fusion protein, and wherein the at least one Cascade polypeptide in the Cascade polypeptide fusion protein is Cas5, Cas6, Cas7, or Cas8b2.

Clause 43. The Type I-B CRISPRa system composition of clause 42, wherein the cell is a eukaryotic cell.

Clause 44. The Type I-B CRISPRa system composition of clause 42 or 43, wherein the nucleic acid of (a)(ii) and/or (b)(ii) is operably linked to a eukaryotic promoter, comprises a nuclear localization signal, and is codon-optimized for eukaryotic expression.

Clause 45. The Type I-B CRISPRa system composition of any one of clauses 42-44, wherein the second polypeptide domain is fused to the N terminus and/or the C terminus of the at least one Cascade polypeptide.

Clause 46. The Type I-B CRISPRa system composition of any one of clauses 42-45, further comprising a linker connecting the at least one Cascade polypeptide to the second polypeptide domain.

Clause 47. The Type I-B CRISPRa system composition of any one of clauses 42-46, wherein the second polypeptide domain comprises a p300 core domain.

Clause 48. The Type I-B CRISPRa system composition of any one of clauses 42-47, wherein the second polypeptide domain comprises an amino acid sequence of SEQ ID NO: 180.

Clause 49. The Type I-B CRISPRa system composition of any one of clauses 42-48, wherein the nucleic acid encoding the Cascade complex comprises: a polynucleotide sequence encoding a Cas5 polypeptide, a polynucleotide sequence encoding a Cas6 polypeptide, a polynucleotide sequence encoding a Cas7 polypeptide and/or a polynucleotide sequence encoding a Cas8b2 polypeptide.

Clause 50. The Type I-B CRISPRa system composition of clause 49, wherein the Cas5 polypeptide comprises an amino acid sequence of SEQ ID NO: 175, the Cas6 polypeptide comprises an amino acid sequence of SEQ ID NO: 176, the Cas7 polypeptide comprises an amino acid sequence of SEQ ID NO: 176, and/or the Cas8b2 polypeptide comprises an amino acid sequence of SEQ ID NO: 177.

Clause 51. The Type I-B CRISPRa system composition of clause 30, wherein the polynucleotide sequence encoding the Cas5 polypeptide comprises a nucleotide sequence of SEQ ID NO: 258, the polynucleotide sequence encoding the Cas6 polypeptide comprises a nucleotide sequence of SEQ ID NO: 259, the polynucleotide sequence encoding the Cas7 polypeptide comprises a nucleotide sequence of SEQ ID NO: 260, and/or the polynucleotide sequence encoding the Cas8b2 polypeptide comprises a nucleotide sequence of SEQ ID NO: 261.

Clause 52. The Type I-B CRISPRa system composition of clause 51, wherein each of the polynucleotide sequences encoding the Cascade polypeptides is operably linked to a eukaryotic promoter, comprises a nuclear localization signal, and is operably linked to a terminator.

Clause 53. The Type I-B CRISPRa system composition of any one of clauses 42-52, wherein two or more Cascade polypeptides, or functional fragments thereof, are fused to form a single polypeptide.

Clause 54. The Type I-B CRISPRa system composition of any one of clauses 42-53, wherein two or more Cascade polypeptides are encoded by a multicistronic polynucleotide sequence and separated by at least one 2A peptide.

Clause 55. The Type I-B CRISPRa system composition of clause 54, wherein a lentiviral vector comprises the multicistronic polynucleotide sequence.

Clause 56. The Type I-B CRISPRa system composition of any one of clauses 42-55, wherein the three or more Cascade polypeptides comprises Cascade polypeptides of a Type I-B CRISPR/Cas system from *Listeria monocytogenes.*

Clause 57. The Type I-B CRISPRa system composition of any one of clauses 42-56, wherein the three or more Cascade polypeptides comprises Cascade polypeptides of a *Listeria monocytogenes* Finland_1998 Type I-B CRISPR/Cas system.

Clause 58. The Type I-B CRISPRa system composition of any one of clauses 42-47, wherein the Cascade polypeptide fusion protein is a Cas5-p300 fusion protein, a Cas6-p300 fusion protein, a Cas7-p300 fusion protein, or a Cas8b2-p300 fusion protein.

Clause 59. The Type I-B CRISPRa system composition of any one of clauses 42-48, wherein the Cascade polypeptide fusion protein comprises an amino acid sequence encoded by a polynucleotide sequence of SEQ ID NO: 171, SEQ ID NO: 172, SEQ ID NO: 173, or SEQ ID NO: 174.

Clause 60. The Type I-B CRISPRa system composition of any one of clauses 42-49, wherein the nucleic acid encoding the Cascade complex comprises at least one polynucleotide sequence of SEQ ID NO: 166, SEQ ID NO: 167, SEQ ID NO: 168, SEQ ID NO: 169, or combinations thereof.

Clause 61. The Type I-B CRISPRa system composition of any one of clauses 42-60, wherein the nucleic acid encoding the at least one crRNA comprises a spacer nucleotide sequence linked to a repeat nucleotide sequence at its 5' end and at its 3' end.

Clause 62. The Type I-B CRISPRa system composition of any one of clauses 42-60, wherein the nucleic acid encoding the at least one crRNA comprises a recombinant CRISPR array comprising two or more repeat nucleotide sequences and one or more spacer nucleotide sequence(s), wherein each spacer nucleotide sequence in said CRISPR array is linked at its 5' end and at its 3' end to a repeat nucleotide sequence.

Clause 63. The Type I-B CRISPRa system composition of clause 62, wherein the recombinant CRISPR array is operably linked to a eukaryotic promoter, comprises a nuclear localization signal, and is operably linked to a terminator.

Clause 64. The Type I-B CRISPRa system of clause 60, wherein at least two of the one or more spacer nucleotide sequence(s) each comprise a 63 sequence that is complementary to a different target nucleotide sequence from a single target gene.

Clause 65. The Type I-B CRISPRa system of clause 63, wherein at least two of the one or more spacer nucleotide sequence(s) each comprise a nucleotide sequence that is complementary to a different target nucleotide sequence from a different target gene.

Clause 66. The Type I-B CRISPRa system of any one of clauses 42-65, wherein the target nucleotide sequence is located on a coding or a plus strand of a double stranded nucleotide sequence.

Clause 67. The Type I-B CRISPRa system of any one of clauses 42-65, wherein the target nucleotide sequence is located on a non-coding or a minus strand of a double stranded nucleotide sequence.

Clause 68. The Type I-B CRISPRa system of any one of clauses 42-67, wherein the target nucleotide sequence comprises all or a part of a nucleotide sequence encoding a promoter region of a gene or a complement thereof, or an enhancer region of a gene or a complement thereof.

Clause 69. The Type I-B CRISPRa system of any one of clauses 42-68, wherein the at least one target gene is an endogenous gene or a transgene.

Clause 70. The Type I-B CRISPRa system of any one of clauses 40-69, wherein the least one crRNA comprises a polynucleotide sequence of SEQ ID NOs 181-197, fragment thereof, or variant thereof.

Clause 71. The Type I-B CRISPRa system of any one of clauses 42-70, wherein the target nucleotide sequence comprises a polynucleotide sequence of SEQ ID Nos: 198-214, fragment thereof, or variant thereof.

Clause 72. The Type I-B CRISPRa system of any one of clauses 42-71, wherein the Cascade complex comprises: a Cas5 polypeptide encoded by a polynucleotide sequence of SEQ ID NO: 166 or 258, a Cas7 polypeptide encoded by a polynucleotide sequence of SEQ ID NO: 168 or 260, a Cas8b2 polypeptide encoded by a polynucleotide sequence of SEQ ID NO: 169 or 261, and a Cas6-p300 fusion protein encoded by a polynucleotide sequence of SEQ ID NO: 174; a Cas6 polypeptide encoded by a polynucleotide sequence of SEQ ID NO: 167 or 259, a Cas7 polypeptide encoded by a polynucleotide sequence of SEQ ID NO: 168 or 260, a Cas8b2 polypeptide encoded by a polynucleotide sequence of SEQ ID NO: 169 or 261, and a Cas5-p300 protein encoded by a polynucleotide sequence of SEQ ID NO: 171; a Cas5 polypeptide encoded by a polynucleotide sequence of SEQ ID NO: 166 or 258, a Cas6 polypeptide encoded by a polynucleotide sequence of SEQ ID NO: 167 or 259, a Cas8b2 polypeptide encoded by a polynucleotide sequence of SEQ ID NO: 169 or 261, and a Cas7 fusion protein encoded by a polynucleotide sequence of SEQ ID NO: 172; or a Cas5 polypeptide encoded by a polynucleotide sequence of SEQ ID NO: 166 or 258, a Cas6 polypeptide encoded by a polynucleotide sequence of SEQ ID NO: 167 or 259, a Cas7 polypeptide encoded by a polynucleotide sequence of SEQ ID NO: 168 or 260, and a Cas8b2 fusion protein encoded by a polynucleotide sequence of SEQ ID NO: 173.

Clause 73. The Type I-B CRISPRa system of any one of clauses 42-72, wherein the nucleic acid of (a)(ii) and/or (b)(ii) comprises DNA or RNA.

Clause 74. An expression cassette or a vector comprising the Type I-B CRISPRa system of any one of clauses 42-73, or subcomponents thereof.

Clause 75. An expression cassette or a vector comprising at least one polynucleotide sequence of SEQ ID NO: 166, SEQ ID NO: 167, SEQ ID NO: 168, SEQ ID NO: 169, SEQ ID NO: 171; SEQ ID NO: 172, SEQ ID NO: 173, SEQ ID NO: 174, SEQ ID NO: 179, SEQ ID NO: 258; SEQ ID NO: 259, SEQ ID NO: 260, SEQ ID NO: 261, or combinations thereof.

Clause 76. A host cell comprising the Type I-B CRISPRa system of any one of clauses 39-69 or the expression cassette or vector of clause 74 or 75.

Clause 77. A pharmaceutical composition comprising the Type I-B CRISPRa system of any one of clauses 42-73, the expression cassette or vector of clause 74 or 75, or the host cell of clause 76.

Clause 78. A kit for activating gene expression of at least one target gene in a cell, the kit comprising the Type I-B CRISPRa system of any one of clauses 42-73 or the expression cassette or vector of clause 74 or 75.

Clause 79. A method of activating the expression of a target gene in a cell, the method comprising introducing to a cell the Type I-B CRISPRa system of any one of clauses 42-73 or the expression cassette or vector of clause 74 or 75.

Clause 80. The method of clause 79, wherein the Type I-B CRISPRa comprises at least one polynucleotide encoding a Cascade complex and at least one crRNA.

Clause 81. The method of clause 79 or 80, wherein the Type I-B CRISPRa system comprises two or more crRNAs.

Clause 82. The method of clause 79 or 80, wherein the Type I-B CRISPRa system comprises between one and ten different crRNAs.

Clause 83. The method of clause 82, wherein the different crRNAs bind to different target nucleotide sequences within the target gene.

Clause 84. The method of clause 83, wherein the different target nucleotide sequences are separated by at least one nucleotide.

Clause 85. The method of clause 83, wherein the different target nucleotide sequences are separated by about 15 to about 700 base pairs.

Clause 86. The method of clause 82, wherein each of the different crRNAs bind to at least one different target genes.

Clause 87. The method of clause 86, wherein the different target genes are located on same chromosome.

Clause 88. The method of clause 86, wherein the different target genes are located on different chromosomes.

Clause 89. The method of clause 88, wherein at least one target nucleotide sequence is within a non-open chromatin region, an open chromatin region, a promoter region of the target gene, an enhancer region of the target gene, or a region upstream of a transcription start site of the target gene.

Clause 90. The method of clause 88, wherein at least one target nucleotide sequence is located between about 1 to about 1000 base pairs upstream of a transcription start site of a target gene.

Clause 91. The method of any one of clauses 79-90, wherein the target nucleotide sequence is immediately 3' to a protospacer adjacent motif (PAM).

Clause 92. The method of clause 91, wherein the PAM comprises CCA, CCT, or CAA.

Clause 93. The method of any one of clauses 79-92, wherein the Type I-B CRISPRa system, or subcomponents thereof, is introduced in one construct or in different constructs Clause 94. A method of activating the expression of a target gene in a cell, the method comprising introducing to a cell: (a)(i) a Cascade complex comprising three or more Cascade polypeptides of a Type I-B CRISPR/Cas system, or functional fragments thereof, or (ii) a nucleic acid encoding a Cascade complex comprising three or more Cascade polypeptides of a Type I-B CRISPR/Cas system, or functional fragments thereof; and/or (b)(i) at least one crRNA or (ii) a nucleic acid encoding at least one crRNA, wherein the crRNA targets a target nucleotide sequence from the at least one target gene, and wherein at least one Cascade polypeptide is fused to a second polypeptide domain having transcription activation activity thereby generating a Cascade polypeptide fusion protein, and wherein the at least one Cascade polypeptide in the Cascade polypeptide fusion protein is Cas5, Cas6, Cas7, or Cas8b2

Clause 95. The method of clause 94, wherein the Cascade complex comprises: [00426] a Cas5 polypeptide encoded by a polynucleotide sequence of SEQ ID NO: 166 or 258, a Cas7 polypeptide encoded by a polynucleotide sequence of SEQ ID NO: 168 or 260, a Cas8b2 polypeptide encoded by a polynucleotide sequence of SEQ ID NO: 169 or 261, and a Cas6-p300 fusion protein encoded by a polynucleotide sequence of SEQ ID NO: 174; a Cas6 polypeptide encoded by a polynucleotide sequence of SEQ ID NO: 167 or 259, a Cas7 polypeptide encoded by a polynucleotide sequence of SEQ ID NO: 168 or 260, a Cas8b2 polypeptide encoded by a polynucleotide sequence of SEQ ID NO: 169 or 261, and a Cas5-p300 protein encoded by a polynucleotide sequence of SEQ ID NO: 171; a Cas5 polypeptide encoded by a polynucleotide sequence of SEQ ID NO: 166 or 258, a Cas6 polypeptide encoded by a polynucleotide sequence of SEQ ID NO: 167 or 259, a Cas8b2 polypeptide encoded by a polynucleotide sequence of SEQ ID NO: 169 or 261, and a Cas7 fusion protein encoded by a polynucleotide sequence of SEQ ID NO: 172; or a Cas5 polypeptide encoded by a polynucleotide sequence of SEQ ID NO: 166 or 258, a Cas6 polypeptide encoded by a polynucleotide sequence of SEQ ID NO: 167 or 259, a Cas7 polypeptide encoded by a polynucleotide sequence of SEQ ID NO: 168 or 260, and a Cas8b2 fusion protein encoded by a polynucleotide sequence of SEQ ID NO:

Clause 96. The method of clause 95, wherein the method comprises introducing to the cell in step (a): a Cas5 expression vector or cassette comprising a polynucleotide sequence encoding a Cas5 polypeptide, a Cas6 expression vector or cassette comprising a polynucleotide sequence encoding a Cas6 polypeptide, a Cas7 expression vector or cassette comprising a polynucleotide sequence encoding a Cas7 polypeptide, a Cas8b2 expression vector or cassette comprising a polynucleotide sequence encoding a Cas8b2 polypeptide, or a combination thereof, and a Cas5 fusion expression vector or cassette comprising a polynucleotide sequence encoding a Cas5 fusion protein, a Cas6 fusion expression vector or cassette comprising a polynucleotide sequence encoding a Cas6 fusion protein, a Cas7 fusion expression vector or cassette comprising a polynucleotide sequence encoding a Cas7 fusion protein, or a Cas8b2 fusion expression vector or cassette comprising a polynucleotide sequence encoding a Cas8b2 fusion protein.

Clause 97. The method of any one of clauses 94-96, wherein the method comprises introducing to the cell in step (b) a crRNA expression vector or cassette comprising the crRNA sequence.

Clause 98. The method of any one of clauses 79-97, wherein the cell is a eukaryotic cell.

Clause 99. The method of any one of clauses 79-98, wherein the at least one polynucleotide sequence is operably linked to a eukaryotic promoter, comprises a nuclear localization signal, and is codon-optimized for eukaryotic expression.

Clause 100. The method of clause 98 or 99, wherein the eukaryotic cell is in a eukaryotic organism.

Clause 101. The method of clause 100, wherein the eukaryotic organism is a mammal, an insect, an amphibian, a reptile, a bird, a fish, a fungus, a plant, or a nematode.

Clause 102. The method of clause 101, wherein the mammal is a human.

Clause 103. The method of any one of clauses 79-102, wherein the nucleic acid of (a)(ii) and/or (b)(ii) comprises DNA or RNA.

Clause 104. A modified lentiviral construct comprising at least one polynucleotide sequence of SEQ ID Nos: 270-275, or a combination thereof.

Clause 105. The Type I-B CRISPRa system of any one of clauses 40-69, wherein the least one crRNA comprises a polynucleotide sequence of SEQ ID Nos: 270-275, fragment thereof, or variant thereof.

EXAMPLES

It will be readily apparent to those skilled in the art that other suitable modifications and adaptations of the methods of the present disclosure described herein are readily applicable and appreciable, and can be made using suitable equivalents without departing from the scope of the present disclosure or the aspects and embodiments disclosed herein. Having now described the present disclosure in detail, the same will be more clearly understood by reference to the following examples, which are merely intended only to illustrate some aspects and embodiments of the disclosure, and should not be viewed as limiting to the scope of the disclosure.

The present disclosure has multiple aspects, illustrated by the following non-limiting examples.

Example 1

Materials and Methods

Figure 9A:
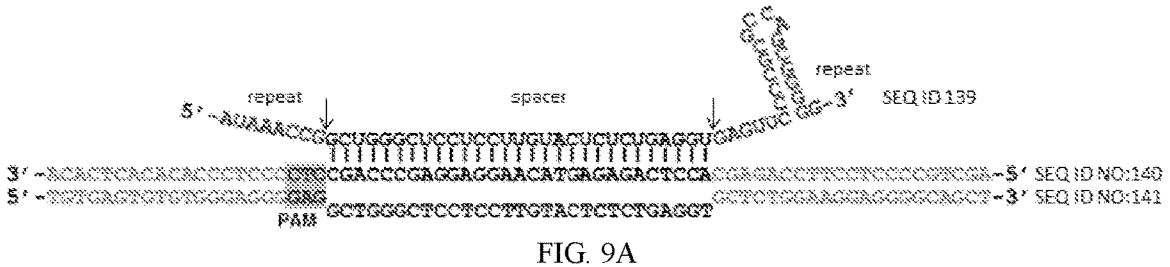
FIG. 9A-FIG. 9D show illustrations of crRNA cloning scheme for expression in mammalian cells.
Figure 9B:
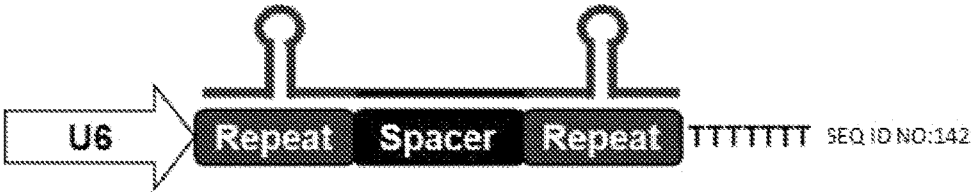
Figure 9C:
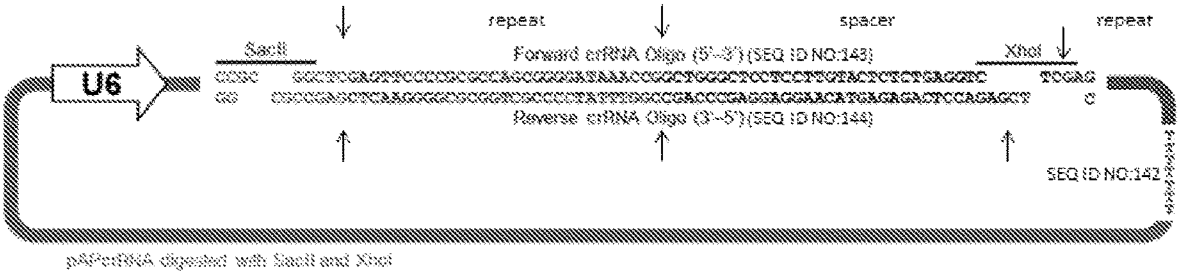
Figure 9D:

Plasmid construction. *E. coli* K-12 Cascade sequences were codon-optimized by human codon usage tables using Integrated DNA technology (IDT), synthesized as gene blocks and integrated into expression plasmids containing a CMV-driven cassette by Gibson cloning strategies. ATUM/DNA2.0 synthesized a second round of human codon-optimized constructs using proprietary methods. See Appendix for gene sequences of *E. coli* K-12 Cascade constructs (SEQ ID NOS: 1-8). For crRNA expression, a cloning vector was constructed (pAPcrRNA) with a U6-driven cassette and digested with SacII and XhoI. To insert repeat-spacer pairs, oligonucleotides encoding the palindromic repeat and crRNA spacers were annealed, 5' phosphorylated with PNK and ligated into digested pAPcrRNA. See FIGS. 9A-9C for an illustration of the cloning scheme. The control crRNA used throughout this study targets Cascade to an irrelevant control locus at HBE1.

Cell culture and transfections. HEK293T cells were maintained in Dulbecco's Modified Eagle's Medium (Invitrogen) with 10% Fetal Bovine Serum (Sigma) and 1% penicillin-streptomycin (Gibco). Cells were incubated at 37° C. with 5% $CO_2$. All transfections were performed using Lipofectamine 2000 (Invitrogen) according to the manufacturer's protocol.

Immunofluorescence staining. Cells were passaged and transfected with 100 ng plasmid DNA on coverslips in 24-well plates. At three days post-transfection, cells were washed with PBS and fixed with 4% paraformaldehyde (Sigma). Cells were incubated with blocking buffer (5% goat serum, 0.2% Triton X-100 in PBS) then incubated with mouse anti-Flag (1:200 dilution, Sigma, M2 clone), followed by incubation with goat anti-mouse Alexa Fluor 647 (1:200 dilution, Life Technologies, A21236), and DAPI nucleic acid stain (Invitrogen). Cells were imaged with a Leica DMI 3000 B fluorescence microscope.

Western blot and co-immunoprecipitation. For protein analysis, HEK293T cells were transfected with 2 μg of individual Cas constructs in 6-well plates. After three days, cells were lysed in RIPA buffer (Sigma) with a proteinase inhibitor cocktail (Roche). Samples were centrifuged at 12,000 rpm for 5 min and the supernatant was isolated and quantified using a bicinchoninic acid assay (BCA) protein standard curve (Thermo Scientific) on the BioTek Synergy 2 Multi-Mode Microplate Reader. Mixed with NuPAGE loading buffer (Invitrogen) and 5% β-mercaptoethanol, 25 μg protein was heated at 100° C. for 10 min. Samples were loaded into 10% NuPAGE Bis-Tris gels (Invitrogen) with IVIES buffer (Invitrogen) and electrophoresed for 70 min at 200V on ice. Protein was transferred to nitrocellulose membranes for 1 hour in 1× tris-glycine transfer buffer containing 10% methanol and 0.01% SDS at 4° C. at 400 mA. The blot was blocked at room temperature for 30 min in 5% milk-TBST (50 mM Tris, 150 mM NaCl and 0.1% Tween-20) and incubated with mouse anti-Flag (1:1,000 dilution, Sigma, M2 clone) in 5% milk-TBST at 4° C. overnight. Blots were then washed in TBST and incubated with goat anti-mouse-conjugated horseradish peroxidase (1:2,500 dilution, Santa-Cruz) in 5% milk-TBST for 45 min at room temperature. Blots were washed in TBST then visualized using Western-C ECL substrate (Bio-Rad) on a ChemiDoc XRS+ System (Bio-Rad). Blots were stripped with Restore PLUS Western Blot Stripping Buffer (Thermo Scientific), blocked, and re-blotted with rabbit anti-GAPDH (1:1,000 dilution, Cell Signaling, 14C10) and goat anti-rabbit-conjugated horseradish peroxidase (1:2,500 dilution, Santa Cruz). Blots were visualized again using the methods described above.

For co-immunoprecipitation analysis, co-transfections were completed using a V5-CasC construct. HEK293T cells were co-transfected in 6-well plates with 425 μg of each Cas construct and crRNA for 2.25 μg total plasmid DNA per condition. At three days post transfection, cells were lysed with IP lysis buffer (Thermo Scientific) with a proteinase inhibitor cocktail (Roche). Samples were centrifuged at 12,000 rpm for 5 min and the supernatant was isolated and subjected to immunoprecipitation using goat anti-V5-agarose conjugate (10 μl, Abcam, ab1229) at 4° C. overnight. The IP products were washed three times with IP lysis buffer, mixed with NuPAGE loading buffer and 5% β-mercaptoethanol, and heated at 100° C. for 10 min. Samples were loaded into 10% NuPAGE Bis-Tris gels, and resolved as described above. Blots were blocked, incubated with mouse anti-Flag (1:1,000 dilution, Sigma, M2 clone) and mouse anti-V5 (1:40,000 dilution, Abcam, SV5-Pk1 clone) then with goat anti-mouse-conjugated horseradish peroxidase (1:2,500 dilution, Santa Cruz). Blots were visualized as described above.

RNA analysis. For quantitative PCR (qPCR), HEK293T cells were co-transfected with 600 ng total plasmid in 24-well plates. After three days, total RNA was isolated using QIAshredder and QIAGEN RNeasy kits (Qiagen). Reverse transcription was carried out using 500 ng total RNA per sample in a 10 μl reaction using the SuperScript VILO Reverse Transcription Kit (Invitrogen). Per qPCR reaction, 1.0 μl of cDNA was used with Perfecta SYBR Green Fastmix (Quanta Biosciences) and ran using the CFX96 Real-Time PCR Detection System (Bio-Rad). All sequences for qPCR primers can be found in Table 1. All qPCR data are presented as fold change in RNA normalized to Gapdh expression and relative to samples targeting Cascade with a crRNA targeted to an irrelevant control locus at HBE1.

TABLE 1

Quantitative RT-PCR and ChIP-qPCR primers and conditions

| Target | Forward Primer (5'-3') | Reverse Primer (5'-3') | Cycling Conditions |
|---|---|---|---|
| IL1RN | GGAATCCATGGAGGGAAGAT (SEQ ID NO: 127) | TGTTCTCGCTCAGGTCAGTG (SEQ ID NO: 133) | 95° C. 10 s<br>60° C. 30 s x45 |
| HBG | GCTGAGTGAACTGCACTGTGA (SEQ ID NO: 128) | GAATTCTTTGCCGAAATGGA (SEQ ID NO: 134) | 95° C. 10 s<br>68° C. 30 s x45 |
| GAPDH | CAATGACCCCTTCATTGACC (SEQ ID NO: 129) | TTGATTTTGGAGGGATCTCG (SEQ ID NO: 135) | 95° C. 10 s<br>53° C. 30 s x45 |
| IL1RN ChIP Region 1 | TGAGTCACCCTCCTGGAAAC (SEQ ID NO: 130) | CTCCTTCCAGAGCACCTCAG (SEQ ID NO: 136) | 95° C. 10 s<br>60° C. 30 s x45 |
| IL1RN ChIP Region 2 | GCTGGGCTCCTCCTTGTACT (SEQ ID NO: 131) | GCTGCTGCCCATAAAGTAGC (SEQ ID NO: 137) | 95° C. 10 s<br>60° C. 30 s x45 |
| Actin ChIP Neg Control | GTTGGGTGCTCCAGCTTTTA (SEQ ID NO: 132) | CCTCAAAACTCCTGGACTCG (SEQ ID NO: 138) | 95° C. 10 s<br>60° C. 30 s x45 |

Chromatin immunoprecipitation qPCR. HEK293T cells were transfected with 40 μg total plasmid in 15 cm dishes. After three days, cells were fixed in 1% formaldehyde for 10 min at room temperature. The reaction was quenched with 0.125M glycine and the cells were lysed using Farnham lysis buffer with a protease inhibitor cocktail (Roche). Nuclei were collected by centrifugation at 2,000 rpm for 5 min at 4° C. and lysed in RIPA buffer with a protease inhibitor cocktail (Roche). Chromatin was sonicated using a Bio-rupter Sonicator (Diagenode, model XL) and immunoprecipitated using anti-Flag (Sigma, M2). The formaldehyde crosslinks were reversed by heating overnight at 65° C. and genomic DNA fragments were purified using a spin column. For qPCR, 500 pg of genomic was used per reaction. qPCR was performed as described above. The data are presented as fold change gDNA normalized to a region of the β-actin locus and relative to samples targeting Cascade with the control crRNA mentioned above. All sequences for qPCR primers can be found in Table 1.

Statistical Analysis. All data analyzed with three biological replicates and presented as mean±SEM. Logarithmic transformations were completed prior to statistical analysis where indicated. All p values calculated by global one-way ANOVA with Tukey post hoc tests ($\alpha$=0.05).

Example 2

Type I-E Cascade Expression and Complex Formation in Human Cells

Figure 1C:
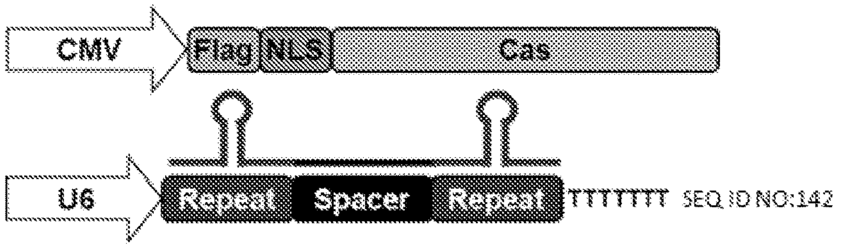
Figure 1D:
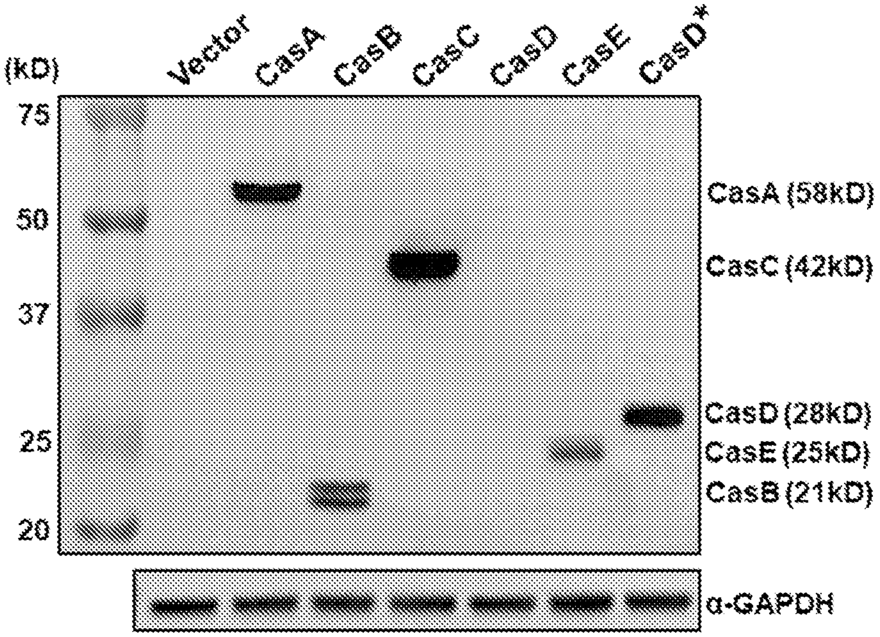
Figure 1E:
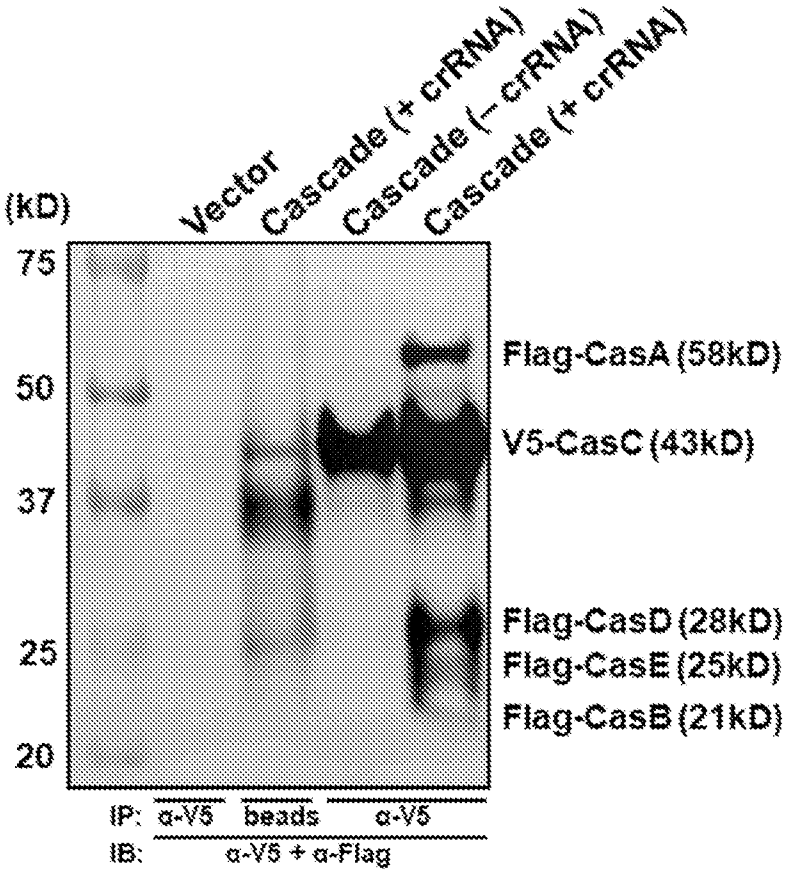
Figure 1F:
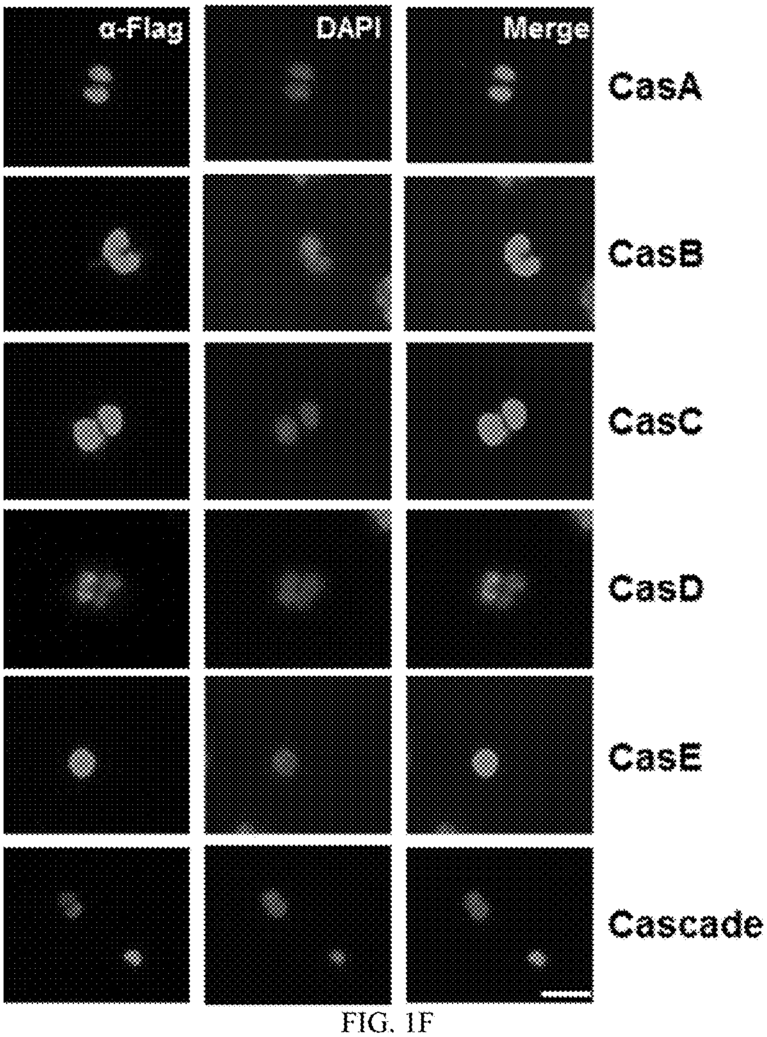
Figure 1G:
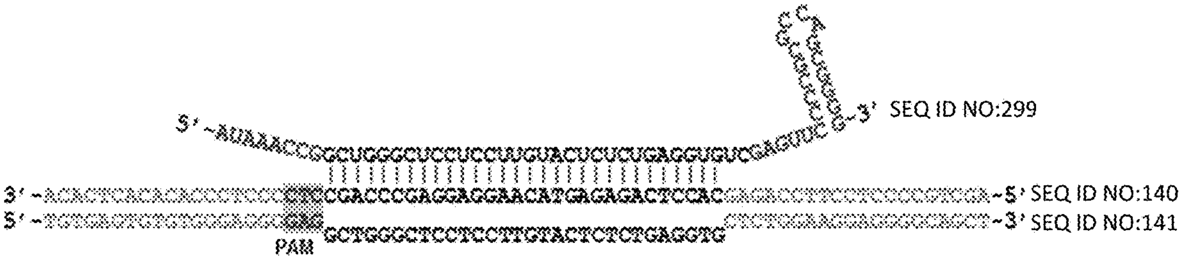

To repurpose Cascade for use in mammalian cells, a CMV promoter was used to express the Cascade subunits of the *E. coli* K12 system with attached N-terminal Flag epitope tags and nuclear localization signals (NLSs). The RNA polymerase III U6 promoter was used to express target spacers flanked by full repeat sequences for crRNA processing (FIG. 1C). Heterologous expression of all Cascade constructs was confirmed by Western blot following transfection of each plasmid individually into human HEK293T cells (FIG. 1D). The Cas genes were originally optimized based on human codon usage, but variable expression of these Cas constructs indicated a need for additional codon-optimization of CasD, which was performed by ATUM/DNA2.0. To determine if Cascade complex formation occurred in human cells, the six plasmids encoding each of the five Cas subunits and the crRNA cassette were co-transfected into HEK293T cells. Co-immunoprecipitation by pull-down of the V5 epitope on CasC and blotting for the Flag epitope on the other subunits confirmed proper complex assembly (FIG. 1E). crRNA-dependent Cascade formation was observed in human cells (FIG. 1E). Additionally, nuclear localization of each subunit with the single NLS was confirmed by immunofluorescence staining of transfected HEK293T cells (FIG. 1F).

Example 3

Figure 2A:
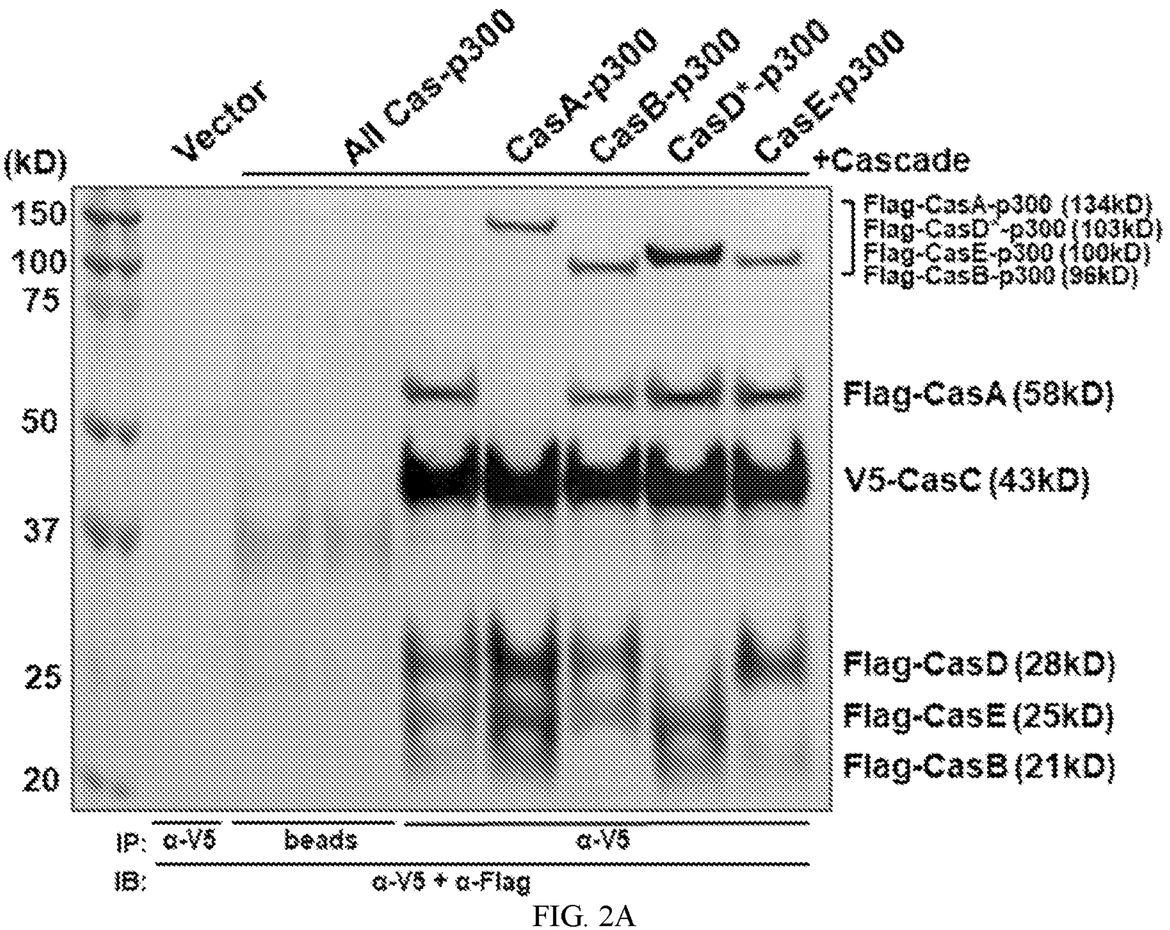
FIG. 2A-FIG. 2E show Type I-E CRISPRa activates transcription of endogenous IL1RN gene in human cells.

Type I-E Cascade Activation of Transcription of Endogenous IL1RN Gene in Human Cells Type I-E Cascade for CRISPR-based programmable transcriptional activation (CRISPRa) was repurposed in mammalian cells. To repurpose Type I-E Cascade as a programmable transcriptional activator, the various Cas-effector subunits was used for tethering of the activation domain and compared to endogenous gene activation with dCas9 fused to the catalytic core domain of the human acetyltransferase p300. The five Cas subunits of Type I-E available at various stoichiometry (FIG. 1A) was fused with transcriptional regulator domains. Following heterologous expression of Cascade with p300 fused to CasA, CasB, CasD, or CasE, Cascade complex formation was confirmed by co-immunoprecipitation (FIG. 2A). The ability of each of these subunits to accommodate the fusion of the large p300 core catalytic domain (72 kDa) without abrogating complex formation suggests that the modular Cascade complex could be particularly useful for multiplexed targeting of regulatory domains at specific loci.

Figure 2B:
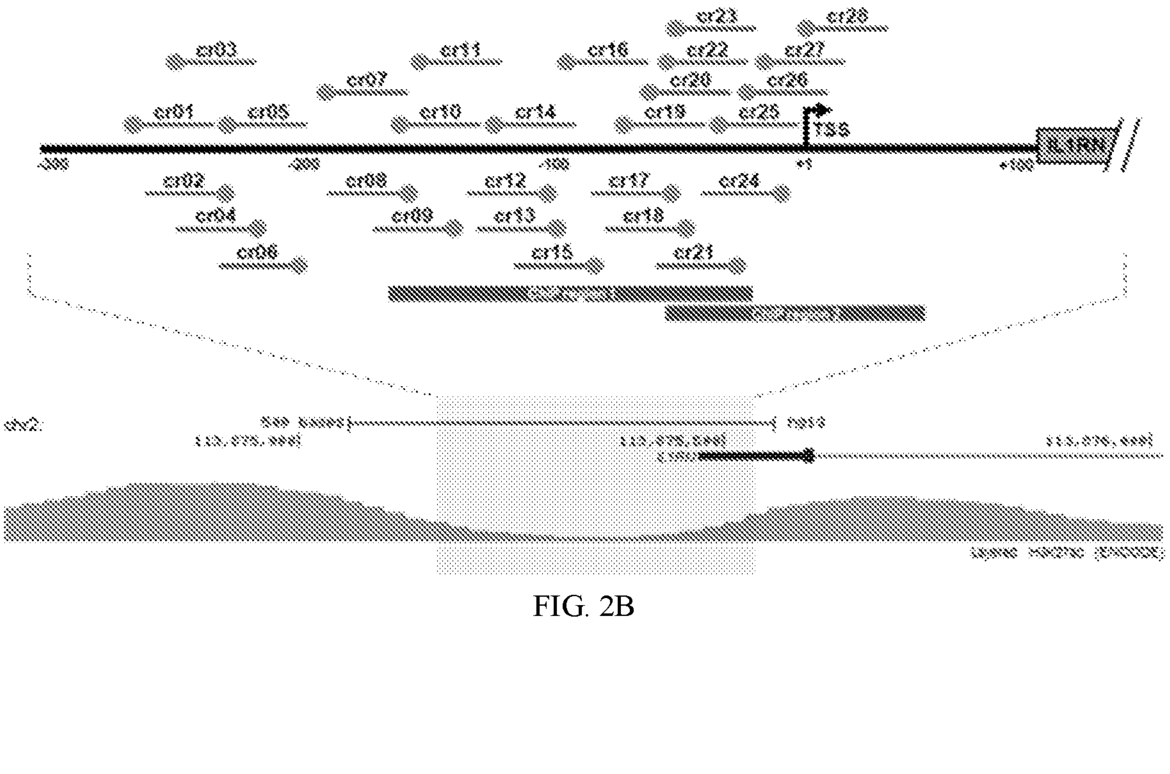
Figure 3A:
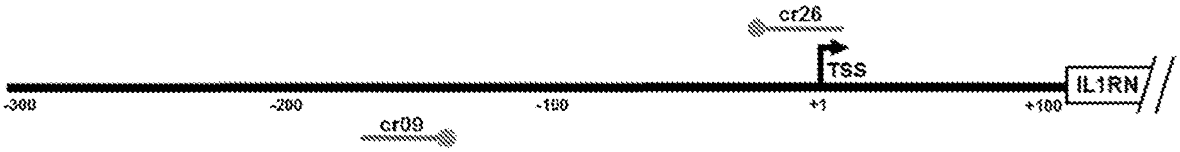
FIG. 3A-FIG. 3B show activation is dependent on targeting Cascade-p300 fusion protein to genomic loci.

To test programmable endogenous gene activation in human cells, a panel of crRNAs were generated tiling the endogenous IL1RN promoter at spacer targets downstream of known PAMs (5'-AAG, AGG, ATG, GAG, TAG-3') (FIG. 2B, Table 2). FIG. 3A shows a schematic of the IL1RN locus along with IL1RN crRNA target sites.

TABLE 2 crRNA target sequences

| crRNA | Target | Strand | PAM | Spacer Sequence (5'-3') | SEQ ID NO: | Target Sequence (5'-3') | SEQ ID NO: | Genomic Location (GRCh37/hg19 Assembly) |
|---|---|---|---|---|---|---|---|---|
| Ctrl crRNA | HBE | + | AGG | CUGACCUGUGUCCCUCAGGGGU GGAGUCAGG | 15 | AGGCTGACCTGTGTCCCTCAGGGG TGGAGTCAGG | 71 | cr11: 5291265-5291257 |
| cr01 | IL1RN | + | GAG | CUGGCGGCAGUCGGGGUUGGGG UAAGCACGUC | 16 | GAGCTGGCGGCAGTCGGGGTTGGG GTAAGCACGTC | 72 | cr2: 113875222-113875251 |
| cr02 | IL1RN | − | GAG | CUGGGCCUUCGUGCUUACCCCA ACCCCGACUC | 17 | GAGCTGGGCCTTCGTGCTTACCCCA ACCCCGACTC | 73 | cr2: 113875230-113875260 |
| cr03 | IL1RN | + | AAG | CACGAAGGCCCAGCUCAGUUCU CUGCAUGUUC | 18 | AAGCACGAAGGCCCAGCTCAGTTC TCTGCATGTTC | 74 | cr2: 113875248-113875277 |
| cr04 | IL1RN | − | GAG | GUCACAUGCAGAGAACUGAGCU GGGCCUUCUC | 19 | GAGGTCACATGCAGAGAACTGAGC TGGGCCTTCTC | 75 | cr2: 113875251-113875280 |
| cr05 | IL1RN | + | AGG | GCCCAGCUCAGUUCUCUGCAUG UGACCUCCUC | 20 | AGGGCCCAGCTCAGTTCTCTGCAT GTGACCTCCTC | 76 | cr2: 113875255-113875284 |
| cr06 | IL1RN | − | AAG | AUGGGAGGUCACAUGCAGAGAA CUGAGCUGUC | 21 | AAGATGGGAGGTCACATGCAGAGA ACTGAGCTGTC | 77 | cr2: 113875258-113875287 |
| cr07 | IL1RN | + | AAG | AACCAGUUUGGUUUCUGCUAGC CUGAGUCAUC | 22 | AAGAACCAGTTTGGTTTCTGCTAGC CTGAGTCATC | 78 | cr2: 113875302-113875333 |
| cr08 | IL1RN | − | GAG | GGUGACUCAGGCUAGCAGAAAC CAAACUGGUC | 23 | GAGGGTGACTCAGGCTAGCAGAAA CCAAACTGGTC | 79 | cr2: 113875303-113875333 |
| cr09 | IL1RN | − | AGG | CCCAGUUUCCAGGAGGGUGACU CAGGCUAGUC | 24 | AGGCCCAGTTTCCAGGAGGGTGAC TCAGGCTAGTC | 80 | cr2: 113875319-113875348 |
| cr10 | IL1RN | + | TAG | CCUGAGUCACCCUCCUGGAAAC UGGGCCUGUC | 25 | TAGCCTGAGTCACCCTCCTGGAAA CTGGGCCTGTC | 81 | cr2: 113875323-113875352 |
| cr11 | IL1RN | + | GAG | UCACCCUCCUGGAAACUGGGCC UGCUUGGCUC | 26 | GAGTCACCCTCCTGGAAACTGGGC CTGCTTGGCTC | 82 | cr2: 113875329-113875358 |
| cr12 | IL1RN | − | GAG | AUGGGCCGGCUGAUGGCUGACU UGAUGCCAUC | 27 | GAGATGGGCCGGCTGATGGCTGAC TTGATGCCATC | 83 | cr2: 113875355-113875384 |
| cr13 | IL1RN | − | AGG | AGAUGGGCCGGCUGAUGGCUGA CUUGAUGCUC | 28 | AGGAGATGGGCCGGCTGATGGCTG ACTTGATGCTC | 84 | cr2: 113875357-113875386 |
| cr14 | IL1RN | + | AAG | UCAGCCAUCAGCCGGCCCAUCU CCUCAUGGUC | 29 | AAGTCAGCCATCAGCCGGCCCATC TCCTCATGGTC | 85 | cr2: 113875365-113875393 |
| cr15 | IL1RN | − | GAG | GGUUGGCCAGCAUGAGGAGAUG GGCCGGCUUC | 30 | GAGGGTTGGCCAGCATGAGGAGAT GGGCCGGCTTC | 86 | cr2: 113875374-113875403 |
| cr16 | IL1RN | + | ATG | CUGGCCAACCCUCUGUGAGUGU GUGGGAGGUC | 31 | ATGCTGGCCAACCCTCTGTGAGTGT GTGGGAGGTC | 87 | cr2: 113875394-113875423 |
| cr17 | IL1RN | − | GAG | CCCAGCCUCCCCUCCCACACAC UCACAGAGUC | 32 | GAGCCCAGCCTCCCCTCCCACACA CTCACAGAGTC | 88 | cr2: 113875404-113875433 |
| cr18 | IL1RN | − | AAG | GAGGAGCCCAGCCUCCCCUCCC ACACACUCUC | 33 | AAGGAGGAGCCCAGCCTCCCCTCC CACACACTCTC | 89 | cr2: 113875408-113875439 |
| cr19 | IL1RN | + | GAG | UGUGUGGGAGGGGAGGCUGGGC UCCUCCUUUC | 34 | GAGTGTGTGGGAGGGGAGGCTGGG CTCCTCCTTTC | 90 | cr2: 113875413-113875442 |
| cr20 | IL1RN | + | AGG | GGAGGCUGGGCUCCUCCUUGUA CUCUCUGAUC | 35 | AGGGGAGGCTGGGCTCCTCCTTGT ACTCTCTGATC | 91 | cr2: 113875424-113875453 |

TABLE 2-continued

| crRNA target sequences | | | | | | | | |
|---|---|---|---|---|---|---|---|---|
| crRNA | Target | Strand | PAM | Spacer Sequence (5'-3') | SEQ ID NO: | Target Sequence (5'-3') | SEQ ID NO: | Genomic Location (GRCh37/hg19 Assembly) |
| cr21 | IL1RN | − | GAG | CACCUCAGAGAGUACAAGGAGGAGCCCAGCUC | 36 | GAGCACCTCAGAGAGTACAAGGAGGAGCCCAGCTC | 92 | cr2: 113875428-113875457 |
| cr22 | IL1RN | + | GAG | GCUGGGCUCCUCCUUGUACUCUCUGAGGUGUC | 37 | GAGGCTGGGCTCCTCCTTGTACTCTCTGAGGTGTC | 93 | cr2: 113875428-113875457 |
| cr23 | IL1RN | + | AGG | CUGGGCUCCUCCUUGUACUCUCUGAGGUGCUC | 38 | AGGCTGGGCTCCTCCTTGTACTCTCTGAGGTGCTC | 94 | cr2: 113875429-113875460 |
| cr24 | IL1RN | − | GAG | CUGCCCCUCCUUCCAGAGCACCUCAGAGAGUC | 39 | GAGCTGCCCCTCCTTCCAGAGCACCTCAGAGAGTC | 95 | cr2: 113875445-113875475 |
| cr25 | IL1RN | + | GAG | GUGCUCUGGAAGGAGGGGCAGCUCCACCCUUC | 40 | GAGGTGCTCTGGAAGGAGGGGCAGCTCCACCCTTC | 96 | cr2: 113875455-113875484 |
| cr26 | IL1RN | + | AAG | GAGGGGCAGCUCCACCCUGGGAGGGACUGUUC | 41 | AAGGAGGGGCAGCTCCACCCTGGGAGGGACTGTTC | 97 | cr2: 113875467-113875496 |
| cr27 | IL1RN | + | GAG | GGGCAGCUCCACCCUGGGAGGGACUGUGGCUC | 42 | GAGGGGCAGCTCCACCCTGGGAGGGACTGTGGCTC | 98 | cr2: 113875470-113875501 |
| cr28 | IL1RN | + | GAG | GGACUGUGGCCCAGGUACUGCCCGGGUGCUUC | 43 | GAGGGACTGTGGCCCAGGTACTGCCCGGGTGCTTC | 99 | cr2: 113875490-113875521 |
| cr01 | HBG | − | ATG | ACUGAAUCGGAACAAGGCAAAGGCUAUAAAUC | 44 | ATGACTGAATCGGAACAAGGCAAAGGCTATAAATC | 100 | cr11: 5271317-5271346 |
| cr02 | HBG | − | AGG | CAAAGGCUAUAAAAAAAAUUAGCAGUAUCCUC | 45 | AGGCAAAGGCTATAAAAAAAATTAGCAGTATCCTC | 101 | cr11: 5271298-5271329 |
| cr03 | HBG | − | AAG | GCUAUAAAAAAAAUUAGCAGUAUCCUCUUGUC | 46 | AAGGCTATAAAAAAAATTAGCAGTATCCTCTTGTC | 102 | cr11: 5271295-5271324 |
| cr04 | HBG | + | GAG | AUAGUGUGGGGAAGGGGCCCCCAAGAGGAUUC | 47 | GAGATAGTGTGGGGAAGGGGCCCCCAAGAGGATTC | 103 | cr11: 5271274-5271305 |
| cr05 | HBG | + | AGG | GACCGUUUCAGACAGAUAUUUGCAUUGAGAUC | 48 | AGGGACCGTTTCAGACAGATATTTGCATTGAGATC | 104 | cr11: 5271245-5271275 |
| cr06 | HBG | − | ATG | CAAAUAUCUGUCUGAAACGGUCCCUGGCUAUC | 49 | ATGCAAATATCTGTCTGAAACGGTCCCTGGCTATC | 105 | cr11: 5271237-5271266 |
| cr07 | HBG | + | GAG | UUUAGCCAGGGACCGUUUCAGACAGAUAUUUC | 50 | GAGTTTAGCCAGGGACCGTTTCAGACAGATATTTC | 106 | cr11: 5271235-5271265 |
| cr08 | HBG | + | ATG | GGUGGAGUUUAGCCAGGGACCGUUUCAGACUC | 51 | ATGGGTGGAGTTTAGCCAGGGACCGTTTCAGACTC | 107 | cr11: 5271228-5271257 |
| cr09 | HBG | + | AGG | CUGGCCAACCCAUGGGUGGAGUUUAGCCAGUC | 52 | AGGCTGGCCAACCCATGGGTGGAGTTTAGCCAGTC | 108 | cr11: 5271214-5271243 |
| cr10 | HBG | + | AAG | GCUGGCCAACCCAUGGGUGGAGUUUAGCCAUC | 53 | AAGGCTGGCCAACCCATGGGTGGAGTTTAGCCATC | 109 | cr11: 5271213-5271242 |
| cr11 | HBG | + | AAG | GCAAGGCUGGCCAACCCAUGGGUGGAGUUUUC | 54 | AAGGCAAGGCTGGCCAACCCATGGGTGGAGTTTTC | 110 | cr11: 5271208-5271237 |
| cr12 | HBG | + | AGG | CUAUUGGUCAAGGCAAGGCUGGCCAACCCAUC | 55 | AGGCTATTGGTCAAGGCAAGGCTGGCCAACCCATC | 111 | cr11: 5271196-5271226 |
| cr13 | HBG | + | AAG | GCUAUUGGUCAAGGCAAGGCUGGCCAACCCUC | 56 | AAGGCTATTGGTCAAGGCAAGGCTGGCCAACCCTC | 112 | cr11: 5271195-5271224 |
| cr14 | HBG | − | ATG | GGUUGGCCAGCCUUGCCUUGACCAAUAGCCUC | 57 | ATGGGTTGGCCAGCCTTGCCTTGACCAATAGCCTC | 113 | cr11: 5271193-5271223 |
| cr15 | HBG | + | AAG | ACUAUUGGUCAAGUUUGCCUUGUCAAGGCUUC | 58 | AAGACTATTGGTCAAGTTTGCCTTGTCAAGGCTTC | 114 | cr11: 5271168-5271197 |
| cr16 | HBG | − | AAG | GCAAACUUGACCAAUAGUCUUAGAGUAUCCUC | 59 | AAGGCAAACTTGACCAATAGTCTTAGAGTATCCTC | 115 | cr11: 5271156-5271185 |

TABLE 2-continued crRNA target sequences

| crRNA | Target | Strand | PAM | Spacer Sequence (5'-3') | SEQ ID NO: | Target Sequence (5'-3') | SEQ ID NO: | Genomic Location (GRCh37/hg19 Assembly) |
|---|---|---|---|---|---|---|---|---|
| cr17 | HBG | − | AGG | CAAACUUGACCAAUAGUCUUAG AGUAUCCAUC | 60 | AGGCAAACTTGACCAATAGTCTTA GAGTATCCATC | 116 | cr11: 5271155-5271184 |
| cr18 | HBG | − | GAG | UAUCCAGUGAGGCCAGGGGCCG GCGGCUGGUC | 61 | AGGCTGACCTGTGTCCCTCAGGGG TGGAGTCAGG | 117 | cr11: 5271131-5271160 |
| cr19 | HBG | − | GAG | GCCAGGGGCCGGCGGCUGGCUA GGGAUGAAUC | 62 | GAGCTGGCGGCAGTCGGGGTTGGG GTAAGCACGTC | 118 | cr11: 5271120-5271149 |
| cr20 | HBG | − | AGG | GGCCGGCGGCUGGCUAGGGAUG AAGAAUAAUC | 63 | GAGCTGGGCCTTCGTGCTTACCCCA ACCCCGACTC | 119 | cr11: 5271114-5271143 |
| cr21 | HBG | + | AAG | GGUGCUUCCUUUUAUUCUUCAU CCCUAGCCUC | 64 | AAGCACGAAGGCCCAGCTCAGTTC TCTGCATGTTC | 120 | cr11: 5271103-5271132 |
| cr22 | HBG | − | ATG | AAGAAUAAAAGGAAGCACCCUU CAGCAGUUUC | 65 | GAGGTCACATGCAGAGAACTGAGC TGGGCCTTCTC | 121 | cr11: 5271090-5271121 |
| cr23 | HBG | − | AAG | AAUAAAAGGAAGCACCCUUCAG CAGUUCCAUC | 66 | AGGGCCCAGCTCAGTTCTCTGCAT GTGACCTCCTC | 122 | cr11: 5271089-5271118 |
| gRNA1 | 1L1RN | + | NGG | UGUACUCUCUGAGGUGCUC | 67 | AAGATGGGAGGTCACATGCAGAGA ACTGAGCTGTC | 123 | chr2: 113875442-113875460 |
| gRNA2 | 1L1RN | + | NGG | ACGCAGAUAAGAACCAGUU | 68 | AAGAACCAGTTTGGTTTCTGCTAGC CTGAGTCATC | 124 | chr2: 113875291-113875309 |
| gRNA3 | 1L1RN | + | NGG | CAUCAAGUCAGCCAUCAGC | 69 | GAGGGTGACTCAGGCTAGCAGAAA CCAAACTGGTC | 125 | chr2: 113875358-113875376 |
| gRNA4 | 1L1RN | + | NGG | GAGUCACCCUCCUGGAAAC | 70 | AGGCCCAGTTTCCAGGAGGGTGAC TCAGGCTAGTC | 126 | chr2: 113875326-113875344 |

Figure 2C:
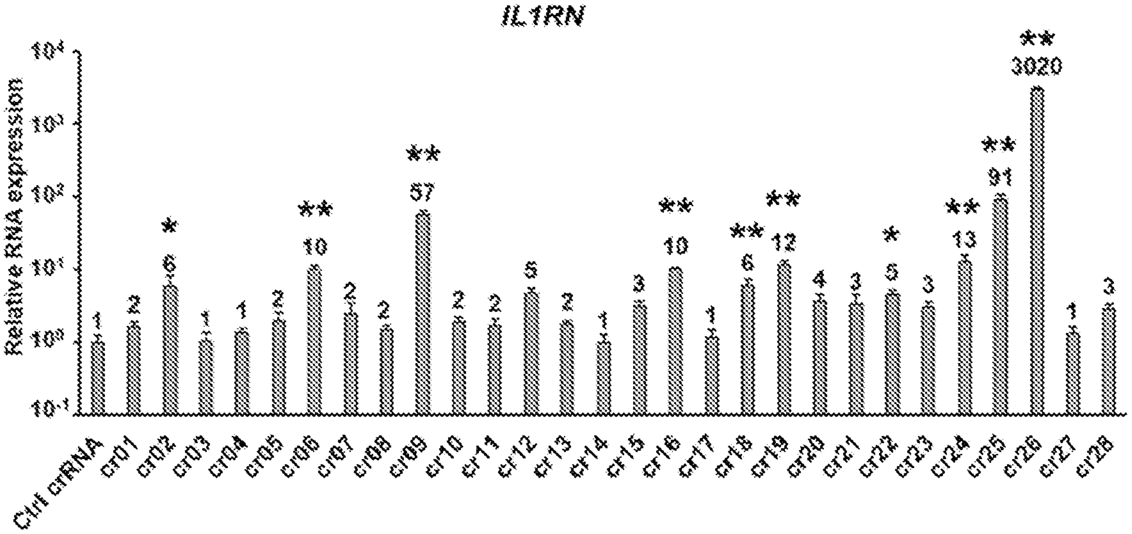
Figure 2D:
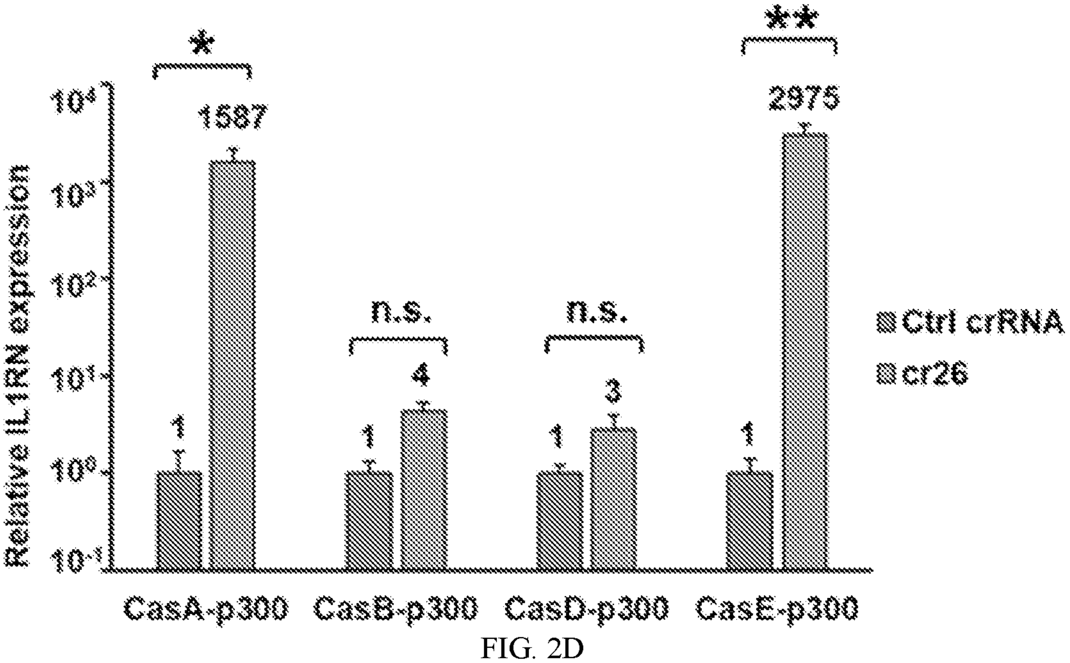
Figure 3B:
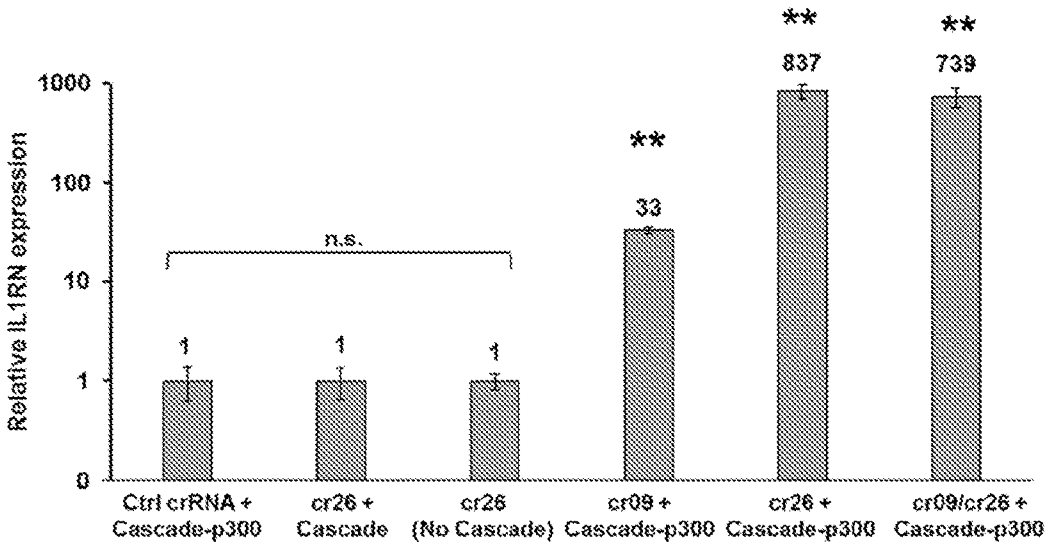
Figure 4:
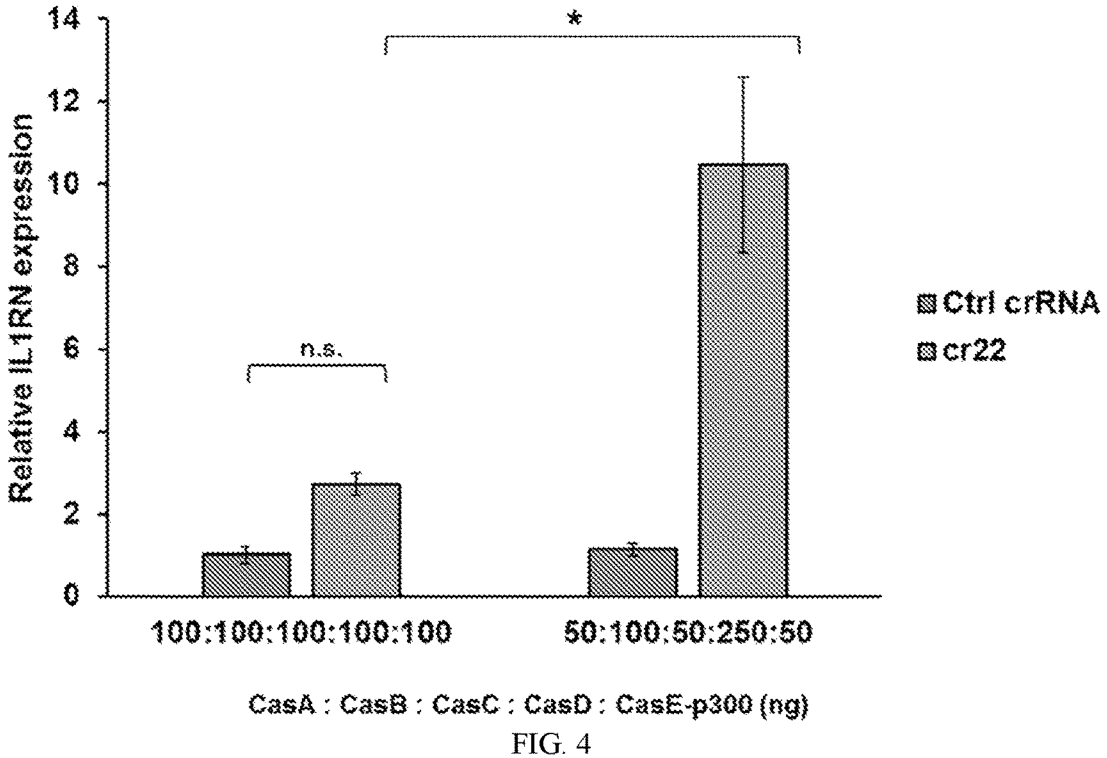
FIG. 4 shows heterologous transfection of Cas constructs reveals optimized transactivation activity. Relative IL1RN expression following co-transfection of 100 ng individual crRNAs (Ctrl crRNA (left bars) and cr22 (right bars)) and 500 ng total Cascade with CasE-p300 in various ratios. All samples processed at 3 days post transfection. (Tukey-test, *P<0.05, n=3 biological replicates; error bars, SEM). TSS, Transcription start site; n.s., non-significant.

Co-transfection of HEK293T cells with plasmids encoding Cascade with CasE-p300 and individual crRNAs revealed robust IL1RN activation with many crRNAs, including >3,000-fold IL1RN activation with cr26 ($P<0.001$, FIG. 2C). Cascade with CasE-p300 is also referred herein as "EcoCascade-p300." cr26 with Cascade, but no p300 domain, or cr26 alone did not activate IL1RN (FIG. 3B), suggesting target-specific activation by Cascade-p300. Based on Cascade stoichiometry (FIG. 1A) and relative Cas construct expression (FIG. 1D), the relative masses of transfected plasmids to maximize gene activation was optimized (FIG. 4**). Additionally, the transactivation potential of all Cas-p300 fusions was explored with cr26. Relative to heterologous expression with a crRNA targeted to an irrelevant control locus, Cascade containing CasA-p300 or CasE-p300 displayed significant IL1RN transactivation (*$P<0.05$, FIG. 2D).

Example 4

Cascade-p300 Interaction with DNA Target

Figure 2E:
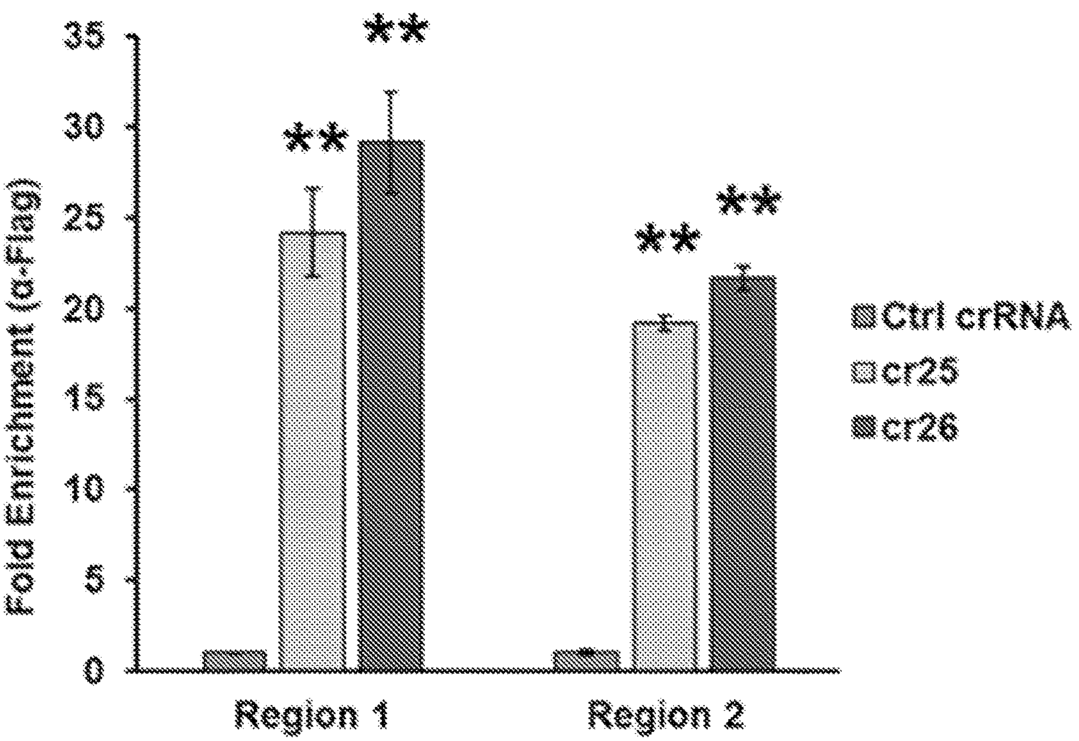
Figure 5A:
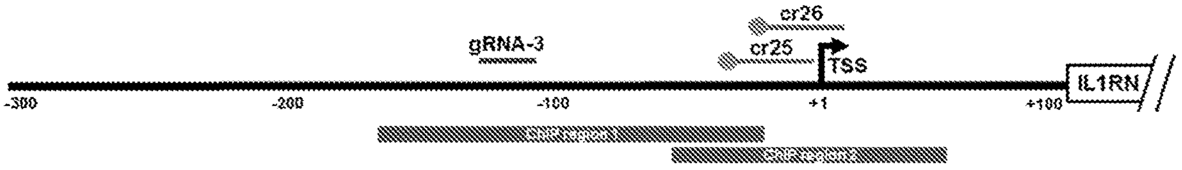
FIG. 5A-FIG. 5B show programmable Cascade-p300 fusion proteins interaction with endogenous DNA target comparable to optimal dCas9 and gRNA-3.
Figure 5B:
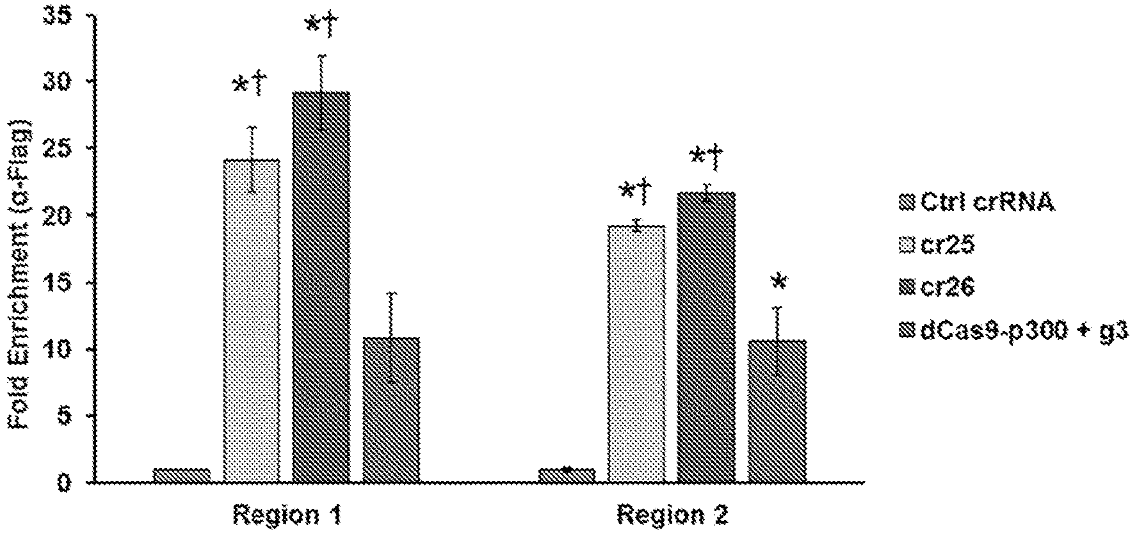
Figure 11A:
FIG. 11A-FIG. 11B show genome-wide specificity of EcoCascade-p300 targeted to IL1RN.
Figure 11B:
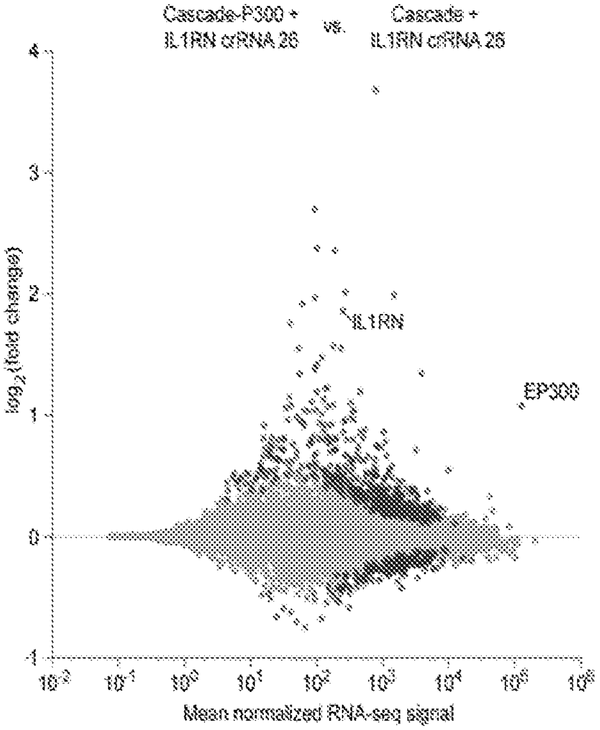

To investigate Cascade-p300 interactions at the target locus, chromatin immunoprecipitation was performed with an anti-Flag antibody followed by quantitative PCR (ChIP-qPCR) of two amplicons adjacent to the target site (FIG. 2B). FIG. 5A shows a schematic of the IL1RN locus along with IL1RN crRNA and gRNA target sites. Table 8 discloses additional target. Significant enrichment of the target regions in Cascade-p300 samples co-transfected with cr25 or cr26 was observed compared to a control crRNA ($P<0.001$, FIG. 2E). These results further confirm Type I-E Cascade as a programmable DNA-binding platform for targeting specific loci in the human genome. Intriguingly, enhanced enrichment of IL1RN signal was observed in samples treated with Flag-tagged Cascade-p300 and an IL1RN-targeted crRNA compared to samples treated with Flag-tagged dCas9-p300 and an IL1RN-targeted gRNA (gRNA-3; "g3") (FIG. 5B). These results can indicate increased occupancy by Cascade relative to dCas9. FIGS. 11A and 11**B show the genome-wide specificity of EcoCascade-p300 targeted to IL1RN.

Example 5

Cascade-Mediated Transactivation Using Different Activation Domains to CasE

Figure 6A:
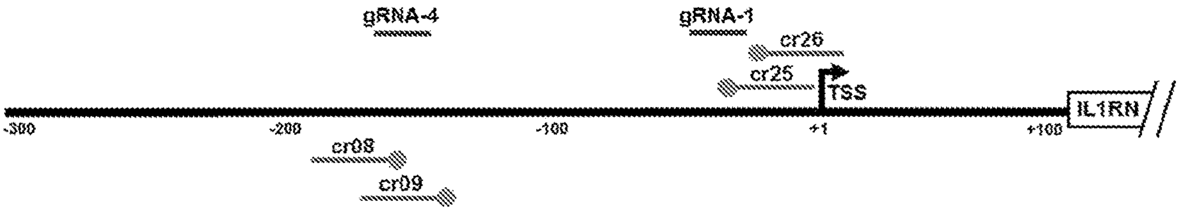
FIG. 6A-FIG. 6C show targeted Cascade-mediated transactivation achieved by tethering different activation domains to CasE.
Figure 6B:
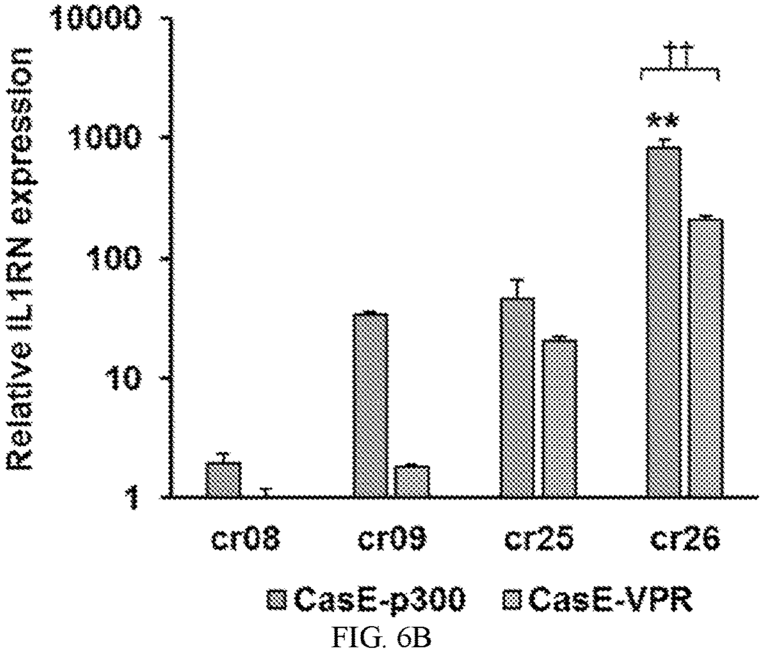
Figure 6C:
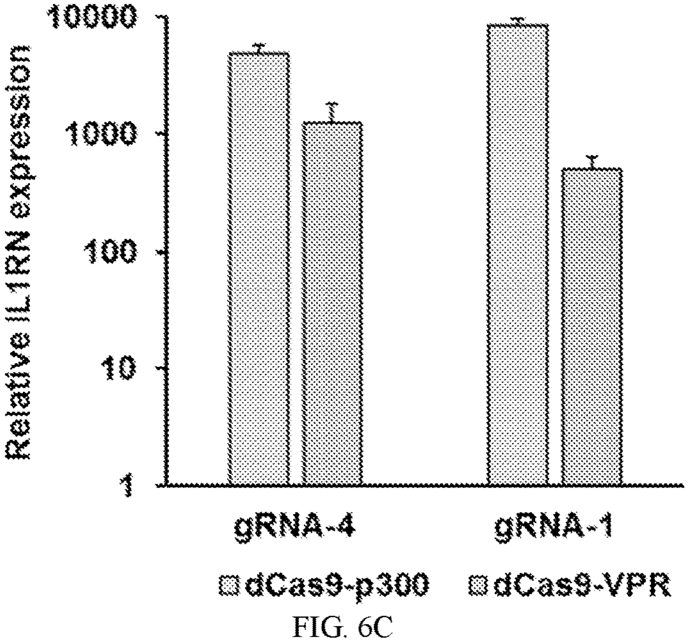
Figure 7A:
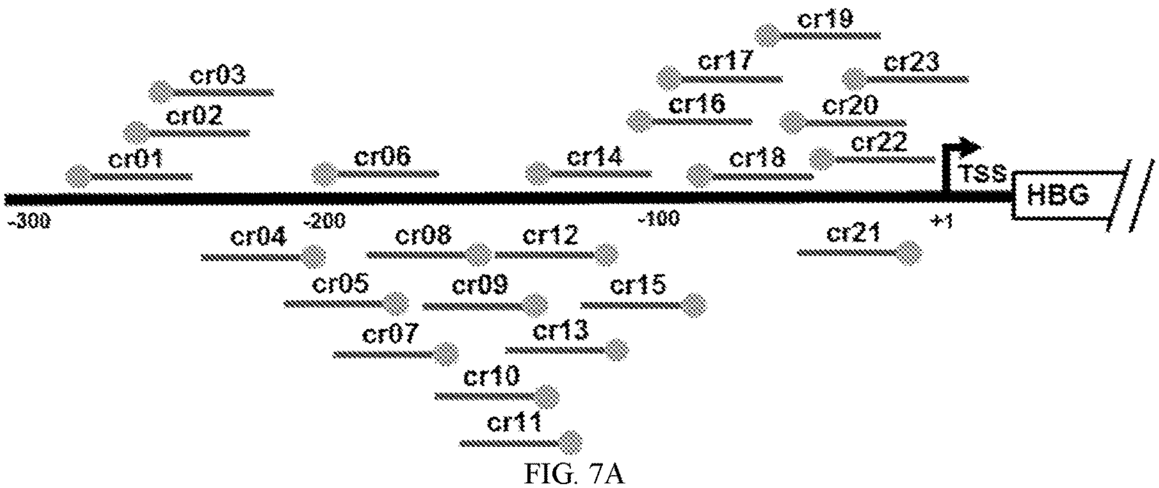
FIG. 7A-FIG. 7B show targeted transactivation by Cascade-p300 at the human HBG locus.
Figure 7B:
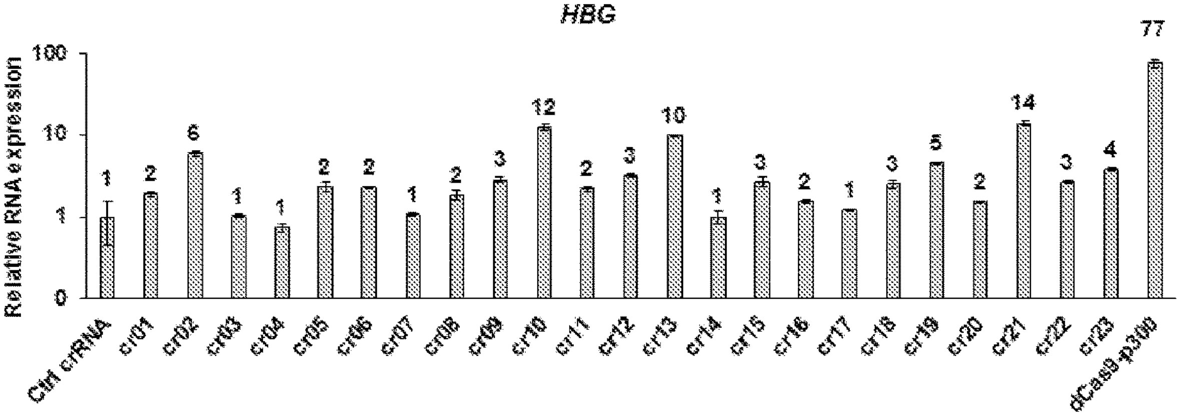
Figure 10A:
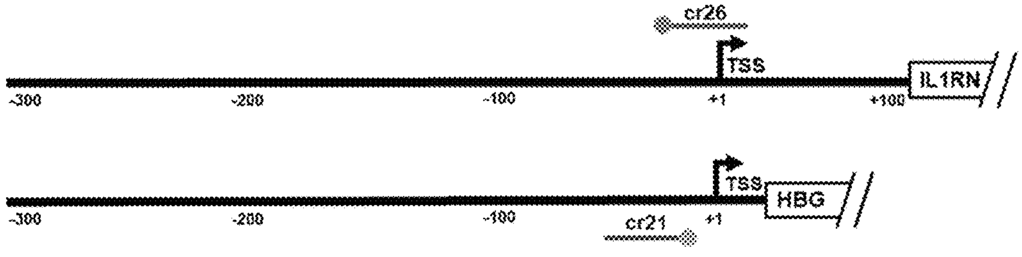
FIG. 10A-FIG. 10B show targeted multiplexed transactivation by EcoCascade-p300 at the human IL1RN and HBG loci.
Figure 10B:
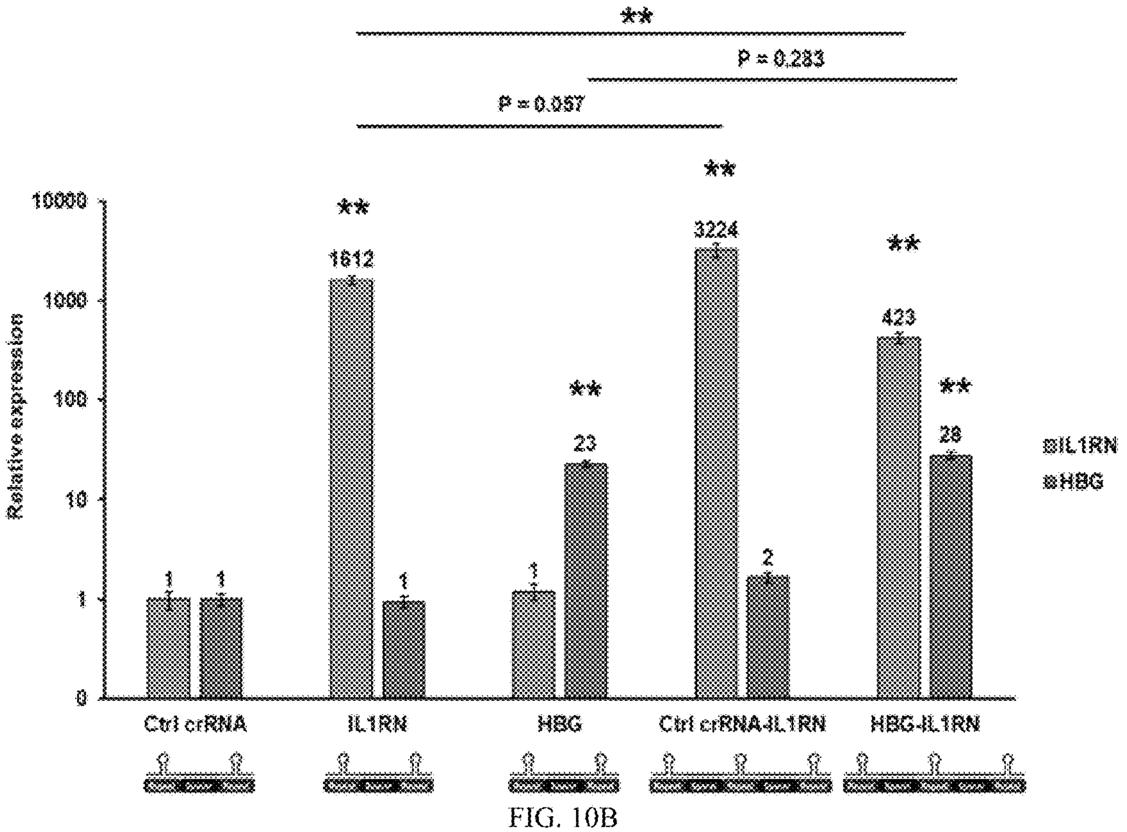

Targeted endogenous IL1RN activation was also achieved by tethering CasE to the tripartite activator, VP64-p65-Rta (VPR). FIG. 6A shows a schematic of the IL1RN locus along with IL1RN crRNA and gRNA target sites used to show that Cascade-mediated transactivation was achieved by tethering different activation domains to CasE. Both p300 and VPR tethered to CasE led to IL1RN activation (FIG. 6B) comparable to fusions with Cas9 (FIG. 6C). Targeted transactivation by Cascade-p300 at the human HBG locus was performed to assess activation of other endogenous targets in the human genome. FIG. 7A shows a schematic of the HBG locus along with HBG crRNA target sites. The HBG promoter was targeted with Cascade-p300 and observed robust transactivation comparable to dCas9-p300 (FIG. 7B). By tiling crRNAs along endogenous promoters, PAM-independent (Table 2) variants in transactivation potential of crRNAs were revealed (FIG. 2A and FIG. 7). Similar differences were observed among gRNAs and crRNAs for other Class 2 systems. FIGS. 10A and 10B show targeted multiplexed transactivation by EcoCascade-p300 at the human IL1RN and HBG loci.

Example 6

Enhanced Cascade-Mediated Transactivation by Co-Targeting with dCas9

Figure 8A:
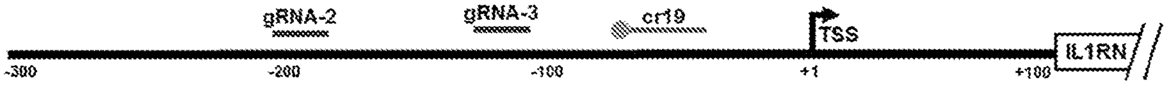
FIG. 8A-FIG. 8B show targeted Cascade-mediated transactivation can be enhanced by co-targeting with dCas9.
Figure 8B:
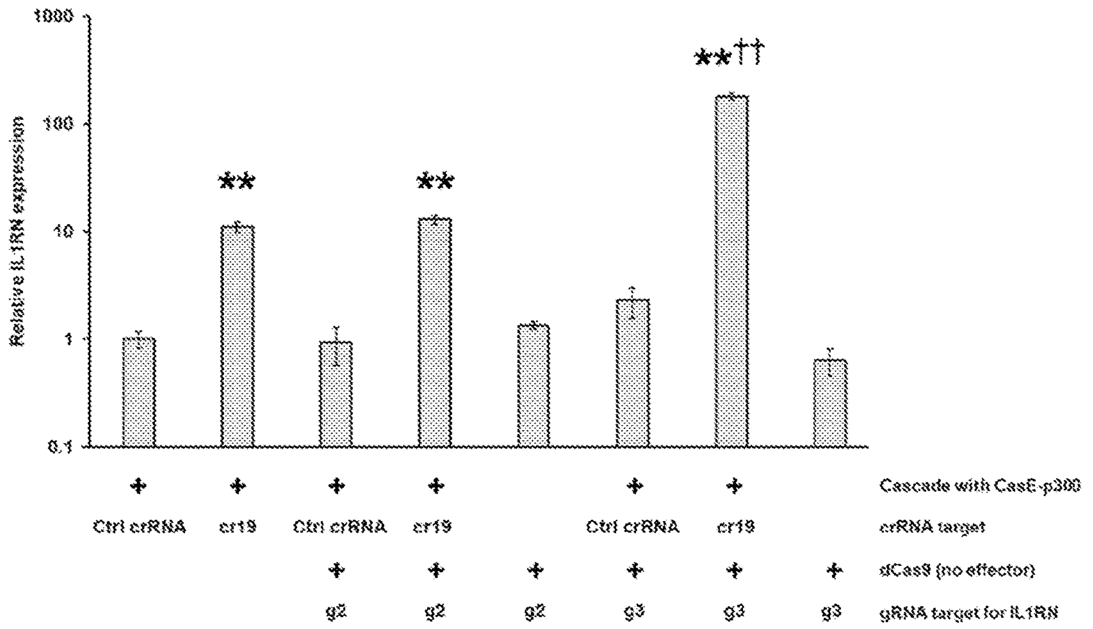

Co-transfection of individual crRNAs, Cascade with CasE-p300, dCas9 (no effector), and individual gRNAs, was performed to determine if transactivation can be enhanced. FIG. 8A shows a schematic of the IL1RN locus along with IL1RN crRNA and gRNA target sites. FIG. 8B shows that an over 16-fold enhanced transactivation was observed with Cascade-p300 and cr22 when dCas9 was co-targeted to IL1RN. These results suggest a narrower ability for Cascade to recognize genomic DNA targets in eukaryotes, which can also serve as a mechanism to increase targeting specificity.

Example 7

Materials and Methods

Plasmid construction. *L. monocytogenes* Finland_1998 Cascade sequences were synthesized by ATUM/DNA2.0 as human codon-optimized constructs using proprietary methods. See Appendix for gene sequences of *L. monocytogenes* Finland_1998 Cascade and Cascade polypeptide fusions (SEQ ID NOS: 166-174). For crRNA expression, a cloning vector was constructed (pAPcrRNA_Lmo) with a U6-driven cassette and digested with SacII and AgeI. To insert repeat-spacer pairs, oligonucleotides encoding the palindromic repeat and crRNA spacers were annealed, 5' phosphorylated with PNK and ligated into digested pAPcrRNA_Lmo. See FIG. 14B and FIG. 14C for an illustration of the cloning scheme. The control crRNA used throughout this study targets Cascade to an irrelevant control locus at HBE1.

Cell culture and transfections. HEK293T cells were maintained in Dulbecco's Modified Eagle's Medium (Invitrogen) with 10% Fetal Bovine Serum (Sigma) and 1% penicillin-streptomycin (Gibco). Cells were incubated at 37° C. with 5% $CO_2$. All transfections were performed using Lipofectamine 2000 (Invitrogen) according to the manufacturer's protocol.

Western blot and co-immunoprecipitation. For protein analysis, HEK293T cells were transfected with 2 μg of individual Cas constructs in 6-well plates. After three days, cells were lysed in RIPA buffer (Sigma) with a proteinase inhibitor cocktail (Roche). Samples were centrifuged at 12,000 rpm for 5 min and the supernatant was isolated and quantified using a bicinchoninic acid assay (BCA) protein standard curve (Thermo Scientific) on the BioTek Synergy 2 Multi-Mode Microplate Reader. Mixed with NuPAGE loading buffer (Invitrogen) and 5% β-mercaptoethanol, 25 μg protein was heated at 100° C. for 10 min. Samples were loaded into 10% NuPAGE Bis-Tris gels (Invitrogen) with IVIES buffer (Invitrogen) and electrophoresed for 70 min at 200V on ice. Protein was transferred to nitrocellulose membranes for 1 hour in 1× tris-glycine transfer buffer containing 10% methanol and 0.01% SDS at 4° C. at 400 mA. The blot was blocked at room temperature for 30 min in 5% milk-TBST (50 mM Tris, 150 mM NaCl and 0.1% Tween-20) and incubated with mouse anti-Flag (1:1,000 dilution, Sigma, M2 clone) in 5% milk-TBST at 4° C. overnight. Blots were then washed in TBST and incubated with goat anti-mouse-conjugated horseradish peroxidase (1:2,500 dilution, Santa-Cruz) in 5% milk-TBST for 45 min at room temperature. Blots were washed in TBST then visualized using Western-C ECL substrate (Bio-Rad) on a ChemiDoc XRS+ System (Bio-Rad). Blots were stripped with Restore PLUS Western Blot Stripping Buffer (Thermo Scientific), blocked, and re-blotted with rabbit anti-Actin (1:1,000 dilution, Sigma, A2066) and goat anti-rabbit-conjugated horseradish peroxidase (1:2,500 dilution, Santa Cruz). Blots were visualized again using the methods described above.

For co-immunoprecipitation analysis, co-transfections were completed using a V5-Cas7 construct. HEK293T cells were co-transfected in 6-well plates with 425 ng of each Cas construct and crRNA for 2.25 μg total plasmid DNA per condition. At three days post transfection, cells were lysed with IP lysis buffer (Thermo Scientific) with a proteinase inhibitor cocktail (Roche). Samples were centrifuged at 12,000 rpm for 5 min and the supernatant was isolated and subjected to immunoprecipitation using goat anti-V5-agarose conjugate (10 μl, Abcam, ab1229) at 4° C. overnight. The IP products were washed three times with IP lysis buffer, mixed with NuPAGE loading buffer and 5% β-mercaptoethanol, and heated at 100° C. for 10 min. Samples were loaded into 10% NuPAGE Bis-Tris gels, and resolved as described above. Blots were blocked, incubated with mouse anti-Flag (1:1,000 dilution, Sigma, M2 clone) and mouse anti-V5 (1:40,000 dilution, Abcam, SV5-Pk1 clone) then with goat anti-mouse-conjugated horseradish peroxidase (1:2,500 dilution, Santa Cruz). Blots were visualized as described above.

RNA analysis. For quantitative PCR (qPCR), HEK293T cells were co-transfected with 600 ng total plasmid in 24-well plates. After three days, total RNA was isolated using QIAshredder and QIAGEN RNeasy kits (Qiagen). Reverse transcription was carried out using 500 ng total RNA per sample in a 10 μl reaction using the SuperScript VILO Reverse Transcription Kit (Invitrogen). Per qPCR reaction, 1.0 μl of cDNA was used with Perfecta SYBR Green Fastmix (Quanta Biosciences) and ran using the CFX96 Real-Time PCR Detection System (Bio-Rad). All sequences for qPCR primers can be found in Table 3. All qPCR data are presented as fold change in RNA normalized to Gapdh expression and relative to samples targeting Cascade with a crRNA targeted to an irrelevant control locus at HBE1.

TABLE 3

Quantitative RT-PCR and ChIP-qPCR primers and conditions

| Target | Foward Primer (5'-3') | Reverse Primer (5'-3') | Cycling Conditions |
|---|---|---|---|
| IL1RN | GGAATCCATGGA GGGAAGAT (SEQ ID NO: 74) | TGTTCTCGCTCAG GTCAGT G (SEQ ID NO: 75) | 95° C. 10 s 60° C. 30 s x45 |
| GAPDH | CAATGACCCCTT CATTGACC (SEQ ID NO: 76) | TTGATTTTGGAGG GATCTC G (SEQ ID NO: 77) | 95° C. 10 s 53° C. 30 s x45 |

Statistical Analysis. All data analyzed with three biological replicates and presented as mean±SEM. Logarithmic transformations were completed prior to statistical analysis where indicated. All p values calculated by global one-way ANOVA with Tukey post hoc tests (α=0.05).

Example 8

Type I-B Cascade Expression and Complex Formation in Human Cells

Figure 14B:
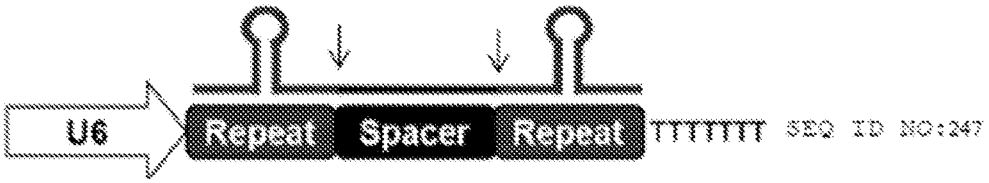
Figure 14C:
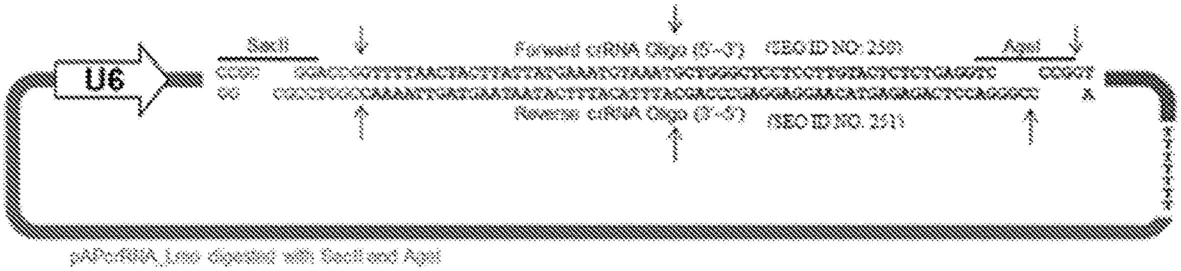
Figure 15:
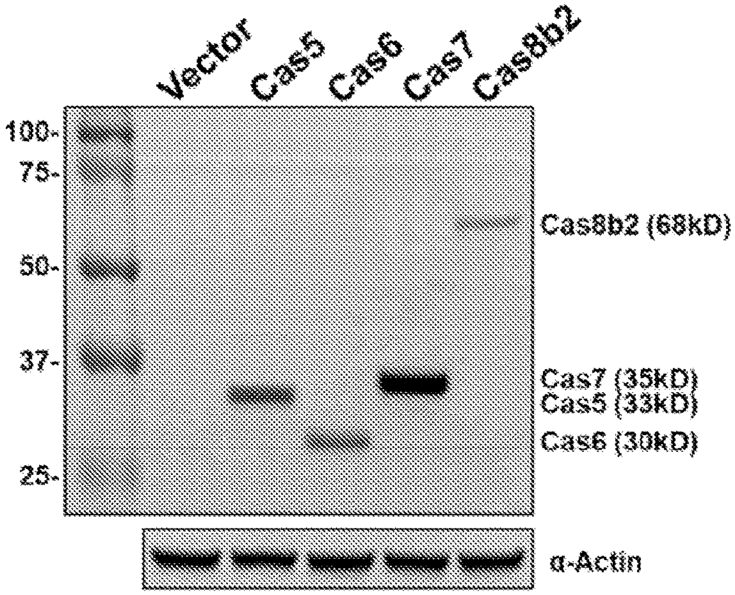
FIG. 15 shows LmoCascade expression in human HEK293T cells.
Figure 16:
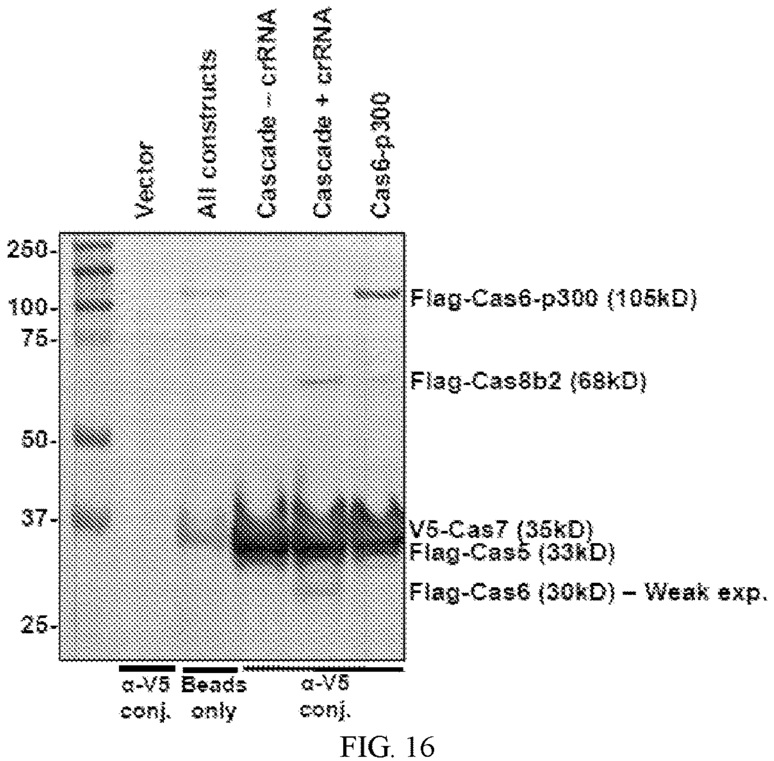
FIG. 16 shows LmoCascade complex formation with crRNA expression in human HEK293T cells.

To repurpose Type I-B Cascade for use in mammalian cells, a CMV promoter was used to express the Cascade subunits Cas5 (SEQ ID NO: 175), Cas6 (SEQ ID NO: 176), Cas7 (SEQ ID NO: 177) and Cas8b2 (SEQ ID NO: 178) of the *L. monocytogenes* Finland_1998 system with attached N-terminal Flag epitope tags and nuclear localization signals (NLSs). The RNA polymerase III U6 promoter was used to express target spacers flanked by full repeat sequences for crRNA processing (FIG. 14B). The Cas genes were human codon optimized and synthesized by ATUM/DNA2.0. To determine if Cascade complex formation occurred in human cells, the five plasmids encoding each of the four Cas subunits and the crRNA cassette were co-transfected into HEK293T cells. Heterologous expression of all Cascade constructs was confirmed by Western blot following transfection of each plasmid individually into human HEK293T cells (FIG. 15). Co-immunoprecipitation by pull-down of the V5 epitope on Cas7 and blotting for the Flag epitope on the other subunits confirmed proper complex assembly (FIG. 16).

Example 9

Type I-B Cascade Activation of Transcription of Endogenous IL1RN Gene in Human Cells Type I-B Cascade for CRISPR-based programmable transcriptional activation (CRISPRa) was repurposed in mammalian cells. To repurpose Type I-B Cascade as a programmable transcriptional activator, the various Cas-effector subunits were separately tether to the activation domain and tested for activity. The polynucleotide sequences encoding four Cas subunits of Type I-B of *L. monocytogenes* Finland_1998, Cas5 (SEQ ID NO: 175), Cas6 (SEQ ID NO: 176), Cas7 (SEQ ID NO: 177), and Cas8b2 (SEQ ID NO: 178) (polynucleotide sequences corresponding to SEQ ID NOs:258-261), were fused with the polynucleotide sequence encoding the transcriptional regulator domain, such as p300 core effector (SEQ ID NO: 180 for amino acid sequence; SEQ ID NO: 179 for polynucleotide sequence), to generate polynucleotide sequence encoding the Type I-B Cascade polypeptide fusion proteins for CRISPRa (SEQ ID NOs: 171-174).

Figure 17:
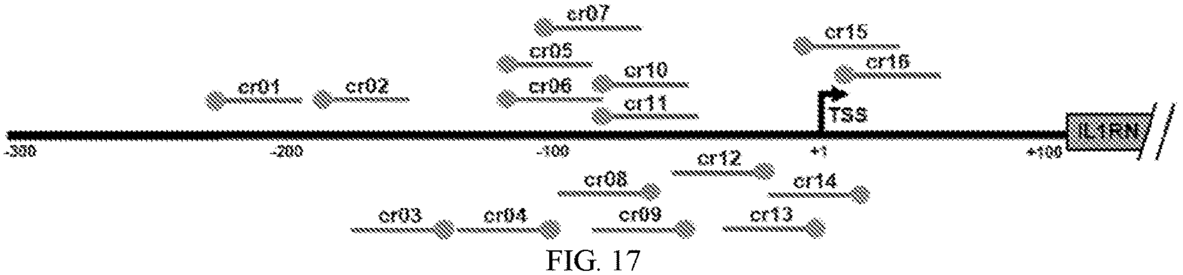
FIG. 17 shows endogenous IL1RN promoter tiling for targeting LmoCascade with Casio-p300 activates IL1RN expression in human HEK293T cells.

To test programmable endogenous gene activation in human cells, a panel of crRNAs was generated tiling the endogenous IL1RN promoter at spacer targets downstream of the putative PAM (5'-CAA-3') (FIG. 17, Table 4). FIG. 17 shows a schematic of the IL1RN locus along with IL1RN crRNA target sites.

TABLE 4 crRNA target sequences

| crRNA | Target | Strand | PAM | Spacer Sequence (5'-3') | SEQ ID NO | Target Sequence (5'-3') | SEQ ID NO | Genomic Location (GRCh37/hg19 Assembly) |
|---|---|---|---|---|---|---|---|---|
| Ctrl crRNA | HBE | + | CCA | UCACUGCUGACCCUCUCCGGACCUGACUCCCG | 181 | TCACTGCTGACCCTCTCCGGACCTGACTCCCG | 198 | chr11: 5270057-5270086 |
| cr01 | IL1RN | + | CCA | GCUCAGUUCUCUGCAUGUGACCUCCCAUCCCG | 182 | GCTCAGTTCTCTGCATGTGACCTCCCATCCCG | 199 | chr2: 113117683-113117711 |
| cr02 | IL1RN | + | CCA | GUUUGGUUUCUGCUAGCCUGAGUCACCCUCCG | 183 | GTTTGGTTTCTGCTAGCCTGAGTCACCCTCCG | 200 | chr2: 113117730-113117760 |
| cr03 | IL1RN | - | CCA | AGCAGGCCCAGUUUCCAGGAGGGUGACUCAGGCCCG | 184 | AGCAGGCCCAGTTTCCAGGAGGGTGACTCAGGCCCG | 201 | chr2: 113117745-113117777 |
| cr04 | IL1RN | - | CCA | GCAUGAGGAGAUGGGCCGGCUGAUGGCUGACUUCCG | 185 | GCATGAGGAGATGGGCCGGCTGATGGCTGACTTCCG | 202 | chr2: 113117785-113117817 |
| cr05 | IL1RN | + | CCA | UCAGCCGGCCCAUCUCCUCAUGCUGGCCAACCCG | 186 | TCAGCCGGCCCATCTCCTCATGCTGGCCAACCCG | 203 | chr2: 113117795-113117827 |
| cr06 | IL1RN | + | CCA | UCAGCCGGCCCAUCUCCUCAUGCUGGCCAACCCCCG | 187 | TCAGCCGGCCCATCTCCTCATGCTGGCCAACCCCCG | 204 | chr2: 113117795-113117827 |
| cr07 | IL1RN | + | CCA | UCUCCUCAUGCUGGCCAACCCUCUGUGAGUGUGCCG | 188 | TCTCCTCATGCTGGCCAACCCTCTGTGAGTGTGCCG | 205 | chr2: 113117807-113117839 |
| cr08 | IL1RN | - | CCA | CACACUCACAGAGGGUUGGCCAGCAUGAGGAGACCG | 189 | CACACTCACAGAGGGTTGGCCAGCATGAGGAGACCG | 206 | chr2: 113117807-113117839 |
| cr09 | IL1RN | - | CCA | GCCUCCCCUCCCACACACUCACAGAGGGUUGGCCCG | 190 | GCCTCCCCTCCCACACACTCACAGAGGGTTGGCCCG | 207 | chr2: 113117817-113117852 |
| cr10 | IL1RN | + | CCA | ACCCUCUGUGAGUGUGUGGGAGGGGAGGCCCG | 191 | ACCCTCTGTGAGTGTGTGGGAGGGGAGGCCCG | 208 | chr2: 113117824-113117852 |

TABLE 4-continued crRNA target sequences

| crRNA | Target | Strand | PAM | Spacer Sequence (5'-3') | SEQ ID NO | Target Sequence (5'-3') | SEQ ID NO | Genomic Location (GRCh37/hg19 Assembly) |
|---|---|---|---|---|---|---|---|---|
| cr11 | IL1RN | + | CCA | ACCCUCUGUGAGUGUGUGGGAGGGGAGGCUGGGCCG | 192 | ACCCTCTGTGAGTGTGTGGGAGGGGAGGCTGGGCCG | 209 | chr2: 113117824-113117857 |
| cr12 | IL1RN | - | CCA | GAGCACCUCAGAGAGUACAAGGAGGAGCCCAGCCCG | 193 | GAGCACCTCAGAGAGTACAAGGAGGAGCCCAGCCCG | 210 | chr2: 113117850-113117883 |
| cr13 | IL1RN | - | CCA | GGGUGGAGCUGCCCCUCCUUCCAGAGCACCUCACCG | 194 | GGGTGGAGCTGCCCCTCCTTCCAGAGCACCTCACCG | 211 | chr2: 113117874-113117906 |
| cr14 | IL1RN | - | CCA | CAGUCCCUCCCAGGGUGGAGCUGCCCCUCCUUCCCG | 195 | CAGTCCCTCCCAGGGTGGAGCTGCCCCTCCTTCCCG | 212 | chr2: 113117883-113117918 |
| cr15 | IL1RN | + | CCA | CCCUGGGAGGGACUGUGGCCCAGGUACUGCCCGCCG | 196 | CCCTGGGAGGGACTGTGGCCCAGGTACTGCCCGCCG | 213 | chr2: 113117904-113117936 |
| cr16 | IL1RN | + | CCA | GGUACUGCCCGGGUGCUACUUUAUGGGCAGCAGCCG | 197 | GGTACTGCCCGGGTGCTACTTTATGGGCAGCAGCCG | 214 | chr2: 113117926-113117959 |

HEK293T cells were co-transfected with plasmids encoding the Cascade components, Cas5, Cas7, and Cas8b2 and a plasmid encoding Cas6-p300 fusion at various stoichiometry with individual crRNA (see Table 5).

TABLE 5

| Ratio A | Ratio B | Ratio C | Radio D | |
|---|---|---|---|---|
| 75 | 60 | 75 | 150 | Cas5 (ng) |
| 150 | 130 | 50 | 50 | Cas7 (ng) |
| 50 | 150 | 150 | 100 | Cas8b2 (ng) |
| 150 | 185 | 150 | 100 | Cas6-p300 (ng) |
| 100 | 100 | 100 | 100 | crRNA (ng) |
| 525 | 625 | 525 | 500 | TOTAL (ng) |

Figure 18:
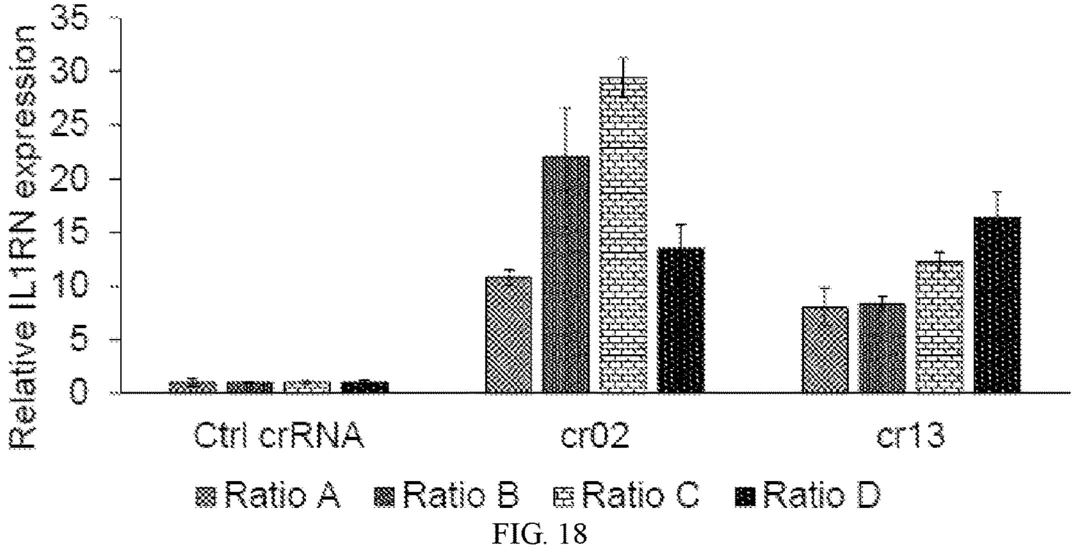
FIG. 18 shows optimization of LmoCascade-p300 activity following transfection of different plasmid ratios and the relative IL1RN expression following co-transfection of individual crRNAs with the LmoCascade-p300 components in the ratios. P<0.001, compared to Ctrl crRNA
Figure 19:
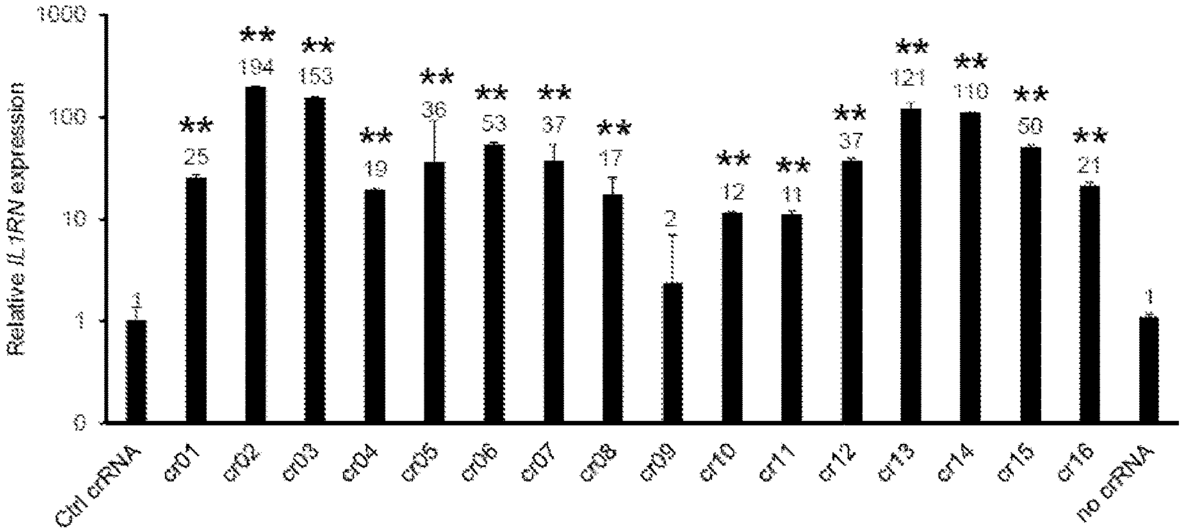
FIG. 19 shows endogenous IL1RN promoter tiling for targeting LmoCascade with Casio-p300 activates IL1RN expression in human HEK293T cells (plasmid ratio A). P<0.001, compared to Ctrl crRNA.
Figure 20:
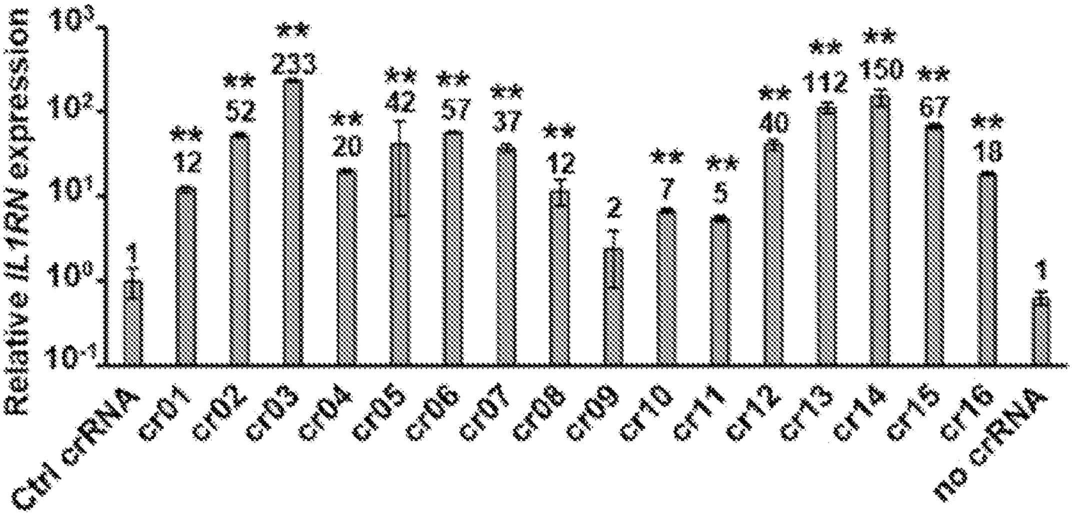
FIG. 20 shows endogenous IL1RN promoter tiling for targeting LmoCascade with Casio-p300 activates IL1RN expression in human HEK293T cells (plasmid ratio C). **P<0.001, compared to Ctrl crRNA.

Co-transfection of HEK293T cells with plasmids encoding Cascade with Cas6-p300 and individual crRNAs revealed robust IL1RN activation with most crRNAs (P<0.001, FIG. 18, FIG. 19, and FIG. 20). FIG. 19 and FIG. 20 show the IL1RN expression in human HEK293T cells using the LmoCascade with Cas6-p300 using plasmid ratio A and C, respectively. Based on predicted Cascade stoichiometry (Table 3) and relative Cas construct expression (FIG. 15), the relative masses of transfected plasmids to maximize gene activation were optimized (FIG. 18, FIG. 19, and FIG. 20**).

Figure 21:
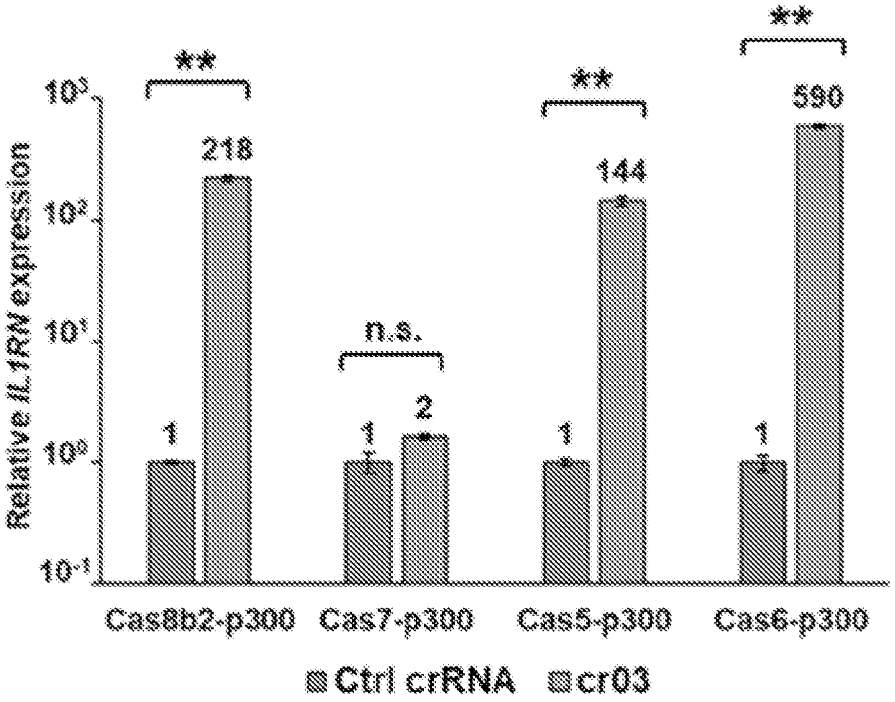
FIG. 21 shows IL1RN expression activated with various LmoCascade subunit fusions with p300 effector in human HEK293T cells. **P<0.001, compared to Ctrl crRNA.

The transactivation potential of all Cas-p300 fusions was explored with cr03. Relative to heterologous expression with a crRNA targeted to an irrelevant control locus, Cascade containing Cas8b2-p300, Cas5-p300 or Cas6-p300 displayed significant IL1RN transactivation (P<0.001, FIG. 21**).

Example 10

Figure 22A:
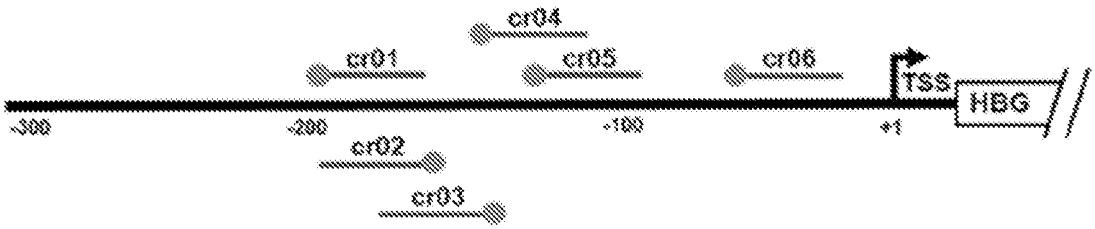
FIG. 22A-FIG. 22B show transactivation of LmoCascade-p300 targeted to HBG in human cells.
Figure 22B:
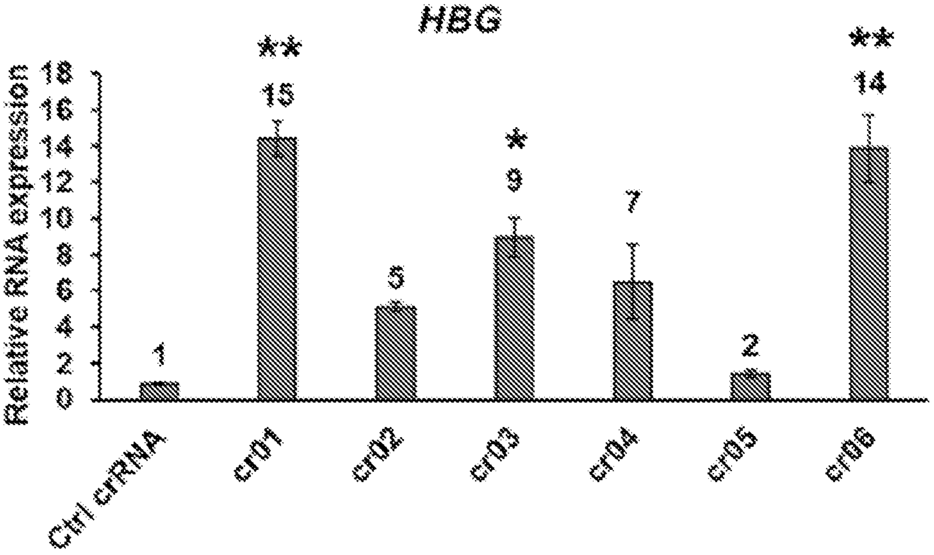
Figure 23:
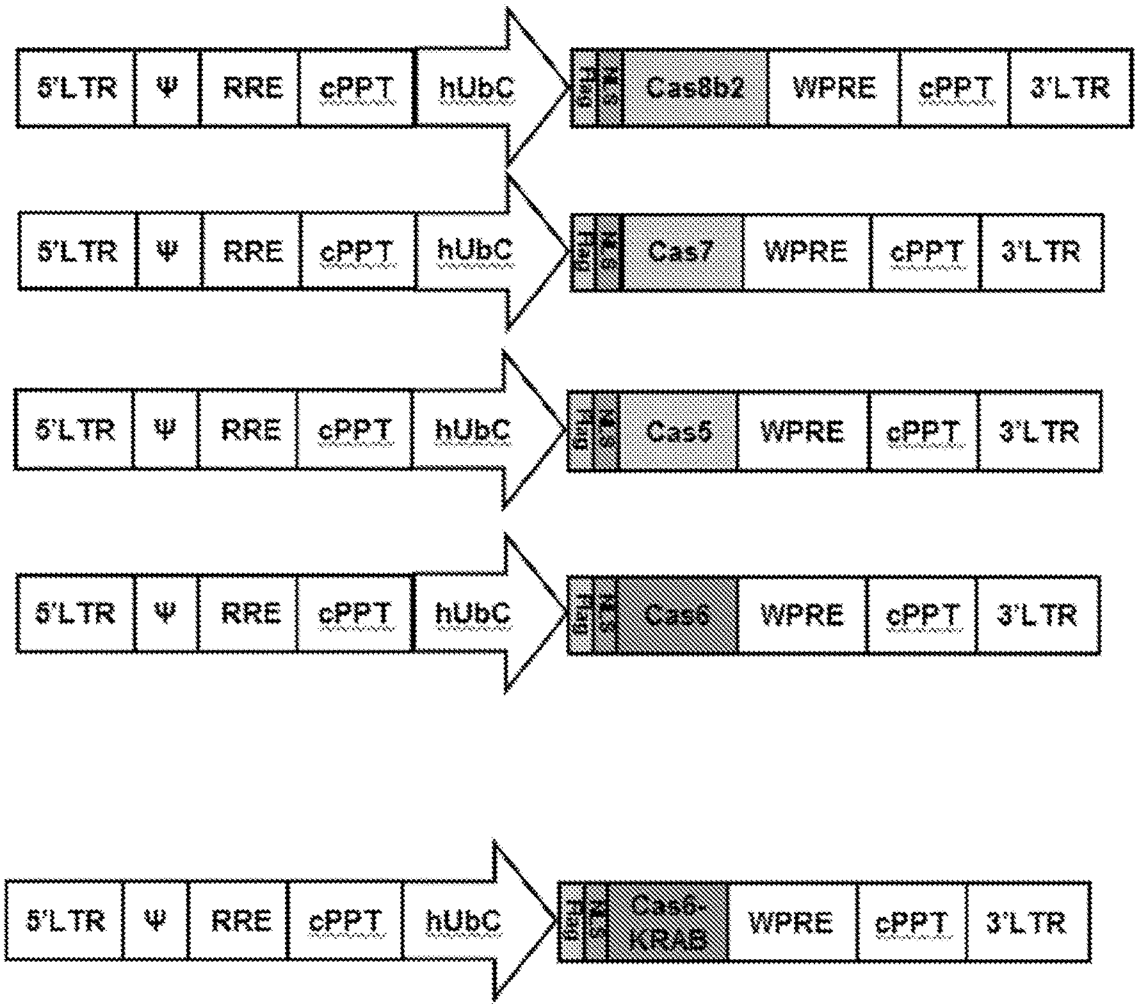
FIG. 23 illustrates LmoCascade lentiviral construct schematics for individual Type I-B LmoCascade subunit expression.
Figure 24:
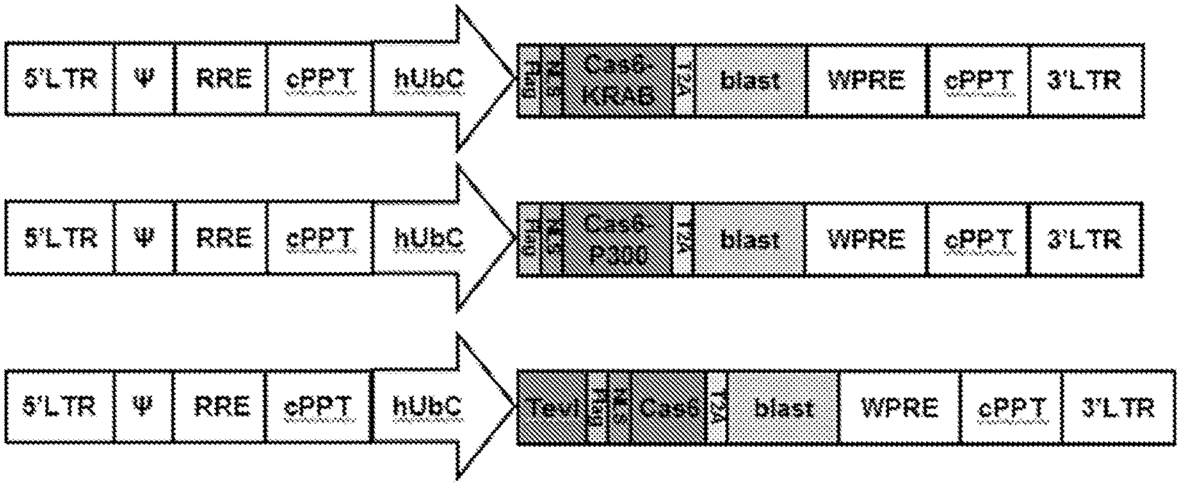
FIG. 24 illustrates LmoCascade lentiviral fusion schematics for individual Type I-B LmoCascade-Cas6 fusion expression. These constructs include 2A sequences to select transduced cells for blasticidin resistance.
Figure 25A:
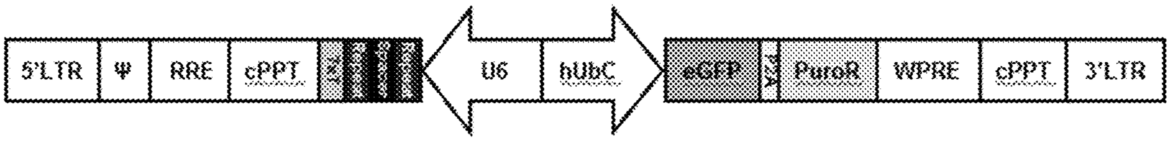
FIG. 25A-FIG. 25B illustrate LmoCascade lentiviral crRNA expression.
Figure 25B:
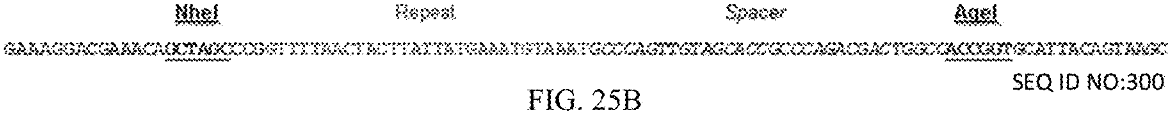
Figure 26A:
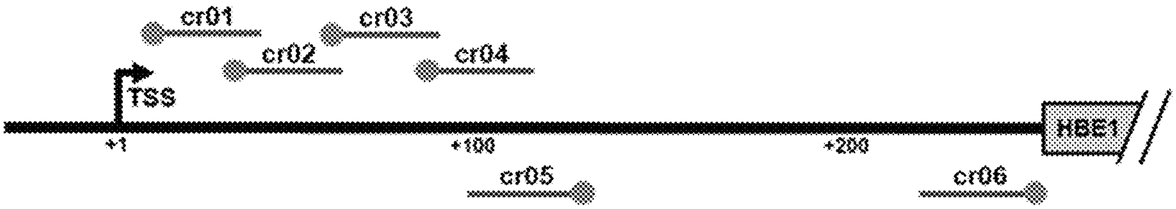
FIG. 26A-FIG. 26E illustrate LmoCascade-KRAB repression of endogenous HBE gene in human cells.
Figure 26B:
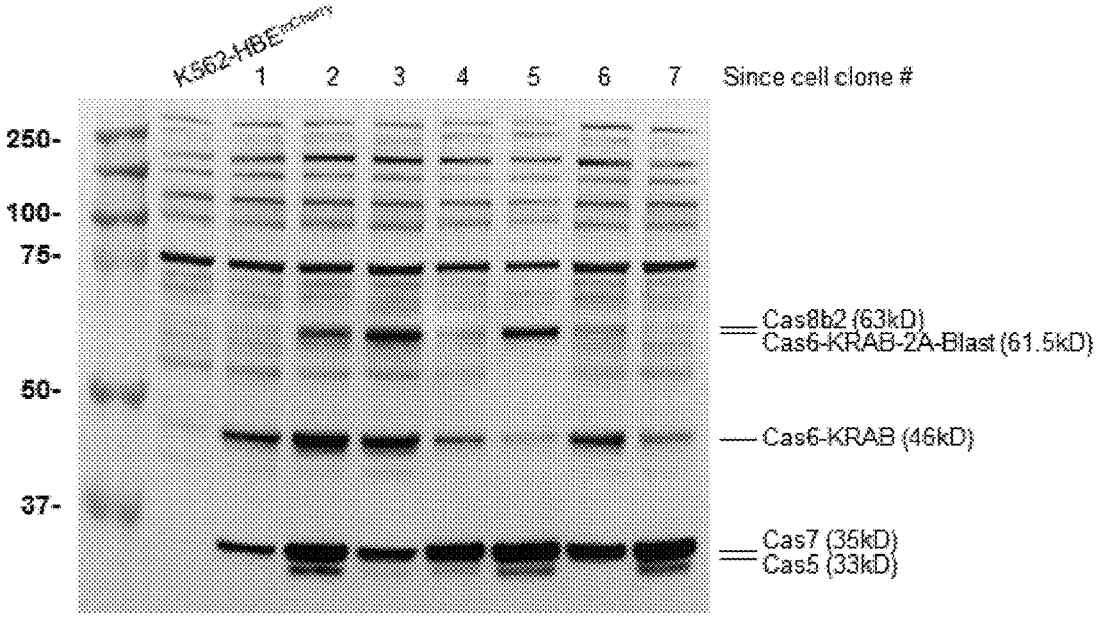
Figure 26C:
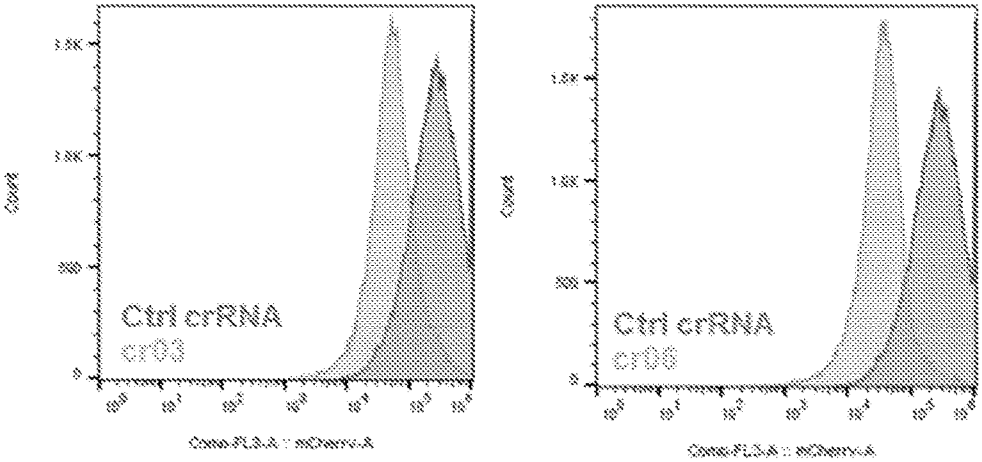
Figure 26D:
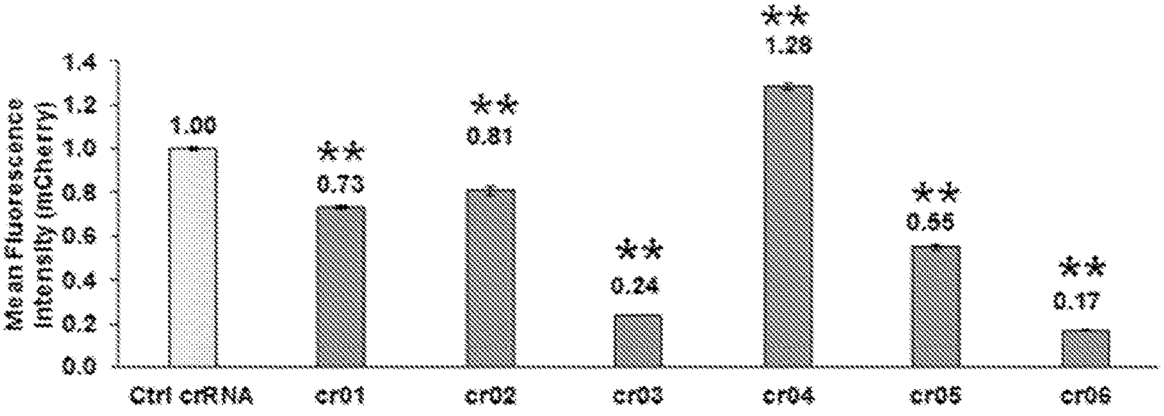
Figure 26E:
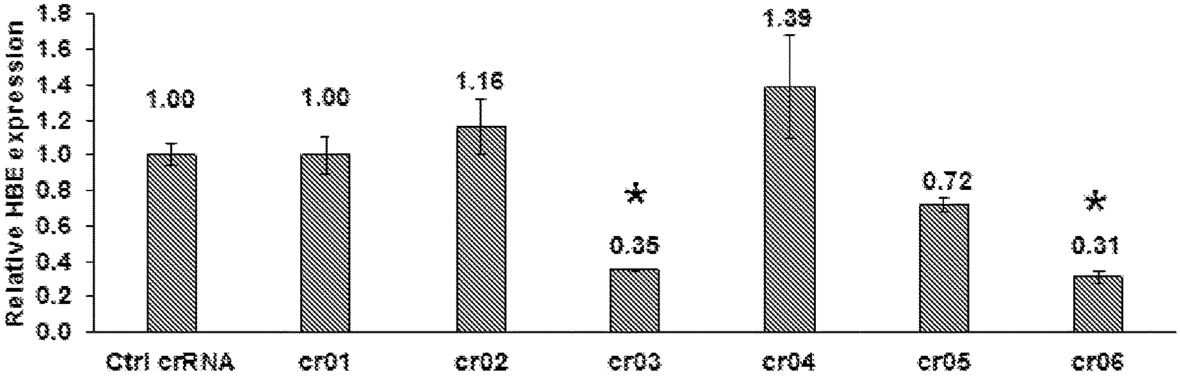
Figure 27:
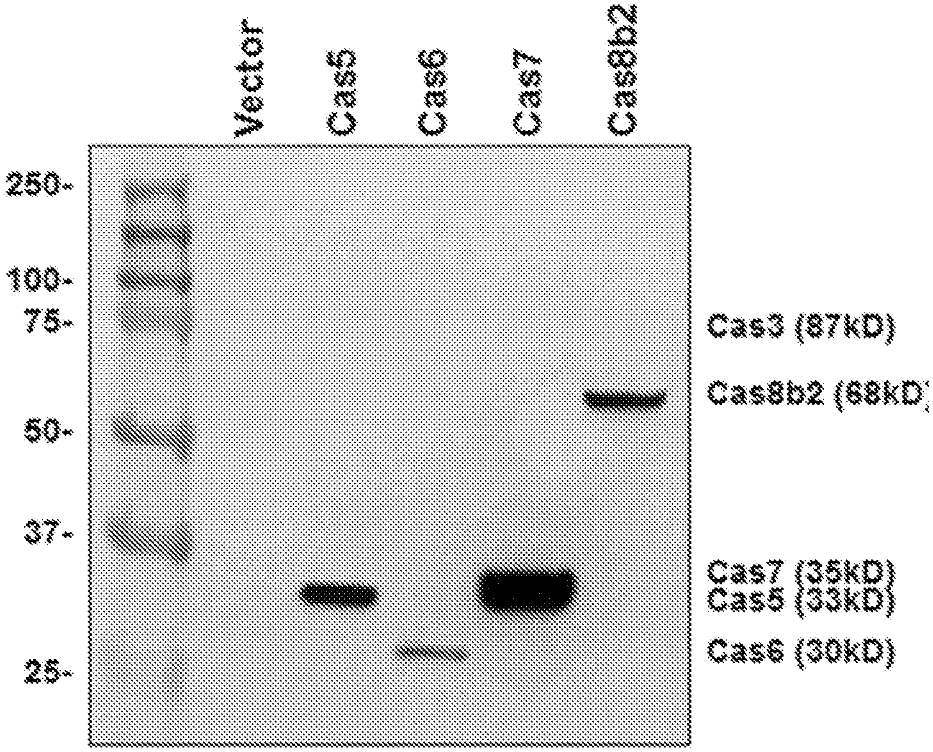
FIG. 27 shows LmoCascade expression following codon optimization in human HEK293T cells.
Figure 28A:
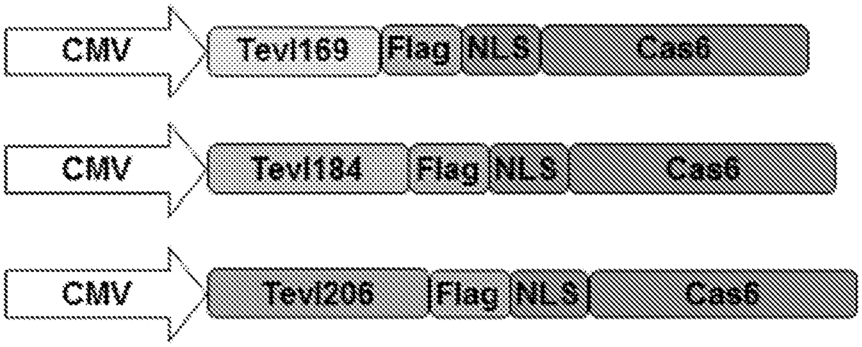
FIG. 28A shows schematic of Cas6 fusions with I-TeVI monomeric nuclease domains of varying length.
Figure 28E:
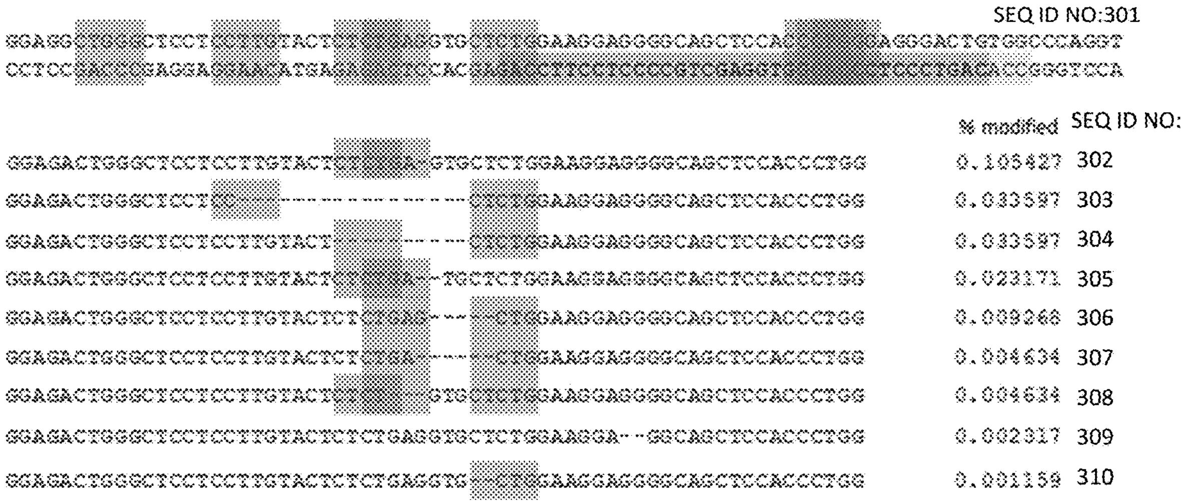
FIG. 28E shows indel footprint of TeVI-LmoCascade-mediated editing following deep sequencing analysis of HEK293 Ts co-transfected with TeVI-LmoCascade and cr14 targeting endogenous IL1RN promoter.
Figure 29:
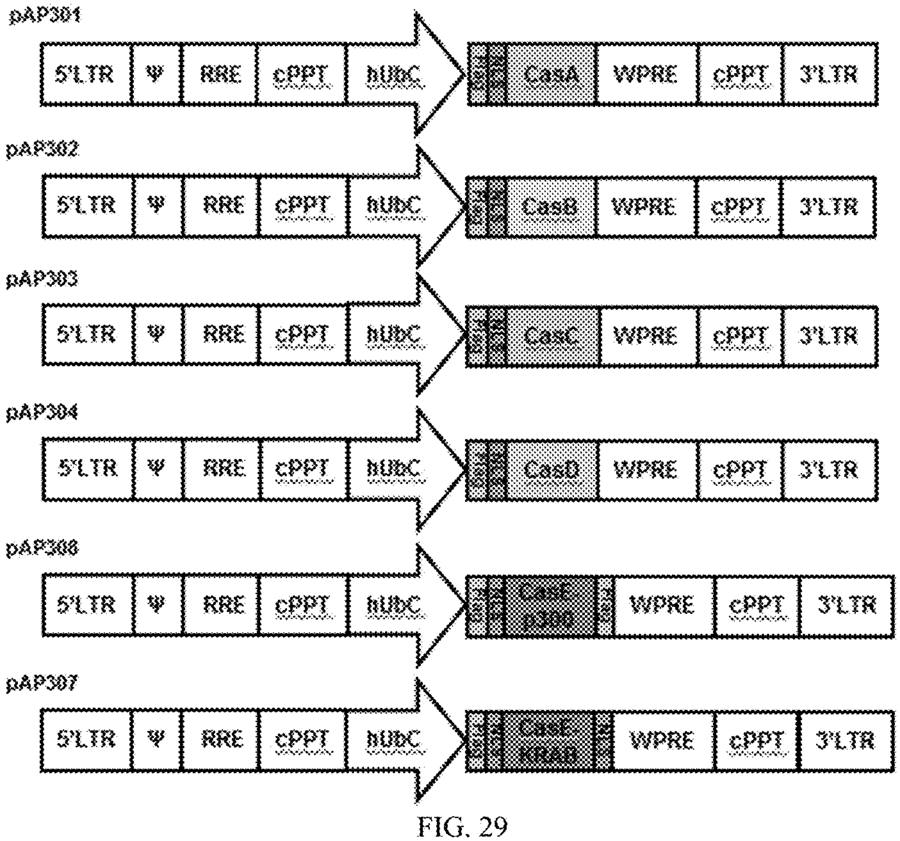
FIG. 29 shows schematic of lentiviral constructs for individual Type I-E EcoCascade subunit expression.
Figure 30:
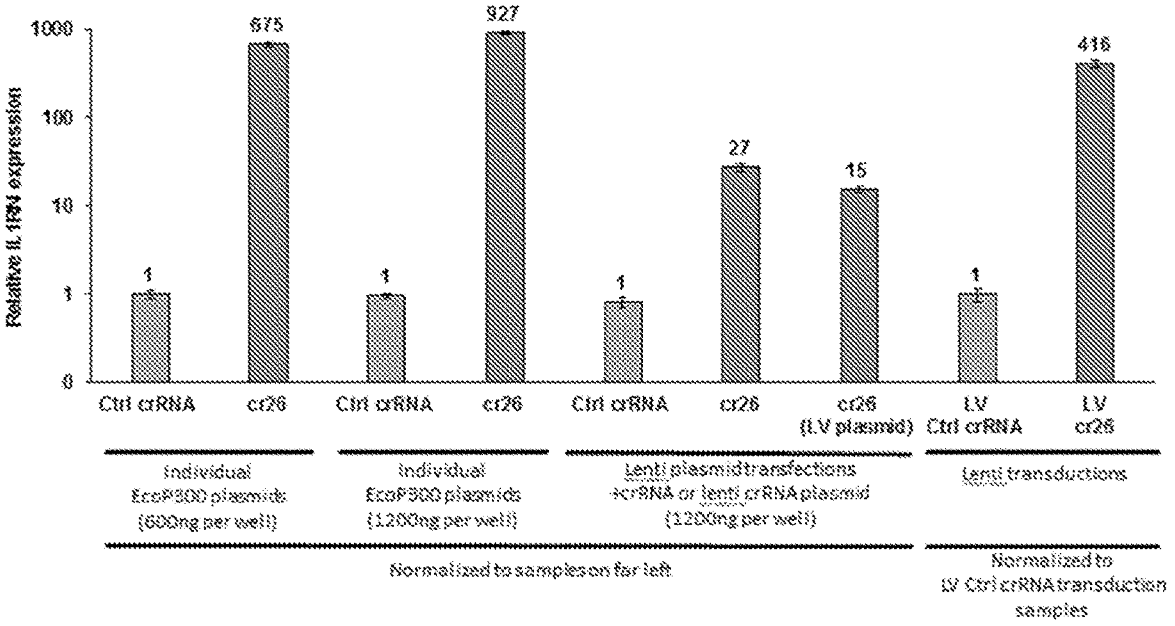
FIG. 30 shows relative IL1RN expression in HEK293 Ts following co-transfection of crRNA and Type I-E EcoCascade expression plasmids, including lentivirus plasmid constructs with CasE-P300. Additionally, HEK293 Ts were transduced with Type I-E EcoCascade and crRNA expressing lentiviruses. All samples processed at 3 days post transfection. Results shows co-transduction with 6 lenti constructs at 1× each results in IL1RN activation; doubling plasmid transfection amounts can enhance activity with minimal toxicity (note: did coat plates beforehand to help cells adhere under these conditions).
Figure 31A:
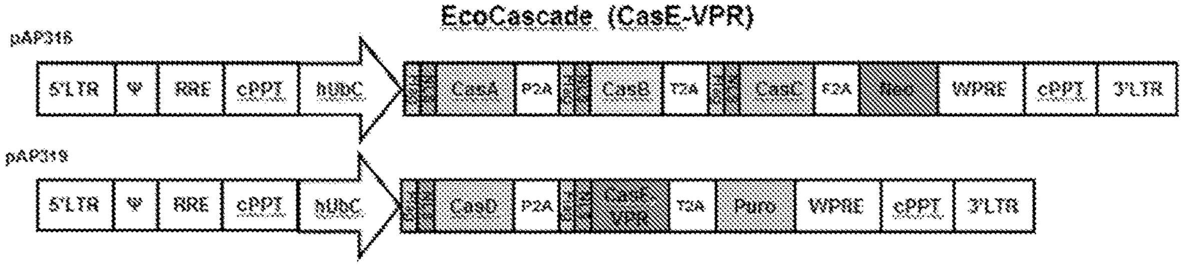
FIG. 31A shows schematic of lentiviral constructs for expression of multiple Type I-E EcoCascade subunits using 2A sequences.
Figure 31B:
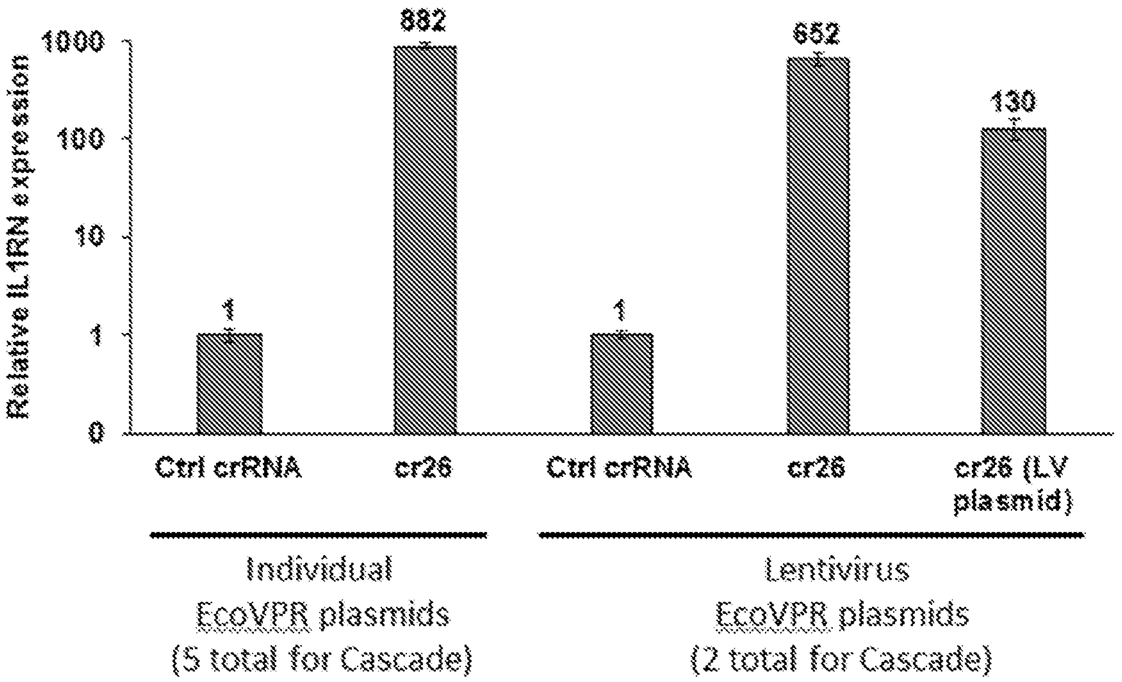
FIG. 31B shows relative IL1RN expression in HEK293 Ts following co-transfection or co-transduction of crRNAs and Type I-E EcoCascade with CasE-VPR. All samples processed at 3 days post transfection.
Figure 32:
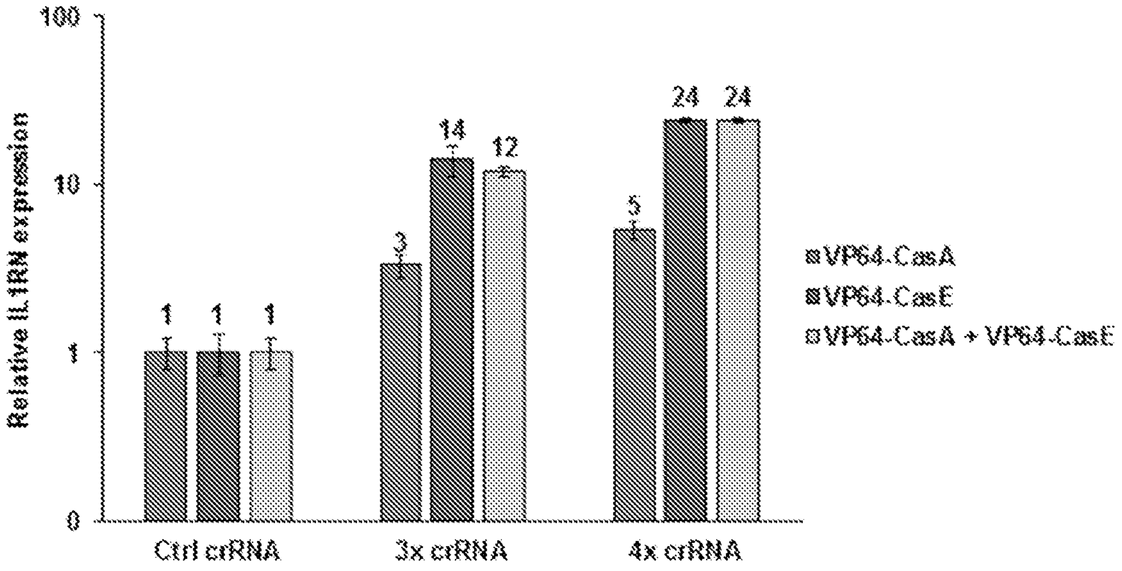
FIG. 32 shows relative IL1RN expression following co-transfection of HEK293T cells with multiple crRNAs and Type I-E EcoCascade with VP64-CasA, VP64-CasE, or both fusions. All samples processed at 3 days post transfection.
Figure 33:
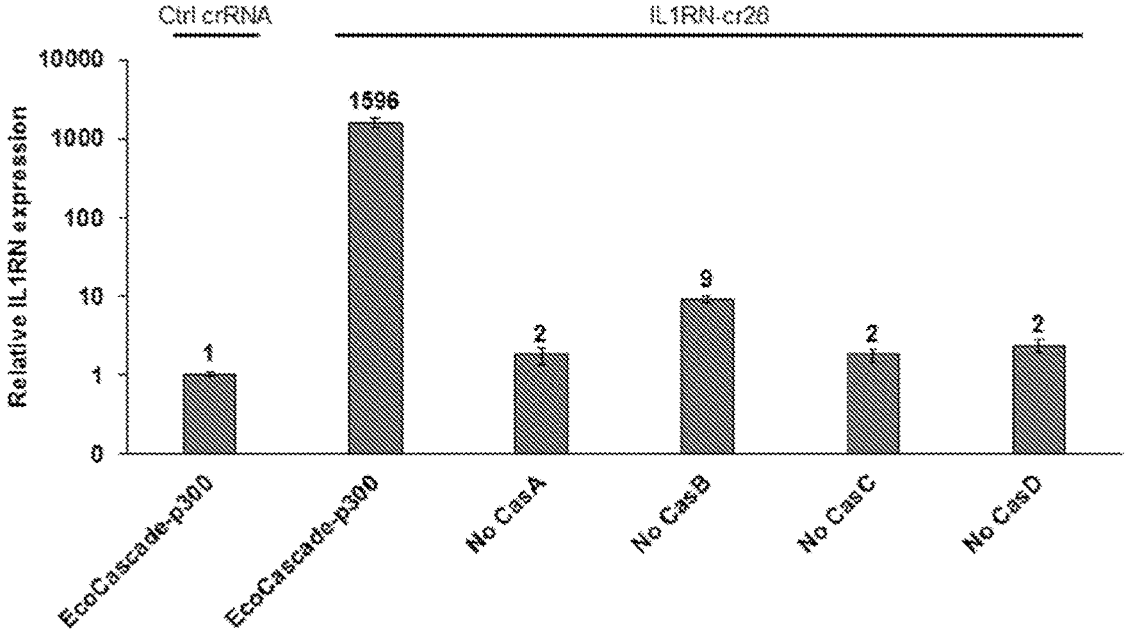
FIG. 33 shows relative IL1RN expression following co-transfection of HEK293T cells with crRNAs and Type I-E EcoCascade, including CasE-p300. Additionally, co-transfections where Cascade subunit expression plasmids were individually replaced with empty vector were tested with cr26. All samples processed at 3 days post transfection.
Figure 34:
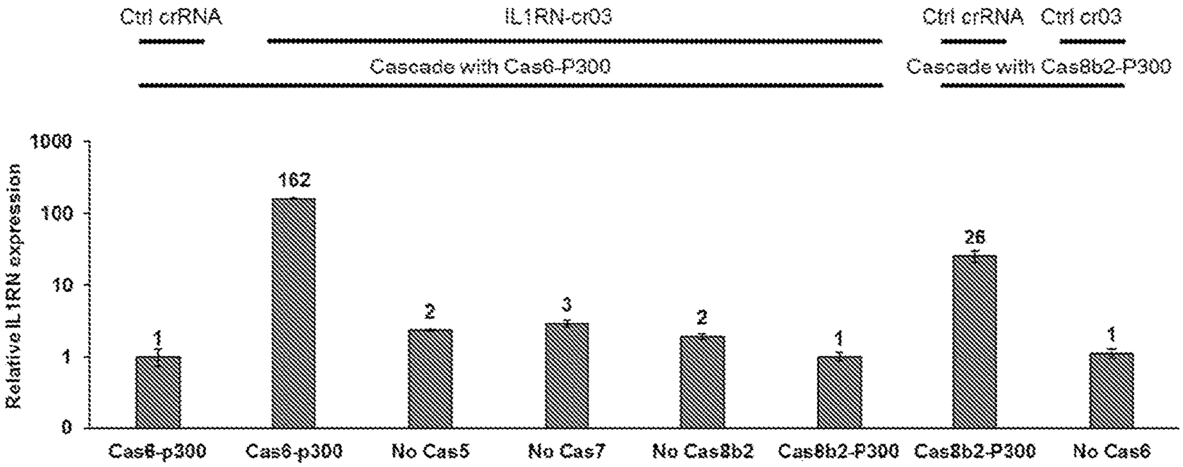
FIG. 34 shows relative IL1RN expression following co-transfection of HEK293T cells with crRNAs and Type I-B LmoCascade, including Cas6-p300 or Cas8b2-P300. Additionally, co-transfections where Cascade subunit expression plasmids were individually replaced with empty vector were tested with cr03. All samples processed at 3 days post transfection.

Type I-B Cascade Activation of Transcription of Endogenous HBG Gene in Human Targeted transactivation by LmoCascade-p300 at the human HBG locus was performed to assess activation of other endogenous targets in the human genome. FIG. 22A shows a schematic of the HBG locus along with HBG crRNA target sites. See also Table 6. Table 7 discloses additional targets. FIG. 22B shows relative HBG expression following co-transfection of individual crRNAs or crRNA arrays and LmoCascade with Casio-p300. All samples processed at 3 days post-transfection. (Tukey-test, **P<0.001 compared to Ctrl crRNA, *P<0.05 compared to Ctrl crRNA n=3 biological replicates; error bars, SEM). Numbers above bars indicate mean relative expression. TSS, transcription start site; Ctrl crRNA, Control crRNA.

TABLE 6

| crRNA | Target | Strand | PAM | Spacer Sequence (5'-3') | SEQ ID NO: | Target sequence (5'-3') | SEQ ID NO: | Genomic Location (GRCh37/hg19 Assembly) |
|---|---|---|---|---|---|---|---|---|
| cr01 | HBG | + | CCA | CACUAUCUCAAUGCAAAUAUCUGUCUGAAACGGCCG | 270 | CACTATCTCAATGCAAATATCTGTCTGAAACGGCCG | 276 | chr11: 5271247-5271279 |
| cr02 | HBG | - | CCA | GGGACCGUUUCAGACAGAUAUUUGCAUUGAGAUCCG | 271 | GGGACCGTTTCAGACAGATATTTGCATTGAGATCCG | 277 | chr11: 5271243-5271275 |

TABLE 6-continued

| crRNA | Target | Strand | PAM | Spacer Sequence (5'-3') | SEQ ID NO: | Target sequence (5'-3') | SEQ ID NO: | Genomic Location (GRCh37/hg19 Assembly) |
|---|---|---|---|---|---|---|---|---|
| cr03 | HBG | - | CCA | ACCCAUGGGUGGAGUUUAGCCAGGGACCGUUUCCCG | 272 | ACCCATGGGTGGAGTTTAGCCAGGGACCGTTTCCCG | 278 | chr11: 5271221-5271253 |
| cr04 | HBG | + | CCA | UGGGUUGGCCAGCCUUGCCUUGACCAAUAGCCUCCG | 273 | TGGGTTGGCCAGCCTTGCCTTGACCAATAGCCTCCG | 279 | chr11: 5271193-5271225 |
| cr05 | HBG | + | CCA | GCCUUGCCUUGACCAAUAGCCUUGACAAGGCAACCG | 274 | GCCTTGCCTTGACCAATAGCCTTGACAAGGCAACCG | 280 | chr11: 5271182-5271214 |
| cr06 | HBG | + | CCA | GGGGCCGGCGGCUGGCUAGGGAUGAAGAAUAAACCG | 275 | GGGGCCGGCGGCTGGCTAGGGATGAAGAATAAACCG | 281 | chr11: 5271113-5271145 |

TABLE 7

Additional LmoCascade crRNA targets

| Target | crRNA | PAM | Spacer Sequence (5'-3') |
|---|---|---|---|
| HBE | cr01 | CCA | ACAAAAAAGAGCCTCAGGATCCAGCACACATTATCA |
| HBE | cr02 | CCA | GCACACATTATCACAAACTTAGTGTCCATCCATCAC |
| HBE | cr03 | CCA | TCACTGCTGACCCTCTCCGGACCTGACTCCACCCCT |
| HBE | cr04 | CCA | CCCCTGAGGGACACAGGTCAGCCTTGACCAATGACT |
| HBE | cr05 | CCA | TGGTACTTAAAAGTCATTGGTCAAGGCTGACCTGTG |
| HBE | cr06 | CCA | GGCCTGAGAGCTTGCTAGTGATTGCAGCTGTGTCGG |
| NEUROG2 | — | CCA | TTGTGATTGGTGGCTCGCGCTCGGCTGGAGCGTGCC |
| NEUROG2 | — | CCA | GCCGAGCGCGAGCCACCAATCACAATGGACAGCGGC |
| NEUROG2 | — | CCA | ATCACAATGGACAGCGGCGGCGACAACAGCCGCAGC |
| NEUROG2 | — | CCA | GCTCCGGCCGCAGCCCGGAGCTCCAACAGGAGCTTT |
| NEUROG2 | — | CCA | ACAGGAGCTTTAGAACCATTTTATGTTGATTAGATA |
| NEUROG2 | — | CCA | AGAAAACAATCAGATCTGCCCCGGGCCCCCTCCTCC |
| MYOD | — | CCA | GCGTTTCCCGCGGATACAGCAGTCGGGTGTTGGAGA |
| MYOD | — | CCA | ACACCCGACTGCTGTATCCGCGGGAAACGCTGGCTG |
| MYOD | — | CCA | AACCTCTCCAACACCCGACTGCTGTATCCGCGGGAA |
| MYOD | — | CCA | AGTGCAGCCGCCTAGGGCTGCCGGTCGCTCCCTCCC |
| MYOD | — | CCA | CACTGGCGTGCGCGCTAGGTCCCCTACCGGGCAGGG |
| MYOD | — | CCA | GCTGCCCGCCTGGGCTCCGGGGCGTTTAGGCTACTA |

TABLE 8

Additional EcoCascade crRNA targets

| Target | PAM | Spacer Sequence (5'-3') |
|---|---|---|
| HBE | AGG | CTGACCTGTGTCCCTCAGGGGTGGAGTCAGGT |
| HBE | AGG | CCTGAGAGCTTGCTAGTGATTGCAGCTGTGTC |
| HBE | ATG | GAGAACAGGGGGCCAGAACTTCGGCAGTAAAG |
| HBE | AGG | ATCCAGCACACATTATCACAAACTTAGTGTCC |
| HBE | TAG | CAAGCTCTCAGGCCTGGCATCATGGTGCATTT |
| HBE | AGG | GGTGGAGTCAGGTCCGGAGAGGGTCAGCAGTG |
| HBE | AAG | AGCCTCAGGATCCAGCACACATTATCACAAAC |
| HBE | AAG | TTTGTGATAATGTGTGCTGGATCCTGAGGCTC |
| HBE | AAG | CAGATATGTGCTGCTGCCTCTCTGTCTGGCCT |
| HBE | AAG | TACCATGGAGAACAGGGGGCCAGAACTTCGGC |
| HBE | GAG | CCTCAGGATCCAGCACACATTATCACAAACTT |
| HBE | GAG | CCAACAAAAAAGAGCCTCAGGATCCAGCACAC |
| HBE | GAG | GAGCCAACAAAAAAGAGCCTCAGGATCCAGCA |
| HBE | GAG | GCTCTTTTTTGTTGGCTCCTCATCTATCTGCA |
| HBE | GAG | GGTCAGCAGTGATGGATGGACACTAAGTTTGT |
| HBE | GAG | GGACACAGGTCAGCCTTGACCAATGACTTTTA |
| HBE | GAG | AACAGGGGGCCAGAACTTCGGCAGTAAAGAAT |
| HBE | TAG | TGTCCATCCATCACTGCTGACCCTCTCCGGAC |
| HBE | TAG | ATGAGGAGCCAACAAAAAAGAGCCTCAGGATC |
| HBE | TAG | TGATTGCAGCTGTGTCGGAAGCAGATATGTGC |
| HBE | ATG | TGTGCTGGATCCTGAGGCTCTTTTTTGTTGGC |
| HBE | ATG | AGGAGCCAACAAAAAAGAGCCTCAGGATCCAG |
| HBE | ATG | ACTTTTAAGTACCATGGAGAACAGGGGGCCAG |
| HBE | ATG | GACACTAAGTTTGTGATAATGTGTGCTGGATC |
| MYOD | AAG | TCAGCTCAGAGGTGAGCGCGCGCAGCCAGCGT |
| MYOD | GAG | CGCGCGCAGCCAGCGTTTCCCGCGGATACAGC |
| MYOD | GAG | AGGTTTGGAAAGGGCGTGCCGGAGAGCCAAGT |

TABLE 8-continued

Additional EcoCascade crRNA targets

| Target | PAM | Spacer Sequence (5'-3') |
|---|---|---|
| MYOD | AGG | CGGCTGCACTTGGCTCTCCGGCACGCCCTTTC |
| MYOD | AAG | GGCGTGCCGGAGAGCCAAGTGCAGCCGCCTAG |
| MYOD | GAG | AGCCAAGTGCAGCCGCCTAGGGCTGCCGGTCG |
| MYOD | AAG | TGCAGCCGCCTAGGGCTGCCGGTCGCTCCCTC |
| MYOD | GAG | GGAGGGAGCGACCGGCAGCCCTAGGCGGCTGC |
| MYOD | AGG | TCCCCTACCGGGCAGGGAGGGAGGGAGCGACC |
| MYOD | GAG | GGGCGGGCTGGCTGGCCAGTCTGCGGGCCCCT |
| MYOD | AAG | CCCCGCCCCGCAGTGTTCCTATTGGCCTCGGA |
| MYOD | AGG | CTACTACGGATAAATAGCCCAGGGCGCCTGGC |
| NEUROG2 | GAG | CGCGAGCCACCAATCACAATGGACAGCGGCGG |
| NEUROG2 | AAG | CTGCGGCTGTTGTCGCCGCCGCTGTCCATTGT |
| NEUROG2 | AGG | CTCAAGCTGCGGCTGTTGTCGCCGCCGCTGTC |
| NEUROG2 | AAG | CCGCAGCGGCCGCAGAGGCTCAAGCTGCGGCT |
| NEUROG2 | GAG | CTGGCGAAGCCGCAGCGGCCGCAGAGGCTCAA |
| NEUROG2 | GAG | CCTCTGCGGCCGCTGCGGCTTCGCCAGCTCCG |
| NEUROG2 | GAG | CTCCGGGCTGCGGCCGGAGCTGGCGAAGCCGC |
| NEUROG2 | AAG | CTCCTGTTGGAGCTCCGGGCTGCGGCCGGAGC |
| NEUROG2 | GAG | CTCCAACAGGAGCTTTAGAACCATTTTATGTT |
| NEUROG2 | AAG | AGAGGCGGGGGTGGTGGGAGGAGGAGGATGGA |
| NEUROG2 | AGG | GGGCCCGGGGCAGATCTGATTGTTTTCTTGGT |
| NEUROG2 | AAG | GGGTTTTAAGGAGAGTCGTGTGCCAGACACGC |

SEQUENCES

Flag-CasA: DNA sequence, *Flag Epitope Tag*, Nuclear localization signal, *E. coli K-12 CasA*

(SEQ ID NO: 1)

ATGGATTACAAAGACGATGACGATAAGATGGCGCCTAAGAAGAAACGCAAAGTGC

GGGGCATGGCCAATCTCCTGATTGACAATTGGATCCCTGTGAGACCGAGGAACGGAG

GGAAGGTTCAGATCATCAACCTGCAAAGTCTCTACTGTAGCAGAGATCAATGGCGACT

CTCATTGCCCAGGGATGATATGGAATTGGCGGCACTTGCACTCTTGGTATGTATTGGG

CAGATCATCGCCCCTGCCAAGGATGATGTCGAGTTTAGGCACAGAATAATGAACCCTC

TTACTGAAGATGAATTCCAGCAATTGATCGCGCCTTGGATAGATATGTTCTATTTGAAT

CACGCCGAACATCCCTTCATGCAGACAAAAGGGGTTAAAGCAAATGATGTCACACCAA

TGGAGAAGCTTTTGGCAGGTGTGTCAGGAGCAACCAACTGCGCTTTCGTTAACCAACC

AGGCCAAGGTGAGGCGTTGTGCGGGGGGTGCACGGCCATAGCGTTGTTTAATCAGGC

GAACCAGGCTCCTGGCTTTGGAGGAGGATTCAAGTCCGGTTTGCGCGGGGGTACACC

CGTAACCACATTCGTTCGCGGAATTGACCTCCGATCAACAGTCCTGTTGAACGTATTG

ACGTTGCCTAGACTTCAGAAGCAATTTCCAAACGAGTCTCACACTGAGAATCAACCGA

CTTGGATTAAGCCCATCAAGTCAAATGAAAGTATACCCGCGTCTTCTATTGGATTTGTT

AGAGGACTTTTTTGGCAGCCCGCTCACATAGAACTCTGTGATCCCATAGGCATTGGAA

AGTGTTCTTGCTGTGGCCAAGAGTCTAACCTTAGATATACGGGCTTTCTCAAGGAGAA

GTTCACGTTCACCGTGAATGGACTTTGGCCACATCCCCATAGCCCGTGCTTGGTCACG

GTCAAGAAGGGGGAGGTTGAAGAGAAATTTCTTGCGTTTACCACATCCGCCCCATCCT

GGACGCAAATATCTCGCGTCGTTGTGGATAAAATCATCCAGAACGAAAATGGTAACCG

CGTTGCCGCGGTAGTGAATCAATTCAGAAACATAGCACCACAGAGCCCGTTGGAGTTG

ATAATGGGCGGGTACCGCAATAATCAAGCTTCCATTCTCGAGCGACGCCATGACGTAC

TTATGTTTAACCAGGGGTGGCAGCAATATGGTAACGTGATAAACGAGATAGTCACAGT

-continued

CGGCCTCGGCTACAAAACTGCGTTGCGCAAAGCTCTGTATACGTTCGCGGAGGGTTTT

AAGAATAAAGACTTTAAAGGCGCTGGGGTGAGTGTGCACGAGACGGCAGAACGCCAT

TTCTATCGCCAGTCTGAACTCTTGATTCCCGACGTTCTGGCGAATGTCAATTTTTCCCA

GGCCGATGAGGTCATTGCGGATCTGCGAGATAAGCTTCACCAGTTGTGTGAGATGCTG

GGCAAGGGCTACGTTGTATAAACACCTTAGAGAACTGAAGCCACAGGGTGGTCCCAG

CAATGGCTGA

Flag-CasB: DNA sequence, *Flag Epitope tag*, Nuclear localization signal, *E. coli K-12 CasB*

(SEQ ID NO: 2)

ATGGATTACAAAGACGATGACGATAAGATGGCGCCTAAGAAAAAGAGGAAAGTAC

GCGGGATGGCCGATGAAATAGACGCAATGGCTCTTTACCGAGCATGGCAACAGCTCG

ACAATGGATCTTGCGCCCAAATACGGCGGGTAAGTGAACCCGATGAACTGCGAGATAT

CCCCGCATTCTACCGATTGGTTCAGCCGTTTGGCTGGGAGAACCCACGGCACCAGCAG

GCGCTTCTTAGGATGGTTTTTTGTCTTAGTGCCGGGAAAAACGTAATCCGCCATCAGG

ATAAGAAGTCCGAACAAACAACAGGGATTTCTCTGGGAAGAGCGCTTGCTAACAGCG

GCAGGATCAATGAACGCCGCATATTTCAGTTGATCCGAGCAGATCGGACTGCTGATAT

GGTCCAGCTCAGGAGGCTCCTTACGCACGCAGAGCCAGTGTTGGATTGGCCACTCAT

GGCAAGAATGCTTACGTGGTGGGGGAAGAGGGAAAGGCAGCAACTGCTTGAAGATTT

TGTATTGACGACGAACAAAAACGCGTAA

Flag-CasC: DNA sequence, *Flag Epitope tag*, Nuclear localization signal, *E. coli K-12 CasC*

(SEQ ID NO: 3)

ATGGATTACAAAGACGATGACGATAAGATGGCGCCTAAGAAGAAGCGCAAGGTGA

GAGGAATGTCAAACTTCATTAATATCCACGTGCTTATCTCACACTCCCCTAGTTGCCT

TAACAGAGACGATATGAACATGCAAAAAGACGCAATTTTTGGCGGCAAAAGGAGAGTC

AGAATTAGTAGCCAGAGCCTGAAGCGCGCTATGAGGAAAAGCGGCTACTATGCTCAA

AACATTGGTGAAAGTTCATTGCGGACCATCCATCTCGCGCAGTTGAGGGACGTCCTGC

GACAGAAGCTTGGGGAAAGATTTGATCAGAAGATCATCGACAAAACGCTTGCCCTTCT

GTCCGGTAAATCAGTGGACGAAGCGGAGAAGATAAGTGCGGATGCTGTTACGCCATG

GGTGGTAGGTGAAATCGCGTGGTTTTGCGAGCAGGTAGCCAAGGCCGAAGCGGATAA

TTTGGATGATAAGAAACTGCTCAAAGTCCTCAAAGAGGACATCGCGGCGATCCGGGTG

AACCTTCAGCAGGGTGTTGATATTGCGCTCTCTGGTCGGATGGCCACGTCTGGAATGA

TGACTGAACTGGGTAAGGTGGACGGAGCTATGTCTATAGCTCATGCTATAACTACCCA

TCAGGTGGATTCTGACATAGACTGGTTCACGGCTGTCGACGATCTCCAGGAACAAGGA

TCCGCACACCTCGGCACGCAAGAATTTTCTTCTGGAGTGTTCTATAGGTATGCCAACA

TCAACCTTGCACAGCTCCAGGAAAACCTCGGTGGGGCAAGCCGGGAACAGGCTCTTG

AAATAGCTACCCATGTGGTTCACATGCTGGCGACCGAAGTGCCAGGGGCCAAGCAGA

GAACGTACGCCGCATTCAATCCGGCGGACATGGTCATGGTGAATTTCTCTGATATGCC

CTTGTCTATGGCAATGCTTTCGAGAAGGCGGTCAAGGCAAAGGACGGTTTTTTGCAA

CCCTCCATCCAAGCCTTTAATCAGTACTGGGATAGAGTAGCTAACGGGTATGGTCTCA

-continued

ATGGCGCGGCTGCTCAGTTTTCTTTGTCCGATGTGGATCCGATAACGGCGCAGGTTAA

ACAGATGCCCACCTTGGAACAACTCAAATCCTGGGTTAGAAACAATGGGGAGGCGTG

A

Flag-CasD: DNA sequence, Flag Epitope tag, Nuclear localization signal, E. coli K-12 CasD (SEQ ID NO: 4)

ATGGATTACAAAGACGATGACGATAAGATGGCGCCTAAGAAAAAGAGGAAAGTAC

GGGGCATGCGATCATACTTGATCCTGCGGCTTGCAGGTCCTATGCAAGCCTGGGGGC

AACCTACCTTTGAAGGTACTCGGCCGACTGGCAGGTTCCCTACGCGGTCTGGTTTGCT

CGGACTCCTCGGCGCCTGTTTGGGGATACAAAGGGATGACACTTCTTCCTTGCAGGCA

CTTTCCGAATCAGTCCAGTTCGCAGTGAGATGTGATGAACTCATACTGGACGACAGAC

GGGTGTCCGTAACTGGACTGAGGGACTATCATACTGTACTCGGCGCAAGAGAAGATTA

TCGAGGTCTTAAGTCACATGAGACTATTCAGACATGGAGGGAATATTTGTGTGACGCC

TCCTTCACGGTGGCCCTCTGGCTTACACCACATGCAACTATGGTGATCTCAGAGCTTG

AGAAAGCCGTTCTTAAACCTCGGTACACACCATATCTGGGGAGGCGGTCTTGCCCACT

TACCCACCCGCTTTTCTTGGGGACTTGTCAGGCCAGCGATCCACAGAAGGCCTTGCTG

GGAATGGTACGTTATTAAGGGGGGAATGGACGTTTCCCAATGA

Flag-CasE: DNA sequence, Flag Epitope tag, Nuclear localization signal, E. coli K-12 CasE (SEQ ID NO: 5)

ATGGATTACAAAGACGATGACGATAAGATGGCGCCTAAGAAGAAGCGCAAGGTGC

GGGGCATGTATCTCAGTAAAGTCATCATTGCCAGGGCCTGGAGCAGGGATCTTTACC

AACTTCACCAGGGATTATGGCATTTATTTCCAAACAGACCGGATGCTGCTCGTGATTTT

CTTTTTCATGTTGAGAAGCGAAACACACCAGAAGGCTGTCATGTTTTATTGCAGTCAG

CGCAAATGCCTGTTTCAACTGCCGTTGCGACAGTCATTAAAACTAAACAGGTTGAATT

TCAACTTCAGGTTGGTGTTCCACTCTATTTTCGGCTTCGGGCAAATCCGATCAAAACTA

TTCTCGACAATCAAAAGCGCCTGGACAGTAAAGGGAATATTAAACGCTGTCGGGTTCC

GTTAATAAAAGAAGCAGAACAAATCGCGTGGTTGCAACGTAAATTGGGCAATGCGGC

GCGCGTTGAAGATGTGCATCCCATATCGGAACGGCCACAGTATTTTTCTGGTGATGGT

AAAAGTGGAAAGATCCAAACGGTTTCGCTTTGAAGGTGTGCTCACCATCAACGACGCGC

CAGCGTTAATAGATCTTGTACAGCAAGGTATTGGGCCAGCTAAATCGATGGGATGTGG

CTTGCTATCTTTGGCTCCACTGTGA

Flag-CasE-p300: DNA sequence, E Epitope tag, Flag Epitope tag, Nuclear localization signal, E. coli K-12 CasE, p300 core effector

(SEQ ID NO: 6)

ATGGGTGCCCCAGTTCCGTATCCGGACCCACTGGAGCCAAGGATGGCGCCTAAGAA

GAAGCGCAAGGTGCGGGGCATGTATCTCAGTAAAGTCATCATTGCCAGGGCCTGGA

GCAGGGATCTTTACCAACTTCACCAGGGATTATGGCATTTATTTCCAAACAGACCGGA

TGCTGCTCGTGATTTTCTTTTTCATGTTGAGAAGCGAAACACACCAGAAGGCTGTCAT

GTTTTATTGCAGTCAGCGCAAATGCCTGTTTCAACTGCCGTTGCGACAGTCATTAAAA

CTAAACAGGTTGAATTTCAACTTCAGGTTGGTGTTCCACTCTATTTTCGGCTTCGGGCA

AATCCGATCAAAACTATTCTCGACAATCAAAAGCGCCTGGACAGTAAAGGGAATATTA

-continued

AACGCTGTCGGGTTCCGTTAATAAAAGAAGCAGAACAAATCGCGTGGTTGCAACGTAA

ATTGGGCAATGCGGCGCGGTTGAAGATGTGCATCCCATATCGGAACGGCCACAGTA

TTTTTCTGGTGATGGTAAAAGTGGAAAGATCCAAACGGTTTGCTTTGAAGGTGTGCTC

ACCATCAACGACGCGCCAGCGTTAATAGATCTTGTACAGCAAGGTATTGGGCCAGCTA

AATCGATGGGATGTGGCTTGCTATCTTTGGCTCCACTGCGGGGCAAGCGACCTGCC

GCCACAAAGAAGGCTGGACAGGCTAAGAAGAAGAAAGGATCCATTTTCAAACC

AGAAGAACTACGACAGGCACTGATGCCAACTTTGGAGGCACTTTACCGTCAGG

ATCCAGAATCCCTTCCCTTTCGTCAACCTGTGGACCCTCAGCTTTTAGGAATCC

CTGATTACTTTGATATTGTGAAGAGCCCCATGGATCTTTCTACCATTAAGAGGA

AGTTAGACACTGGACAGTATCAGGAGCCCTGGCAGTATGTCGATGATATTTGG

CTTATGTTCAATAATGCCTGGTTATATAACCGGAAAACATCACGGGTATACAAA

TACTGCTCCAAGCTCTCTGAGGTCTTTGAACAAGAAATTGACCCAGTGATGCAA

AGCCTTGGATACTGTTGTGGCAGAAAGTTGGAGTTCTCTCCACAGACACTGTGT

TGCTACGGCAAACAGTTGTGCACAATACCTCGTGATGCCACTTATTACAGTTAC

CAGAACAGGTATCATTTCTGTGAGAAGTGTTTCAATGAGATCCAAGGGGAGAG

CGTTTCTTTGGGGGATGACCCTTCCCAGCCTCAAACTACAATAAATAAAGAACA

ATTTTCCAAGAGAAAAAATGACACACTGGATCCTGAACTGTTTGTTGAATGTAC

AGAGTGCGGAAGAAAGATGCATCAGATCTGTGTCCTTCACCAATGAGATCATCT

GGCCTGCTGGATTCGTCTGTGATGGCTGTTTAAAGAAAAGTGCACGAACTAGG

AAAGAAAATAAGTTTTCTGCTAAAAGGTTGCCATCTACCAGACTTGGCACCTTT

CTAGAGAATCGTGTGAATGACTTTCTGAGGCGACAGAATCACCCTGAGTCAGG

AGAGGTCACTGTTAGAGTAGTTCATGCTTCTGACAAAACCGTGGAAGTAAAAC

CAGGCATGAAAGCAAGGTTTGTGGACAGTGGAGAGATGGCAGAATCCTTTCCA

TACCGAACCAAAGCCCTCTTTGCCTTTGAAGAAATTGATGGTGTTGACCTGTGC

TTCTTTGGCATGCATGTTCAAGAGTATGGCTCTGACTGCCCTCCACCCAACCAG

AGGAGAGTATACATATCTTACCTCGATAGTGTTCATTTCTTCCGTCCTAAATGC

TTGAGGACTGCAGTCTATCATGAAATCCTAATTGGATATTTAGAATATGTCAAG

AAATTAGGTTACACAACAGGGCATATTTGGGCATGTCCACCAAGTGAGGGAGA

TGATTATATCTTCCATTGCCATCCTCCTGACCAGAAGATACCCAAGCCCAAGCG

ACTGCAGGAATGGTACAAAAAAATGCTTGACAAGGCTGTATCAGAGCGTATTG

TCCATGACTACAAGGATATTTTTAAACAAGCTACTGAAGATAGATTAACAAGTG

CAAAGGAATTGCCTTATTTCGAGGGTGATTTCTGGCCCAATGTTCTGGAAGAAA

GCATTAAGGAACTGGAACAGGAGGAAGAAGAGAGAAAACGAGAGGAAAACAC

CAGCAATGAAAGCACAGATGTGACCAAGGGAGACAGCAAAAATGCTAAAAAGA

AGAATAATAAGAAAACCAGCAAAAATAAGAGCAGCCTGAGTAGGGGCAACAAG

AAGAAACCCGGGATGCCCAATGTATCTAACGACCTCTCACAGAAACTATATGCC

-continued

ACCATGGAGAAGCATAAAGAGGTCTTCTTTGTGATCCGCCTCATTGCTGGCCCT

GCTGCCAACTCCCTGCCTCCCATTGTTGATCCTGATCCTCTCATCCCCTGCGAT

CTGATGGATGGTCGGGATGCGTTTCTCACGCTGGCAAGGGACAAGCACCTGGA

GTTCTCTTCACTCCGAAGAGCCCAGTGGTCCACCATGTGCATGCTGGTGGAGC

TGCACACGGCAGAGCCAGGACGGATCCGATTACAAAGACGATGACGATAAGTGA

Flag-CasA-p300: DNA sequence, Myc Epitope tag, Flag Epitope tag, Nuclear localization signal, E. coli K-12 CasA, p300 core effector (SEQ ID NO: 8)

ATGGAGCAAAAATTGATCAGTGAAGAAGACCTGATGGCACCAAAAAAGAAACGCAA

AGTGCGGGGCATGGCCAATCTCCTGATTGACAATTGGATCCCTGTGAGACCGAGGA

ACGGAGGGAAGGTTCAGATCATCAACCTGCAAAGTCTCTACTGTAGCAGAGATCAA

TGGCGACTCTCATTGCCCAGGGATGATATGGAATTGGCGGCACTTGCACTCTTGGTA

TGTATTGGGCAGATCATCGCCCCTGCCAAGGATGATGTCGAGTTTAGGCACAGAATA

ATGAACCCTCTTACTGAAGATGAATTCCAGCAATTGATCGCGCCTTGGATAGATATG

TTCTATTTGAATCACGCCGAACATCCCTTCATGCAGACAAAAGGGGTTAAAGCAAAT

GATGTCACACCAATGGAGAAGCTTTTGGCAGGTGTGTCAGGAGCAACCAACTGCGC

TTTCGTTAACCAACCAGGCCAAGGTGAGGCGTTGTGCGGGGGGTGCACGGCCATAG

CGTTGTTTAATCAGGCGAACCAGGCTCCTGGCTTTGGAGGAGGATTCAAGTCCGGTT

TGCGCGGGGGTACACCCGTAACCACATTCGTTCGCGGAATTGACCTCCGATCAACAG

TCCTGTTGAACGTATTGACGTTGCCTAGACTTCAGAAGCAATTTCCAAACGAGTCTC

ACACTGAGAATCAACCGACTTGGATTAAGCCCATCAAGTCAAATGAAAGTATACCC

GCGTCTTCTATTGGATTTGTTAGAGGACTTTTTTGGCAGCCCGCTCACATAGAACTCT

GTGATCCCATAGGCATTGGAAAGTGTTCTTGCTGTGGCCAAGAGTCTAACCTTAGAT

ATACGGGCTTTCTCAAGGAGAAGTTCACGTTCACCGTGAATGGACTTTGGCCACATC

CCCATAGCCCGTGCTTGGTCACGGTCAAGAAGGGGGAGGTTGAAGAGAAATTTCTT

GCGTTTACCACATCCGCCCCATCCTGGACGCAAATATCTCGCGTCGTTGTGGATAAA

GTGATCCCATAGGCATTGGAAAGTGTTCTTGCTGTGGCCAAGAGTCTAACCTTAGAT

CATAGCACCACAGAGCCCGTTGGAGTTGATAATGGGCGGGTACCGCAATAATCAAG

CTTCCATTCTCGAGCGACGCCATGACGTACTTATGTTTAACCAGGGGTGGCAGCAAT

ATGGTAACGTGATAAACGAGATAGTCACAGTCGGCCTCGGCTACAAAACTGCGTTG

CGCAAAGCTCTGTATACGTTCGCGGAGGGTTTAAGAATAAAGACTTTAAAGGCGCT

GGGGTGAGTGTGCACGAGACGGCAGAACGCCATTTCTATCGCCAGTCTGAACTCTTG

ATTCCCGACGTTCTGGCGAATGTCAATTTTTCCCAGGCCGATGAGGTCATTGCGGAT

CTGCGAGATAAGCTTCACCAGTTGTGTGAGATGCTGTTCAACCAGTCTGTGGCTCCT

TATGCTCATCATCCCAAACTGATTTCAACTCTCGCTTTGGCAAGGGCTACGTTGTATA

AACACCTTAGAGAACTGAAGCCACAGGGTGGTCCCAGCAATGGCCGGGGCAAGCG

ACCTGCCGCCACAAAGAAGGCTGGACAGGCTAAGAAGAAGAAAGGATCCATTTT

CAAACCAGAAGAACTACGACAGGCACTGATGCCAACTTTGGAGGCACTTTACCGTC

AGGATCCAGAATCCCTTCCCTTTCGTCAACCTGTGGACCCTCAGCTTTTAGGAATCC

-continued

CTGATTACTTTGATATTGTGAAGAGCCCCATGGATCTTTCTACCATTAAGAGGAAGT
TAGACACTGGACAGTATCAGGAGCCCTGGCAGTATGTCGATGATATTTGGCTTATGT
TCAATAATGCCTGGTTATATAACCGGAAAACATCACGGGTATACAAATACTGCTCCA
AGCTCTCTGAGGTCTTTGAACAAGAAATTGACCCAGTGATGCAAAGCCTTGGATACT
GTTGTGGCAGAAAGTTGGAGTTCTCTCCACAGACACTGTGTTGCTACGGCAAACAGT
TGTGCACAATACCTCGTGATGCCACTTATTACAGTTACCAGAACAGGTATCATTTCT
GTGAGAAGTGTTTCAATGAGATCCAAGGGGAGAGCGTTTCTTTGGGGGATGACCCTT
CCCAGCCTCAAACTACAATAAATAAAGAACAATTTTCCAAGAGAAAAAATGACACA
CTGGATCCTGAACTGTTTGTTGAATGTACAGAGTGCGGAAGAAAGATGCATCAGATC
AGAAAAGTGCACGAACTAGGAAAGAAAATAAGTTTTCTGCTAAAAGGTTGCCATCT
ACCAGACTTGGCACCTTTCTAGAGAATCGTGTGAATGACTTTCTGAGGCCGACAGAAT
CACCCTGAGTCAGGAGAGGTCACTGTTAGAGTAGTTCATGCTTCTGACAAAACCGTG
GAAGTAAAACCAGGCATGAAAGCAAGGTTTGTGGACAGTGGAGAGATGGCAGAAT
CCTTTCCATACCGAACCAAAGCCCTCTTTGCCTTTGAAGAAATTGATGGTGTTGACCT
GTGCTTCTTTGGCATGCATGTTCAAGAGTATGGCTCTGACTGCCCTCCACCCAACCA
GAGGAGAGTATACATATCTTACCTCGATAGTGTTCATTTCTTCCGTCCTAAATGCTTG
AGGACTGCAGTCTATCATGAAATCCTAATTGGATATTTAGAATATGTCAAGAAATTA
GGTTACACAACAGGGCATATTTGGGCATGTCCACCAAGTGAGGGAGATGATTATAT
CTTCCATTGCCATCCTCCTGACCAGAAGATACCCAAGCCCAAGCGACTGCAGGAATG
GTACAAAAAAATGCTTGACAAGGCTGTATCAGAGCGTATTGTCCATGACTACAAGG
ATATTTTTAAACAAGCTACTGAAGATAGATTAACAAGTGCAAAGGAATTGCCTTATT
TCGAGGGTGATTTCTGGCCCAATGTTCTGGAAGAAAGCATTAAGGAACTGGAACAG
GAGGAAGAAGAGAGAAAACGAGAGGAAAACACCAGCAATGAAAGCACAGATGTGA
CCAAGGGAGACAGCAAAAATGCTAAAAAGAAGAATAATAAGAAAACCAGCAAAAA
TAAGAGCAGCCTGAGTAGGGGCAACAAGAAGAAACCCGGGATGCCCAATGTATCTA
ACGACCTCTCACAGAAACTATGCCACCATGGAGAAGCATAAAGAGGTCTTCTTTG
TGATCCGCCTCATTGCTGGCCCTGCTGCCAACTCCCTGCCTCCCATTGTTGATCCTGA
TCCTCTCATCCCCTGCGATCTGATGGATGGTCGGGATGCGTTTCTCACGCTGGCAAG
GGACAAGCACCTGGAGTTCTCTTCACTCCGAAGAGCCCAGTGGTCCACCATGTGCAT
GCTGGTGGAGCTGCACACGCAGAGCCAGGACGGATCCGATTACAAA*GACGATGACG*
*ATAAG*TGA

**Flag-CasE-VPR: DNA sequence, *Flag Epitope tag,* Nuclear localization signal,** *E. coli K-12 CasE*, VPR (SEQ ID NO: 7)

ATG***GATTACAAAGACGATGACG*ATAAGATGGCGCCTAAGAAGAAGCGCAAGGTGC**
GGGGC*ATGTATCTCAGTAAAGTCATCATTGCCAGGGCCTGGAGCAGGGATCTTTACC*
*AACTTCACCAGGGATTATGGCATTTATTTCCAAACAGACCGGATGCTGCTCGTGATTTT*
*CTTTTTCATGTTGAGAAGCGAAACACACCAGAAGGCTGTCATGTTTTATTGCAGTCAG*
*CGCAAATGCCTGTTTCAACTGCCGTTGCGACAGTCATTAAAACTAAACAGGTTGAATT*
*TCAACTTCAGGTTGGTGTTCCACTCTATTTTCGGCTTCGGGCAAATCCGATCAAAACTA*

-continued

*TTCTCGACAATCAAAAGCGCCTGGACAGTAAAGGGAATATTAAACGCTGTCGGGTTCC*

*GTTAATAAAAGAAGCAGAACAAATCGCGTGGTTGCAACGTAAATTGGGCAATGCGGC*

*GCGCGTTGAAGATGTGCATCCCATATCGGAACGGCCACAGTATTTTTCTGGTGATGGT*

*AAAAGTGGAAAGATCCAAACGGTTTGCTTTGAAGGTGTGCTCACCATCAACGACGCGC*

*CAGCGTTAATAGATCTTGTACAGCAAGGTATTGGGCCAGCTAAATCGATGGGATGTGG*

*CTTGCTATCTTTGGCTCCACTGCGGGGC*AAGCGACCTGCCGCCACAAAGAAGGCT

GGACAGGCTAAGAAGAAGAAAggatccTCGCCAGGGATCCGTCGACTTGACGCGTTG

ATATCAACAAGTTTGTACAAAAAAGCAGGCTACAAAGAGGCCAGCGGTTCCGGACG

GGCTGACGCATTGGACGATTTTGATCTGGATATGCTGGGAAGTGACGCCCTCGATGA

TTTTGACCTTGACATGCTTGGTTCGGATGCCCTTGATGACTTTGACCTCGACATGCTC

GGCAGTGACGCCCTTGATGATTTCGACCTGGACATGCTGATTAACTCTAGAAGTTCC

GGATCTCCGAAAAAGAAACGCAAAGTTGGTAGCCAGTACCTGCCCGACACCGACGA

CCGGCACCGGATCGAGGAAAAGCGGAAGCGGACCTACGAGACATTCAAGAGCATC

ATGAAGAAGTCCCCCTTCAGCGGCCCCACCGACCCTAGACCTCCACCTAGAAGAAT

CGCCGTGCCCAGCAGATCCAGCGCCAGCGTGCCAAAACCTGCCCCCCAGCCTTACCC

CTTCACCAGCAGCCTGAGCACCATCAACTACGACGAGTTCCCTACCATGGTGTTCCC

CAGCGGCCAGATCTCTCAGGCCTCTGCTCTGGCTCCAGCCCCTCCTCAGGTGCTGCC

TCAGGCTCCTGCTCCTGCACCAGCTCCAGCCATGGTGTCTGCACTGGCTCAGGCACC

AGCACCCGTGCCTGTGCTGGCTCCTGGACCTCCACAGGCTGTGGCTCCACCAGCCCC

TAAACCTACACAGGCCGGCGAGGGCACACTGTCTGAAGCTCTGCTGCAGCTGCAGT

TCGACGACGAGGATCTGGGAGCCCTGCTGGGAAACAGCACCGATCCTGCCGTGTTC

ACCGACCTGGCCAGCGTGGACAACAGCGAGTTCCAGCAGCTGCTGAACCAGGGCAT

CCCTGTGGCCCCTCACACCACCGAGCCCATGCTGATGGAATACCCCGAGGCCATCAC

CCGGCTCGTGACAGGCGCTCAGAGGCCTCCTGATCCAGCTCCTGCCCCTCTGGGAGC

ACCAGGCCTGCCTAATGGACTGCTGTCTGGCGACGAGGACTTCAGCTCTATCGCCGA

TATGGATTTCTCAGCCTTGCTGGGCTCTGGCAGCGGCAGCCGGGATTCCAGGGAAGG

GATGTTTTTGCCGAAGCCTGAGGCCGGCTCCGCTATTAGTGACGTGTTTGAGGGCCG

CGAGGTGTGCCAGCCAAAACGAATCCGGCCATTTCATCCTCCAGGAAGTCCATGGG

CCAACCGCCCACTCCCCGCCAGCCTCGCACCAACACCAACCGGTCCAGTACATGAG

CCAGTCGGGTCACTGACCCCGGCACCAGTCCCTCAGCCACTGGATCCAGCGCCCGCA

GTGACTCCCGAGGCCAGTCACCTGTTGGAGGATCCCGATGAAGAGACGAGCCAGGC

TGTCAAAGCCCTTCGGGAGATGGCCGATACTGTGATTCCCCAGAAGGAAGAGGCTG

CAATCTGTGGCCAAATGGACCTTTCCCATCCGCCCCCAAGGGGCCATCTGGATGAGC

TGACAACCACACTTGAGTCCATGACCGAGGATCTGAACCTGGACTCACCCCTGACCC

CGGAATTGAACGAGATTCTGGATACCTTCCTGAACGACGAGTGCCTCTTGCATGCCA

TGCATATCAGCACAGGACTGTCCATCTTCGACACATCTCTGTTCTGA

**V5-CasC: DNA sequence, *V5 Epitope tag,* Nuclear localization signal,** *E. coli K-12 CasC*

(SEQ ID NO: 163)

**ATG*GGCAAGCCTATACCTAACCCTTTGCTCGGGCTGGACTCCACC*ATGGCTCCTAAG**

AAGAAGCGCAAGGTGAGAGGA*ATGTCAAACTTCATTAATATCCACGTGCTTATCTC*

-continued

*ACACTCCCCTAGTTGCCTTAACAGAGACGATATGAACATGCAAAAAGACGCAATTTTT*

*GGCGGCAAAAGGAGAGTCAGAATTAGTAGCCAGAGCCTGAAGCGCGCTATGAGGAAA*

*AGCGGCTACTATGCTCAAAACATTGGTGAAAGTTCATTGCGGACCATCCATCTCGCGC*

*AGTTGAGGGACGTCCTGCGACAGAAGCTTGGGGAAAGATTTGATCAGAAGATCATCG*

*ACAAAACGCTTGCCCTTCTGTCCGGTAAATCAGTGGACGAAGCGGAGAAGATAAGTGC*

*GGATGCTGTTACGCCATGGGTGGTAGGTGAAATCGCGTGGTTTTGCGAGCAGGTAGC*

*CAAGGCCGAAGCGGATAATTTGGATGATAAGAAACTGCTCAAAGTCCTCAAAGAGGAC*

*ATCGCGGCGATCCGGGTGAACCTTCAGCAGGGTGTTGATATTGCGCTCTCTGGTCGGA*

*TGGCCACGTCTGGAATGATGACTGAACTGGGTAAGGTGGACGGAGCTATGTCTATAG*

*CTCATGCTATAACTACCCATCAGGTGGATTCTGACATAGACTGGTTCACGGCTGTCGA*

*CGATCTCCAGGAACAAGGATCCGCACACCTCGGCACGCAAGAATTTTCTTCTGGAGTG*

*TTCTATAGGTATGCCAACATCAACCTTGCACAGCTCCAGGAAAACCTCGGTGGGGCAA*

*GCCGGGAACAGGCTCTTGAAATAGCTACCCATGTGGTTCACATGCTGGCGACCGAAGT*

*GCCAGGGGCCAAGCAGAGAACGTACGCCGCATTCAATCCGGCGGACATGGTCATGGT*

*GAATTTCTCTGATATGCCCTTGTCTATGGCAAATGCTTTCGAGAAGGCGGTCAAGGCA*

*AAGGACGGTTTTTTGCAACCCTCCATCCAAGCCTTTAATCAGTACTGGGATAGAGTAG*

*CTAACGGGTATGGTCTCAATGGCGCGGCTGCTCAGTTTTCTTTGTCCGATGTGGATCC*

*GATAACGGCGCAGGTTAAACAGATGCCCACCTTGGAACAACTCAAATCCTGGGTTAGA*

*AACAATGGGGAGGCGTGA* p300 Core Effector (SEQ ID NO: 9)

IFKPEELRQALMPTLEALYRQDPESLPFRQPVDPQLLGIPDYFDIVKSPMDLSTIKRKLDT

GQYQEPWQYVDDIWLMFNNAWLYNRKTSRVYKYCSKLSEVFEQEIDPVMQSLGYCCG

RKLEFSPQTLCCYGKQLCTIPRDATYYSYQNRYHFCEKCFNEIQGESVSLGDDPSQPQTT

INKEQFSKRKNDTLDPELFVECTECGRKMHQICVLHHEIIWPAGFVCDGCLKKSARTRK

ENKFSAKRLPSTRLGTFLENRVNDFLRRQNHPESGEVTVRVVHASDKTVEVKPGMKAR

FVDSGEMAESFPYRTKALFAFEEIDGVDLCFFGMHVQEYGSDCPPPNQRRVYISYLDSV

EIFFRPKCLRTAVYHHLIGYLEYVKKLGYTTGHIWACPPSEGDDYIFHCHPPDQKIPKPK

RLQEWYKKMLDKAVSERIVHDYKDIFKQATEDRLTSAKELPYFEGDFWPNVLEESIKEL

EQEEEERKREENTSNESTDVTKGDSKNAKKKNNKKTSKNKSSLSRGNKKKPGMPNVSN

DLSQKLYATMEKHKEVFFVIRLIAGPAANSLPPIVDPDPLIPCDLMDGRDAFLTLARDKH

LEFSSLRRAQWSTMCMLVELHTQSQD

*Streptococcus pyogenes* Cas 9 (with D10A, H849A)

(SEQ ID NO: 10)

MDKKYSIGLAIGTNSVGWAVITDEYKVPSKKFKVLGNTDRHSIKKNLIGALLFDSGETA

EATRLKRTARRRYTRRKNRICYLQEIFSNEMAKVDDSFFHRLEESFLVEEDKKHERHPIF

GNIVDEVAYHEKYPTIYHLRKKLVDSTDKADLRLIYLALAHMIKFRGHFLIEGDLNPDNS

DVDKLFIQLVQTYNQLFEENPINASGVDAKAILSARLSKSRRLENLIAQLPGEKKNGLFG

NLIALSLGLTPNFKSNFDLAEDAKLQLSKDTYDDDLDNLLAQIGDQYADLFLAAKNLSD

AILLSDILRVNTEITKAPLSASMIKRYDEHHQDLTLLKALVRQQLPEKYKEIFFDQSKNGY

AGYIDGGASQEEFYKFIKPILEKMDGTEELLVKLNREDLLRKQRTFDNGSIPHQIHLGEL

-continued

HAILRRQEDFYPFLKDNREKIEKILTFRIPYYVGPLARGNSRFAWMTRKSEETITPWNFEE

VVDKGASAQSFIERMTNFDKNLPNEKVLPKHSLLYEYFTVYNELTKVKYVTEGMRKPA

FLSGEQKKAWDLLFKTNRKVTVKQLKEDYFKKIECFDSVEISGVEDRFNASLGTYHDLL

KIIKDKDFLDNEENEDILEDIVLTLTLFEDREMIEERLKTYAHLFDDKVMKQLKRRRYTG

WGRLSRKLINGIRDKQSGKTILDFLKSDGFANRNFMQLIHDDSLTFKEDIQKAQVSGQG

DSLHEHIANLAGSPAIKKGILQTVKVVDELVKVMGRHKPENIVIEMARENQTTQKGQKN

SRERMKRIEEGIKELGSQILKEHPVENTQLQNEKLYLYYLQNGRDMYVDQELDINRLSD

YDVDAIVPQSFLKDDSIDNKVLTRSDKNRGKSDNVPSEEVVKKMKNYVVRQLLNAKLIT

QRKFDNLTKAERGGLSELDKAGFIKRQLVETRQITKHVAQILDSRMNTKYDENDKLIRE

VKVITLKSKLVSDFRKDFQFYKVREINNYHHAHDAYLNAVVGTALIKKYPKLESEFVYG

DYKVYDVRKMIAKSEQEIGKATAKYFFYSNIMNFFKTEITLANGEIRKRPLIETNGETGEI

VWDKGRDFATVRKVLSMPQVNIVKKTEVQTGGFSKESILPKRNSDKLIARKKDWDPKK

YGGFDSPTVAYSVLVVAKVEKGKSKKLKSVKELLGITIMERSSFEKNPIDFLEAKGYKE

VKKDLIIKLPKYSLFELENGRKRMLASAGELQKGNELALPSKYVNFLYLASHYEKLKGS

PEDNEQKQLFVEQHKHYLDEIIEQISEFSKRVILADANLDKVLSAYNKHRDKPIREQAENI

IHLFTLTNLGAPAAFKYFDTTIDRKRYTSTKEVLDATLIHQSITGLYETRIDLSQLGGD

VP64-p65-Rta tripartite activator (SEQ ID NO: 11)

SPGIRRLDALISTSLYKKAGYKEASGSGRADALDDFDLDMLGSDALDDFDLDMLGSDA

LDDFDLDMLGSDALDDFDLDMLINSRSSGSPKKKRKVGSQYLPDTDDRHRIEEKRKRTY

ETFKSIMKKSPFSGPTDPRPPPRRIAVPSRSSASVPKPAPQPYPFTSSLSTINYDEFPTMVFP

SGQISQASALAPAPPQVLPQAPAPAPAPAMVSALAQAPAPVPVLAPGPPQAVAPPAPKPT

QAGEGTLSEALLQLQFDDEDLGALLGNSTDPAVFTDLASVDNSEFQQLLNQGIPVAPHT

TEPMLMEYPEAITRLVTGAQRPPDPAPAPLGAPGLPNGLLSGDEDFSSIADMDFSALLGS

GSGSRDSREGMFLPKPEAGSAISDVFEGREVCQPKRIRPFHPPGSPWANRPLPASLAPTPT

GPVHEPVGSLTPAPVPQPLDPAPAVTPEASHLLEDPDEETSQAVKALREMADTVIPQKEE

AAICGQMDLSHPPPRGHLDELTTTLESMTEDLNLDSPLTPELNEILDTFLNDECLLHAMH

ISTGLSIFDTSLF

Flag-Cas5: DNA sequence, Flag Epitope Tag, Nuclear localization signal, L. monocytogenes Finland 1998 Cas5

(SEQ ID NO: 166)

ATGGACTATAAGGATGATGACGACAAGATGGCCCCCAAGAAGAAGCGCAAAGTCC

GCGGGATGAAGGCTATTAGGGTCCGGCTGTGGCAGGATCTCGTGAACTTCAAGAAGC

CTACCAGCTTCCAACTGAAGGAAACCTACCCTCTGCCGCCGTACTCTACCGTGATCGG

CATGGTGCATACACTGTGCGGCTTTACCTCCTACCACGAGATGAAGATCAGCATTCAG

GGAAAGTACTTTAGCAAGGTCAACGACCTCGCGACTAGATACGAATTCAAGAATGGCT

CAAAATACGACGTGGAACGCCACCAGATCAAAGTGGACAAATACGGAGTGTCGAGAG

GCGTCAGCACCGTGGAGCTCCTTGTGGACCTCGAACTGCTGCTGCACATCATTCCGGA

AGATCCATCCTTGGTGCCGATCATTGAAAAGGCATTCCGGGAACCCATCGAGTTCCCT

TCCCTGGGACGCAGAGAGGACATCGCCACGATTCAGAAGGTCGAAGTGGTGGACGTC

GAGAAGCGACAGCCCAAGAAGTCCACCGAGATCTCCGACGGTTATAACGCCTACGTG

CCGATCAGCTTGACCGAGAACAACTCGGTGCATTTCAAGTCCCACGAGTCCTCAGTGG

-continued

GACGGGATAAGCTGCTGGGGACTCGGTACCTTCTGACTGAGAAATACGAGCGCGTGA

ACCACGGAACCGAAAAGGCCCCTAAGTTCTTCCGGAAGTGGCGGAAGAAGGACGTCA

TCTACTCCTCGCGCATCTTCGTGTCCAAGAAGGATGTGTTCTTTTTCGACGAGGACGA

TTACCTGGTGTTCATCGAAGAAGAAGAGTGA

Flag-Cas6: DNA sequence, Flag Epitope Tag, Nuclear localization signal, L. monocytogenes Finland 1998 Cas6

(SEQ ID NO: 167)

ATGGACTACAAGGACGACGACGATAAGATGGCGCCAAAGAAAAAGCGCAAGGTC

CGCGGAATGCGGCTGAAGATTAACTGCGACTTCGACAGCAAGATCATCCCCAAGGAC

TTCCAGTCCAAGGTCGTGTCCCTGTTCAAAGCCGGAATTATGAAAAGCTCCCCGGAGA

GATACGAGAACCTGTTTGGTGGAAACAAGCACAAGCAGTACACTTTCTCGGTGTATCT

CCCAAAACCTCAGAACAAGGGCGCCGAAATTCAGCTGAACGAGGCGAACTGTATCATC

AACTTCTCCACCGGCGATGCTGAAACCGGTATTATCTTCTACAACGCCCTGATTAGCC

TGAGAGGCTCCAAGGTCCTGTTTGGGGCCGGAAATCACATCACCGTGAAGAACATCCA

GATCGTGCCTGAGAAGAAGATCATCGGGAAGCAAACCATTCTGCGGACCCTTTCGCCG

GTGGTGTCGAGGGATCACAACCGGGAAACCTTCAAGAATTGGTTCTACTCATTCGAGG

ACGAAGAATTCGAGCCTACTTTGAAGCGGAACATGCTGCCGTACCTCATCGACGCCTT

TGGAGAACAGGCTCGCTACGATCTGGAAAAGCTGAAGATCACGCCCATTTCCATGAAG

AAAGTCGTGGTGTACTGCCATGAGATCCACATCGAGAGCTCCGTGGGCATCTTCGAGC

TGGAAGCCGAGGCATACCTCCAAAAGTACCTCGTGGAAAACGGAATCGGCACTATGA

CTGGCTCAGGGTTCGGAATGATTGAACAGTTCTGA

Flag-Cas7: DNA sequence, Flag Epitope Tag, Nuclear localization signal, L. monocytogenes Finland_1998 Cas7

(SEQ ID NO: 168)

ATGGACTACAAGGACGATGATGACAAGATGGCCCCCAAGAAGAAACGGAAAGTCC

GCGGCATGAAGAACAAGGGACTGGCAATGACTATCATTTTCCAAGCCGAAAGCGCCA

ATTACGGCGAATCCCTGGGGAACATTTCAAGCCTGAAGAAGATCTCTAGGAACAACGG

AGATCAGTACACCTACATCTCCCGCCAAGCGATCCGGTACAATCTTATGGATCAGATC

GGAGAAAAGGAAGCCCCTGTGAAGGCTGAAGGCGGCGGAGACAAAAAGGTCATCCAG

TTCCTGTCCGAGGCCACGATCACCGACTTCCCGGAACTCGACTTTTTCGGCTACCTGA

AAACCGAAAAGGGTTCCGGGGGACAGAAGCGCAGCGCCAAAGTCCGACTGTCGAACG

CCATCTCGCTGGAGACTTTTAAGGGCGACCTGGATTTCCTCACTAACAAGGGACAGGC

CGACAAGCTGAACGAAAACATGAACATTGCGCAGGCAGAGATCCACAAGTCCTACTAC

CGCTACACCATCACCATCGACCTCGACCAGATCGGTATCGACGGGGAGATTGCTCTGG

ACAACAAGGAAAAGGCCCGGAGAGTGAAGAAGCTGATGGACACTGTGGCGTTCCTCT

ATCGGGACATTAGGGGCAGACGGGAGGACCTCAAGCCCCTGTTCGTGATCGGTGGAG

TGTATGACGTGAAGAACCCGGTGTTCCAAAACATTGTGGATGTGGCCGACAACAATAT

-continued

TGTGATCAAGAACATTAAGGATTTGCTGACCTACGAGGACATCAAGGAGAACACCAGA

GTCGGCATCATTGATGGGCAGTTCGCCAACTCCGACGAAGTGAAAGTCGAGCTGAAG

GCCGAGTCCGTGCCAGCTTTCTTCAACGACATCAAGGGAAAGATTGATGCGTACTACG

AGAGCAACTGA

Flag-Cas8b2: DNA sequence, *Flag Epitope Tag*, Nuclear localization signal, *L. monocytogenes Finland 1998 Cas8b2*

(SEQ ID NO: 169)

**ATG*GATTACAAGGACGATGACGACAAAAT*GGCACCGAAGAAGAAGCGGAAGGTC**

**CGCGGA*ATGCAGACCGAAATCGAAGTCAGGGCAGACGACTGGCTCATCAACACCGGA***

*CTGACCGGCTTCCTGAACATTGTGGGAAAAGAGAACGTCCGGATTGACGGGCAGTCT*

*ATCTACTTCACCGCTGACCTCCTGGAAGATTTCGAAACTAAGTACTTTAACTTCTTCAT*

*CCAAGAGTACAAAGAAACTCTCTCATGGTACAAGATCGTCAGCTACAAAGAGACTATG*

*GAGCAGTTCAGAATTGATGAATTCGCGTCCTTTGACGAAGTGGCCCTGGGGAACCTGA*

*ACAAGTACATGAAGGACGTCGTGAAGTTCTATCTGAAAAAGGCCAACTATATCAAAGT*

*GTTCCCCTTGATTGACCCTAGCGCCAACGTGACCAAGTGGCTCGAAAAGCTGAACACC*

*ATTAATCTGACCAAGAAGCAGAAATGGGATGAGGTCAAGGCTGACATTATTGAGGAG*

*GTCAAACAGACCTACACCCAACTCGACCTGATTATTGACTTCTGTGCCTCCGAAAAGG*

*GACTGCAGTACCTGGGAGCCAAGAACCTGATCTATTCCGTCATTAACAAGGGCTGGAG*

*CGGAGTCTCCTTCCTGTTCAAGCAAACCAAGTTCATTGACCCGTATCTGGACTACAAG*

*ACGACCTTCGTGGATCCTGTGCTGGAGTACCTGGATACCGATCTGTCCAAGGCCAAGT*

*ACAACTGCTTCAACTGCAACCAGCCCATCAAGAACCTCAAGCTCGACCTCTCGTTCAT*

*GAATGACGTGGGCTTTGACACCGCCCGCAAGACTGCGCACGTCTGGGATTTCAACAAC*

*GATGTGGCCACTTGTCCAATCTGCCGGCTGATCTACTCATGCGTGCCTGCCGGGTTCA*

*CCTACGTGTATGGAGAGGGAATGTTCGTGAACGACTCCTACGGCGTGGAAGAACTGC*

*ACAGAGTGAACGAACGGATGCGGAACAGCATCCTGAGGTTTAACAAGGACGGTATCA*

*ATTCCACCAACACTTACCGCGCGCTTGTGGAGTCCATTACCATGGAACACGAAAACAA*

*CAGACGCTACGAATTGGCTGACATCCAGCTCGTGCGATACGAGAACGAGCATTACCG*

*GTTCAATCTGTTGTCAAAGAAGATGCTTCACATCGTGAACGATTCCAAGGGTATCCTG*

*AAGTCGCTGATACGCTGCGGTTACAAGGAGGGGAACCTCAACGTGAACCTCTACAAG*

*GAAGTGATCCAGCATCTGATGAACAACGAAAACCTCTTCACCCTTATCCACAAGTTGA*

*TCTACTACAAGCAGACCAGCGTGAACGGCCTGTACTACAACATGGGCCACGTGTCCGG*

*AATCCTGGATATCAACACCAAGTTCCTGAAAGAAATGGAGGTCATGACGAACATCTCA*

*CAGAACCAGCTGTGGTTCGTGCAAAATTGTGGCAAAGAATTCAAGGAGGGTTACGTGA*

*AGAAGAAGTCCGAGAACAAGATCTCCGGAATCACTTACAAGCTGCTGAATTCGCTGAA*

*GGTCAACGACAAGGACGGATTCATGGACACCCTGCTGAACTCCTACTCGTACCTGTCC*

-continued

ATGCCGATCCCCGACGTGTTCATCAAGATGTTCTCCAACAACGAAGCCTTCAAGAGCG

TGGGCTACGCTTTTATGCTTGGCGTGGGTGGAGAAAAGACTAAGAAGGAAGATGGGG

GCAACACCGATGAGAAGTGA

V5-Cas7: DNA sequence, *V5 Epitope Tag*, Nuclear localization signal, L. monocytogenes Finland_1998 Cas7

(SEQ ID NO: 170)

ATGGGCAAGCCTATACCTAACCCTTTGCTCGGGCTGGACTCCACCATGGCCCCCAAG

AAGAAACGGAAAGTCCGCGGCATGAAGAACAAGGGACTGGCAATGACTATCATTTT

CCAAGCCGAAAGCGCCAATTACGGCGAATCCCTGGGGAACATTTCAAGCCTGAAGAA

GATCTCTAGGAACAACGGAGATCAGTACACCTACATCTCCCGCCAAGCGATCCGGTAC

AATCTTATGGATCAGATCGGAGAAAAGGAAGCCCCTGTGAAGGCTGAAGGCGGCGGA

GACAAAAAGGTCATCCAGTTCCTGTCCGAGGCCACGATCACCGACTTCCCGGAACTCG

ACTTTTTCGGCTACCTGAAAACCGAAAAGGGTTCCGGGGGACAGAAGCGCAGCGCCA

AAGTCCGACTGTCGAACGCCATCTCGCTGGAGACTTTTAAGGGCGACCTGGATTTCCT

CACTAACAAGGGACAGGCCGACAAGCTGAACGAAAACATGAACATTGCGCAGGCAGA

GATCCACAAGTCCTACTACCGCTACACCATCACCATCGACCTCGACCAGATCGGTATC

GACGGGGAGATTGCTCTGGACAACAAGGAAAAGGCCCGGAGAGTGAAGAAGCTGATG

GACACTGTGGCGTTCCTCTATCGGGACATTAGGGGCAGACGGGAGGACCTCAAGCCC

CTGTTCGTGATCGGTGGAGTGTATGACGTGAAGAACCCGGTGTTCCAAAACATTGTGG

ATGTGGCCGACAACAATATTGTGATCAAGAACATTAAGGATTTGCTGACCTACGAGGA

CATCAAGGAGAACACCAGAGTCGGCATCATTGATGGGCAGTTCGCCAACTCCGACGA

AGTGAAAGTCGAGCTGAAGGCCGAGTCCGTGCCAGCTTTCTTCAACGACATCAAGGG

AGTGAAAGTCGAGCTGAAGGCCGAGTCCGTGCCAGCTTTCTTCAACGACATCAAGGG

AAAGATTGATGCGTACTACGAGAGCAACTGA

Flag-Cas5-p300: DNA sequence, *Flag Epitope Tag*, Nuclear localization signal, L. monocytogenes Finland_1998 Cas5, p300 core effector (SEQ ID NO: 171)

ATGGACTATAAGGATGATGACGACAAGATGGCCCCCAAGAAGAAGCGCAAAGTCC

GCGGGATGAAGGCTATTAGGGTCCGGCTGTGGCAGGATCTCGTGAACTTCAAGAAGC

CTACCAGCTTCCAACTGAAGGAAACCTACCCTCTGCCGCCGTACTCTACCGTGATCGG

CATGGTGCATACACTGTGCGGCTTTACCTCCTACCACGAGATGAAGATCAGCATTCAG

GGAAAGTACTTTAGCAAGGTCAACGACCTCGCGACTAGATACGAATTCAAGAATGGCT

CAAAATACGACGTGGAACGCCACCAGATCAAAGTGGACAAATACGGAGTGTCGAGAG

GCGTCAGCACCGTGGAGCTCCTTGTGGACCTCGAACTGCTGCTGCACATCATTCCGGA

AGATCCATCCTTGGTGCCGATCATTGAAAAGGCATTCCGGGAACCCATCGAGTTCCCT

TCCCTGGGACGCAGAGAGGACATCGCCACGATTCAGAAGGTCGAAGTGGTGGACGTC

GAGAAGCGACAGCCCAAGAAGTCCACCGAGATCTCCGACGGTTATAACGCCTACGTG

CCGATCAGCTTGACCGAGAACAACTCGGTGCATTTCAAGTCCCACGAGTCCTCAGTGG

GACGGGATAAGCTGCTGGGGACTCGGTACCTTCTGACTGAGAAATACGAGCGCGTGA

-continued

*ACCACGGAACCGAAAAGGCCCCTAAGTTCTTCCGGAAGTGGCGGAAGAAGGACGTCA*

*TCTACTCCTCGCGCATCTTCGTGTCCAAGAAGGATGTGTTCTTTTTCGACGAGGACGA*

*TTACCTGGTGTTCATCGAAGAAGAAGAGCGGGGC*AAGCGACCTGCCGCCACAAAG

AAGGCTGGACAGGCTAAGAAGAAGAAAGGATCCATTTTCAAACCAGAAGAACT

ACGACAGGCACTGATGCCAACTTTGGAGGCACTTTACCGTCAGGATCCAGAAT

CCCTTCCCTTTCGTCAACCTGTGGACCCTCAGCTTTTAGGAATCCCTGATTACT

TTGATATTGTGAAGAGCCCCATGGATCTTTCTACCATTAAGAGGAAGTTAGACA

CTGGACAGTATCAGGAGCCCTGGCAGTATGTCGATGATATTTGGCTTATGTTCA

ATAATGCCTGGTTATATAACCGGAAAACATCACGGGTATACAAATACTGCTCCA

AGCTCTCTGAGGTCTTTGAACAAGAAATTGACCCAGTGATGCAAAGCCTTGGAT

ACTGTTGTGGCAGAAAGTTGGAGTTCTCTCCACAGACACTGTGTTGCTACGGC

AAACAGTTGTGCACAATACCTCGTGATGCCACTTATTACAGTTACCAGAACAGG

TATCATTTCTGTGAGAAGTGTTTCAATGAGATCCAAGGGGAGAGCGTTTCTTTG

GGGGATGACCCTTCCCAGCCTCAAACTACAATAAATAAAGAACAATTTTCCAAG

AGAAAAAATGACACACTGGATCCTGAACTGTTTGTTGAATGTACAGAGTGCGG

AAGAAAGATGCATCAGATCTGTGTCCTTCACCATGAGATCATCTGGCCTGCTGG

ATTCGTCTGTGATGGCTGTTTAAAGAAAAGTGCACGAACTAGGAAAGAAAATA

AGTTTTCTGCTAAAAGGTTGCCATCTACCAGACTTGGCACCTTTCTAGAGAATC

GTGTGAATGACTTTCTGAGGCGACAGAATCACCCTGAGTCAGGAGAGGTCACT

GTTAGAGTAGTTCATGCTTCTGACAAAACCGTGGAAGTAAAACCAGGCATGAA

AGCAAGGTTTGTGGACAGTGGAGAGATGGCAGAATCCTTTCCATACCGAACCA

AAGCCCTCTTTGCCTTTGAAGAAATTGATGGTGTTGACCTGTGCTTCTTTGGCA

TGCATGTTCAAGAGTATGGCTCTGACTGCCCTCCACCCAACCAGAGGAGAGTA

TACATATCTTACCTCGATAGTGTTCATTTCTTCCGTCCTAAATGCTTGAGGACT

GCAGTCTATCATGAAATCCTAATTGGATATTTAGAATATGTCAAGAAATTAGGT

TACACAACAGGGCATATTTGGGCATGTCCACCAAGTGAGGGAGATGATTATAT

CTTCCATTGCCATCCTCCTGACCAGAAGATACCCAAGCCCAAGCGACTGCAGG

AATGGTACAAAAAAATGCTTGACAAGGCTGTATCAGAGCGTATTGTCCATGACT

ACAAGGATATTTTTAAACAAGCTACTGAAGATAGATTAACAAGTGCAAAGGAAT

TGCCTTATTTCGAGGGTGATTTCTGGCCCAATGTTCTGGAAGAAAGCATTAAGG

AACTGGAACAGGAGGAAGAAGAGAGAAAACGAGAGGAAAACACCAGCAATGA

AAGCACAGATGTGACCAAGGGAGACAGCAAAAATGCTAAAAAGAAGAATAATA

AGAAAACCAGCAAAAATAAGAGCAGCCTGAGTAGGGGCAACAAGAAGAAACCC

GGGATGCCCAATGTATCTAACGACCTCTCACAGAAACTATATGCCACCATGGA

GAAGCATAAAGAGGTCTTCTTTGTGATCCGCCTCATTGCTGGCCCTGCTGCCAA

CTCCCTGCCTCCCATTGTTGATCCTGATCCTCTCATCCCCTGCGATCTGATGGA

-continued

TGGTCGGGATGCGTTTCTCACGCTGGCAAGGGACAAGCACCTGGAGTTCTCTT

CACTCCGAAGAGCCCAGTGGTCCACCATGTGCATGCTGGTGGAGCTGCACACG

CAGAGCCAGGACGGGATCCGATTACAAAGACGATGACGATAAGTGA

Flag-Cas7-p300: DNA sequence, *Flag Epitope Tag*, Nuclear localization signal, *L. monocytogenes Finland 1998 Cas7*, p300 core effector (SEQ ID NO: 172)

ATG*GACTACAAGGACGATGATGACAAG*ATGGCCCCCAAGAAGAAACGGAAAGTCC

GCGGC*ATGAAGAACAAGGGACTGGCAATGACTATCATTTTCCAAGCCGAAAGCGCCA*

*ATTACGGCGAATCCCTGGGGAACATTTCAAGCCTGAAGAAGATCTCTAGCAACAACGG*

*AGATCAGTACACCTACATCTCCCGCCAAGCGATCCGGTACAATCTTATGGATCAGATC*

*GGAGAAAAGGAAGCCCCTGTGAAGGCTGAAGGCGGCGGAGACAAAAAGGTCATCCAG*

*TTCCTGTCCGAGGCCACGATCACCGACTTCCCGGAACTCGACTTTTTCGGCTACCTGA*

*AAACCGAAAAGGGGTTCCGGGGGACAGAAGCGCAGCGCCAAAGTCCGACTGTCGAACG*

*CCATCTCGCTGGAGACTTTTAAGGGCGACCTGGATTTCCTCACTAACAAGGGACAGGC*

*CGACAAGCTGAACGAAAACATGAACATTGCGCAGGCAGAGATCCACAAGTCCTACTAC*

*CGCTACACCATCACCATCGACCTCGACCAGATCGGTATCGACGGGGAGATTGCTCTGG*

*ACAACAAGGAAAAGGCCCGGAGAGTGAAGAAGCTGATGGACACTGTGGCGTTCCTCT*

*ATCGGGACATTAGGGGCAGACGGGAGGACCTCAAGCCCCTGTTCGTGATCGGTGGAG*

*TGTATGACGTGAAGAACCCGGTGTTCCAAAACATTGTGGATGTGGCCGACAACAATAT*

*TGTGATCAAGAACATTAAGGATTTGCTGACCTACGAGGACATCAAGGAGAACACCAGA*

*GTCGGCATCATTGATGGGCAGTTCGCCAACTCCGACGAAGTGAAAGTCGAGCTGAAG*

*GCCGAGTCCGTGCCAGCTTTCTTCAACGACATCAAGGGAAAGATTGATGCGTACTACG*

*AGAGCAACC*GGGGCAAGCGACCTGCCGCCACAAAGAAGGCTGGACAGGCTAAG

AAGAAGAAA*GGATCCATTTTCAAACCAGAAGAACTACGACAGGCACTGATGCC*

AACTTTGGAGGCACTTTACCGTCAGGATCCAGAATCCCTTCCCTTTCGTCAACC

TGTGGACCCTCAGCTTTTAGGAATCCCTGATTACTTTGATATTGTGAAGAGCCC

CATGGATCTTTCTACCATTAAGAGGAAGTTAGACACTGGACAGTATCAGGAGC

CCTGGCAGTATGTCGATGATATTTGGCTTATGTTCAATAATGCCTGGTTATATA

ACCGGAAAACATCACGGGTATACAAATACTGCTCCAAGCTCTCTGAGGTCTTTG

AACAAGAAATTGACCCAGTGATGCAAAGCCTTGGATACTGTTGTGGCAGAAAG

TTGGAGTTCTCTCCACAGACACTGTGTTGCTACGGCAAACAGTTGTGCACAATA

CCTCGTGATGCCACTTATTACAGTTACCAGAACAGGTATCATTTCTGTGAGAAG

TGTTTCAATGAGATCCAAGGGGAGAGCGTTTCTTTGGGGGATGACCCTTCCCA

GCCTCAAACTACAATAAATAAAGAACAATTTTCCAAGAGAAAAAATGACACACT

GGATCCTGAACTGTTTGTTGAATGTACAGAGTGCGGAAGAAAGATGCATCAGA

TCTGTGTCCTTCACCATGAGATCATCTGGCCTGCTGGATTCGTCTGTGATGGCT

GTTTAAAGAAAAGTGCACGAACTAGGAAAGAAAATAAGTTTTCTGCTAAAAGGT

-continued

TGCCATCTACCAGACTTGGCACCTTTCTAGAGAATCGTGTGAATGACTTTCTGA

GGCGACAGAATCACCCTGAGTCAGGAGAGGTCACTGTTAGAGTAGTTCATGCT

TCTGACAAAACCGTGGAAGTAAAACCAGGCATGAAAGCAAGGTTTGTGGACAG

TGGAGAGATGGCAGAATCCTTTCCATACCGAACCAAAGCCCTCTTTGCCTTTGA

AGAAATTGATGGTGTTGACCTGTGCTTCTTTGGCATGCATGTTCAAGAGTATGG

CTCTGACTGCCCTCCACCCAACCAGAGGAGAGTATACATATCTTACCTCGATAG

TGTTCATTTCTTCCGTCCTAAATGCTTGAGGACTGCAGTCTATCATGAAATCCT

AATTGGATATTTAGAATATGTCAAGAAATTAGGTTACACAACAGGGCATATTTG

GGCATGTCCACCAAGTGAGGGAGATGATTATATCTTCCATTGCCATCCTCCTGA

CCAGAAGATACCCAAGCCCAAGCGACTGCAGGAATGGTACAAAAAAATGCTTG

ACAAGGCTGTATCAGAGCGTATTGTCCATGACTACAAGGATATTTTTAAACAAG

CTACTGAAGATAGATTAACAAGTGCAAAGGAATTGCCTTATTTCGAGGGTGATT

CTACTGAAGATAGATTAACAAGTGCAAAGGAATTGCCTTATTTCGAGGGTGATT

TCTGGCCCAATGTTCTGGAAGAAAGCATTAAGGAACTGGAACAGGAGGAAGAA

AGACAGCAAAAAATGCTAAAAAGAAGAATAATAAGAAAACCAGCAAAAATAAGA

GCAGCCTGAGTAGGGGCAACAAGAAGAAACCCGGGATGCCCAATGTATCTAAC

GACCTCTCACAGAAACTATATGCCACCATGGAGAAGCATAAAGAGGTCTTCTTT

GTGATCCGCCTCATTGCTGGCCCTGCTGCCAACTCCCTGCCTCCCATTGTTGAT

GTGATCCGCCTCATTGCTGGCCCTGCTGCCAACTCCCTGCCTCCCATTGTTGAT

CCTGATCCTCTCATCCCCTGCGATCTGATGGATGGTCGGGATGCGTTTCTCACG

CACCATGTGCATGCTGGTGGAGCTGCACACGCAGAGCCAGGACGGATCC*GATT*

ACAAAGACGATGACGATAAGTGA

Flag-Cas8b2-p300: DNA sequence, *Flag epitope Tag*, Nuclear localization signal, *L. monocytogenes Finland_1998 Cas8b2*, p300 core effector (SEQ ID NO: 173)

ATG*GATTACAAGGACGATGACGACAAAA*TGGCACCGAAGAAGAAGCGGAAGGTC

CGCGGA*ATGCAGACCGAAATCGAAGTCAGGGCAGACGACTGGCTCATCAACACCGGA*

*CTGACCGGCTTCCTGAACATTGTGGGAAAAGAGAACGTCCGGATTGACGGGCAGTCT*

*ATCTACTTCACCGCTGACCTCCTGGAAGATTTCGAAACTAAGTACTTTAACTTCTTCAT*

*CCAAGAGTACAAAGAAACTCTCTCATGGTACAAGATCGTCAGCTACAAAGAGACTATG*

*GAGCAGTTCAGAATTGATGAATTCGCGTCCTTTGACGAAGTGGCCCTGGGGAACCTGA*

*ACAAGTACATGAAGGACGTCGTGAAGTTCTATCTGAAAAAGGCCAACTATATCAAAGT*

*GTTCCCCTTGATTGACCCTAGCGCCAACGTGACCAAGTGGCTCGAAAAGCTGAACACC*

*ATTAATCTGACCAAGAAGCAGAAATGGGATGAGGTCAAGGCTGACATTATTGAGGAG*

*GTCAAACAGACCTACACCCAACTCGACCTGATTATTGACTTCTGTGCCTCCGAAAAGG*

*GACTGCAGTACCTGGGAGCCAAGAACCTGATCTATTCCGTCATTAACAAGGGCTGGAG*

*CGGAGTCTCCTTCCTGTTCAAGCAAACCAAGTTCATTGACCCGTATCTGGACTACAAG*

-continued

ACGACCTTCGTGGATCCTGTGCTGGAGTACCTGGATACCGATCTGTCCAAGGCCAAGT

ACAACTGCTTCAACTGCAACCAGCCCATCAAGAACCTCAAGCTCGACCTCTCGTTCAT

GAATGACGTGGGCTTTGACACCGCCCGCAAGACTGCGCACGTCTGGGATTTCAACAAC

GATGTGGCCACTTGTCCAATCTGCCGGCTGATCTACTCATGCGTGCCTGCCGGGTTCA

CCTACGTGTATGGAGAGGGAATGTTCGTGAACGACTCCTACGGCGTGGAAGAACTGC

ACAGAGTGAACGAACGGATGCGGAACAGCATCCTGAGGTTTAACAAGGACGGTATCA

ATTCCACCAACACTTACCGCGCGCTTGTGGAGTCCATTACCATGGAACACGAAAACAA

CAGACGCTACGAATTGGCTGACATCCAGCTCGTGCGATACGAGAACGAGCATTACCG

GTTCAATCTGTTGTCAAAGAAGATGCTTCACATCGTGAACGATTCCAAGGGTATCCTG

AAGTCGCTGATACGCTGCGGTTACAAGGAGGGGAACCTCAACGTGAACCTCTACAAG

GAAGTGATCCAGCATCTGATGAACAACGAAAACCTCTTCACCCTTATCCACAAGTTGA

TCTACTACAAGCAGACCAGCGTGAACGGCCTGTACTACAACATGGGCCACGTGTCCGG

AATCCTGGATATCAACACCAAGTTCCTGAAAGAAATGGAGGTCATGACGAACATCTCA

CAGAACCAGCTGTGGTTCGTGCAAAATTGTGGCAAAGAATTCAAGGAGGGTTACGTGA

AGAAGAAGTCCGAGAACAAGATCTCCGGAATCACTTACAAGCTGCTGAATTCGCTGAA

GGTCAACGACAAGGACGGATTCATGGACACCCTGCTGAACTCCTACTCGTACCTGTCC

ATGCCGATCCCCGACGTGTTCATCAAGATGTTCTCCAACAACGAAGCCTTCAAGAGCG

TGGGCTACGCTTTTATGCTTGGCGTGGGTGGAGAAAAGACTAAGAAGGAAGATGGGG

GCAACACTGATGAGAAGCGGGGCAAGCGACCTGCCGCCACAAAGAAGGCTGGACAGG

CTAAGAAGAAGAAAGGATCCATTTTCAAACCAGAAGAACTACGACAGGCACTGATGCC

AACTTTGGAGGCACTTTACCGTCAGGATCCAGAATCCCTTCCCTTTCGTCAACCTGTG

GACCCTCAGCTTTTAGGAATCCCTGATTACTTTGATATTGTGAAGAGCCCCATGGATCT

TTCTACCATTAAGAGGAAGTTAGACACTGGACAGTATCAGGAGCCCTGGCAGTATGTC

GATGATATTTGGCTTATGTTCAATAATGCCTGGTTATATAACCGGAAAACATCACGGG

TATACAAATACTGCTCCAAGCTCTCTGAGGTCTTTGAACAAGAAATTGACCCAGTGAT

GCAAAGCCTTGGATACTGTTGTGGCAGAAAGTTGGAGTTCTCTCCACAGACACTGTGT

TGCTACGGCAAACAGTTGTGCACAATACCTCGTGATGCCACTTATTACAGTTACCAGA

ACAGGTATCATTTCTGTGAGAAGTGTTTCAATGAGATCCAAGGGGAGAGCGTTTCTTT

GGGGGATGACCCTTCCCAGCCTCAAACTACAATAAATAAAGAACAATTTTCCAAGAGA

GGGGGATGACCCTTCCCAGCCTCAAACTACAATAAATAAAGAACAATTTTCCAAGAGA

AAAAATGACACACTGGATCCTGAACTGTTTGTTGAATGTACAGAGTGCGGAAGAAAGA

TGCATCAGATCTGTGTCCTTCACCATGAGATCATCTGGCCTGCTGGATTCGTCTGTGA

TGGCTGTTTAAAGAAAAGTGCACGAACTAGGAAAGAAAATAAGTTTTCTGCTAAAAGG

TTGCCATCTACCAGACTTGGCACCTTTCTAGAGAATCGTGTGAATGACTTTCTGAGGC

GACAGAATCACCCTGAGTCAGGAGAGGTCACTGTTAGAGTAGTTCATGCTTCTGACAA

AACCGTGGAAGTAAAACCAGGCATGAAAGCAAGGTTTGTGGACAGTGGAGAGATGGC

-continued

AGAATCCTTTCCATACCGAACCAAAGCCCTCTTTGCCTTTGAAGAAATTGATGGTGTTG

ACCTGTGCCTTCTTTGGCATGCATGTTCAAGAGTATGGCTCTGACTGCCCTCCACCCAA

CCAGAGGAGAGTATACATATCTTACCTCGATAGTGTTCATTTCTTCCGTCCTAAATGCT

TGAGGACTGCAGTCTATCATGAAATCCTAATTGGATATTTAGAATATGTCAAGAAATTA

GGTTACACAACAGGGCATATTTGGGCATGTCCACCAAGTGAGGGAGATGATTATATCT

TCCATTGCCATCCTCCTGACCAGAAGATACCCAAGCCCAAGCGACTGCAGGAATGGTA

CAAAAAAATGCTTGACAAGGCTGTATCAGAGCGTATTGTCCATGACTACAAGGATATT

TTTAAACAAGCTACTGAAGATAGATTAACAAGTGCAAAGGAATTGCCTTATTTCGAGG

GTGATTTCTGGCCCAATGTTCTGGAAGAAAGCATTAAGGAACTGGAACAGGAGGAAG

AAGAGAGAAAACGAGAGGAAAACACCAGCAATGAAAGCACAGATGTGACCAAGGGAG

ACAGCAAAAATGCTAAAAAGAAGAATAATAAGAAAACCAGCAAAAATAAGAGCAGCCT

GAGTAGGGGCAACAAGAAGAAACCCGGGATGCCCAATGTATCTAACGACCTCTCACA

GAAACTATATGCCACCATGGAGAAGCATAAAGAGGTCTTCTTTGTGATCCGCCTCATT

GCTGGCCCTGCTGCCAACTCCCTGCCTCCCATTGTTGATCCTGATCCTCTCATCCCCTG

CGATCTGATGGATGGTCGGGATGCGTTTCTCACGCTGGCAAGGGACAAGCACCTGGA

GTTCTCTTCACTCCGAAGAGCCCAGTGGTCCACCATGTGCATGCTGGTGGAGCTGCAC

ACGCAGAGCCAGGACGGATCCGATTACAAAGACGATGACGATAAGTGA

Flag-Cas6-p300: DNA sequence, Flag Epitope Tag, Nuclear localization signal, L. monocytogenes Finland_1998 Cas6, p300 core effector (SEQ ID NO: 174)

ATGGACTACAAGGACGACGACGATAAGATGGCGCCAAAGAAAAAGCGCAAGGTC

CGCGGAATGCGGCTGAAGATTAACTGCGACTTCGACAGCAAGATCATCCCCAAGGAC

TTCCAGTCCAAGGTCGTGTCCCTGTTCAAAGCCGGAATTATGAAAAGCTCCCCGGAGA

GATACGAGAACCTGTTTGGTGGAAACAAGCACAAGCAGTACACTTTCTCGGTGTATCT

CCCAAAACCTCAGAACAAGGGCGCCGAAATTCAGCTGAACGAGGCGAACTGTATCATC

AACTTCTCCACCGGCGATGCTGAAACCGGTATTATCTTCTACAACGCCCTGATTAGCC

TGAGAGGCTCCAAGGTCCTGTTTGGGGCCGGAAATCACATCACCGTGAAGAACATCCA

GATCGTGCCTGAGAAGAAGATCATCGGGAAGCAAACCATTCTGCGGACCCTTTCGCCG

GTGGTGTCGAGGGATCACAACCGGGAAACCTTCAAGAATTGGTTCTACTCATTCGAGG

ACGAAGAATTCGAGCCTACTTTGAAGCGGAACATGCTGCCGTACCTCATCGACGCCTT

TGGAGAACAGGCTCGCTACGATCTGGAAAAGCTGAAGATCACGCCCATTTCCATGAAG

AAAGTCGTGGTGTACTGCCATGAGATCCACATCGAGAGCTCCGTGGGCATCTTCGAGC

TGGAAGCCGAGGCATACCTCCAAAAGTACCTCGTGGAAAACGGAATCGGCACTATGA

CTGGCTCAGGGTTCGGAATGATTGAACAGTTCCGGGGCAAGCGACCTGCCGCCAC

AAAGAAGGCTGGACAGGCTAAGAAGAAGAAAGGATCCATTTTCAAACCAGAAG

AACTACGACAGGCACTGATGCCAACTTTGGAGGCACTTTACCGTCAGGATCCA

GAATCCCTTCCCTTTCGTCAACCTGTGGACCCTCAGCTTTTAGGAATCCCTGAT

-continued

TACTTTGATATTGTGAAGAGCCCCATGGATCTTTCTACCATTAAGAGGAAGTTA

GACACTGGACAGTATCAGGAGCCCTGGCAGTATGTCGATGATATTTGGCTTAT

GTTCAATAATGCCTGGTTATATAACCGGAAAACATCACGGGTATACAAATACTG

CTCCAAGCTCTCTGAGGTCTTTGAACAAGAAATTGACCCAGTGATGCAAAGCCT

TGGATACTGTTGTGGCAGAAAGTTGGAGTTCTCTCCACAGACACTGTGTTGCTA

CGGCAAACAGTTGTGCACAATACCTCGTGATGCCACTTATTACAGTTACCAGAA

CAGGTATCATTTCTGTGAGAAGTGTTTCAATGAGATCCAAGGGGAGAGCGTTT

CTTTGGGGGATGACCCTTCCCAGCCTCAAACTACAATAAATAAAGAACAATTTT

CCAAGAGAAAAAATGACACACTGGATCCTGAACTGTTTGTTGAATGTACAGAGT

GCGGAAGAAAGATGCATCAGATCTGTGTCCTTCACCATGAGATCATCTGGCCT

GCTGGATTCGTCTGTGATGGCTGTTTAAAGAAAAGTGCACGAACTAGGAAAGA

AAATAAGTTTTCTGCTAAAAGGTTGCCATCTACCAGACTTGGCACCTTTCTAGA

GAATCGTGTGAATGACTTTCTGAGGCGACAGAATCACCCTGAGTCAGGAGAGG

TCACTGTTAGAGTAGTTCATGCTTCTGACAAAACCGTGGAAGTAAAACCAGGCA

TGAAAGCAAGGTTTGTGGACAGTGGAGAGATGGCAGAATCCTTTCCATACCGA

ACCAAAGCCCTCTTTGCCTTTGAAGAAATTGATGGTGTTGACCTGTGCTTCTTT

GGCATGCATGTTCAAGAGTATGGCTCTGACTGCCCTCCACCCAACCAGAGGAG

AGTATACATATCTTACCTCGATAGTGTTCATTTCTTCCGTCCTAAATGCTTGAG

GACTGCAGTCTATCATGAAATCCTAATTGGATATTTAGAAATATGTCAAGAAATT

AGGTTACACAACAGGGCATATTTGGGCATGTCCACCAAGTGAGGGAGATGATT

ATATCTTCCATTGCCATCCTCCTGACCAGAAGATACCCAAGCCCAAGCGACTGC

AGGAATGGTACAAAAAAATGCTTGACAAGGCTGTATCAGAGCGTATTGTCCAT

GACTACAAGGATATTTTTAAACAAGCTACTGAAGATAGATTAACAAGTGCAAAG

GAATTGCCTTATTTCGAGGGTGATTTCTGGCCCAATGTTCTGGAAGAAAGCATT

AAGGAACTGGAACAGGAGGAAGAAGAGAGAAAACGAGAGGAAAACACCAGCA

ATGAAAGCACAGATGTGACCAAGGGAGACAGCAAAAATGCTAAAAAGAAGAAT

AATAAGAAAACCAGCAAAAATAAGAGCAGCCTGAGTAGGGGCAACAAGAAGAA

ACCCGGGATGCCCAATGTATCTAACGACCTCTCACAGAAACTATATGCCACCAT

GGAGAAGCATAAAGAGGTCTTCTTTGTGATCCGCCTCATTGCTGGCCCTGCTG

CCAACTCCCTGCCTCCCATTGTTGATCCTGATCCTCTCATCCCCTGCGATCTGA

TGGATGGTCGGGATGCGTTTCTCACGCTGGCAAGGGACAAGCACCTGGAGTTC

TCTTCACTCCGAAGAGCCCAGTGGTCCACCATGTGCATGCTGGTGGAGCTGCA

CACGCAGAGCCAGGACGGATCC*GATTACAAAGACGATGACGATAAG*TGA

Cas5 amino acid sequence (SEQ ID NO: 175)

MKAIRVRLWQDLVNFKKPTSFQLKETYPLPPYSTVIGMVHTLCGFTSYHEMKISIQGY

FSKVNDLATRYEFKNGSKYDVERHQIKVDKYGVSRGVSTVELLVDLELLLHIIPEDPSLV

-continued

PIIEKAFREPIEFPSLGRREDIATIQKVEVVDVEKRQPKKSTEISDGYNAYVPISLTENNSV

HFKSHESSVGRDKLLGTRYLLTEKYERVNHGTEKAPKFFRKWRKKDVIYSSRIFVSKKD

VFFFDEDDYLVFIEEEE

Cas6 amino acid sequence (SEQ ID NO: 176)

MRLKINCDFDSKIIPKDFQSKVVSLFKAGIMKSSPERYENLFGGNKHKQYTFSVYLPKPQ

NKGAEIQLNEANCIINFSTGDAETGIIFYNALISLRGSKVLFGAGNHITVKNIQIVPEKKIIG

KQTILRTLSPVVSRDHNRETFKNVVFYSFEDEEFEPTLKRNMLPYLIDAFGEQARYDLEKL

KITPISMKKVVVYCHEIHIES SVGIFELEAEAYLQKYLVENGIGTMTGSGFGMIEQF

Cas7 amino acid sequence (SEQ ID NO: 177)

MKNKGLAMTIIFQAESANYGESLGNISSLKKISRNNGDQYTYISRQAIRYNLMDQIGEKE

APVKAEGGGDKKVIQFLSEATITDEPELDFFGYLKTEKGSGGQKRSAKVRLSNAISLETF

KGDLDFLTNKGQADKLNENMNIAQAEIHKSYYRYTITIDLDQIGIDGEIALDNKEKARRV

KKLMDTVAFLYRDIRGRREDLKPLEVIGGVYDVKNPVFQNIVDVADNNIVIKNIKDLLT

YEDIKENTRVGIIDGQFANSDEVKVELKAESVPAFFNDIKGKIDAYYESN

Cas8b2 amino acid sequence (SEQ ID NO: 178)

MQTEIEVRADDWLINTGLTGELNIVGKENVRIDGQSIYFTADLLEDFETKYFNEFIQEYKE

TLSWYKIVSYKETMEQFRIDEFASEDEVALGNLNKYMKDVVKFYLKKANYIKVFPLIDP

SANVTKWLEKLNTINLTKKQKWDEVKADIIEEVKQTYTQLDLIIDFCASEKGLQYLGAK

NLIYSVINKGWSGVSFLEKQTKFIDPYLDYKTTFVDPVLEYLDTDLSKAKYNCFNCNQPI

KNLKLDLSFMNDVGFDTARKTAHVWDENNDVATCPICRLIYSCVPAGETYVYGEGMFV

NDSYGVEELEIRVNERMRNSILRENKDGINSTNTYRALVESITMEHENNRRYELADIQLV

RYENEHYRFNLLSKKMLIIIVNDSKGILKSLIRCGYKEGNLNVNLYKEVIQHLMNNENLF

TLIHKLIYYKQTSVNGLYYNMGHVSGILDINTKELKEMEVIVITNISQNQLWFVQNCGKEF

KEGYVKKKSENKISGITYKLLNSLKVNDKDGEMDTLLNSYSYLSMPIPDVFIKMESNNE

AFKSVGYAFMLGVGGEKTKKEDGGNTDEK p300 core effector polynucleotide sequence (SEQ ID NO: 179)

ATTTTCAAACCAGAAGAACTACGACAGGCACTGATGCCAACTTTGGAGGCACTTTAC

CGTCAGGATCCAGAATCCCTTCCCTTTCGTCAACCTGTGGACCCTCAGCTTTTAGGA

ATCCCTGATTACTTTGATATTGTGAAGAGCCCCATGGATCTTTCTACCATTAAGAGG

AAGTTAGACACTGGACAGTATCAGGAGCCCTGGCAGTATGTCGATGATATTTGGCTT

ATGTTCAATAATGCCTGGTTATATAACCGGAAAACATCACGGGTATACAAATACTGC

TCCAAGCTCTCTGAGGTCTTTGAACAAGAAATTGACCCAGTGATGCAAAGCCTTGGA

TACTGTTGTGGCAGAAAGTTGGAGTTCTCTCCACAGACACTGTGTTGCTACGGCAAA

CAGTTGTGCACAATACCTCGTGATGCCACTTATTACAGTTACCAGAACAGGTATCAT

TTCTGTGAGAAGTGTTTCAATGAGATCCAAGGGGAGAGCGTTTCTTTGGGGGATGAC

CCTTCCCAGCCTCAAACTACAATAAATAAAGAACAATTTTCCAAGAGAAAAAATGA

CACACTGGATCCTGAACTGTTTGTTGAATGTACAGAGTGCGGAAGAAAGATGCATC

AGATCTGTGTCCTTCACCATGAGATCATCTGGCCTGCTGGATTCGTCTGTGATGGCTG

TTTAAAGAAAAGTGCACGAACTAGGAAAGAAAATAAGTTTTCTGCTAAAAGGTTGC

CATCTACCAGACTTGGCACCTTTCTAGAGAATCGTGTGAATGACTTTCTGAGGCGAC

AGAATCACCCTGAGTCAGGAGAGGTCACTGTTAGAGTAGTTCATGCTTCTGACAAAA

CCGTGGAAGTAAAACCAGGCATGAAAGCAAGGTTTGTGGACAGTGGAGAGATGGCA

GAATCCTTTCCATACCGAACCAAAGCCCTCTTTGCCTTTGAAGAAATTGATGGTGTT

-continued

GACCTGTGCTTCTTTGGCATGCATGTTCAAGAGTATGGCTCTGACTGCCCTCCACCCA

ACCAGAGGAGAGTATACATATCTTACCTCGATAGTGTTCATTTCTTCCGTCCTAAAT

GCTTGAGGACTGCAGTCTATCATGAAATCCTAATTGGATATTTAGAATATGTCAAGA

AATTAGGTTACACAACAGGGCATATTTGGGCATGTCCACCAAGTGAGGGAGATGAT

TATATCTTCCATTGCCATCCTCCTGACCAGAAGATACCCAAGCCCAAGCGACTGCAG

GAATGGTACAAAAAAATGCTTGACAAGGCTGTATCAGAGCGTATTGTCCATGACTA

CAAGGATATTTTTAAACAAGCTACTGAAGATAGATTAACAAGTGCAAAGGAATTGC

CTTATTTCGAGGGTGATTTCTGGCCCAATGTTCTGGAAGAAAGCATTAAGGAACTGG

AACAGGAGGAAGAAGAGAGAAAACGAGAGGAAAACACCAGCAATGAAAGCACAG

ATGTGACCAAGGGAGACAGCAAAAATGCTAAAAAGAAGAATAATAAGAAAACCAG

CAAAAATAAGAGCAGCCTGAGTAGGGGCAACAAGAAGAAACCCGGGATGCCCAAT

GTATCTAACGACCTCTCACAGAAACTATATGCCACCATGGAGAAGCATAAAGAGGT

CTTCTTTGTGATCCGCCTCATTGCTGGCCCTGCTGCCAACTCCCTGCCTCCCATTGTT

GATCCTGATCCTCTCATCCCCTGCGATCTGATGGATGGTCGGGATGCGTTTCTCACGC

TGGCAAGGGACAAGCACCTGGAGTTCTCTTCACTCCGAAGAGCCCAGTGGTCCACC

ATGTGCATGCTGGTGGAGCTGCACACGCAGAGCCAGGAC p300 core effector amino acid sequence (SEQ ID NO: 180)

IFKPEELRQALMPTLEALYRQDPESLPFRQPVDPQLLGIPDYFDIVKSPMDLSTIKRKLDT

GQYQEPWQYVDDIWLMFNNAWLYNRKTSRVYKYCSKLSEVFEQEIDPVIVIQSLGYCCG

RKLEFSPQTLCCYGKQLCTIPRDATYYSYQNRYHFCEKCFNEIQGESVSLGDDPSQPQTT

INKEQFSKRKNDTLDPELFVECTECGRKMEIQICVLHHEIIWPAGFVCDGCLKKSARTRK

ENKFSAKRLPSTRLGTFLENRVNDFLRRQNHPESGEVTVRVVHASDKTVEVKPGMKAR

FVDSGEMAESFPYRTKALFAFEEIDGVDLCFFGMHVQEYGSDCPPPNQRRVYISYLDSV

EIFFRPKCLRTAVYHEILIGYLEYVKKLGYTTGHIWACPPSEGDDYIFHCHPPDQKIPKPK

RLQEWYKKMLDKAVSERIVHDYKDIFKQATEDRLTSAKELPYFEGDFWPNVLEESIKEL

EQEEEERKREENTSNESTDVTKGDSKNAKKKNNKKTSKNKSSLSRGNKKKPGMPNVSN

DLSQKLYATMEKHKEVFFVIRLIAGPAANSLPPIVDPDPLIPCDLMDGRDAFLTLARDKH

LEFSSLRRAQWSTMCMLVELHTQSQD

Cas5 polynucleotide sequence (SEQ ID NO: 258)

ATGAAGGCTATTAGGGTCCGGCTGTGGCAGGATCTCGTGAACTTCAAGAAGCCTACC

AGCTTCCAACTGAAGGAAACCTACCCTCTGCCGCCGTACTCTACCGTGATCGGCATG

GTGCATACACTGTGCGGCTTTACCTCCTACCACGAGATGAAGATCAGCATTCAGGGA

AAGTACTTTAGCAAGGTCAACGACCTCGCGACTAGATACGAATTCAAGAATGGCTC

AAAATACGACGTGGAACGCCACCAGATCAAAGTGGACAAATACGGAGTGTCGAGA

GGCGTCAGCACCGTGGAGCTCCTTGTGGACCTCGAACTGCTGCTGCACATCATTCCG

GAAGATCCATCCTTGGTGCCGATCATTGAAAAGGCATTCCGGGAACCCATCGAGTTC

CCTTCCCTGGGACGCAGAGAGGACATCGCCACGATTCAGAAGGTCGAAGTGGTGGA

CGTCGAGAAGCGACAGCCCAAGAAGTCCACCGAGATCTCCGACGGTTATAACGCCT

ACGTGCCGATCAGCTTGACCGAGAACAACTCGGTGCATTTCAAGTCCCACGAGTCCT

CAGTGGGACGGGATAAGCTGCTGGGGACTCGGTACCTTCTGACTGAGAAATACGAG

CGCGTGAACCACGGAACCGAAAAGGCCCCTAAGTTCTTCCGGAAGTGGCGGAAGAA

-continued

GGACGTCATCTACTCCTCGCGCATCTTCGTGTCCAAGAAGGATGTGTTCTTTTTCGAC

GAGGACGATTACCTGGTGTTCATCGAAGAAGAAGAGTGA

Cas6 polynucleotide sequence (SEQ ID NO: 259)

ATGCGGCTGAAGATTAACTGCGACTTCGACAGCAAGATCATCCCCAAGGACTTCCA

GTCCAAGGTCGTGTCCCTGTTCAAAGCCGGAATTATGAAAAGCTCCCCGGAGAGAT

ACGAGAACCTGTTTGGTGGAAACAAGCACAAGCAGTACACTTTCTCGGTGTATCTCC

CAAAACCTCAGAACAAGGGCGCCGAAATTCAGCTGAACGAGGCGAACTGTATCATC

AACTTCTCCACCGGCGATGCTGAAACCGGTATTATCTTCTACAACGCCCTGATTAGC

CTGAGAGGCTCCAAGGTCCTGTTTGGGGCCGGAAATCACATCACCGTGAAGAACAT

CCAGATCGTGCCTGAGAAGAAGATCATCGGGAAGCAAACCATTCTGCGGACCCTTT

CGCCGGTGGTGTCGAGGGATCACAACCGGGAAACCTTCAAGAATTGGTTCTACTCAT

TCGAGGACGAAGAATTCGAGCCTACTTTGAAGCGGAACATGCTGCCGTACCTCATCG

ACGCCTTTGGAGAACAGGCTCGCTACGATCTGGAAAAGCTGAAGATCACGCCCATTT

CCATGAAGAAAGTCGTGGTGTACTGCCATGAGATCCACATCGAGAGCTCCGTGGGC

ATCTTCGAGCTGGAAGCCGAGGCATACCTCCAAAAGTACCTCGTGGAAAACGGAAT

CGGCACTATGACTGGCTCAGGGTTCGGAATGATTGAACAGTTCTGA

Cas7 polynucleotide sequence (SEQ ID NO: 260)

ATGAAGAACAAGGGACTGGCAATGACTATCATTTTCCAAGCCGAAAGCGCCAATTA

CGGCGAATCCCTGGGGAACATTTCAAGCCTGAAGAAGATCTCTAGGAACAACGGAG

ATCAGTACACCTACATCTCCCGCCAAGCGATCCGGTACAATCTTATGGATCAGATCG

GAGAAAAGGAAGCCCCTGTGAAGGCTGAAGGCGGCGGAGACAAAAAGGTCATCCA

GTTCCTGTCCGAGGCCACGATCACCGACTTCCCGGAACTCGACTTTTTCGGCTACCT

GAAAACCGAAAAGGGTTCCGGGGGACAGAAGCGCAGCGCCAAAGTCCGACTGTCG

AACGCCATCTCGCTGGAGACTTTTAAGGGCGACCTGGATTTCCTCACTAACAAGGGA

CAGGCCGACAAGCTGAACGAAAACATGAACATTGCGCAGGCAGAGATCCACAAGTC

CTACTACCGCTACACCATCACCATCGACCTCGACCAGATCGGTATCGACGGGGAGAT

TGCTCTGGACAACAAGGAAAAGGCCCGGAGAGTGAAGAAGCTGATGGACACTGTGG

CGTTCCTCTATCGGGACATTAGGGGCAGACGGGAGGACCTCAAGCCCCTGTTCGTGA

TCGGTGGAGTGTATGACGTGAAGAACCCGGTGTTCCAAAACATTGTGGATGTGGCC

GACAACAATATTGTGATCAAGAACATTAAGGATTTGCTGACCTACGAGGACATCAA

GGAGAACACCAGAGTCGGCATCATTGATGGGCAGTTCGCCAACTCCGACGAAGTGA

AAGTCGAGCTGAAGGCCGAGTCCGTGCCAGCTTTCTTCAACGACATCAAGGGAAAG

ATTGATGCGTACTACGAGAGCAACTGA

Cas8b2 polynucleotide sequence (SEQ ID NO: 261)

ATGCAGACCGAAATCGAAGTCAGGGCAGACGACTGGCTCATCAACACCGGACTGAC

CGGCTTCCTGAACATTGTGGGAAAAGAGAACGTCCGGATTGACGGGCAGTCTATCT

ACTTCACCGCTGACCTCCTGGAAGATTTCGAAACTAAGTACTTTAACTTCTTCATCCA

AGAGTACAAAGAAACTCTCTCATGGTACAAGATCGTCAGCTACAAAGAGACTATGG

AGCAGTTCAGAATTGATGAATTCGCGTCCTTTGACGAAGTGGCCCTGGGGAACCTGA

ACAAGTACATGAAGGACGTCGTGAAGTTCTATCTGAAAAAGGCCAACTATATCAAA

GTGTTCCCCTTGATTGACCCTAGCGCCAACGTGACCAAGTGGCTCGAAAAGCTGAAC

ACCATTAATCTGACCAAGAAGCAGAAATGGGATGAGGTCAAGGCTGACATTATTGA

-continued

GGAGGTCAAACAGACCTACACCCAACTCGACCTGATTATTGACTTCTGTGCCTCCGA

AAAGGGACTGCAGTACCTGGGAGCCAAGAACCTGATCTATTCCGTCATTAACAAGG

GCTGGAGCGGAGTCTCCTTCCTGTTCAAGCAAACCAAGTTCATTGACCCGTATCTGG

ACTACAAGACGACCTTCGTGGATCCTGTGCTGGAGTACCTGGATACCGATCTGTCCA

AGGCCAAGTACAACTGCTTCAACTGCAACCAGCCCATCAAGAACCTCAAGCTCGAC

CTCTCGTTCATGAATGACGTGGGCTTTGACACCGCCCGCAAGACTGCGCACGTCTGG

GATTTCAACAACGATGTGGCCACTTGTCCAATCTGCCGGCTGATCTACTCATGCGTG

CCTGCCGGGTTCACCTACGTGTATGGAGAGGGAATGTTCGTGAACGACTCCTACGGC

GTGGAAGAACTGCACAGAGTGAACGAACGGATGCGGAACAGCATCCTGAGGTTTAA

CAAGGACGGTATCAATTCCACCAACACTTACCGCGCGCTTGTGGAGTCCATTACCAT

GGAACACGAAAACAACAGACGCTACGAATTGGCTGACATCCAGCTCGTGCGATACG

AGAACGAGCATTACCGGTTCAATCTGTTGTCAAAGAAGATGCTTCACATCGTGAACG

ATTCCAAGGGTATCCTGAAGTCGCTGATACGCTGCGGTTACAAGGAGGGGAACCTC

AACGTGAACCTCTACAAGGAAGTGATCCAGCATCTGATGAACAACGAAAACCTCTT

CACCCTTATCCACAAGTTGATCTACTACAAGCAGACCAGCGTGAACGGCCTGTACTA

CAACATGGGCCACGTGTCCGGAATCCTGGATATCAACACCAAGTTCCTGAAAGAAA

TGGAGGTCATGACGAACATCTCACAGAACCAGCTGTGGTTCGTGCAAAATTGTGGC

AAAGAATTCAAGGAGGGTTACGTGAAGAAGAAGTCCGAGAACAAGATCTCCGGAAT

CACTTACAAGCTGCTGAATTCGCTGAAGGTCAACGACAAGGACGGATTCATGGACA

CCCTGCTGAACTCCTACTCGTACCTGTCCATGCCGATCCCCGACGTGTTCATCAAGA

TGTTCTCCAACAACGAAGCCTTCAAGAGCGTGGGCTACGCTTTTATGCTTGGCGTGG

GTGGAGAAAAGACTAAGAAGGAAGATGGGGGCAACACCGATGAGAAGTGA

Full lentiviral example (Cas8b2):

LTR, HIV-1 Ψ, RPE, cPPT, hUbC promoter, AgeI restriction enzyme site, EcoRI restriction enzyme site, WPRE, Flag Epitope tag, Nuclear localization signal, *L. monocytogenes* Finland 1998 Cas8b2

(SEQ ID NO: 282)

GGGTCTCTCTGGTTAGACCAGATCTGAGCCTGGGAGCTCTCTGGCTAACTAGG

GAACCCACTGCTTAAGCCTCAATAAAGCTTGCCTTGAGTGCTTCAAGTAGTGTG

TGCCCGTCTGTTGTGTGACTCTGGTAACTAGAGATCCCTCAGACCCTTTTAGTC

AGTGTGGAAAATCTCTAGCAGTGGCGCCCGAACAGGGACTTGAAAGCGAAAGG

GAAACCAGAGGAGCTCTCTCGACGCAGGACTCGGCTTGCTGAAGCGCGCACGG

CAAGAGGCGAGGGGCGGCGACTGGTGAGTACGCCAAAAATTTTGACTAGCGGA

GGCTAGAAGGAGAGAGATGGGTGCGAGAGCGTCAGTATTAAGCGGGGGAGAA

TTAGATCGCGATGGGAAAAAATTCGGTTAAGGCCAGGGGGAAAGAAAAAATAT

AAATTAAAACATATAGTATGGGCAAGCAGGGAGCTAGAACGATTCGCAGTTAA

TCCTGGCCTGTTAGAAACATCAGAAGGCTGTAGACAAATACTGGGACAGCTAC

AACCATCCCTTCAGACAGGATCAGAAGAACTTAGATCATTATATAATACAGTAG

CAACCCTCTATTGTGTGCATCAAAGGATAGAGATAAAAGACACCAAGGAAGCT

TTAGACAAGATAGAGGAAGAGCAAAACAAAAGTAAGACCACCGCACAGCAAGC

GGCCGCTGATCTTCAGACCTGGAGGAGGAGATATGAGGGACAATTGGAGAAGT

GAATTATATAAATATAAAGTAGTAAAAATTGAACCATTAGGAGTAGCACCCACC

-continued

AAGGCAAAGAGAAGAGTGGTGCAGAGAGAAAAAAGAGCAGTGGGAATAGGAG

CTTTGTTCCTTGGGTTCTTGGGAGCAGCAGGAAGCACTATGGGCGCAGCGTCA

ATGACGCTGACGGTACAGGCCAGACAATTATTGTCTGGTATAGTGCAGCAGCA

GAACAATTTGCTGAGGGCTATTGAGGCGCAACAGCATCTGTTGCAACTCACAG

TCTGGGGCATCAAGCAGCTCCAGGCAAGAATCCTGGCTGTGGAAAGATACCTA

AAGGATCAACAGCTCCTGGGATTTGGGGTTGCTCTGGAAAACTCATTTGCAC

CACTGCTGTGCCTTGGAATGCTAGTTGGAGTAATAAATCTCTGGAACAGATTTG

GAATCACACGACCTGGATGGAGTGGGACAGAGAAATTAACAATTACACAAGCT

TAATACACTCCTTAATTGAAGAATCGCAAAACCAGCAAGAAAAGAATGAACAAG

AATTATTGGAATTAGATAAATGGGCAAGTTTGTGGAATTGGTTTAACATAACAA

ATTGGCTGTGGTATATAAAATTATTCATAATGATAGTAGGAGGCTTGGTAGGTT

TAAGAATAGTTTTTGCTGTACTTTCTATAGTGAATAGAGTTAGGCAGGGATATT

CACCATTATCGTTTCAGACCCACCTCCCAACCCCGAGGGGACCCGACAGGCCC

GAAGGAATAGAAGAAGAAGGTGGAGAGAGAGACAGAGACAGATCCATTCGATT

AGTGAACGGATCGGCACTGCGTGCGCCAATTCTGCAGACAAATGGCAGTATTC

ATCCACAATTTTAAAAGAAAAGGGGGGATTGGGGGGTACAGTGCAGGGGAAAG

AATAGTAGACATAATAGCAACAGACATACAAACTAAAGAATTACAAAAACAAAT

TACAAAAATTCAAAATTTTCGGGTTTATTACAGGGACAGCAGAGATCCAGTTTG

GTTAATTAAGGGTGCAGCCGCCTCCGCGCCGGGTTTTCGCGCCTCCCGCGGGC

GCCCCCCTCCTCACGGCGAGCGCTGCCACGTCAGACGAAGGGCGCAGGAGCG

TTCCTGATCCTTCCGCCCGGACGCTCAGGACAGCGGCCCGCTGCTCATAAGAC

TCGGCCTTAGAACCCCAGTATCAGCAGAAGGACATTTTAGGACGGGACTTGGC

TGACTCTAGGGCACTGGTTTTCTTTCCAGAGAGCGGAACAGGCGAGGAAAAGT

AGTCCCTTCTCGGCGATTCTGCGGAGGGATCTCCGTGGGGCGGTGAACGCCGA

TGATTATATAAGGACGCGCCGGGTGTGGCACAGCTAGTTCCGTCGCAGCCGGG

ATTTGGGTCGCGGTTCTTGTTTGTGGATCGCTGTGATCGTCACTTGGTGAGTTG

CGGGCTGCTGGGCTGGCCGGGGCTTTCGTGGCCGCCGGGCCGCTCGGTGGGA

CGGAAGCGTGTGGAGAGACCGCCAAGGGCTGTAGTCTGGGTCCGCGAGCAAG

GTTGCCCTGAACTGGGGGTTGGGGGGAGCGCACAAAATGGCGGCTGTTCCCGA

GTCTTGAATGGAAGACGCTTGTAAGGCGGGCTGTGAGGTCGTTGAAACAAGGT

GGGGGGCATGGTGGGCGGCAAGAACCCAAGGTCTTGAGGCCTTCGCTAATGC

GGGAAAGCTCTTATTCGGGTGAGATGGGCTGGGGCACCATCTGGGGACCCTGA

CGTGAAGTTTGTCACTGACTGGAGAACTCGGGTTTGTCGTCTGGTTGCGGGGG

CGGCAGTTATGCGGTGCCGTTGGGCAGTGCACCCGTACCTTTGGGAGCGCGCG

CCTCGTCGTGTCGTGACGTCACCCGTTCTGTTGGCTTATAATGCAGGGTGGGG

CCACCTGCCGGTAGGTGTGCGGTAGGCTTTTCTCCGTCGCAGGACGCAGGGTT

CGGGCCTAGGGTAGGCTCTCCTGAATCGACAGGCGCCGGACCTCTGGTGAGGG

GAGGGATAAGTGAGGCGTCAGTTTCTTTGGTCGGTTTTATGTACCTATCTTCTT

-continued

AAGTAGCTGAAGCTCCGGTTTTGAACTATGCGCTCGGGGTTGGCGAGTGTGTT

TTGTGAAGTTTTTTAGGCACCTTTTGAAATGTAATCATTTGGGTCAATATGTAA

TTTTCAGTGTTAGACTAGTAAATTGTCCGCTAAATTCTGGCCGTTTTTGGCTTTT

TTGTTAGACGAAGCTTGGGCTGCAGGTCGACTCTAGAGGATCCCCGGGTACCG

GTCGCCACCGCCGCCACCATGGATTACAAGGACGATGACGACAAAATGGCGCC

GAAGAAGAAGCGGAAGGTCCGGGGCATGCAGACCCGAAATCGAAGTCAGGGCA

GACCGACTGGCTCATCAACACCGGACTGACCGGCTTCCTGAACATTGTGGGAAA

AGAGAACGTCCGGATTGACGGGCAGTCTATCTACTTCACCGCTGACCTCCTGG

AAGATTTCGAAACTAAGTACTTTAACTTCTTCATCCAAGAGTACAAAGAAACTC

TCTCATGGTACAAGATCGTCAGCTACAAAGAGACTATGGAGCAGTTCAGAATT

GATGAATTCGCGTCCTTTGACGAAGTGGCCCTGGGGAACCTGAACAAGTACAT

GAAGGACGTCGTGAAGTTCTATCTGAAAAAGGCCAACTATATCAAAGTGTTCCC

CTTGATTGACCCTAGCGCCAACGTGACCAAGTGGCTCGAAAAGCTGAACACCA

TTAATCTGACCAAGAAGCAGAAATGGGATGAGGTCAAGGCTGACATTATTGAG

GAGGTCAAACAGACCTACACCCAACTCGACCTGATTATTGACTTCTGTGCCTCC

GAAAAGGACTGCAGTACCTGGGAGCCAAGAACCTGATCTATTCCGTCATTAA

CAAGGGCTGGAGCGGAGTCTCCTTCCTGTTCAAGCAAACCAAGTTCATTGACC

CGTATCTGGACTACAAGACGACCTTCGTGGATCCTGTGCTGGAGTACCTGGAT

ACCGATCTGTCCAAGGCCAAGTACAACTGCTTCAACTGCAACCAGCCCATCAA

GAACCTCAAGCTCGACCTCTCGTTCATGAATGACGTGGGCTTTGACACCGCCC

GCAAGACTGCGCACGTCTGGGATTTCAACAACGATGTGGCCACTTGTCCAATC

TGCCGGCTGATCTACTCATGCGTGCCTGCCGGGTTCACCTACGTGTATGGAGA

GGGAATGTTCGTGAACGACTCCTACGGCGTGGAAGAACTGCACAGAGTGAACG

AACGGATGCGGAACAGCATCCTGAGGTTTAACAAGGACGGTATCAATTCCACC

AACACTTACCGCGCGCTTGTGGAGTCCATTACCATGGAACACGAAAACAACAG

ACGCTACGAATTGGCTGACATCCAGCTCGTGCGATACGAGAACGAGCATTACC

GGTTCAATCTGTTGTCAAAGAAGATGCTTCACATCGTGAACGATTCCAAGGGTA

TCCTGAAGTCGCTGATACGCTGCGGTTACAAGGAGGGGAACCTCAACGTGAAC

CTCTACAAGGAAGTGATCCAGCATCTGATGAACAACGAAAACCTCTTCACCCTT

ATCCACAAGTTGATCTACTACAAGCAGACCAGCGTGAACGGCCTGTACTACAA

CATGGGCCACGTGTCCGGAATCCTGGATATCAACACCAAGTTCCTGAAAGAAA

TGGAGGTCATGACGAACATCTCACAGAACCAGCTGTGGTTCGTGCAAAATTGT

GGCAAAGAATTCAAGGACGGTTACGTGAAGAACAAGTCCGAGAACAAGATCTC

CGGAATCACTTACAAGCTGCTGAATTCGCTGAAGGTCAACGACAAGGACGGAT

TCATGGACACCCTGCTGAACTCCTACTCGTACCTGTCCATGCCGATCCCCGACG

TGTTCATCAAGATGTTCTCCAACAACGAAGCCTTCAAGAGCGTGGCTACGCTT

TTATGCTTGGCGTGGGTGGAGAAAAGACTAAGAAGGAAGATGGGGGCAACACC

GATGAGAAGTGAGAATTCGATATCAAGCTTATCGATAATCAACCTCTGGATTAC

-continued

AAAATTTGTGAAAGATTGACTGGTATTCTTAACTATGTTGCTCCTTTTACGCTAT

GTGGATACGCTGCTTTAATGCCTTTGTATCATGCTATTGCTTCCCGTATGGCTT

TCATTTTCTCCTCCTTGTATAAATCCTGGTTGCTGTCTCTTTATGAGGAGTTGTG

GCCCGTTGTCAGGCAACGTGGCGTGGTGTGCACTGTGTTTGCTGACGCAACCC

CCACTGGTTGGGGCATTGCCACCACCTGTCAGCTCCTTTCCGGGACTTTCGCTT

TCCCCCTCCCTATTGCCACGGCGGAACTCATCGCCGCCTGCCTTGCCCGCTGCT

GGACAGGGGCTCGGCTGTTGGGCACTGACAATTCCGTGGTGTTGTCGGGGAAA

TCATCGTCCTTTCCTTGGCTGCTCGCCTGTGTTGCCACCTGGATTCTGCGCGGG

ACGTCCTTCTGCTACGTCCCTTCGGCCCTCAATCCAGCGGACCTTCCTTCCCGC

GGCCTGCTGCCGGCTCTGCGGCCTCTTCCGCGTCTTCGCCTTCGCCCTCAGAC

GAGTCGGATCTCCCTTTGGGCCGCCTCCCCGCATCGATACCGTCGACCTCGAG

ACCTAGAAAAACATGGAGCAATCACAAGTAGCAATACAGCAGCTACCAATGCT

GATTGTGCCTGGCTAGAAGCACAAGAGGAGGAGGAGGTGGGTTTTCCAGTCAC

ACCTCAGGTACCTTTAAGACCAATGACTTACAAGCAGCTGTAGATCTTAGCCA

CTTTTTAAAAGAAAAGGGGGGACTGGAAGGGCTAATTCACTCCCAACGAAGAC

AAGATATCCTTGATCTGTGGATCTACCACACACAAGGCTACTTCCCTGATTGGC

AGAACTACACACCAGGGCCAGGGATCAGATATCCACTGACCTTTGGATGGTGC

TACAAGCTAGTACCAGTTGAGCAAGAGAAGGTAGAAGAAGCCAATGAAGGAGA

GAACACCCGCTTGTTACACCCTGTGAGCCTGCATGGGATGGATGACCCGGAGA

GAGAAGTATTAGAGTGGAGGTTTGACAGCCGCCTAGCATTTCATCACATGGCC

CGAGAGCTGCATCCGGACTGTACTGGGTCTCTCTGGTTAGACCAGATCTGAGC

CTGGGAGCTCTCTGGCTAACTAGGGAACCCACTGCTTAAGCCTCAATAAAGCTT

GCCTTGAGTGCTTCAAGTAGTGTGTGCCCGTCTGTTGTGTGACTCTGGTAACTA

GAGATCCCTCAGACCCTTTTAGTCAGTGTGGAAAATCTCTAGCA

AgeI restriction enzyme site, EcoRI restriction enzyme site, Flag Epitope tag, Nuclear localization signal, *L. monocytogenes* Finland_1998 Cas7

(SEQ ID NO: 283)

ACCGGTCGCCACCGCCGCCACCATGGACTACAAGGACGATGATGACAAGATGGCG

CCCAAGAAGAAACGGAAAGTCCGCGGGATGAAGAACAAGGGACTGGCAATGACTA

TCATTTTCCAAGCCGAAAGCGCCAATTACGGCGAATCCCTGGGGAACATTTCAAGCC

TGAAGAAGATCTCTAGGAACAACGGAGATCAGTACACCTACATCTCCCGCCAAGCG

ATCCGGTACAATCTTATGGATCAGATCGGAGAAAAGGAAGCCCCTGTGAAGGCTGA

AGGCGGCGGAGACAAAAAGGTCATCCAGTTCCTGTCCGAGGCCACGATCACCGACT

TCCCGGAACTCGACTTTTTCGGCTACCTGAAAACCGAAAAGGGTTCCGGCGGACAG

AAGCGCAGCGCCAAAGTCCGACTGTCGAACGCCATCTCGCTGGAGACTTTTAAGGG

CGACCTGGATTTCCTCACTAACAAGGGACAGGCCGACAAGCTGAACGAAAACATGA

ACATTGCGCAGGCAGAGATCCACAAGTCCTACTACCGCTACACCATCACCATCGACC

TCGACCAGATCGGTATCGACGGGGACATTGCTCTGGACAACAAGGAAAAGGCCCGG

AGAGTGAAGAAGCTGATGGACACTGTGGCGTTCCTCTATCGGCACATTAGGGGCAG

-continued

ACGGGAGGACCTCAAGCCCCTGTTCGTGATCGTGGAGTGTATGACGTGAAGAACC

CGGTGTTCCAAAACATTGTGGATGTGGCCGACAACAATATTGTGATCAAGAACATTA

AGGATTTGCTGACCTACGAGGACATCAAGGAGAACACCAGAGTCGGCATCATTGAT

GGGCAGTTCGCCAACTCCGACGAAGTGAAAGTCGAGCTGAAGGCCGAGTCCGTGCC

AGCTTTCTTCAACGACATCAAGCGAAAGATTGATGCGTACTACGAGAGCAACTGAG

AATTC

AgeI restriction enzyme site, EcoRI restriction enzyme site, Flag Epitope tag, Nuclear localization signal, *L. monocytogenes* Finland_1998 Cas5

(SEQ ID NO: 284)

ACCGGTCGCCACCGCCGCCACCATGGACTACAAGGACGATGATGACAAGATGGCG

CCCAAGAAGAAGCGCAAGTCCGCGGGATGAAGGCTATTAGGGTCCGGCTGTGGCA

GGATCTCGTGAACTTCAAGAAGCCTACCAGCTTCCAACTGAAGGAAACCTACCCTCT

GCCGCCGTACTCTACCGTGATCGGCATGGTGCATACACTGTGCGGCTTTACCTCCTA

CCACGAGATGAAGATCAGCATTCAGGGAAAGTACTTTAGCAAGGTCAACGACCTCG

CGACTAGATACGAATTCAAGAATGGCTCAAAATACGACGTGGAACGCCACCAGATC

AAAGTGGACAAATACGGAGTGTCGAGAGGCGTCAGCACCGTGGAGCTCCTTGTGGA

CCTCGAACTGCTGCTGCACATCATTCCGGAAGATCCATCCTTGGTGCCGATCATTGA

AAAGGCATTCCGGGAACCCATCGAGTTCCCTTCCCTGGGACGCAGAGAGGACATCG

CCACGATTCAGAAGGTCGAAGTGGTGGACGTCGAGAAGCGACAGCCCAAGAAGTCC

ACCGAGATCTCCCGACGGTTATAACGCCTACGTGCCGATCAGCTTGACCGAGAACAA

CTCGGTGCATTTCAAGTCCCACGAGTCCTCAGTGGGACGGGATAAGCTGCTGGGAC

TCGGTACCTTCTGACTGAGAAATACGAGCGCGTGAACCACGGAACCGAAAAGGCCC

CTAAGTTCTTCCGGAAGTGGCGGAAGAAGGACGTCATCTACTCCTCGCGCATCTTCG

TGTCCAAGAAGGATGTGTTCTTTTTCGACGAGGACGATTACCTGGTGTTCATCGAAG

AAGAAGAGTGAGAATTC

AgeI restriction enzyme site, EcoRI restriction enzyme site, Flag Epitope tag, Nuclear localization signal, *L. monocytogenes* Finland_1998 Cas6

(SEQ ID NO: 285)

ACCGGTCGCCACCGCCGCCACCATGGACTACAAGGACGACGACGATAAGATGGCG

CCAAAGAAAAAGCGCAAGGTCCGCGGGATGCCGGCTGAAGATTAACTGCCGACTTCGA

CAGCAAGATCATCCCCAAGGACTTCCAGTCCAAGGTCGTGTCCCTGTTCAAAGCCGG

AATTATGAAAAGCTCCCCGGAGAGATACGAGAACCTGTTTGGTGGAAACAAGCACA

AGCAGTACACTTTCTCGGTGTATCTCCCAAAACCTCAGAACAAGGGCGCCGAAATTC

AGCTGAACGAGGCGAACTGTATCATCAACTTCTCCACCGGCGATGCTGAAACCGGT

ATTATCTTCTACAACGCCCTGATTAGCCTGAGAGGCTCCAAGGTCCTGTTTGGGGCC

GGAAATCACATCACCGTGAAGAACATCCAGATCGTGCCTGAGAAGAAGATCATCGG

GAAGCAAACCATTCTGCGGACCCTTTCGCCGGTGGTGTCGAGGGATCACAACCGGG

AAACCTTCAAGAATTGGTTCTACTCATTCGAGGACGAAGAATTCGAGCCTACTTTGA

-continued

AGCGGAACATGCTGCCGTACCTCATCGACGCCTTTGGAGAACAGGCTCGCTACGATC

TGGAAAAGCTGAAGATCACGCCCATTTCCATGAAGAAAGTCGTGGTGTACTGCCAT

GAGATCCACATCGAGAGCTCCGTGGGCATCTTCGAGCTGGAAGCCGAGGCATACCT

CCAAAAGTACCTCGTGGAAAACGGAATCGGCACTATGACTGGCTCAGGGTTCGGAA

TGATTGAACAGTTCTGAGAATTC

AgeI restriction enzyme site, EcoRI restriction enzyme site, Flag Epitope tag, Nuclear localization signal, *L. monocytogenes* Finland_1998 Cas6, KRAB effector

(SEQ ID NO: 286)

ACCGGTCGCCACCGCCGCCACCATGGACTACAAGGACGACGACGATAAGATGGCG

CCAAAGAAAAAGCGCAAGGTCCGGGGCATGCGGCTGAAGATTAACTGCGACTTCGA

CAGCAAGATCATCCCCAAGGACTTCCAGTCCAAGGTCGTGTCCCTGTTCAAAGCCGG

AATTATGAAAAGCTCCCCGGAGAGATACGAGAACCTGTTTGGTGGAAACAAGCACA

AGCAGTACACTTTCTCGGTGTATCTCCCAAAACCTCAGAACAAGGGCGCCGAAATTC

AGCTGAACGAGGCGAACTGTATCATCAACTTCTCCACCGGCGATGCTGAAACCGGT

ATTATCTTCTACAACGCCCTGATTAGCCTGAGAGGCTCCAAGGTCCTGTTTGGGGCC

GGAAATCACATCACCGTGAAGAACATCCAGATCGTGCCTGAGAAGAAGATCATCGG

GAAGCAAACCATTCTGCGGACCCTTTCGCCGGTGGTGTCGAGGGATCACAACCGGG

AAACCTTCAAGAATTGGTTCTACTCATTCGAGGACGAAGAATTCGAGCCTACTTTGA

AGCGGAACATGCTGCCGTACCTCATCGACGCCTTTGGAGAACAGGCTCGCTACGATC

TGGAAAAGCTGAAGATCACGCCCATTTCCATGAAGAAAGTCGTGGTGTACTGCCAT

GAGATCCACATCGAGAGCTCCGTGGGCATCTTCGAGCTGGAAGCCGAGGCATACCT

CCAAAAGTACCTCGTGGAAAACGGAATCGGCACTATGACTGGCTCAGGGTTCGGAA

TGATTGAACAGTTCCGGGGCAAAAGGCCGGCGGCCACGAAAAAGGCCGGCCAGGC

AAAAAAGAAAAAGGGATCCGATGCTAAGTCACTGACTGCCTGGTCCCGGACACTGG

TGACCTTCAAGGATGTGTTTGTGGACTTCACCAGGGAGGAGTGGAAGCTGCTGGAC

ACTGCTCAGCAGATCCTGTACAGAAATGTGATGCTGGAGAACTATAAGAACCTGGTT

TCCTTGGGTTATCAGCTTACTAAGCCAGATGTGATCCTCCGGTTGGAGAAGGGAGAA

GAGCCCTGGCTGGTGGAGAGAGAAATTCACCAAGAGACCCATCCTGATTCAGAGAC

TGCATTTGAAATCAAATCATCAGTTCCGAAAAAGAAACGCAAAGTTTGAGAATTC

AgeI restriction enzyme site, EcoRI restriction enzyme site, Flag Epitope tag, Nuclear localization signal, *L. monocytogenes* Finland_1998 Cas6, KRAB effector, Blasticidin resistance, 2A sequences

(SEQ ID NO: 287)

ACCGGTCGCCACCGCCGCCACCATGGACTACAAGGACGACGACGATAAGATGGCG

CCAAAGAAAAAGCGCAAGGTCCGGGGCATGCGGCTGAAGATTAACTGCGACTTCGA

CAGCAAGATCATCCCCAAGGACTTCCAGTCCAAGGTCGTGTCCCTGTTCAAAGCCGG

AATTATGAAAAGCTCCCCGGAGAGATACGAGAACCTGTTTGGTGGAAACAAGCACA

AGCAGTACACTTTCTCGGTGTATCTCCCAAAACCTCAGAACAAGGGCGCCGAAATTC

AGCTGAACGAGGCGAACTGTATCATCAACTTCTCCACCGGCGATGCTGAAACCGGT

-continued

ATTATCTTCTACAACGCCCTGATTAGCCTGAGAGGCTCCAAGGTCCTGTTTGGGGCC

GGAAATCACATCACCGTGAAGAACATCCAGATCGTGCCTGAGAAGAAGATCATCCG

GAAGCAAACCATTCTGCGGACCCTTTCGCCGGTGGTGTCGAGGGATCACAACCGGG

AAACCTTCAAGAATTGGTTCTACTCATTCGAGGACGAAGAATTCGAGCCTACTTTGA

AGCGGAACATGCTGCCGTACCTCATCGACGCCTTTGGAGAACAGGCTCGCTACGATC

TGGAAAAGCTGAAGATCACGCCCATTTCCATGAAGAAAGTCGTGGTGTACTGCCAT

GAGATCCACATCGAGAGCTCCGTGGGCATCTTCGAGCTGGAAGCCGAGGCATACCT

CCAAAAGTACCTCGTGGAAAACGGAATCGGCACTATGACTGGCTCAGGGTTCGGAA

TGATTGAACAGTTCCGGGGCAAAAGGCCGGCGGCCACGAAAAAGGCCGGCCAGGC

AAAAAAGAAAAAGGGATCCGATGCTAAGTCACTGACTGCCTGGTCCCGGACACTGG

TGACCTTCAAGGATGTGTTTGTGGACTTCACCAGGGAGGAGTGGAAGCTGCTGGAC

ACTGCTCAGCAGATCCTGTACAGAAATGTGATGCTGGAGAACTATAAGAACCTGGTT

TCCTTGGGTTATCAGCTTACTAAGCCAGATGTGATCCTCCGGTTGGAGAAGGGAGAA

GAGCCCTGGCTGGTGGAGAGAGAAATTCACCAAGAGACCCATCCTGATTCAGAGAC

TGCATTTGAAATCAAATCATCAGTTCCGAAAAAGAAACGCAAAGTTGGAAGCGGAG

AGGGCAGAGGAAGTCTTCTCACATGCGGTGACGTGGAGGAGAATCCTGGACCTAAG

ACCTTCAACATCTCTCAGCAGGATCTGGAGCTGGTGGAGGTCGCCACTGAGAAGATC

ACCATGCTCTATGAGGACAACAAGCACCATGTCGGGGCGGCCATCAGGACCAAGAC

TGGGGAGATCATCTCTGCTGTCCACATTGAGGCCTACATTGGCAGGGTCACTGTCTG

TGCTGAAGCCATTGCCATTGGGTCTGCTGTGAGCAACGGGCAGAAGGACTTTGACAC

CATTGTGGCTGTCAGGCACCCCTACTCTGATGAGGTGGACAGATCCATCAGGGTGGT

CAGCCCCTGTGGCATGTGCAGAGAGCTCATCTCTGACTATGCTCCTGACTGCTTTGT

GCTCATTGAGATGAATGGCAAGCTGGTCAAAACCACCATTGAGGAACTCATCCCCCT

CAAGTACACCAGGAACTAAAGGAATTC

AgeI restriction enzyme site, EcoRI restriction enzyme site, Flag Epitope tag, Nuclear localization signal, *L. monocytogenes* Finland_1998 Cas6, I-TevI effector, Blasticidin resistance, 2A sequences

(SEQ ID NO: 288)

ACCGGTCGCCACCGCCGCCACCATGATGGGCAAGAGTGGGATATACCAAATTAAAA

ACACACTGAATAATAAGGTTTACGTGGGATCTGCGAAGGATTTTGAGAAACGATGG

AAACGACACTTCAAGGATCTGGAAAAGGGCTGCCATTCCAGCATAAAACTGCAGAG

GTCTTTTTAATAAACACGGCAACGTGTTTGAGTGCTCAATCCTGGAAGAAATTCCGTA

CGAAAAGGACTTGATTATAGAACGGGAGAATTTCTGGATTAAAGAGCTCAACAGCA

AGATCAATGGCTATAACATCGCCGATGCCACTTTTGGGGACACGTGTTCAACCCACC

CCCTCAAAGAAGAAATCATTAAAAAACGGAGCGAAACGGTCAAAGCAAAAATGTTG

AAGCTCGGACCCGACGGGCGCAAAGCCCTTTACTCAAAACCCGGCAGCAAAAACGG

ACGGTGGAACCCTGAAACTCATAAGTTTTGCAAATGTGGCGTTAGAATACAAACGTC

-continued

CGCTTACACGTGCTCCAAATGTCGCAACCGCTCAGGCGAAAACAACAGTTTTTTCAA

TCATAAACATTCTGATATCACCAAGAGTAAGATATCTGAGAAGATGAAAGGCAAAA

AGCCGTCTAACATAAAGAAGATCAGCGGTGGGTCAGGTGGATCAGACTACAAGGAC

GACGACGATAAGATGGCGCCAAAGAAAAAGCGCAAGGTCCGGGGCATGCGGCTGA

AGATTAACTGCGACTTCGACAGCAAGATCATCCCCAAGGACTTCCAGTCCAAGGTC

GTGTCCCTGTTCAAAGCCGGAATTATGAAAAGCTCCCCGGAGAGATACGAGAACCT

GTTTGGTGGAAACAAGCACAAGCAGTACACTTTCTCGGTGTATCTCCCAAAACCTCA

GAACAAGGGCGCCGAAATTCAGCTGAACGAGGCGAACTGTATCATCAACTTCTCCA

CCGGCGATGCTGAAACCGGTATTATCTTCTACAACGCCCTGATTAGCCTGAGAGGCT

CCAAGGTCCTGTTTGGGGCCGGAAATCACATCACCGTGAAGAACATCCAGATCGTG

CCTGAGAAGAAGATCATCGGGAAGCAAACCATTCTGCGGACCCTTTCGCCGGTGGT

GTCGAGGGATCACAACCGGGAAACCTTCAAGAATTGGTTCTACTCATTCGAGGACG

AAGAATTCGAGCCTACTTTGAAGCGGAACATGCTGCCGTACCTCATCGACGCCTTTG

GAGAACAGGCTCGCTACGATCTGGAAAAGCTGAAGATCACGCCCATTTCCATGAAG

AAAGTCGTGGTGTACTGCCATGAGATCCACATCCAGAGCTCCGTGGGCATCTTCGAG

CTGGAAGCCGAGGCATACCTCCAAAAGTACCTCGTGGAAAACGGAATCGGCACTAT

GACTGGCTCAGGGTTCGGAATGATTGAACAGTTCGGAAGCGGAGAGGGCAGAGGAA

GTCTTCTCACATGCGGTGACGTGGAGGAGAATCCTGGACCTAAGACCTTCAACATCT

CTCAGCAGGATCTGGAGCTGGTGGAGGTCGCCACTGAGAAGATCACCATGCTCTAT

GAGGACAACAAGCACCATGTCGGGGCGGCCATCAGGACCAAGACTGGGGAGATCA

TCTCTGCTGTCCACATTGAGGCCTACATTGGCAGGGTCACTGTCTGTGCTGAAGCCA

TTGCCATTGGGTCTGCTGTGAGCAACGGGCAGAAGGACTTTGACACCATTGTGGCTG

TCAGGCACCCCTACTCTGATGAGGTGGACAGATCCATCAGGGTGGTCAGCCCCTGTG

GCATGTGCAGAGAGCTCATCTCTGACTATGCTCCTGACTGCTTTGTGCTCATTGAGAT

GCATGTGCAGAGAGCTCATCTCTGACTATGCTCCTGACTGCTTTGTGCTCATTGAGAT

GAATGGCAAGCTGGTCAAAACCACCATTGAGGAACTCATCCCCCTCAAGTACACCA

GGAACTAAAGGAATTC

Full lentiviral example with crRNA spacer

LTR, HIV-1 ψ, RPE, cPPT, hUbC promoter, AgeI restriction enzyme site, NheI restriction enzyme site, WPRE, Repeat, Spacer, U6 promoter, 2A sequence, eGFP, PuroR

(SEQ ID NO: 289)

GGGTCTCTCTGGTTAGACCAGATCTGAGCCTGGGAGCTCTCTGGCTAACTAGG

GAACCCACTGCTTAAGCCTCAATAAAGCTTGCCTTGAGTGCTTCAAGTAGTGTG

TGCCCGTCTGTTGTGTGACTCTGGTAACTAGAGATCCCTCAGACCCTTTTAGTC

AGTGTGGAAAATCTCTAGCAGTGGCGCCCGAACAGGGACTTGAAAGCGAAAGG

GAAACCAGAGGAGCTCTCTCGACGCAGGACTCGGCTTGCTGAAGCGCGCACGG

CAAGAGGCGAGGGGCGGCGACTGGTGAGTACGCCAAAAATTTTGACTAGCGGA

GGCTAGAAGGAGAGAGATGGGTGCGAGAGCGTCAGTATTAAGCGGGGGAGAA

TTAGATCGCGATGGGAAAAAATTCGGTTAAGGCCAGGGGGAAAGAAAAAATAT

-continued

AAATTAAAACATATAGTATGGGCAAGCAGGGAGCTAGAACGATTCGCAGTTAA

TCCTGGCCTGTTAGAAACATCAGAAGGCTGTAGACAAATACTGGGACAGCTAC

AACCATCCCTTCAGACAGGATCAGAAGAACTTAGATCATTATATAATACAGTAG

CAACCCTCTATTGTGTGCATCAAAGGATAGAGATAAAAGACACCAAGGAAGCT

TTAGACAAGATAGAGGAAGAGCAAAACAAAAGTAAGACCACCGCACAGCAAGC

GGCCGCTGATCTTCAGACCTGGAGGAGGAGATATGAGGGACAATTGGAGAAGT

GAATTATATAAATATAAAGTAGTAAAAATTGAACCATTAGGAGTAGCACCCACC

AAGGCAAAGAGAAGAGTGGTGCAGAGAGAAAAAAGAGCAGTGGGAATAGGAG

CTTTGTTCCTTGGGTTCTTGGGAGCAGCAGGAAGCACTATGGGCGCAGCGTCA

ATGACGCTGACGGTACAGGCCAGACAATTATTGTCTGGTATAGTGCAGCAGCA

GAACAATTTGCTGAGGGCTATTGAGGCGCAACAGCATCTGTTGCAACTCACAG

TCTGGGGCATCAAGCAGCTCCAGGCAAGAATCCTGGCTGTGGAAAGATACCTA

AAGGATCAACAGCTCCTGGGGATTTGGGGTTGCTCTGGAAAACTCATTTGCAC

CACTGCTGTGCCTTGGAATGCTAGTTGGAGTAATAAATCTCTGGAACAGATTTG

GAATCACACGACCTGGATGGAGTGGGACAGAGAAATTAACAATTACACAAGCT

TAATACACTCCTTAATTGAAGAATCGCAAAACCAGCAAGAAAAGAATGAACAAG

AATTATTGGAATTAGATAAATGGGCAAGTTTGTGGAATTGGTTTAACATAACAA

ATTGGCTGTGGTATATAAAATTATTCATAATGATAGTAGGAGGCTTGGTAGGTT

TAAGAATAGTTTTTGCTGTACTTTCTATAGTGAATAGAGTTAGGCAGGGATATT

CACCATTATCGTTTCAGACCCACCTCCCAACCCCGAGGGGACCCGACAGGCC

GAAGGAATAGAAGAAGAAGGTGGAGAGAGAGACAGAGACAGATCCATTCGATT

AGTGAACGGATCGGCACTGCGTGCGCCAATTCTGCAGACAAATGGCAGTATTC

ATCCACAATTTTAAAAGAAAAGGGGGGATTGGGGGGTACAGTGCAGGGGAAAG

AATAGTAGACATAATAGCAACAGACATACAAACTAAAGAATTACAAAAACAAAT

TACAAAAATTCAAAATTTTCGGGTTTATTACAGGGACAGCAGAGATCCAGTTTG

GTTAATACACAGGAAACAGCTATGACCATGATTACGCCAAGCGCGCAATTAAC

CCTCACTAAAGGGAACAAAAGCTGGAGCTCGGAAAAAAAATTTACATTTCATAA

TAAGTAGTTAAACCGGTGGCCAGTCGTCTGGGCGGTGCTACAACTGGGCATT

TACATTTCATAATAAGTAGTTAAAACCGGGCTAGCTGTTTCGTCCTTTCCACAA

GATATATAAAGCCAAGAAATCGAAATACTTTCAAGTTACGGTAAGCATATGATA

GTCCATTTTAAAACATAATTTTAAAACTGCAAACTACCCAAGAAATTATTACTTT

CTACGTCACGTATTTTGTACTAATATCTTTGTGTTTACAGTCAAATTAATTCCAA

TTATCTCTCTAACAGCCTTGTATCGTATATGCAAATATGAAGGAATCATGGGAA

ATAGGCCCTCGGTACCCAATTCGCCCTATAGTGAGTCGTATTACGCGCGCTCAC

TGGCCGTCGTTTTACAACATTAACCCGTGTCGGCTCCAGATCTGGCCTCCGCGC

CGGGTTTTGGCGCCTCCCGCGGGCGCCCCCCTCCTCACGGCGAGCGCTGCCAC

GTCAGACGAAGGGCGCAGGAGCGTTCCTGATCCTTCCGCCCGGACGCTCAGGA

-continued

CAGCGGCCCGCTGCTCATAAGACTCGGCCTTAGAACCCCAGTATCAGCAGAAG

GACATTTTAGGACGGGACTTGGGTGACTCTAGGGCACTGGTTTTCTTTCCAGA

GAGCGGAACAGGCGAGGAAAAGTAGTCCCTTCTCGGCGATTCTGCGGAGGGAT

CTCCGTGGGGCGGTGAACGCCGATGATTATATAAGGACGCGCCGGGTGTGGCA

CAGCTAGTTCCGTCGCAGCCGGGATTTGGGTCGCGGTTCTTGTTTGTGGATCG

CTGTGATCGTCACTTGGTGAGTTGCGGGCTGCTGGGCTGGCCGGGGCTTTCGT

GGCCGCCGGGCCGCTCGGTGGGACGGAAGCGTGTGGAGAGACCGCCAAGGGC

TGTAGTCTGGGTCCGCGAGCAAGGTTGCCCTGAACTGGGGGTTGGGGGGAGC

GGACAAAATGGCGGCTGTTCCCGAGTCTTGAATGGAAGACGCTTGTAAGGCGG

GCTGTGAGGTCGTTGAAACAAGGTGGGGGGCATGGTGGGCGGCAAGAACCCA

AGGTCTTGAGGCCTTCGCTAATGCGGGAAAGCTCTTATTCGGGTGAGATGGGC

TGGGGCACCATCTGGGGACCCTGACGTGAAGTTTGTCACTGACTGGAGAACTC

GGGTTTGTCGTCTGGTTGCGGGGGCGGCAGTTATGCGGTGCCGTTGGGCAGTG

CACCCGTACCTTTGGGAGCGCGCGCCTCGTCGTGTCGTGACGTCACCCGTTCT

GTTGGCTTATAATGCAGGGTGGGGCCACCTGCCGGTAGGTGTGCGGTAGGCTT

TTCTCCGTCGCAGGACGCAGGGTTCGGGCCTAGGGTAGGCTCTCCTGAATCGA

CAGGCGCCGGACCTCTGGTGAGGGGAGGCATAAGTGACGCGTCAGTTTCTTTC

GTCGGTTTTATGTACCTATCTTCTTAACTAGCTGAAGCTCCGGTTTTGAACTAT

GCGCTCGCGGTTGGCGAGTGTGTTTTGTGAACTTTTTTAGGCACCTTTTGAAAT

GTAATCATTTGGGTCAATATCTAATTTTCAGTGTTAGACTAGTAAATTGTCCCC

TAAATTCTGGCCGTTTTTGGCTTTTTTGTTAGACGAAGCTTGGGCTGCAGGTCG

ACTCTAGAATGGTGAGCAAGGGCGAGGAGCTGTTCACCGGGGTGGTGCCCATC

CTGGTCGAGCTGGACGGCGACGTAAACGGCCACAAGTTCAGCGTGTCCGGCGA

GGGCGAGGGCGATGCCACCTACGGCAAGCTGACCCTGAAGTTCATCTGCACCA

CCGGCAAGCTGCCCGTGCCCTGGCCCACCCTCGTGACCACCCTGACCTACGGC

GTGCAGTGCTTCAGCCGCTACCCCGACCACATGAAGCAGCACGACTTCTTCAA

GTCCGCCATGCCCGAAGGCTACGTCCAGGAGCGCACCATCTTCTTCAAGGACG

ACGGCAACTACAAGACCCGCGCCGAGGTGAAGTTCGAGGGCGACACCCTGGTG

AACCGCATCGAGCTGAAGGGCATCGACTTCAAGGAGGACGGCAACATCCTGGG

GCACAAGCTGGAGTACAACTACAACAGCCACAACGTCTATATCATGGCCGACA

AGCAGAAGAACGGCATCAAGGTGAACTTCAAGATCCGCCACAACATCGAGGAC

GGCAGCGTGCAGCTCGCCGACCACTACCAGCAGAACACCCCCATCGGCGACGG

CCCCGTGCTGCTGCCCGACAACCACTACCTGAGCACCCAGTCCGCCCTGAGCA

AAGACCCCAACGAGAAGCGCGATCACATGGTCCTGCTGGAGTTCGTGACCGCC

GCCGGGATCACTCTCGGCATGGACGAGCTGTACAAGGGATCCGGCGCAACAAA

CTTCTCTCTGCTGAAACAAGCCGGAGATGTCGAAGAGAATCCTGGACCGATGA

-continued

CCGAGTACAAGCCCACGGTGCGCCTCGCCACCCGCGACGACGTCCCCAGGGCC

GTACGCACCCTCGCCGCCGCGTTCGCCGACTACCCCGCCACGCGCCACACCGT

CGATCCGGACCGCCACATCGAGCGGGTCACCGAGCTGCAAGAACTCTTCCTCA

CGCGCGTCGGGCTCGACATCGGCAAGGTGTGGGTCGCGGACGACGGCGCCGC

GGTGGCGGTCTGGACCACGCCGGAGAGCGTCGAAGCGGGGGCGGTGTTCGCC

GAGATCGGCCCGCGCATGGCCGAGTTGAGCGGTTCCCGGCTGGCCGCGCAGC

AACAGATGGAAGGCCTCCTGGCGCCGCACCGGCCCAAGGAGCCCGCGTGGTTC

CTGGCCACCGTCGGCGTGTCGCCCGACCACCAGGGCAAGGGTCTGGGCAGCG

CCGTCGTGCTCCCCGGAGTGGAGGCGGCCGAGCGCGCCGGGGTGCCCGCCTT

CCTGGAGACCTCCGCGCCCCGCAACCTCCCCTTCTACGAGCGGCTCGGCTTCA

CCGTCACCGCCGACGTCGAGGTGCCCGAAGGACCGCGCACCTGGTGCATGACC

CGCAAGCCCGGTGCCTAAAGTTGATAATAGATAACTTCGTATAGCATACATTAT

ACGAAGTTATGAATTCGATATCAAGCTTATCGATAATCAACCTCTGGATTACAA

AATTTGTGAAAGATTGACTGGTATTCTTAACTATGTTGCTCCTTTTACGCTATGT

GGATACGCTGCTTTAATGCCTTTGTATCATGCTATTGCTTCCCGTATGGCTTTC

ATTTTCTCCTCCTTGTATAAATCCTGGTTGCTGTCTCTTTATGAGGAGTTGTGG

CCCGTTGTCAGGCAACGTGGCGTGGTGTGCACTGTGTTTGCTGACGCAACCCC

CACTGGTTGGGGCATTGCCACCACCTGTCAGCTCCTTTCCGGGACTTTCGCTTT

CCCCCTCCCTATTGCCACGGCGGAACTCATCGCCGCCTGCCTTGCCCGCTGCT

GGACAGGGGCTCGGCTGTTGGGCACTGACAATTCCGTGGTGTTGTCGGGGAAA

TCATCGTCCTTTCCTTGGCTGCTCGCCTGTGTTGCCACCTGGATTCTGCGCGGG

ACGTCCTTCTGCTACGTCCCTTCGGCCCTCAATCCAGCGGACCTTCCTTCCCGG

GGCCTGCTGCCGGCTCTGCGGCCTCTTCCGCGTCTTCGCCTTCGCCCTCAGAC

GAGTCGGATCTCCCTTTGGGCCGCCTCCCCGCATCGATACCGTCGACCTCGAG

ACCTAGAAAAACATGGAGCAATCACAAGTAGCAATACAGCAGCTACCAATGCT

GATTGTGCCTGGCTAGAAGCACAAGAGGAGGAGGAGGTGGGTTTTCCGTCAC

ACCTCAGGTACCTTTAAGACCAATGACTTACAAGGCAGCTGTAGATCTTAGCCA

CTTTTTAAAAGAAAAGGGGGGACTGGAAGGGCTAATTCACTCCCAACGAAGAC

AAGATATCCTTGATCTGTGGATCTACCACACACAAGGCTACTTCCCTGATTGGC

AGAACTACACACCAGGGCCAGGGATCAGATATCCACTGACCTTTGGATGGTGC

TACAAGCTAGTACCAGTTGAGCAAGAGAAGGTAGAAGAAGCCAATGAAGGAGA

GAACACCCGCTTGTTACACCCTGTGAGCCTGCATGGGATGGATGACCCGGAGA

GAGAAGTATTAGAGTGGAGGTTTGACAGCCGCCTAGCATTTCATCACATGGCC

CGAGAGCTGCATCCGGACTGTACTGGGTCTCTCTGGTTAGACCAGATCTGAGC

-continued

CTGGGAGCTCTCTGGCTAACTAGGGAACCCACTGCTTAAGCCTCAATAAAGCTT

GCCTTGAGTGCTTCAAGTAGTGTGTGCCCGTCTGTTGTGTGACTCTGGTAACTA

GAGATCCCTCAGACCCTTTTAGTCAGTGTGGAAAATCTCTAGCA

Full lentiviral example (CasA):

LTR, HIV-1Ψ, RPE, cPPT, hUbC promoter, AgeI restriction enzyme site, EcoRI restriction enzyme site, WPRE, Flag Epitope tag, Nuclear localization signal, *E. coli* K-12 CasA (SEQ ID NO: 290)

GGGTCTCTCTGGTTAGACCAGATCTGAGCCTGGGAGCTCTCTGGCTAACTAGG

GAACCCACTGCTTAAGCCTCAATAAAGCTTGCCTTGAGTGCTTCAAGTAGTGTG

TGCCCGTCTGTTGTGTGACTCTGGTAACTAGAGATCCCTCAGACCCTTTTAGTC

AGTGTGGAAAATCTCTAGCAGTGGCGCCCGAACAGGGACTTGAAAGCGAAAGG

GAAACCAGAGGAGCTCTCTCGACGCAGGACTCGGCTTGCTGAAGCGCGCACGG

CAAGAGGCGAGGGGCGGCGACTGGTGAGTACGCCAAAAATTTTGACTAGCGGA

GGCTAGAAGGAGAGAGATGGGTGCGAGAGCGTCAGTATTAAGCGGGGGAGAA

TTAGATCGCGATGGGAAAAAATTCGGTTAAGGCCAGGGGGAAAGAAAAAATAT

AAATTAAAACATATAGTATGGGCAAGCAGGGAGCTAGAACGATTCGCAGTTAA

TCCTGGCCTGTTAGAAACATCAGAAGGCTGTAGACAAATACTGGGACAGCTAC

AACCATCCCTTCAGACAGGATCAGAAGAACTTAGATCATTATATAATACAGTAG

CAACCCTCTATTGTGTGCATCAAAGGATAGAGATAAAAGACACCAAGGAAGCT

TTAGACAAGATAGAGGAAGAGCAAAACAAAAGTAAGACCACCGCACAGCAAGC

GGCCGCTGATCTTCAGACCTGGAGGAGGAGATATGAGGGACAATTGGAGAAGT

GAATTATATAAATATAAAGTAGTAAAAATTGAACCATTAGGAGTAGCACCCACC

AAGGCAAAGAGAAGAGTGGTGCAGAGAGAAAAAAGAGCAGTGGGAATAGGAG

CTTTGTTCCTTGGGTTCTTGGGAGCAGCAGGAAGCACTATGGGCGCAGCGTCA

ATGACGCTGACGGTACAGGCCAGACAATTATTGTCTGGTATAGTGCAGCAGCA

GAACAATTTGCTGAGGGCTATTGAGGCGCAACAGCATCTGTTGCAACTCACAG

TCTGGGGCATCAAGCAGCTCCAGGCAAGAATCCTGGCTGTGGAAAGATACCTA

AAGGATCAACAGCTCCTGGGGATTTGGGGTTGCTCTGGAAAACTCATTTGCAC

CACTGCTGTGCCTTGGAATGCTAGTTGGAGTAATAAATCTCTGGAACAGATTTG

GAATCACACGACCTGGATGGAGTGGGACAGAGAAATTAACAATTACACAAGCT

TAATACACTCCTTAATTGAAGAATCGCAAAACCAGCAAGAAAAGAATGAACAAG

AATTATTGGAATTAGATAAATGGGCAAGTTTGTGGAATTGGTTTAACATAACAA

ATTGGCTGTGGTATATAAAATTATTCATAATGATAGTAGGAGGCTTGGTAGGTT

TAAGAATAGTTTTTGCTGTACTTTCTATAGTGAATAGAGTTAGGCAGGGATATT

CACCATTATCGTTTCAGACCCACCTCCCAACCCCGAGGGGACCCGACAGGCCC

GAAGGAATAGAAGAAGAAGGTGGAGAGAGAGACAGAGACAGATCCATTCGATT

AGTGAACGGATCGGCACTGCGTGCGCCAATTCTGCAGACAAATGGCAGTATTC

ATCCACAATTTTAAAAGAAAAGGGGGGATTGGGGGGTACAGTGCAGGGGAAAG

AATAGTAGACATAATAGCAACAGACATACAAACTAAAGAATTACAAAAACAAAT

TACAAAAATTCAAAATTTTCGGGTTTATTACAGGGACAGCAGAGATCCAGTTTG

-continued

GTTAATTAAGGGTGCAGCGGCCTCCGCGCCGGGTTTTGGCGCCTCCCGCGGGC

GCCCCCCTCCTCACGGCGAGCGCTGCCACGTCAGACGAAGGGCGCAGGAGCG

TTCCTGATCCTTCCGCCCGGACGCTCAGGACAGCGGCCCGCTGCTCATAAGAC

TCGGCCTTAGAACCCCAGTATCAGCAGAAGGACATTTTAGGACGGGACTTGGG

TGACTCTAGGGCACTGGTTTTCTTTCCAGAGAGCGGAACAGGCGAGGAAAAGT

AGTCCCTTCTCGGCGATTCTGCGGAGGGATCTCCGTGGGGCGGTGAACGCCGA

TGATTATATAAGGACGCGCCGGGTGTGGCACAGCTAGTTCCGTCGCAGCCGGG

ATTTGGGTCGCGGTTCTTGTTTGTGGATCGCTGTGATCGTCACTTGGTGAGTTG

CGGGCTGCTGGGCTGGCCGGGGCTTTCGTGGCCGCCGGGCCGCTCGGTGGGA

CGGAAGCGTGTGGAGAGACCGCCAAGGGCTGTAGTCTGGGTCCGCGAGCAAG

GTTGCCCTGAACTGGGGGTTGGGGGGAGCGCACAAAATGGCGGCTGTTCCCGA

GTCTTGAATGGAAGACGCTTGTAAGGCGGGCTGTGAGGTCGTTGAAACAAGGT

GGGGGGCATGGTGGGCGGCAAGAACCCAAGGTCTTGAGGCCTTCGCTAATGC

GGGAAAGCTCTTATTCGGGTGAGATGGGCTGGGGCACCATCTGGGGACCCTGA

CGTGAAGTTTGTCACTGACTGGAGAACTCGGGTTTGTCGTCTGGTTGCGGGGG

CGGCAGTTATGCGGTGCCGTTGGGCAGTGCACCCGTACCTTTGGGAGCGCGCG

CCTCGTCGTGTCGTGACGTCACCCGTTCTGTTGGCTTATAATGCAGGGTGGGG

CCACCTGCCGGTAGGTGTGCGGTAGGCTTTTCTCCGTCGCAGGACGCAGGGTT

CGGGCCTAGGGTAGGCTCTCCTGAATCGACAGGCGCCGGACCTCTGGTGAGGG

GAGGGATAAGTGAGGCGTCAGTTTCTTTGGTCGGTTTTATGTACCTATCTTCTT

AAGTAGCTGAAGCTCCGGTTTTGAACTATGCGCTCGGGGTTGGCGAGTGTGTT

TTGTGAAGTTTTTTAGGCACCTTTTGAAATGTAATCATTTGGGTCAATATGTAA

TTTTCAGTGTTAGACTAGTAAATTGTCCGCTAAATTCTGGCCGTTTTTGGCTTTT

TTGTTAGACGAAGCTTGGGCTGCAGGTCGACTCTAGAGGATCCCCGGGTACCG

GTCGCCACCGCCGCCACCATGGATTACAAAGACGATGACGATAAGATGGCGCC

TAAGAAGAAgCGCAAgGTGCGGGGCATGGCCAATCTCCTGATTGACAATTGGAT

CCCTGTGAGACCGAGGAACGGAGGGAAGGTTCAGATCATCAACCTGCAAAGTC

TCTACTGTAGCAGAGATCAATGGCGACTCTCATTGCCCAGGGATGATATGGAA

TTGGCGGCACTTGCACTCTTGGTATGTATTGGGCAGATCATCGCCCCTGCCAA

GGATGATGTCGAGTTTAGGCACAGAATAATGAACCCTCTTACTGAAGATGAATT

CCAGCAATTGATCGCGCCTTGGATAGATATGTTCTATTTGAATCACGCCGAACA

TCCCTTCATGCAGACAAAAGGGGTTAAAGCAAATGATGTCACACCAATGGAGA

AGCTTTTGGCAGGTGTGTCAGGAGCAACCAACTGCGCTTTCGTTAACCAACCA

GGCCAAGGTGAGGCGTTGTGCGGGGGGTGCACGGCCATAGCGTTGTTTAATCA

GGCGAACCAGGCTCCTGGCTTTGGAGGAGGATTCAAGTCCGGTTTGCGCGGGG

GTACACCCGTAACCACATTCGTTCGCGGAATTGACCTCCGATCAACAGTCCTGT

TGAACGTATTGACGTTGCCTAGACTTCAGAAGCAATTTCCAAACGAGTCTCACA

CTGAGAATCAACCGACTTGGATTAAGCCCATCAAGTCAAATGAAGTATACCCC

-continued

CGTCTTCTATTGGATTTGTTAGAGGACTTTTTTGGCAGCCCGCTCACATAGAAC

TCTGTGATCCCATAGGCATTGGAAAGTGTTCTTGCTGTGGCCAAGAGTCTAACC

TTAGATATACGGGCTTTCTCAAGGAGAAGTTCACGTTCACCGTGAATGGACTTT

GGCCACATCCCCATAGCCCGTGCTTGGTCACGGTCAAGAAGGGGGAGGTTGAA

GAGAAATTTCTTGCGTTTACCACATCCGCCCCATCCTGGACGCAAATATCTCGC

GTCGTTGTGGATAAAATCATCCAGAACGAAAATGGTAACCGCGTTGCCGCGGT

AGTGAATCAATTCAGAAACATAGCACCACAGAGCCCGTTGGAGTTGATAATGG

GCGGGTACCGCAATAATCAAGCTTCCATTCTCGAGCGACGCCATGACGTACTT

ATGTTTAACCAGGGGTGGCAGCAATATGGTAACGTGATAAACGAGATAGTCAC

AGTCGGCCTCGGCTACAAAACTGCGTTGCGCAAAGCTCTGTATACGTTCGCGG

AGGGTTTTAAGAATAAAGACTTTAAAGGCGCTGGGGTGAGTGTGCACGAGACG

GCAGAACGCCATTTCTATCGCCAGTCTGAACTCTTGATTCCCGACGTTCTGGCG

AATGTCAATTTTTCCCAGGCCGATGAGGTCATTGCGGATCTGCGAGATAAGCTT

CACCAGTTGTGTGAGATGCTGTTCAACCAGTCTGTGGCTCCTTATGCTCATCAT

AGAGAACTGAAGCCACAGGGTGGTCCCAGCAATGGCTGAGAATTCGATATCAA

GCTTATCGATAATCAACCTCTGGATTACAAAATTTGTGAAAGATTGACTGGTAT

TCTTAACTATGTTGCTCCTTTTACGCTATGTGGATACGCTGCTTTAATGCCTTTG

TATCATGCTATTGCTTCCCGTATGGCTTTCATTTTCTCCTCCTTGTATAAATCCT

GGTTGCTGTCTCTTTATGAGGAGTTGTGGCCCGTTGTCAGGCAACGTGGCGTG

GTGTGCACTGTGTTTGCTGACGCAACCCCCACTGGTTGGGGCATTGCCACCAC

CTGTCAGCTCCTTTCCGGGACTTTCGCTTTCCCCCTCCCTATTGCCACGGCGGA

ACTCATCGCCGCCTGCCTTGCCCGCTGCTGGACAGGGGCTCGGCTGTTGGGCA

CTGACAATTCCGTGGTGTTGTCGGGGAAATCATCGTCCTTTCCTTGGCTGCTCG

CCTGTGTTGCCACCTGGATTCTGCGCGGGACGTCCTTCTGCTACGTCCCTTCGG

CCCTCAATCCAGCGGACCTTCCTTCCCGCGGCCTGCTGCCGGCTCTGCGGCCT

CTTCCGCGTCTTCGCCTTCGCCCTCAGACGAGTCGGATCTCCCTTTGGGCCGCC

TCCCCGCATCGATACCGTCGACCTCGAGACCTAGAAAAACATGGAGCAATCAC

AAGTAGCAATACAGCAGCTACCAATGCTGATTGTGCCTGGCTAGAAGCACAAG

AGGAGGAGGAGGTGGGTTTTCCAGTCACACCTCAGGTACCTTTAAGACCAATG

ACTTACAAGGCAGCTGTAGATCTTAGCCACTTTTTAAAAGAAAAGGGGGGACT

GGAAGGGCTAATTCACTCCCAACGAAGACAAGATATCCTTGATCTGTGGATCTA

CCACACACAAGGCTACTTCCCTGATTGGCAGAACTACACACCAGGGCCAGGGA

TCAGATATCCACTGACCTTTGGATGGTGCTACAAGCTAGTACCAGTTGAGCAAG

AGAAGGTAGAAGAAGCCAATGAAGGAGAGAACACCCGCTTGTTACACCCTGTG

AGCCTGCATGGGATGGATGACCCGGAGAGAGAAGTATTAGAGTGGAGGTTTGA

CAGCCGCCTAGCATTTCATCACATGGCCCGAGAGCTGCATCCGGACTGTACTG

-continued

GGTCTCTCTGGTTAGACCAGATCTGAGCCTGGGAGCTCTCTGGCTAACTAGGG

AACCCACTGCTTAAGCCTCAATAAAGCTTGCCTTGAGTGCTTCAAGTAGTGTGT

GCCCGTCTGTTGTGTGACTCTGGTAACTAGAGATCCCTCAGACCCTTTTAGTCA

GTGTGGAAAATCTCTAGCA

AgeI restriction enzyme site, EcoRI restriction enzyme site, Flag Epitope tag, Nuclear localization signal, *E. coli* K-12 CasB (SEQ ID NO: 291)

ACCGGTCGCCACCGCCGCCACCATGGATTACAAAGACGATGACGATAAGATGGCGC

CTAAGAAAAAGAGGAAAGTACGCGGGATGGCCGATGAAATAGACGCAATGGCTCTT

TACCGAGCATGGCAACAGCTCGACAATGGATCTTGCGCCCAAATACGGCGGGTAAG

TGAACCCGATGAACTGCGAGATATCCCCGCATTCTACCGATTGGTTCAGCCGTTTGG

CTGGGAGAACCCACGGCACCAGCAGGCGCTTCTTAGGATGGTTTTTTGTCTTAGTGC

CGGGAAAAACGTAATCCGCCATCAGGATAAGAAGTCCGAACAAACAACAGGGATTT

CTCTGGCAAGAGCGCTTGCTAACAGCGGCAGGATCAATGAACGCCGCATATTTCAG

TTGATCCGAGCAGATCGGACTGCTGATATGGTCCAGCTCAGGAGGCTCCTTACGCAC

GCAGAGCCAGTGTTGGATTGGCCACTCATGGCAAGAATGCTTACGTGGTGGGGAA

GAGGGAAAGGCAGCAACTGCTTGAAGATTTTGTATTGACGACGAACAAAAACGCGT

AAGAATTC

AgeI restriction enzyme site, EcoRI restriction enzyme site, Flag Epitope tag, Nuclear localization signal, *E. coli* K-12 CasC (SEQ ID NO: 292)

ACCGGTCGCCACCGCCGCCACCATGGATTACAAAGACGATGACGATAAGATGGCGC

CTAAGAAGAAGCGCAAGGTGAGAGGAATGTCAAACTTCATTAATATCCACGTGCTT

ATCTCACACTCCCCTAGTTGCCTTAACAGAGACGATATGAACATGCAAAAAGACGC

AATTTTTGGCGGCAAAAGGAGAGTCAGAATTAGTAGCCAGAGCCTGAAGCGCGCTA

TGAGGAAAAGCGGCTACTATGCTCAAAACATTGGTGAAAGTTCATTGCGGACCATC

CATCTCGCGCAGTTGAGGGACGTCCTGCGACAGAAGCTTGGGGAAAGATTTGATCA

GAAGATCATCGACAAAACGCTTGCCCTTCTGTCCGGTAAATCAGTGGACGAAGCGG

AGAAGATAAGTGCGGATGCTGTTACGCCATGGGTGGTAGGTGAAATCGCGTGGTTTT

GCGAGCAGGTAGCCAAGGCCGAAGCGGATAATTTGGATGATAAGAAACTGCTCAAA

GTCCTCAAAGAGGACATCGCGGCGATCCGGGTGAACCTTCAGCAGGGTGTTGATATT

GCGCTCTCTGGTCGGATGGCCACGTCTGGAATGATGACTGAACTGGGTAAGGTGGA

CGGAGCTATGTCTATAGCTCATGCTATAACTACCCATCAGGTGGATTCTGACATAGA

CTGGTTCACGGCTGTCGACGATCTCCAGGAACAAGGATCCGCACACCTCGGCACGC

AAGAATTTTCTTCTGGAGTGTTCTATAGGTATGCCAACATCAACCTTGCACAGCTCC

AGGAAAACCTCGGTGGGGCAAGCCGGGAACAGGCTCTTGAAATAGCTACCCATGTG

GTTCACATGCTGGCGACCGAAGTGCCAGGGGCCAAGCAGAGAACGTACGCCGCATT

CAATCCGGCGGACATGGTCATGGTGAATTTCTCTGATATGCCCTTGTCTATGGCAAA

TGCTTTCGAGAAGGCGGTCAAGGCAAAGGACGGTTTTTTGCAACCCTCCATCCAAGC

CTTTAATCAGTACTGGGATAGAGTAGCTAACGGGTATGGTCTCAATGGCGCGGCTGC

-continued

TCAGTTTTCTTTGTCCGATGTGGATCCGATAACGGCGCAGGTTAAACAGATGCCCAC

CTTGGAACAACTCAAATCCTGGGTTAGAAACAATGGGGAGGCGTGAGAATTC

AgeI restriction enzyme site, EcoRI restriction enzyme site, Flag Epitope tag, Nuclear localization signal, *E. coli* K-12 CasD (SEQ ID NO: 293)

ACCGGTCGCCACCGCCGCCACCATGGATTACAAAGACGATGACGATAAGATGGCGC

CGAAGAAGAAGCGGAAAGTCCGGGGCATGAGATCCTACCTCATCCTGCGCCTGGCC

GGGCCGATGCAGGCCTGGGGCCAGCCTACATTTGAGGGTACCCGGCCCACCGGACG

GTTCCCGACCCGCTCGGGGCTTCTGGGACTTCTGGGCGCATGTCTGGGCATCCAGCG

GGATGACACTAGCAGCCTGCAGGCCCTGAGCGAATCCGTGCAGTTCGCCGTGCGCT

GCGATGAACTGATCCTCGACGACCGCAGGGTGTCAGTGACTGGACTGAGAGACTAC

CACACCGTGCTGGGAGCCCGCGAGGATTACAGGGGCCTGAAGTCCCATGAAACCAT

TCAGACCTGGAGAGAGTACCTCTGCGACGCGTCGTTCACTGTGGCACTGTGGCTCAC

GCCGCACGCGACCATGGTCATCTCCGAACTGGAAAAAGCCGTGCTCAAGCCTCGGT

ACACCCCCTATCTCGGACGACGCTCCTGCCCACTGACCCATCCCCTGTTCCTCGGTA

CTTGCCAAGCCAGCGACCCTCAAAAGGCTCTGTTGAACTACGAACCCGTGGGGGGA

GACATCTACTCCGAGGAATCCGTCACCGGCCACCACTTGAAGTTCACCGCCCGGGAC

GAGCCGATGATTACTCTGCCAAGACAGTTCGCTTCACGGGAGTGGTACGTGATTAAG

GCTGGAATGGACGTGTCGCAGTGAGAATTC

AgeI restriction enzyme site, EcoRI restriction enzyme site, E. Epitope tag, Flag Epitope tag, Nuclear localization signal, *E. coli* K-12 CasE, p300 core effector (SEQ ID NO: 294)

ACCGGTCGCCACCGCCGCCACCATGGGTGCCCCAGTTCCCTATCCCGACCCACTGGA

GCCAAGGATGGCGCCTAAGAAGAAGCGCAAGGTGCGGGGCATGTATCTCAGTAAAG

TCATCATTGCCAGGGCCTGGAGCAGGGATCTTTACCAACTTCACCAGGGATTATGGC

ATTTATTTCCAAACAGACCGGATGCTGCTCGTGATTTTCTTTTTCATGTTGAGAAGCG

AAACACACCAGAAGGCTGTCATGTTTTATTGCAGTCAGCGCAAATGCCTGTTTCAAC

TGCCGTTGCGACAGTCATTAAAACTAAACAGGTTGAATTTCAACTTCACGTTGGTGT

TCCACTCTATTTTCGGCTTCGGGCAAATCCGATCAAAACTATTCTCGACAATCAAAA

GCGCCTGGACAGTAAAGGGAATATTAAACGCTGTCGGGTTCCGTTAATAAAAGAAG

CAGAACAAATCGCGTGGTTGCAACGTAAATTGGGCAATGCGGCGCGCGTTGAAGAT

GTGCATCCCATATCGGAACGGCCACAGTATTTTTCTGGTGATGGTAAAAGTGGAAAG

ATCCAAACGGTTTGCTTTGAAGGTGTGCTCACCATCAACGACGCGCCAGCGTTAATA

GATCTTGTACAGCAAGGTATTGGGCCAGCTAAATCGATGGGATGTGGCTTGCTATCT

TTGGCTCCACTGCGGGGCAAGCGACCTGCCGCCACAAAGAAGGCTGGACAGGCTAA

GAAGAAGAAAGGATCCATTTTTCAAACCAGAAGAACTACGACAGGCACTGATGCCAA

CTTTGGAGGCACTTTACCGTCAGGATCCAGAATCCCTTCCCTTTCGTCAACCTGTGGA

CCCTCAGCTTTTAGGAATCCCTGATTACTTTGATATTGTGAAGAGCCCCATGGATCTT

TCTACCATTAAGAGGAAGTTAGACACTGGACAGTATCAGGAGCCCTGGCAGTATGT

-continued

CGATGATATTTGGCTTATGTTCAATAATGCCTGGTTATATAACCGGAAAACATCACG

GGTATACAAATACTGCTCCAAGCTCTCTGAGGTCTTTGAACAAGAAATTGACCCAGT

GATGCAAAGCCTTGGATACTGTTGTGGCAGAAAGTTGGAGTTCTCTCCACAGACACT

GTGTTGCTACGGCAAACAGTTGTGCACAATACCTCGTGATGCCACTTATTACAGTTA

CCAGAACAGGTATCATTTCTGTGAGAAGTGTTTCAATGAGATCCAAGGGGAGAGCG

TTTCTTTGGGGGATGACCCTTCCCAGCCTCAAACTACAATAAATAAAGAACAATTTT

CCAAGAGAAAAAATGACACACTGGATCCTGAACTGTTTGTTGAATGTACAGAGTGC

GGAAGAAAGATGCATCAGATCTGTGTCCTTCACCATGAGATCATCTGGCCTGCTGGA

TTCGTCTGTGATGGCTGTTTAAAGAAAAGTGCACGAACTAGGAAAGAAAATAAGTT

TTCTGCTAAAAGGTTGCCATCTACCAGACTTGGCACCTTTCTAGAGAATCGTGTGAA

TGACTTTCTGAGGCGACAGAATCACCCTGAGTCAGGAGAGGTCACTGTTAGAGTAGT

TCATGCTTCTGACAAAACCGTGGAAGTAAAACCAGGCATGAAAGCAAGGTTTGTGG

ACAGTGGAGAGATGGCAGAATCCTTTCCATACCGAACCAAAGCCCTCTTTGCCTTTG

AAGAAATTGATGGTGTTGACCTGTGCTTCTTTGGCATGCATGTTCAAGAGTATGGCT

CTGACTGCCCTCCACCCAACCAGAGGAGAGTATACATATCTTACCTCGATAGTGTTC

ATTTCTTCCGTCCTAAATGCTTGAGGACTGCAGTCTATCATGAAATCCTAATTGGATA

TTTAGAATATGTCAAGAAATTAGGTTACACAACAGGGCATATTTGGGCATGTCCACC

AAGTGAGGGAGATGATTATATCTTCCATTGCCATCCTCCTGACCAGAAGATACCCAA

GCCCAAGCGACTGCAGGAATGGTACAAAAAAATGCTTGACAAGGCTGTATCAGAGC

GTATTGTCCATGACTACAAGGATATTTTTAAACAAGCTACTGAAGATAGATTAACAA

GTGCAAAGGAATTGCCTTATTTCGAGGGTGATTTCTGGCCCAATGTTCTGGAAGAAA

GCATTAAGGAACTGGAACAGGAGGAAGAAGAGAGAAAACGAGAGGAAAACACCAG

CAATGAAAGCACAGATGTGACCAAGGGAGACAGCAAAAATGCTAAAAAGAAGAAT

AATAAGAAAACCAGCAAAAATAAGAGCAGCCTGAGTAGGGGCAACAAGAAGAAAC

CCGGGATGCCCAATGTATCTAACGACCTCTCACAGAAACTATATGCCACCATGGAG

AAGCATAAAGAGGTCTTCTTTGTGATCCGCCTCATTGCTGGCCCTGCTGCCAACTCC

CTGCCTCCCATTGTTGATCCTGATCCTCTCATCCCCTGCGATCTGATGGATGGTCGGG

ATGCGTTTCTCACGCTGGCAAGGGACAAGCACCTGGAGTTCTCTTCACTCCGAAGAG

CCCAGTGGTCCACCATGTGCATGCTGGTGGAGCTGCACACGCAGAGCCAGGACGGA

TCCGATTACAAAGACGATGACGATAAGTGAGAATTC

AgeI restriction enzyme site, EcoRI restriction enzyme site, Flag Epitope tag, Nuclear localization signal, *E. coli* K-12 CasE, KRAB effector (SEQ ID NO: 295)

ACCGGTCGCCACCGCCGCCACCATGGATTACAAAGACGATGACGATAAGATGGCGC

CTAAGAAGAAGCGCAAGGTGCGGGGCATGTATCTCAGTAAAGTCATCATTGCCAGG

GCCTGGAGCAGGGATCTTTACCAACTTCACCAGGGATTATGGCATTTATTTCCAAAC

AGACCGGATGCTGCTCGTGATTTTCTTTTTCATGTTGAGAAGCGAAACACACCAGAA

-continued

GGCTGTCATGTTTTATTGCAGTCAGCGCAAATGCCTGTTTCAACTGCCGTTGGCGACA

GTCATTAAAACTAAACAGGTTGAATTTCAACTTCAGGTTGGTGTTCCACTCTATTTTC

GGCTTCGGGCAAATCCGATCAAAACTATTCTCGACAATCAAAAGCGCCTGGACAGT

AAAGGGAATATTAAACGCTGTCGGGTTCCGTTAATAAAAGAAGCAGAACAAATCGC

GTGGTTGCAACGTAAATTGGGCAATGCGGCGCGCGTTGAAGATGTGCATCCCATATC

GGAACGGCCACAGTATTTTTCTGGTGATGGTAAAAGTGGAAAGATCCAAACGGTTT

GCTTTGAAGGTGTGCTCACCATCAACGACGCGCCAGCGTTAATAGATCTTGTACAGC

AAGGTATTGGGCCAGCTAAATCGATGGGATGTGGCTTGCTATCTTTGGCTCCACTGC

GGGGCAAGCGACCTGCCGCCACAAAGAAGGCTGGACAGGCTAAGAAGAAGAAAGG

ATCCGATGCTAAGTCACTGACTGCCTGGTCCCGGACACTGGTGACCTTCAAGGATGT

GTTTGTGGACTTCACCAGGGAGGAGTGGAAGCTGCTGGACACTGCTCAGCAGATCCT

GTACAGAAATGTGATGCTGGAGAACTATAAGAACCTGGTTTCCTTGGGTTATCAGCT

TACTAAGCCAGATGTGATCCTCCGGTTGGAGAAGGGAGAAGAGCCCTGGCTGGTGG

AGAGAGAAATTCACCAAGAGACCCATCCTGATTCAGAGACTGCATTTGAAATCAAA
TCATCAGTTCCGAAAAAGAAACGCAAGTTTGAGAATTC

AgeI restriction enzyme site, EcoRI restriction enzyme site, Flag Epitope tag, Nuclear localization signal, *E. coli* K-12 CasA, *E. coli* K-12 CasB, *E. coli* K-12 CasC, Neomycin resistance, 2A sequences (SEQ ID NO: 296)

ACCGGTCGCCACCGCCGCCACCATGGATTACAAAGACGATGACGATAAGATGGCGC

CTAAGAAGAAGCGCAAGGTGCGGGGCATGGCCAATCTCCTGATTGACAATTGGATC

CCTGTGAGACCGAGGAACGGAGGGAAGGTTCAGATCATCAACCTGCAAAGTCTCTA

CTGTAGCAGAGATCAATGGCGACTCTCATTGCCCAGGGATGATATGGAATTGGCGG

CACTTGCACTCTTGGTATGTATTGGGCAGATCATCGCCCCTGCCAAGGATGATGTCG

AGTTTAGGCACAGAATAATGAACCCTCTTACTGAAGATGAATTCCAGCAATTGATCG

CGCCTTGGATAGATATGTTCTATTTGAATCACGCCGAACATCCCTTCATGCAGACAA

AAGGGGTTAAAGCAAATGATGTCACACCAATGGAGAAGCTTTTGGCAGGTGTGTCA

GGAGCAACCAACTGCGCTTTCGTTAACCAACCAGGCCAAGGTGAGGCGTTGTGCGG

GGGGTGCACGGCCATAGCGTTGTTTAATCAGGCGAACCAGGCTCCTGGCTTTGGAGG

AGGATTCAAGTCCGGTTTGCGCGGGGGTACACCCGTAACCACATTCGTTCGCGGAAT

TGACCTCCGATCAACAGTCCTGTTGAACGTATTGACGTTGCCTAGACTTCAGAAGCA

ATTTCCAAACGAGTCTCACACTGAGAATCAACCGACTTGGATTAAGCCCATCAAGTC

AAATGAAAGTATACCCGCGTCTTCTATTGGATTTGTTAGAGGACTTTTTTGGCAGCC

CGCTCACATAGAACTCTGTGATCCCATAGGCATTGGAAAGTGTTCTTGCTGTGGCCA

AGAGTCTAACCTTAGATATACGGGCTTTCTCAAGGAGAAGTTCACGTTCACCGTGAA

TGGACTTTGGCCACATCCCCATAGCCCGTGCTTGGTCACGGTCAAGAAGGGGGAGGT

TGAAGAGAAATTTCTTGCGTTTACCACATCCGCCCCATCCTGGACGCAAATATCTCG

CGTCGTTGTGGATAAAATCATCCAGAACGAAAATGGTAACCGCGTTGCCGCGGTAC

TGAATCAATTCAGAAACATAGCACCACAGAGCCCGTTGGAGTTGATAATGGGCGGG

-continued

TACCGCAATAATCAAGCTTCCATTCTCGAGCGACGCCATGACGTACTTATGTTTAAC

CAGGGGTGGCAGCAATATGGTAACGTGATAAACGAGATAGTCACAGTCGGCCTCGG

CTACAAAACTGCGTTGCGCAAAGCTCTGTATACGTTCGCGGAGGGTTTTAAGAATAA

AGACTTTAAAGGCGCTGGGGTGAGTGTGCACGAGACGGCAGAACGCCATTTCTATC

GCCAGTCTGAACTCTTGATTCCCGACGTTCTGGCGAATGTCAATTTTTCCCAGGCCG

ATGAGGTCATTGCGGATCTGCGAGATAAGCTTCACCAGTTGTGTGAGATGCTGTTCA

ACCAGTCTGTGGCTCCTTATGCTCATCATCCCAAACTGATTTCAACTCTCGCTTTGGC

AAGGGCTACGTTGTATAAACACCTTAGAGAACTGAAGCCACAGGGTGGTCCCAGCA

ATGGCGGAAGCGGAGCTACTAACTTCAGCCTGCTGAAGCAGGCTGGAGACGTGGAG

GAGAACCCTGGACCTATGGATTACAAAGACGATGACGATAAGATGGCGCCTAAGAA

AAAGAGGAAAGTACGCGGGATGGCCGATGAAATAGACGCAATGGCTCTTTACCGAG

CATGGCAACAGCTCGACAATGGATCTTGCGCCCAAATACGGCGGGTAAGTGAACCC

GATGAACTGCGAGATATCCCCGCATTCTACCGATTGGTTCAGCCGTTTGGCTGGGAG

AACCCACGGCACCAGCAGGCGCTTCTTAGGATGGTTTTTTGTCTTAGTGCCGGGAAA

AACGTAATCCGCCATCAGGATAAGAAGTCCGAACAAACAACAGGGATTTCTCTGGG

AAGAGCGCTTGCTAACAGCGGCAGGATCAATGAACGCCGCATATTTCAGTTGATCC

GAGCAGATCGGACTGCTGATATGGTCCAGCTCAGGAGGCTCCTTACGCACGCAGAG

CCAGTGTTGGATTGGCCACTCATGGCAAGAATGCTTACGTGGTGGGGGAAGAGGGA

AAGGCAGCAACTGCTTGAAGATTTTGTATTGACGACGAACAAAAACGCGGGAAGCG

ATGGATTACAAAGACGATGACGATAAGATGGCGCCTAAGAAGAAGCGCAAGGTGA

GAGGAATGTCAAACTTCATTAATATCCACGTGCTTATCTCACACTCCCCTAGTTGCCT

TAACAGAGACGATATGAACATGCAAAAAGACGCAATTTTTGGCGGCAAAAGGAGAG

TCAGAATTAGTAGCCAGAGCCTGAAGCGCGCTATGAGGAAAAGCGGCTACTATGCT

CAAAACATTGGTGAAAGTTCATTGCGGACCATCCATCTCGCGCAGTTGAGGGACGTC

CTGCGACAGAAGCTTGGGGAAAGATTTGATCAGAAGATCATCGACAAAACGCTTGC

CCTTCTGTCCGGTAAATCAGTGGACGAAGCGGAGAAGATAAGTGCGGATGCTGTTA

CGCCATGGGTGGTAGGTGAAATCGCGTGGTTTTGCGAGCAGGTAGCCAAGGCCGAA

GCGGATAATTTGGATGATAAGAAACTGCTCAAAGTCCTCAAAGAGGACATCGCGGC

GATCCGGGTGAACCTTCAGCAGGGTGTTGATATTGCGCTCTCTGGTCGGATGGCCAC

GTCTGGAATGATGACTGAACTGGGTAAGGTGGACGGAGCTATGTCTATAGCTCATGC

TATAACTACCCATCAGGTGGATTCTGACATAGACTGGTTCACGGCTGTCGACGATCT

CCAGGAACAAGGATCCGCACACCTCGGCACGCAAGAATTTTCTTCTGGAGTGTTCTA

TAGGTATGCCAACATCAACCTTGCACAGCTCCAGGAAAACCTCGGTGGGGCAAGCC

GGGAACAGGCTCTTGAAATAGCTACCCATGTGGTTCACATGCTGGCGACCGAAGTG

CCAGGGGCCAAGCAGAGAACGTACGCCGCATTCAATCCGGCGGACATGGTCATGGT

GAATTTCTCTGATATGCCCTTGTCTATGGCAAATGCTTTCGAGAAGGCGGTCAAGGC

-continued

AAAGGACGGTTTTTTGCAACCCTCCATCCAAGCCTTTAATCAGTACTGGGATAGAGT

AGCTAACGGGTATGGTCTCAATGGCGCGGCTGCTCAGTTTTCTTTGTCCGATGTGGA

TCCGATAACGGCGCAGGTTAAACAGATGCCCACCTTGGAACAACTCAAATCCTGGG

TTAGAAACAATGGGGAGGCGGGAAGCGGAGTGAAACAGACTTTGAACTTTGACTTG

CTCAAGTTGGCAGGAGACGTGGAGTCCAACCCTGGACCTATGGGATCGGCCATTGA

ACAAGATGGATTGCACGCAGGTTCTCCGGCCGCTTGGGTGGAGAGGCTATTCGGCTA

TGACTGGGCACAACAGACAATCGGCTGCTCTGATGCCGCCGTGTTCCGGCTGTCAGC

GCAGGGGCGCCCGGTTCTTTTTGTCAAGACCGACCTGTCCGGTGCCCTGAATGAACT

GCAGGACGAGGCAGCGCGGCTATCGTGGCTGGCCACGACGGGCGTTCCTTGCGCAG

CTGTGCTCGACGTTGTCACTGAAGCGGGAAGGGACTGGCTGCTATTGGGCGAAGTG

CCGGGGCAGGATCTCCTGTCATCTCACCTTGCTCCTGCCGAGAAAGTATCCATCATG

GCTGATGCAATGCGGCGGCTGCATACGCTTGATCCGGCTACCTGCCCATTCGACCAC

CAAGCGAAACATCGCATCGAGCGAGCACGTACTCGGATGGAAGCCGGTCTTGTCGA

TCAGGATGATCTGGACGAAGAGCATCAGGGGCTCGCGCCAGCCGAACTGTTCGCCA

GGCTCAAGGCGCGCATGCCCGACGGCGATGATCTCGTCGTGACCCATGGCGATGCC

TGCTTGCCGAATATCATGGTGGAAAATGGCCGCTTTTCTGGATTCATCGACTGTGGC

CGGCTGGGTGTGGCGGACCGCTATCAGGACATAGCGTTGGCTACCCGTGATATTGCT

GAAGAGCTTGGCGGCGAATGGGCTGACCGCTTCCTCGTGCTTTACGGTATCGCCGCT

CCCGATTCGCAGCGCATCGCCTTCTATCGCCTTCTTGACGAGTTCTTCT

AgeI restriction enzyme site, EcoRI restriction enzyme site, Flag Epitope tag, Nuclear localization signal, *E. coli* K-12 CasD, *E. coli* K-12 CasE, VPR, Blast resistance, 2A sequences (SEQ ID NO: 297)

ACCGGTCGCCACCGCCGCCACCATGGATTACAAGGACGACGACGATAAGATGGCGC

CGAAGAAGAAGCGGAAAGTCCGGGGCATGAGATCCTACCTCATCCTGCGCCTGGCC

GGGCCGATGCAGGCCTGGGGCCAGCCTACATTTGAGGGTACCCGGCCCACCGGACG

GTTCCCGACCCGCTCGGGGCTTCTGGGACTTCTGGGCGCATGTCTGGGCATCCAGCG

GGATGACACTAGCAGCCTGCAGGCCCTGAGCGAATCCGTGCAGTTCGCCCGTGCGCT

GCGATGAACTGATCCTCGACGACCGCAGGGTGTCAGTGACTGGACTGAGAGACTAC

CACACCGTGCTGGGAGCCCGCGAGGATTACAGGGGCCTGAAGTCCCATGAAACCAT

TCAGACCTGGAGAGAGTACCTCTGCGACGCGTCGTTCACTGTGGCACTGTGGCTCAC

GCCGCACGCGACCATGGTCATCTCCGAACTGGAAAAAGCCGTGCTCAAGCCTCGGT

ACACCCCCTATCTCGGACGACGCTCCTGCCCACTGACCCATCCCCTGTTCCTCGGTA

CTTGCCAAGCCAGCGACCCTCAAAGGCTCTGTTGAACTACGAACCCGTGGGGGA

GACATCTACTCCGAGGAATCCGTCACCGGCCACCACTTGAAGTTCACCGCCCGGGAC

GAGCCGATGATTACTCTGCCAAGACAGTTCGCTTCACGGGAGTGGTACGTGATTAAG

GGTGGAATGGACGTGTCGCAGGGAAGCGGAGCTACTAACTTCAGCCTGCTGAAGCA

-continued

GGCTGGAGACGTGGAGGAGAACCCTGGACCTATGGATTACAAAGACGATGACGATA

AGATGGCGCCTAAGAAGAAGCGCAAGGTGCGGGGCATGTATCTCAGTAAAGTCATC

ATTGCCAGGGCCTGGAGCAGGGATCTTTACCAACTTCACCAGGGATTATGGCATTTA

TTTCCAAACAGACCGGATGCTGCTCGTGATTTTCTTTTTCATGTTGAGAAGCGAAAC

ACACCAGAAGGCTGTCATGTTTTATTGCAGTCAGCGCAAATGCCTGTTTCAACTGCC

GTTGCGACAGTCATTAAAACTAAACAGGTTGAATTTCAACTTCAGGTTGGTGTTCCA

CTCTATTTTCGGCTTCGGGCAAATCCGATCAAAACTATTCTCGACAATCAAAAGCGC

CTGGACAGTAAAGGGAATATTAAACGCTGTCGCGTTCCGTTAATAAAAGAAGCAGA

ACAAATCGCGTGGTTGCAACGTAAATTGGGCAATGCGGCGCGCGTTGAAGATGTGC

ATCCCATATCGGAACGGCCACAGTATTTTTCTGGTGATGGTAAAAGTGGAAAGATCC

AAACGGTTTGCTTTGAAGGTGTGCTCACCATCAACGACGCGCCAGCGTTAATAGATC

TTGTACAGCAAGGTATTGGGCCAGCTAAATCGATGGGATGTGGCTTGCTATCTTTGG

CTCCACTGCGGGGCAAGCGACCTGCCGCCACAAAGAAGGCTGGACAGGCTAAGAAG

AAGAAAGGATCCTCGCCAGGGATCCGTCGACTTGACGCGTTGATATCAACAAGTTTG

TACAAAAAAGCAGGCTACAAAGAGGCCAGCGGTTCCGGACGGGCTGACGCATTGGA

CGATTTTGATCTGGATATGCTGGGAAGTGACGCCCTCGATGATTTTGACCTTGACAT

GCTTGGTTCGGATGCCCTTGATGACTTTGACCTCGACATGCTCGGCAGTGACGCCCT

TGATGATTTCGACCTGGACATGCTGATTAACTCTAGAAGTTCCGGATCTGGAAAAAA

GAAAGGTAAAGTTGGTAGCCAGTACCTGCCCGACACCGACGACCGGCACCGGATCG

AGGAAAAGCGGAAGCGGACCTACGAGACATTCAAGAGCATCATGAAGAAGTCCCC

CTTCAGCGGCCCCACCGACCCTAGACCTCCACCTAGAAGAATCGCCGTGCCCAGCA

GATCCAGCGCCAGCGTGCCAAAACCTGCCCCCCAGCCTTACCCCTTCACCAGCAGCC

TGAGCACCATCAACTACGACGAGTTCCCTACCATGGTGTTCCCCAGCGGCCAGATCT

CTCAGGCCTCTGCTCTGGCTCCAGCCCCTCCTCAGGTGCTGCCTCAGGCTCCTGCTCC

TGCACCAGCTCCAGCCATGGTGTCTGCACTGGCTCAGGCACCAGCACCCGTGCCTGT

GCTGGCTCCTGGACCTCCACAGGCTGTGGCTCCACCAGCCCCTAAACCTACACAGGC

CGGCGAGGGCACACTGTCTGAAGCTCTGCTGCAGCTGCAGTTCGACGACGAGGATC

TGGGAGCCCTGCTGGGAAACAGCACCGATCCTGCCGTGTTCACCGACCTGGCCAGC

GTGGACAACAGCGAGTTCCAGCAGCTGCTGAACCAGGGCATCCCTGTGGCCCCTCA

CACCACCGAGCCCATGCTGATGGAATACCCCGAGGCCATCACCCGGCTCGTGACAG

GCGCTCAGAGGCCTCCTGATCCAGCTCCTGCCCCTCTGGGAGCACCAGGCCTGCCTA

ATGGACTGCTGTCTGGCGACGAGGACTTCAGCTCTATCGCCGATATGGATTTCTCAG

CCTTGCTGGGCTCTGGCAGCGGCAGCCGGGATTCCAGGGAAGGGATGTTTTTGCCGA

AGCCTGAGGCCGGCTCCGCTATTAGTGACGTGTTTGAGGGCCGCGAGGTGTGCCAGC

CAAAACGAATCCGGCCATTTCATCCTCCAGGAAGTCCATGGGCCAACCGCCCCACTCC

CCGCCAGCCTCGCACCAACACCAACCGGTCCAGTACATGAGCCAGTCGGGTCACTC

-continued

ACCCCGGCACCAGTCCCTCAGCCACTGGATCCAGCGCCCGCAGTGACTCCCGAGGC

CAGTCACCTGTTGGAGGATCCCGATGAAGAGACCGAGCCAGGCTGTCAAAGCCCTTC

GGGAGATGGCCGATACTGTGATTCCCCAGAAGGAAGAGGCTGCAATCTGTGGCCAA

ATGGACCTTTCCCATCCGCCCCCAAGGGGCCATCTGGATGAGCTGACAACCACACTT

GAGTCCATGACCGAGGATCTGAACCTGGACTCACCCCTGACCCCGGAATTGAACGA

GATTCTGGATACCTTCCTGAACGACGAGTGCCTCTTGCATGCCATGCATATCAGCAC

AGGACTGTCCATCTTCGACACATCTCTGTTCGGAAGCGGAGAGGGCAGAGGAAGTC

TTCTCACATGCGGTGACGTGGAGGAGAATCCTGGACCTAAGACCTTCAACATCTCTC

AGCAGGATCTGGAGCTGGTGGAGGTCGCCACTGAGAAGATCACCATGCTCTATGAG

GACAACAAGCACCATGTCGGGGCGGCCATCAGGACCAAGACTGGGGAGATCATCTC

TGCTGTCCACATTGAGGCCTACATTGGCAGGGTCACTGTCTGTGCTGAAGCCATTGC

CATTGGGTCTGCTGTGAGCAACGGGCAGAAGGACTTTGACACCATTGTGGCTGTCAG

GCACCCCTACTCTGATGAGGTGGACAGATCCATCAGGGTGGTCAGCCCCTGTGGCAT

GTGCAGAGAGCTCATCTCTGACTATGCTCCTGACTGCTTTGTGCTCATTGAGATGAA

TGGCAAGCTGGTCAAAACCACCATTGAGGAACTCATCCCCCTCAAGTACACCAGGA

ACTAAGAATTC

It is understood that the foregoing detailed description and accompanying examples are merely illustrative and are not to be taken as limitations upon the scope of the disclosure, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the disclosure, can be made without departing from the spirit and scope thereof.

What is claimed is:

1. A method of activating the expression of a target gene in a eukaryotic cell in vitro, the method comprising introducing to the eukaryotic cell a composition comprising at least one polynucleotide sequence encoding:

(a) a Cascade complex comprising three or more Cascade polypeptides selected from a CasA polypeptide, a CasB polypeptide, a CasC polypeptide, a CasD polypeptide, and a CasE polypeptide, wherein at least one Cascade polypeptide is fused to a polypeptide domain having transcription activation activity, wherein the CasA polypeptide is encoded by a polynucleotide comprising SEQ ID NO: 377, wherein the CasB polypeptide is encoded by a polynucleotide comprising SEQ ID NO: 378, wherein the CasC polypeptide is encoded by a polynucleotide comprising SEQ ID NO: 379, wherein the CasD polypeptide is encoded by a polynucleotide comprising SEQ ID NO: 380, and wherein the CasE polypeptide is encoded by a polynucleotide comprising SEQ ID NO: 381; and (b) at least one crRNA, wherein the crRNA targets a target nucleotide sequence in the target gene, wherein the at least one polynucleotide sequence is operably linked to a eukaryotic promoter, comprises a nuclear localization signal, and is codon-optimized.

2. The method of claim 1, the method further comprising introducing to the eukaryotic cell:

a dCas9 protein or a polynucleotide sequence encoding a dCas9 protein; and a guide RNA (gRNA).

3. The method of claim 1, wherein the polypeptide domain having transcription activation activity is fused to the N terminus and/or the C terminus of at least one of the three or more Cascade polypeptides.

4. The method of claim 1, wherein the polypeptide domain having transcription activation activity comprises a p300 core domain, a VP64-p65-Rta tripartite activator (VPR) domain, an amino acid sequence of SEQ ID NO: 9, or an amino acid sequence of SEQ ID NO: 11.

5. The method of claim 1, wherein each polynucleotide sequence encoding each Cascade polypeptide is operably linked to a eukaryotic promoter, comprises a nuclear localization signal, and is operably linked to a terminator.

6. The method of claim 1, wherein two or more Cascade polypeptides, or functional fragments thereof, are fused to form a single polypeptide.

7. The method of claim 1, wherein two or more Cascade polypeptides are encoded by a multicistronic polynucleotide sequence and separated by at least one 2A peptide.

8. The method of claim 1, wherein the at least one Cascade polypeptide fused to a polypeptide domain having transcription activation activity is encoded by a polynucleotide comprising the sequence of SEQ ID NO: 6, SEQ ID NO: 7, or SEQ ID NO: 8.

9. The method of claim 1, wherein the at least one Cascade polypeptide fused to a polypeptide domain having transcription activation activity further comprises an epitope tag.

10. The method of claim 1, wherein the at least one polynucleotide sequence encoding the at least one crRNA comprises a spacer nucleotide sequence linked to a repeat nucleotide sequence at its 5' end and at its 3' end.

11. The method of claim 1, wherein the at least one polynucleotide sequence encoding the at least one crRNA comprises a recombinant CRISPR array comprising two or more repeat nucleotide sequences and two or more spacer nucleotide sequence(s), wherein each spacer nucleotide sequence in said CRISPR array is linked at its 5' end and at its 3' end to a repeat nucleotide sequence, wherein the recombinant CRISPR array is operably linked to a eukaryotic promoter, comprises a nuclear localization signal, and is operably linked to a terminator, and wherein at least two of the two or more spacer nucleotide sequence(s) each comprise a nucleotide sequence that is complementary to a different target nucleotide sequence from a single target gene or a different target gene.

12. The method of claim 1, wherein the at least one crRNA comprises a polynucleotide sequence selected from SEQ ID NOs: 15-66.

* * * * *

SEQUENCE LISTING

```
<160> NUMBER OF SEQ ID NOS: 381

<210> SEQ ID NO 1
<211> LENGTH: 1572
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1

atggattaca aagacgatga cgataagatg gcgcctaaga agaaacgcaa agtgcggggc     60

atggccaatc tcctgattga caattggatc cctgtgagac cgaggaacgg agggaaggtt    120

cagatcatca acctgcaaag tctctactgt agcagagatc aatggcgact ctcattgccc    180

agggatgata tggaattggc ggcacttgca ctcttggtat gtattgggca gatcatcgcc    240

cctgccaagg atgatgtcga gtttaggcac agaataatga accctcttac tgaagatgaa    300

ttccagcaat tgatcgcgcc ttggatagat atgttctatt tgaatcacgc cgaacatccc    360

ttcatgcaga caaaaggggt taaagcaaat gatgtcacac caatggagaa gcttttggca    420

ggtgtgtcag gagcaaccaa ctgcgctttc gttaaccaac caggccaagg tgaggcgttg    480

tgcggggggt gcacggccat agcgttgttt aatcaggcga accaggctcc tggctttgga    540
```

```
ggaggattca agtccggttt gcgcgggggt acacccgtaa ccacattcgt tcgcggaatt    600

gacctccgat caacagtcct gttgaacgta ttgacgttgc ctagacttca gaagcaattt    660

ccaaacgagt ctcacactga gaatcaaccg acttggatta agcccatcaa gtcaaatgaa    720

agtatacccg cgtcttctat tggatttgtt agaggacttt tttggcagcc cgctcacata    780

gaactctgtg atcccatagg cattggaaag tgttcttgct gtggccaaga gtctaacctt    840

agatatacgg gctttctcaa ggagaagttc acgttcaccg tgaatggact ttggccacat    900

ccccatagcc cgtgcttggt cacggtcaag aagggggagg ttgaagagaa atttcttgcg    960

tttaccacat ccgccccatc ctggacgcaa atatctcgcg tcgttgtgga taaaatcatc   1020

cagaacgaaa atggtaaccg cgttgccgcg gtagtgaatc aattcagaaa catagcacca   1080

cagagcccgt tggagttgat aatgggcggg taccgcaata atcaagcttc cattctcgag   1140

cgacgccatg acgtacttat gtttaaccag gggtggcagc aatatggtaa cgtgataaac   1200

gagatagtca cagtcggcct cggctacaaa actgcgttgc gcaaagctct gtatacgttc   1260

gcggagggtt ttaagaataa agactttaaa ggcgctgggg tgagtgtgca cgagacggca   1320

gaacgccatt tctatcgcca gtctgaactc ttgattcccg acgttctggc gaatgtcaat   1380

ttttcccagg ccgatgaggt cattgcggat ctgcgagata agcttcacca gttgtgtgag   1440

atgctgttca accagtctgt ggctccttat gctcatcatc ccaaactgat ttcaactctc   1500

gctttggcaa gggctacgtt gtataaacac cttagagaac tgaagccaca gggtggtccc   1560

agcaatggct ga                                                       1572


<210> SEQ ID NO 2
<211> LENGTH: 543
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2

atggattaca aagacgatga cgataagatg gcgcctaaga aaaagaggaa agtacgcggg     60

atggccgatg aaatagacgc aatggctctt taccgagcat ggcaacagct cgacaatgga    120

tcttgcgccc aaatacggcg ggtaagtgaa cccgatgaac tgcgagatat ccccgcattc    180

taccgattgg ttcagccgtt tggctgggag aacccacggc accagcaggc gcttcttagg    240

atggtttttt gtcttagtgc cgggaaaaac gtaatccgcc atcaggataa gaagtccgaa    300

caaacaacag ggatttctct gggaagagcg cttgctaaca gcggcaggat caatgaacgc    360

cgcatatttc agttgatccg agcagatcgg actgctgata tggtccagct caggaggctc    420

cttacgcacg cagagccagt gttggattgg ccactcatgg caagaatgct tacgtggtgg    480

gggaagaggg aaaggcagca actgcttgaa gattttgtat tgacgacgaa caaaaacgcg    540

taa                                                                  543


<210> SEQ ID NO 3
<211> LENGTH: 1152
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3

atggattaca aagacgatga cgataagatg gcgcctaaga agaagcgcaa ggtgagagga     60
```

```
atgtcaaact tcattaatat ccacgtgctt atctcacact cccctagttg ccttaacaga    120

gacgatatga acatgcaaaa agacgcaatt tttggcggca aaaggagagt cagaattagt    180

agccagagcc tgaagcgcgc tatgaggaaa agcggctact atgctcaaaa cattggtgaa    240

agttcattgc ggaccatcca tctcgcgcag ttgagggacg tcctgcgaca gaagcttggg    300

gaaagatttg atcagaagat catcgacaaa acgcttgccc ttctgtccgg taaatcagtg    360

gacgaagcgg agaagataag tgcggatgct gttacgccat gggtggtagg tgaaatcgcg    420

tggttttgcg agcaggtagc caaggccgaa gcggataatt tggatgataa gaaactgctc    480

aaagtcctca aagaggacat cgcggcgatc cgggtgaacc ttcagcaggg tgttgatatt    540

gcgctctctg gtcggatggc cacgtctgga atgatgactg aactgggtaa ggtggacgga    600

gctatgtcta tagctcatgc tataactacc catcaggtgg attctgacat agactggttc    660

acggctgtcg acgatctcca ggaacaagga tccgcacacc tcggcacgca agaattttct    720

tctggagtgt tctataggta tgccaacatc aaccttgcac agctccagga aaacctcggt    780

ggggcaagcc gggaacaggc tcttgaaata gctacccatg tggttcacat gctggcgacc    840

gaagtgccag gggccaagca gagaacgtac gccgcattca atccggcgga catggtcatg    900

gtgaatttct ctgatatgcc cttgtctatg gcaaatgctt tcgagaaggc ggtcaaggca    960

aaggacggtt ttttgcaacc ctccatccaa gcctttaatc agtactggga tagagtagct   1020

aacgggtatg gtctcaatgg cgcggctgct cagttttctt tgtccgatgt ggatccgata   1080

acggcgcagg ttaaacagat gcccaccttg gaacaactca aatcctgggt tagaaacaat   1140

ggggaggcgt ga                                                       1152
```

<210> SEQ ID NO 4
<211> LENGTH: 735
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 4

```
atggattaca aagacgatga cgataagatg gcgcctaaga aaaagaggaa agtacggggc     60

atgcgatcat acttgatcct gcggcttgca ggtcctatgc aagcctgggg gcaacctacc    120

tttgaaggta ctcggccgac tggcaggttc cctacgcggt ctggtttgct cggactcctc    180

ggcgcctgtt tggggataca aagggatgac acttcttcct tgcaggcact ttccgaatca    240

gtccagttcg cagtgagatg tgatgaactc atactggacg acagacgggt gtccgtaact    300

ggactgaggg actatcatac tgtactcggc gcaagagaag attatcgagg tcttaagtca    360

catgagacta ttcagacatg gagggaatat ttgtgtgacg cctccttcac ggtggccctc    420

tggcttacac cacatgcaac tatggtgatc tcagagcttg agaaagccgt tcttaaacct    480

cggtacacac catatctggg gaggcggtct tgcccactta cccacccgct tttcttgggg    540

acttgtcagg ccagcgatcc acagaaggcc ttgctgaact atgaacccgt tggtggcgat    600

atatacagtg aagagagcgt cacgggccat cacttgaagt tcactgctag ggatgagccg    660

atgattacgc tcccgagaca gttcgctagt agggaatggt acgttattaa ggggggaatg    720

gacgtttccc aatga                                                     735
```

<210> SEQ ID NO 5
<211> LENGTH: 660

<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 5
atggattaca aagacgatga cgataagatg gcgcctaaga agaagcgcaa ggtgcggggc 60
atgtatctca gtaaagtcat cattgccagg gcctggagca gggatcttta ccaacttcac 120
cagggattat ggcatttatt tccaaacaga ccggatgctg ctcgtgattt tctttttcat 180
gttgagaagc gaaacacacc agaaggctgt catgttttat tgcagtcagc gcaaatgcct 240
gtttcaactg ccgttgcgac agtcattaaa actaaacagg ttgaatttca acttcaggtt 300
ggtgttccac tctattttcg gcttcgggca aatccgatca aaactattct cgacaatcaa 360
aagcgcctgg acagtaaagg gaatattaaa cgctgtcggg ttccgttaat aaaagaagca 420
gaacaaatcg cgtggttgca acgtaaattg ggcaatgcgg cgcgcgttga agatgtgcat 480
cccatatcgg aacggccaca gtatttttct ggtgatggta aaagtggaaa gatccaaacg 540
gtttgctttg aaggtgtgct caccatcaac gacgcgccag cgttaataga tcttgtacag 600
caaggtattg ggccagctaa atcgatggga tgtggcttgc tatctttggc tccactgtga 660

<210> SEQ ID NO 6
<211> LENGTH: 2616
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 6
atgggtgccc cagttcccta tcccgaccca ctggagccaa ggatggcgcc taagaagaag 60
cgcaaggtgc ggggcatgta tctcagtaaa gtcatcattg ccagggcctg gagcagggat 120
ctttaccaac ttcaccaggg attatggcat ttatttccaa acagaccgga tgctgctcgt 180
gattttcttt ttcatgttga gaagcgaaac acaccagaag gctgtcatgt tttattgcag 240
tcagcgcaaa tgcctgtttc aactgccgtt gcgacagtca ttaaaactaa acaggttgaa 300
tttcaacttc aggttggtgt tccactctat tttcggcttc gggcaaatcc gatcaaaact 360
attctcgaca atcaaaagcg cctggacagt aaagggaata ttaaacgctg tcgggttccg 420
ttaataaaag aagcagaaca aatcgcgtgg ttgcaacgta aattgggcaa tgcggcgcgc 480
gttgaagatg tgcatcccat atcggaacgg ccacagtatt tttctggtga tggtaaaagt 540
ggaaagatcc aaacggtttg ctttgaaggt gtgctcacca tcaacgacgc gccagcgtta 600
atagatcttg tacagcaagg tattgggcca gctaaatcga tgggatgtgg cttgctatct 660
ttggctccac tgcggggcaa gcgacctgcc gccacaaaga aggctggaca ggctaagaag 720
aagaaaggat ccattttcaa accagaagaa ctacgacagg cactgatgcc aactttggag 780
gcactttacc gtcaggatcc agaatccctt ccctttcgtc aacctgtgga ccctcagctt 840
ttaggaatcc ctgattactt tgatattgtg aagagcccca tggatctttc taccattaag 900
aggaagttag acactggaca gtatcaggag ccctggcagt atgtcgatga tatttggctt 960
atgttcaata atgcctggtt atataaccgg aaaacatcac gggtatacaa atactgctcc 1020
aagctctctg aggtctttga acaagaaatt gacccagtga tgcaaagcct tggatactgt 1080
tgtggcagaa agttggagtt ctctccacag acactgtgtt gctacggcaa acagttgtgc 1140
acaatacctc gtgatgccac ttattacagt taccagaaca ggtatcattt ctgtgagaag 1200
tgtttcaatg agatccaagg ggagagcgtt tctttggggg atgacccttc ccagcctcaa 1260
actacaataa ataaagaaca attttccaag agaaaaaatg acacactgga tcctgaactg 1320
tttgttgaat gtacagagtg cggaagaaag atgcatcaga tctgtgtcct tcaccatgag 1380
atcatctggc ctgctggatt cgtctgtgat ggctgtttaa agaaaagtgc acgaactagg 1440
aaagaaaata agttttctgc taaaaggttg ccatctacca gacttggcac ctttctagag 1500
aatcgtgtga atgactttct gaggcgacag aatcaccctg agtcaggaga ggtcactgtt 1560
agagtagttc atgcttctga caaaaccgtg gaagtaaaac caggcatgaa agcaaggttt 1620
gtggacagtg gagagatggc agaatccttt ccataccgaa ccaaagccct ctttgccttt 1680
gaagaaattg atggtgttga cctgtgcttc tttggcatgc atgttcaaga gtatggctct 1740
gactgccctc cacccaacca gaggagagta tacatatctt acctcgatag tgttcatttc 1800
ttccgtccta aatgcttgag gactgcagtc tatcatgaaa tcctaattgg atatttagaa 1860
tatgtcaaga aattaggtta cacaacaggg catatttggg catgtccacc aagtgaggga 1920
gatgattata tcttccattg ccatcctcct gaccagaaga tacccaagcc caagcgactg 1980
caggaatggt acaaaaaaat gcttgacaag gctgtatcag agcgtattgt ccatgactac 2040
aaggatattt ttaaacaagc tactgaagat agattaacaa gtgcaaagga attgccttat 2100
ttcgagggtg atttctggcc caatgttctg gaagaaagca ttaaggaact ggaacaggag 2160
gaagaagaga gaaaacgaga ggaaaacacc agcaatgaaa gcacagatgt gaccaaggga 2220
gacagcaaaa atgctaaaaa gaagaataat aagaaaacca gcaaaaataa gagcagcctg 2280
agtaggggca acaagaagaa acccgggatg cccaatgtat ctaacgacct ctcacagaaa 2340
ctatatgcca ccatggagaa gcataaagag gtcttctttg tgatccgcct cattgctggc 2400
cctgctgcca actccctgcc tcccattgtt gatcctgatc ctctcatccc ctgcgatctg 2460
atggatggtc gggatgcgtt tctcacgctg gcaagggaca agcacctgga gttctcttca 2520
ctccgaagag cccagtggtc caccatgtgc atgctggtgg agctgcacac gcagagccag 2580
gacggatccg attacaaaga cgatgacgat aagtga 2616

<210> SEQ ID NO 7
<211> LENGTH: 2379
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 7
atggattaca aagacgatga cgataagatg gcgcctaaga agaagcgcaa ggtgcggggc 60
atgtatctca gtaaagtcat cattgccagg gcctggagca gggatcttta ccaacttcac 120
cagggattat ggcatttatt tccaaacaga ccggatgctg ctcgtgattt tctttttcat 180
gttgagaagc gaaacacacc agaaggctgt catgttttat tgcagtcagc gcaaatgcct 240
gtttcaactg ccgttgcgac agtcattaaa actaaacagg ttgaatttca acttcaggtt 300
ggtgttccac tctattttcg gcttcgggca aatccgatca aaactattct cgacaatcaa 360
aagcgcctgg acagtaaagg gaatattaaa cgctgtcggg ttccgttaat aaaagaagca 420
gaacaaatcg cgtggttgca acgtaaattg ggcaatgcgg cgcgcgttga agatgtgcat 480
cccatatcgg aacggccaca gtatttttct ggtgatggta aaagtggaaa gatccaaacg 540

```
gtttgctttg aaggtgtgct caccatcaac gacgcgccag cgttaataga tcttgtacag    600
caaggtattg ggccagctaa atcgatggga tgtggcttgc tatctttggc tccactgcgg    660
ggcaagcgac ctgccgccac aaagaaggct ggacaggcta agaagaagaa aggatcctcg    720
ccagggatcc gtcgacttga cgcgttgata tcaacaagtt tgtacaaaaa agcaggctac    780
aaagaggcca gcggttccgg acgggctgac gcattggacg attttgatct ggatatgctg    840
ggaagtgacg ccctcgatga ttttgacctt gacatgcttg gttcggatgc ccttgatgac    900
tttgacctcg acatgctcgg cagtgacgcc cttgatgatt tcgacctgga catgctgatt    960
aactctagaa gttccggatc tccgaaaaag aaacgcaaag ttggtagcca gtacctgccc   1020
gacaccgacg accggcaccg gatcgaggaa aagcggaagc ggacctacga gacattcaag   1080
agcatcatga agaagtcccc cttcagcggc cccaccgacc ctagacctcc acctagaaga   1140
atcgccgtgc ccagcagatc cagcgccagc gtgccaaaac ctgcccccca gccttacccc   1200
ttcaccagca gcctgagcac catcaactac gacgagttcc ctaccatggt gttccccagc   1260
ggccagatct ctcaggcctc tgctctggct ccagcccctc ctcaggtgct gcctcaggct   1320
cctgctcctg caccagctcc agccatggtg tctgcactgg ctcaggcacc agcacccgtg   1380
cctgtgctgg ctcctggacc tccacaggct gtggctccac cagcccctaa acctacacag   1440
gccggcgagg gcacactgtc tgaagctctg ctgcagctgc agttcgacga cgaggatctg   1500
ggagccctgc tgggaaacag caccgatcct gccgtgttca ccgacctggc cagcgtggac   1560
aacagcgagt tccagcagct gctgaaccag ggcatccctg tggcccctca caccaccgag   1620
cccatgctga tggaataccc cgaggccatc acccggctcg tgacaggcgc tcagaggcct   1680
cctgatccag ctcctgcccc tctgggagca ccaggcctgc ctaatggact gctgtctggc   1740
gacgaggact tcagctctat cgccgatatg gatttctcag ccttgctggg ctctggcagc   1800
ggcagccggg attccaggga agggatgttt ttgccgaagc ctgaggccgg ctccgctatt   1860
agtgacgtgt ttgagggccg cgaggtgtgc cagccaaaac gaatccggcc atttcatcct   1920
ccaggaagtc catgggccaa ccgcccactc cccgccagcc tcgcaccaac accaaccggt   1980
ccagtacatg agccagtcgg gtcactgacc ccggcaccag tccctcagcc actggatcca   2040
gcgcccgcag tgactcccga ggccagtcac ctgttggagg atcccgatga agagacgagc   2100
caggctgtca aagcccttcg ggagatggcc gatactgtga ttccccagaa ggaagaggct   2160
gcaatctgtg gccaaatgga cctttcccat ccgcccccaa ggggccatct ggatgagctg   2220
acaaccacac ttgagtccat gaccgaggat ctgaacctgg actcacccct gaccccggaa   2280
ttgaacgaga ttctggatac cttcctgaac gacgagtgcc tcttgcatgc catgcatatc   2340
agcacaggac tgtccatctt cgacacatct ctgttctga                          2379
```

<210> SEQ ID NO 8
<211> LENGTH: 3519
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 8

```
atggagcaaa aattgatcag tgaagaagac ctgatggcac caaaaaagaa acgcaaagtg     60
cggggcatgg ccaatctcct gattgacaat tggatccctg tgagaccgag gaacggaggg    120
aaggttcaga tcatcaacct gcaaagtctc tactgtagca gagatcaatg gcgactctca    180
```

-continued

```
ttgcccaggg atgatatgga attggcggca cttgcactct tggtatgtat tgggcagatc    240
atcgcccctg ccaaggatga tgtcgagttt aggcacagaa taatgaaccc tcttactgaa    300
gatgaattcc agcaattgat cgcgccttgg atagatatgt tctatttgaa tcacgccgaa    360
catcccttca tgcagacaaa aggggttaaa gcaaatgatg tcacaccaat ggagaagctt    420
ttggcaggtg tgtcaggagc aaccaactgc gctttcgtta accaaccagg ccaaggtgag    480
gcgttgtgcg gggggtgcac ggccatagcg ttgtttaatc aggcgaacca ggctcctggc    540
tttggaggag gattcaagtc cggtttgcgc gggggtacac ccgtaaccac attcgttcgc    600
ggaattgacc tccgatcaac agtcctgttg aacgtattga cgttgcctag acttcagaag    660
caatttccaa acgagtctca cactgagaat caaccgactt ggattaagcc catcaagtca    720
aatgaaagta tacccgcgtc ttctattgga tttgttagag gactttttttg gcagcccgct    780
cacatagaac tctgtgatcc cataggcatt ggaaagtgtt cttgctgtgg ccaagagtct    840
aaccttagat atacgggctt tctcaaggag aagttcacgt tcaccgtgaa tggactttgg    900
ccacatcccc atagcccgtg cttggtcacg gtcaagaagg gggaggttga agagaaattt    960
cttgcgttta ccacatccgc cccatcctgg acgcaaatat ctcgcgtcgt tgtggataaa   1020
atcatccaga acgaaaatgg taaccgcgtt gccgcggtag tgaatcaatt cagaaacata   1080
gcaccacaga gcccgttgga gttgataatg ggcgggtacc gcaataatca agcttccatt   1140
ctcgagcgac gccatgacgt acttatgttt aaccaggggt ggcagcaata tggtaacgtg   1200
ataaacgaga tagtcacagt cggcctcggc tacaaaaactg cgttgcgcaa agctctgtat   1260
acgttcgcgg agggttttaa gaataaagac tttaaaggcg ctggggtgag tgtgcacgag   1320
acggcagaac gccatttcta tcgccagtct gaactcttga ttcccgacgt tctggcgaat   1380
gtcaattttt cccaggccga tgaggtcatt gcggatctgc gagataagct tcaccagttg   1440
tgtgagatgc tgttcaacca gtctgtggct ccttatgctc atcatcccaa actgatttca   1500
actctcgctt tggcaagggc tacgttgtat aaacacctta gagaactgaa gccacagggt   1560
ggtcccagca atggccgggg caagcgacct gccgccacaa agaaggctgg acaggctaag   1620
aagaagaaag gatccatttt caaaccagaa gaactacgac aggcactgat gccaactttg   1680
gaggcacttt accgtcagga tccagaatcc cttccctttc gtcaacctgt ggaccctcag   1740
cttttaggaa tccctgatta ctttgatatt gtgaagagcc ccatggatct ttctaccatt   1800
aagaggaagt tagacactgg acagtatcag gagccctggc agtatgtcga tgatatttgg   1860
cttatgttca ataatgcctg gttatataac cggaaaacat cacgggtata caaatactgc   1920
tccaagctct ctgaggtctt tgaacaagaa attgacccag tgatgcaaag ccttggatac   1980
tgttgtggca gaaagttgga gttctctcca cagacactgt gttgctacgg caaacagttg   2040
tgcacaatac ctcgtgatgc cacttattac agttaccaga acaggtatca tttctgtgag   2100
aagtgtttca atgagatcca aggggagagc gtttctttgg gggatgaccc ttcccagcct   2160
caaactacaa taaataaaga acaattttcc aagagaaaaa atgacacact ggatcctgaa   2220
ctgtttgttg aatgtacaga gtgcggaaga aagatgcatc agatctgtgt ccttcaccat   2280
gagatcatct ggcctgctgg attcgtctgt gatggctgtt taaagaaaag tgcacgaact   2340
aggaaagaaa ataagttttc tgctaaaagg ttgccatcta ccagacttgg cacctttcta   2400
gagaatcgtg tgaatgactt tctgaggcga cagaatcacc ctgagtcagg agaggtcact   2460
gttagagtag ttcatgcttc tgacaaaacc gtggaagtaa aaccaggcat gaaagcaagg   2520
tttgtggaca gtggagagat ggcagaatcc tttccatacc gaaccaaagc cctctttgcc   2580
```

```
tttgaagaaa ttgatggtgt tgacctgtgc ttctttggca tgcatgttca agagtatggc   2640

tctgactgcc ctccacccaa ccagaggaga gtatacatat cttacctcga tagtgttcat   2700

ttcttccgtc ctaaatgctt gaggactgca gtctatcatg aaatcctaat tggatattta   2760

gaatatgtca agaaattagg ttacacaaca gggcatattt gggcatgtcc accaagtgag   2820

ggagatgatt atatcttcca ttgccatcct cctgaccaga agatacccaa gcccaagcga   2880

ctgcaggaat ggtacaaaaa aatgcttgac aaggctgtat cagagcgtat tgtccatgac   2940

tacaaggata tttttaaaca agctactgaa gatagattaa caagtgcaaa ggaattgcct   3000

tatttcgagg gtgatttctg gcccaatgtt ctggaagaaa gcattaagga actggaacag   3060

gaggaagaag agagaaaacg agaggaaaac accagcaatg aaagcacaga tgtgaccaag   3120

ggagacagca aaaatgctaa aaagaagaat aataagaaaa ccagcaaaaa taagagcagc   3180

ctgagtaggg gcaacaagaa gaaacccggg atgcccaatg tatctaacga cctctcacag   3240

aaactatatg ccaccatgga gaagcataaa gaggtcttct ttgtgatccg cctcattgct   3300

ggccctgctg ccaactccct gcctcccatt gttgatcctg atcctctcat cccctgcgat   3360

ctgatggatg gtcgggatgc gtttctcacg ctggcaaggg acaagcacct ggagttctct   3420

tcactccgaa gagcccagtg gtccaccatg tgcatgctgg tggagctgca cacgcagagc   3480

caggacggat ccgattacaa agacgatgac gataagtga                          3519
```

```
<210> SEQ ID NO 9
<211> LENGTH: 617
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Ile Phe Lys Pro Glu Glu Leu Arg Gln Ala Leu Met Pro Thr Leu Glu
1               5                   10                  15

Ala Leu Tyr Arg Gln Asp Pro Glu Ser Leu Pro Phe Arg Gln Pro Val
            20                  25                  30

Asp Pro Gln Leu Leu Gly Ile Pro Asp Tyr Phe Asp Ile Val Lys Ser
        35                  40                  45

Pro Met Asp Leu Ser Thr Ile Lys Arg Lys Leu Asp Thr Gly Gln Tyr
    50                  55                  60

Gln Glu Pro Trp Gln Tyr Val Asp Asp Ile Trp Leu Met Phe Asn Asn
65                  70                  75                  80

Ala Trp Leu Tyr Asn Arg Lys Thr Ser Arg Val Tyr Lys Tyr Cys Ser
                85                  90                  95

Lys Leu Ser Glu Val Phe Glu Gln Glu Ile Asp Pro Val Met Gln Ser
            100                 105                 110

Leu Gly Tyr Cys Cys Gly Arg Lys Leu Glu Phe Ser Pro Gln Thr Leu
        115                 120                 125

Cys Cys Tyr Gly Lys Gln Leu Cys Thr Ile Pro Arg Asp Ala Thr Tyr
    130                 135                 140

Tyr Ser Tyr Gln Asn Arg Tyr His Phe Cys Glu Lys Cys Phe Asn Glu
145                 150                 155                 160

Ile Gln Gly Glu Ser Val Ser Leu Gly Asp Asp Pro Ser Gln Pro Gln
                165                 170                 175

Thr Thr Ile Asn Lys Glu Gln Phe Ser Lys Arg Lys Asn Asp Thr Leu
            180                 185                 190
```

```
Asp Pro Glu Leu Phe Val Glu Cys Thr Glu Cys Gly Arg Lys Met His
        195                 200                 205

Gln Ile Cys Val Leu His His Glu Ile Ile Trp Pro Ala Gly Phe Val
    210                 215                 220

Cys Asp Gly Cys Leu Lys Lys Ser Ala Arg Thr Arg Lys Glu Asn Lys
225                 230                 235                 240

Phe Ser Ala Lys Arg Leu Pro Ser Thr Arg Leu Gly Thr Phe Leu Glu
                245                 250                 255

Asn Arg Val Asn Asp Phe Leu Arg Arg Gln Asn His Pro Glu Ser Gly
            260                 265                 270

Glu Val Thr Val Arg Val Val His Ala Ser Asp Lys Thr Val Glu Val
        275                 280                 285

Lys Pro Gly Met Lys Ala Arg Phe Val Asp Ser Gly Glu Met Ala Glu
    290                 295                 300

Ser Phe Pro Tyr Arg Thr Lys Ala Leu Phe Ala Phe Glu Glu Ile Asp
305                 310                 315                 320

Gly Val Asp Leu Cys Phe Phe Gly Met His Val Gln Glu Tyr Gly Ser
                325                 330                 335

Asp Cys Pro Pro Pro Asn Gln Arg Arg Val Tyr Ile Ser Tyr Leu Asp
            340                 345                 350

Ser Val His Phe Phe Arg Pro Lys Cys Leu Arg Thr Ala Val Tyr His
        355                 360                 365

Glu Ile Leu Ile Gly Tyr Leu Glu Tyr Val Lys Lys Leu Gly Tyr Thr
    370                 375                 380

Thr Gly His Ile Trp Ala Cys Pro Pro Ser Glu Gly Asp Asp Tyr Ile
385                 390                 395                 400

Phe His Cys His Pro Pro Asp Gln Lys Ile Pro Lys Pro Lys Arg Leu
                405                 410                 415

Gln Glu Trp Tyr Lys Lys Met Leu Asp Lys Ala Val Ser Glu Arg Ile
            420                 425                 430

Val His Asp Tyr Lys Asp Ile Phe Lys Gln Ala Thr Glu Asp Arg Leu
        435                 440                 445

Thr Ser Ala Lys Glu Leu Pro Tyr Phe Glu Gly Asp Phe Trp Pro Asn
    450                 455                 460

Val Leu Glu Glu Ser Ile Lys Glu Leu Glu Gln Glu Glu Glu Glu Arg
465                 470                 475                 480

Lys Arg Glu Glu Asn Thr Ser Asn Glu Ser Thr Asp Val Thr Lys Gly
                485                 490                 495

Asp Ser Lys Asn Ala Lys Lys Lys Asn Asn Lys Lys Thr Ser Lys Asn
            500                 505                 510

Lys Ser Ser Leu Ser Arg Gly Asn Lys Lys Lys Pro Gly Met Pro Asn
        515                 520                 525

Val Ser Asn Asp Leu Ser Gln Lys Leu Tyr Ala Thr Met Glu Lys His
    530                 535                 540

Lys Glu Val Phe Phe Val Ile Arg Leu Ile Ala Gly Pro Ala Ala Asn
545                 550                 555                 560

Ser Leu Pro Pro Ile Val Asp Pro Asp Pro Leu Ile Pro Cys Asp Leu
                565                 570                 575

Met Asp Gly Arg Asp Ala Phe Leu Thr Leu Ala Arg Asp Lys His Leu
            580                 585                 590

Glu Phe Ser Ser Leu Arg Arg Ala Gln Trp Ser Thr Met Cys Met Leu
        595                 600                 605
```

Val Glu Leu His Thr Gln Ser Gln Asp
610 615

<210> SEQ ID NO 10
<211> LENGTH: 1368
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 10

Met Asp Lys Lys Tyr Ser Ile Gly Leu Ala Ile Gly Thr Asn Ser Val
1 5 10 15

Gly Trp Ala Val Ile Thr Asp Glu Tyr Lys Val Pro Ser Lys Lys Phe
20 25 30

Lys Val Leu Gly Asn Thr Asp Arg His Ser Ile Lys Lys Asn Leu Ile
35 40 45

Gly Ala Leu Leu Phe Asp Ser Gly Glu Thr Ala Glu Ala Thr Arg Leu
50 55 60

Lys Arg Thr Ala Arg Arg Arg Tyr Thr Arg Arg Lys Asn Arg Ile Cys
65 70 75 80

Tyr Leu Gln Glu Ile Phe Ser Asn Glu Met Ala Lys Val Asp Asp Ser
85 90 95

Phe Phe His Arg Leu Glu Glu Ser Phe Leu Val Glu Glu Asp Lys Lys
100 105 110

His Glu Arg His Pro Ile Phe Gly Asn Ile Val Asp Glu Val Ala Tyr
115 120 125

His Glu Lys Tyr Pro Thr Ile Tyr His Leu Arg Lys Lys Leu Val Asp
130 135 140

Ser Thr Asp Lys Ala Asp Leu Arg Leu Ile Tyr Leu Ala Leu Ala His
145 150 155 160

Met Ile Lys Phe Arg Gly His Phe Leu Ile Glu Gly Asp Leu Asn Pro
165 170 175

Asp Asn Ser Asp Val Asp Lys Leu Phe Ile Gln Leu Val Gln Thr Tyr
180 185 190

Asn Gln Leu Phe Glu Glu Asn Pro Ile Asn Ala Ser Gly Val Asp Ala
195 200 205

Lys Ala Ile Leu Ser Ala Arg Leu Ser Lys Ser Arg Arg Leu Glu Asn
210 215 220

Leu Ile Ala Gln Leu Pro Gly Glu Lys Lys Asn Gly Leu Phe Gly Asn
225 230 235 240

Leu Ile Ala Leu Ser Leu Gly Leu Thr Pro Asn Phe Lys Ser Asn Phe
245 250 255

Asp Leu Ala Glu Asp Ala Lys Leu Gln Leu Ser Lys Asp Thr Tyr Asp
260 265 270

Asp Asp Leu Asp Asn Leu Leu Ala Gln Ile Gly Asp Gln Tyr Ala Asp
275 280 285

Leu Phe Leu Ala Ala Lys Asn Leu Ser Asp Ala Ile Leu Leu Ser Asp
290 295 300

Ile Leu Arg Val Asn Thr Glu Ile Thr Lys Ala Pro Leu Ser Ala Ser
305 310 315 320

Met Ile Lys Arg Tyr Asp Glu His His Gln Asp Leu Thr Leu Leu Lys
325 330 335

Ala Leu Val Arg Gln Gln Leu Pro Glu Lys Tyr Lys Glu Ile Phe Phe
340 345 350

-continued

```
Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
    610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
    690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
        755                 760                 765
```

-continued

```
Thr Thr Gln Lys Gly Gln Lys Asn Ser Arg Glu Arg Met Lys Arg Ile
    770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp Ala Ile Val Pro Gln Ser Phe Leu Lys
        835                 840                 845

Asp Asp Ser Ile Asp Asn Lys Val Leu Thr Arg Ser Asp Lys Asn Arg
    850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
    930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
            980                 985                 990

Val Gly Thr Ala Leu Ile Lys Lys  Tyr Pro Lys Leu Glu  Ser Glu Phe
        995                 1000                1005

Val Tyr  Gly Asp Tyr Lys Val  Tyr Asp Val Arg Lys  Met Ile Ala
    1010                1015                1020

Lys Ser  Glu Gln Glu Ile Gly  Lys Ala Thr Ala Lys  Tyr Phe Phe
    1025                1030                1035

Tyr Ser  Asn Ile Met Asn Phe  Phe Lys Thr Glu Ile  Thr Leu Ala
    1040                1045                1050

Asn Gly  Glu Ile Arg Lys Arg  Pro Leu Ile Glu Thr  Asn Gly Glu
    1055                1060                1065

Thr Gly  Glu Ile Val Trp Asp  Lys Gly Arg Asp Phe  Ala Thr Val
    1070                1075                1080

Arg Lys  Val Leu Ser Met Pro  Gln Val Asn Ile Val  Lys Lys Thr
    1085                1090                1095

Glu Val  Gln Thr Gly Gly Phe  Ser Lys Glu Ser Ile  Leu Pro Lys
    1100                1105                1110

Arg Asn  Ser Asp Lys Leu Ile  Ala Arg Lys Lys Asp  Trp Asp Pro
    1115                1120                1125

Lys Lys  Tyr Gly Gly Phe Asp  Ser Pro Thr Val Ala  Tyr Ser Val
    1130                1135                1140

Leu Val  Val Ala Lys Val Glu  Lys Gly Lys Ser Lys  Lys Leu Lys
    1145                1150                1155

Ser Val  Lys Glu Leu Leu Gly  Ile Thr Ile Met Glu  Arg Ser Ser
    1160                1165                1170

Phe Glu  Lys Asn Pro Ile Asp  Phe Leu Glu Ala Lys  Gly Tyr Lys
```

```
    1175                1180                1185

Glu Val  Lys Lys Asp Leu Ile  Ile Lys Leu Pro Lys  Tyr Ser Leu
    1190                1195                1200

Phe Glu  Leu Glu Asn Gly Arg  Lys Arg Met Leu Ala  Ser Ala Gly
    1205                1210                1215

Glu Leu  Gln Lys Gly Asn Glu  Leu Ala Leu Pro Ser  Lys Tyr Val
    1220                1225                1230

Asn Phe  Leu Tyr Leu Ala Ser  His Tyr Glu Lys Leu  Lys Gly Ser
    1235                1240                1245

Pro Glu  Asp Asn Glu Gln Lys  Gln Leu Phe Val Glu  Gln His Lys
    1250                1255                1260

His Tyr  Leu Asp Glu Ile Ile  Glu Gln Ile Ser Glu  Phe Ser Lys
    1265                1270                1275

Arg Val  Ile Leu Ala Asp Ala  Asn Leu Asp Lys Val  Leu Ser Ala
    1280                1285                1290

Tyr Asn  Lys His Arg Asp Lys  Pro Ile Arg Glu Gln  Ala Glu Asn
    1295                1300                1305

Ile Ile  His Leu Phe Thr Leu  Thr Asn Leu Gly Ala  Pro Ala Ala
    1310                1315                1320

Phe Lys  Tyr Phe Asp Thr Thr  Ile Asp Arg Lys Arg  Tyr Thr Ser
    1325                1330                1335

Thr Lys  Glu Val Leu Asp Ala  Thr Leu Ile His Gln  Ser Ile Thr
    1340                1345                1350

Gly Leu  Tyr Glu Thr Arg Ile  Asp Leu Ser Gln Leu  Gly Gly Asp
    1355                1360                1365


<210> SEQ ID NO 11
<211> LENGTH: 553
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Ser Pro Gly Ile Arg Arg Leu Asp Ala Leu Ile Ser Thr Ser Leu Tyr
1               5                   10                  15

Lys Lys Ala Gly Tyr Lys Glu Ala Ser Gly Ser Gly Arg Ala Asp Ala
            20                  25                  30

Leu Asp Asp Phe Asp Leu Asp Met Leu Gly Ser Asp Ala Leu Asp Asp
        35                  40                  45

Phe Asp Leu Asp Met Leu Gly Ser Asp Ala Leu Asp Asp Phe Asp Leu
    50                  55                  60

Asp Met Leu Gly Ser Asp Ala Leu Asp Asp Phe Asp Leu Asp Met Leu
65                  70                  75                  80

Ile Asn Ser Arg Ser Ser Gly Ser Pro Lys Lys Lys Arg Lys Val Gly
                85                  90                  95

Ser Gln Tyr Leu Pro Asp Thr Asp Asp Arg His Arg Ile Glu Glu Lys
            100                 105                 110

Arg Lys Arg Thr Tyr Glu Thr Phe Lys Ser Ile Met Lys Lys Ser Pro
        115                 120                 125

Phe Ser Gly Pro Thr Asp Pro Arg Pro Pro Pro Arg Arg Ile Ala Val
    130                 135                 140

Pro Ser Arg Ser Ser Ala Ser Val Pro Lys Pro Ala Pro Gln Pro Tyr
145                 150                 155                 160
```

-continued

```
Pro Phe Thr Ser Ser Leu Ser Thr Ile Asn Tyr Asp Glu Phe Pro Thr
                165                 170                 175

Met Val Phe Pro Ser Gly Gln Ile Ser Gln Ala Ser Ala Leu Ala Pro
            180                 185                 190

Ala Pro Pro Gln Val Leu Pro Gln Ala Pro Ala Pro Ala Pro Ala Pro
        195                 200                 205

Ala Met Val Ser Ala Leu Ala Gln Ala Pro Ala Pro Val Pro Val Leu
    210                 215                 220

Ala Pro Gly Pro Pro Gln Ala Val Ala Pro Pro Ala Pro Lys Pro Thr
225                 230                 235                 240

Gln Ala Gly Glu Gly Thr Leu Ser Glu Ala Leu Leu Gln Leu Gln Phe
                245                 250                 255

Asp Asp Glu Asp Leu Gly Ala Leu Leu Gly Asn Ser Thr Asp Pro Ala
            260                 265                 270

Val Phe Thr Asp Leu Ala Ser Val Asp Asn Ser Glu Phe Gln Gln Leu
        275                 280                 285

Leu Asn Gln Gly Ile Pro Val Ala Pro His Thr Thr Glu Pro Met Leu
    290                 295                 300

Met Glu Tyr Pro Glu Ala Ile Thr Arg Leu Val Thr Gly Ala Gln Arg
305                 310                 315                 320

Pro Pro Asp Pro Ala Pro Ala Pro Leu Gly Ala Pro Gly Leu Pro Asn
                325                 330                 335

Gly Leu Leu Ser Gly Asp Glu Asp Phe Ser Ser Ile Ala Asp Met Asp
            340                 345                 350

Phe Ser Ala Leu Leu Gly Ser Gly Ser Gly Ser Arg Asp Ser Arg Glu
        355                 360                 365

Gly Met Phe Leu Pro Lys Pro Glu Ala Gly Ser Ala Ile Ser Asp Val
    370                 375                 380

Phe Glu Gly Arg Glu Val Cys Gln Pro Lys Arg Ile Arg Pro Phe His
385                 390                 395                 400

Pro Pro Gly Ser Pro Trp Ala Asn Arg Pro Leu Pro Ala Ser Leu Ala
                405                 410                 415

Pro Thr Pro Thr Gly Pro Val His Glu Pro Val Gly Ser Leu Thr Pro
            420                 425                 430

Ala Pro Val Pro Gln Pro Leu Asp Pro Ala Pro Ala Val Thr Pro Glu
        435                 440                 445

Ala Ser His Leu Leu Glu Asp Pro Asp Glu Glu Thr Ser Gln Ala Val
    450                 455                 460

Lys Ala Leu Arg Glu Met Ala Asp Thr Val Ile Pro Gln Lys Glu Glu
465                 470                 475                 480

Ala Ala Ile Cys Gly Gln Met Asp Leu Ser His Pro Pro Pro Arg Gly
                485                 490                 495

His Leu Asp Glu Leu Thr Thr Thr Leu Glu Ser Met Thr Glu Asp Leu
            500                 505                 510

Asn Leu Asp Ser Pro Leu Thr Pro Glu Leu Asn Glu Ile Leu Asp Thr
        515                 520                 525

Phe Leu Asn Asp Glu Cys Leu Leu His Ala Met His Ile Ser Thr Gly
    530                 535                 540

Leu Ser Ile Phe Asp Thr Ser Leu Phe
545                 550
```

<210> SEQ ID NO 12
<211> LENGTH: 21
<212> TYPE: DNA

<213> ORGANISM: Unknown
<220> FEATURE:
<223> OTHER INFORMATION: Description of Unknown: Nuclear localization
      signal sequence

<400> SEQUENCE: 12
cctaagaaga aacgcaaagt g 21

<210> SEQ ID NO 13
<211> LENGTH: 21
<212> TYPE: DNA
<213> ORGANISM: Unknown
<220> FEATURE:
<223> OTHER INFORMATION: Description of Unknown: Nuclear localization
      signal sequence

<400> SEQUENCE: 13
cctaagaaaa agaggaaagt a 21

<210> SEQ ID NO 14
<211> LENGTH: 21
<212> TYPE: DNA
<213> ORGANISM: Unknown
<220> FEATURE:
<223> OTHER INFORMATION: Description of Unknown: Nuclear localization
      signal sequence

<400> SEQUENCE: 14
cctaagaaga agcgcaaggt g 21

<210> SEQ ID NO 15
<211> LENGTH: 31
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 15
cugaccugug ucccucaggg guggagucag g 31

<210> SEQ ID NO 16
<211> LENGTH: 32
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 16
cuggcggcag ucggguuggg gguaagcacg uc 32

<210> SEQ ID NO 17
<211> LENGTH: 32
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 17
cugggccuuc gugcuuaccc caaccccgac uc 32

<210> SEQ ID NO 18
<211> LENGTH: 32
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 18
cacgaaggcc cagcucaguu cucugcaugu uc                                32

<210> SEQ ID NO 19
<211> LENGTH: 32
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 19
gucacaugca gagaacugag cugggccuuc uc                                32

<210> SEQ ID NO 20
<211> LENGTH: 32
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 20
gcccagcuca guucucugca ugugaccucc uc                                32

<210> SEQ ID NO 21
<211> LENGTH: 32
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 21
augggagguc acaugcagag aacugagcug uc                                32

<210> SEQ ID NO 22
<211> LENGTH: 32
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 22
aaccaguuug guuucugcua gccugaguca uc                                32

<210> SEQ ID NO 23
<211> LENGTH: 32
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 23
ggugacucag gcuagcagaa accaaacugg uc                                32

<210> SEQ ID NO 24
<211> LENGTH: 32
<212> TYPE: RNA
<213> ORGANISM: Artificial Sequence
<220> FEATURE:

<223> OTHER INFORMATION: Description of Artificial Sequence: Synthetic
      oligonucleotide

<400> SEQUENCE: 24
cccaguuucc aggaggguga cucaggcuag uc 32

<210> SEQ ID NO 25
<211> LENGTH: 32
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 25
ccugagucac ccuccuggaa acugggccug uc 32

<210> SEQ ID NO 26
<211> LENGTH: 32
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 26
ucacccuccu ggaaacuggg ccugcuuggc uc 32

<210> SEQ ID NO 27
<211> LENGTH: 32
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 27
augggccggc ugauggcuga cuugaugcca uc 32

<210> SEQ ID NO 28
<211> LENGTH: 32
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 28
agaugggccg gcugauggcu gacuugaugc uc 32

<210> SEQ ID NO 29
<211> LENGTH: 32
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 29
ucagccauca gccggcccau cuccucaugg uc 32

<210> SEQ ID NO 30
<211> LENGTH: 32
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 30
gguuggccag caugaggaga ugggccggcu uc 32

<210> SEQ ID NO 31
<211> LENGTH: 32
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 31
cuggccaacc cucugugagu gugugggagg uc 32

<210> SEQ ID NO 32
<211> LENGTH: 32
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 32
cccagccucc ccucccacac acucacagag uc 32

<210> SEQ ID NO 33
<211> LENGTH: 32
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 33
gaggagccca gccuccccuc ccacacacuc uc 32

<210> SEQ ID NO 34
<211> LENGTH: 32
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 34
ugugugggag gggaggcugg gcuccuccuu uc 32

<210> SEQ ID NO 35
<211> LENGTH: 32
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 35
ggaggcuggg cuccuccuug uacucucuga uc 32

<210> SEQ ID NO 36
<211> LENGTH: 32
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 36
caccucagag aguacaagga ggagcccagc uc 32

<210> SEQ ID NO 37
<211> LENGTH: 32
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 37
gcugggcucc uccuuguacu cucugaggug uc 32

<210> SEQ ID NO 38
<211> LENGTH: 32
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 38
cugggcuccu ccuuguacuc ucugaggugc uc 32

<210> SEQ ID NO 39
<211> LENGTH: 32
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 39
cugccccucc uuccagagca ccucagagag uc 32

<210> SEQ ID NO 40
<211> LENGTH: 32
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 40
gugcucugga aggaggggca gcuccacccu uc 32

<210> SEQ ID NO 41
<211> LENGTH: 32
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 41
gaggggcagc uccacccugg gagggacugu uc 32

<210> SEQ ID NO 42
<211> LENGTH: 32
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 42
gggcagcucc acccugggag ggacuguggc uc 32

<210> SEQ ID NO 43
<211> LENGTH: 32
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 43
ggacuguggc ccagguacug cccgggugcu uc 32

<210> SEQ ID NO 44
<211> LENGTH: 32
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 44
acugaaucgg aacaaggcaa aggcuauaaa uc 32

<210> SEQ ID NO 45
<211> LENGTH: 32
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 45
caaaggcuau aaaaaaaauu agcaguaucc uc 32

<210> SEQ ID NO 46
<211> LENGTH: 32
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 46
gcuauaaaaa aaauuagcag uauccucuug uc 32

<210> SEQ ID NO 47
<211> LENGTH: 32
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 47
auaguguggg gaaggggccc ccaagaggau uc 32

<210> SEQ ID NO 48
<211> LENGTH: 32
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 48
gaccguuuca gacagauauu ugcauugaga uc 32

<210> SEQ ID NO 49
<211> LENGTH: 32
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 49
caaauaucug ucugaaacgg ucccuggcua uc 32

<210> SEQ ID NO 50
<211> LENGTH: 32
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 50
uuuagccagg gaccguuuca gacagauauu uc 32

<210> SEQ ID NO 51
<211> LENGTH: 32
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 51
gguggaguuu agccagggac cguuucagac uc 32

<210> SEQ ID NO 52
<211> LENGTH: 32
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 52
cuggccaacc caugggugga guuuagccag uc 32

<210> SEQ ID NO 53
<211> LENGTH: 32
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 53
gcuggccaac ccaugggugg aguuuagcca uc 32

<210> SEQ ID NO 54
<211> LENGTH: 32
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 54
gcaaggcugg ccaacccaug gguggaguuu uc 32

<210> SEQ ID NO 55
<211> LENGTH: 32
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 55
cuauugguca aggcaaggcu ggccaaccca uc 32

<210> SEQ ID NO 56
<211> LENGTH: 32
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 56
gcuauugguc aaggcaaggc uggccaaccc uc 32

<210> SEQ ID NO 57
<211> LENGTH: 32
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 57
gguuggccag ccuugccuug accaauagcc uc 32

<210> SEQ ID NO 58
<211> LENGTH: 32
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 58
acuauugguc aaguuugccu ugucaaggcu uc 32

<210> SEQ ID NO 59
<211> LENGTH: 32
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 59
gcaaacuuga ccaauagucu uagaguaucc uc 32

<210> SEQ ID NO 60
<211> LENGTH: 32
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 60
caaacuugac caauagucuu agaguaucca uc 32

<210> SEQ ID NO 61
<211> LENGTH: 32
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 61
uauccaguga ggccaggggc cggcggcugg uc 32

<210> SEQ ID NO 62
<211> LENGTH: 32
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 62
gccaggggcc ggcggcuggc uagggaugaa uc 32

<210> SEQ ID NO 63
<211> LENGTH: 32
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 63
ggccggcggc uggcuaggga ugaagaauaa uc 32

<210> SEQ ID NO 64
<211> LENGTH: 32
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 64
ggugcuuccu uuuauucuuc aucccuagcc uc 32

<210> SEQ ID NO 65
<211> LENGTH: 32
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 65
aagaauaaaa ggaagcaccc uucagcaguu uc 32

<210> SEQ ID NO 66
<211> LENGTH: 32
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 66
aauaaaagga agcacccuuc agcaguucca uc 32

<210> SEQ ID NO 67
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 67
uguacucucu gaggugcuc 19

<210> SEQ ID NO 68
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 68
acgcagauaa gaaccaguu 19

<210> SEQ ID NO 69
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 69
caucaaguca gccaucagc 19

<210> SEQ ID NO 70
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 70
gagucacccu ccuggaaac 19

<210> SEQ ID NO 71
<211> LENGTH: 34
<212> TYPE: DNA
<213> ORGANISM: Homo sapiens

<400> SEQUENCE: 71
aggctgacct gtgtccctca ggggtggagt cagg 34

<210> SEQ ID NO 72
<211> LENGTH: 35
<212> TYPE: DNA
<213> ORGANISM: Homo sapiens

<400> SEQUENCE: 72
gagctggcgg cagtcggggt tggggtaagc acgtc 35

<210> SEQ ID NO 73
<211> LENGTH: 35
<212> TYPE: DNA
<213> ORGANISM: Homo sapiens

<400> SEQUENCE: 73
gagctgggcc ttcgtgctta ccccaacccc gactc 35

<210> SEQ ID NO 74
<211> LENGTH: 35
<212> TYPE: DNA
<213> ORGANISM: Homo sapiens

<400> SEQUENCE: 74
aagcacgaag gcccagctca gttctctgca tgttc 35

<210> SEQ ID NO 75
<211> LENGTH: 35
<212> TYPE: DNA
<213> ORGANISM: Homo sapiens

<400> SEQUENCE: 75
gaggtcacat gcagagaact gagctgggcc ttctc 35

<210> SEQ ID NO 76
<211> LENGTH: 35
<212> TYPE: DNA
<213> ORGANISM: Homo sapiens

<400> SEQUENCE: 76
agggcccagc tcagttctct gcatgtgacc tcctc 35

<210> SEQ ID NO 77
<211> LENGTH: 35
<212> TYPE: DNA
<213> ORGANISM: Homo sapiens

<400> SEQUENCE: 77
aagatgggag gtcacatgca gagaactgag ctgtc 35

<210> SEQ ID NO 78
<211> LENGTH: 35
<212> TYPE: DNA
<213> ORGANISM: Homo sapiens

<400> SEQUENCE: 78
aagaaccagt ttggtttctg ctagcctgag tcatc 35

<210> SEQ ID NO 79
<211> LENGTH: 35
<212> TYPE: DNA
<213> ORGANISM: Homo sapiens

<400> SEQUENCE: 79
gagggtgact caggctagca gaaaccaaac tggtc 35

<210> SEQ ID NO 80
<211> LENGTH: 35
<212> TYPE: DNA
<213> ORGANISM: Homo sapiens

<400> SEQUENCE: 80
aggcccagtt tccaggaggg tgactcaggc tagtc 35

<210> SEQ ID NO 81
<211> LENGTH: 35
<212> TYPE: DNA
<213> ORGANISM: Homo sapiens

<400> SEQUENCE: 81
tagcctgagt caccctcctg gaaactgggc ctgtc 35

<210> SEQ ID NO 82
<211> LENGTH: 35
<212> TYPE: DNA
<213> ORGANISM: Homo sapiens

<400> SEQUENCE: 82
gagtcaccct cctggaaact gggcctgctt ggctc 35

<210> SEQ ID NO 83
<211> LENGTH: 35
<212> TYPE: DNA
<213> ORGANISM: Homo sapiens

<400> SEQUENCE: 83
gagatgggcc ggctgatggc tgacttgatg ccatc 35

<210> SEQ ID NO 84
<211> LENGTH: 35
<212> TYPE: DNA
<213> ORGANISM: Homo sapiens

<400> SEQUENCE: 84
aggagatggg ccggctgatg gctgacttga tgctc 35

<210> SEQ ID NO 85
<211> LENGTH: 35
<212> TYPE: DNA
<213> ORGANISM: Homo sapiens

<400> SEQUENCE: 85
aagtcagcca tcagccggcc catctcctca tggtc 35

<210> SEQ ID NO 86
<211> LENGTH: 35
<212> TYPE: DNA
<213> ORGANISM: Homo sapiens

<400> SEQUENCE: 86
gagggttggc cagcatgagg agatgggccg gcttc 35

<210> SEQ ID NO 87
<211> LENGTH: 35
<212> TYPE: DNA
<213> ORGANISM: Homo sapiens

<400> SEQUENCE: 87
atgctggcca accctctgtg agtgtgtggg aggtc 35

<210> SEQ ID NO 88
<211> LENGTH: 35
<212> TYPE: DNA
<213> ORGANISM: Homo sapiens

<400> SEQUENCE: 88
gagcccagcc tcccctccca cacactcaca gagtc 35

<210> SEQ ID NO 89
<211> LENGTH: 35
<212> TYPE: DNA
<213> ORGANISM: Homo sapiens -continued

<400> SEQUENCE: 89
aaggaggagc ccagcctccc ctcccacaca ctctc 35

<210> SEQ ID NO 90
<211> LENGTH: 35
<212> TYPE: DNA
<213> ORGANISM: Homo sapiens

<400> SEQUENCE: 90
gagtgtgtgg gaggggaggc tgggctcctc ctttc 35

<210> SEQ ID NO 91
<211> LENGTH: 35
<212> TYPE: DNA
<213> ORGANISM: Homo sapiens

<400> SEQUENCE: 91
aggggaggct gggctcctcc ttgtactctc tgatc 35

<210> SEQ ID NO 92
<211> LENGTH: 35
<212> TYPE: DNA
<213> ORGANISM: Homo sapiens

<400> SEQUENCE: 92
gagcacctca gagagtacaa ggaggagccc agctc 35

<210> SEQ ID NO 93
<211> LENGTH: 35
<212> TYPE: DNA
<213> ORGANISM: Homo sapiens

<400> SEQUENCE: 93
gaggctgggc tcctccttgt actctctgag gtgtc 35

<210> SEQ ID NO 94
<211> LENGTH: 35
<212> TYPE: DNA
<213> ORGANISM: Homo sapiens

<400> SEQUENCE: 94
aggctgggct cctccttgta ctctctgagg tgctc 35

<210> SEQ ID NO 95
<211> LENGTH: 35
<212> TYPE: DNA
<213> ORGANISM: Homo sapiens

<400> SEQUENCE: 95
gagctgcccc tccttccaga gcacctcaga gagtc 35

<210> SEQ ID NO 96
<211> LENGTH: 35
<212> TYPE: DNA
<213> ORGANISM: Homo sapiens

<400> SEQUENCE: 96
gaggtgctct ggaaggaggg gcagctccac ccttc 35

<210> SEQ ID NO 97
<211> LENGTH: 35
<212> TYPE: DNA

<213> ORGANISM: Homo sapiens

<400> SEQUENCE: 97
aaggaggggc agctccaccc tgggagggac tgttc 35

<210> SEQ ID NO 98
<211> LENGTH: 35
<212> TYPE: DNA
<213> ORGANISM: Homo sapiens

<400> SEQUENCE: 98
gaggggcagc tccaccctgg gagggactgt ggctc 35

<210> SEQ ID NO 99
<211> LENGTH: 35
<212> TYPE: DNA
<213> ORGANISM: Homo sapiens

<400> SEQUENCE: 99
gagggactgt ggcccaggta ctgcccgggt gcttc 35

<210> SEQ ID NO 100
<211> LENGTH: 35
<212> TYPE: DNA
<213> ORGANISM: Homo sapiens

<400> SEQUENCE: 100
atgactgaat cggaacaagg caaaggctat aaatc 35

<210> SEQ ID NO 101
<211> LENGTH: 35
<212> TYPE: DNA
<213> ORGANISM: Homo sapiens

<400> SEQUENCE: 101
aggcaaaggc tataaaaaaa attagcagta tcctc 35

<210> SEQ ID NO 102
<211> LENGTH: 35
<212> TYPE: DNA
<213> ORGANISM: Homo sapiens

<400> SEQUENCE: 102
aaggctataa aaaaaattag cagtatcctc ttgtc 35

<210> SEQ ID NO 103
<211> LENGTH: 35
<212> TYPE: DNA
<213> ORGANISM: Homo sapiens

<400> SEQUENCE: 103
gagatagtgt ggggaagggg cccccaagag gattc 35

<210> SEQ ID NO 104
<211> LENGTH: 35
<212> TYPE: DNA
<213> ORGANISM: Homo sapiens

<400> SEQUENCE: 104
agggaccgtt tcagacagat atttgcattg agatc 35

<210> SEQ ID NO 105
<211> LENGTH: 35

-continued

<212> TYPE: DNA
<213> ORGANISM: Homo sapiens

<400> SEQUENCE: 105
atgcaaatat ctgtctgaaa cggtccctgg ctatc 35

<210> SEQ ID NO 106
<211> LENGTH: 35
<212> TYPE: DNA
<213> ORGANISM: Homo sapiens

<400> SEQUENCE: 106
gagtttagcc agggaccgtt tcagacagat atttc 35

<210> SEQ ID NO 107
<211> LENGTH: 35
<212> TYPE: DNA
<213> ORGANISM: Homo sapiens

<400> SEQUENCE: 107
atgggtggag tttagccagg gaccgtttca gactc 35

<210> SEQ ID NO 108
<211> LENGTH: 35
<212> TYPE: DNA
<213> ORGANISM: Homo sapiens

<400> SEQUENCE: 108
aggctggcca acccatgggt ggagtttagc cagtc 35

<210> SEQ ID NO 109
<211> LENGTH: 35
<212> TYPE: DNA
<213> ORGANISM: Homo sapiens

<400> SEQUENCE: 109
aaggctggcc aacccatggg tggagtttag ccatc 35

<210> SEQ ID NO 110
<211> LENGTH: 35
<212> TYPE: DNA
<213> ORGANISM: Homo sapiens

<400> SEQUENCE: 110
aaggcaaggc tggccaaccc atgggtggag ttttc 35

<210> SEQ ID NO 111
<211> LENGTH: 35
<212> TYPE: DNA
<213> ORGANISM: Homo sapiens

<400> SEQUENCE: 111
aggctattgg tcaaggcaag gctggccaac ccatc 35

<210> SEQ ID NO 112
<211> LENGTH: 35
<212> TYPE: DNA
<213> ORGANISM: Homo sapiens

<400> SEQUENCE: 112
aaggctattg gtcaaggcaa ggctggccaa ccctc 35

<210> SEQ ID NO 113

<211> LENGTH: 35
<212> TYPE: DNA
<213> ORGANISM: Homo sapiens

<400> SEQUENCE: 113
atgggttggc cagccttgcc ttgaccaata gcctc 35

<210> SEQ ID NO 114
<211> LENGTH: 35
<212> TYPE: DNA
<213> ORGANISM: Homo sapiens

<400> SEQUENCE: 114
aagactattg gtcaagtttg ccttgtcaag gcttc 35

<210> SEQ ID NO 115
<211> LENGTH: 35
<212> TYPE: DNA
<213> ORGANISM: Homo sapiens

<400> SEQUENCE: 115
aaggcaaact tgaccaatag tcttagagta tcctc 35

<210> SEQ ID NO 116
<211> LENGTH: 35
<212> TYPE: DNA
<213> ORGANISM: Homo sapiens

<400> SEQUENCE: 116
aggcaaactt gaccaatagt cttagagtat ccatc 35

<210> SEQ ID NO 117
<211> LENGTH: 34
<212> TYPE: DNA
<213> ORGANISM: Homo sapiens

<400> SEQUENCE: 117
aggctgacct gtgtccctca ggggtggagt cagg 34

<210> SEQ ID NO 118
<211> LENGTH: 35
<212> TYPE: DNA
<213> ORGANISM: Homo sapiens

<400> SEQUENCE: 118
gagctggcgg cagtcggggt tggggtaagc acgtc 35

<210> SEQ ID NO 119
<211> LENGTH: 35
<212> TYPE: DNA
<213> ORGANISM: Homo sapiens

<400> SEQUENCE: 119
gagctgggcc ttcgtgctta ccccaacccc gactc 35

<210> SEQ ID NO 120
<211> LENGTH: 35
<212> TYPE: DNA
<213> ORGANISM: Homo sapiens

<400> SEQUENCE: 120
aagcacgaag gcccagctca gttctctgca tgttc 35

<210> SEQ ID NO 121
<211> LENGTH: 35
<212> TYPE: DNA
<213> ORGANISM: Homo sapiens

<400> SEQUENCE: 121
gaggtcacat gcagagaact gagctgggcc ttctc 35

<210> SEQ ID NO 122
<211> LENGTH: 35
<212> TYPE: DNA
<213> ORGANISM: Homo sapiens

<400> SEQUENCE: 122
agggcccagc tcagttctct gcatgtgacc tcctc 35

<210> SEQ ID NO 123
<211> LENGTH: 35
<212> TYPE: DNA
<213> ORGANISM: Homo sapiens

<400> SEQUENCE: 123
aagatgggag gtcacatgca gagaactgag ctgtc 35

<210> SEQ ID NO 124
<211> LENGTH: 35
<212> TYPE: DNA
<213> ORGANISM: Homo sapiens

<400> SEQUENCE: 124
aagaaccagt ttggtttctg ctagcctgag tcatc 35

<210> SEQ ID NO 125
<211> LENGTH: 35
<212> TYPE: DNA
<213> ORGANISM: Homo sapiens

<400> SEQUENCE: 125
gagggtgact caggctagca gaaaccaaac tggtc 35

<210> SEQ ID NO 126
<211> LENGTH: 35
<212> TYPE: DNA
<213> ORGANISM: Homo sapiens

<400> SEQUENCE: 126
aggcccagtt tccaggaggg tgactcaggc tagtc 35

<210> SEQ ID NO 127
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 127
ggaatccatg gagggaagat 20

<210> SEQ ID NO 128
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 128
gctgagtgaa ctgcactgtg a 21

<210> SEQ ID NO 129
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 129
caatgacccc ttcattgacc 20

<210> SEQ ID NO 130
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 130
tgagtcaccc tcctggaaac 20

<210> SEQ ID NO 131
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 131
gctgggctcc tccttgtact 20

<210> SEQ ID NO 132
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 132
gttgggtgct ccagctttta 20

<210> SEQ ID NO 133
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 133
tgttctcgct caggtcagtg 20

<210> SEQ ID NO 134
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 134
gaattctttg ccgaaatgga 20

<210> SEQ ID NO 135
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 135
ttgattttgg agggatctcg 20

<210> SEQ ID NO 136
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 136
ctccttccag agcacctcag 20

<210> SEQ ID NO 137
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 137
gctgctgccc ataaagtagc 20

<210> SEQ ID NO 138
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 138
cctcaaaact cctggactcg 20

<210> SEQ ID NO 139
<211> LENGTH: 59
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 139
auaaaccggc ugggcuccuc cuuguacucu cugaggugag uuccccgcgc cagcggggg 59

<210> SEQ ID NO 140
<211> LENGTH: 71
<212> TYPE: DNA
<213> ORGANISM: Homo sapiens

<400> SEQUENCE: 140
agctgcccct ccttccagag cacctcagag agtacaagga ggagcccagc ctcccctccc 60
acacactcac a 71

<210> SEQ ID NO 141
<211> LENGTH: 71
<212> TYPE: DNA
<213> ORGANISM: Homo sapiens

<400> SEQUENCE: 141
tgtgagtgtg tgggagggga ggctgggctc ctccttgtac tctctgaggt gctctggaag 60
gaggggcagc t 71

<210> SEQ ID NO 142
<211> LENGTH: 7
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 142 ttttttt 7

<210> SEQ ID NO 143
<211> LENGTH: 64
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 143
ggctcgagtt ccccgcgcca gcggggataa accggctggg ctcctccttg tactctctga 60
ggtc 64

<210> SEQ ID NO 144
<211> LENGTH: 70
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 144
tcgagacctc agagagtaca aggaggagcc cagccggttt atccccgctg gcgcggggaa 60
ctcgagccgc 70

<210> SEQ ID NO 145

<400> SEQUENCE: 145

000

<210> SEQ ID NO 146

<400> SEQUENCE: 146

000

<210> SEQ ID NO 147
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 147

Asp Tyr Lys Asp Asp Asp Asp Lys
1               5

<210> SEQ ID NO 148
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Tyr Pro Tyr Asp Val Pro Asp Tyr Ala Cys
1               5                   10

<210> SEQ ID NO 149
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

Glu Gln Lys Leu Ile Ser Glu Glu Asp Leu Cys
1               5                   10

<210> SEQ ID NO 150
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

Gly Lys Pro Ile Pro Asn Pro Leu Leu Gly Leu Asp Ser Thr
1               5                   10

<210> SEQ ID NO 151
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

Gly Ala Pro Val Pro Tyr Pro Asp Pro Leu Glu Pro Arg
1               5                   10

<210> SEQ ID NO 152
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Tyr Thr Asp Ile Glu Met Asn Arg Leu Gly Lys
1               5                   10

<210> SEQ ID NO 153

<211> LENGTH: 6
<212> TYPE: PRT
<213> ORGANISM: Artificial Sequence
<220> FEATURE:
<223> OTHER INFORMATION: Description of Artificial Sequence: Synthetic 6xHis tag

<400> SEQUENCE: 153

His His His His His His
1 5

<210> SEQ ID NO 154
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 154

Gln Pro Glu Leu Ala Pro Glu Asp Pro Glu Asp Cys
1 5 10

<210> SEQ ID NO 155
<211> LENGTH: 7
<212> TYPE: PRT
<213> ORGANISM: Simian virus 40

<400> SEQUENCE: 155

Pro Lys Lys Lys Arg Lys Val
1 5

<210> SEQ ID NO 156
<211> LENGTH: 20
<212> TYPE: PRT
<213> ORGANISM: Unknown
<220> FEATURE:
<223> OTHER INFORMATION: Description of Unknown: Nucleoplasmin sequence

<400> SEQUENCE: 156

Ala Val Lys Arg Pro Ala Ala Thr Lys Lys Ala Gly Gln Ala Lys Lys
1 5 10 15

Lys Lys Leu Asp
20

<210> SEQ ID NO 157
<211> LENGTH: 25
<212> TYPE: PRT
<213> ORGANISM: Unknown
<220> FEATURE:
<223> OTHER INFORMATION: Description of Unknown: EGL-13 sequence

<400> SEQUENCE: 157

Met Ser Arg Arg Arg Lys Ala Asn Pro Thr Lys Leu Ser Glu Asn Ala
1 5 10 15

Lys Lys Leu Ala Lys Glu Val Glu Asn
20 25

<210> SEQ ID NO 158
<211> LENGTH: 9
<212> TYPE: PRT
<213> ORGANISM: Unknown
<220> FEATURE:
<223> OTHER INFORMATION: Description of Unknown: c-Myc sequence

<400> SEQUENCE: 158

Pro Ala Ala Lys Arg Val Lys Leu Asp
1 5

<210> SEQ ID NO 159
<211> LENGTH: 9
<212> TYPE: PRT
<213> ORGANISM: Unknown
<220> FEATURE:
<223> OTHER INFORMATION: Description of Unknown: TUS-protein sequence

<400> SEQUENCE: 159

Lys Leu Lys Ile Lys Arg Pro Val Lys
1 5

<210> SEQ ID NO 160
<211> LENGTH: 10
<212> TYPE: PRT
<213> ORGANISM: Unknown
<220> FEATURE:
<223> OTHER INFORMATION: Description of Unknown: Nuclear localization signal sequence

<400> SEQUENCE: 160

Val Gln Arg Lys Arg Gln Lys Leu Met Pro
1 5 10

<210> SEQ ID NO 161
<211> LENGTH: 8
<212> TYPE: PRT
<213> ORGANISM: Unknown
<220> FEATURE:
<223> OTHER INFORMATION: Description of Unknown: Nuclear localization signal sequence

<400> SEQUENCE: 161

Ser Lys Lys Lys Lys Thr Lys Val
1 5

<210> SEQ ID NO 162
<211> LENGTH: 8
<212> TYPE: PRT
<213> ORGANISM: Unknown
<220> FEATURE:
<223> OTHER INFORMATION: Description of Unknown: Nuclear localization signal sequence

<400> SEQUENCE: 162

Gly Arg Lys Arg Lys Lys Arg Thr
1 5

<210> SEQ ID NO 163
<211> LENGTH: 1170
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 163
atgggcaagc ctatacctaa ccctttgctc gggctggact ccaccatggc tcctaagaag 60
aagcgcaagg tgagaggaat gtcaaacttc attaatatcc acgtgcttat ctcacactcc 120
cctagttgcc ttaacagaga cgatatgaac atgcaaaaag acgcaatttt tggcggcaaa 180
aggagagtca gaattagtag ccagagcctg aagcgcgcta tgaggaaaag cggctactat 240
gctcaaaaca ttggtgaaag ttcattgcgg accatccatc tcgcgcagtt gagggacgtc 300

```
ctgcgacaga agcttgggga aagatttgat cagaagatca tcgacaaaac gcttgccctt    360

ctgtccggta aatcagtgga cgaagcggag aagataagtg cggatgctgt tacgccatgg    420

gtggtaggtg aaatcgcgtg gttttgcgag caggtagcca aggccgaagc ggataatttg    480

gatgataaga aactgctcaa agtcctcaaa gaggacatcg cggcgatccg ggtgaacctt    540

cagcagggtg ttgatattgc gctctctggt cggatggcca cgtctggaat gatgactgaa    600

ctgggtaagg tggacggagc tatgtctata gctcatgcta taactaccca tcaggtggat    660

tctgacatag actggttcac ggctgtcgac gatctccagg aacaaggatc cgcacacctc    720

ggcacgcaag aatttcttc tggagtgttc tataggtatg ccaacatcaa ccttgcacag     780

ctccaggaaa acctcggtgg ggcaagccgg gaacaggctc ttgaaatagc tacccatgtg    840

gttcacatgc tggcgaccga agtgccaggg gccaagcaga gaacgtacgc cgcattcaat    900

ccggcggaca tggtcatggt gaatttctct gatatgccct tgtctatggc aaatgctttc    960

gagaaggcgg tcaaggcaaa ggacggtttt ttgcaaccct ccatccaagc ctttaatcag   1020

tactgggata gagtagctaa cggtatggt ctcaatggcg cggctgctca gttttctttg    1080

tccgatgtgg atccgataac ggcgcaggtt aaacagatgc ccaccttgga acaactcaaa   1140

tcctgggtta gaaacaatgg ggaggcgtga                                    1170
```

<210> SEQ ID NO 164
<211> LENGTH: 16
<212> TYPE: PRT
<213> ORGANISM: Unknown
<220> FEATURE:
<223> OTHER INFORMATION: Description of Unknown: Nucleoplasmin sequence

<400> SEQUENCE: 164

```
Lys Arg Pro Ala Ala Thr Lys Lys Ala Gly Gln Ala Lys Lys Lys Lys
1               5                   10                  15
```

<210> SEQ ID NO 165
<211> LENGTH: 48
<212> TYPE: DNA
<213> ORGANISM: Unknown
<220> FEATURE:
<223> OTHER INFORMATION: Description of Unknown: Nuclear localization signal sequence

<400> SEQUENCE: 165

```
aagcgacctg ccgccacaaa gaaggctgga caggctaaga agaagaaa                  48
```

<210> SEQ ID NO 166
<211> LENGTH: 834
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 166

```
atggactata aggatgatga cgacaagatg gcccccaaga agaagcgcaa agtccgcggg     60

atgaaggcta ttagggtccg gctgtggcag gatctcgtga acttcaagaa gcctaccagc    120

ttccaactga aggaaaccta ccctctgccg ccgtactcta ccgtgatcgg catggtgcat    180

acactgtgcg gctttacctc ctaccacgag atgaagatca gcattcaggg aaagtacttt    240

agcaaggtca acgacctcgc gactagatac gaattcaaga atggctcaaa atacgacgtg    300

gaacgccacc agatcaaagt ggacaaatac ggagtgtcga gaggcgtcag caccgtggag    360
```

ctccttgtgg acctcgaact gctgctgcac atcattccgg aagatccatc cttggtgccg 420
atcattgaaa aggcattccg ggaacccatc gagttccctt ccctgggacg cagagaggac 480
atcgccacga ttcagaaggt cgaagtggtg gacgtcgaga agcgacagcc caagaagtcc 540
accgagatct ccgacggtta taacgcctac gtgccgatca gcttgaccga gaacaactcg 600
gtgcatttca agtcccacga gtcctcagtg ggacgggata agctgctggg gactcggtac 660
cttctgactg agaaatacga gcgcgtgaac cacggaaccg aaaaggcccc taagttcttc 720
cggaagtggc ggaagaagga cgtcatctac tcctcgcgca tcttcgtgtc caagaaggat 780
gtgttctttt tcgacgagga cgattacctg gtgttcatcg aagaagaaga gtga 834

<210> SEQ ID NO 167
<211> LENGTH: 783
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 167
atggactaca aggacgacga cgataagatg gcgccaaaga aaaagcgcaa ggtccgcgga 60
atgcggctga agattaactg cgacttcgac agcaagatca tccccaagga cttccagtcc 120
aaggtcgtgt ccctgttcaa agccggaatt atgaaaagct ccccggagag atacgagaac 180
ctgtttggtg gaaacaagca caagcagtac actttctcgg tgtatctccc aaaacctcag 240
aacaagggcg ccgaaattca gctgaacgag gcgaactgta tcatcaactt ctccaccggc 300
gatgctgaaa ccggtattat cttctacaac gccctgatta gcctgagagg ctccaaggtc 360
ctgtttgggg ccggaaatca catcaccgtg aagaacatcc agatcgtgcc tgagaagaag 420
atcatcggga agcaaaccat tctgcggacc ctttcgccgg tggtgtcgag ggatcacaac 480
cgggaaacct tcaagaattg gttctactca ttcgaggacg aagaattcga gcctactttg 540
aagcggaaca tgctgccgta cctcatcgac gcctttggag aacaggctcg ctacgatctg 600
gaaaagctga agatcacgcc catttccatg aagaaagtcg tggtgtactg ccatgagatc 660
cacatcgaga gctccgtggg catcttcgag ctggaagccg aggcatacct ccaaaagtac 720
ctcgtggaaa acggaatcgg cactatgact ggctcagggt tcggaatgat tgaacagttc 780
tga 783

<210> SEQ ID NO 168
<211> LENGTH: 930
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 168
atggactaca aggacgatga tgacaagatg gcccccaaga agaaacggaa agtccgcggc 60
atgaagaaca agggactggc aatgactatc attttccaag ccgaaagcgc caattacggc 120
gaatccctgg ggaacatttc aagcctgaag aagatctcta ggaacaacgg agatcagtac 180
acctacatct cccgccaagc gatccggtac aatcttatgg atcagatcgg agaaaaggaa 240
gcccctgtga aggctgaagg cggcggagac aaaaaggtca tccagttcct gtccgaggcc 300
acgatcaccg acttcccgga actcgacttt ttcggctacc tgaaaaccga aaagggttcc 360
gggggacaga agcgcagcgc caaagtccga ctgtcgaacg ccatctcgct ggagactttt 420
aagggcgacc tggatttcct cactaacaag ggacaggccg acaagctgaa cgaaaacatg 480
aacattgcgc aggcagagat ccacaagtcc tactaccgct acaccatcac catcgacctc 540
gaccagatcg gtatcgacgg ggagattgct ctggacaaca aggaaaaggc ccggagagtg 600
aagaagctga tggacactgt ggcgttcctc tatcgggaca ttaggggcag acgggaggac 660
ctcaagcccc tgttcgtgat cggtggagtg tatgacgtga agaacccggt gttccaaaac 720
attgtggatg tggccgacaa caatattgtg atcaagaaca ttaaggattt gctgacctac 780
gaggacatca aggagaacac cagagtcggc atcattgatg ggcagttcgc caactccgac 840
gaagtgaaag tcgagctgaa ggccgagtcc gtgccagctt tcttcaacga catcaaggga 900
aagattgatg cgtactacga gagcaactga 930

<210> SEQ ID NO 169
<211> LENGTH: 1749
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 169
atggattaca aggacgatga cgacaaaatg gcaccgaaga agaagcggaa ggtccgcgga 60
atgcagaccg aaatcgaagt cagggcagac gactggctca tcaacaccgg actgaccggc 120
ttcctgaaca ttgtgggaaa agagaacgtc cggattgacg ggcagtctat ctacttcacc 180
gctgacctcc tggaagattt cgaaactaag tactttaact tcttcatcca agagtacaaa 240
gaaactctct catggtacaa gatcgtcagc tacaaagaga ctatggagca gttcagaatt 300
gatgaattcg cgtcctttga cgaagtggcc ctggggaacc tgaacaagta catgaaggac 360
gtcgtgaagt tctatctgaa aaaggccaac tatatcaaag tgttcccctt gattgaccct 420
agcgccaacg tgaccaagtg gctcgaaaag ctgaacacca ttaatctgac caagaagcag 480
aaatgggatg aggtcaaggc tgacattatt gaggaggtca aacagaccta cacccaactc 540
gacctgatta ttgacttctg tgcctccgaa aagggactgc agtacctggg agccaagaac 600
ctgatctatt ccgtcattaa caagggctgg agcggagtct ccttcctgtt caagcaaacc 660
aagttcattg acccgtatct ggactacaag acgaccttcg tggatcctgt gctggagtac 720
ctggataccg atctgtccaa ggccaagtac aactgcttca actgcaacca gcccatcaag 780
aacctcaagc tcgacctctc gttcatgaat gacgtgggct ttgacaccgc ccgcaagact 840
gcgcacgtct gggatttcaa caacgatgtg gccacttgtc caatctgccg gctgatctac 900
tcatgcgtgc ctgccgggtt cacctacgtg tatggagagg gaatgttcgt gaacgactcc 960
tacggcgtgg aagaactgca cagagtgaac gaacggatgc ggaacagcat cctgaggttt 1020
aacaaggacg gtatcaattc caccaacact taccgcgcgc ttgtggagtc cattaccatg 1080
gaacacgaaa acaacagacg ctacgaattg gctgacatcc agctcgtgcg atacgagaac 1140
gagcattacc ggttcaatct gttgtcaaag aagatgcttc acatcgtgaa cgattccaag 1200
ggtatcctga agtcgctgat acgctgcggt tacaaggagg ggaacctcaa cgtgaacctc 1260
tacaaggaag tgatccagca tctgatgaac aacgaaaacc tcttcaccct tatccacaag 1320
ttgatctact acaagcagac cagcgtgaac ggcctgtact acaacatggg ccacgtgtcc 1380
ggaatcctgg atatcaacac caagttcctg aaagaaatgg aggtcatgac gaacatctca 1440
cagaaccagc tgtggttcgt gcaaaattgt ggcaaagaat tcaaggaggg ttacgtgaag 1500

```
aagaagtccg agaacaagat ctccggaatc acttacaagc tgctgaattc gctgaaggtc   1560

aacgacaagg acggattcat ggacaccctg ctgaactcct actcgtacct gtccatgccg   1620

atccccgacg tgttcatcaa gatgttctcc aacaacgaag ccttcaagag cgtgggctac   1680

gcttttatgc ttggcgtggg tggagaaaag actaagaagg aagatggggg caacaccgat   1740

gagaagtga                                                           1749
```

<210> SEQ ID NO 170
<211> LENGTH: 948
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 170

```
atgggcaagc ctatacctaa ccctttgctc gggctggact ccaccatggc ccccaagaag     60

aaacggaaag tccgcggcat gaagaacaag ggactggcaa tgactatcat tttccaagcc    120

gaaagcgcca attacggcga atccctgggg aacatttcaa gcctgaagaa gatctctagg    180

aacaacggag atcagtacac ctacatctcc cgccaagcga tccggtacaa tcttatggat    240

cagatcggag aaaaggaagc ccctgtgaag gctgaaggcg gcggagacaa aaaggtcatc    300

cagttcctgt ccgaggccac gatcaccgac ttcccggaac tcgacttttt cggctacctg    360

aaaaccgaaa agggttccgg gggacagaag cgcagcgcca aagtccgact gtcgaacgcc    420

atctcgctgg agacttttaa gggcgacctg gatttcctca ctaacaaggg acaggccgac    480

aagctgaacg aaaacatgaa cattgcgcag gcagagatcc acaagtccta ctaccgctac    540

accatcacca tcgacctcga ccagatcggt atcgacgggg agattgctct ggacaacaag    600

gaaaaggccc ggagagtgaa gaagctgatg gacactgtgg cgttcctcta tcgggacatt    660

aggggcagac gggaggacct caagcccctg ttcgtgatcg gtggagtgta tgacgtgaag    720

aacccggtgt tccaaaacat tgtggatgtg gccgacaaca atattgtgat caagaacatt    780

aaggatttgc tgacctacga ggacatcaag gagaacacca gagtcggcat cattgatggg    840

cagttcgcca actccgacga agtgaaagtc gagctgaagg ccgagtccgt gccagctttc    900

ttcaacgaca tcaagggaaa gattgatgcg tactacgaga gcaactga                 948
```

<210> SEQ ID NO 171
<211> LENGTH: 2776
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 171

```
atggactata aggatgatga cgacaagatg gcccccaaga agaagcgcaa agtccgcggg     60

atgaaggcta ttagggtccg gctgtggcag gatctcgtga acttcaagaa gcctaccagc    120

ttccaactga aggaaaccta ccctctgccg ccgtactcta ccgtgatcgg catggtgcat    180

acactgtgcg gctttacctc ctaccacgag atgaagatca gcattcaggg aaagtacttt    240

agcaaggtca acgacctcgc gactagatac gaattcaaga atggctcaaa atacgacgtg    300

gaacgccacc agatcaaagt ggacaaatac ggagtgtcga gaggcgtcag caccgtggag    360

ctccttgtgg acctcgaact gctgctgcac atcattccgg aagatccatc cttggtgccg    420
```

```
atcattgaaa aggcattccg ggaacccatc gagttccctt ccctgggacg cagagaggac    480
atcgccacga ttcagaaggt cgaagtggtg gacgtcgaga agcgacagcc caagaagtcc    540
accgagatct ccgacggtta taacgcctac gtgccgatca gcttgaccga gaacaactcg    600
gtgcatttca agtcccacga gtcctcagtg ggacgggata agctgctggg gactcggtac    660
cttctgactg agaaatacga gcgcgtgaac cacggaaccg aaaaggcccc taagttcttc    720
cggaagtggc ggaagaagga cgtcatctac tcctcgcgca tcttcgtgtc caagaaggat    780
gtgttctttt tcgacgagga cgattacctg gtgttcatcg aagaagaaga gcggggcaag    840
cgacctgccg ccacaaagaa ggctggacag gctaagaaga agaaaggatc cattttcaaa    900
ccagaagaac tacgacaggc actgatgcca actttggagg cactttaccg tcaggatcca    960
gaatcccttc cctttcgtca acctgtggac cctcagcttt taggaatccc tgattacttt   1020
gatattgtga agagccccat ggatctttct accattaaga ggaagttaga cactggacag   1080
tatcaggagc cctggcagta tgtcgatgat atttggctta tgttcaataa tgcctggtta   1140
tataaccgga aaacatcacg ggtatacaaa tactgctcca agctctctga ggtctttgaa   1200
caagaaattg acccagtgat gcaaagcctt ggatactgtt gtggcagaaa gttggagttc   1260
tctccacaga cactgtgttg ctacggcaaa cagttgtgca caatacctcg tgatgccact   1320
tattacagtt accagaacag gtatcatttc tgtgagaagt gtttcaatga gatccaaggg   1380
gagagcgttt ctttgggggga tgacccttcc cagcctcaaa ctacaataaa taaagaacaa   1440
ttttccaaga gaaaaaatga cacactggat cctgaactgt ttgttgaatg tacagagtgc   1500
ggaagaaaga tgcatcagat ctgtgtcctt caccatgaga tcatctggcc tgctggattc   1560
gtctgtgatg gctgtttaaa gaaaagtgca cgaactagga aagaaaataa gttttctgct   1620
aaaaggttgc catctaccag acttggcacc tttctagaga atcgtgtgaa tgactttctg   1680
aggcgacaga atcaccctga gtcaggagag gtcactgtta gagtagttca tgcttctgac   1740
aaaaccgtgg aagtaaaacc aggcatgaaa gcaaggtttg tggacagtgg agagatggca   1800
gaatcctttc cataccgaac caaagccctc tttgcctttg aagaaattga tggtgttgac   1860
ctgtgcttct ttggcatgca tgttcaagag tatggctctg actgccctcc acccaaccag   1920
aggagagtat acatatctta cctcgatagt gttcatttct tccgtcctaa atgcttgagg   1980
actgcagtct atcatgaaat cctaattgga tatttagaat atgtcaagaa attaggttac   2040
acaacagggc atatttgggc atgtccacca agtgagggag atgattatat cttccattgc   2100
catcctcctg accagaagat acccaagccc aagcgactgc aggaatggta caaaaaaatg   2160
cttgacaagg ctgtatcaga gcgtattgtc catgactaca aggatatttt taaacaagct   2220
actgaagata gattaacaag tgcaaaggaa ttgccttatt tcgagggtga tttctggccc   2280
aatgttctgg aagaaagcat taaggaactg gaacaggagg aagaagagag aaaacgagag   2340
gaaaacacca gcaatgaaag cacagatgtg accaagggag acagcaaaaa tgctaaaaag   2400
aagaataata agaaaaccag caaaaataag agcagcctga gtaggggcaa caagaagaaa   2460
cccgggatgc ccaatgtatc taacgacctc tcacagaaac tatatgccac catggagaag   2520
cataaagagg tcttctttgt gatccgcctc attgctggcc ctgctgccaa ctccctgcct   2580
cccattgttg atcctgatcc tctcatcccc tgcgatctga tggatggtcg ggatgcgttt   2640
ctcacgctgg caagggacaa gcacctggag ttctcttcac tccgaagagc ccagtggtcc   2700
accatgtgca tgctggtgga gctgcacacg cagagccagg acgggatccg attacaaaga   2760
cgatgacgat aagtga                                                   2776
```

<210> SEQ ID NO 172
<211> LENGTH: 2871
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 172
atggactaca aggacgatga tgacaagatg gcccccaaga agaaacggaa agtccgcggc 60
atgaagaaca agggactggc aatgactatc attttccaag ccgaaagcgc caattacggc 120
gaatccctgg ggaacatttc aagcctgaag aagatctcta ggaacaacgg agatcagtac 180
acctacatct cccgccaagc gatccggtac aatcttatgg atcagatcgg agaaaaggaa 240
gcccctgtga aggctgaagg cggcggagac aaaaaggtca tccagttcct gtccgaggcc 300
acgatcaccg acttcccgga actcgacttt ttcggctacc tgaaaaccga aaagggttcc 360
gggggacaga agcgcagcgc caaagtccga ctgtcgaacg ccatctcgct ggagactttt 420
aagggcgacc tggatttcct cactaacaag ggacaggccg acaagctgaa cgaaaacatg 480
aacattgcgc aggcagagat ccacaagtcc tactaccgct acaccatcac catcgacctc 540
gaccagatcg gtatcgacgg ggagattgct ctggacaaca aggaaaaggc ccggagagtg 600
aagaagctga tggacactgt ggcgttcctc tatcgggaca ttaggggcag acgggaggac 660
ctcaagcccc tgttcgtgat cggtggagtg tatgacgtga agaacccggt gttccaaaac 720
attgtggatg tggccgacaa caatattgtg atcaagaaca ttaaggattt gctgacctac 780
gaggacatca aggagaacac cagagtcggc atcattgatg ggcagttcgc caactccgac 840
gaagtgaaag tcgagctgaa ggccgagtcc gtgccagctt tcttcaacga catcaaggga 900
aagattgatg cgtactacga gagcaaccgg ggcaagcgac ctgccgccac aaagaaggct 960
ggacaggcta agaagaagaa aggatccatt ttcaaaccag aagaactacg acaggcactg 1020
atgccaactt tggaggcact ttaccgtcag gatccagaat cccttccctt tcgtcaacct 1080
gtggaccctc agcttttagg aatccctgat tactttgata ttgtgaagag ccccatggat 1140
ctttctacca ttaagaggaa gttagacact ggacagtatc aggagccctg gcagtatgtc 1200
gatgatattt ggcttatgtt caataatgcc tggttatata accggaaaac atcacgggta 1260
tacaaatact gctccaagct ctctgaggtc tttgaacaag aaattgaccc agtgatgcaa 1320
agccttggat actgttgtgg cagaaagttg gagttctctc cacagacact gtgttgctac 1380
ggcaaacagt tgtgcacaat acctcgtgat gccacttatt acagttacca gaacaggtat 1440
catttctgtg agaagtgttt caatgagatc caaggggaga gcgtttcttt gggggatgac 1500
ccttcccagc ctcaaactac aataaataaa gaacaatttt ccaagagaaa aaatgacaca 1560
ctggatcctg aactgtttgt tgaatgtaca gagtgcggaa gaaagatgca tcagatctgt 1620
gtccttcacc atgagatcat ctggcctgct ggattcgtct gtgatggctg tttaaagaaa 1680
agtgcacgaa ctaggaaaga aaataagttt tctgctaaaa ggttgccatc taccagactt 1740
ggcacctttc tagagaatcg tgtgaatgac tttctgaggc gacagaatca ccctgagtca 1800
ggagaggtca ctgttagagt agttcatgct tctgacaaaa ccgtggaagt aaaaccaggc 1860
atgaaagcaa ggtttgtgga cagtggagag atggcagaat cctttccata ccgaaccaaa 1920
gccctctttg cctttgaaga aattgatggt gttgacctgt gcttctttgg catgcatgtt 1980
caagagtatg gctctgactg ccctccaccc aaccagagga gagtatacat atcttacctc 2040
gatagtgttc atttcttccg tcctaaatgc ttgaggactg cagtctatca tgaaatccta 2100
attggatatt tagaatatgt caagaaatta ggttacacaa cagggcatat ttgggcatgt 2160
ccaccaagtg agggagatga ttatatcttc cattgccatc ctcctgacca gaagataccc 2220
aagcccaagc gactgcagga atggtacaaa aaaatgcttg acaaggctgt atcagagcgt 2280
attgtccatg actacaagga tatttttaaa caagctactg aagatagatt aacaagtgca 2340
aaggaattgc cttatttcga gggtgatttc tggcccaatg ttctggaaga aagcattaag 2400
gaactggaac aggaggaaga agagagaaaa cgagaggaaa acaccagcaa tgaaagcaca 2460
gatgtgacca agggagacag caaaaatgct aaaaagaaga ataataagaa aaccagcaaa 2520
aataagagca gcctgagtag ggcaacaag aagaaacccg ggatgcccaa tgtatctaac 2580
gacctctcac agaaactata tgccaccatg gagaagcata aagaggtctt ctttgtgatc 2640
cgcctcattg ctggccctgc tgccaactcc ctgcctccca ttgttgatcc tgatcctctc 2700
atcccctgcg atctgatgga tggtcgggat gcgtttctca cgctggcaag ggacaagcac 2760
ctggagttct cttcactccg aagagcccag tggtccacca tgtgcatgct ggtggagctg 2820
cacacgcaga gccaggacgg atccgattac aaagacgatg acgataagtg a 2871

<210> SEQ ID NO 173
<211> LENGTH: 3690
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 173
atggattaca aggacgatga cgacaaaatg gcaccgaaga agaagcggaa ggtccgcgga 60
atgcagaccg aaatcgaagt cagggcagac gactggctca tcaacaccgg actgaccggc 120
ttcctgaaca ttgtgggaaa agagaacgtc cggattgacg ggcagtctat ctacttcacc 180
gctgacctcc tggaagattt cgaaactaag tactttaact tcttcatcca agagtacaaa 240
gaaactctct catggtacaa gatcgtcagc tacaaagaga ctatggagca gttcagaatt 300
gatgaattcg cgtcctttga cgaagtggcc ctggggaacc tgaacaagta catgaaggac 360
gtcgtgaagt tctatctgaa aaaggccaac tatatcaaag tgttcccctt gattgaccct 420
agcgccaacg tgaccaagtg gctcgaaaag ctgaacacca ttaatctgac caagaagcag 480
aaatgggatg aggtcaaggc tgacattatt gaggaggtca aacagaccta cacccaactc 540
gacctgatta ttgacttctg tgcctccgaa aagggactgc agtacctggg agccaagaac 600
ctgatctatt ccgtcattaa caagggctgg agcggagtct ccttcctgtt caagcaaacc 660
aagttcattg acccgtatct ggactacaag acgaccttcg tggatcctgt gctggagtac 720
ctggataccg atctgtccaa ggccaagtac aactgcttca actgcaacca gcccatcaag 780
aacctcaagc tcgacctctc gttcatgaat gacgtgggct ttgacaccgc ccgcaagact 840
gcgcacgtct gggatttcaa caacgatgtg gccacttgtc caatctgccg gctgatctac 900
tcatgcgtgc ctgccgggtt cacctacgtg tatggagagg gaatgttcgt gaacgactcc 960
tacggcgtgg aagaactgca cagagtgaac gaacggatgc ggaacagcat cctgaggttt 1020
aacaaggacg gtatcaattc caccaacact taccgcgcgc ttgtggagtc cattaccatg 1080
gaacacgaaa acaacagacg ctacgaattg gctgacatcc agctcgtgcg atacgagaac 1140
gagcattacc ggttcaatct gttgtcaaag aagatgcttc acatcgtgaa cgattccaag 1200

```
ggtatcctga agtcgctgat acgctgcggt tacaaggagg ggaacctcaa cgtgaacctc   1260
tacaaggaag tgatccagca tctgatgaac aacgaaaacc tcttcaccct tatccacaag   1320
ttgatctact acaagcagac cagcgtgaac ggcctgtact acaacatggg ccacgtgtcc   1380
ggaatcctgg atatcaacac caagttcctg aaagaaatgg aggtcatgac gaacatctca   1440
cagaaccagc tgtggttcgt gcaaaattgt ggcaaagaat tcaaggaggg ttacgtgaag   1500
aagaagtccg agaacaagat ctccggaatc acttacaagc tgctgaattc gctgaaggtc   1560
aacgacaagg acggattcat ggacaccctg ctgaactcct actcgtacct gtccatgccg   1620
atccccgacg tgttcatcaa gatgttctcc aacaacgaag ccttcaagag cgtgggctac   1680
gcttttatgc ttggcgtggg tggagaaaag actaagaagg aagatggggg caacactgat   1740
gagaagcggg gcaagcgacc tgccgccaca aagaaggctg gacaggctaa gaagaagaaa   1800
ggatccattt tcaaaccaga agaactacga caggcactga tgccaacttt ggaggcactt   1860
taccgtcagg atccagaatc ccttcccttt cgtcaacctg tggaccctca gcttttagga   1920
atccctgatt actttgatat tgtgaagagc cccatggatc tttctaccat taagaggaag   1980
ttagacactg gacagtatca ggagccctgg cagtatgtcg atgatatttg gcttatgttc   2040
aataatgcct ggttatataa ccggaaaaca tcacgggtat acaaatactg ctccaagctc   2100
tctgaggtct ttgaacaaga aattgaccca gtgatgcaaa gccttggata ctgttgtggc   2160
agaaagttgg agttctctcc acagacactg tgttgctacg gcaaacagtt gtgcacaata   2220
cctcgtgatg ccacttatta cagttaccag aacaggtatc atttctgtga gaagtgtttc   2280
aatgagatcc aaggggagag cgtttctttg gggatgacc cttcccagcc tcaaactaca   2340
ataaataaag aacaatttc caagagaaaa aatgacacac tggatcctga actgtttgtt   2400
gaatgtacag agtgcggaag aaagatgcat cagatctgtg tccttcacca tgagatcatc   2460
tggcctgctg gattcgtctg tgatggctgt ttaaagaaaa gtgcacgaac taggaaagaa   2520
aataagtttt ctgctaaaag gttgccatct accagacttg gcacctttct agagaatcgt   2580
gtgaatgact ttctgaggcg acagaatcac cctgagtcag gagaggtcac tgttagagta   2640
gttcatgctt ctgacaaaac cgtggaagta aaaccaggca tgaaagcaag gtttgtggac   2700
agtggagaga tggcagaatc ctttccatac cgaaccaaag ccctctttgc ctttgaagaa   2760
attgatggtg ttgacctgtg cttctttggc atgcatgttc aagagtatgg ctctgactgc   2820
cctccaccca accagaggag agtatacata tcttacctcg atagtgttca tttcttccgt   2880
cctaaatgct tgaggactgc agtctatcat gaaatcctaa ttggatattt agaatatgtc   2940
aagaaattag gttacacaac agggcatatt tgggcatgtc caccaagtga gggagatgat   3000
tatatcttcc attgccatcc tcctgaccag aagataccca agcccaagcg actgcaggaa   3060
tggtacaaaa aaatgcttga caaggctgta tcagagcgta ttgtccatga ctacaaggat   3120
atttttaaac aagctactga agatagatta acaagtgcaa aggaattgcc ttatttcgag   3180
ggtgatttct ggcccaatgt tctggaagaa agcattaagg aactggaaca ggaggaagaa   3240
gagagaaaac gagaggaaaa caccagcaat gaaagcacag atgtgaccaa gggagacagc   3300
aaaaatgcta aaaagaagaa taataagaaa accagcaaaa ataagagcag cctgagtagg   3360
ggcaacaaga agaaacccgg gatgcccaat gtatctaacg acctctcaca gaaactatat   3420
gccaccatgg agaagcataa agaggtcttc tttgtgatcc gcctcattgc tggccctgct   3480
gccaactccc tgcctcccat tgttgatcct gatcctctca tcccctgcga tctgatggat   3540
```

ggtcgggatg cgtttctcac gctggcaagg gacaagcacc tggagttctc ttcactccga 3600
agagcccagt ggtccaccat gtgcatgctg gtggagctgc acacgcagag ccaggacgga 3660
tccgattaca aagacgatga cgataagtga 3690

<210> SEQ ID NO 174
<211> LENGTH: 2724
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 174
atggactaca aggacgacga cgataagatg gcgccaaaga aaaagcgcaa ggtccgcgga 60
atgcggctga agattaactg cgacttcgac agcaagatca tccccaagga cttccagtcc 120
aaggtcgtgt ccctgttcaa agccggaatt atgaaaagct ccccggagag atacgagaac 180
ctgtttggtg gaaacaagca caagcagtac actttctcgg tgtatctccc aaaacctcag 240
aacaagggcg ccgaaattca gctgaacgag gcgaactgta tcatcaactt ctccaccggc 300
gatgctgaaa ccggtattat cttctacaac gccctgatta gcctgagagg ctccaaggtc 360
ctgtttgggg ccggaaatca catcaccgtg aagaacatcc agatcgtgcc tgagaagaag 420
atcatcggga agcaaaccat tctgcggacc ctttcgccgg tggtgtcgag ggatcacaac 480
cgggaaacct tcaagaattg gttctactca ttcgaggacg aagaattcga gcctactttg 540
aagcggaaca tgctgccgta cctcatcgac gcctttggag aacaggctcg ctacgatctg 600
gaaaagctga agatcacgcc catttccatg aagaaagtcg tggtgtactg ccatgagatc 660
cacatcgaga gctccgtggg catcttcgag ctggaagccg aggcatacct ccaaaagtac 720
ctcgtggaaa acggaatcgg cactatgact ggctcagggt tcggaatgat tgaacagttc 780
cggggcaagc gacctgccgc cacaaagaag gctggacagg ctaagaagaa gaaaggatcc 840
attttcaaac cagaagaact acgacaggca ctgatgccaa ctttggaggc actttaccgt 900
caggatccag aatcccttcc ctttcgtcaa cctgtggacc ctcagctttt aggaatccct 960
gattactttg atattgtgaa gagccccatg gatctttcta ccattaagag gaagttagac 1020
actggacagt atcaggagcc ctggcagtat gtcgatgata tttggcttat gttcaataat 1080
gcctggttat ataaccggaa aacatcacgg gtatacaaat actgctccaa gctctctgag 1140
gtctttgaac aagaaattga cccagtgatg caaagccttg gatactgttg tggcagaaag 1200
ttggagttct ctccacagac actgtgttgc tacggcaaac agttgtgcac aatacctcgt 1260
gatgccactt attacagtta ccagaacagg tatcatttct gtgagaagtg tttcaatgag 1320
atccaagggg agagcgtttc tttgggggat gacccttccc agcctcaaac tacaataaat 1380
aaagaacaat tttccaagag aaaaaatgac acactggatc ctgaactgtt tgttgaatgt 1440
acagagtgcg gaagaaagat gcatcagatc tgtgtccttc accatgagat catctggcct 1500
gctggattcg tctgtgatgg ctgtttaaag aaaagtgcac gaactaggaa agaaaataag 1560
ttttctgcta aaaggttgcc atctaccaga cttggcacct ttctagagaa tcgtgtgaat 1620
gactttctga ggcgacagaa tcaccctgag tcaggagagg tcactgttag agtagttcat 1680
gcttctgaca aaaccgtgga agtaaaacca ggcatgaaag caaggtttgt ggacagtgga 1740
gagatggcag aatcctttcc ataccgaacc aaagccctct ttgcctttga agaaattgat 1800
ggtgttgacc tgtgcttctt tggcatgcat gttcaagagt atggctctga ctgccctcca 1860

```
cccaaccaga ggagagtata catatcttac ctcgatagtg ttcatttctt ccgtcctaaa   1920

tgcttgagga ctgcagtcta tcatgaaatc ctaattggat atttagaata tgtcaagaaa   1980

ttaggttaca caacagggca tatttgggca tgtccaccaa gtgagggaga tgattatatc   2040

ttccattgcc atcctcctga ccagaagata cccaagccca agcgactgca ggaatggtac   2100

aaaaaaatgc ttgacaaggc tgtatcagag cgtattgtcc atgactacaa ggatattttt   2160

aaacaagcta ctgaagatag attaacaagt gcaaaggaat tgccttattt cgagggtgat   2220

ttctggccca atgttctgga agaaagcatt aaggaactgg aacaggagga agaagagaga   2280

aaacgagagg aaaacaccag caatgaaagc acagatgtga ccaagggaga cagcaaaaat   2340

gctaaaaaga agaataataa gaaaaccagc aaaaataaga gcagcctgag taggggcaac   2400

aagaagaaac ccgggatgcc caatgtatct aacgacctct cacagaaact atatgccacc   2460

atggagaagc ataaagaggt cttctttgtg atccgcctca ttgctggccc tgctgccaac   2520

tccctgcctc ccattgttga tcctgatcct ctcatcccct gcgatctgat ggatggtcgg   2580

gatgcgtttc tcacgctggc aagggacaag cacctggagt tctcttcact ccgaagagcc   2640

cagtggtcca ccatgtgcat gctggtggag ctgcacacgc agagccagga cggatccgat   2700

tacaaagacg atgacgataa gtga                                          2724
```

```
<210> SEQ ID NO 175
<211> LENGTH: 257
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 175

Met Lys Ala Ile Arg Val Arg Leu Trp Gln Asp Leu Val Asn Phe Lys
1               5                   10                  15

Lys Pro Thr Ser Phe Gln Leu Lys Glu Thr Tyr Pro Leu Pro Pro Tyr
            20                  25                  30

Ser Thr Val Ile Gly Met Val His Thr Leu Cys Gly Phe Thr Ser Tyr
        35                  40                  45

His Glu Met Lys Ile Ser Ile Gln Gly Lys Tyr Phe Ser Lys Val Asn
    50                  55                  60

Asp Leu Ala Thr Arg Tyr Glu Phe Lys Asn Gly Ser Lys Tyr Asp Val
65                  70                  75                  80

Glu Arg His Gln Ile Lys Val Asp Lys Tyr Gly Val Ser Arg Gly Val
                85                  90                  95

Ser Thr Val Glu Leu Leu Val Asp Leu Glu Leu Leu Leu His Ile Ile
            100                 105                 110

Pro Glu Asp Pro Ser Leu Val Pro Ile Ile Glu Lys Ala Phe Arg Glu
        115                 120                 125

Pro Ile Glu Phe Pro Ser Leu Gly Arg Arg Glu Asp Ile Ala Thr Ile
    130                 135                 140

Gln Lys Val Glu Val Val Asp Val Glu Lys Arg Gln Pro Lys Lys Ser
145                 150                 155                 160

Thr Glu Ile Ser Asp Gly Tyr Asn Ala Tyr Val Pro Ile Ser Leu Thr
                165                 170                 175

Glu Asn Asn Ser Val His Phe Lys Ser His Glu Ser Ser Val Gly Arg
            180                 185                 190

Asp Lys Leu Leu Gly Thr Arg Tyr Leu Leu Thr Glu Lys Tyr Glu Arg
        195                 200                 205
```

-continued

Val Asn His Gly Thr Glu Lys Ala Pro Lys Phe Phe Arg Lys Trp Arg
    210                 215                 220

Lys Lys Asp Val Ile Tyr Ser Ser Arg Ile Phe Val Ser Lys Lys Asp
225                 230                 235                 240

Val Phe Phe Phe Asp Glu Asp Asp Tyr Leu Val Phe Ile Glu Glu Glu
                245                 250                 255

Glu

<210> SEQ ID NO 176
<211> LENGTH: 240
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 176

Met Arg Leu Lys Ile Asn Cys Asp Phe Asp Ser Lys Ile Ile Pro Lys
1               5                   10                  15

Asp Phe Gln Ser Lys Val Val Ser Leu Phe Lys Ala Gly Ile Met Lys
            20                  25                  30

Ser Ser Pro Glu Arg Tyr Glu Asn Leu Phe Gly Gly Asn Lys His Lys
        35                  40                  45

Gln Tyr Thr Phe Ser Val Tyr Leu Pro Lys Pro Gln Asn Lys Gly Ala
    50                  55                  60

Glu Ile Gln Leu Asn Glu Ala Asn Cys Ile Ile Asn Phe Ser Thr Gly
65                  70                  75                  80

Asp Ala Glu Thr Gly Ile Ile Phe Tyr Asn Ala Leu Ile Ser Leu Arg
                85                  90                  95

Gly Ser Lys Val Leu Phe Gly Ala Gly Asn His Ile Thr Val Lys Asn
            100                 105                 110

Ile Gln Ile Val Pro Glu Lys Lys Ile Ile Gly Lys Gln Thr Ile Leu
        115                 120                 125

Arg Thr Leu Ser Pro Val Val Ser Arg Asp His Asn Arg Glu Thr Phe
    130                 135                 140

Lys Asn Trp Phe Tyr Ser Phe Glu Asp Glu Glu Phe Glu Pro Thr Leu
145                 150                 155                 160

Lys Arg Asn Met Leu Pro Tyr Leu Ile Asp Ala Phe Gly Glu Gln Ala
                165                 170                 175

Arg Tyr Asp Leu Glu Lys Leu Lys Ile Thr Pro Ile Ser Met Lys Lys
            180                 185                 190

Val Val Val Tyr Cys His Glu Ile His Ile Glu Ser Ser Val Gly Ile
        195                 200                 205

Phe Glu Leu Glu Ala Glu Ala Tyr Leu Gln Lys Tyr Leu Val Glu Asn
    210                 215                 220

Gly Ile Gly Thr Met Thr Gly Ser Gly Phe Gly Met Ile Glu Gln Phe
225                 230                 235                 240

<210> SEQ ID NO 177
<211> LENGTH: 289
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 177

```
Met Lys Asn Lys Gly Leu Ala Met Thr Ile Ile Phe Gln Ala Glu Ser
1               5                   10                  15

Ala Asn Tyr Gly Glu Ser Leu Gly Asn Ile Ser Ser Leu Lys Lys Ile
            20                  25                  30

Ser Arg Asn Asn Gly Asp Gln Tyr Thr Tyr Ile Ser Arg Gln Ala Ile
        35                  40                  45

Arg Tyr Asn Leu Met Asp Gln Ile Gly Glu Lys Glu Ala Pro Val Lys
    50                  55                  60

Ala Glu Gly Gly Gly Asp Lys Lys Val Ile Gln Phe Leu Ser Glu Ala
65                  70                  75                  80

Thr Ile Thr Asp Phe Pro Glu Leu Asp Phe Phe Gly Tyr Leu Lys Thr
                85                  90                  95

Glu Lys Gly Ser Gly Gly Gln Lys Arg Ser Ala Lys Val Arg Leu Ser
            100                 105                 110

Asn Ala Ile Ser Leu Glu Thr Phe Lys Gly Asp Leu Asp Phe Leu Thr
        115                 120                 125

Asn Lys Gly Gln Ala Asp Lys Leu Asn Glu Asn Met Asn Ile Ala Gln
    130                 135                 140

Ala Glu Ile His Lys Ser Tyr Tyr Arg Tyr Thr Ile Thr Ile Asp Leu
145                 150                 155                 160

Asp Gln Ile Gly Ile Asp Gly Glu Ile Ala Leu Asp Asn Lys Glu Lys
                165                 170                 175

Ala Arg Arg Val Lys Lys Leu Met Asp Thr Val Ala Phe Leu Tyr Arg
            180                 185                 190

Asp Ile Arg Gly Arg Arg Glu Asp Leu Lys Pro Leu Phe Val Ile Gly
        195                 200                 205

Gly Val Tyr Asp Val Lys Asn Pro Val Phe Gln Asn Ile Val Asp Val
    210                 215                 220

Ala Asp Asn Asn Ile Val Ile Lys Asn Ile Lys Asp Leu Leu Thr Tyr
225                 230                 235                 240

Glu Asp Ile Lys Glu Asn Thr Arg Val Gly Ile Ile Asp Gly Gln Phe
                245                 250                 255

Ala Asn Ser Asp Glu Val Lys Val Glu Leu Lys Ala Glu Ser Val Pro
            260                 265                 270

Ala Phe Phe Asn Asp Ile Lys Gly Lys Ile Asp Ala Tyr Tyr Glu Ser
        275                 280                 285

Asn


<210> SEQ ID NO 178
<211> LENGTH: 562
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 178

Met Gln Thr Glu Ile Glu Val Arg Ala Asp Asp Trp Leu Ile Asn Thr
1               5                   10                  15

Gly Leu Thr Gly Phe Leu Asn Ile Val Gly Lys Glu Asn Val Arg Ile
            20                  25                  30

Asp Gly Gln Ser Ile Tyr Phe Thr Ala Asp Leu Leu Glu Asp Phe Glu
        35                  40                  45

Thr Lys Tyr Phe Asn Phe Phe Ile Gln Glu Tyr Lys Glu Thr Leu Ser
    50                  55                  60
```

-continued

```
Trp Tyr Lys Ile Val Ser Tyr Lys Glu Thr Met Glu Gln Phe Arg Ile
65                  70                  75                  80

Asp Glu Phe Ala Ser Phe Asp Glu Val Ala Leu Gly Asn Leu Asn Lys
                85                  90                  95

Tyr Met Lys Asp Val Val Lys Phe Tyr Leu Lys Lys Ala Asn Tyr Ile
            100                 105                 110

Lys Val Phe Pro Leu Ile Asp Pro Ser Ala Asn Val Thr Lys Trp Leu
        115                 120                 125

Glu Lys Leu Asn Thr Ile Asn Leu Thr Lys Lys Gln Lys Trp Asp Glu
    130                 135                 140

Val Lys Ala Asp Ile Ile Glu Glu Val Lys Gln Thr Tyr Thr Gln Leu
145                 150                 155                 160

Asp Leu Ile Ile Asp Phe Cys Ala Ser Glu Lys Gly Leu Gln Tyr Leu
                165                 170                 175

Gly Ala Lys Asn Leu Ile Tyr Ser Val Ile Asn Lys Gly Trp Ser Gly
            180                 185                 190

Val Ser Phe Leu Phe Lys Gln Thr Lys Phe Ile Asp Pro Tyr Leu Asp
        195                 200                 205

Tyr Lys Thr Thr Phe Val Asp Pro Val Leu Glu Tyr Leu Asp Thr Asp
    210                 215                 220

Leu Ser Lys Ala Lys Tyr Asn Cys Phe Asn Cys Asn Gln Pro Ile Lys
225                 230                 235                 240

Asn Leu Lys Leu Asp Leu Ser Phe Met Asn Asp Val Gly Phe Asp Thr
                245                 250                 255

Ala Arg Lys Thr Ala His Val Trp Asp Phe Asn Asn Asp Val Ala Thr
            260                 265                 270

Cys Pro Ile Cys Arg Leu Ile Tyr Ser Cys Val Pro Ala Gly Phe Thr
        275                 280                 285

Tyr Val Tyr Gly Glu Gly Met Phe Val Asn Asp Ser Tyr Gly Val Glu
    290                 295                 300

Glu Leu His Arg Val Asn Glu Arg Met Arg Asn Ser Ile Leu Arg Phe
305                 310                 315                 320

Asn Lys Asp Gly Ile Asn Ser Thr Asn Thr Tyr Arg Ala Leu Val Glu
                325                 330                 335

Ser Ile Thr Met Glu His Glu Asn Asn Arg Arg Tyr Glu Leu Ala Asp
            340                 345                 350

Ile Gln Leu Val Arg Tyr Glu Asn Glu His Tyr Arg Phe Asn Leu Leu
        355                 360                 365

Ser Lys Lys Met Leu His Ile Val Asn Asp Ser Lys Gly Ile Leu Lys
    370                 375                 380

Ser Leu Ile Arg Cys Gly Tyr Lys Glu Gly Asn Leu Asn Val Asn Leu
385                 390                 395                 400

Tyr Lys Glu Val Ile Gln His Leu Met Asn Asn Glu Asn Leu Phe Thr
                405                 410                 415

Leu Ile His Lys Leu Ile Tyr Tyr Lys Gln Thr Ser Val Asn Gly Leu
            420                 425                 430

Tyr Tyr Asn Met Gly His Val Ser Gly Ile Leu Asp Ile Asn Thr Lys
        435                 440                 445

Phe Leu Lys Glu Met Glu Val Met Thr Asn Ile Ser Gln Asn Gln Leu
    450                 455                 460

Trp Phe Val Gln Asn Cys Gly Lys Glu Phe Lys Glu Gly Tyr Val Lys
465                 470                 475                 480

Lys Lys Ser Glu Asn Lys Ile Ser Gly Ile Thr Tyr Lys Leu Leu Asn
```

-continued

```
                485                 490                 495

Ser Leu Lys Val Asn Asp Lys Asp Gly Phe Met Asp Thr Leu Leu Asn
            500                 505                 510

Ser Tyr Ser Tyr Leu Ser Met Pro Ile Pro Asp Val Phe Ile Lys Met
        515                 520                 525

Phe Ser Asn Asn Glu Ala Phe Lys Ser Val Gly Tyr Ala Phe Met Leu
    530                 535                 540

Gly Val Gly Gly Glu Lys Thr Lys Lys Glu Asp Gly Gly Asn Thr Asp
545                 550                 555                 560

Glu Lys
```

<210> SEQ ID NO 179
<211> LENGTH: 1851
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 179

```
attttcaaac cagaagaact acgacaggca ctgatgccaa ctttggaggc actttaccgt     60

caggatccag aatcccttcc ctttcgtcaa cctgtggacc ctcagctttt aggaatccct    120

gattactttg atattgtgaa gagccccatg gatctttcta ccattaagag gaagttagac    180

actggacagt atcaggagcc ctggcagtat gtcgatgata tttggcttat gttcaataat    240

gcctggttat ataaccggaa aacatcacgg gtatacaaat actgctccaa gctctctgag    300

gtctttgaac aagaaattga cccagtgatg caaagccttg gatactgttg tggcagaaag    360

ttggagttct ctccacagac actgtgttgc tacggcaaac agttgtgcac aatacctcgt    420

gatgccactt attacagtta ccagaacagg tatcatttct gtgagaagtg tttcaatgag    480

atccaagggg agagcgtttc tttgggggat gacccttccc agcctcaaac tacaataaat    540

aaagaacaat tttccaagag aaaaaatgac acactggatc ctgaactgtt tgttgaatgt    600

acagagtgcg gaagaaagat gcatcagatc tgtgtccttc accatgagat catctggcct    660

gctggattcg tctgtgatgg ctgtttaaag aaaagtgcac gaactaggaa agaaaataag    720

ttttctgcta aaaggttgcc atctaccaga cttggcacct ttctagagaa tcgtgtgaat    780

gactttctga ggcgacagaa tcaccctgag tcaggagagg tcactgttag agtagttcat    840

gcttctgaca aaaccgtgga agtaaaacca ggcatgaaag caaggtttgt ggacagtgga    900

gagatggcag aatcctttcc ataccgaacc aaagccctct ttgcctttga agaaattgat    960

ggtgttgacc tgtgcttctt tggcatgcat gttcaagagt atggctctga ctgccctcca   1020

cccaaccaga ggagagtata catatcttac ctcgatagtg ttcatttctt ccgtcctaaa   1080

tgcttgagga ctgcagtcta tcatgaaatc ctaattggat atttagaata tgtcaagaaa   1140

ttaggttaca caacagggca tatttgggca tgtccaccaa gtgagggaga tgattatatc   1200

ttccattgcc atcctcctga ccagaagata cccaagccca agcgactgca ggaatggtac   1260

aaaaaaatgc ttgacaaggc tgtatcagag cgtattgtcc atgactacaa ggatattttt   1320

aaacaagcta ctgaagatag attaacaagt gcaaaggaat tgccttattt cgagggtgat   1380

ttctggccca atgttctgga agaaagcatt aaggaactgg aacaggagga agaagagaga   1440

aaacgagagg aaaacaccag caatgaaagc acagatgtga ccaagggaga cagcaaaaat   1500

gctaaaaaga agaataataa gaaaaccagc aaaaataaga gcagcctgag taggggcaac   1560
```

-continued

```
aagaagaaac ccgggatgcc caatgtatct aacgacctct cacagaaact atatgccacc   1620

atggagaagc ataaagaggt cttctttgtg atccgcctca ttgctggccc tgctgccaac   1680

tccctgcctc ccattgttga tcctgatcct ctcatcccct gcgatctgat ggatggtcgg   1740

gatgcgtttc tcacgctggc aagggacaag cacctggagt tctcttcact ccgaagagcc   1800

cagtggtcca ccatgtgcat gctggtggag ctgcacacgc agagccagga c            1851


<210> SEQ ID NO 180
<211> LENGTH: 617
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 180

Ile Phe Lys Pro Glu Glu Leu Arg Gln Ala Leu Met Pro Thr Leu Glu
1               5                   10                  15

Ala Leu Tyr Arg Gln Asp Pro Glu Ser Leu Pro Phe Arg Gln Pro Val
            20                  25                  30

Asp Pro Gln Leu Leu Gly Ile Pro Asp Tyr Phe Asp Ile Val Lys Ser
        35                  40                  45

Pro Met Asp Leu Ser Thr Ile Lys Arg Lys Leu Asp Thr Gly Gln Tyr
    50                  55                  60

Gln Glu Pro Trp Gln Tyr Val Asp Asp Ile Trp Leu Met Phe Asn Asn
65                  70                  75                  80

Ala Trp Leu Tyr Asn Arg Lys Thr Ser Arg Val Tyr Lys Tyr Cys Ser
                85                  90                  95

Lys Leu Ser Glu Val Phe Glu Gln Glu Ile Asp Pro Val Met Gln Ser
            100                 105                 110

Leu Gly Tyr Cys Cys Gly Arg Lys Leu Glu Phe Ser Pro Gln Thr Leu
        115                 120                 125

Cys Cys Tyr Gly Lys Gln Leu Cys Thr Ile Pro Arg Asp Ala Thr Tyr
    130                 135                 140

Tyr Ser Tyr Gln Asn Arg Tyr His Phe Cys Glu Lys Cys Phe Asn Glu
145                 150                 155                 160

Ile Gln Gly Glu Ser Val Ser Leu Gly Asp Asp Pro Ser Gln Pro Gln
                165                 170                 175

Thr Thr Ile Asn Lys Glu Gln Phe Ser Lys Arg Lys Asn Asp Thr Leu
            180                 185                 190

Asp Pro Glu Leu Phe Val Glu Cys Thr Glu Cys Gly Arg Lys Met His
        195                 200                 205

Gln Ile Cys Val Leu His His Glu Ile Ile Trp Pro Ala Gly Phe Val
    210                 215                 220

Cys Asp Gly Cys Leu Lys Lys Ser Ala Arg Thr Arg Lys Glu Asn Lys
225                 230                 235                 240

Phe Ser Ala Lys Arg Leu Pro Ser Thr Arg Leu Gly Thr Phe Leu Glu
                245                 250                 255

Asn Arg Val Asn Asp Phe Leu Arg Arg Gln Asn His Pro Glu Ser Gly
            260                 265                 270

Glu Val Thr Val Arg Val Val His Ala Ser Asp Lys Thr Val Glu Val
        275                 280                 285

Lys Pro Gly Met Lys Ala Arg Phe Val Asp Ser Gly Glu Met Ala Glu
    290                 295                 300

Ser Phe Pro Tyr Arg Thr Lys Ala Leu Phe Ala Phe Glu Glu Ile Asp
```

```
305                 310                 315                 320

Gly Val Asp Leu Cys Phe Phe Gly Met His Val Gln Glu Tyr Gly Ser
                325                 330                 335

Asp Cys Pro Pro Pro Asn Gln Arg Arg Val Tyr Ile Ser Tyr Leu Asp
            340                 345                 350

Ser Val His Phe Phe Arg Pro Lys Cys Leu Arg Thr Ala Val Tyr His
        355                 360                 365

Glu Ile Leu Ile Gly Tyr Leu Glu Tyr Val Lys Lys Leu Gly Tyr Thr
    370                 375                 380

Thr Gly His Ile Trp Ala Cys Pro Pro Ser Glu Gly Asp Asp Tyr Ile
385                 390                 395                 400

Phe His Cys His Pro Pro Asp Gln Lys Ile Pro Lys Pro Lys Arg Leu
                405                 410                 415

Gln Glu Trp Tyr Lys Lys Met Leu Asp Lys Ala Val Ser Glu Arg Ile
            420                 425                 430

Val His Asp Tyr Lys Asp Ile Phe Lys Gln Ala Thr Glu Asp Arg Leu
        435                 440                 445

Thr Ser Ala Lys Glu Leu Pro Tyr Phe Glu Gly Asp Phe Trp Pro Asn
    450                 455                 460

Val Leu Glu Glu Ser Ile Lys Glu Leu Glu Gln Glu Glu Glu Glu Arg
465                 470                 475                 480

Lys Arg Glu Glu Asn Thr Ser Asn Glu Ser Thr Asp Val Thr Lys Gly
                485                 490                 495

Asp Ser Lys Asn Ala Lys Lys Lys Asn Asn Lys Lys Thr Ser Lys Asn
            500                 505                 510

Lys Ser Ser Leu Ser Arg Gly Asn Lys Lys Lys Pro Gly Met Pro Asn
        515                 520                 525

Val Ser Asn Asp Leu Ser Gln Lys Leu Tyr Ala Thr Met Glu Lys His
    530                 535                 540

Lys Glu Val Phe Phe Val Ile Arg Leu Ile Ala Gly Pro Ala Ala Asn
545                 550                 555                 560

Ser Leu Pro Pro Ile Val Asp Pro Asp Pro Leu Ile Pro Cys Asp Leu
                565                 570                 575

Met Asp Gly Arg Asp Ala Phe Leu Thr Leu Ala Arg Asp Lys His Leu
            580                 585                 590

Glu Phe Ser Ser Leu Arg Arg Ala Gln Trp Ser Thr Met Cys Met Leu
        595                 600                 605

Val Glu Leu His Thr Gln Ser Gln Asp
    610                 615
```

<210> SEQ ID NO 181
<211> LENGTH: 32
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 181
ucacugcuga cccucuccgg accugacucc cg 32

<210> SEQ ID NO 182
<211> LENGTH: 32
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 182
gcucaguucu cugcauguga ccucccaucc cg 32

<210> SEQ ID NO 183
<211> LENGTH: 32
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 183
guuugguuuc ugcuagccug agucacccuc cg 32

<210> SEQ ID NO 184
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 184
agcaggccca guuuccagga gggugacuca ggcccg 36

<210> SEQ ID NO 185
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 185
gcaugaggag augggccggc ugauggcuga cuuccg 36

<210> SEQ ID NO 186
<211> LENGTH: 34
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 186
ucagccggcc caucuccuca ugcuggccaa cccg 34

<210> SEQ ID NO 187
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 187
ucagccggcc caucuccuca ugcuggccaa cccccg 36

<210> SEQ ID NO 188
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 188
ucuccucaug cuggccaacc cucugugagu gugccg 36

<210> SEQ ID NO 189
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 189
cacacucaca gaggguuggc cagcaugagg agaccg 36

<210> SEQ ID NO 190
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 190
gccuccccuc ccacacacuc acagaggguu ggcccg 36

<210> SEQ ID NO 191
<211> LENGTH: 32
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 191
acccucugug agugugcggg aggggaggcc cg 32

<210> SEQ ID NO 192
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 192
acccucugug agugugcggg aggggaggcu gggccg 36

<210> SEQ ID NO 193
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 193
gagcaccuca gagaguacaa ggaggagccc agcccg 36

<210> SEQ ID NO 194
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 194 gggugggagcu gccccuccuu ccagagcacc ucaccg 36

<210> SEQ ID NO 195
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 195 caguccucc cagggguggag cugccccucc uucccg 36

<210> SEQ ID NO 196
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 196
cccugggagg gacuguggcc cagguacugc ccgccg 36

<210> SEQ ID NO 197
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 197
gguacugccc gggugcuacu uuaugggcag cagccg 36

<210> SEQ ID NO 198
<211> LENGTH: 32
<212> TYPE: DNA
<213> ORGANISM: Homo sapiens

<400> SEQUENCE: 198
tcactgctga ccctctccgg acctgactcc cg 32

<210> SEQ ID NO 199
<211> LENGTH: 32
<212> TYPE: DNA
<213> ORGANISM: Homo sapiens

<400> SEQUENCE: 199
gctcagttct ctgcatgtga cctcccatcc cg 32

<210> SEQ ID NO 200
<211> LENGTH: 32
<212> TYPE: DNA
<213> ORGANISM: Homo sapiens

<400> SEQUENCE: 200
gtttggtttc tgctagcctg agtcaccctc cg 32

<210> SEQ ID NO 201
<211> LENGTH: 36
<212> TYPE: DNA
<213> ORGANISM: Homo sapiens

<400> SEQUENCE: 201
agcaggccca gtttccagga gggtgactca ggcccg 36

<210> SEQ ID NO 202
<211> LENGTH: 36
<212> TYPE: DNA
<213> ORGANISM: Homo sapiens

<400> SEQUENCE: 202
gcatgaggag atgggccggc tgatggctga cttccg 36

<210> SEQ ID NO 203
<211> LENGTH: 34
<212> TYPE: DNA
<213> ORGANISM: Homo sapiens

<400> SEQUENCE: 203
tcagccggcc catctcctca tgctggccaa cccg 34

<210> SEQ ID NO 204
<211> LENGTH: 36
<212> TYPE: DNA
<213> ORGANISM: Homo sapiens

<400> SEQUENCE: 204
tcagccggcc catctcctca tgctggccaa cccccg 36

<210> SEQ ID NO 205
<211> LENGTH: 36
<212> TYPE: DNA
<213> ORGANISM: Homo sapiens

<400> SEQUENCE: 205
tctcctcatg ctggccaacc ctctgtgagt gtgccg 36

<210> SEQ ID NO 206
<211> LENGTH: 36
<212> TYPE: DNA
<213> ORGANISM: Homo sapiens

<400> SEQUENCE: 206
cacactcaca gagggttggc cagcatgagg agaccg 36

<210> SEQ ID NO 207
<211> LENGTH: 36
<212> TYPE: DNA
<213> ORGANISM: Homo sapiens

<400> SEQUENCE: 207
gcctcccctc ccacacactc acagagggtt ggcccg 36

<210> SEQ ID NO 208
<211> LENGTH: 32
<212> TYPE: DNA
<213> ORGANISM: Homo sapiens

<400> SEQUENCE: 208
accctctgtg agtgtgtggg aggggaggcc cg 32

<210> SEQ ID NO 209
<211> LENGTH: 36
<212> TYPE: DNA
<213> ORGANISM: Homo sapiens

<400> SEQUENCE: 209
accctctgtg agtgtgtggg aggggaggct gggccg 36

<210> SEQ ID NO 210
<211> LENGTH: 36
<212> TYPE: DNA
<213> ORGANISM: Homo sapiens

<400> SEQUENCE: 210
gagcacctca gagagtacaa ggaggagccc agcccg 36

<210> SEQ ID NO 211
<211> LENGTH: 36
<212> TYPE: DNA
<213> ORGANISM: Homo sapiens

<400> SEQUENCE: 211
gggtggagct gcccctcctt ccagagcacc tcaccg 36

<210> SEQ ID NO 212
<211> LENGTH: 36
<212> TYPE: DNA
<213> ORGANISM: Homo sapiens

<400> SEQUENCE: 212
cagtccctcc cagggtggag ctgcccctcc ttcccg 36

<210> SEQ ID NO 213
<211> LENGTH: 36
<212> TYPE: DNA
<213> ORGANISM: Homo sapiens

<400> SEQUENCE: 213
ccctgggagg gactgtggcc caggtactgc ccgccg 36

<210> SEQ ID NO 214
<211> LENGTH: 36
<212> TYPE: DNA
<213> ORGANISM: Homo sapiens

<400> SEQUENCE: 214
ggtactgccc gggtgctact ttatgggcag cagccg 36

<210> SEQ ID NO 215
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 215
gactataagg atgatgacga caag 24

<210> SEQ ID NO 216
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 216

-continued gactacaagg acgacgacga taag 24

<210> SEQ ID NO 217
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 217
gactacaagg acgatgatga caag 24

<210> SEQ ID NO 218
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 218
gattacaagg acgatgacga caaa 24

<210> SEQ ID NO 219
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 219
gattacaaag acgatgacga taag 24

<210> SEQ ID NO 220
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 220

Asp Tyr Lys Asp Asp Asp Asp Lys
1               5

<210> SEQ ID NO 221
<211> LENGTH: 42
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 221
ggcaagccta tacctaaccc tttgctcggg ctggactcca cc 42

<210> SEQ ID NO 222
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 222

-continued

Gly Lys Pro Ile Pro Asn Pro Leu Leu Gly Leu Asp Ser Thr
1 5 10

<210> SEQ ID NO 223
<211> LENGTH: 21
<212> TYPE: DNA
<213> ORGANISM: Unknown
<220> FEATURE:
<223> OTHER INFORMATION: Description of Unknown: Nuclear localization signal sequence

<400> SEQUENCE: 223
cccaagaaga agcgcaaagt c 21

<210> SEQ ID NO 224
<211> LENGTH: 21
<212> TYPE: DNA
<213> ORGANISM: Unknown
<220> FEATURE:
<223> OTHER INFORMATION: Description of Unknown: Nuclear localization signal sequence

<400> SEQUENCE: 224
ccaaagaaaa agcgcaaggt c 21

<210> SEQ ID NO 225
<211> LENGTH: 21
<212> TYPE: DNA
<213> ORGANISM: Unknown
<220> FEATURE:
<223> OTHER INFORMATION: Description of Unknown: Nuclear localization signal sequence

<400> SEQUENCE: 225
cccaagaaga aacggaaagt c 21

<210> SEQ ID NO 226
<211> LENGTH: 21
<212> TYPE: DNA
<213> ORGANISM: Unknown
<220> FEATURE:
<223> OTHER INFORMATION: Description of Unknown: Nuclear localization signal sequence

<400> SEQUENCE: 226
ccgaagaaga agcggaaggt c 21

<210> SEQ ID NO 227
<211> LENGTH: 7
<212> TYPE: PRT
<213> ORGANISM: Simian virus 40

<400> SEQUENCE: 227

Pro Lys Lys Lys Arg Lys Val
1 5

<210> SEQ ID NO 228
<211> LENGTH: 48
<212> TYPE: DNA
<213> ORGANISM: Unknown
<220> FEATURE:
<223> OTHER INFORMATION: Description of Unknown: Nuclear localization signal sequence

<400> SEQUENCE: 228
aagcgacctg ccgccacaaa gaaggctgga caggctaaga agaagaaa 48

<210> SEQ ID NO 229
<211> LENGTH: 16
<212> TYPE: PRT
<213> ORGANISM: Unknown
<220> FEATURE:
<223> OTHER INFORMATION: Description of Unknown: Nuclear localization signal sequence

<400> SEQUENCE: 229

Lys Arg Pro Ala Ala Thr Lys Lys Ala Gly Gln Ala Lys Lys Lys Lys
1 5 10 15

<210> SEQ ID NO 230
<211> LENGTH: 43
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 230
tcaaaccaac agatcaaact ccggaagggt gattgtaaat ggc 43

<210> SEQ ID NO 231
<211> LENGTH: 44
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 231
aatacccaaa aataggagga aataaattat gactatcaaa ttaa 44

<210> SEQ ID NO 232
<211> LENGTH: 45
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 232
cttggccaag agtttccagc tgtaaggcca gatattgata atttc 45

<210> SEQ ID NO 233
<211> LENGTH: 45
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 233
atattccacc tccacaatca ctcggctttc ttcgtcttta tcgac 45

<210> SEQ ID NO 234
<211> LENGTH: 45
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 234
aagatccagt cgctagagct aaaaaatgga tagaggaaca acaag 45

<210> SEQ ID NO 235
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 235
ccaaacaagt tgaaaagcgc accattgttt taattttttt aatt 44

<210> SEQ ID NO 236
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 236
caagtccatt ttgtcgcata aattctttga tgtggcggac tgacg 45

<210> SEQ ID NO 237
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 237
cggagccttc gttaatcata attgatgaaa gtcatcatgt gttag 45

<210> SEQ ID NO 238

<400> SEQUENCE: 238

000

<210> SEQ ID NO 239

<400> SEQUENCE: 239

000

<210> SEQ ID NO 240

<400> SEQUENCE: 240

000

<210> SEQ ID NO 241

<400> SEQUENCE: 241

000

<210> SEQ ID NO 242

<400> SEQUENCE: 242

000

<210> SEQ ID NO 243
<211> LENGTH: 29
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 243
guuuuaacua cuuauuauga aauguaaau 29

<210> SEQ ID NO 244
<211> LENGTH: 68
<212> TYPE: DNA
<213> ORGANISM: Homo sapiens

<400> SEQUENCE: 244
atggctgact tgatgccaag caggcccagt ttccaggagg gtgactcagg ctagcagaaa 60
ccaaacca 68

<210> SEQ ID NO 245
<211> LENGTH: 68
<212> TYPE: DNA
<213> ORGANISM: Homo sapiens

<400> SEQUENCE: 245
tggtttggtt tctgctagcc tgagtcaccc tcctggaaac tgggcctgct tggcatcaag 60
tcagccat 68

<210> SEQ ID NO 246
<211> LENGTH: 66
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 246
uagcaggccc aguuuccagg agggugacuc aggcccgguu uuaacuacuu auuaugaaau 60
guaaau 66

<210> SEQ ID NO 247
<211> LENGTH: 7
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 247 ttttttt 7

<210> SEQ ID NO 248
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 248
gttttaacta cttattatga aatgtaaat 29

<210> SEQ ID NO 249
<211> LENGTH: 29
<212> TYPE: DNA
<213> ORGANISM: Artificial Sequence
<220> FEATURE:

<223> OTHER INFORMATION: Description of Artificial Sequence: Synthetic
      oligonucleotide

<400> SEQUENCE: 249
atttacattt cataataagt agttaaaac 29

<210> SEQ ID NO 250
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 250
ggaccggttt taactactta ttatgaaatg taaatgctgg gctcctcctt gtactctctg 60
aggtc 65

<210> SEQ ID NO 251
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 251
ccgggacctc agagagtaca aggaggagcc cagcatttac atttcataat aagtagttaa 60
aaccggtccg c 71

<210> SEQ ID NO 252
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 252

Tyr Pro Tyr Asp Val Pro Asp Tyr Ala Cys
1               5                   10

<210> SEQ ID NO 253
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 253

Glu Gln Lys Leu Ile Ser Glu Glu Asp Leu Cys
1               5                   10

<210> SEQ ID NO 254
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 254

Gly Ala Pro Val Pro Tyr Pro Asp Pro Leu Glu Pro Arg
1               5                   10

<210> SEQ ID NO 255
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 255

Tyr Thr Asp Ile Glu Met Asn Arg Leu Gly Lys
1 5 10

<210> SEQ ID NO 256
<211> LENGTH: 6
<212> TYPE: PRT
<213> ORGANISM: Artificial Sequence
<220> FEATURE:
<223> OTHER INFORMATION: Description of Artificial Sequence: Synthetic 6xHis tag

<400> SEQUENCE: 256

His His His His His His
1 5

<210> SEQ ID NO 257
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 257

Gln Pro Glu Leu Ala Pro Glu Asp Pro Glu Asp Cys
1 5 10

<210> SEQ ID NO 258
<211> LENGTH: 774
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 258
atgaaggcta ttagggtccg gctgtggcag gatctcgtga acttcaagaa gcctaccagc 60
ttccaactga aggaaaccta ccctctgccg ccgtactcta ccgtgatcgg catggtgcat 120
acactgtgcg gctttacctc ctaccacgag atgaagatca gcattcaggg aaagtacttt 180
agcaaggtca acgacctcgc gactagatac gaattcaaga atggctcaaa atacgacgtg 240
gaacgccacc agatcaaagt ggacaaatac ggagtgtcga gaggcgtcag caccgtggag 300
ctccttgtgg acctcgaact gctgctgcac atcattccgg aagatccatc cttggtgccg 360
atcattgaaa aggcattccg ggaacccatc gagttccctt ccctgggacg cagagaggac 420
atcgccacga ttcagaaggt cgaagtggtg gacgtcgaga agcgacagcc caagaagtcc 480
accgagatct ccgacggtta taacgcctac gtgccgatca gcttgaccga gaacaactcg 540
gtgcatttca agtcccacga gtcctcagtg ggacgggata agctgctggg gactcggtac 600
cttctgactg agaaatacga gcgcgtgaac cacggaaccg aaaaggcccc taagttcttc 660
cggaagtggc ggaagaagga cgtcatctac tcctcgcgca tcttcgtgtc caagaaggat 720
gtgttctttt tcgacgagga cgattacctg gtgttcatcg aagaagaaga gtga 774

<210> SEQ ID NO 259
<211> LENGTH: 723
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 259
atgcggctga agattaactg cgacttcgac agcaagatca tccccaagga cttccagtcc 60
aaggtcgtgt ccctgttcaa agccggaatt atgaaaagct ccccggagag atacgagaac 120
ctgtttggtg gaaacaagca caagcagtac actttctcgg tgtatctccc aaaacctcag 180
aacaagggcg ccgaaattca gctgaacgag gcgaactgta tcatcaactt ctccaccggc 240
gatgctgaaa ccggtattat cttctacaac gccctgatta gcctgagagg ctccaaggtc 300
ctgtttgggg ccggaaatca catcaccgtg aagaacatcc agatcgtgcc tgagaagaag 360
atcatcggga agcaaaccat tctgcggacc ctttcgccgg tggtgtcgag ggatcacaac 420
cgggaaacct tcaagaattg gttctactca ttcgaggacg aagaattcga gcctactttg 480
aagcggaaca tgctgccgta cctcatcgac gcctttggag aacaggctcg ctacgatctg 540
gaaaagctga agatcacgcc catttccatg aagaaagtcg tggtgtactg ccatgagatc 600
cacatcgaga gctccgtggg catcttcgag ctggaagccg aggcatacct ccaaaagtac 660
ctcgtggaaa acggaatcgg cactatgact ggctcagggt tcggaatgat tgaacagttc 720
tga 723

<210> SEQ ID NO 260
<211> LENGTH: 870
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 260
atgaagaaca agggactggc aatgactatc attttccaag ccgaaagcgc caattacggc 60
gaatccctgg ggaacatttc aagcctgaag aagatctcta ggaacaacgg agatcagtac 120
acctacatct cccgccaagc gatccggtac aatcttatgg atcagatcgg agaaaaggaa 180
gcccctgtga aggctgaagg cggcggagac aaaaaggtca tccagttcct gtccgaggcc 240
acgatcaccg acttcccgga actcgacttt ttcggctacc tgaaaaccga aaagggttcc 300
gggggacaga agcgcagcgc caaagtccga ctgtcgaacg ccatctcgct ggagactttt 360
aagggcgacc tggatttcct cactaacaag ggacaggccg acaagctgaa cgaaaacatg 420
aacattgcgc aggcagagat ccacaagtcc tactaccgct acaccatcac catcgacctc 480
gaccagatcg gtatcgacgg ggagattgct ctggacaaca aggaaaaggc ccggagagtg 540
aagaagctga tggacactgt ggcgttcctc tatcgggaca ttaggggcag acgggaggac 600
ctcaagcccc tgttcgtgat cggtggagtg tatgacgtga agaacccggt gttccaaaac 660
attgtggatg tggccgacaa caatattgtg atcaagaaca ttaaggattt gctgacctac 720
gaggacatca aggagaacac cagagtcggc atcattgatg ggcagttcgc caactccgac 780
gaagtgaaag tcgagctgaa ggccgagtcc gtgccagctt tcttcaacga catcaaggga 840
aagattgatg cgtactacga gagcaactga 870

<210> SEQ ID NO 261
<211> LENGTH: 1689
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 261
atgcagaccg aaatcgaagt cagggcagac gactggctca tcaacaccgg actgaccggc 60
ttcctgaaca ttgtgggaaa agagaacgtc cggattgacg ggcagtctat ctacttcacc 120
gctgacctcc tggaagattt cgaaactaag tactttaact tcttcatcca agagtacaaa 180
gaaactctct catggtacaa gatcgtcagc tacaaagaga ctatggagca gttcagaatt 240
gatgaattcg cgtcctttga cgaagtggcc ctggggaacc tgaacaagta catgaaggac 300
gtcgtgaagt tctatctgaa aaaggccaac tatatcaaag tgttcccctt gattgaccct 360
agcgccaacg tgaccaagtg gctcgaaaag ctgaacacca ttaatctgac caagaagcag 420
aaatgggatg aggtcaaggc tgacattatt gaggaggtca aacagaccta cacccaactc 480
gacctgatta ttgacttctg tgcctccgaa aagggactgc agtacctggg agccaagaac 540
ctgatctatt ccgtcattaa caagggctgg agcggagtct ccttcctgtt caagcaaacc 600
aagttcattg acccgtatct ggactacaag acgaccttcg tggatcctgt gctggagtac 660
ctggataccg atctgtccaa ggccaagtac aactgcttca actgcaacca gcccatcaag 720
aacctcaagc tcgacctctc gttcatgaat gacgtgggct ttgacaccgc ccgcaagact 780
gcgcacgtct gggatttcaa caacgatgtg gccacttgtc caatctgccg gctgatctac 840
tcatgcgtgc ctgccgggtt cacctacgtg tatggagagg gaatgttcgt gaacgactcc 900
tacggcgtgg aagaactgca cagagtgaac gaacggatgc ggaacagcat cctgaggttt 960
aacaaggacg gtatcaattc caccaacact taccgcgcgc ttgtggagtc cattaccatg 1020
gaacacgaaa acaacagacg ctacgaattg gctgacatcc agctcgtgcg atacgagaac 1080
gagcattacc ggttcaatct gttgtcaaag aagatgcttc acatcgtgaa cgattccaag 1140
ggtatcctga agtcgctgat acgctgcggt tacaaggagg ggaacctcaa cgtgaacctc 1200
tacaaggaag tgatccagca tctgatgaac aacgaaaacc tcttcaccct tatccacaag 1260
ttgatctact acaagcagac cagcgtgaac ggcctgtact acaacatggg ccacgtgtcc 1320
ggaatcctgg atatcaacac caagttcctg aaagaaatgg aggtcatgac gaacatctca 1380
cagaaccagc tgtggttcgt gcaaaattgt ggcaaagaat tcaaggaggg ttacgtgaag 1440
aagaagtccg agaacaagat ctccggaatc acttacaagc tgctgaattc gctgaaggtc 1500
aacgacaagg acggattcat ggacaccctg ctgaactcct actcgtacct gtccatgccg 1560
atccccgacg tgttcatcaa gatgttctcc aacaacgaag ccttcaagag cgtgggctac 1620
gcttttatgc ttggcgtggg tggagaaaag actaagaagg aagatggggg caacaccgat 1680
gagaagtga 1689

<210> SEQ ID NO 262
<211> LENGTH: 20
<212> TYPE: PRT
<213> ORGANISM: Unknown
<220> FEATURE:
<223> OTHER INFORMATION: Description of Unknown: Nucleoplasmin sequence

<400> SEQUENCE: 262

Ala Val Lys Arg Pro Ala Ala Thr Lys Lys Ala Gly Gln Ala Lys Lys 1 5 10 15

Lys Lys Leu Asp
20

<210> SEQ ID NO 263
<211> LENGTH: 16
<212> TYPE: PRT
<213> ORGANISM: Unknown
<220> FEATURE:
<223> OTHER INFORMATION: Description of Unknown: Nucleoplasmin sequence

<400> SEQUENCE: 263

Lys Arg Pro Ala Ala Thr Lys Lys Ala Gly Gln Ala Lys Lys Lys Lys
1 5 10 15

<210> SEQ ID NO 264
<211> LENGTH: 25
<212> TYPE: PRT
<213> ORGANISM: Unknown
<220> FEATURE:
<223> OTHER INFORMATION: Description of Unknown: EGL-13 sequence

<400> SEQUENCE: 264

Met Ser Arg Arg Arg Lys Ala Asn Pro Thr Lys Leu Ser Glu Asn Ala
1 5 10 15

Lys Lys Leu Ala Lys Glu Val Glu Asn
20 25

<210> SEQ ID NO 265
<211> LENGTH: 9
<212> TYPE: PRT
<213> ORGANISM: Unknown
<220> FEATURE:
<223> OTHER INFORMATION: Description of Unknown: c-Myc sequence

<400> SEQUENCE: 265

Pro Ala Ala Lys Arg Val Lys Leu Asp
1 5

<210> SEQ ID NO 266
<211> LENGTH: 9
<212> TYPE: PRT
<213> ORGANISM: Unknown
<220> FEATURE:
<223> OTHER INFORMATION: Description of Unknown: TUS-protein sequence

<400> SEQUENCE: 266

Lys Leu Lys Ile Lys Arg Pro Val Lys
1 5

<210> SEQ ID NO 267
<211> LENGTH: 10
<212> TYPE: PRT
<213> ORGANISM: Unknown
<220> FEATURE:
<223> OTHER INFORMATION: Description of Unknown: Nuclear localization signal sequence

<400> SEQUENCE: 267

Val Gln Arg Lys Arg Gln Lys Leu Met Pro
1 5 10

<210> SEQ ID NO 268
<211> LENGTH: 8
<212> TYPE: PRT
<213> ORGANISM: Unknown

<220> FEATURE:
<223> OTHER INFORMATION: Description of Unknown: Nuclear localization
      signal sequence

<400> SEQUENCE: 268

Ser Lys Lys Lys Lys Thr Lys Val
1               5

<210> SEQ ID NO 269
<211> LENGTH: 8
<212> TYPE: PRT
<213> ORGANISM: Unknown
<220> FEATURE:
<223> OTHER INFORMATION: Description of Unknown: Nuclear localization
      signal sequence

<400> SEQUENCE: 269

Gly Arg Lys Arg Lys Lys Arg Thr
1               5

<210> SEQ ID NO 270
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 270
cacuaucuca augcaaauau cugucugaaa cggccg 36

<210> SEQ ID NO 271
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 271
gggaccguuu cagacagaua uuugcauuga gauccg 36

<210> SEQ ID NO 272
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 272
acccaugggu ggaguuuagc cagggaccgu uucccg 36

<210> SEQ ID NO 273
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 273
uggguuggcc agccuugccu ugaccaauag ccuccg 36

<210> SEQ ID NO 274
<211> LENGTH: 36
<212> TYPE: RNA

<213> ORGANISM: Artificial Sequence
<220> FEATURE:
<223> OTHER INFORMATION: Description of Artificial Sequence: Synthetic
oligonucleotide

<400> SEQUENCE: 274
gccuugccuu gaccaauagc cuugacaagg caaccg 36

<210> SEQ ID NO 275
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 275
ggggccggcg gcuggcuagg gaugaagaau aaaccg 36

<210> SEQ ID NO 276
<211> LENGTH: 36
<212> TYPE: DNA
<213> ORGANISM: Homo sapiens

<400> SEQUENCE: 276
cactatctca atgcaaatat ctgtctgaaa cggccg 36

<210> SEQ ID NO 277
<211> LENGTH: 36
<212> TYPE: DNA
<213> ORGANISM: Homo sapiens

<400> SEQUENCE: 277
gggaccgttt cagacagata tttgcattga gatccg 36

<210> SEQ ID NO 278
<211> LENGTH: 36
<212> TYPE: DNA
<213> ORGANISM: Homo sapiens

<400> SEQUENCE: 278
acccatgggt ggagtttagc cagggaccgt ttcccg 36

<210> SEQ ID NO 279
<211> LENGTH: 36
<212> TYPE: DNA
<213> ORGANISM: Homo sapiens

<400> SEQUENCE: 279
tgggttggcc agccttgcct tgaccaatag cctccg 36

<210> SEQ ID NO 280
<211> LENGTH: 36
<212> TYPE: DNA
<213> ORGANISM: Homo sapiens

<400> SEQUENCE: 280
gccttgcctt gaccaatagc cttgacaagg caaccg 36

<210> SEQ ID NO 281
<211> LENGTH: 36
<212> TYPE: DNA
<213> ORGANISM: Homo sapiens

<400> SEQUENCE: 281

```
gggggccggcg gctggctagg gatgaagaat aaaccg                              36


<210> SEQ ID NO 282
<211> LENGTH: 6116
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 282

gggtctctct ggttagacca gatctgagcc tgggagctct ctggctaact agggaaccca     60

ctgcttaagc ctcaataaag cttgccttga gtgcttcaag tagtgtgtgc ccgtctgttg    120

tgtgactctg gtaactagag atccctcaga cccttttagt cagtgtggaa aatctctagc    180

agtggcgccc gaacagggac ttgaaagcga aagggaaacc agaggagctc tctcgacgca    240

ggactcggct tgctgaagcg cgcacggcaa gaggcgaggg gcggcgactg gtgagtacgc    300

caaaaatttt gactagcgga ggctagaagg agagagatgg gtgcgagagc gtcagtatta    360

agcgggggag aattagatcg cgatgggaaa aaattcggtt aaggccaggg ggaaagaaaa    420

aatataaatt aaaacatata gtatgggcaa gcagggagct agaacgattc gcagttaatc    480

ctggcctgtt agaaacatca gaaggctgta gacaaatact gggacagcta caaccatccc    540

ttcagacagg atcagaagaa cttagatcat tatataatac agtagcaacc ctctattgtg    600

tgcatcaaag gatagagata aaagacacca aggaagcttt agacaagata gaggaagagc    660

aaaacaaaag taagaccacc gcacagcaag cggccgctga tcttcagacc tggaggagga    720

gatatgaggg acaattggag aagtgaatta tataaatata aagtagtaaa aattgaacca    780

ttaggagtag cacccaccaa ggcaaagaga agagtggtgc agagagaaaa aagagcagtg    840

ggaataggag ctttgttcct tgggttcttg ggagcagcag gaagcactat gggcgcagcg    900

tcaatgacgc tgacggtaca ggccagacaa ttattgtctg gtatagtgca gcagcagaac    960

aatttgctga gggctattga ggcgcaacag catctgttgc aactcacagt ctggggcatc   1020

aagcagctcc aggcaagaat cctggctgtg gaaagatacc taaaggatca acagctcctg   1080

gggatttggg gttgctctgg aaaactcatt tgcaccactg ctgtgccttg gaatgctagt   1140

tggagtaata aatctctgga acagatttgg aatcacacga cctggatgga gtgggacaga   1200

gaaattaaca attacacaag cttaatacac tccttaattg aagaatcgca aaaccagcaa   1260

gaaaagaatg aacaagaatt attggaatta gataaatggg caagtttgtg gaattggttt   1320

aacataacaa attggctgtg gtatataaaa ttattcataa tgatagtagg aggcttggta   1380

ggtttaagaa tagtttttgc tgtactttct atagtgaata gagttaggca gggatattca   1440

ccattatcgt ttcagaccca cctcccaacc ccgaggggac ccgacaggcc cgaaggaata   1500

gaagaagaag gtggagagag agacagagac agatccattc gattagtgaa cggatcggca   1560

ctgcgtgcgc caattctgca gacaaatggc agtattcatc cacaatttta aaagaaaagg   1620

ggggattggg gggtacagtg caggggaaag aatagtagac ataatagcaa cagacataca   1680

aactaaagaa ttacaaaaac aaattacaaa aattcaaaat tttcgggttt attacaggga   1740

cagcagagat ccagtttggt taattaaggg tgcagcggcc tccgcgccgg gttttggcgc   1800

ctcccgcggg cgcccccctc ctcacggcga gcgctgccac gtcagacgaa gggcgcagga   1860

gcgttcctga tccttccgcc cggacgctca ggacagcggc ccgctgctca taagactcgg   1920

ccttagaacc ccagtatcag cagaaggaca ttttaggacg ggacttgggt gactctaggg   1980
```

```
cactggtttt ctttccagag agcggaacag gcgaggaaaa gtagtccctt ctcggcgatt   2040
ctgcggaggg atctccgtgg ggcggtgaac gccgatgatt atataaggac gcgccgggtg   2100
tggcacagct agttccgtcg cagccgggat ttgggtcgcg gttcttgttt gtggatcgct   2160
gtgatcgtca cttggtgagt tgcgggctgc tgggctggcc ggggctttcg tggccgccgg   2220
gccgctcggt gggacggaag cgtgtggaga gaccgccaag ggctgtagtc tgggtccgcg   2280
agcaaggttg ccctgaactg ggggttgggg ggagcgcaca aaatggcggc tgttcccgag   2340
tcttgaatgg aagacgcttg taaggcgggc tgtgaggtcg ttgaaacaag gtgggggggca   2400
tggtgggcgg caagaaccca aggtcttgag gccttcgcta atgcgggaaa gctcttattc   2460
gggtgagatg ggctggggca ccatctgggg accctgacgt gaagtttgtc actgactgga   2520
gaactcgggt ttgtcgtctg gttgcggggg cggcagttat gcggtgccgt tgggcagtgc   2580
acccgtacct ttgggagcgc gcgcctcgtc gtgtcgtgac gtcacccgtt ctgttggctt   2640
ataatgcagg gtggggccac ctgccggtag gtgtgcggta ggcttttctc cgtcgcagga   2700
cgcagggttc gggcctaggg taggctctcc tgaatcgaca ggcgccggac ctctggtgag   2760
gggagggata agtgaggcgt cagtttcttt ggtcggtttt atgtacctat cttcttaagt   2820
agctgaagct ccggttttga actatgcgct cggggttggc gagtgtgttt tgtgaagttt   2880
tttaggcacc ttttgaaatg taatcatttg ggtcaatatg taattttcag tgttagacta   2940
gtaaattgtc cgctaaattc tggccgtttt tggctttttt gttagacgaa gcttgggctg   3000
caggtcgact ctagaggatc cccgggtacc ggtcgccacc gccgccacca tggattacaa   3060
ggacgatgac gacaaaatgg cgccgaagaa gaagcggaag gtccggggca tgcagaccga   3120
aatcgaagtc agggcagacg actggctcat caacaccgga ctgaccggct tcctgaacat   3180
tgtgggaaaa gagaacgtcc ggattgacgg gcagtctatc tacttcaccg ctgacctcct   3240
ggaagatttc gaaactaagt actttaactt cttcatccaa gagtacaaag aaactctctc   3300
atggtacaag atcgtcagct acaaagagac tatggagcag ttcagaattg atgaattcgc   3360
gtcctttgac gaagtggccc tggggaacct gaacaagtac atgaaggacg tcgtgaagtt   3420
ctatctgaaa aaggccaact atatcaaagt gttccccttg attgacccta gcgccaacgt   3480
gaccaagtgg ctcgaaaagc tgaacaccat taatctgacc aagaagcaga aatgggatga   3540
ggtcaaggct gacattattg aggaggtcaa acagacctac acccaactcg acctgattat   3600
tgacttctgt gcctccgaaa agggactgca gtacctggga gccaagaacc tgatctattc   3660
cgtcattaac aagggctgga gcggagtctc cttcctgttc aagcaaacca agttcattga   3720
cccgtatctg gactacaaga cgaccttcgt ggatcctgtg ctggagtacc tggataccga   3780
tctgtccaag gccaagtaca actgcttcaa ctgcaaccag cccatcaaga acctcaagct   3840
cgacctctcg ttcatgaatg acgtgggctt tgacaccgcc cgcaagactg cgcacgtctg   3900
ggatttcaac aacgatgtgg ccacttgtcc aatctgccgg ctgatctact catgcgtgcc   3960
tgccgggttc acctacgtgt atggagaggg aatgttcgtg aacgactcct acggcgtgga   4020
agaactgcac agagtgaacg aacggatgcg gaacagcatc ctgaggttta acaaggacgg   4080
tatcaattcc accaacactt accgcgcgct tgtggagtcc attaccatgg aacacgaaaa   4140
caacagacgc tacgaattgg ctgacatcca gctcgtgcga tacgagaacg agcattaccg   4200
gttcaatctg ttgtcaaaga agatgcttca catcgtgaac gattccaagg gtatcctgaa   4260
gtcgctgata cgctgcggtt acaaggaggg gaacctcaac gtgaacctct acaaggaagt   4320
```

gatccagcat ctgatgaaca acgaaaacct cttcaccctt atccacaagt tgatctacta 4380
caagcagacc agcgtgaacg gcctgtacta caacatgggc cacgtgtccg gaatcctgga 4440
tatcaacacc aagttcctga aagaaatgga ggtcatgacg aacatctcac agaaccagct 4500
gtggttcgtg caaaattgtg gcaaagaatt caaggagggt tacgtgaaga agaagtccga 4560
gaacaagatc tccggaatca cttacaagct gctgaattcg ctgaaggtca acgacaagga 4620
cggattcatg gacaccctgc tgaactccta ctcgtacctg tccatgccga tccccgacgt 4680
gttcatcaag atgttctcca acaacgaagc cttcaagagc gtgggctacg cttttatgct 4740
tggcgtgggt ggagaaaaga ctaagaagga agatgggggc aacaccgatg agaagtgaga 4800
attcgatatc aagcttatcg ataatcaacc tctggattac aaaatttgtg aaagattgac 4860
tggtattctt aactatgttg ctccttttac gctatgtgga tacgctgctt taatgccttt 4920
gtatcatgct attgcttccc gtatggcttt cattttctcc tccttgtata aatcctggtt 4980
gctgtctctt tatgaggagt tgtggcccgt tgtcaggcaa cgtggcgtgg tgtgcactgt 5040
gtttgctgac gcaaccccca ctggttgggg cattgccacc acctgtcagc tcctttccgg 5100
gactttcgct ttccccctcc ctattgccac ggcggaactc atcgccgcct gccttgcccg 5160
ctgctggaca ggggctcggc tgttgggcac tgacaattcc gtggtgttgt cggggaaatc 5220
atcgtccttt ccttggctgc tcgcctgtgt tgccacctgg attctgcgcg ggacgtcctt 5280
ctgctacgtc ccttcggccc tcaatccagc ggaccttcct tcccgcggcc tgctgccggc 5340
tctgcggcct cttccgcgtc ttcgccttcg ccctcagacg agtcggatct ccctttgggc 5400
cgcctccccg catcgatacc gtcgacctcg agacctagaa aaacatggag caatcacaag 5460
tagcaataca gcagctacca atgctgattg tgcctggcta gaagcacaag aggaggagga 5520
ggtgggtttt ccagtcacac ctcaggtacc tttaagacca atgacttaca aggcagctgt 5580
agatcttagc cactttttaa aagaaaaggg gggactggaa gggctaattc actcccaacg 5640
aagacaagat atccttgatc tgtggatcta ccacacacaa ggctacttcc ctgattggca 5700
gaactacaca ccagggccag ggatcagata tccactgacc tttggatggt gctacaagct 5760
agtaccagtt gagcaagaga aggtagaaga agccaatgaa ggagagaaca cccgcttgtt 5820
acaccctgtg agcctgcatg ggatggatga cccggagaga gaagtattag agtggaggtt 5880
tgacagccgc ctagcatttc atcacatggc ccgagagctg catccggact gtactgggtc 5940
tctctggtta gaccagatct gagcctggga gctctctggc taactaggga acccactgct 6000
taagcctcaa taaagcttgc cttgagtgct tcaagtagtg tgtgcccgtc tgttgtgtga 6060
ctctggtaac tagagatccc tcagaccctt ttagtcagtg tggaaaatct ctagca 6116

<210> SEQ ID NO 283
<211> LENGTH: 958
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 283
accggtcgcc accgccgcca ccatggacta caaggacgat gatgacaaga tggcgcccaa 60
gaagaaacgg aaagtccgcg ggatgaagaa caagggactg gcaatgacta tcattttcca 120
agccgaaagc gccaattacg gcgaatccct ggggaacatt tcaagcctga agaagatctc 180
taggaacaac ggagatcagt acacctacat ctcccgccaa gcgatccggt acaatcttat 240

```
ggatcagatc ggagaaaagg aagcccctgt gaaggctgaa ggcggcggag acaaaaaggt    300

catccagttc ctgtccgagg ccacgatcac cgacttcccg gaactcgact ttttcggcta    360

cctgaaaacc gaaaagggtt ccgggggaca gaagcgcagc gccaaagtcc gactgtcgaa    420

cgccatctcg ctggagactt ttaagggcga cctggatttc ctcactaaca agggacaggc    480

cgacaagctg aacgaaaaca tgaacattgc gcaggcagag atccacaagt cctactaccg    540

ctacaccatc accatcgacc tcgaccagat cggtatcgac ggggagattg ctctggacaa    600

caaggaaaag gcccggagag tgaagaagct gatggacact gtggcgttcc tctatcggga    660

cattaggggc agacgggagg acctcaagcc cctgttcgtg atcggtggag tgtatgacgt    720

gaagaacccg gtgttccaaa acattgtgga tgtggccgac aacaatattg tgatcaagaa    780

cattaaggat ttgctgacct acgaggacat caaggagaac accagagtcg gcatcattga    840

tgggcagttc gccaactccg acgaagtgaa agtcgagctg aaggccgagt ccgtgccagc    900

tttcttcaac gacatcaagg gaaagattga tgcgtactac gagagcaact gagaattc      958
```

```
<210> SEQ ID NO 284
<211> LENGTH: 862
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 284

accggtcgcc accgccgcca ccatggacta taaggatgat gacgacaaga tggcgcccaa     60

gaagaagcgc aaagtccgcg ggatgaaggc tattagggtc cggctgtggc aggatctcgt    120

gaacttcaag aagcctacca gcttccaact gaaggaaacc taccctctgc cgccgtactc    180

taccgtgatc ggcatggtgc atacactgtg cggctttacc tcctaccacg agatgaagat    240

cagcattcag ggaaagtact ttagcaaggt caacgacctc gcgactagat acgaattcaa    300

gaatggctca aaatacgacg tggaacgcca ccagatcaaa gtggacaaat acggagtgtc    360

gagaggcgtc agcaccgtgg agctccttgt ggacctcgaa ctgctgctgc acatcattcc    420

ggaagatcca tccttggtgc cgatcattga aaaggcattc cgggaaccca tcgagttccc    480

ttccctggga cgcagagagg acatcgccac gattcagaag gtcgaagtgg tggacgtcga    540

gaagcgacag cccaagaagt ccaccgagat ctccgacggt tataacgcct acgtgccgat    600

cagcttgacc gagaacaact cggtgcattt caagtcccac gagtcctcag tgggacggga    660

taagctgctg gggactcggt accttctgac tgagaaatac gagcgcgtga accacggaac    720

cgaaaaggcc cctaagttct tccggaagtg gcggaagaag gacgtcatct actcctcgcg    780

catcttcgtg tccaagaagg atgtgttctt tttcgacgag gacgattacc tggtgttcat    840

cgaagaagaa gagtgagaat tc                                             862
```

```
<210> SEQ ID NO 285
<211> LENGTH: 811
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 285

accggtcgcc accgccgcca ccatggacta caaggacgac gacgataaga tggcgccaaa     60

gaaaaagcgc aaggtccgcg ggatgcggct gaagattaac tgcgacttcg acagcaagat    120
```

```
catccccaag gacttccagt ccaaggtcgt gtccctgttc aaagccggaa ttatgaaaag    180

ctccccggag agatacgaga acctgtttgg tggaaacaag cacaagcagt acactttctc    240

ggtgtatctc ccaaaacctc agaacaaggg cgccgaaatt cagctgaacg aggcgaactg    300

tatcatcaac ttctccaccg gcgatgctga aaccggtatt atcttctaca acgccctgat    360

tagcctgaga ggctccaagg tcctgtttgg ggccggaaat cacatcaccg tgaagaacat    420

ccagatcgtg cctgagaaga agatcatcgg gaagcaaacc attctgcgga ccctttcgcc    480

ggtggtgtcg agggatcaca accgggaaac cttcaagaat tggttctact cattcgagga    540

cgaagaattc gagcctactt tgaagcggaa catgctgccg tacctcatcg acgcctttgg    600

agaacaggct cgctacgatc tggaaaagct gaagatcacg cccatttcca tgaagaaagt    660

cgtggtgtac tgccatgaga tccacatcga gagctccgtg ggcatcttcg agctggaagc    720

cgaggcatac ctccaaaagt acctcgtgga aaacggaatc ggcactatga ctggctcagg    780

gttcggaatg attgaacagt tctgagaatt c                                   811
```

```
<210> SEQ ID NO 286
<211> LENGTH: 1180
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 286

accggtcgcc accgccgcca ccatggacta caaggacgac gacgataaga tggcgccaaa     60

gaaaaagcgc aaggtccggg gcatgcggct gaagattaac tgcgacttcg acagcaagat    120

catccccaag gacttccagt ccaaggtcgt gtccctgttc aaagccggaa ttatgaaaag    180

ctccccggag agatacgaga acctgtttgg tggaaacaag cacaagcagt acactttctc    240

ggtgtatctc ccaaaacctc agaacaaggg cgccgaaatt cagctgaacg aggcgaactg    300

tatcatcaac ttctccaccg gcgatgctga aaccggtatt atcttctaca acgccctgat    360

tagcctgaga ggctccaagg tcctgtttgg ggccggaaat cacatcaccg tgaagaacat    420

ccagatcgtg cctgagaaga agatcatcgg gaagcaaacc attctgcgga ccctttcgcc    480

ggtggtgtcg agggatcaca accgggaaac cttcaagaat tggttctact cattcgagga    540

cgaagaattc gagcctactt tgaagcggaa catgctgccg tacctcatcg acgcctttgg    600

agaacaggct cgctacgatc tggaaaagct gaagatcacg cccatttcca tgaagaaagt    660

cgtggtgtac tgccatgaga tccacatcga gagctccgtg ggcatcttcg agctggaagc    720

cgaggcatac ctccaaaagt acctcgtgga aaacggaatc ggcactatga ctggctcagg    780

gttcggaatg attgaacagt tccggggcaa aaggccggcg gccacgaaaa aggccggcca    840

ggcaaaaaag aaaaagggat ccgatgctaa gtcactgact gcctggtccc ggacactggt    900

gaccttcaag gatgtgtttg tggacttcac cagggaggag tggaagctgc tggacactgc    960

tcagcagatc ctgtacagaa atgtgatgct ggagaactat aagaacctgg tttccttggg   1020

ttatcagctt actaagccag atgtgatcct ccggttggag aagggagaag agccctggct   1080

ggtggagaga gaaattcacc aagagaccca tcctgattca gagactgcat ttgaaatcaa   1140

atcatcagtt ccgaaaaaga aacgcaaagt ttgagaattc                         1180

<210> SEQ ID NO 287
<211> LENGTH: 1662
```

<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 287
accggtcgcc accgccgcca ccatggacta caaggacgac gacgataaga tggcgccaaa 60
gaaaaagcgc aaggtccggg gcatgcggct gaagattaac tgcgacttcg acagcaagat 120
catccccaag gacttccagt ccaaggtcgt gtccctgttc aaagccggaa ttatgaaaag 180
ctccccggag agatacgaga acctgtttgg tggaaacaag cacaagcagt acactttctc 240
ggtgtatctc ccaaaacctc agaacaaggg cgccgaaatt cagctgaacg aggcgaactg 300
tatcatcaac ttctccaccg gcgatgctga aaccggtatt atcttctaca acgccctgat 360
tagcctgaga ggctccaagg tcctgtttgg ggccggaaat cacatcaccg tgaagaacat 420
ccagatcgtg cctgagaaga agatcatcgg gaagcaaacc attctgcgga ccctttcgcc 480
ggtggtgtcg agggatcaca accgggaaac cttcaagaat tggttctact cattcgagga 540
cgaagaattc gagcctactt tgaagcggaa catgctgccg tacctcatcg acgcctttgg 600
agaacaggct cgctacgatc tggaaaagct gaagatcacg cccatttcca tgaagaaagt 660
cgtggtgtac tgccatgaga tccacatcga gagctccgtg ggcatcttcg agctggaagc 720
cgaggcatac ctccaaaagt acctcgtgga aaacggaatc ggcactatga ctggctcagg 780
gttcggaatg attgaacagt tccggggcaa aaggccggcg gccacgaaaa aggccggcca 840
ggcaaaaaag aaaaagggat ccgatgctaa gtcactgact gcctggtccc ggacactggt 900
gaccttcaag gatgtgtttg tggacttcac cagggaggag tggaagctgc tggacactgc 960
tcagcagatc ctgtacagaa atgtgatgct ggagaactat aagaacctgg tttccttggg 1020
ttatcagctt actaagccag atgtgatcct ccggttggag aagggagaag agccctggct 1080
ggtggagaga gaaattcacc aagagaccca tcctgattca gagactgcat ttgaaatcaa 1140
atcatcagtt ccgaaaaaga aacgcaaagt tggaagcgga gagggcagag gaagtcttct 1200
cacatgcggt gacgtggagg agaatcctgg acctaagacc ttcaacatct ctcagcagga 1260
tctggagctg gtggaggtcg ccactgagaa gatcaccatg ctctatgagg acaacaagca 1320
ccatgtcggg gcggccatca ggaccaagac tggggagatc atctctgctg tccacattga 1380
ggcctacatt ggcagggtca ctgtctgtgc tgaagccatt gccattgggt ctgctgtgag 1440
caacgggcag aaggactttg acaccattgt ggctgtcagg caccccctact ctgatgaggt 1500 ggacagatcc atcagggtgg tcagcccctg tggcatgtgc agagagctca tctctgacta 1560
tgctcctgac tgctttgtgc tcattgagat gaatggcaag ctggtcaaaa ccaccattga 1620
ggaactcatc cccctcaagt acaccaggaa ctaaaggaat tc 1662

<210> SEQ ID NO 288
<211> LENGTH: 1932
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 288
accggtcgcc accgccgcca ccatgatggg caagagtggg atataccaaa ttaaaaacac 60
actgaataat aaggtttacg tgggatctgc gaaggatttt gagaaacgat ggaaacgaca 120

-continued

```
cttcaaggat ctggaaaagg gctgccattc cagcataaaa ctgcagaggt cttttaataa    180

acacggcaac gtgtttgagt gctcaatcct ggaagaaatt ccgtacgaaa aggacttgat    240

tatagaacgg gagaatttct ggattaaaga gctcaacagc aagatcaatg gctataacat    300

cgccgatgcc acttttgggg acacgtgttc aacccacccc ctcaaagaag aaatcattaa    360

aaaacggagc gaaacggtca aagcaaaaat gttgaagctc ggacccgacg ggcgcaaagc    420

cctttactca aaacccggca gcaaaaacgg acggtggaac cctgaaactc ataagttttg    480

caaatgtggc gttagaatac aaacgtccgc ttacacgtgc tccaaatgtc gcaaccgctc    540

aggcgaaaac aacagttttt tcaatcataa acattctgat atcaccaaga gtaagatatc    600

tgagaagatg aaaggcaaaa agccgtctaa cataaagaag atcagcggtg ggtcaggtgg    660

atcagactac aaggacgacg acgataagat ggcgccaaag aaaaagcgca aggtccgggg    720

catgcggctg aagattaact gcgacttcga cagcaagatc atccccaagg acttccagtc    780

caaggtcgtg tccctgttca aagccggaat tatgaaaagc tccccggaga gatacgagaa    840

cctgtttggt ggaaacaagc acaagcagta cactttctcg gtgtatctcc caaaacctca    900

gaacaagggc gccgaaattc agctgaacga ggcgaactgt atcatcaact tctccaccgg    960

cgatgctgaa accggtatta tcttctacaa cgccctgatt agcctgagag gctccaaggt   1020

cctgtttggg gccggaaatc acatcaccgt gaagaacatc cagatcgtgc ctgagaagaa   1080

gatcatcggg aagcaaacca ttctgcggac cctttcgccg gtggtgtcga gggatcacaa   1140

ccgggaaacc ttcaagaatt ggttctactc attcgaggac gaagaattcg agcctacttt   1200

gaagcggaac atgctgccgt acctcatcga cgcctttgga gaacaggctc gctacgatct   1260

ggaaaagctg aagatcacgc ccatttccat gaagaaagtc gtggtgtact gccatgagat   1320

ccacatcgag agctccgtgg gcatcttcga gctggaagcc gaggcatacc tccaaaagta   1380

cctcgtggaa aacggaatcg gcactatgac tggctcaggg ttcggaatga ttgaacagtt   1440

cggaagcgga gagggcagag gaagtcttct cacatgcggt gacgtggagg agaatcctgg   1500

acctaagacc ttcaacatct ctcagcagga tctggagctg gtggaggtcg ccactgagaa   1560

gatcaccatg ctctatgagg acaacaagca ccatgtcggg gcggccatca ggaccaagac   1620

tggggagatc atctctgctg tccacattga ggcctacatt ggcagggtca ctgtctgtgc   1680

tgaagccatt gccattgggt ctgctgtgag caacgggcag aaggactttg acaccattgt   1740

ggctgtcagg cacccctact ctgatgaggt ggacagatcc atcagggtgg tcagcccctg   1800

tggcatgtgc agagagctca tctctgacta tgctcctgac tgctttgtgc tcattgagat   1860

gaatggcaag ctggtcaaaa ccaccattga ggaactcatc cccctcaagt acaccaggaa   1920

ctaaaggaat tc                                                       1932
```

<210> SEQ ID NO 289
<211> LENGTH: 6273
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 289

```
gggtctctct ggttagacca gatctgagcc tgggagctct ctggctaact agggaaccca     60

ctgcttaagc ctcaataaag cttgccttga gtgcttcaag tagtgtgtgc ccgtctgttg    120

tgtgactctg gtaactagag atccctcaga cccttttagt cagtgtggaa aatctctagc    180
```

-continued

```
agtggcgccc gaacagggac ttgaaagcga aagggaaacc agaggagctc tctcgacgca    240
ggactcggct tgctgaagcg cgcacggcaa gaggcgaggg gcggcgactg gtgagtacgc    300
caaaaatttt gactagcgga ggctagaagg agagagatgg gtgcgagagc gtcagtatta    360
agcgggggag aattagatcg cgatgggaaa aaattcggtt aaggccaggg ggaaagaaaa    420
aatataaatt aaaacatata gtatgggcaa gcagggagct agaacgattc gcagttaatc    480
ctggcctgtt agaaacatca gaaggctgta gacaaatact gggacagcta caaccatccc    540
ttcagacagg atcagaagaa cttagatcat tatataatac agtagcaacc ctctattgtg    600
tgcatcaaag gatagagata aaagacacca aggaagcttt agacaagata gaggaagagc    660
aaaacaaaag taagaccacc gcacagcaag cggccgctga tcttcagacc tggaggagga    720
gatatgaggg acaattggag aagtgaatta tataaatata aagtagtaaa aattgaacca    780
ttaggagtag cacccaccaa ggcaaagaga agagtggtgc agagagaaaa aagagcagtg    840
ggaataggag ctttgttcct tgggttcttg ggagcagcag gaagcactat gggcgcagcg    900
tcaatgacgc tgacggtaca ggccagacaa ttattgtctg gtatagtgca gcagcagaac    960
aatttgctga gggctattga ggcgcaacag catctgttgc aactcacagt ctggggcatc   1020
aagcagctcc aggcaagaat cctggctgtg gaaagatacc taaaggatca acagctcctg   1080
gggatttggg gttgctctgg aaaactcatt tgcaccactg ctgtgccttg gaatgctagt   1140
tggagtaata aatctctgga acagatttgg aatcacacga cctggatgga gtgggacaga   1200
gaaattaaca attacacaag cttaatacac tccttaattg aagaatcgca aaaccagcaa   1260
gaaaagaatg aacaagaatt attggaatta gataaatggg caagtttgtg gaattggttt   1320
aacataacaa attggctgtg gtatataaaa ttattcataa tgatagtagg aggcttggta   1380
ggtttaagaa tagtttttgc tgtactttct atagtgaata gagttaggca gggatattca   1440
ccattatcgt ttcagaccca cctcccaacc ccgaggggac ccgacaggcc cgaaggaata   1500
gaagaagaag gtggagagag agacagagac agatccattc gattagtgaa cggatcggca   1560
ctgcgtgcgc caattctgca gacaaatggc agtattcatc cacaatttta aaagaaaagg   1620
ggggattggg gggtacagtg caggggaaag aatagtagac ataatagcaa cagacataca   1680
aactaaagaa ttacaaaaac aaattacaaa aattcaaaat tttcgggttt attacaggga   1740
cagcagagat ccagtttggt taatacacag gaaacagcta tgaccatgat tacgccaagc   1800
gcgcaattaa ccctcactaa agggaacaaa agctggagct cggaaaaaaa atttacattt   1860
cataataagt agttaaaacc ggtggccagt cgtctgggcg gtgctacaac tgggcattta   1920
catttcataa taagtagtta aaaccgggct agctgtttcg tcctttccac aagatatata   1980
aagccaagaa atcgaaatac tttcaagtta cggtaagcat atgatagtcc attttaaaac   2040
ataattttaa aactgcaaac tacccaagaa attattactt tctacgtcac gtattttgta   2100
ctaatatctt tgtgtttaca gtcaaattaa ttccaattat ctctctaaca gccttgtatc   2160
gtatatgcaa atatgaagga atcatgggaa ataggccctc ggtacccaat tcgccctata   2220
gtgagtcgta ttacgcgcgc tcactggccg tcgttttaca acattaaccc gtgtcggctc   2280
cagatctggc ctccgcgccg ggttttggcg cctcccgcgg gcgccccct cctcacggcg    2340
agcgctgcca cgtcagacga agggcgcagg agcgttcctg atccttccgc ccggacgctc   2400
aggacagcgg cccgctgctc ataagactcg gccttagaac cccagtatca gcagaaggac   2460
attttaggac gggacttggg tgactctagg gcactggttt tctttccaga gagcggaaca   2520
ggcgaggaaa agtagtccct tctcggcgat tctgcggagg gatctccgtg ggcggtgaa    2580
```

```
cgccgatgat tatataagga cgcgccgggt gtggcacagc tagttccgtc gcagccggga   2640
tttgggtcgc ggttcttgtt tgtggatcgc tgtgatcgtc acttggtgag ttgcgggctg   2700
ctgggctggc cggggctttc gtggccgccg ggccgctcgg tgggacggaa gcgtgtggag   2760
agaccgccaa gggctgtagt ctgggtccgc gagcaaggtt gccctgaact gggggttggg   2820
gggagcgcac aaaatggcgg ctgttcccga gtcttgaatg gaagacgctt gtaaggcggg   2880
ctgtgaggtc gttgaaacaa ggtgggggc atggtgggcg gcaagaaccc aaggtcttga   2940
ggccttcgct aatgcgggaa agctcttatt cgggtgagat gggctggggc accatctggg   3000
gaccctgacg tgaagtttgt cactgactgg agaactcggg tttgtcgtct ggttgcgggg   3060
gcggcagtta tgcggtgccg ttgggcagtg cacccgtacc tttgggagcg cgcgcctcgt   3120
cgtgtcgtga cgtcacccgt tctgttggct tataatgcag ggtggggcca cctgccggta   3180
ggtgtgcggt aggcttttct ccgtcgcagg acgcagggtt cgggcctagg gtaggctctc   3240
ctgaatcgac aggcgccgga cctctggtga ggggagggat aagtgaggcg tcagtttctt   3300
tggtcggttt tatgtaccta tcttcttaag tagctgaagc tccggttttg aactatgcgc   3360
tcggggttgg cgagtgtgtt ttgtgaagtt ttttaggcac cttttgaaat gtaatcattt   3420
gggtcaatat gtaattttca gtgttagact agtaaattgt ccgctaaatt ctggccgttt   3480
ttggcttttt tgttagacga agcttgggct gcaggtcgac tctagaatgg tgagcaaggg   3540
cgaggagctg ttcaccgggg tggtgcccat cctggtcgag ctggacggcg acgtaaacgg   3600
ccacaagttc agcgtgtccg gcgagggcga gggcgatgcc acctacggca agctgaccct   3660
gaagttcatc tgcaccaccg gcaagctgcc cgtgccctgg cccaccctcg tgaccaccct   3720
gacctacggc gtgcagtgct tcagccgcta ccccgaccac atgaagcagc acgacttctt   3780
caagtccgcc atgcccgaag gctacgtcca ggagcgcacc atcttcttca aggacgacgg   3840
caactacaag acccgcgccg aggtgaagtt cgagggcgac accctggtga accgcatcga   3900
gctgaagggc atcgacttca aggaggacgg caacatcctg gggcacaagc tggagtacaa   3960
ctacaacagc cacaacgtct atatcatggc cgacaagcag aagaacggca tcaaggtgaa   4020
cttcaagatc cgccacaaca tcgaggacgg cagcgtgcag ctcgccgacc actaccagca   4080
gaacaccccc atcggcgacg gccccgtgct gctgcccgac aaccactacc tgagcaccca   4140
gtccgccctg agcaaagacc ccaacgagaa gcgcgatcac atggtcctgc tggagttcgt   4200
gaccgccgcc gggatcactc tcggcatgga cgagctgtac aagggatccg gcgcaacaaa   4260
cttctctctg ctgaaacaag ccggagatgt cgaagagaat cctggaccga tgaccgagta   4320
caagcccacg gtgcgcctcg ccacccgcga cgacgtcccc agggccgtac gcaccctcgc   4380
cgccgcgttc gccgactacc ccgccacgcg ccacaccgtc gatccggacc gccacatcga   4440
gcgggtcacc gagctgcaag aactcttcct cacgcgcgtc gggctcgaca tcggcaaggt   4500
gtgggtcgcg gacgacggcg ccgcggtggc ggtctggacc acgccggaga gcgtcgaagc   4560
gggggcggtg ttcgccgaga tcggcccgcg catggccgag ttgagcggtt cccggctggc   4620
cgcgcagcaa cagatggaag gcctcctggc gccgcaccgg cccaaggagc ccgcgtggtt   4680
cctggccacc gtcggcgtgt cgcccgacca ccagggcaag ggtctgggca gcgccgtcgt   4740
gctccccgga gtggaggcgg ccgagcgcgc cggggtgccc gccttcctgg agacctccgc   4800
gccccgcaac ctccccttct acgagcggct cggcttcacc gtcaccgccg acgtcgaggt   4860
gcccgaagga ccgcgcacct ggtgcatgac ccgcaagccc ggtgcctaaa gttgataata   4920
```

```
gataacttcg tatagcatac attatacgaa gttatgaatt cgatatcaag cttatcgata   4980
atcaacctct ggattacaaa atttgtgaaa gattgactgg tattcttaac tatgttgctc   5040
cttttacgct atgtggatac gctgctttaa tgcctttgta tcatgctatt gcttcccgta   5100
tggctttcat tttctcctcc ttgtataaat cctggttgct gtctctttat gaggagttgt   5160
ggcccgttgt caggcaacgt ggcgtggtgt gcactgtgtt tgctgacgca acccccactg   5220
gttggggcat tgccaccacc tgtcagctcc tttccgggac tttcgctttc cccctcccta   5280
ttgccacggc ggaactcatc gccgcctgcc ttgcccgctg ctggacaggg gctcggctgt   5340
tgggcactga caattccgtg gtgttgtcgg ggaaatcatc gtcctttcct tggctgctcg   5400
cctgtgttgc cacctggatt ctgcgcggga cgtccttctg ctacgtccct tcggccctca   5460
atccagcgga ccttccttcc cgcggcctgc tgccggctct gcggcctctt ccgcgtcttc   5520
gccttcgccc tcagacgagt cggatctccc tttgggccgc ctccccgcat cgataccgtc   5580
gacctcgaga cctagaaaaa catggagcaa tcacaagtag caatacagca gctaccaatg   5640
ctgattgtgc ctggctagaa gcacaagagg aggaggaggt gggttttcca gtcacacctc   5700
aggtaccttt aagaccaatg acttacaagg cagctgtaga tcttagccac tttttaaaag   5760
aaaagggggg actggaaggg ctaattcact cccaacgaag acaagatatc cttgatctgt   5820
ggatctacca cacacaaggc tacttccctg attggcagaa ctacacacca gggccaggga   5880
tcagatatcc actgaccttt ggatggtgct acaagctagt accagttgag caagagaagg   5940
tagaagaagc caatgaagga gagaacaccc gcttgttaca ccctgtgagc ctgcatggga   6000
tggatgaccc ggagagagaa gtattagagt ggaggtttga cagccgccta gcatttcatc   6060
acatggcccg agagctgcat ccggactgta ctgggtctct ctggttagac cagatctgag   6120
cctgggagct ctctggctaa ctagggaacc cactgcttaa gcctcaataa agcttgcctt   6180
gagtgcttca agtagtgtgt gcccgtctgt tgtgtgactc tggtaactag agatccctca   6240
gaccctttta gtcagtgtgg aaaatctcta gca                                6273
```

<210> SEQ ID NO 290
<211> LENGTH: 5939
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 290

```
gggtctctct ggttagacca gatctgagcc tgggagctct ctggctaact agggaaccca     60
ctgcttaagc ctcaataaag cttgccttga gtgcttcaag tagtgtgtgc ccgtctgttg    120
tgtgactctg gtaactagag atccctcaga cccttttagt cagtgtggaa aatctctagc    180
agtggcgccc gaacagggac ttgaaagcga aagggaaacc agaggagctc tctcgacgca    240
ggactcggct tgctgaagcg cgcacggcaa gaggcgaggg gcggcgactg gtgagtacgc    300
caaaaatttt gactagcgga ggctagaagg agagagatgg gtgcgagagc gtcagtatta    360
agcgggggag aattagatcg cgatgggaaa aaattcggtt aaggccaggg ggaaagaaaa    420
aatataaatt aaaacatata gtatgggcaa gcagggagct agaacgattc gcagttaatc    480
ctggcctgtt agaaacatca gaaggctgta gacaaatact gggacagcta caaccatccc    540
ttcagacagg atcagaagaa cttagatcat tatataatac agtagcaacc ctctattgtg    600
tgcatcaaag gatagagata aaagacacca aggaagcttt agacaagata gaggaagagc    660
```

-continued

```
aaaacaaaag taagaccacc gcacagcaag cggccgctga tcttcagacc tggaggagga    720
gatatgaggg acaattggag aagtgaatta tataaatata aagtagtaaa aattgaacca    780
ttaggagtag cacccaccaa ggcaaagaga agagtggtgc agagagaaaa aagagcagtg    840
ggaataggag ctttgttcct tgggttcttg ggagcagcag gaagcactat gggcgcagcg    900
tcaatgacgc tgacggtaca ggccagacaa ttattgtctg gtatagtgca gcagcagaac    960
aatttgctga gggctattga ggcgcaacag catctgttgc aactcacagt ctggggcatc   1020
aagcagctcc aggcaagaat cctggctgtg gaaagatacc taaaggatca acagctcctg   1080
gggatttggg gttgctctgg aaaactcatt tgcaccactg ctgtgccttg gaatgctagt   1140
tggagtaata aatctctgga acagatttgg aatcacacga cctggatgga gtgggacaga   1200
gaaattaaca attacacaag cttaatacac tccttaattg aagaatcgca aaaccagcaa   1260
gaaaagaatg aacaagaatt attggaatta gataaatggg caagtttgtg gaattggttt   1320
aacataacaa attggctgtg gtatataaaa ttattcataa tgatagtagg aggcttggta   1380
ggtttaagaa tagtttttgc tgtactttct atagtgaata gagttaggca gggatattca   1440
ccattatcgt ttcagaccca cctcccaacc ccgaggggac ccgacaggcc cgaaggaata   1500
gaagaagaag gtggagagag agacagagac agatccattc gattagtgaa cggatcggca   1560
ctgcgtgcgc caattctgca gacaaatggc agtattcatc cacaatttta aaagaaaagg   1620
ggggattggg gggtacagtg caggggaaag aatagtagac ataatagcaa cagacataca   1680
aactaaagaa ttacaaaaac aaattacaaa aattcaaaat tttcgggttt attacaggga   1740
cagcagagat ccagtttggt taattaaggg tgcagcggcc tccgcgccgg gttttggcgc   1800
ctcccgcggg cgcccccctc ctcacggcga gcgctgccac gtcagacgaa gggcgcagga   1860
gcgttcctga tccttccgcc cggacgctca ggacagcggc ccgctgctca taagactcgg   1920
ccttagaacc ccagtatcag cagaaggaca ttttaggacg ggacttgggt gactctaggg   1980
cactggtttt ctttccagag agcggaacag gcgaggaaaa gtagtccctt ctcggcgatt   2040
ctgcggaggg atctccgtgg ggcggtgaac gccgatgatt atataaggac gcgccgggtg   2100
tggcacagct agttccgtcg cagccgggat ttgggtcgcg gttcttgttt gtggatcgct   2160
gtgatcgtca cttggtgagt tgcgggctgc tgggctggcc ggggctttcg tggccgccgg   2220
gccgctcggt gggacggaag cgtgtggaga gaccgccaag ggctgtagtc tgggtccgcg   2280
agcaaggttg ccctgaactg ggggttgggg ggagcgcaca aaatggcggc tgttcccgag   2340
tcttgaatgg aagacgcttg taaggcgggc tgtgaggtcg ttgaaacaag gtgggggca    2400
tggtgggcgg caagaaccca aggtcttgag gccttcgcta atgcgggaaa gctcttattc   2460
gggtgagatg ggctggggca ccatctgggg accctgacgt gaagtttgtc actgactgga   2520
gaactcgggt ttgtcgtctg gttgcggggg cggcagttat gcggtgccgt tgggcagtgc   2580
acccgtacct ttgggagcgc gcgcctcgtc gtgtcgtgac gtcacccgtt ctgttggctt   2640
ataatgcagg gtggggccac ctgccggtag gtgtgcggta ggcttttctc cgtcgcagga   2700
cgcagggttc gggcctaggg taggctctcc tgaatcgaca ggcgccggac ctctggtgag   2760
gggagggata agtgaggcgt cagtttcttt ggtcggtttt atgtacctat cttcttaagt   2820
agctgaagct ccggttttga actatgcgct cggggttggc gagtgtgttt tgtgaagttt   2880
tttaggcacc ttttgaaatg taatcatttg ggtcaatatg taattttcag tgttagacta   2940
gtaaattgtc cgctaaattc tggccgtttt tggctttttt gttagacgaa gcttgggctg   3000
caggtcgact ctagaggatc cccgggtacc ggtcgccacc gccgccacca tggattacaa   3060
```

agacgatgac gataagatgg cgcctaagaa gaagcgcaag gtgcggggca tggccaatct 3120
cctgattgac aattggatcc ctgtgagacc gaggaacgga gggaaggttc agatcatcaa 3180
cctgcaaagt ctctactgta gcagagatca atggcgactc tcattgccca gggatgatat 3240
ggaattggcg gcacttgcac tcttggtatg tattgggcag atcatcgccc ctgccaagga 3300
tgatgtcgag tttaggcaca gaataatgaa ccctcttact gaagatgaat tccagcaatt 3360
gatcgcgcct tggatagata tgttctattt gaatcacgcc gaacatccct tcatgcagac 3420
aaaaggggtt aaagcaaatg atgtcacacc aatggagaag cttttggcag gtgtgtcagg 3480
agcaaccaac tgcgctttcg ttaaccaacc aggccaaggt gaggcgttgt gcggggggtg 3540
cacggccata gcgttgttta atcaggcgaa ccaggctcct ggctttggag gaggattcaa 3600
gtccggtttg cgcgggggta cacccgtaac cacattcgtt cgcggaattg acctccgatc 3660
aacagtcctg ttgaacgtat tgacgttgcc tagacttcag aagcaatttc caaacgagtc 3720
tcacactgag aatcaaccga cttggattaa gcccatcaag tcaaatgaaa gtatacccgc 3780
gtcttctatt ggatttgtta gaggactttt ttggcagccc gctcacatag aactctgtga 3840
tcccataggc attggaaagt gttcttgctg tggccaagag tctaacctta gatatacggg 3900
ctttctcaag gagaagttca cgttcaccgt gaatggactt tggccacatc cccatagccc 3960
gtgcttggtc acggtcaaga agggggaggt tgaagagaaa tttcttgcgt ttaccacatc 4020
cgccccatcc tggacgcaaa tatctcgcgt cgttgtggat aaaatcatcc agaacgaaaa 4080
tggtaaccgc gttgccgcgg tagtgaatca attcagaaac atagcaccac agagcccgtt 4140
ggagttgata atgggcgggt accgcaataa tcaagcttcc attctcgagc gacgccatga 4200
cgtacttatg tttaaccagg ggtggcagca atatggtaac gtgataaacg agatagtcac 4260
agtcggcctc ggctacaaaa ctgcgttgcg caaagctctg tatacgttcg cggagggttt 4320
taagaataaa gactttaaag gcgctggggt gagtgtgcac gagacggcag aacgccattt 4380
ctatcgccag tctgaactct tgattcccga cgttctggcg aatgtcaatt tttcccaggc 4440
cgatgaggtc attgcggatc tgcgagataa gcttcaccag ttgtgtgaga tgctgttcaa 4500
ccagtctgtg gctccttatg ctcatcatcc caaactgatt tcaactctcg ctttggcaag 4560
ggctacgttg tataaacacc ttagagaact gaagccacag ggtggtccca gcaatggctg 4620
agaattcgat atcaagctta tcgataatca acctctggat tacaaaattt gtgaaagatt 4680
gactggtatt cttaactatg ttgctccttt tacgctatgt ggatacgctg ctttaatgcc 4740
tttgtatcat gctattgctt cccgtatggc tttcattttc tcctccttgt ataaatcctg 4800
gttgctgtct ctttatgagg agttgtggcc cgttgtcagg caacgtggcg tggtgtgcac 4860
tgtgtttgct gacgcaaccc ccactggttg gggcattgcc accacctgtc agctcctttc 4920
cgggactttc gctttccccc tccctattgc cacggcggaa ctcatcgccg cctgccttgc 4980
ccgctgctgg acaggggctc ggctgttggg cactgacaat tccgtggtgt tgtcggggaa 5040
atcatcgtcc tttccttggc tgctcgcctg tgttgccacc tggattctgc gcgggacgtc 5100
cttctgctac gtcccttcgg ccctcaatcc agcggacctt ccttcccgcg gcctgctgcc 5160
ggctctgcgg cctcttccgc gtcttcgcct tcgccctcag acgagtcgga tctccctttg 5220
ggccgcctcc ccgcatcgat accgtcgacc tcgagaccta gaaaaacatg gagcaatcac 5280
aagtagcaat acagcagcta ccaatgctga ttgtgcctgg ctagaagcac aagaggagga 5340
ggaggtgggt tttccagtca cacctcaggt acctttaaga ccaatgactt acaaggcagc 5400

-continued

```
tgtagatctt agccactttt taaaagaaaa ggggggactg gaagggctaa ttcactccca   5460

acgaagacaa gatatccttg atctgtggat ctaccacaca caaggctact tccctgattg   5520

gcagaactac acaccagggc cagggatcag atatccactg acctttggat ggtgctacaa   5580

gctagtacca gttgagcaag agaaggtaga agaagccaat gaaggagaga acacccgctt   5640

gttacaccct gtgagcctgc atgggatgga tgacccggag agagaagtat tagagtggag   5700

gtttgacagc cgcctagcat ttcatcacat ggcccgagag ctgcatccgg actgtactgg   5760

gtctctctgg ttagaccaga tctgagcctg ggagctctct ggctaactag ggaacccact   5820

gcttaagcct caataaagct tgccttgagt gcttcaagta gtgtgtgccc gtctgttgtg   5880

tgactctggt aactagagat ccctcagacc cttttagtca gtgtggaaaa tctctagca    5939
```

<210> SEQ ID NO 291
<211> LENGTH: 571
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 291

```
accggtcgcc accgccgcca ccatggatta caaagacgat gacgataaga tggcgcctaa     60

gaaaaagagg aaagtacgcg ggatggccga tgaaatagac gcaatggctc tttaccgagc    120

atggcaacag ctcgacaatg gatcttgcgc ccaaatacgg cgggtaagtg aacccgatga    180

actgcgagat atccccgcat tctaccgatt ggttcagccg tttggctggg agaacccacg    240

gcaccagcag gcgcttctta ggatggtttt ttgtcttagt gccgggaaaa acgtaatccg    300

ccatcaggat aagaagtccg aacaaacaac agggatttct ctgggaagag cgcttgctaa    360

cagcggcagg atcaatgaac gccgcatatt tcagttgatc cgagcagatc ggactgctga    420

tatggtccag ctcaggaggc tccttacgca cgcagagcca gtgttggatt ggccactcat    480

ggcaagaatg cttacgtggt gggggaagag ggaaaggcag caactgcttg aagattttgt    540

attgacgacg aacaaaaacg cgtaagaatt c                                   571
```

<210> SEQ ID NO 292
<211> LENGTH: 1180
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 292

```
accggtcgcc accgccgcca ccatggatta caaagacgat gacgataaga tggcgcctaa     60

gaagaagcgc aaggtgagag gaatgtcaaa cttcattaat atccacgtgc ttatctcaca    120

ctcccctagt tgccttaaca gagacgatat gaacatgcaa aaagacgcaa tttttggcgg    180

caaaaggaga gtcagaatta gtagccagag cctgaagcgc gctatgagga aaagcggcta    240

ctatgctcaa aacattggtg aaagttcatt gcggaccatc catctcgcgc agttgaggga    300

cgtcctgcga cagaagcttg ggaaaagatt tgatcagaag atcatcgaca aaacgcttgc    360

ccttctgtcc ggtaaatcag tggacgaagc ggagaagata agtgcggatg ctgttacgcc    420

atgggtggta ggtgaaatcg cgtggttttg cgagcaggta gccaaggccg aagcggataa    480

tttggatgat aagaaactgc tcaaagtcct caaagaggac atcgcggcga tccgggtgaa    540

ccttcagcag ggtgttgata ttgcgctctc tggtcggatg gccacgtctg gaatgatgac    600
```

tgaactgggt aaggtggacg gagctatgtc tatagctcat gctataacta cccatcaggt 660
ggattctgac atagactggt tcacggctgt cgacgatctc caggaacaag gatccgcaca 720
cctcggcacg caagaatttt cttctggagt gttctatagg tatgccaaca tcaaccttgc 780
acagctccag gaaaacctcg gtggggcaag ccgggaacag gctcttgaaa tagctaccca 840
tgtggttcac atgctggcga ccgaagtgcc aggggccaag cagagaacgt acgccgcatt 900
caatccggcg gacatggtca tggtgaattt ctctgatatg cccttgtcta tggcaaatgc 960
tttcgagaag gcggtcaagg caaaggacgg ttttttgcaa ccctccatcc aagcctttaa 1020
tcagtactgg gatagagtag ctaacgggta tggtctcaat ggcgcggctg ctcagttttc 1080
tttgtccgat gtggatccga taacggcgca ggttaaacag atgcccacct tggaacaact 1140
caaatcctgg gttagaaaca atggggaggc gtgagaattc 1180

<210> SEQ ID NO 293
<211> LENGTH: 763
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 293
accggtcgcc accgccgcca ccatggatta caaggacgac gacgataaga tggcgccgaa 60
gaagaagcgg aaagtccggg gcatgagatc ctacctcatc ctgcgcctgg ccgggccgat 120
gcaggcctgg ggccagccta catttgaggg tacccggccc accggacggt tcccgacccg 180
ctcggggctt ctgggacttc tgggcgcatg tctgggcatc cagcgggatg acactagcag 240
cctgcaggcc ctgagcgaat ccgtgcagtt cgccgtgcgc tgcgatgaac tgatcctcga 300
cgaccgcagg gtgtcagtga ctggactgag agactaccac accgtgctgg gagcccgcga 360
ggattacagg ggcctgaagt cccatgaaac cattcagacc tggagagagt acctctgcga 420
cgcgtcgttc actgtggcac tgtggctcac gccgcacgcg accatggtca tctccgaact 480
ggaaaaagcc gtgctcaagc ctcggtacac cccctatctc ggacgacgct cctgcccact 540
gacccatccc ctgttcctcg gtacttgcca agccagcgac cctcaaaagg ctctgttgaa 600
ctacgaaccc gtggggggag acatctactc cgaggaatcc gtcaccggcc accacttgaa 660
gttcaccgcc cgggacgagc cgatgattac tctgccaaga cagttcgctt cacgggagtg 720
gtacgtgatt aagggtggaa tggacgtgtc gcagtgagaa ttc 763

<210> SEQ ID NO 294
<211> LENGTH: 2644
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 294
accggtcgcc accgccgcca ccatgggtgc cccagttccc tatcccgacc cactggagcc 60
aaggatggcg cctaagaaga agcgcaaggt gcggggcatg tatctcagta aagtcatcat 120
tgccagggcc tggagcaggg atctttacca acttcaccag ggattatggc atttatttcc 180
aaacagaccg gatgctgctc gtgattttct ttttcatgtt gagaagcgaa acacaccaga 240
aggctgtcat gttttattgc agtcagcgca aatgcctgtt tcaactgccg ttgcgacagt 300

-continued

```
cattaaaact aaacaggttg aatttcaact tcaggttggt gttccactct attttcggct    360
tcgggcaaat ccgatcaaaa ctattctcga caatcaaaag cgcctggaca gtaaagggaa    420
tattaaacgc tgtcgggttc cgttaataaa agaagcagaa caaatcgcgt ggttgcaacg    480
taaattgggc aatgcggcgc gcgttgaaga tgtgcatccc atatcggaac ggccacagta    540
tttttctggt gatggtaaaa gtggaaagat ccaaacggtt tgctttgaag gtgtgctcac    600
catcaacgac gcgccagcgt taatagatct tgtacagcaa ggtattgggc cagctaaatc    660
gatgggatgt ggcttgctat ctttggctcc actgcggggc aagcgacctg ccgccacaaa    720
gaaggctgga caggctaaga agaagaaagg atccattttc aaaccagaag aactacgaca    780
ggcactgatg ccaactttgg aggcacttta ccgtcaggat ccagaatccc ttccctttcg    840
tcaacctgtg gaccctcagc ttttaggaat ccctgattac tttgatattg tgaagagccc    900
catggatctt tctaccatta agaggaagtt agacactgga cagtatcagg agccctggca    960
gtatgtcgat gatatttggc ttatgttcaa taatgcctgg ttatataacc ggaaaacatc   1020
acgggtatac aaatactgct ccaagctctc tgaggtcttt gaacaagaaa ttgacccagt   1080
gatgcaaagc cttggatact gttgtggcag aaagttggag ttctctccac agacactgtg   1140
ttgctacggc aaacagttgt gcacaatacc tcgtgatgcc acttattaca gttaccagaa   1200
caggtatcat ttctgtgaga agtgtttcaa tgagatccaa ggggagagcg tttctttggg   1260
ggatgaccct tcccagcctc aaactacaat aaataaagaa caattttcca agagaaaaaa   1320
tgacacactg gatcctgaac tgtttgttga atgtacagag tgcggaagaa agatgcatca   1380
gatctgtgtc cttcaccatg agatcatctg gcctgctgga ttcgtctgtg atggctgttt   1440
aaagaaaagt gcacgaacta ggaaagaaaa taagttttct gctaaaaggt tgccatctac   1500
cagacttggc acctttctag agaatcgtgt gaatgacttt ctgaggcgac agaatcaccc   1560
tgagtcagga gaggtcactg ttagagtagt tcatgcttct gacaaaaccg tggaagtaaa   1620
accaggcatg aaagcaaggt ttgtggacag tggagagatg gcagaatcct ttccataccg   1680
aaccaaagcc ctctttgcct ttgaagaaat tgatggtgtt gacctgtgct tctttggcat   1740
gcatgttcaa gagtatggct ctgactgccc tccacccaac cagaggagag tatacatatc   1800
ttacctcgat agtgttcatt tcttccgtcc taaatgcttg aggactgcag tctatcatga   1860
aatcctaatt ggatatttag aatatgtcaa gaaattaggt tacacaacag ggcatatttg   1920
ggcatgtcca ccaagtgagg gagatgatta tatcttccat tgccatcctc ctgaccagaa   1980
gatacccaag cccaagcgac tgcaggaatg gtacaaaaaa atgcttgaca aggctgtatc   2040
agagcgtatt gtccatgact acaaggatat ttttaaacaa gctactgaag atagattaac   2100
aagtgcaaag gaattgcctt atttcgaggg tgatttctgg cccaatgttc tggaagaaag   2160
cattaaggaa ctggaacagg aggaagaaga gagaaaacga gaggaaaaca ccagcaatga   2220
aagcacagat gtgaccaagg gagacagcaa aaatgctaaa aagaagaata ataagaaaac   2280
cagcaaaaat aagagcagcc tgagtagggg caacaagaag aaacccggga tgcccaatgt   2340
atctaacgac ctctcacaga aactatatgc caccatggag aagcataaag aggtcttctt   2400
tgtgatccgc ctcattgctg gccctgctgc caactccctg cctcccattg ttgatcctga   2460
tcctctcatc ccctgcgatc tgatggatgg tcgggatgcg tttctcacgc tggcaaggga   2520
caagcacctg gagttctctt cactccgaag agcccagtgg tccaccatgt gcatgctggt   2580
ggagctgcac acgcagagcc aggacggatc cgattacaaa gacgatgacg ataagtgaga   2640
attc                                                                2644
```

<210> SEQ ID NO 295
<211> LENGTH: 1057
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 295
accggtcgcc accgccgcca ccatggatta caaagacgat gacgataaga tggcgcctaa 60
gaagaagcgc aaggtgcggg gcatgtatct cagtaaagtc atcattgcca gggcctggag 120
cagggatctt taccaacttc accagggatt atggcattta tttccaaaca gaccggatgc 180
tgctcgtgat tttctttttc atgttgagaa gcgaaacaca ccagaaggct gtcatgtttt 240
attgcagtca gcgcaaatgc ctgtttcaac tgccgttgcg acagtcatta aaactaaaca 300
ggttgaattt caacttcagg ttggtgttcc actctatttt cggcttcggg caaatccgat 360
caaaactatt ctcgacaatc aaaagcgcct ggacagtaaa gggaatatta aacgctgtcg 420
ggttccgtta ataaaagaag cagaacaaat cgcgtggttg caacgtaaat tgggcaatgc 480
ggcgcgcgtt gaagatgtgc atcccatatc ggaacggcca cagtattttt ctggtgatgg 540
taaaagtgga aagatccaaa cggtttgctt tgaaggtgtg ctcaccatca acgacgcgcc 600
agcgttaata gatcttgtac agcaaggtat tgggccagct aaatcgatgg gatgtggctt 660
gctatctttg gctccactgc ggggcaagcg acctgccgcc acaaagaagg ctggacaggc 720
taagaagaag aaaggatccg atgctaagtc actgactgcc tggtcccgga cactggtgac 780
cttcaaggat gtgtttgtgg acttcaccag ggaggagtgg aagctgctgg acactgctca 840
gcagatcctg tacagaaatg tgatgctgga gaactataag aacctggttt ccttgggtta 900
tcagcttact aagccagatg tgatcctccg gttggagaag ggagaagagc cctggctggt 960
ggagagagaa attcaccaag agacccatcc tgattcagag actgcatttg aaatcaaatc 1020
atcagttccg aaaaagaaac gcaaagtttg agaattc 1057

<210> SEQ ID NO 296
<211> LENGTH: 4294
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 296
accggtcgcc accgccgcca ccatggatta caaagacgat gacgataaga tggcgcctaa 60
gaagaagcgc aaggtgcggg gcatggccaa tctcctgatt gacaattgga tccctgtgag 120
accgaggaac ggagggaagg ttcagatcat caacctgcaa agtctctact gtagcagaga 180
tcaatggcga ctctcattgc ccagggatga tatggaattg gcggcacttg cactcttggt 240
atgtattggg cagatcatcg cccctgccaa ggatgatgtc gagtttaggc acagaataat 300
gaaccctctt actgaagatg aattccagca attgatcgcg ccttggatag atatgttcta 360
tttgaatcac gccgaacatc ccttcatgca gacaaaaggg gttaaagcaa atgatgtcac 420
accaatggag aagcttttgg caggtgtgtc aggagcaacc aactgcgctt tcgttaacca 480
accaggccaa ggtgaggcgt tgtgcggggg gtgcacggcc atagcgttgt ttaatcaggc 540
gaaccaggct cctggctttg gaggaggatt caagtccggt ttgcgcgggg gtacacccgt 600

```
aaccacattc gttcgcggaa ttgacctccg atcaacagtc ctgttgaacg tattgacgtt    660
gcctagactt cagaagcaat ttccaaacga gtctcacact gagaatcaac cgacttggat    720
taagcccatc aagtcaaatg aaagtatacc cgcgtcttct attggatttg ttagaggact    780
tttttggcag cccgctcaca tagaactctg tgatcccata ggcattggaa agtgttcttg    840
ctgtggccaa gagtctaacc ttagatatac gggctttctc aaggagaagt tcacgttcac    900
cgtgaatgga ctttggccac atccccatag cccgtgcttg gtcacggtca agaaggggga    960
ggttgaagag aaatttcttg cgtttaccac atccgcccca tcctggacgc aaatatctcg   1020
cgtcgttgtg gataaaatca tccagaacga aaatggtaac cgcgttgccg cggtagtgaa   1080
tcaattcaga aacatagcac cacagagccc gttggagttg ataatgggcg ggtaccgcaa   1140
taatcaagct tccattctcg agcgacgcca tgacgtactt atgtttaacc aggggtggca   1200
gcaatatggt aacgtgataa acgagatagt cacagtcggc ctcggctaca aaactgcgtt   1260
gcgcaaagct ctgtatacgt tcgcggaggg ttttaagaat aaagacttta aaggcgctgg   1320
ggtgagtgtg cacgagacgg cagaacgcca tttctatcgc cagtctgaac tcttgattcc   1380
cgacgttctg gcgaatgtca atttttccca ggccgatgag gtcattgcgg atctgcgaga   1440
taagcttcac cagttgtgtg agatgctgtt caaccagtct gtggctcctt atgctcatca   1500
tcccaaactg atttcaactc tcgctttggc aagggctacg ttgtataaac accttagaga   1560
actgaagcca cagggtggtc ccagcaatgg cggaagcgga gctactaact tcagcctgct   1620
gaagcaggct ggagacgtgg aggagaaccc tggacctatg gattacaaag acgatgacga   1680
taagatggcg cctaagaaaa agaggaaagt acgcgggatg gccgatgaaa tagacgcaat   1740
ggctctttac cgagcatggc aacagctcga caatggatct tgcgcccaaa tacggcgggt   1800
aagtgaaccc gatgaactgc gagatatccc cgcattctac cgattggttc agccgtttgg   1860
ctgggagaac ccacggcacc agcaggcgct tcttaggatg gttttttgtc ttagtgccgg   1920
gaaaaacgta atccgccatc aggataagaa gtccgaacaa acaacaggga tttctctggg   1980
aagagcgctt gctaacagcg gcaggatcaa tgaacgccgc atatttcagt tgatccgagc   2040
agatcggact gctgatatgg tccagctcag gaggctcctt acgcacgcag agccagtgtt   2100
ggattggcca ctcatggcaa gaatgcttac gtggtggggg aagagggaaa ggcagcaact   2160
gcttgaagat tttgtattga cgacgaacaa aaacgcggga agcggagagg gcagaggaag   2220
tcttctcaca tgcggtgacg tggaggagaa tcctggacct atggattaca aagacgatga   2280
cgataagatg gcgcctaaga agaagcgcaa ggtgagagga atgtcaaact tcattaatat   2340
ccacgtgctt atctcacact cccctagttg ccttaacaga gacgatatga acatgcaaaa   2400
agacgcaatt tttggcggca aaaggagagt cagaattagt agccagagcc tgaagcgcgc   2460
tatgaggaaa agcggctact atgctcaaaa cattggtgaa agttcattgc ggaccatcca   2520
tctcgcgcag ttgagggacg tcctgcgaca gaagcttggg gaaagatttg atcagaagat   2580
catcgacaaa acgcttgccc ttctgtccgg taaatcagtg gacgaagcgg agaagataag   2640
tgcggatgct gttacgccat gggtggtagg tgaaatcgcg tggttttgcg agcaggtagc   2700
caaggccgaa gcggataatt tggatgataa gaaactgctc aaagtcctca aagaggacat   2760
cgcggcgatc cgggtgaacc ttcagcaggg tgttgatatt gcgctctctg gtcggatggc   2820
cacgtctgga atgatgactg aactgggtaa ggtggacgga gctatgtcta tagctcatgc   2880
tataactacc catcaggtgg attctgacat agactggttc acggctgtcg acgatctcca   2940
ggaacaagga tccgcacacc tcggcacgca agaattttct tctggagtgt tctataggta   3000
```

tgccaacatc aaccttgcac agctccagga aaacctcggt ggggcaagcc gggaacaggc 3060
tcttgaaata gctacccatg tggttcacat gctggcgacc gaagtgccag gggccaagca 3120
gagaacgtac gccgcattca atccggcgga catggtcatg gtgaatttct ctgatatgcc 3180
cttgtctatg gcaaatgctt tcgagaaggc ggtcaaggca aaggacggtt ttttgcaacc 3240
ctccatccaa gcctttaatc agtactggga tagagtagct aacgggtatg gtctcaatgg 3300
cgcggctgct cagttttctt tgtccgatgt ggatccgata acggcgcagg ttaaacagat 3360
gcccaccttg gaacaactca aatcctgggt tagaaacaat ggggaggcgg gaagcggagt 3420
gaaacagact ttgaactttg acttgctcaa gttggcagga gacgtggagt ccaaccctgg 3480
acctatggga tcggccattg aacaagatgg attgcacgca ggttctccgg ccgcttgggt 3540
ggagaggcta ttcggctatg actgggcaca acagacaatc ggctgctctg atgccgccgt 3600
gttccggctg tcagcgcagg ggcgcccggt tctttttgtc aagaccgacc tgtccggtgc 3660
cctgaatgaa ctgcaggacg aggcagcgcg gctatcgtgg ctggccacga cgggcgttcc 3720
ttgcgcagct gtgctcgacg ttgtcactga agcgggaagg gactggctgc tattgggcga 3780
agtgccgggg caggatctcc tgtcatctca ccttgctcct gccgagaaag tatccatcat 3840
ggctgatgca atgcggcggc tgcatacgct tgatccggct acctgcccat tcgaccacca 3900
agcgaaacat cgcatcgagc gagcacgtac tcggatggaa gccggtcttg tcgatcagga 3960
tgatctggac gaagagcatc aggggctcgc gccagccgaa ctgttcgcca ggctcaaggc 4020
gcgcatgccc gacggcgatg atctcgtcgt gacccatggc gatgcctgct tgccgaatat 4080
catggtggaa aatggccgct tttctggatt catcgactgt ggccggctgg gtgtggcgga 4140
ccgctatcag gacatagcgt tggctacccg tgatattgct gaagagcttg gcggcgaatg 4200
ggctgaccgc ttcctcgtgc tttacggtat cgccgctccc gattcgcagc gcatcgcctt 4260
ctatcgcctt cttgacgagt tcttctgaga attc 4294

<210> SEQ ID NO 297
<211> LENGTH: 3685
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 297
accggtcgcc accgccgcca ccatggatta caaggacgac gacgataaga tggcgccgaa 60
gaagaagcgg aaagtccggg gcatgagatc ctacctcatc ctgcgcctgg ccgggccgat 120
gcaggcctgg ggccagccta catttgaggg tacccggccc accggacggt tcccgacccg 180
ctcggggctt ctgggacttc tgggcgcatg tctgggcatc cagcgggatg acactagcag 240
cctgcaggcc ctgagcgaat ccgtgcagtt cgccgtgcgc tgcgatgaac tgatcctcga 300
cgaccgcagg gtgtcagtga ctggactgag agactaccac accgtgctgg gagcccgcga 360
ggattacagg ggcctgaagt cccatgaaac cattcagacc tggagagagt acctctgcga 420
cgcgtcgttc actgtggcac tgtggctcac gccgcacgcg accatggtca tctccgaact 480
ggaaaaagcc gtgctcaagc ctcggtacac cccctatctc ggacgacgct cctgcccact 540
gacccatccc ctgttcctcg gtacttgcca agccagcgac cctcaaaagg ctctgttgaa 600
ctacgaaccc gtggggggag acatctactc cgaggaatcc gtcaccggcc accacttgaa 660
gttcaccgcc cgggacgagc cgatgattac tctgccaaga cagttcgctt cacgggagtg 720
gtacgtgatt aagggtggaa tggacgtgtc gcagggaagc ggagctacta acttcagcct 780
gctgaagcag gctggagacg tggaggagaa ccctggacct atggattaca aagacgatga 840
cgataagatg gcgcctaaga agaagcgcaa ggtgcggggc atgtatctca gtaaagtcat 900
cattgccagg gcctggagca gggatcttta ccaacttcac cagggattat ggcatttatt 960
tccaaacaga ccggatgctg ctcgtgattt tctttttcat gttgagaagc gaaacacacc 1020
agaaggctgt catgttttat tgcagtcagc gcaaatgcct gtttcaactg ccgttgcgac 1080
agtcattaaa actaaacagg ttgaatttca acttcaggtt ggtgttccac tctattttcg 1140
gcttcgggca aatccgatca aaactattct cgacaatcaa aagcgcctgg acagtaaagg 1200
gaatattaaa cgctgtcggg ttccgttaat aaaagaagca gaacaaatcg cgtggttgca 1260
acgtaaattg ggcaatgcgg cgcgcgttga agatgtgcat cccatatcgg aacggccaca 1320
gtatttttct ggtgatggta aaagtggaaa gatccaaacg gtttgctttg aaggtgtgct 1380
caccatcaac gacgcgccag cgttaataga tcttgtacag caaggtattg ggccagctaa 1440
atcgatggga tgtggcttgc tatctttggc tccactgcgg ggcaagcgac ctgccgccac 1500
aaagaaggct ggacaggcta agaagaagaa aggatcctcg ccagggatcc gtcgacttga 1560
cgcgttgata tcaacaagtt tgtacaaaaa agcaggctac aaagaggcca gcggttccgg 1620
acgggctgac gcattggacg attttgatct ggatatgctg ggaagtgacg ccctcgatga 1680
ttttgacctt gacatgcttg gttcggatgc ccttgatgac tttgacctcg acatgctcgg 1740
cagtgacgcc cttgatgatt tcgacctgga catgctgatt aactctagaa gttccggatc 1800
tccgaaaaag aaacgcaaag ttggtagcca gtacctgccc gacaccgacg accggcaccg 1860
gatcgaggaa aagcggaagc ggacctacga gacattcaag agcatcatga agaagtcccc 1920
cttcagcggc cccaccgacc ctagacctcc acctagaaga atcgccgtgc ccagcagatc 1980
cagcgccagc gtgccaaaac ctgcccccca gccttacccc ttcaccagca gcctgagcac 2040
catcaactac gacgagttcc ctaccatggt gttccccagc ggccagatct ctcaggcctc 2100
tgctctggct ccagcccctc ctcaggtgct gcctcaggct cctgctcctg caccagctcc 2160
agccatggtg tctgcactgg ctcaggcacc agcacccgtg cctgtgctgg ctcctggacc 2220
tccacaggct gtggctccac cagcccctaa acctacacag gccggcgagg gcacactgtc 2280
tgaagctctg ctgcagctgc agttcgacga cgaggatctg ggagccctgc tgggaaacag 2340
caccgatcct gccgtgttca ccgacctggc cagcgtggac aacagcgagt tccagcagct 2400
gctgaaccag ggcatccctg tggcccctca caccaccgag cccatgctga tggaataccc 2460
cgaggccatc acccggctcg tgacaggcgc tcagaggcct cctgatccag ctcctgcccc 2520
tctgggagca ccaggcctgc ctaatggact gctgtctggc gacgaggact tcagctctat 2580
cgccgatatg gatttctcag ccttgctggg ctctggcagc ggcagccggg attccaggga 2640
agggatgttt ttgccgaagc ctgaggccgg ctccgctatt agtgacgtgt ttgagggccg 2700
cgaggtgtgc cagccaaaac gaatccggcc atttcatcct ccaggaagtc catgggccaa 2760
ccgcccactc cccgccagcc tcgcaccaac accaaccggt ccagtacatg agccagtcgg 2820
gtcactgacc ccggcaccag tccctcagcc actggatcca gcgcccgcag tgactcccga 2880
ggccagtcac ctgttggagg atcccgatga agagacgagc caggctgtca aagcccttcg 2940
ggagatggcc gatactgtga ttccccagaa ggaagaggct gcaatctgtg gccaaatgga 3000
cctttcccat ccgcccccaa ggggccatct ggatgagctg acaaccacac ttgagtccat 3060

-continued

```
gaccgaggat ctgaacctgg actcacccct gaccccggaa ttgaacgaga ttctggatac   3120

cttcctgaac gacgagtgcc tcttgcatgc catgcatatc agcacaggac tgtccatctt   3180

cgacacatct ctgttcggaa gcggagaggg cagaggaagt cttctcacat gcggtgacgt   3240

ggaggagaat cctggaccta agaccttcaa catctctcag caggatctgg agctggtgga   3300

ggtcgccact gagaagatca ccatgctcta tgaggacaac aagcaccatg tcggggcggc   3360

catcaggacc aagactgggg agatcatctc tgctgtccac attgaggcct acattggcag   3420

ggtcactgtc tgtgctgaag ccattgccat tgggtctgct gtgagcaacg ggcagaagga   3480

ctttgacacc attgtggctg tcaggcaccc ctactctgat gaggtggaca gatccatcag   3540

ggtggtcagc ccctgtggca tgtgcagaga gctcatctct gactatgctc ctgactgctt   3600

tgtgctcatt gagatgaatg gcaagctggt caaaaccacc attgaggaac tcatcccccct   3660

caagtacacc aggaactaag aattc                                         3685
```

<210> SEQ ID NO 298
<211> LENGTH: 5
<212> TYPE: PRT
<213> ORGANISM: Unknown
<220> FEATURE:
<223> OTHER INFORMATION: Description of Unknown: Yeast transcription repressor Mat-alpha-2 sequence

<400> SEQUENCE: 298

```
Lys Ile Pro Ile Lys
1               5
```

<210> SEQ ID NO 299
<211> LENGTH: 61
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 299

```
auaaaccggc ugggcuccuc cuuguacucu cugaggugu c gaguuccccg cgccagcggg     60

g                                                                     61
```

<210> SEQ ID NO 300
<211> LENGTH: 104
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 300

```
gaaaggacga aacagctagc ccggttttaa ctacttatta tgaaatgtaa atgcccagtt     60

gtagcaccgc ccagacgact ggccaccggt gcattacagt aagc                     104
```

<210> SEQ ID NO 301
<211> LENGTH: 82
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 301

```
ggaggctggg ctcctccttg tactctctga ggtgctctgg aaggaggggc agctccaccc     60
```

-continued tgggagggac tgtggcccag gt 82

<210> SEQ ID NO 302
<211> LENGTH: 62
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 302
ggagactggg ctcctccttg tactctctga gtgctctgga aggaggggca gctccaccct 60
gg 62

<210> SEQ ID NO 303
<211> LENGTH: 46
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 303
ggagactggg ctcctccctc tggaaggagg ggcagctcca ccctgg 46

<210> SEQ ID NO 304
<211> LENGTH: 53
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 304
ggagactggg ctcctccttg tactctctgg aaggaggggc agctccaccc tgg 53

<210> SEQ ID NO 305
<211> LENGTH: 61
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 305
ggagactggg ctcctccttg tactctctga tgctctggaa ggaggggcag ctccaccctg 60
g 61

<210> SEQ ID NO 306
<211> LENGTH: 58
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 306
ggagactggg ctcctccttg tactctctga gctggaagga ggggcagctc caccctgg 58

<210> SEQ ID NO 307
<211> LENGTH: 57
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 307
ggagactggg ctcctccttg tactctctga ctggaaggag gggcagctcc accctgg 57

<210> SEQ ID NO 308
<211> LENGTH: 60
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 308
ggagactggg ctcctccttg tactctctgt gctctggaag gaggggcagc tccaccctgg 60

<210> SEQ ID NO 309
<211> LENGTH: 61
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 309
ggagactggg ctcctccttg tactctctga ggtgctctgg aaggaggcag ctccaccctg 60
g 61

<210> SEQ ID NO 310
<211> LENGTH: 61
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 310
ggagactggg ctcctccttg tactctctga ggtgctggaa ggaggggcag ctccaccctg 60
g 61

<210> SEQ ID NO 311
<211> LENGTH: 36
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 311
acaaaaaaga gcctcaggat ccagcacaca ttatca 36

<210> SEQ ID NO 312
<211> LENGTH: 36
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 312
gcacacatta tcacaaactt agtgtccatc catcac 36

<210> SEQ ID NO 313
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 313
tcactgctga ccctctccgg acctgactcc acccct 36

<210> SEQ ID NO 314
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 314
cccctgaggg acacaggtca gccttgacca atgact 36

<210> SEQ ID NO 315
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 315
tggtacttaa aagtcattgg tcaaggctga cctgtg 36

<210> SEQ ID NO 316
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 316
ggcctgagag cttgctagtg attgcagctg tgtcgg 36

<210> SEQ ID NO 317
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 317
ttgtgattgg tggctcgcgc tcggctggag cgtgcc 36

<210> SEQ ID NO 318
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 318
gccgagcgcg agccaccaat cacaatggac agcggc 36

<210> SEQ ID NO 319
<211> LENGTH: 36
<212> TYPE: DNA
<213> ORGANISM: Artificial Sequence
<220> FEATURE:

<223> OTHER INFORMATION: Description of Artificial Sequence: Synthetic oligonucleotide

<400> SEQUENCE: 319
atcacaatgg acagcggcgg cgacaacagc cgcagc 36

<210> SEQ ID NO 320
<211> LENGTH: 36
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 320
gctccggccg cagcccggag ctccaacagg agcttt 36

<210> SEQ ID NO 321
<211> LENGTH: 36
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 321
acaggagctt tagaaccatt ttatgttgat tagata 36

<210> SEQ ID NO 322
<211> LENGTH: 36
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 322
agaaaacaat cagatctgcc ccgggccccc tcctcc 36

<210> SEQ ID NO 323
<211> LENGTH: 36
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 323
gcgtttcccg cggatacagc agtcgggtgt tggaga 36

<210> SEQ ID NO 324
<211> LENGTH: 36
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 324
acacccgact gctgtatccg cgggaaacgc tggctg 36

<210> SEQ ID NO 325
<211> LENGTH: 36
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 325
aacctctcca acacccgact gctgtatccg cgggaa 36

<210> SEQ ID NO 326
<211> LENGTH: 36
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 326
agtgcagccg cctagggctg ccggtcgctc cctccc 36

<210> SEQ ID NO 327
<211> LENGTH: 36
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 327
cactggcgtg cgcgctaggt cccctaccgg gcaggg 36

<210> SEQ ID NO 328
<211> LENGTH: 36
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 328
gctgcccgcc tgggctccgg ggcgtttagg ctacta 36

<210> SEQ ID NO 329
<211> LENGTH: 32
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 329
ctgacctgtg tccctcaggg gtggagtcag gt 32

<210> SEQ ID NO 330
<211> LENGTH: 32
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 330
cctgagagct tgctagtgat tgcagctgtg tc 32

<210> SEQ ID NO 331
<211> LENGTH: 32
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 331
gagaacaggg ggccagaact tcggcagtaa ag 32

<210> SEQ ID NO 332
<211> LENGTH: 32
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 332
atccagcaca cattatcaca aacttagtgt cc 32

<210> SEQ ID NO 333
<211> LENGTH: 32
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 333
caagctctca ggcctggcat catggtgcat tt 32

<210> SEQ ID NO 334
<211> LENGTH: 32
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 334
ggtggagtca ggtccggaga gggtcagcag tg 32

<210> SEQ ID NO 335
<211> LENGTH: 32
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 335
agcctcagga tccagcacac attatcacaa ac 32

<210> SEQ ID NO 336
<211> LENGTH: 32
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 336
tttgtgataa tgtgtgctgg atcctgaggc tc 32

<210> SEQ ID NO 337
<211> LENGTH: 32
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 337
cagatatgtg ctgctgcctc tctgtctggc ct 32

<210> SEQ ID NO 338
<211> LENGTH: 32
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 338
taccatggag aacagggggc cagaacttcg gc 32

<210> SEQ ID NO 339
<211> LENGTH: 32
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 339
cctcaggatc cagcacacat tatcacaaac tt 32

<210> SEQ ID NO 340
<211> LENGTH: 32
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 340
ccaacaaaaa agagcctcag gatccagcac ac 32

<210> SEQ ID NO 341
<211> LENGTH: 32
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 341
gagccaacaa aaaagagcct caggatccag ca 32

<210> SEQ ID NO 342
<211> LENGTH: 32
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 342
gctctttttt gttggctcct catctatctg ca 32

<210> SEQ ID NO 343
<211> LENGTH: 32
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 343
ggtcagcagt gatggatgga cactaagttt gt 32

<210> SEQ ID NO 344
<211> LENGTH: 32
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 344
ggacacaggt cagccttgac caatgacttt ta 32

<210> SEQ ID NO 345
<211> LENGTH: 32
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 345
aacagggggc cagaacttcg gcagtaaaga at 32

<210> SEQ ID NO 346
<211> LENGTH: 32
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 346
tgtccatcca tcactgctga ccctctccgg ac 32

<210> SEQ ID NO 347
<211> LENGTH: 32
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 347
atgaggagcc aacaaaaaag agcctcagga tc 32

<210> SEQ ID NO 348
<211> LENGTH: 32
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 348
tgattgcagc tgtgtcggaa gcagatatgt gc 32

<210> SEQ ID NO 349
<211> LENGTH: 32
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 349
tgtgctggat cctgaggctc ttttttgttg gc 32

<210> SEQ ID NO 350
<211> LENGTH: 32
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 350
aggagccaac aaaaaagagc ctcaggatcc ag 32

<210> SEQ ID NO 351
<211> LENGTH: 32
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 351
acttttaagt accatggaga acagggggcc ag 32

<210> SEQ ID NO 352
<211> LENGTH: 32
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 352
gacactaagt ttgtgataat gtgtgctgga tc 32

<210> SEQ ID NO 353
<211> LENGTH: 32
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 353
tcagctcaga ggtgagcgcg cgcagccagc gt 32

<210> SEQ ID NO 354
<211> LENGTH: 32
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 354
cgcgcgcagc cagcgtttcc cgcggataca gc 32

<210> SEQ ID NO 355
<211> LENGTH: 32
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 355
aggtttggaa agggcgtgcc ggagagccaa gt 32

<210> SEQ ID NO 356
<211> LENGTH: 32
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 356
cggctgcact tggctctccg gcacgccctt tc 32

<210> SEQ ID NO 357
<211> LENGTH: 32
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 357
ggcgtgccgg agagccaagt gcagccgcct ag 32

<210> SEQ ID NO 358
<211> LENGTH: 32
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 358
agccaagtgc agccgcctag ggctgccggt cg 32

<210> SEQ ID NO 359
<211> LENGTH: 32
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 359
tgcagccgcc tagggctgcc ggtcgctccc tc 32

<210> SEQ ID NO 360
<211> LENGTH: 32
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 360
ggagggagcg accggcagcc ctaggcggct gc 32

<210> SEQ ID NO 361
<211> LENGTH: 32
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 361
tcccctaccg ggcagggagg gagggagcga cc 32

<210> SEQ ID NO 362
<211> LENGTH: 32
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 362
gggcgggctg gctggccagt ctgcgggccc ct 32

<210> SEQ ID NO 363
<211> LENGTH: 32
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 363
ccccgccccg cagtgttcct attggcctcg ga 32

<210> SEQ ID NO 364
<211> LENGTH: 32
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 364
ctactacgga taaatagccc agggcgcctg gc 32

<210> SEQ ID NO 365
<211> LENGTH: 32
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 365
cgcgagccac caatcacaat ggacagcggc gg 32

<210> SEQ ID NO 366
<211> LENGTH: 32
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 366
ctgcggctgt tgtcgccgcc gctgtccatt gt 32

<210> SEQ ID NO 367
<211> LENGTH: 32
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 367
ctcaagctgc ggctgttgtc gccgccgctg tc 32

<210> SEQ ID NO 368
<211> LENGTH: 32
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 368
ccgcagcggc cgcagaggct caagctgcgg ct 32

<210> SEQ ID NO 369
<211> LENGTH: 32
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 369
ctggcgaagc cgcagcggcc gcagaggctc aa 32

<210> SEQ ID NO 370
<211> LENGTH: 32
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 370
cctctgcggc cgctgcggct tcgccagctc cg 32

<210> SEQ ID NO 371
<211> LENGTH: 32
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 371
ctccgggctg cggccggagc tggcgaagcc gc 32

<210> SEQ ID NO 372
<211> LENGTH: 32
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 372
ctcctgttgg agctccgggc tgcggccgga gc 32

<210> SEQ ID NO 373
<211> LENGTH: 32
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 373
ctccaacagg agctttagaa ccattttatg tt 32

<210> SEQ ID NO 374

<211> LENGTH: 32
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 374
agaggcgggg gtggtgggag gaggaggatg ga 32

<210> SEQ ID NO 375
<211> LENGTH: 32
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 375
gggcccgggg cagatctgat tgttttcttg gt 32

<210> SEQ ID NO 376
<211> LENGTH: 32
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 376
gggttttaag gagagtcgtg tgccagacac gc 32

<210> SEQ ID NO 377
<211> LENGTH: 1512
<212> TYPE: DNA
<213> ORGANISM: Artificial Sequence
<220> FEATURE:
<223> OTHER INFORMATION: Synthetic

<400> SEQUENCE: 377
atggccaatc tcctgattga caattggatc cctgtgagac cgaggaacgg agggaaggtt 60
cagatcatca acctgcaaag tctctactgt agcagagatc aatggcgact ctcattgccc 120
agggatgata tggaattggc ggcacttgca ctcttggtat gtattgggca gatcatcgcc 180
cctgccaagg atgatgtcga gtttaggcac agaataatga accctcttac tgaagatgaa 240
ttccagcaat tgatcgcgcc ttggatagat atgttctatt tgaatcacgc cgaacatccc 300
ttcatgcaga caaaaggggt taaagcaaat gatgtcacac caatggagaa gcttttggca 360
ggtgtgtcag gagcaaccaa ctgcgctttc gttaaccaac caggccaagg tgaggcgttg 420 tgcgggggggt gcacggccat agcgttgttt aatcaggcga accaggctcc tggctttgga 480
ggaggattca agtccggttt gcgcgggggt acacccgtaa ccacattcgt tcgcggaatt 540
gacctccgat caacagtcct gttgaacgta ttgacgttgc ctagacttca gaagcaattt 600
ccaaacgagt ctcacactga gaatcaaccg acttggatta agcccatcaa gtcaaatgaa 660
agtatacccg cgtcttctat tggatttgtt agaggacttt tttggcagcc cgctcacata 720
gaactctgtg atcccatagg cattggaaag tgttcttgct gtggccaaga gtctaacctt 780
agatatacgg gctttctcaa ggagaagttc acgttcaccg tgaatggact ttggccacat 840
ccccatagcc cgtgcttggt cacggtcaag aagggggagg ttgaagagaa atttcttgcg 900
tttaccacat ccgccccatc ctggacgcaa atatctcgcg tcgttgtgga taaaatcatc 960
cagaacgaaa atggtaaccg cgttgccgcg gtagtgaatc aattcagaaa catagcacca 1020
cagagcccgt tggagttgat aatgggcggg taccgcaata atcaagcttc cattctcgag 1080
cgacgccatg acgtacttat gtttaaccag gggtggcagc aatatggtaa cgtgataaac 1140
gagatagtca cagtcggcct cggctacaaa actgcgttgc gcaaagctct gtatacgttc 1200
gcggagggtt ttaagaataa agactttaaa ggcgctgggg tgagtgtgca cgagacggca 1260
gaacgccatt tctatcgcca gtctgaactc ttgattcccg acgttctggc gaatgtcaat 1320
ttttcccagg ccgatgaggt cattgcggat ctgcgagata agcttcacca gttgtgtgag 1380
atgctgttca accagtctgt ggctccttat gctcatcatc ccaaactgat ttcaactctc 1440
gctttggcaa gggctacgtt gtataaacac cttagagaac tgaagccaca gggtggtccc 1500
agcaatggct ga 1512

<210> SEQ ID NO 378
<211> LENGTH: 483
<212> TYPE: DNA
<213> ORGANISM: Artificial Sequence
<220> FEATURE:
<223> OTHER INFORMATION: Synthetic

<400> SEQUENCE: 378
atggccgatg aaatagacgc aatggctctt taccgagcat ggcaacagct cgacaatgga 60
tcttgcgccc aaatacggcg ggtaagtgaa cccgatgaac tgcgagatat ccccgcattc 120
taccgattgg ttcagccgtt tggctgggag aacccacggc accagcaggc gcttcttagg 180
atggtttttt gtcttagtgc cgggaaaaac gtaatccgcc atcaggataa gaagtccgaa 240
caaacaacag ggatttctct gggaagagcg cttgctaaca gcggcaggat caatgaacgc 300
cgcatatttc agttgatccg agcagatcgg actgctgata tggtccagct caggaggctc 360
cttacgcacg cagagccagt gttggattgg ccactcatgg caagaatgct tacgtggtgg 420
gggaagaggg aaaggcagca actgcttgaa gattttgtat tgacgacgaa caaaaacgcg 480
taa 483

<210> SEQ ID NO 379
<211> LENGTH: 1092
<212> TYPE: DNA
<213> ORGANISM: Artificial Sequence
<220> FEATURE:
<223> OTHER INFORMATION: Sytthetic

<400> SEQUENCE: 379
atgtcaaact tcattaatat ccacgtgctt atctcacact cccctagttg ccttaacaga 60
gacgatatga acatgcaaaa agacgcaatt tttggcggca aaaggagagt cagaattagt 120
agccagagcc tgaagcgcgc tatgaggaaa agcggctact atgctcaaaa cattggtgaa 180
agttcattgc ggaccatcca tctcgcgcag ttgagggacg tcctgcgaca gaagcttggg 240
gaaagatttg atcagaagat catcgacaaa acgcttgccc ttctgtccgg taaatcagtg 300

```
gacgaagcgg agaagataag tgcggatgct gttacgccat gggtggtagg tgaaatcgcg    360

tggttttgcg agcaggtagc caaggccgaa gcggataatt tggatgataa gaaactgctc    420

aaagtcctca aagaggacat cgcggcgatc cgggtgaacc ttcagcaggg tgttgatatt    480

gcgctctctg gtcggatggc cacgtctgga atgatgactg aactgggtaa ggtggacgga    540

gctatgtcta tagctcatgc tataactacc catcaggtgg attctgacat agactggttc    600

acggctgtcg acgatctcca ggaacaagga tccgcacacc tcggcacgca agaattttct    660

tctggagtgt tctataggta tgccaacatc aaccttgcac agctccagga aaacctcggt    720

ggggcaagcc gggaacaggc tcttgaaata gctacccatg tggttcacat gctggcgacc    780

gaagtgccag gggccaagca gagaacgtac gccgcattca atccggcgga catggtcatg    840

gtgaatttct ctgatatgcc cttgtctatg gcaaatgctt tcgagaaggc ggtcaaggca    900

aaggacggtt ttttgcaacc ctccatccaa gcctttaatc agtactggga tagagtagct    960

aacgggtatg gtctcaatgg cgcggctgct cagttttctt tgtccgatgt ggatccgata   1020

acggcgcagg ttaaacagat gcccaccttg gaacaactca aatcctgggt tagaaacaat   1080

ggggaggcgt ga                                                       1092


<210> SEQ ID NO 380
<211> LENGTH: 675
<212> TYPE: DNA
<213> ORGANISM: Artificial Sequence
<220> FEATURE:
<223> OTHER INFORMATION: Synthetic

<400> SEQUENCE: 380

atgcgatcat acttgatcct gcggcttgca ggtcctatgc aagcctgggg gcaacctacc     60

tttgaaggta ctcggccgac tggcaggttc cctacgcggt ctggtttgct cggactcctc    120

ggcgcctgtt tggggataca aagggatgac acttcttcct tgcaggcact ttccgaatca    180

gtccagttcg cagtgagatg tgatgaactc atactggacg acagacgggt gtccgtaact    240

ggactgaggg actatcatac tgtactcggc gcaagagaag attatcgagg tcttaagtca    300

catgagacta ttcagacatg gagggaatat ttgtgtgacg cctccttcac ggtggccctc    360

tggcttacac cacatgcaac tatggtgatc tcagagcttg agaaagccgt tcttaaacct    420

cggtacacac catatctggg gaggcggtct tgcccactta cccacccgct tttcttgggg    480

acttgtcagg ccagcgatcc acagaaggcc ttgctgaact atgaacccgt tggtggcgat    540

atatacagtg aagagagcgt cacgggccat cacttgaagt tcactgctag ggatgagccg    600

atgattacgc tcccgagaca gttcgctagt agggaatggt acgttattaa gggggggaatg    660

gacgtttccc aatga                                                     675


<210> SEQ ID NO 381
<211> LENGTH: 600
<212> TYPE: DNA
<213> ORGANISM: Artificial Sequence
<220> FEATURE:
<223> OTHER INFORMATION: Synthetic

<400> SEQUENCE: 381

atgtatctca gtaaagtcat cattgccagg gcctggagca gggatcttta ccaacttcac     60

cagggattat ggcatttatt tccaaacaga ccggatgctg ctcgtgattt tctttttcat    120

gttgagaagc gaaacacacc agaaggctgt catgttttat tgcagtcagc gcaaatgcct    180

gtttcaactg ccgttgcgac agtcattaaa actaaacagg ttgaatttca acttcaggtt    240
```

-continued

```
ggtgttccac tctattttcg gcttcgggca aatccgatca aaactattct cgacaatcaa    300

aagcgcctgg acagtaaagg gaatattaaa cgctgtcggg ttccgttaat aaaagaagca    360

gaacaaatcg cgtggttgca acgtaaattg ggcaatgcgg cgcgcgttga agatgtgcat    420

cccatatcgg aacggccaca gtatttttct ggtgatggta aaagtggaaa gatccaaacg    480

gtttgctttg aaggtgtgct caccatcaac gacgcgccag cgttaataga tcttgtacag    540

caaggtattg ggccagctaa atcgatggga tgtggcttgc tatctttggc tccactgtga    600
```